US010596172B2

(12) United States Patent
Singh et al.

(10) Patent No.: US 10,596,172 B2
(45) Date of Patent: Mar. 24, 2020

(54) 2,4-DISUBSTITUTED PYRIMIDINES USEFUL AS KINASE INHIBITORS

(71) Applicant: Celgene CAR LLC, Pembroke (BM)

(72) Inventors: Juswinder Singh, Southborough, MA (US); Russell C. Petter, Stow, MA (US); Richland Wayne Tester, Marlborough, MA (US); Arthur F. Kluge, Lincoln, MA (US); Hormoz Mazdiyasni, Marlborough, MA (US); William Frederick Westlin, III, Boxborough, MA (US); Deqiang Niu, Lexington, MA (US); Lixin Qiao, Andover, MA (US)

(73) Assignee: Celgene CAR LLC, Pembroke (BM)

(*) Notice: Subject to any disclaimer, the term of this patent is extended or adjusted under 35 U.S.C. 154(b) by 0 days.

(21) Appl. No.: 16/024,514

(22) Filed: Jun. 29, 2018

(65) Prior Publication Data

US 2019/0192512 A1 Jun. 27, 2019

Related U.S. Application Data

(60) Division of application No. 15/221,421, filed on Jul. 27, 2016, now Pat. No. 10,010,548, which is a division of application No. 14/253,903, filed on Apr. 16, 2014, now Pat. No. 9,409,921, which is a continuation of application No. 13/667,396, filed on Nov. 2, 2012, now Pat. No. 8,710,222, which is a division of application No. 12/648,693, filed on Dec. 29, 2009, now Pat. No. 8,338,439, which is a continuation-in-part of application No. 12/492,180, filed on Jun. 26, 2009, now Pat. No. 8,450,335.

(60) Provisional application No. 61/170,874, filed on Apr. 20, 2009, provisional application No. 61/148,388, filed on Jan. 29, 2009, provisional application No. 61/076,450, filed on Jun. 27, 2008.

(51) Int. Cl.

| | |
|---|---|
| ***C07D 239/48*** | (2006.01) |
| ***A61K 31/505*** | (2006.01) |
| ***C07D 239/47*** | (2006.01) |
| ***C07D 401/14*** | (2006.01) |
| ***C07D 403/12*** | (2006.01) |
| ***C07D 407/12*** | (2006.01) |
| ***C07D 413/12*** | (2006.01) |
| ***C07D 413/14*** | (2006.01) |
| ***C07D 471/04*** | (2006.01) |
| ***C07D 487/04*** | (2006.01) |
| ***C07D 487/18*** | (2006.01) |
| ***A61K 31/506*** | (2006.01) |
| ***A61K 31/519*** | (2006.01) |
| ***A61K 31/5377*** | (2006.01) |
| ***A61K 31/538*** | (2006.01) |
| ***A61K 31/541*** | (2006.01) |
| ***A61K 45/06*** | (2006.01) |
| ***C07D 401/12*** | (2006.01) |
| ***C07D 405/12*** | (2006.01) |
| ***C07D 405/14*** | (2006.01) |
| ***C07D 487/08*** | (2006.01) |
| ***C07D 495/04*** | (2006.01) |

(52) U.S. Cl.

CPC .......... *A61K 31/505* (2013.01); *A61K 31/506* (2013.01); *A61K 31/519* (2013.01); *A61K 31/538* (2013.01); *A61K 31/5377* (2013.01); *A61K 31/541* (2013.01); *A61K 45/06* (2013.01); *C07D 239/47* (2013.01); *C07D 239/48* (2013.01); *C07D 401/12* (2013.01); *C07D 401/14* (2013.01); *C07D 403/12* (2013.01); *C07D 405/12* (2013.01); *C07D 405/14* (2013.01); *C07D 407/12* (2013.01); *C07D 413/12* (2013.01); *C07D 413/14* (2013.01); *C07D 471/04* (2013.01); *C07D 487/04* (2013.01); *C07D 487/08* (2013.01); *C07D 487/18* (2013.01); *C07D 495/04* (2013.01)

(58) Field of Classification Search

CPC .................................................... C07D 239/48
USPC .......................................................... 544/323
See application file for complete search history.

(56) References Cited

U.S. PATENT DOCUMENTS

| | | | |
|---|---|---|---|
| 4,032,637 | A | 6/1977 | Spiegel et al. |
| 4,879,303 | A | 11/1989 | Davison et al. |
| 5,453,510 | A | 9/1995 | Hill et al. |
| 5,958,935 | A | 9/1999 | Davis et al. |
| 6,093,716 | A | 7/2000 | Davis et al. |
| 6,114,333 | A | 9/2000 | Davis et al. |
| 6,127,376 | A | 10/2000 | Davey et al. |
| 6,160,010 | A | 12/2000 | Uckun et al. |
| 6,262,088 | B1 | 7/2001 | Phillips |
| 6,432,963 | B1 | 8/2002 | Hisamichi et al. |
| 6,469,168 | B1 | 10/2002 | Ratzne Simonek et al. |
| 6,579,983 | B1 | 6/2003 | Batchelor et al. |
| 6,593,326 | B1 | 7/2003 | Bradbury et al. |

(Continued)

FOREIGN PATENT DOCUMENTS

| | | |
|---|---|---|
| CN | 102558149 A | 7/2012 |
| CN | 103159742 A | 6/2013 |

(Continued)

OTHER PUBLICATIONS

U.S. Appl. No. 13/518,833, filed Jun. 22, 2012, Gray et al.

(Continued)

*Primary Examiner* — Douglas M Willis

(74) *Attorney, Agent, or Firm* — Choate, Hall & Stewart LLP; Kristen C. Buteau; Erica M. D'Amato

(57) ABSTRACT

The present invention provides 2,4-disubstituted pyrimidine compounds useful as kinase inhibitors, pharmaceutically (Continued)

acceptable compositions thereof, and methods of using the same.

3 Claims, 29 Drawing Sheets

Specification includes a Sequence Listing.

(56) References Cited

U.S. PATENT DOCUMENTS

| | | | |
|---|---|---|---|
| 6,838,464 | B2 | 1/2005 | Pease et al. |
| 6,939,874 | B2 | 9/2005 | Harmange et al. |
| 7,060,827 | B2 | 6/2006 | Singh et al. |
| 7,122,542 | B2 | 10/2006 | Singh et al. |
| 7,125,879 | B2 | 10/2006 | Guillemont et al. |
| 7,176,212 | B2 | 2/2007 | Breault et al. |
| 7,202,033 | B2 | 4/2007 | Prescott et al. |
| 7,241,769 | B2 | 7/2007 | Stadtmueller et al. |
| 7,282,504 | B2 | 10/2007 | Armistead et al. |
| 7,329,671 | B2 | 2/2008 | Singh et al. |
| 7,329,672 | B2 | 2/2008 | Singh et al. |
| 7,332,484 | B2 | 2/2008 | Singh et al. |
| 7,435,814 | B2 | 10/2008 | Singh et al. |
| 7,452,879 | B2 | 11/2008 | Singh et al. |
| 7,485,724 | B2 | 2/2009 | Singh et al. |
| 7,491,732 | B2 | 2/2009 | Li et al. |
| 7,498,435 | B2 | 3/2009 | Singh et al. |
| 7,504,396 | B2 | 3/2009 | Nunes et al. |
| 7,514,444 | B2 | 4/2009 | Honigberg et al. |
| 7,514,445 | B2 | 4/2009 | Freyne et al. |
| 7,514,446 | B2 | 4/2009 | Davis-Ward et al. |
| 7,517,886 | B2 | 4/2009 | Singh et al. |
| 7,528,143 | B2 | 5/2009 | Noronha et al. |
| 7,531,548 | B2 | 5/2009 | Guillemont et al. |
| 7,550,460 | B2 | 6/2009 | Singh et al. |
| 7,557,210 | B2 | 7/2009 | Singh et al. |
| 7,582,648 | B2 | 9/2009 | Singh et al. |
| 7,589,200 | B2 | 9/2009 | Singh et al. |
| 7,642,351 | B2 | 1/2010 | Singh et al. |
| 7,655,797 | B2 | 2/2010 | Singh et al. |
| 7,718,662 | B1 | 5/2010 | Chen et al. |
| 7,741,330 | B1 | 6/2010 | Chen et al. |
| 7,803,939 | B2 | 9/2010 | Singh et al. |
| 7,812,029 | B1 | 10/2010 | Singh et al. |
| 7,820,819 | B2 | 10/2010 | Singh et al. |
| 7,825,116 | B2 | 11/2010 | Singh et al. |
| 7,858,633 | B2 | 12/2010 | Li et al. |
| 7,884,111 | B2 | 2/2011 | Argade et al. |
| 7,906,644 | B2 | 3/2011 | Singh et al. |
| 8,088,781 | B2 | 1/2012 | Honigberg et al. |
| 8,148,525 | B2 | 4/2012 | Singh et al. |
| 8,158,621 | B2 | 4/2012 | Singh et al. |
| 8,188,276 | B2 | 5/2012 | Singh et al. |
| 8,334,296 | B2 | 12/2012 | Singh et al. |
| 8,338,439 | B2 | 12/2012 | Singh et al. |
| 8,450,335 | B2 | 5/2013 | Singh et al. |
| 8,501,751 | B2 | 8/2013 | Honigberg et al. |
| 8,557,806 | B2 | 10/2013 | Singh et al. |
| 8,563,568 | B2 | 10/2013 | Witowski et al. |
| 8,609,679 | B2 | 12/2013 | Singh et al. |
| 8,710,222 | B2 | 4/2014 | Singh et al. |
| 8,735,404 | B2 | 5/2014 | Honigberg et al. |
| 8,748,438 | B2 | 6/2014 | Honigberg et al. |
| 8,748,597 | B2 | 6/2014 | Singh et al. |
| 8,796,255 | B2 | 8/2014 | Lee et al. |
| 8,822,685 | B2 | 9/2014 | Singh et al. |
| 8,835,430 | B2 | 9/2014 | Singh et al. |
| 8,853,397 | B2 | 10/2014 | Singh et al. |
| 8,883,435 | B2 | 11/2014 | Honigberg et al. |
| 8,883,803 | B2 | 11/2014 | Honigberg et al. |
| 8,975,249 | B2 | 3/2015 | Lee et al. |
| 9,212,181 | B2 | 12/2015 | Singh et al. |
| 9,238,629 | B2 | 1/2016 | Lee et al. |
| 9,296,737 | B2 | 3/2016 | Singh et al. |
| 9,375,431 | B2 | 6/2016 | Lee et al. |
| 9,409,887 | B2 | 8/2016 | Lee et al. |
| 9,409,921 | B2 | 8/2016 | Singh et al. |
| 9,604,936 | B2 | 3/2017 | Witowski et al. |
| 9,765,038 | B2 | 9/2017 | Lee et al. |
| 9,867,824 | B2 | 1/2018 | Lee et al. |
| 9,868,723 | B2 | 1/2018 | Lee et al. |
| 9,987,276 | B2 | 6/2018 | Singh et al. |
| 10,010,548 | B2 | 7/2018 | Singh et al. |
| 10,081,606 | B2 | 9/2018 | Lee et al. |
| 2004/0019067 | A1 | 1/2004 | Armistead et al. |
| 2004/0023957 | A1 | 2/2004 | Wang et al. |
| 2004/0077661 | A1 | 4/2004 | Arbiser |
| 2005/0004125 | A1 | 1/2005 | Freyne et al. |
| 2005/0014753 | A1 | 1/2005 | Ding et al. |
| 2005/0085637 | A1 | 4/2005 | Cheung et al. |
| 2005/0209221 | A1 | 9/2005 | Nunes et al. |
| 2005/0272083 | A1 | 12/2005 | Seshagiri |
| 2006/0030018 | A1 | 2/2006 | Zuccola et al. |
| 2006/0079543 | A1 | 4/2006 | Sum et al. |
| 2006/0084644 | A1 | 4/2006 | Pal et al. |
| 2006/0084645 | A1 | 4/2006 | Pal et al. |
| 2006/0100227 | A1 | 5/2006 | Baenteli et al. |
| 2006/0148800 | A1 | 7/2006 | Stadtmueller et al. |
| 2006/0160803 | A1 | 7/2006 | Adams et al. |
| 2006/0247241 | A1 | 11/2006 | Garcia-Echeverria et al. |
| 2006/0247262 | A1 | 11/2006 | Baenteli et al. |
| 2006/0270694 | A1 | 11/2006 | Wong |
| 2006/0293311 | A1 | 12/2006 | Li et al. |
| 2007/0010668 | A1 | 1/2007 | Davis-Ward et al. |
| 2007/0032493 | A1 | 2/2007 | Foley et al. |
| 2007/0066658 | A1 | 3/2007 | Chappell |
| 2007/0105839 | A1 | 5/2007 | Imbach et al. |
| 2007/0203161 | A1 | 8/2007 | Argade et al. |
| 2007/0203162 | A1 | 8/2007 | Li et al. |
| 2007/0259904 | A1 | 11/2007 | Noronha et al. |
| 2008/0009484 | A1 | 1/2008 | Argade et al. |
| 2008/0009494 | A1 | 1/2008 | Li et al. |
| 2008/0021020 | A1 | 1/2008 | Argade et al. |
| 2008/0027045 | A1 | 1/2008 | Argade et al. |
| 2008/0039622 | A1 | 2/2008 | Singh et al. |
| 2008/0058358 | A1 | 3/2008 | Luecking et al. |
| 2008/0076921 | A1 | 3/2008 | Honigberg et al. |
| 2008/0132504 | A1 | 6/2008 | Garcia-Echeverria et al. |
| 2008/0139582 | A1 | 6/2008 | Honigberg et al. |
| 2008/0167330 | A1 | 7/2008 | Luecking et al. |
| 2008/0176866 | A1 | 7/2008 | Jautelat et al. |
| 2008/0182852 | A1 | 7/2008 | Johnson et al. |
| 2008/0194603 | A1 | 8/2008 | Li et al. |
| 2008/0194605 | A1 | 8/2008 | Heinrich et al. |
| 2008/0207613 | A1 | 8/2008 | Styles et al. |
| 2008/0214501 | A1 | 9/2008 | Pan et al. |
| 2008/0260754 | A1 | 10/2008 | Li et al. |
| 2008/0279867 | A1 | 11/2008 | Atuegbu et al. |
| 2008/0300268 | A1 | 12/2008 | Singh et al. |
| 2008/0312438 | A1 | 12/2008 | Singh et al. |
| 2009/0131436 | A1 | 5/2009 | Imbach et al. |
| 2009/0137588 | A1 | 5/2009 | Singh et al. |
| 2009/0156622 | A1 | 6/2009 | Singh et al. |
| 2009/0171086 | A1 | 7/2009 | Singh et al. |
| 2009/0181987 | A1 | 7/2009 | Honigberg et al. |
| 2009/0215803 | A1 | 8/2009 | Rice et al. |
| 2009/0286778 | A1 | 11/2009 | Combs et al. |
| 2009/0298830 | A1 | 12/2009 | Mann et al. |
| 2009/0318407 | A1 | 12/2009 | Bauer et al. |
| 2010/0004270 | A1 | 1/2010 | Honigberg et al. |
| 2010/0016296 | A1 | 1/2010 | Singh et al. |
| 2010/0022561 | A1 | 1/2010 | Honigberg et al. |
| 2010/0029610 | A1 | 2/2010 | Singh et al. |
| 2010/0041677 | A1 | 2/2010 | Honigberg et al. |
| 2010/0081679 | A1 | 4/2010 | Greul et al. |
| 2010/0088912 | A1 | 4/2010 | Higgs et al. |
| 2010/0144732 | A1 | 6/2010 | Krueger et al. |
| 2010/0173285 | A1 | 7/2010 | Varmus et al. |
| 2010/0197918 | A1 | 8/2010 | Singh et al. |
| 2010/0249092 | A1 | 9/2010 | Singh et al. |
| 2010/0254905 | A1 | 10/2010 | Honigberg et al. |
| 2011/0039868 | A1 | 2/2011 | Honigberg et al. |
| 2011/0105472 | A1 | 5/2011 | Greul et al. |
| 2011/0144330 | A1 | 6/2011 | Singh et al. |

(56) References Cited

U.S. PATENT DOCUMENTS

2011/0207736 A1 8/2011 Gray et al.
2011/0224235 A1 9/2011 Honigberg et al.
2011/0245156 A1 10/2011 Sielecki-Dzurdz
2011/0245284 A1 10/2011 Greul et al.
2011/0281322 A1 11/2011 Honigberg et al.
2011/0281850 A1 11/2011 Flynn et al.
2012/0040968 A1 2/2012 Shimada et al.
2012/0065201 A1 3/2012 Honigberg et al.
2012/0071497 A1 3/2012 Buggy et al.
2012/0077832 A1 3/2012 Witowski et al.
2012/0083006 A1 4/2012 Ramsden et al.
2012/0087915 A1 4/2012 Buggy et al.
2012/0088912 A1 4/2012 Honigberg et al.
2012/0094999 A1 4/2012 Gray et al.
2012/0101113 A1 4/2012 Honigberg et al.
2012/0101114 A1 4/2012 Honigberg et al.
2012/0149687 A1 6/2012 Lee et al.
2012/0149722 A1 6/2012 Lee et al.
2012/0157426 A1 6/2012 Lee et al.
2012/0165328 A1 6/2012 Honigberg et al.
2012/0165332 A1 6/2012 Major et al.
2012/0184013 A1 7/2012 Honigberg et al.
2012/0184567 A1 7/2012 Honigberg et al.
2012/0202264 A1 8/2012 Honigberg et al.
2012/0270237 A9 10/2012 Ramsden et al.
2012/0296089 A1 11/2012 Honigberg et al.
2012/0316135 A1 12/2012 Dalgarno et al.
2012/0329130 A1 12/2012 Honigberg et al.
2013/0035334 A1 2/2013 Honigberg et al.
2013/0065879 A1 3/2013 Singh et al.
2013/0065899 A1 3/2013 Singh et al.
2013/0072469 A1 3/2013 Singh et al.
2013/0137708 A1 5/2013 Garske et al.
2013/0165462 A1 6/2013 Singh et al.
2014/0057929 A1 2/2014 Witowski et al.
2014/0134265 A1 5/2014 Buggy et al.
2014/0142123 A1 5/2014 Honigberg et al.
2014/0163027 A1 6/2014 Verner et al.
2014/0163046 A1 6/2014 Honigberg et al.
2014/0187564 A1 7/2014 Honigberg et al.
2014/0187565 A1 7/2014 Honigberg et al.
2014/0213574 A1 7/2014 Singh et al.
2014/0303154 A1 10/2014 Singh et al.
2014/0303191 A1 10/2014 Buggy et al.
2014/0330007 A1 11/2014 Singh et al.
2014/0371241 A1 12/2014 Buggy et al.
2015/0005297 A1 1/2015 Singh et al.
2015/0025055 A1 1/2015 Lee et al.
2015/0038518 A1 2/2015 Balasubramanian
2015/0126504 A1 5/2015 Singh et al.
2015/0158823 A1 6/2015 Singh et al.
2015/0246040 A1 9/2015 Lee et al.
2016/0130236 A1 5/2016 Lee et al.
2016/0303121 A1 10/2016 Singh et al.
2016/0332994 A1 11/2016 Lee et al.
2017/0027937 A1 2/2017 Lee et al.
2017/0100397 A1 4/2017 Singh et al.
2017/0281623 A1 10/2017 Lai
2018/0072687 A1 3/2018 Lee et al.
2018/0353508 A1 12/2018 Lee et al.

FOREIGN PATENT DOCUMENTS

EP 1 054 004 A1 11/2000
JP H0741461 A 2/1995
WO WO-96/28427 A1 9/1996
WO WO-97/19065 A1 5/1997
WO WO-99/31073 A1 6/1999
WO WO-00/027825 A1 5/2000
WO WO-00/046203 A2 8/2000
WO WO-00/078731 A1 12/2000
WO WO-01/047897 A1 7/2001
WO WO-01/060816 A1 8/2001
WO WO-01/064654 A1 9/2001
WO WO-01/064655 A1 9/2001
WO WO-01/085699 A2 11/2001
WO WO-02/04429 A1 1/2002
WO WO-02/083653 A1 10/2002
WO WO-03/016306 A1 2/2003
WO WO-03/030909 A1 4/2003
WO WO-03/063794 A2 8/2003
WO WO-03/066601 A1 8/2003
WO WO-2004/014382 A1 2/2004
WO WO-2004/031232 A1 4/2004
WO WO-2004/050068 A1 6/2004
WO WO-2004/056786 A2 7/2004
WO WO-2004/069812 A1 8/2004
WO WO-2004/074244 A2 9/2004
WO WO-2004/080980 A1 9/2004
WO WO-2004/096224 A2 11/2004
WO WO-2005/009443 A1 2/2005
WO WO-2005/013996 A2 2/2005
WO WO-2005/016893 A2 2/2005
WO WO-2005/016894 A1 2/2005
WO WO-2005/026130 A1 3/2005
WO WO-2005/026158 A1 3/2005
WO WO-2005/063722 A1 7/2005
WO WO-2005/070890 A2 8/2005
WO WO-2006/021544 A1 3/2006
WO WO-2006/045066 A2 4/2006
WO WO-2006/053109 A1 5/2006
WO WO-2006/055561 A2 5/2006
WO WO-2006/061415 A1 6/2006
WO WO-2006/068770 A1 6/2006
WO WO-2006/074057 A2 7/2006
WO WO-2006/076706 A1 7/2006
WO WO-2006/078846 A1 7/2006
WO WO-2006/101977 A2 9/2006
WO WO-2006/108487 A1 10/2006
WO WO-2006/124874 A2 11/2006
WO WO-2006/128129 A2 11/2006
WO WO-2006/129100 A1 12/2006
WO WO-2006/133426 A2 12/2006
WO WO-2007/027238 A2 3/2007
WO WO-2007/048064 A2 4/2007
WO WO-2007/053452 A1 5/2007
WO WO-2007/056151 A2 5/2007
WO WO-2007/085833 A2 8/2007
WO WO-2007/089768 A2 8/2007
WO WO-2007/113254 A1 10/2007
WO WO-2007/113256 A1 10/2007
WO WO-2007/120339 A1 10/2007
WO WO-2007/120980 A2 10/2007
WO WO-2007/125351 A1 11/2007
WO WO-2008/005538 A2 1/2008
WO WO-2008/009458 A1 1/2008
WO WO-2008/025556 A1 3/2008
WO WO-2008/049123 A2 4/2008
WO WO-2008/064274 A1 5/2008
WO WO-2008/073687 A2 6/2008
WO WO-2008/074515 A1 6/2008
WO WO-2008/079719 A1 7/2008
WO WO-2008/079907 A1 7/2008
WO WO-2008/080964 A1 7/2008
WO WO-2008/080965 A2 7/2008
WO WO-2008/088303 A1 7/2008
WO WO-2008/092199 A1 8/2008
WO WO-2008/107096 A1 9/2008
WO WO-2008/115738 A1 9/2008
WO WO-2008/115742 A1 9/2008
WO WO-2008/118822 A1 10/2008
WO WO-2008/118823 A2 10/2008
WO WO-2009/012421 A1 1/2009
WO WO-2009/017838 A2 2/2009
WO WO-2009/029682 A1 3/2009
WO WO-2009/032668 A2 3/2009
WO WO-2009/032694 A1 3/2009
WO WO-2009/032703 A1 3/2009
WO WO-2009/080638 A2 7/2009
WO WO-2009/105675 A1 8/2009
WO WO-2009/112490 A1 9/2009
WO WO-2009/115267 A2 9/2009
WO WO-2009/127642 A2 10/2009
WO WO-2009/132202 A2 10/2009

(56) References Cited

FOREIGN PATENT DOCUMENTS

| | | | |
|---|---|---|---|
| WO | WO-2009/136995 | A2 | 11/2009 |
| WO | WO-2009/143389 | A1 | 11/2009 |
| WO | WO-2009/158571 | A1 | 12/2009 |
| WO | WO-2010/025833 | A1 | 3/2010 |
| WO | WO-2010/081679 | A2 | 7/2010 |
| WO | WO-2010/129053 | A2 | 11/2010 |
| WO | WO-2011/079231 | A1 | 6/2011 |
| WO | WO-2011/090760 | A1 | 7/2011 |
| WO | WO-2011/140338 | A1 | 11/2011 |
| WO | WO-2011/153514 | A2 | 12/2011 |
| WO | WO-2012/021444 | A1 | 2/2012 |
| WO | WO-2012/061299 | A1 | 5/2012 |
| WO | WO-2012/061303 | A1 | 5/2012 |
| WO | WO-2012/061415 | A1 | 5/2012 |
| WO | WO-2012/064706 | A1 | 5/2012 |
| WO | WO-2012/158843 | A2 | 11/2012 |

OTHER PUBLICATIONS

U.S. Appl. No. 15/996,162, filed Jun. 1, 2018, Singh et al.

A to Z list of Cancers, National Cancer Institute, 22 pages URL: http://www.cancer.gov/. (Downloaded May 29, 2014).

Aliagas-Martin, I. et al., A class of 2,4-bisanilinopyrimidine Aurora A inhibitors with unusually high selectivity against Aurora B, J. Med. Chem. 52:3300-3307 (2009).

Andrulis, I. et al., Neu/ErbB-2 amplification identifies a poor-prognosis group of women with node-negative breast cancer, J Clin Oncol 16:1340-9 (1998).

Angiolelli, M. E. et al., Palladium-catalyzed cross-coupling of benzylzinc reagents with methylthio N-heterocycles: a new coupling reaction with unusual selectivity, Synlett, 6: 905-907 (2000).

Bamborough, P. et al., N-4-Pyrimidinyl-1H-indazol-4-amine inhibitors of Lck: Indazoles as phenol isosteres with improved pharmacokinetics, Bioorg. & Med. Chem. Lett. 17:4363-4368 (2007).

Bunz, F., The Genetic Basis of Cancer, Principles of Cancer Genetics, Chapter 1: 1-47 (2008).

Calvo, E. et al., Administration of CI-1033, an Irreversible Pan-erbB Tyrosine Kinase Inhibitor, Is Feasible on a 7-Day Off Schedule: A Phase I Pharmacokinetic and Food Effect Study, Clinical Cancer Research, 10: 7112-7120 (2004).

Carter, T. et al, Inhibition of drug-resistant mutants of ABL, KIT, and EGF receptor kinases, Proc. Natl. Acad. Sci. USA 102(31):11011-11016 (2005).

Cashman, J.D. et al., Fucoidan Film Safely Inhibits Surgical Adhesions in a Rat Model, Journal of Surgical Research, Journal of Surgical Research, 171: 495-503 (2011).

Ciardiello, F. et al., Antitumor Effect and Potentiation of Cytotoxic Drugs Activity in Human Cancer Cells by ZD-1839 (Iressa), an Epidermal Growth Factor Receptor-selective Tyrosine Kinase Inhibitor, Clinical Cancer Research, 6: 2053-2063 (2000).

Cohen, M. et al., Structural bioinformatics-based design of selective, irreversible inhibitors, Science 308:1318-1321 (2005).

Coughlin, C.M. et al., Approaches and limitations of phosphatidylinositol-3-kinase pathway activation status as a predictive biomarker in the clinical development of targeted therapy, Breast Cancer Research Treatment, 124: 1-11 (2010).

Curto, M. et al., Contact-dependent inhibition of EGFR signaling by Nf2/Merlin, J Cell Biol 177:893-903 (2007).

Database Registry No. 303145-52-0, Chemical Abstracts Service (Nov. 17, 2000).

Database Registry No. 321433-25-4, Chemical Abstracts Service (Feb. 12, 2001).

Database Registry No. 344594-36-1, Chemical Abstracts Service (Jul. 5, 2001).

Ding, K. et al., Design, Synthesis and Biological Evaluation of Novel Conformationally Constrained Inhibitors Targeting Epidermal Growth Factor Receptor T790M mutant, J. Med. Chem., Just Accepted Manuscript, 1-36 (2012).

European Search Report for EP10844293.0, 8 pages (dated Jun. 27, 2013).

European Search Report for EP11816874.9, 5 pages (dated Dec. 12, 2014).

European Search Report for EP11838624.2, 5 pages (dated Jun. 6, 2014).

European Search Report for EP11838628.3, 7 pages (dated Jun. 20, 2014).

European Search Report for EP11839800.7, 8 pages (dated Jun. 24, 2014).

Fabian, M. et al., A small molecule-kinase interaction map for clinical kinase inhibitors, Nature Biotechnology, 23(3): 329 (2005).

Fallon, K. et al., Constitutive activation of the neuregulin-1/erbB signaling pathway promotes the proliferation of a human peripheral neuroepithelioma cell line, J Neuro Oncol 66:273-84 (2004).

Frank, D., STAT signaling in the pathogenesis and treatment of cancer, Mol. Med. 5 :432-456 (1999).

Fry, D. et al., Specific, irreversible inactivation of the epidermal growth factor receptor and erbB2, by a new class of tyrosine kinase inhibitor, Proc. Natl. Acad. Sci. USA 95:12022-12027 (1998).

Ghiassi-Nejad, Z. and Friedman, S.L., Advances in Antifibrotic therapy, Expert Review of Gastroenterology & Hepatology, 2(6):803-816 (2008).

Ghoneim, K., Synthesis and evaluation of some 2-, 4-, di-substituted-6-methylpyrimidine derivatives for antimicrobial activity, J. Indian Chem. Soc. 63(10):914-917 (1986).

Ghosh, D., 2-4-bis (arylamino)-5-methylpyrimidines as antimicrobial agents, J. Med. Chem. 10(5):974 (1967).

Ghosh, D., 2-4-bis (arylamino)-6-methylpyrimidines as antimicrobial agents, J. Indian Chem. Soc. 58(5):512-573 (1981).

Gonzales, A. et al, Antitumor activity and pharmacokinetic properties of PF-00299804, a second-generation, irreversible pan-erbB receptor tyrosine kinase inhibitor, Mol. Cancer Ther. 7(7):1880-1889 (2008).

Hackman, D.G. and Redlmeier, D.A., Translation of Research Evidence from Animals to Humans, JAMA, 295(14):1731-1732 (2006).

Hur, W. et al., Clinical stage EGFR inhibitors irreversibly alkylate Bmx kinase, Bioorg. Med. Chem. Lett. 18:5916-5919 (2008).

International Search Report for PCT/US10/31714, 4 pages (dated Aug. 13, 2010).

International Search Report for PCT/US11/46926, 2 pages (dated Dec. 22, 2011).

International Search Report for PCT/US11/58610, 4 pages (dated Mar. 27, 2012).

International Search Report for PCT/US11/58616, 3 pages (dated Mar. 27, 2012).

International Search Report for PCT/US11/59726, 3 pages (dated Mar. 20, 2012).

International Search Report for PCT/US2009/048784, 8 pages (dated Nov. 16, 2009).

International Search Report for PCT/US2010/062432, 4 pages (dated May 26, 2011).

Itai, A. and Tomioka, N., Lead generation wo shikou sita computer graphics (Computer graphics directed to lead generation), Shinyaku no lead generation (Lead generation of new drug)—Saishin drug design (Latest drug design), Tokyo Kagaku Dojin, 57-72 (1987). Japanese and English Translation.

Jordan, V. C., Tamoxifen: A Most Unlikely Pioneering Medicine, Nature Reviews: Drug Discovery, 2: 205-213 (2003).

Kim, J. et al., A Signaling Network in Phenylephrine-Induced Benign Prostatic Hyperplasia, Endocrinology, 150(8): 3576-3583 (2009).

Kirken, R., Targeting Jak3 for immune suppression and allograft acceptance, Transplant. Proc. 33 :3268-3270 (2001).

Kok, R.J. Targets in Fibrotic Disorders, Pharmaceutical Research, 25(10): 2413-2415 (2008).

Kumar, A., et al, Structure and Clinical Relevance of the Epidermal Growth Factor Receptor in Human Cancer, Journal of Clinical Oncology 26(10):1742-1751 (2008).

Kuppen, P.J.K. et al., Tumor structure and extracellular matrix as a possible barrier for therapeutic approaches uding immune cells or adenoviruses in colorectal cancer, Histochemistry and Cell Biology, 115: 67-72 (2001).

(56) References Cited

OTHER PUBLICATIONS

Kuster, B. (ed.), Kinase Inhibitors, Methods and Protocols, Methods in Molecular Biology, 795: 1-44 (2012).
Kwak, E. et al., Irreversible inhibitors of the EGF receptor may circumvent acquired resistance to gefitinib, Proc. Natl. Acad. Sci. USA 102:7665-7670 (2005).
Lajeunesse, D. et al., A systematic screen for dominant second-site modifiers of Merlin/NF2 phenotypes reveals an interaction with blistered/DSRF and scribbler, Genetics 158:667-79 (2001).
Li, D. et al., BIBW2992, an irreversible EGFR/HER2 inhibitor highly effective in preclinical lung cancer models, Oncogene 27:4702-4711 (2008).
Lim, A.K.H., Diabetic nephrophathy—complications and treatment, International Journal of Nephrology and Renovascular Disease, 7: 361-381 (2014).
Lin, N. and Winer, E., New targets for therapy in breast cancer: Small molecule tyrosine kinase inhibitors, Breast Cancer Res 6:204-210 (2004).
Lissoni, P. et al., Biotherapy with the pineal hormone melatonin plus aloe and myrrh tincture in untreatable metastatic cancer patients as an essence therapy of cancer, Cancer Research, 7: 397-401 (2009).
Ludovici, D. W. et al., Evolution of anti-HIV drug candidates. Part 3: Diarylpyrimidine (DAPY) analogues, Bioorganic & Medicinal Chemistry Letters, 11(17): 2235-2239 (2001).
Luo, J. et al., Principles of Cancer Therapy: Oncogene and Non-oncogene Addition, Cell, 36: 823-837 (2009).
Malaviya, R. et al., Targeting Janus Kinase 3 in Mast Cells Prevents Immediate Hypersensitivity Reactions and Anaphylaxis, J. Biol. Chem. 274 :27028-27038 (1999).
Mcclatchey, A. and Giovannini, M., Membrane organization and tumorigenesis—the NF2 tumor suppressor, Merlin, Genes Dev 19:2265-77 (2005).
McDermott, U. and Settleman, J. Personalized Cancer Therapy with Selective Kinase Inhibitors: An Emerging Paradigm in Medical Oncology, Journal of Clinical Oncology, 27(33): 5650-5659 (2009).
Minkovsky, N. and Berezov, A., BIBW-2992, a dual receptor tyrosine kinase inhibitor for the treatment of solid tumors, Curr Opin Invest Drugs 9:1336-1346 (2008).
Mordant, C. et al., Synthesis of novel diarylpyrimidine analogues of TMC278 and their antiviral activity against HIV-1 wild-type and mutant strains, Eur. J. Med. Chem., 42(5): 567-579 (2006).
Nandeesha, H. et al., Hyperinsulinemia and dyslipidemia in non-diabetic benign prostatic hyperplasia, Clinica Chimica Acta, 370: 89-93 (2006).
O'Brien, C.J., Current Management of Benign Parotid Tumors—the Role of Limited Superficial Parotidectomy, Head and Neck, 946-952 (2003).
Pacifico, F. and Leonard!, A., Role of NF-κB in thyroid cancer, Molecular and Cellular Endocrinology, 321: 29-35 (2010).
Pearlstein, R. et al., Understanding the structure-activity relationship of the human ether-a-go-go-related gene cardiac K+ channel. A model for bad behavior, Journal of Medicinal Chemistry, 46(11):2017-2022 (2003).
Pelton, P. et al., Ruffling membrane, stress fiber, cell spreading and proliferation abnormalities in human Schwann cells, Oncogene 17:2195-2209 (1998).
Portnyagina, V. A. et al., Pyrimidine derivatives as possible anticandidiasis agents. Farmakologiya i Toksikologiya, (Russian, Kiev), 13(70-1): 109-25 (1978).
PubChem CID 44594695. Feb. 1, 2010. [Retrieved from the Internet May 15, 2011: http://pubchem.ncbi.nlm.nih.gov/summary.cgi?cid=44594695&loc=ec_rcs].
Readinger, J. et al., Selective Targeting of ITK Blocks Multiple Steps of HIV Replication, Proc. Natl. Acad. Sci. USA 105: 6684-6689 (2008).
Rebehmed, J. et al., 2D and 3D QSAR studies of diarylpyrimidine HIV-1 reverse transcriptase inhibitors, Journal of Computer-Aided Molecular Design, 22(11): 831-841 (2008).
Saltz, L.B. et al., Phase II Trial of Cetuximab in Patients with Refractory Colorectal Cancer that Expresses the Epidermal Growth Factor Receptor, Journal of Clinical Oncology, 22(7): 1201-1208 (2004).
Sawanishi, H. et al., Drug Design of Condensed Purines for PDE4 Isoenzyme Inhibitors—Transformation from Xanthines to Imidazo [2,1-i] purines-, Bulletin of Hokuriku University, 28: 1-15 (2004). Japanese and English Translation.
Sawyers, C.L., The cancer biomarker problem, Nature, 452(7187): 548-552 (2008).
Seidel, H. et al., Pharmaceutical intervention in the JAK/STAT signaling pathway, Oncogene 19: 2645-2656 (2000).
Sequist, L., Second-Generation Epidermal Growth Factor Receptor Tyrosine Kinase Inhibitors in Non-Small Cell Lung Cancer, The Oncologist 12(3):325-330 (2007).
Singh, J. et al, Structure-based design of a potent, selective, and irreversible inhibitor of the catalytic domain of the erbB receptor subfamily of protein tyrosine kinases, J. Med. Chem. 40:1130-1135 (1997).
Sjin, R. et al., In vitro and in vivo characterization of irreversible mutant-selective EGFR inhibitors that are wild-type sparing, Molecular Cancer Therapeutics, 13(6):1468-1479 (2014).
Soussi, T., p53 Antibodies in the Sera of Patients with Various Types of Cancer: A Review, Cancer Research, 60: 1777-1788 (2000).
Stonecypher, M. et al., Activation of the neuregulin-1/ErbB signaling pathway promotes the proliferation of neoplastic Schwann cells in human malignant peripheral nerve sheath tumors, Oncogene 24:5589-5605 (2005).
Sudbeck, E. et al., Structure-based Design of Specific Inhibitors of Janus Kinase 3 as Apoptosis-inducing Antileukemic Agents, Clin. Cancer Res. 5: 1569-1582 (1999).
Sun,Y-M. et al., Recent advances in understanding the biochemical and molecular mechanism of diabetic nephropathy, Biochemical and Biophysical Research Communications, 433: 359-361 (2013).
Thakur, A. et al., SAR and QSAR studies: Modelling of new DAPY derivatives, European Journal of Medicinal Chemistry, 43(3): 471-477 (2008).
Tremblay, T. and Hamet, P., Role of genomics on the path to personalized medicine, Metabolism Clinical and Experimental, 62:S2-S5 (2013).
Trieu, V. et al., A specific inhibitor of janus kinase-3 increases survival in a transgenic mouse model of amyotrophic lateral sclerosis, Biochem. Biophys. Res. Commun. 267 :22-25 (2000).
Wong, K. et al, A phase I study with neratinib (HKI-272), an irreversible pan Erb B receptor tyrosine kinase inhibitor, in patients with solid tumors, Clin. Cancer Res. 15(7):2552-2558 (2009).
Written Opinion for PCT/US10/31714, 7 pages (dated Aug. 13, 2010).
Written Opinion for PCT/US11/46926, 9 pages (dated Dec. 22, 2011).
Written Opinion for PCT/US11/58610, 8 pages (dated Mar. 27, 2012).
Written Opinion for PCT/US11/58616, 9 pages (dated Mar. 27, 2012).
Written Opinion for PCT/US11/59726, 7 pages (dated Mar. 20, 2012).
Written Opinion for PCT/US2009/048784, 9 pages (dated Nov. 16, 2009).
Written Opinion for PCT/US2010/062432, 6 pages (dated May 26, 2011).
Yamada, S. et al., Alpha-1 Adrenoceptors in Human Prostate: Characterization and Alteration in Genign Prostatic Hypertrophy, The Journal of Pharmacology and Experimental Therapeutics, 242: 326-330 (1987).
Yamamoto, T. et al., Expression of transforming growth factor B is elecated in human and experimental diabetic nephropathy, Proceedings of the National Academy of Sciences, 90: 1814-1818 (1993).
Zhang, J. et al., Targeting Cancer with Small Molecule Kinase Inhibitors, Nature Rev. Cancer 9:28-39 (2009).
Zhang, Y. et al., Antitumor Activity of Epidermal Growth Factor Receptor-Related Protein Is Mediated by Inactivation of ErbB Receptors and Nuclear Factor-kB in Pancreatic Cancer, Cancer Res 66:1025-1032 (2006).

(56) References Cited

OTHER PUBLICATIONS

Zhou, W. et al. Novel mutant-selective EGFR kinase inhibitors against EGFR T790M, Nature, 462(7276): 1070-1074 (2009).

Dose-Response with Compound I-2 in Ramos cells

Washout with 1 μM Compound I-2 in Ramos cells

Dose-Response with Compound I-4 in Ramos cells

Washout with 1 μM Compound I-4 in Ramos cells

Dose-Response with Compound I-7 in Ramos cells

Washout Experiment with 1 μM Compound I-7 in Ramos Cells

Dose-Response with Compound I-35 in Ramos cells

Dose-Response with Compound I-38 in Ramos cells

TEC Kinase - Compound I-4 Tryptic Digest Results

Washout Experiments with Compounds I-2, I-4, and I-7 in HCC827 cells containing EGFR Deletion mutant

**Concentration of compound used is 1 μM in all cases

Phospho Y1068 EGFR (deletion mutant)

Phospho Y1068 EGFR (deletion mutant)

Phospho Y1068 EGFR (deletion mutant)

Washout Experiment with 1 μM Compound I-7 in A431 Cells (EGFR wt)

JAK3 Kinase – Compound I-7 Tryptic Digest Results

Dose Response with Compound I-2 in CTLL-2 cells

Dose Response with Compound I-4 in CTLL-2 Cells

Dose Response with Compound I-7 in CTLL-2 Cells

SEQ ID 1: FULL LENGTH BTK PROTEIN:

MAAVILESIFLKRSQQKKKTSPLNFKKRLFLLTVHKLSYYEYDFERGRRGSKKGSIDVEK
ITCVETVVPEKNPPPERQIPRRGEESSEMEQISIIERFPYPFQVVYDEGPLYVFSPTEEL
RKRWIHQLKNVIRYNSDLVQKYHPCFWIDGQYLCCSQTAKNAMGCQILENRNGSLKPGSSHRKTKKPLPPTPEEDQILKKPL
PPEPAAAPVSTSELKKVVALYDYMPMNANDLQLRKGDEYFILEESNLPWWRARDKNGQEGYIPSNYVTEAEDSIEMYEWY
SKHMTRSQAEQLLKQEGKEGGFIVRDSSKAGKYTVSVFAKSTGDPQGVIRHYVVCSTPQSQYYLAEKHLFSTIPELINYHQH
NSAGLISRLKYPVSQQNKNAPSTAGLGYGSWEIDPKDLTFLKELGTGQFGVVKYGKWRGQYDVAIKMIKEGSMSEDEFIEEA
KVMMNLSHEKLVQLYGVCTKQRPIFIITEYMANGCLLNYLREMRHRFQTQQLLEMCKDVCEAMEYLESKQFLHRDLAARN
CLVNDQGVVKVSDF

Cys=481

Figure 20

SEQ ID 2: FULL LENGTH TEC PROTEIN NP_003206 631 aa

MNFNTILEEILIKRSQQKKKTSPLNYKERLFVLTKSMLTYYEGRAEKKYRKGFIDVSKIKCVEIVKNDDGVIPCQNKYPFQVV
HDANTLYIFAPSPQSRDLWVKKLKEEIKNNNNIMIKYHPKFWTDGSYQCCRQTEKLAPGCEKYNLFESSIRKALPPAPETKKR
RPPPPIPLEEEDNSEEIVVAMYDFQAAEGHDLRLERGQEYLILEKNDVHWWRARDKYGNEGYIPSNYVTGKKSNNLDQYEW
YCRNMNRSKAEQLLRSEDKEGGFMVRDSSQPGLYTVSLYTKFGGEGSSGFRHYHIKETTTSPKKYYLAEKHAFGSIPEIIEYH
KHNAAGLVTRLRYPVSVKGK
NAPTTAGFSYEKWEINPSELTFMRELGSGLFGVVRLGKWRAQYKVAIKAIREGAMCEEDFIEEAKVMMKLTHPKLVQLYGV
CTQQKPIYIVTEFMERGCLLNFLRQRQGHFSRDVLLSMCQDVCEGMEYLERNSFIHRDLAARNCLVSEAGVVKVSDFGMAR
YVLDDQYTSSSGAKFPVKWCPPEVFNYSRFSSKSDVWSFGVLMWEVFTEGRMPFEKYTNYEVVTMVTRGHRLYQPKLASN
YVYEVMLRCWQEKPEGRPSFEDLLRTIDELVECEETFGR

Cys=449

Figure 21

SEQ ID 3: FULL LENGTH ITK PROTEIN NP 005537 620aa

MNNFILLEEQLIKKSQQKRRTSPSNFKVRFFVLTKASLAYFEDRHGKKRTLKGSIELSRIKCVEIVKSDISIPCHYKYPFQVVHD
NYLLYVFAPDRESRQRWVLALKEETRNNNSLVPKYHPNFWMDGKWRCCSQLEKLATGCAQYDPTKNASKKPLPPTPEDNR
RPLWEPEETVVIALYDYQTNDPQELALRRNEEYCLLDSSEIHWWRVQDRNGHEGYVPSSYLVEKSPNNLETYEWYNKSISR
DKAEKLLLDTGKEGAFMVRDSRTAGTYTVSVFTKAVVSENNPCIKHYHIKETNDNPKRYYVAEKYVFDSIPLLINYHQHNG
GGLVTRLRYPVCFGRQKAPVTAGLRYGKWVIDPSELTFVQEIGSGQFGLVHLGYWLNKDKVAIKTIREGAMSEEDFIEEAEV
MMKLSHPKLVQLYGVCLEQAPICLVFEFMEHGCLSDYLRTQRGLFAAETLLGMCLDVCEGMAYLEEACVIHRDLAARNCL
VGENQVIKVSDFGMTRFVLDDQYTSSTGTKFPVKWASPEVFSFSRYSSKSDVWSFGVLMWEVFSEGKIPYENRSNSEVVEDI
STGFRLYKPRLASTHVYQIMNHCWKERPEDRPAFSRLLRQLAEIAESGL

Cys=442

Figure 22

SEQ ID 4: FULL LENGTH BMX PROTEIN NP_001712_675aa

MDTKSILEELLLKRSQQKKKMSPNNYKERLFVLTKTNLSYYEYDKMKRGSRKGSIEIKKIRCVEKVNLEEQTPVERQYPFQIV
YKDGLLYVYASNEESRSQWLKALQKEIRGNPHLLVKYHSGFFVDGKFLCCQQSCKAAPGCTLWEAYANLHTAVNEEKHRV
PTFPDRVLKIPRAVPVLKMDAPSSSTTLAQYDNESKKNYGSQPPSSSTSLAQYDSNSKKIYGSQPNFNMQYIPREDFPDWWQ
VRKLKSSSSSEDVASSNQKERNVNHTTSKISWEFPESSSSEEEENLDDYDWFAGNISRSQSEQLLRQKGKEGAFMVRNSSQV
GMYTVSLFSKAVNDKKGTVKHYH
VHTNAENKLYLAENYCFDSIPKLIHYHQHNSAGMITRLRHPVSTKANKVPDSVSLGNGIWELKREEITLLKELGSGQFGVVQ
LGKWKGQYDVAVKMIKEGSMSEDEFFQEAQTMMKLSHPKLVKFYGVCSKEYPIYIVTEYISNGCLLNYLRSHGKGLEPSQL
LEMCYDVCEGMAFLESHQFIHRDLAARNCLVDRDLCVKVSDFGMTRYVLDDQYVSSVGTKFPVKWSAPEVFHYFKYSSKS
DVWAFGILMWEVFSLGKQPYDLYDNSQVVLKVSQGHRLYRPHLASDTIYQIMYSCWHELPEKRPTFQQLLSSIEPLREKDK
H

Cys=496

Figure 23

SEQ ID 5: FULL LENGTH TXK PROTEIN NP_003319 527 aa

MILSSYNTIQSVFCCCCCCSVQKRQMRTQISLSTDEELPEKYTQRRRPWLSQLSNKKQSNTGRVQPSKRKPLPPLPPSEVAEE
KIQVKALYDFLPREPCNLALRRAEEYLILEKYNPHWWKARDRLGNEGLIPSNYVTENKITNLEIYEWYHRNITRNQAEHLLR
QESKEGAFIVRDSRHLGSYTISVFMGARRSTEAAIKHYQIKKNDSGQWYVAERHAFQSIPELIWYHQHNAAGLMTRLRYPVG
LMGSCLPATAGFSYEKWEIDPSELAFIKEIGSGQFGVVHLGEWRSHIQVAIKAINEGSMSEEDFIEEAKVMMKLSHSKLVQLY
GVCIQRKPLYIVTEFMENGCLLNYLRENKGKLRKEMLLSVCQDICEGMEYLERNGYIHRDLAARNCLVSSTCIVKISDFGMT
RYVLDDEYVSSFGAKFPIKWSPPEVFLFNKYSSKSDVWSFGVLMWEVFTEGKMPFENKSNLQVVEAISEGFRLYRPHLAPMS
IYEVMYSCWHEKPEGRPTFAELLRAVTEIAETW

Cys 350

Figure 24

SEQ ID 6: FULL LENGTH JAK3 PROTEIN NP 000206 1124 aa

MAPPSEETPLIPQRSCSLLSTEAGALHVLLPARGPGPPQRLSFSFGDHLAEDLCVQAAKASGILPVYHSLFALATEDLSCWFPP
SHIFSVEDASTQVLLYRIRFYFPNWFGLEKCHRFGLRKDLASAILDLPVLEHLFAQHRSDLVSGRLPVGLSLKEQGECLSLAV
LDLARMAREQAQRPGELLKTVSYKACLPPSLRDLIQGLSFVTRRRIRRTVRRALRRVAACQADRHSLMAKYIMDLERLDPA
GAAETFHVGLPGALGGHDGLGLLRVAGDGGIAWTQGEQEVLQPFCDFPEIVDISIKQAPRVGPAGEHRLVTVTRTDNQILEA
EFPGLPEALSFVALVDGYFRLTTDSQHFFCKEVAPPRLLEEVAEQCHGPITLDFAINKLKTGGSRPGSYVLRRSPQDFDSFLLT
VCVQNPLGPDYKGCLIRRSPTGTFLLVGLSRPHSSLRELLATCWDGGLHVDGVAVTLTSCCIPRPKEKSNLIVVQRGHSPPTS
SLVQPQSQYQLSQMTFHKIPADSLEWHENLGHGSFTKIYRGCRHEVVDGEARKTEVLLKVMDAKHKNCMESFLEAASLMS
QVSYRHLVLLHGVCMAGDSTMVQEFVHLGAIDMYLRKRGHLVPASWKLQVVKQLAYALNYLEDKGLPHGNVSARKVLL
AREGADGSPPFIKLSDPGVSPAVLSLEMLTDRIPWVAPECLREAQTLSLEADKWGFGATVWEVFSGVTMPISALDPAKKLQF
YEDRQQLPAPKWTELALLIQQCMAYEPVQRPSFRAVIRDLNSLISSDYELLSDPTPGALAPRDGLWNGAQLYACQDPTIFEER
HLKYISQLGKGNFGSVELCRYDPLGDNTGALVAVKQLQHSGPDQQRDFQREIQILKALHSDFIVKYRGVSYGPGRQSLRLV
MEYLPSGCLRDFLQRHRARLDASRLLLYSSQICKGMEYLGSRRCVHRDLAARNILVESEAHVKIADFGLAKLLPLDKDYYV
VREPGQSPIFWYAPESLSDNIFSRQSDVWSFGVVLYELFTYCDKSCSPSAEFLRMMGCERDVPALCRLLELLEEGQRLPAPPA
CPAEVHELMKLCWAPSPQDRPSFSALGPQLDMLWSGSRGCETHAFTAHPEGKHHSLSFS

Cys=909

Figure 25

SEQUENCE LISTING

```
<160> NUMBER OF SEQ ID NOS: 6

<210> SEQ ID NO 1
<211> LENGTH: 540
<212> TYPE: PRT
<213> ORGANISM: Homo sapiens

<400> SEQUENCE: 1

Met Ala Ala Val Ile Leu Glu Ser Ile Phe Leu Lys Arg Ser Gln Gln
1               5                   10                  15

Lys Lys Lys Thr Ser Pro Leu Asn Phe Lys Lys Arg Leu Phe Leu Leu
            20                  25                  30

Thr Val His Lys Leu Ser Tyr Tyr Glu Tyr Asp Phe Glu Arg Gly Arg
        35                  40                  45

Arg Gly Ser Lys Lys Gly Ser Ile Asp Val Glu Lys Ile Thr Cys Val
    50                  55                  60
```

-continued

Glu Thr Val Val Pro Glu Lys Asn Pro Pro Pro Glu Arg Gln Ile Pro
65 70 75 80

Arg Arg Gly Glu Glu Ser Ser Glu Met Glu Gln Ile Ser Ile Ile Glu
85 90 95

Arg Phe Pro Tyr Pro Phe Gln Val Val Tyr Asp Glu Gly Pro Leu Tyr
100 105 110

Val Phe Ser Pro Thr Glu Glu Leu Arg Lys Arg Trp Ile His Gln Leu
115 120 125

Lys Asn Val Ile Arg Tyr Asn Ser Asp Leu Val Gln Lys Tyr His Pro
130 135 140

Cys Phe Trp Ile Asp Gly Gln Tyr Leu Cys Cys Ser Gln Thr Ala Lys
145 150 155 160

Asn Ala Met Gly Cys Gln Ile Leu Glu Asn Arg Asn Gly Ser Leu Lys
165 170 175

Pro Gly Ser Ser His Arg Lys Thr Lys Lys Pro Leu Pro Pro Thr Pro
180 185 190

Glu Glu Asp Gln Ile Leu Lys Lys Pro Leu Pro Pro Glu Pro Ala Ala
195 200 205

Ala Pro Val Ser Thr Ser Glu Leu Lys Lys Val Val Ala Leu Tyr Asp
210 215 220

Tyr Met Pro Met Asn Ala Asn Asp Leu Gln Leu Arg Lys Gly Asp Glu
225 230 235 240

Tyr Phe Ile Leu Glu Glu Ser Asn Leu Pro Trp Trp Arg Ala Arg Asp
245 250 255

Lys Asn Gly Gln Glu Gly Tyr Ile Pro Ser Asn Tyr Val Thr Glu Ala
260 265 270

Glu Asp Ser Ile Glu Met Tyr Glu Trp Tyr Ser Lys His Met Thr Arg
275 280 285

Ser Gln Ala Glu Gln Leu Leu Lys Gln Glu Gly Lys Glu Gly Gly Phe
290 295 300

Ile Val Arg Asp Ser Ser Lys Ala Gly Lys Tyr Thr Val Ser Val Phe
305 310 315 320

Ala Lys Ser Thr Gly Asp Pro Gln Gly Val Ile Arg His Tyr Val Val
325 330 335

Cys Ser Thr Pro Gln Ser Gln Tyr Tyr Leu Ala Glu Lys His Leu Phe
340 345 350

Ser Thr Ile Pro Glu Leu Ile Asn Tyr His Gln His Asn Ser Ala Gly
355 360 365

Leu Ile Ser Arg Leu Lys Tyr Pro Val Ser Gln Gln Asn Lys Asn Ala
370 375 380

Pro Ser Thr Ala Gly Leu Gly Tyr Gly Ser Trp Glu Ile Asp Pro Lys
385 390 395 400

Asp Leu Thr Phe Leu Lys Glu Leu Gly Thr Gly Gln Phe Gly Val Val
405 410 415

Lys Tyr Gly Lys Trp Arg Gly Gln Tyr Asp Val Ala Ile Lys Met Ile
420 425 430

Lys Glu Gly Ser Met Ser Glu Asp Glu Phe Ile Glu Glu Ala Lys Val
435 440 445

Met Met Asn Leu Ser His Glu Lys Leu Val Gln Leu Tyr Gly Val Cys
450 455 460

Thr Lys Gln Arg Pro Ile Phe Ile Ile Thr Glu Tyr Met Ala Asn Gly
465 470 475 480

```
Cys Leu Leu Asn Tyr Leu Arg Glu Met Arg His Arg Phe Gln Thr Gln
                485                 490                 495

Gln Leu Leu Glu Met Cys Lys Asp Val Cys Glu Ala Met Glu Tyr Leu
            500                 505                 510

Glu Ser Lys Gln Phe Leu His Arg Asp Leu Ala Ala Arg Asn Cys Leu
        515                 520                 525

Val Asn Asp Gln Gly Val Val Lys Val Ser Asp Phe
    530                 535                 540


<210> SEQ ID NO 2
<211> LENGTH: 631
<212> TYPE: PRT
<213> ORGANISM: Homo sapiens

<400> SEQUENCE: 2

Met Asn Phe Asn Thr Ile Leu Glu Glu Ile Leu Ile Lys Arg Ser Gln
1               5                   10                  15

Gln Lys Lys Lys Thr Ser Pro Leu Asn Tyr Lys Glu Arg Leu Phe Val
            20                  25                  30

Leu Thr Lys Ser Met Leu Thr Tyr Tyr Glu Gly Arg Ala Glu Lys Lys
        35                  40                  45

Tyr Arg Lys Gly Phe Ile Asp Val Ser Lys Ile Lys Cys Val Glu Ile
    50                  55                  60

Val Lys Asn Asp Asp Gly Val Ile Pro Cys Gln Asn Lys Tyr Pro Phe
65                  70                  75                  80

Gln Val Val His Asp Ala Asn Thr Leu Tyr Ile Phe Ala Pro Ser Pro
                85                  90                  95

Gln Ser Arg Asp Leu Trp Val Lys Lys Leu Lys Glu Glu Ile Lys Asn
            100                 105                 110

Asn Asn Asn Ile Met Ile Lys Tyr His Pro Lys Phe Trp Thr Asp Gly
        115                 120                 125

Ser Tyr Gln Cys Cys Arg Gln Thr Glu Lys Leu Ala Pro Gly Cys Glu
    130                 135                 140

Lys Tyr Asn Leu Phe Glu Ser Ser Ile Arg Lys Ala Leu Pro Pro Ala
145                 150                 155                 160

Pro Glu Thr Lys Lys Arg Arg Pro Pro Pro Pro Ile Pro Leu Glu Glu
                165                 170                 175

Glu Asp Asn Ser Glu Glu Ile Val Val Ala Met Tyr Asp Phe Gln Ala
            180                 185                 190

Ala Glu Gly His Asp Leu Arg Leu Glu Arg Gly Gln Glu Tyr Leu Ile
        195                 200                 205

Leu Glu Lys Asn Asp Val His Trp Trp Arg Ala Arg Asp Lys Tyr Gly
    210                 215                 220

Asn Glu Gly Tyr Ile Pro Ser Asn Tyr Val Thr Gly Lys Lys Ser Asn
225                 230                 235                 240

Asn Leu Asp Gln Tyr Glu Trp Tyr Cys Arg Asn Met Asn Arg Ser Lys
                245                 250                 255

Ala Glu Gln Leu Leu Arg Ser Glu Asp Lys Glu Gly Gly Phe Met Val
            260                 265                 270

Arg Asp Ser Ser Gln Pro Gly Leu Tyr Thr Val Ser Leu Tyr Thr Lys
        275                 280                 285

Phe Gly Gly Glu Gly Ser Ser Gly Phe Arg His Tyr His Ile Lys Glu
    290                 295                 300

Thr Thr Thr Ser Pro Lys Lys Tyr Tyr Leu Ala Glu Lys His Ala Phe
305                 310                 315                 320
```

Gly Ser Ile Pro Glu Ile Ile Glu Tyr His Lys His Asn Ala Ala Gly
325 330 335

Leu Val Thr Arg Leu Arg Tyr Pro Val Ser Val Lys Gly Lys Asn Ala
340 345 350

Pro Thr Thr Ala Gly Phe Ser Tyr Glu Lys Trp Glu Ile Asn Pro Ser
355 360 365

Glu Leu Thr Phe Met Arg Glu Leu Gly Ser Gly Leu Phe Gly Val Val
370 375 380

Arg Leu Gly Lys Trp Arg Ala Gln Tyr Lys Val Ala Ile Lys Ala Ile
385 390 395 400

Arg Glu Gly Ala Met Cys Glu Glu Asp Phe Ile Glu Glu Ala Lys Val
405 410 415

Met Met Lys Leu Thr His Pro Lys Leu Val Gln Leu Tyr Gly Val Cys
420 425 430

Thr Gln Gln Lys Pro Ile Tyr Ile Val Thr Glu Phe Met Glu Arg Gly
435 440 445

Cys Leu Leu Asn Phe Leu Arg Gln Arg Gln Gly His Phe Ser Arg Asp
450 455 460

Val Leu Leu Ser Met Cys Gln Asp Val Cys Glu Gly Met Glu Tyr Leu
465 470 475 480

Glu Arg Asn Ser Phe Ile His Arg Asp Leu Ala Ala Arg Asn Cys Leu
485 490 495

Val Ser Glu Ala Gly Val Val Lys Val Ser Asp Phe Gly Met Ala Arg
500 505 510

Tyr Val Leu Asp Asp Gln Tyr Thr Ser Ser Ser Gly Ala Lys Phe Pro
515 520 525

Val Lys Trp Cys Pro Pro Glu Val Phe Asn Tyr Ser Arg Phe Ser Ser
530 535 540

Lys Ser Asp Val Trp Ser Phe Gly Val Leu Met Trp Glu Val Phe Thr
545 550 555 560

Glu Gly Arg Met Pro Phe Glu Lys Tyr Thr Asn Tyr Glu Val Val Thr
565 570 575

Met Val Thr Arg Gly His Arg Leu Tyr Gln Pro Lys Leu Ala Ser Asn
580 585 590

Tyr Val Tyr Glu Val Met Leu Arg Cys Trp Gln Glu Lys Pro Glu Gly
595 600 605

Arg Pro Ser Phe Glu Asp Leu Leu Arg Thr Ile Asp Glu Leu Val Glu
610 615 620

Cys Glu Glu Thr Phe Gly Arg
625 630

<210> SEQ ID NO 3
<211> LENGTH: 620
<212> TYPE: PRT
<213> ORGANISM: Homo sapiens

<400> SEQUENCE: 3

Met Asn Asn Phe Ile Leu Leu Glu Glu Gln Leu Ile Lys Lys Ser Gln
1 5 10 15

Gln Lys Arg Arg Thr Ser Pro Ser Asn Phe Lys Val Arg Phe Phe Val
20 25 30

Leu Thr Lys Ala Ser Leu Ala Tyr Phe Glu Asp Arg His Gly Lys Lys
35 40 45

Arg Thr Leu Lys Gly Ser Ile Glu Leu Ser Arg Ile Lys Cys Val Glu

-continued

```
    50                  55                  60

Ile Val Lys Ser Asp Ile Ser Ile Pro Cys His Tyr Lys Tyr Pro Phe
65                  70                  75                  80

Gln Val Val His Asp Asn Tyr Leu Leu Tyr Val Phe Ala Pro Asp Arg
                85                  90                  95

Glu Ser Arg Gln Arg Trp Val Leu Ala Leu Lys Glu Glu Thr Arg Asn
            100                 105                 110

Asn Asn Ser Leu Val Pro Lys Tyr His Pro Asn Phe Trp Met Asp Gly
        115                 120                 125

Lys Trp Arg Cys Cys Ser Gln Leu Glu Lys Leu Ala Thr Gly Cys Ala
    130                 135                 140

Gln Tyr Asp Pro Thr Lys Asn Ala Ser Lys Lys Pro Leu Pro Pro Thr
145                 150                 155                 160

Pro Glu Asp Asn Arg Arg Pro Leu Trp Glu Pro Glu Glu Thr Val Val
                165                 170                 175

Ile Ala Leu Tyr Asp Tyr Gln Thr Asn Asp Pro Gln Glu Leu Ala Leu
            180                 185                 190

Arg Arg Asn Glu Glu Tyr Cys Leu Leu Asp Ser Ser Glu Ile His Trp
        195                 200                 205

Trp Arg Val Gln Asp Arg Asn Gly His Glu Gly Tyr Val Pro Ser Ser
    210                 215                 220

Tyr Leu Val Glu Lys Ser Pro Asn Asn Leu Glu Thr Tyr Glu Trp Tyr
225                 230                 235                 240

Asn Lys Ser Ile Ser Arg Asp Lys Ala Glu Lys Leu Leu Leu Asp Thr
                245                 250                 255

Gly Lys Glu Gly Ala Phe Met Val Arg Asp Ser Arg Thr Ala Gly Thr
            260                 265                 270

Tyr Thr Val Ser Val Phe Thr Lys Ala Val Val Ser Glu Asn Asn Pro
        275                 280                 285

Cys Ile Lys His Tyr His Ile Lys Glu Thr Asn Asp Asn Pro Lys Arg
    290                 295                 300

Tyr Tyr Val Ala Glu Lys Tyr Val Phe Asp Ser Ile Pro Leu Leu Ile
305                 310                 315                 320

Asn Tyr His Gln His Asn Gly Gly Gly Leu Val Thr Arg Leu Arg Tyr
                325                 330                 335

Pro Val Cys Phe Gly Arg Gln Lys Ala Pro Val Thr Ala Gly Leu Arg
            340                 345                 350

Tyr Gly Lys Trp Val Ile Asp Pro Ser Glu Leu Thr Phe Val Gln Glu
        355                 360                 365

Ile Gly Ser Gly Gln Phe Gly Leu Val His Leu Gly Tyr Trp Leu Asn
    370                 375                 380

Lys Asp Lys Val Ala Ile Lys Thr Ile Arg Glu Gly Ala Met Ser Glu
385                 390                 395                 400

Glu Asp Phe Ile Glu Glu Ala Glu Val Met Met Lys Leu Ser His Pro
                405                 410                 415

Lys Leu Val Gln Leu Tyr Gly Val Cys Leu Glu Gln Ala Pro Ile Cys
            420                 425                 430

Leu Val Phe Glu Phe Met Glu His Gly Cys Leu Ser Asp Tyr Leu Arg
        435                 440                 445

Thr Gln Arg Gly Leu Phe Ala Ala Glu Thr Leu Leu Gly Met Cys Leu
    450                 455                 460

Asp Val Cys Glu Gly Met Ala Tyr Leu Glu Glu Ala Cys Val Ile His
465                 470                 475                 480
```

Arg Asp Leu Ala Ala Arg Asn Cys Leu Val Gly Glu Asn Gln Val Ile
485 490 495

Lys Val Ser Asp Phe Gly Met Thr Arg Phe Val Leu Asp Asp Gln Tyr
500 505 510

Thr Ser Ser Thr Gly Thr Lys Phe Pro Val Lys Trp Ala Ser Pro Glu
515 520 525

Val Phe Ser Phe Ser Arg Tyr Ser Ser Lys Ser Asp Val Trp Ser Phe
530 535 540

Gly Val Leu Met Trp Glu Val Phe Ser Glu Gly Lys Ile Pro Tyr Glu
545 550 555 560

Asn Arg Ser Asn Ser Glu Val Val Glu Asp Ile Ser Thr Gly Phe Arg
565 570 575

Leu Tyr Lys Pro Arg Leu Ala Ser Thr His Val Tyr Gln Ile Met Asn
580 585 590

His Cys Trp Lys Glu Arg Pro Glu Asp Arg Pro Ala Phe Ser Arg Leu
595 600 605

Leu Arg Gln Leu Ala Glu Ile Ala Glu Ser Gly Leu
610 615 620

<210> SEQ ID NO 4
<211> LENGTH: 675
<212> TYPE: PRT
<213> ORGANISM: Homo sapiens

<400> SEQUENCE: 4

Met Asp Thr Lys Ser Ile Leu Glu Glu Leu Leu Leu Lys Arg Ser Gln
1 5 10 15

Gln Lys Lys Lys Met Ser Pro Asn Asn Tyr Lys Glu Arg Leu Phe Val
20 25 30

Leu Thr Lys Thr Asn Leu Ser Tyr Tyr Glu Tyr Asp Lys Met Lys Arg
35 40 45

Gly Ser Arg Lys Gly Ser Ile Glu Ile Lys Lys Ile Arg Cys Val Glu
50 55 60

Lys Val Asn Leu Glu Glu Gln Thr Pro Val Glu Arg Gln Tyr Pro Phe
65 70 75 80

Gln Ile Val Tyr Lys Asp Gly Leu Leu Tyr Val Tyr Ala Ser Asn Glu
85 90 95

Glu Ser Arg Ser Gln Trp Leu Lys Ala Leu Gln Lys Glu Ile Arg Gly
100 105 110

Asn Pro His Leu Leu Val Lys Tyr His Ser Gly Phe Phe Val Asp Gly
115 120 125

Lys Phe Leu Cys Cys Gln Gln Ser Cys Lys Ala Ala Pro Gly Cys Thr
130 135 140

Leu Trp Glu Ala Tyr Ala Asn Leu His Thr Ala Val Asn Glu Glu Lys
145 150 155 160

His Arg Val Pro Thr Phe Pro Asp Arg Val Leu Lys Ile Pro Arg Ala
165 170 175

Val Pro Val Leu Lys Met Asp Ala Pro Ser Ser Ser Thr Thr Leu Ala
180 185 190

Gln Tyr Asp Asn Glu Ser Lys Lys Asn Tyr Gly Ser Gln Pro Pro Ser
195 200 205

Ser Ser Thr Ser Leu Ala Gln Tyr Asp Ser Asn Ser Lys Lys Ile Tyr
210 215 220

Gly Ser Gln Pro Asn Phe Asn Met Gln Tyr Ile Pro Arg Glu Asp Phe

-continued 225 230 235 240

Pro Asp Trp Trp Gln Val Arg Lys Leu Lys Ser Ser Ser Ser Ser Glu
245 250 255

Asp Val Ala Ser Ser Asn Gln Lys Glu Arg Asn Val Asn His Thr Thr
260 265 270

Ser Lys Ile Ser Trp Glu Phe Pro Glu Ser Ser Ser Ser Glu Glu Glu
275 280 285

Glu Asn Leu Asp Asp Tyr Asp Trp Phe Ala Gly Asn Ile Ser Arg Ser
290 295 300

Gln Ser Glu Gln Leu Leu Arg Gln Lys Gly Lys Glu Gly Ala Phe Met
305 310 315 320

Val Arg Asn Ser Ser Gln Val Gly Met Tyr Thr Val Ser Leu Phe Ser
325 330 335

Lys Ala Val Asn Asp Lys Lys Gly Thr Val Lys His Tyr His Val His
340 345 350

Thr Asn Ala Glu Asn Lys Leu Tyr Leu Ala Glu Asn Tyr Cys Phe Asp
355 360 365

Ser Ile Pro Lys Leu Ile His Tyr His Gln His Asn Ser Ala Gly Met
370 375 380

Ile Thr Arg Leu Arg His Pro Val Ser Thr Lys Ala Asn Lys Val Pro
385 390 395 400

Asp Ser Val Ser Leu Gly Asn Gly Ile Trp Glu Leu Lys Arg Glu Glu
405 410 415

Ile Thr Leu Leu Lys Glu Leu Gly Ser Gly Gln Phe Gly Val Val Gln
420 425 430

Leu Gly Lys Trp Lys Gly Gln Tyr Asp Val Ala Val Lys Met Ile Lys
435 440 445

Glu Gly Ser Met Ser Glu Asp Glu Phe Phe Gln Glu Ala Gln Thr Met
450 455 460

Met Lys Leu Ser His Pro Lys Leu Val Lys Phe Tyr Gly Val Cys Ser
465 470 475 480

Lys Glu Tyr Pro Ile Tyr Ile Val Thr Glu Tyr Ile Ser Asn Gly Cys
485 490 495

Leu Leu Asn Tyr Leu Arg Ser His Gly Lys Gly Leu Glu Pro Ser Gln
500 505 510

Leu Leu Glu Met Cys Tyr Asp Val Cys Glu Gly Met Ala Phe Leu Glu
515 520 525

Ser His Gln Phe Ile His Arg Asp Leu Ala Ala Arg Asn Cys Leu Val
530 535 540

Asp Arg Asp Leu Cys Val Lys Val Ser Asp Phe Gly Met Thr Arg Tyr
545 550 555 560

Val Leu Asp Asp Gln Tyr Val Ser Ser Val Gly Thr Lys Phe Pro Val
565 570 575

Lys Trp Ser Ala Pro Glu Val Phe His Tyr Phe Lys Tyr Ser Ser Lys
580 585 590

Ser Asp Val Trp Ala Phe Gly Ile Leu Met Trp Glu Val Phe Ser Leu
595 600 605

Gly Lys Gln Pro Tyr Asp Leu Tyr Asp Asn Ser Gln Val Val Leu Lys
610 615 620

Val Ser Gln Gly His Arg Leu Tyr Arg Pro His Leu Ala Ser Asp Thr
625 630 635 640

Ile Tyr Gln Ile Met Tyr Ser Cys Trp His Glu Leu Pro Glu Lys Arg
645 650 655

Pro Thr Phe Gln Gln Leu Leu Ser Ser Ile Glu Pro Leu Arg Glu Lys
660 665 670

Asp Lys His
675

<210> SEQ ID NO 5
<211> LENGTH: 1124
<212> TYPE: PRT
<213> ORGANISM: Homo sapiens

<400> SEQUENCE: 5

Met Ala Pro Pro Ser Glu Glu Thr Pro Leu Ile Pro Gln Arg Ser Cys
1 5 10 15

Ser Leu Leu Ser Thr Glu Ala Gly Ala Leu His Val Leu Leu Pro Ala
20 25 30

Arg Gly Pro Gly Pro Pro Gln Arg Leu Ser Phe Ser Phe Gly Asp His
35 40 45

Leu Ala Glu Asp Leu Cys Val Gln Ala Ala Lys Ala Ser Gly Ile Leu
50 55 60

Pro Val Tyr His Ser Leu Phe Ala Leu Ala Thr Glu Asp Leu Ser Cys
65 70 75 80

Trp Phe Pro Pro Ser His Ile Phe Ser Val Glu Asp Ala Ser Thr Gln
85 90 95

Val Leu Leu Tyr Arg Ile Arg Phe Tyr Phe Pro Asn Trp Phe Gly Leu
100 105 110

Glu Lys Cys His Arg Phe Gly Leu Arg Lys Asp Leu Ala Ser Ala Ile
115 120 125

Leu Asp Leu Pro Val Leu Glu His Leu Phe Ala Gln His Arg Ser Asp
130 135 140

Leu Val Ser Gly Arg Leu Pro Val Gly Leu Ser Leu Lys Glu Gln Gly
145 150 155 160

Glu Cys Leu Ser Leu Ala Val Leu Asp Leu Ala Arg Met Ala Arg Glu
165 170 175

Gln Ala Gln Arg Pro Gly Glu Leu Leu Lys Thr Val Ser Tyr Lys Ala
180 185 190

Cys Leu Pro Pro Ser Leu Arg Asp Leu Ile Gln Gly Leu Ser Phe Val
195 200 205

Thr Arg Arg Arg Ile Arg Arg Thr Val Arg Arg Ala Leu Arg Arg Val
210 215 220

Ala Ala Cys Gln Ala Asp Arg His Ser Leu Met Ala Lys Tyr Ile Met
225 230 235 240

Asp Leu Glu Arg Leu Asp Pro Ala Gly Ala Ala Glu Thr Phe His Val
245 250 255

Gly Leu Pro Gly Ala Leu Gly Gly His Asp Gly Leu Gly Leu Leu Arg
260 265 270

Val Ala Gly Asp Gly Gly Ile Ala Trp Thr Gln Gly Glu Gln Glu Val
275 280 285

Leu Gln Pro Phe Cys Asp Phe Pro Glu Ile Val Asp Ile Ser Ile Lys
290 295 300

Gln Ala Pro Arg Val Gly Pro Ala Gly Glu His Arg Leu Val Thr Val
305 310 315 320

Thr Arg Thr Asp Asn Gln Ile Leu Glu Ala Glu Phe Pro Gly Leu Pro
325 330 335

Glu Ala Leu Ser Phe Val Ala Leu Val Asp Gly Tyr Phe Arg Leu Thr

-continued

```
            340                 345                 350

Thr Asp Ser Gln His Phe Phe Cys Lys Glu Val Ala Pro Pro Arg Leu
        355                 360                 365

Leu Glu Glu Val Ala Glu Gln Cys His Gly Pro Ile Thr Leu Asp Phe
    370                 375                 380

Ala Ile Asn Lys Leu Lys Thr Gly Gly Ser Arg Pro Gly Ser Tyr Val
385                 390                 395                 400

Leu Arg Arg Ser Pro Gln Asp Phe Asp Ser Phe Leu Leu Thr Val Cys
                405                 410                 415

Val Gln Asn Pro Leu Gly Pro Asp Tyr Lys Gly Cys Leu Ile Arg Arg
            420                 425                 430

Ser Pro Thr Gly Thr Phe Leu Leu Val Gly Leu Ser Arg Pro His Ser
        435                 440                 445

Ser Leu Arg Glu Leu Leu Ala Thr Cys Trp Asp Gly Gly Leu His Val
    450                 455                 460

Asp Gly Val Ala Val Thr Leu Thr Ser Cys Cys Ile Pro Arg Pro Lys
465                 470                 475                 480

Glu Lys Ser Asn Leu Ile Val Val Gln Arg Gly His Ser Pro Pro Thr
                485                 490                 495

Ser Ser Leu Val Gln Pro Gln Ser Gln Tyr Gln Leu Ser Gln Met Thr
            500                 505                 510

Phe His Lys Ile Pro Ala Asp Ser Leu Glu Trp His Glu Asn Leu Gly
        515                 520                 525

His Gly Ser Phe Thr Lys Ile Tyr Arg Gly Cys Arg His Glu Val Val
    530                 535                 540

Asp Gly Glu Ala Arg Lys Thr Glu Val Leu Leu Lys Val Met Asp Ala
545                 550                 555                 560

Lys His Lys Asn Cys Met Glu Ser Phe Leu Glu Ala Ala Ser Leu Met
                565                 570                 575

Ser Gln Val Ser Tyr Arg His Leu Val Leu Leu His Gly Val Cys Met
            580                 585                 590

Ala Gly Asp Ser Thr Met Val Gln Glu Phe Val His Leu Gly Ala Ile
        595                 600                 605

Asp Met Tyr Leu Arg Lys Arg Gly His Leu Val Pro Ala Ser Trp Lys
    610                 615                 620

Leu Gln Val Val Lys Gln Leu Ala Tyr Ala Leu Asn Tyr Leu Glu Asp
625                 630                 635                 640

Lys Gly Leu Pro His Gly Asn Val Ser Ala Arg Lys Val Leu Leu Ala
                645                 650                 655

Arg Glu Gly Ala Asp Gly Ser Pro Pro Phe Ile Lys Leu Ser Asp Pro
            660                 665                 670

Gly Val Ser Pro Ala Val Leu Ser Leu Glu Met Leu Thr Asp Arg Ile
        675                 680                 685

Pro Trp Val Ala Pro Glu Cys Leu Arg Glu Ala Gln Thr Leu Ser Leu
    690                 695                 700

Glu Ala Asp Lys Trp Gly Phe Gly Ala Thr Val Trp Glu Val Phe Ser
705                 710                 715                 720

Gly Val Thr Met Pro Ile Ser Ala Leu Asp Pro Ala Lys Lys Leu Gln
                725                 730                 735

Phe Tyr Glu Asp Arg Gln Gln Leu Pro Ala Pro Lys Trp Thr Glu Leu
            740                 745                 750

Ala Leu Leu Ile Gln Gln Cys Met Ala Tyr Glu Pro Val Gln Arg Pro
        755                 760                 765
```

Ser Phe Arg Ala Val Ile Arg Asp Leu Asn Ser Leu Ile Ser Ser Asp
    770                 775                 780

Tyr Glu Leu Leu Ser Asp Pro Thr Pro Gly Ala Leu Ala Pro Arg Asp
785                 790                 795                 800

Gly Leu Trp Asn Gly Ala Gln Leu Tyr Ala Cys Gln Asp Pro Thr Ile
                805                 810                 815

Phe Glu Glu Arg His Leu Lys Tyr Ile Ser Gln Leu Gly Lys Gly Asn
            820                 825                 830

Phe Gly Ser Val Glu Leu Cys Arg Tyr Asp Pro Leu Gly Asp Asn Thr
        835                 840                 845

Gly Ala Leu Val Ala Val Lys Gln Leu Gln His Ser Gly Pro Asp Gln
    850                 855                 860

Gln Arg Asp Phe Gln Arg Glu Ile Gln Ile Leu Lys Ala Leu His Ser
865                 870                 875                 880

Asp Phe Ile Val Lys Tyr Arg Gly Val Ser Tyr Gly Pro Gly Arg Gln
                885                 890                 895

Ser Leu Arg Leu Val Met Glu Tyr Leu Pro Ser Gly Cys Leu Arg Asp
            900                 905                 910

Phe Leu Gln Arg His Arg Ala Arg Leu Asp Ala Ser Arg Leu Leu Leu
        915                 920                 925

Tyr Ser Ser Gln Ile Cys Lys Gly Met Glu Tyr Leu Gly Ser Arg Arg
    930                 935                 940

Cys Val His Arg Asp Leu Ala Ala Arg Asn Ile Leu Val Glu Ser Glu
945                 950                 955                 960

Ala His Val Lys Ile Ala Asp Phe Gly Leu Ala Lys Leu Leu Pro Leu
                965                 970                 975

Asp Lys Asp Tyr Tyr Val Val Arg Glu Pro Gly Gln Ser Pro Ile Phe
            980                 985                 990

Trp Tyr Ala Pro Glu Ser Leu Ser  Asp Asn Ile Phe Ser  Arg Gln Ser
        995                 1000                1005

Asp Val  Trp Ser Phe Gly Val  Val Leu Tyr Glu Leu  Phe Thr Tyr
    1010                1015                1020

Cys Asp  Lys Ser Cys Ser Pro  Ser Ala Glu Phe Leu  Arg Met Met
    1025                1030                1035

Gly Cys  Glu Arg Asp Val Pro  Ala Leu Cys Arg Leu  Leu Glu Leu
    1040                1045                1050

Leu Glu  Glu Gly Gln Arg Leu  Pro Ala Pro Pro Ala  Cys Pro Ala
    1055                1060                1065

Glu Val  His Glu Leu Met Lys  Leu Cys Trp Ala Pro  Ser Pro Gln
    1070                1075                1080

Asp Arg  Pro Ser Phe Ser Ala  Leu Gly Pro Gln Leu  Asp Met Leu
    1085                1090                1095

Trp Ser  Gly Ser Arg Gly Cys  Glu Thr His Ala Phe  Thr Ala His
    1100                1105                1110

Pro Glu  Gly Lys His His Ser  Leu Ser Phe Ser
    1115                1120

<210> SEQ ID NO 6
<211> LENGTH: 527
<212> TYPE: PRT
<213> ORGANISM: Homo sapiens

<400> SEQUENCE: 6

Met Ile Leu Ser Ser Tyr Asn Thr Ile Gln Ser Val Phe Cys Cys Cys

-continued

```
1               5                   10                  15

Cys Cys Cys Ser Val Gln Lys Arg Gln Met Arg Thr Gln Ile Ser Leu
            20                  25                  30

Ser Thr Asp Glu Glu Leu Pro Glu Lys Tyr Thr Gln Arg Arg Arg Pro
        35                  40                  45

Trp Leu Ser Gln Leu Ser Asn Lys Lys Gln Ser Asn Thr Gly Arg Val
    50                  55                  60

Gln Pro Ser Lys Arg Lys Pro Leu Pro Pro Leu Pro Pro Ser Glu Val
65                  70                  75                  80

Ala Glu Glu Lys Ile Gln Val Lys Ala Leu Tyr Asp Phe Leu Pro Arg
                85                  90                  95

Glu Pro Cys Asn Leu Ala Leu Arg Arg Ala Glu Glu Tyr Leu Ile Leu
            100                 105                 110

Glu Lys Tyr Asn Pro His Trp Trp Lys Ala Arg Asp Arg Leu Gly Asn
        115                 120                 125

Glu Gly Leu Ile Pro Ser Asn Tyr Val Thr Glu Asn Lys Ile Thr Asn
    130                 135                 140

Leu Glu Ile Tyr Glu Trp Tyr His Arg Asn Ile Thr Arg Asn Gln Ala
145                 150                 155                 160

Glu His Leu Leu Arg Gln Glu Ser Lys Glu Gly Ala Phe Ile Val Arg
                165                 170                 175

Asp Ser Arg His Leu Gly Ser Tyr Thr Ile Ser Val Phe Met Gly Ala
            180                 185                 190

Arg Arg Ser Thr Glu Ala Ala Ile Lys His Tyr Gln Ile Lys Lys Asn
        195                 200                 205

Asp Ser Gly Gln Trp Tyr Val Ala Glu Arg His Ala Phe Gln Ser Ile
    210                 215                 220

Pro Glu Leu Ile Trp Tyr His Gln His Asn Ala Ala Gly Leu Met Thr
225                 230                 235                 240

Arg Leu Arg Tyr Pro Val Gly Leu Met Gly Ser Cys Leu Pro Ala Thr
                245                 250                 255

Ala Gly Phe Ser Tyr Glu Lys Trp Glu Ile Asp Pro Ser Glu Leu Ala
            260                 265                 270

Phe Ile Lys Glu Ile Gly Ser Gly Gln Phe Gly Val Val His Leu Gly
        275                 280                 285

Glu Trp Arg Ser His Ile Gln Val Ala Ile Lys Ala Ile Asn Glu Gly
    290                 295                 300

Ser Met Ser Glu Glu Asp Phe Ile Glu Glu Ala Lys Val Met Met Lys
305                 310                 315                 320

Leu Ser His Ser Lys Leu Val Gln Leu Tyr Gly Val Cys Ile Gln Arg
                325                 330                 335

Lys Pro Leu Tyr Ile Val Thr Glu Phe Met Glu Asn Gly Cys Leu Leu
            340                 345                 350

Asn Tyr Leu Arg Glu Asn Lys Gly Lys Leu Arg Lys Glu Met Leu Leu
        355                 360                 365

Ser Val Cys Gln Asp Ile Cys Glu Gly Met Glu Tyr Leu Glu Arg Asn
    370                 375                 380

Gly Tyr Ile His Arg Asp Leu Ala Ala Arg Asn Cys Leu Val Ser Ser
385                 390                 395                 400

Thr Cys Ile Val Lys Ile Ser Asp Phe Gly Met Thr Arg Tyr Val Leu
                405                 410                 415

Asp Asp Glu Tyr Val Ser Ser Phe Gly Ala Lys Phe Pro Ile Lys Trp
            420                 425                 430
```

-continued

Ser Pro Pro Glu Val Phe Leu Phe Asn Lys Tyr Ser Ser Lys Ser Asp
435 440 445

Val Trp Ser Phe Gly Val Leu Met Trp Glu Val Phe Thr Glu Gly Lys
450 455 460

Met Pro Phe Glu Asn Lys Ser Asn Leu Gln Val Val Glu Ala Ile Ser
465 470 475 480

Glu Gly Phe Arg Leu Tyr Arg Pro His Leu Ala Pro Met Ser Ile Tyr
485 490 495

Glu Val Met Tyr Ser Cys Trp His Glu Lys Pro Glu Gly Arg Pro Thr
500 505 510

Phe Ala Glu Leu Leu Arg Ala Val Thr Glu Ile Ala Glu Thr Trp
515 520 525

2,4-DISUBSTITUTED PYRIMIDINES USEFUL AS KINASE INHIBITORS

CROSS-REFERENCE TO RELATED APPLICATIONS

The present application is a continuation-in-part of U.S. Ser. No. 12/492,180, filed Jun. 26, 2009, which claims priority to U.S. provisional application Ser. No. 61/076,450, filed Jun. 27, 2008, U.S. provisional application Ser. No. 61/148,388, filed Jan. 29, 2009, and U.S. provisional application Ser. No. 61/170,874, filed Apr. 20, 2009, the entirety of each of which is hereby incorporated by reference.

SEQUENCE LISTING

In accordance with 37 CFR 1.52(e)(5), a Sequence Listing in the form of a text file (entitled "Sequence Listing.txt," created on Dec. 29, 2009, and 36 kilobytes) is incorporated herein by reference in its entirety.

TECHNICAL FIELD OF THE INVENTION

The present invention relates to compounds useful as inhibitors of protein kinases. The invention also provides pharmaceutically acceptable compositions comprising compounds of the present invention and methods of using said compositions in the treatment of various disorders.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is protein kinases.

Protein kinases constitute a large family of structurally related enzymes that are responsible for the control of a variety of signal transduction processes within the cell. Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxin, and $H_2O_2$), cytokines (e.g., interleukin-1 (IL-1) and tumor necrosis factor α (TNF-α)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by protein kinase-mediated events as described above. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases. Accordingly, there remains a need to find protein kinase inhibitors useful as therapeutic agents.

SUMMARY OF THE INVENTION

It has now been found that compounds of this invention, and pharmaceutically acceptable compositions thereof, are effective as inhibitors of one or more protein kinases. Such compounds have general formulae I-a and I-b:

I-a

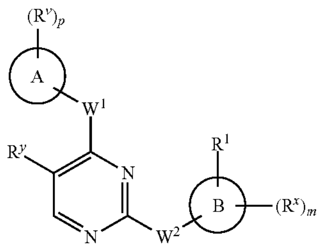

I-b

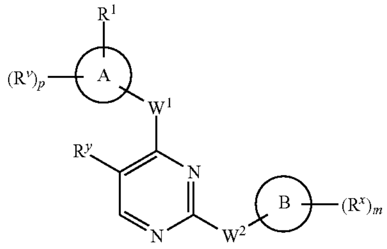

or a pharmaceutically acceptable salt thereof, wherein Ring A, Ring B, m, p, $R^x$, $R^y$, $R^v$, $W^1$, $W^2$, and $R^1$ are as defined herein.

Compounds of the present invention, and pharmaceutically acceptable compositions thereof, are useful for treating a variety of diseases, disorders or conditions, associated with abnormal cellular responses triggered by protein kinase-mediated events. Such diseases, disorders, or conditions include those described herein.

Compounds provided by this invention are also useful for the study of kinases in biological and pathological phenomena; the study of intracellular signal transduction pathways mediated by such kinases; and the comparative evaluation of new kinase inhibitors.

BRIEF DESCRIPTION OF THE DRAWINGS

FIG. 20 depicts an amino acid sequence for BTK (SEQ ID 1).

FIG. 21 depicts an amino acid sequence for TEC (SEQ ID 2).

FIG. 22 depicts an amino acid sequence for ITK (SEQ ID 3).

FIG. 23 depicts an amino acid sequence for BMX (SEQ ID 4).

FIG. 24 depicts an amino acid sequence for TXK (SEQ ID 5).

FIG. 25 depicts an amino acid sequence for JAK3 (SEQ ID 6).

DETAILED DESCRIPTION OF CERTAIN EMBODIMENTS

Figure 1:
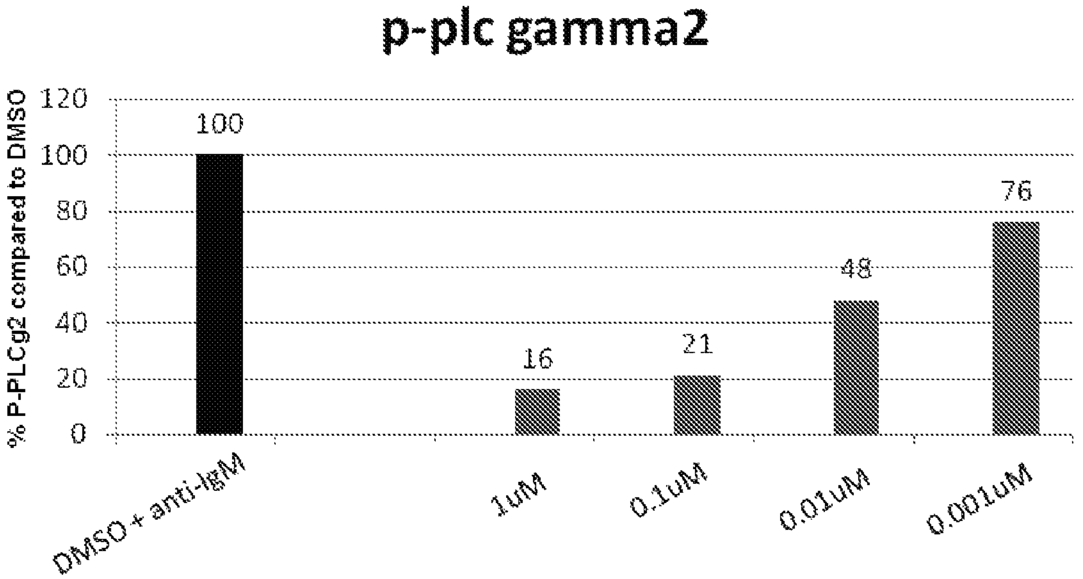
FIG. 1 depicts dose-response inhibition of phospho-plc gamma2 (p-plc gamma 2) with compound I-2 in Ramos Cells; and the results of compound I-2 in a "washout" experiment.
Figure 1:
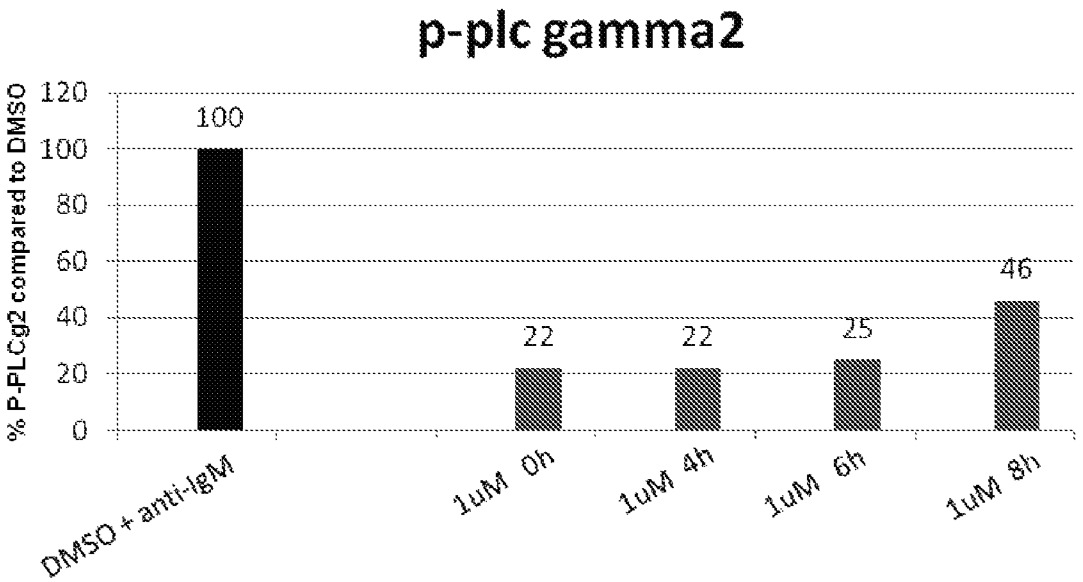

1. General Description of Compounds of the Invention

In certain embodiments, the present invention provides a compound of formula I-a or I-b:

I-a

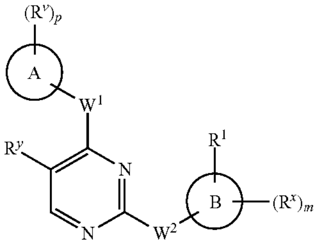

I-b

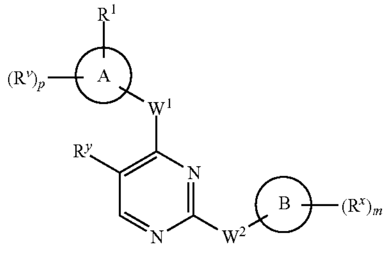

or a pharmaceutically acceptable salt thereof, wherein:

Ring A is an optionally substituted group selected from phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;

Ring B is an optionally substituted group selected from phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;

$R^1$ is a warhead group;

$R^y$ is hydrogen, halogen, —CN, —$CF_3$, $C_{1-4}$ aliphatic, $C_{1-4}$ haloaliphatic, —OR, —C(O)R, or —C(O)N(R)$_2$;

each R group is independently hydrogen or an optionally substituted group selected from $C_{1-6}$ aliphatic, phenyl, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur;

$W^1$ and $W^2$ are each independently a covalent bond or a bivalent $C_{1-3}$ alkylene chain wherein one methylene unit of $W^1$ or $W^2$ is optionally replaced by —$NR^2$—, —$N(R^2)C(O)$—, —$C(O)N(R^2)$—, —$N(R^2)SO_2$—, —$SO_2N(R^2)$—, —O—, —C(O)—, —OC(O)—, —C(O)O—, —S—, —SO— or —$SO_2$—;

$R^2$ is hydrogen, optionally substituted $C_{1-6}$ aliphatic, or —C(O)R, or:

$R^2$ and a substituent on Ring A are taken together with their intervening atoms to form a 4-6 membered saturated, partially unsaturated, or aromatic fused ring, or:

$R^2$ and $R^y$ are taken together with their intervening atoms to form a 4-7 membered partially unsaturated or aromatic fused ring;

m and p are independently 0-4; and $R^x$ and $R^v$ are independently selected from —R, halogen, —OR, —$O(CH_2)_qOR$, —CN, —$NO_2$, —$SO_2R$, —$SO_2N(R)_2$, —SOR, —C(O)R, —$CO_2R$, —C(O)N$(R)_2$, —NRC(O)R, —NRC(O)$NR_2$, —$NRSO_2R$, or —$N(R)_2$, wherein q is 1-4; or:

$R^x$ and $R^1$ when concurrently present on Ring B are taken together with their intervening atoms to form a 5-7 membered saturated, partially unsaturated, or aryl ring having 0-3 heteroatoms independently selected from nitrogen, oxygen, or sulfur, wherein said ring is substituted with a warhead group and 0-3 groups independently selected from oxo, halogen, —CN, or $C_{1-6}$ aliphatic; or $R^v$ and $R^1$ when concurrently present on Ring A are taken together with their intervening atoms to form a 5-7 membered saturated, partially unsaturated, or aryl ring having 0-3 heteroatoms independently selected from nitrogen, oxygen, or sulfur, wherein said ring is substituted with a warhead group and 0-3 groups independently selected from oxo, halogen, —CN, or $C_{1-6}$ aliphatic.

2. Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, $75^{th}$ Ed. Additionally, general principles of organic chemistry are described in "Organic Chemistry", Thomas Sorrell, University Science Books, Sausalito: 1999, and "March's Advanced Organic Chemistry", $5^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated", as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —$(CH_2)_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the following structure:

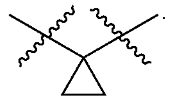 [SMILES: *C1(*)CC1]

The term "halogen" means F, Cl, Br, or I.

The term "aryl" used alone or as part of a larger moiety as in "aralkyl", "aralkoxy", or "aryloxyalkyl", refers to monocyclic and bicyclic ring systems having a total of five to fourteen ring members, wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl", as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-", used alone or as part of a larger moiety, e.g., "heteroaralkyl", or "heteroaralkoxy", refer to groups having 5 to 10 ring atoms, preferably 5, 6, or 9 ring atoms; having 6, 10, or 14 $\pi$ electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^{+}NR$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $—(CH_2)_{0-4}R^\circ$; $—(CH_2)_{0-4}OR^\circ$; $—O(CH_2)_{0-4}R^\circ$, $—O—(CH_2)_{0-4}C(O)OR^\circ$; $—(CH_2)_{0-4}CH(OR^\circ)_2$; $—(CH_2)_{0-4}SR^\circ$; $—(CH_2)_{0-4}Ph$, which may be substituted with $R^\circ$; $—(CH_2)_{0-4}O(CH_2)_{0-1}$-Ph which may be substituted with $R^\circ$; $—CH{=}CHPh$, which may be substituted with $R^\circ$; $—(CH_2)_{0-4}O(CH_2)_{0-1}$-pyridyl which may be substituted with $R^\circ$; $—NO_2$; $—CN$; $—N_3$; $—(CH_2)_{0-4}N(R^\circ)_2$; $—(CH_2)_{0-4}N(R^\circ)C(O)R^\circ$; $—N(R^\circ)C(S)R^\circ$; $—(CH_2)_{0-4}N(R^\circ)C(O)NR^\circ_2$; $—N(R^\circ)C(S)NR^\circ_2$; $—(CH_2)_{0-4}N(R^\circ)C(O)OR^\circ$; $—N(R^\circ)N(R^\circ)C(O)R^\circ$; $—N(R^\circ)N(R^\circ)C(O)NR^\circ_2$; $—N(R^\circ)N(R^\circ)C(O)OR^\circ$; $—(CH_2)_{0-4}C(O)R^\circ$; $—C(S)R^\circ$; $—(CH_2)_{0-4}C(O)OR^\circ$; $—(CH_2)_{0-4}C(O)SR^\circ$; $—(CH_2)_{0-4}C(O)OSiR^\circ_3$; $—(CH_2)_{0-4}OC(O)R^\circ$; $—OC(O)(CH_2)_{0-4}SR^\circ$, $SC(S)SR^\circ$; $—(CH_2)_{0-4}SC(O)R^\circ$; $—(CH_2)_{0-4}C(O)NR^\circ_2$; $—C(S)NR^\circ_2$; $—C(S)SR^\circ$; $—SC(S)SR^\circ$, $—(CH_2)_{0-4}OC(O)NR^\circ_2$; $—C(O)N(OR^\circ)R^\circ$; $—C(O)C(O)R^\circ$; $—C(O)CH_2C(O)R^\circ$; $—C(NOR^\circ)R^\circ$; $—(CH_2)_{0-4}SSR^\circ$; $—(CH_2)_{0-4}S(O)_2R^\circ$; $—(CH_2)_{0-4}S(O)_2OR^\circ$; $—(CH_2)_{0-4}OS(O)_2R^\circ$; $—S(O)_2NR^\circ_2$, $—(CH_2)_{0-4}S(O)R^\circ$; $—N(R^\circ)S(O)_2NR^\circ_2$; $—N(R^\circ)S(O)_2R^\circ$; $—N(OR^\circ)R^\circ$; $—C(NH)NR^\circ_2$; $—P(O)_2R^\circ$; $—P(O)R^\circ_2$; $—OP(O)R^\circ_2$; $—OP(O)(OR^\circ)_2$; $SiR^\circ_3$; $—(C_{1-4}$ straight or branched)alkylene)O—$N(R^\circ)_2$; or $—(C_{1-4}$ straight or branched)alkylene)C(O)O—$N(R^\circ)_2$, wherein each $R^\circ$ may be substituted as defined below and is independently hydrogen, $C_{1-6}$ aliphatic, $—CH_2Ph$, $—O(CH_2)_{0-1}Ph$, $—CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $—(CH_2)_{0-2}R^\bullet$, -(halo$R^\bullet$), $—(CH_2)_{0-2}OH$, —$(CH_2)_{0-2}OR^{\bullet}$, —$(CH_2)_{0-2}CH(OR^{\bullet})_2$; —O(halo$R^{\bullet}$), —CN, —$N_3$, —$(CH_2)_{0-2}C(O)R^{\bullet}$, —$(CH_2)_{0-2}C(O)OH$, —$(CH_2)_{0-2}C(O)OR^{\bullet}$, —$(CH_2)_{0-2}SR^{\bullet}$, —$(CH_2)_{0-2}SH$, —$(CH_2)_{0-2}NH_2$, —$(CH_2)_{0-2}NHR^{\bullet}$, —$(CH_2)_{0-2}NR^{\bullet}_2$, —$NO_2$, —$SiR^{\bullet}_3$, —$OSiR^{\bullet}_3$, —$C(O)SR^{\bullet}$, —($C_{1-4}$ straight or branched alkylene)$C(O)OR^{\bullet}$, or —$SSR^{\bullet}$ wherein each $R^{\bullet}$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^{\circ}$ include =O and =S.

Suitable divalent substituents on a saturated carbon atom of an "optionally substituted" group include the following: =O, =S, =$NNR^*_2$, =NNHC(O)R*, =NNHC(O)OR*, =$NNHS(O)_2R^*$, =NR*, =NOR*, —$O(C(R^*_2))_{2-3}O$—, or —$S(C(R^*_2))_{2-3}S$—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —$O(CR^*_2)_{2-3}O$—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —$R^{\bullet}$, -(halo$R^{\bullet}$), —OH, —$OR^{\bullet}$, —O(halo$R^{\bullet}$), —CN, —C(O)OH, —$C(O)OR^{\bullet}$, —$NH_2$, —$NHR^{\bullet}$, —$NR^{\bullet}_2$, or —$NO_2$, wherein each $R^{\bullet}$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —$R^{\dagger}$, —$NR^{\dagger}_2$, —$C(O)R^{\dagger}$, —$C(O)OR^{\dagger}$, —$C(O)C(O)R^{\dagger}$, —$C(O)CH_2C(O)R^{\dagger}$, —$S(O)_2R^{\dagger}$, —$S(O)_2NR^{\dagger}_2$, —$C(S)NR^{\dagger}_2$, —$C(NH)NR^{\dagger}_2$, or —$N(R^{\dagger})S(O)_2R^{\dagger}$; wherein each $R^{\dagger}$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^{\dagger}$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^{\dagger}$ are independently halogen, —$R^{\bullet}$, -(halo$R^{\bullet}$), —OH, —$OR^{\bullet}$, —O(halo$R^{\bullet}$), —CN, —C(O)OH, —$C(O)OR^{\bullet}$, —$NH_2$, —$NHR^{\bullet}$, —$NR^{\bullet}_2$, or —$NO_2$, wherein each $R^{\bullet}$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention. In some embodiments, the $R^1$ group of formula I-a and I-b comprises one or more deuterium atoms.

As used herein, the term "irreversible" or "irreversible inhibitor" refers to an inhibitor (i.e. a compound) that is able to be covalently bonded to a target protein kinase in a substantially non-reversible manner. That is, whereas a reversible inhibitor is able to bind to (but is generally unable to form a covalent bond) the target protein kinase, and therefore can become dissociated from the target protein kinase, an irreversible inhibitor will remain substantially bound to the target protein kinase once covalent bond formation has occurred. Irreversible inhibitors usually display time dependency, whereby the degree of inhibition increases with the time with which the inhibitor is in contact with the enzyme. Methods for identifying if a compound is acting as an irreversible inhibitor are known to one of ordinary skill in the art. Such methods include, but are not limited to, enzyme kinetic analysis of the inhibition profile of the compound with the protein kinase target, the use of mass spectrometry of the protein drug target modified in the presence of the inhibitor compound, discontinuous exposure, also known as "washout," experiments, and the use of labeling, such as radiolabelled inhibitor, to show covalent modification of the enzyme, as well as other methods known to one of skill in the art.

One of ordinary skill in the art will recognize that certain reactive functional groups can act as "warheads." As used herein, the term "warhead" or "warhead group" refers to a functional group present on a compound of the present invention wherein that functional group is capable of covalently binding to an amino acid residue (such as cysteine, lysine, histidine, or other residues capable of being covalently modified) present in the binding pocket of the target protein, thereby irreversibly inhibiting the protein. It will be appreciated that the -L-Y group, as defined and described herein, provides such warhead groups for covalently, and irreversibly, inhibiting the protein.

As used herein, the term "inhibitor" is defined as a compound that binds to and/or inhibits the target protein kinase with measurable affinity. In certain embodiments, an inhibitor has an $IC_{50}$ and/or binding constant of less about 50 μM, less than about 1 μM, less than about 500 nM, less than about 100 nM, or less than about 10 nM.

The terms "measurable affinity" and "measurably inhibit," as used herein, means a measurable change in at least one of ErbB1, ErbB2, ErbB3, ErbB4, a TEC-kinase, and/or JAK3 activity between a sample comprising a compound of the present invention, or composition thereof, and at least one of ErbB1, ErbB2, ErbB3, ErbB4, a TEC-kinase, and/or JAK3, and an equivalent sample comprising at least one of ErbB1, ErbB2, ErbB3, ErbB4, a TEC-kinase, and/or JAK3, in the absence of said compound, or composition thereof.

3. Description of Exemplary Compounds

According to one aspect, the present invention provides a compound of formula I-a or I-b, I-a

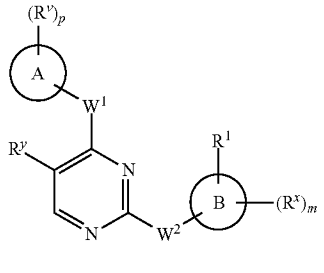

-continued

I-b

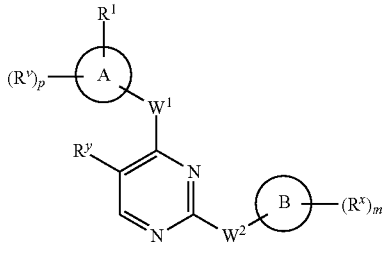

or a pharmaceutically acceptable salt thereof, wherein:

Ring A is an optionally substituted group selected from phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;

Ring B is an optionally substituted group selected from phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;

$R^1$ is -L-Y, wherein:

L is a covalent bond or a bivalent $C_{1-8}$ saturated or unsaturated, straight or branched, hydrocarbon chain, wherein one, two, or three methylene units of L are optionally and independently replaced by cyclopropylene, —NR—, —N(R)C(O)—, —C(O)N(R)—, —N(R)$SO_2$—, —$SO_2$N(R)—, —O—, —C(O)—, —OC(O)—, —C(O)O—, —S—, —SO—, —$SO_2$—, —C(=S)—, —C(=NR)—, —N=N—, or —C(=$N_2$)—;

Y is hydrogen, $C_{1-6}$ aliphatic optionally substituted with oxo, halogen, or CN, or a 3-10 membered monocyclic or bicyclic, saturated, partially unsaturated, or aryl ring having 0-3 heteroatoms independently selected from nitrogen, oxygen, or sulfur, and wherein said ring is substituted with at 1-4 groups independently selected from -Q-Z, oxo, $NO_2$, halogen, CN, or $C_{1-6}$ aliphatic, wherein:

Q is a covalent bond or a bivalent $C_{1-6}$ saturated or unsaturated, straight or branched, hydrocarbon chain, wherein one or two methylene units of Q are optionally and independently replaced by —NR—, —S—, —O—, —C(O)—, —SO—, or —$SO_2$—; and Z is hydrogen or $C_{1-6}$ aliphatic optionally substituted with oxo, halogen, or CN;

$R^y$ is hydrogen, halogen, —CN, —$CF_3$, $C_{1-4}$ aliphatic, $C_{1-4}$ haloaliphatic, —OR, —C(O)R, or —C(O)N(R)$_2$;

each R group is independently hydrogen or an optionally substituted group selected from $C_{1-6}$ aliphatic, phenyl, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur;

$W^1$ and $W^2$ are each independently a covalent bond or a bivalent $C_{1-3}$ alkylene chain wherein one methylene unit of $W^1$ or $W^2$ is optionally replaced by —$NR^2$—, —N($R^2$)C(O)—, —C(O)N($R^2$)—, —N($R^2$)$SO_2$—, —$SO_2$N($R^2$)—, —O—, —C(O)—, —OC(O)—, —C(O)O—, —S—, —SO— or —$SO_2$—;

$R^2$ is hydrogen, optionally substituted $C_{1-6}$ aliphatic, or —C(O)R, or:

$R^2$ and a substituent on Ring A are taken together with their intervening atoms to form a 4-6 membered partially unsaturated or aromatic fused ring; or $R^2$ and $R^y$ are taken together with their intervening atoms to form a 4-6 membered saturated, partially unsaturated, or aromatic fused ring;

m and p are independently 0-4; and $R^x$ and $R^v$ are independently selected from —R, halogen, —OR, —O($CH_2$)$_q$OR, —CN, —$NO_2$, —$SO_2$R, —$SO_2$N(R)$_2$, —SOR, —C(O)R, —$CO_2$R, —C(O)N(R)$_2$, —NRC(O)R, —NRC(O)$NR_2$, —$NRSO_2$R, or —N(R)$_2$, or:

$R^x$ and $R^1$ when concurrently present on Ring B are taken together with their intervening atoms to form a 5-7 membered saturated, partially unsaturated, or aryl ring having 0-3 heteroatoms independently selected from nitrogen, oxygen, or sulfur, wherein said ring is substituted with a warhead group and 0-3 groups independently selected from oxo, halogen, —CN, or $C_{1-6}$ aliphatic; or $R^v$ and $R^1$ when concurrently present on Ring A are taken together with their intervening atoms to form a 5-7 membered saturated, partially unsaturated, or aryl ring having 0-3 heteroatoms independently selected from nitrogen, oxygen, or sulfur, wherein said ring is substituted with a warhead group and 0-3 groups independently selected from oxo, halogen, —CN, or $C_{1-6}$ aliphatic.

As defined generally above, Ring A is an optionally substituted group selected from phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur. In certain embodiments, Ring A is an optionally substituted phenyl group. In some embodiments, Ring A is an optionally substituted naphthyl ring or a bicyclic 8-10 membered heteroaryl ring having 1-4 heteroatoms independently selected from nitrogen, oxygen, or sulfur. In certain other embodiments, Ring A is an optionally substituted 3-7 membered carbocyclic ring. In yet other embodiments, Ring A is an optionally substituted 4-7 membered heterocyclic ring having 1-3 heteroatoms independently selected from nitrogen, oxygen, or sulfur.

In certain embodiments, Ring A is substituted as defined herein. In some embodiments, Ring A is substituted with one, two, or three groups independently selected from halogen, R°, or —($CH_2$)$_{0-4}$OR°, or —O($CH_2$)$_{0-4}$R°, wherein each R° is as defined herein. Exemplary substituents on Ring A include Br, I, Cl, methyl, —$CF_3$, —C≡CH, —$OCH_2$phenyl, —$OCH_2$(fluorophenyl), or —$OCH_2$pyridyl.

Exemplary Ring A groups are set forth in Table 1.

TABLE 1

| Exemplary Ring A Groups | |
|---|---|
| 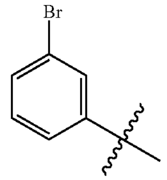 [SMILES: *c1cccc(Br)c1] | i |
| 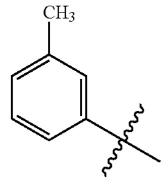 [SMILES: *c1cccc(C)c1] | ii |
| 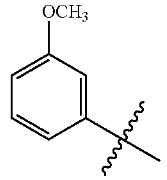 [SMILES: *c1cccc(OC)c1] | iii |
| 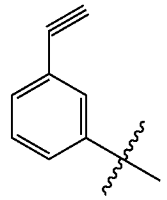 [SMILES: *c1cccc(C#C)c1] | iv |
| 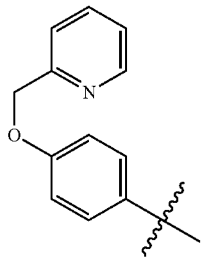 [SMILES: *c1ccc(OCc2ccccn2)cc1] | v |

TABLE 1-continued
| Exemplary Ring A Groups | |
|---|---|
| 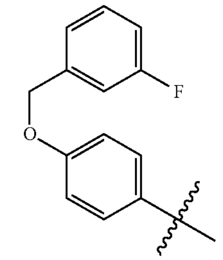 [SMILES: *c1ccc(OCc2cccc(F)c2)cc1] | vi |
| 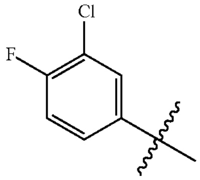 [SMILES: *c1ccc(F)c(Cl)c1] | vii |
| 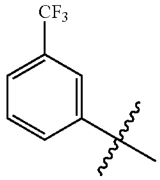 [SMILES: *c1cccc(C(F)(F)F)c1] | viii |
| 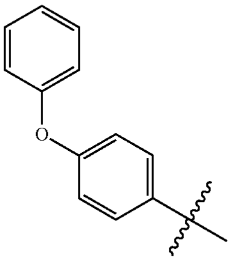 [SMILES: *c1ccc(Oc2ccccc2)cc1] | ix |
| 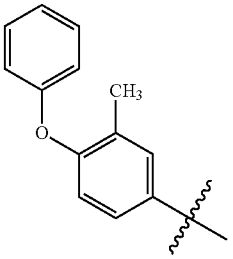 [SMILES: *c1ccc(Oc2ccccc2)c(C)c1] | x |
| 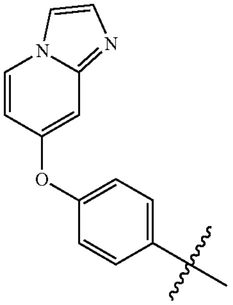 [SMILES: *c1ccc(Oc2ccn3ccnc3c2)cc1] | xi |
TABLE 1-continued
| Exemplary Ring A Groups | |
|---|---|
| 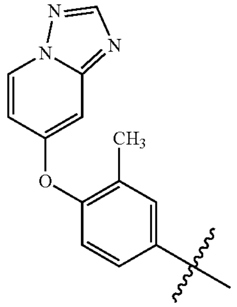 [SMILES: *c1ccc(Oc2ccn3ncnc3c2)c(C)c1] | xii |
| 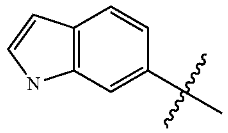 [SMILES: *c1ccc2cc[nH]c2c1] | xiii |
| 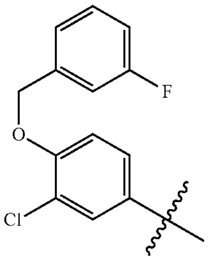 [SMILES: *c1ccc(OCc2cccc(F)c2)c(Cl)c1] | xiv |
| 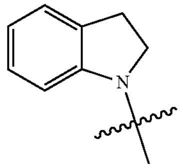 [SMILES: *N1CCc2ccccc21] | xv |
| 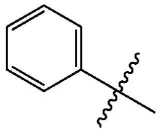 [SMILES: *c1ccccc1] | xvi |
| 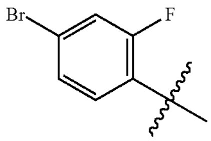 [SMILES: *c1ccc(Br)cc1F] | xvii |
| 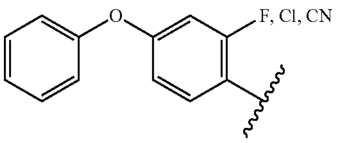 | xviii |
| 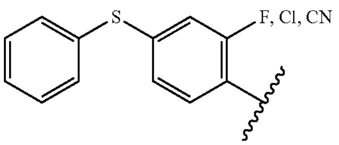 | xix |

TABLE 1-continued
| Exemplary Ring A Groups | |
|---|---|
| 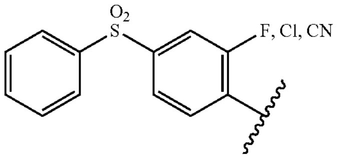 | xx |
| 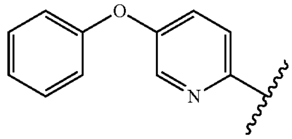 [SMILES: *c1ccc(Oc2ccccc2)cn1] | xxi |
| 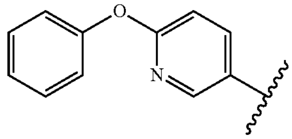 [SMILES: *c1ccc(Oc2ccccc2)nc1] | xxii |
| 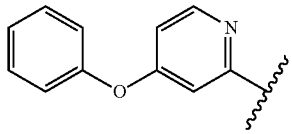 [SMILES: *c1cc(Oc2ccccc2)ccn1] | xxiii |
| 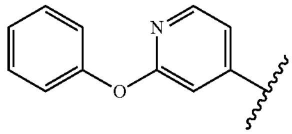 [SMILES: *c1ccnc(Oc2ccccc2)c1] | xxiv |
| 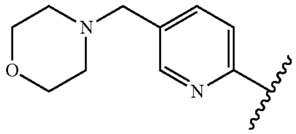 [SMILES: *c1ccc(CN2CCOCC2)cn1] | xxv |
| 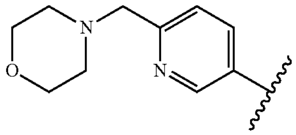 [SMILES: *c1ccc(CN2CCOCC2)nc1] | xxvi |
| 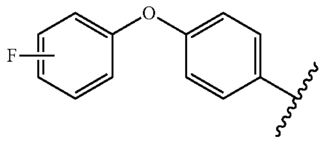 | xxvii |
| 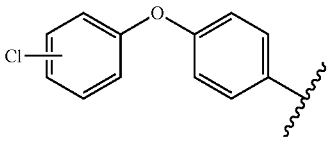 | xxviii |
| 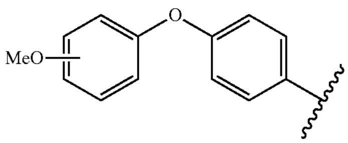 | xxix |
TABLE 1-continued
| Exemplary Ring A Groups | |
|---|---|
| 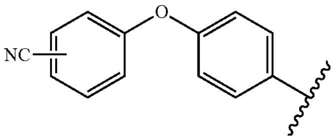 | xxx |
| 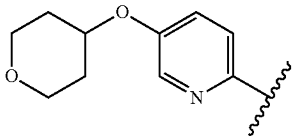 [SMILES: *c1ccc(OC2CCOCC2)cn1] | xxxi |
| 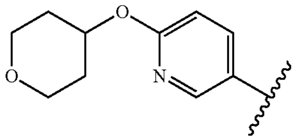 [SMILES: *c1ccc(OC2CCOCC2)nc1] | xxxii |
| 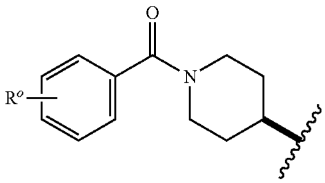 | xxxiii |
| 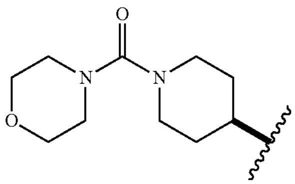 | xxxiv |
| 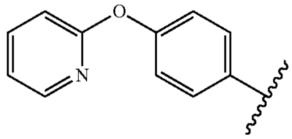 [SMILES: *c1ccc(Oc2ccccn2)cc1] | xxxv |
| 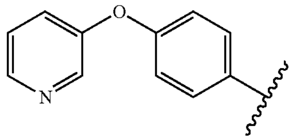 [SMILES: *c1ccc(Oc2cccnc2)cc1] | xxxvi |
| 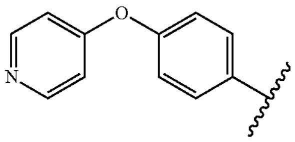 [SMILES: *c1ccc(Oc2ccncc2)cc1] | xxxvii |
| 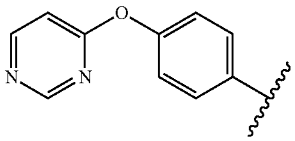 [SMILES: *c1ccc(Oc2ccncn2)cc1] | xxxviii |
| 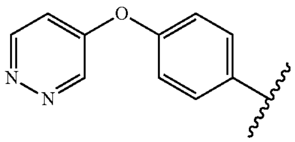 [SMILES: *c1ccc(Oc2ccnnc2)cc1] | xxxix |

TABLE 1-continued
| Exemplary Ring A Groups | |
|---|---|
| 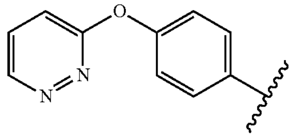 [SMILES: *c1ccc(Oc2cccnn2)cc1] | xl |
| 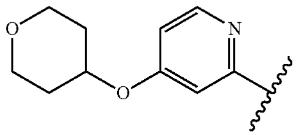 [SMILES: *c1cc(OC2CCOCC2)ccn1] | xli |
| 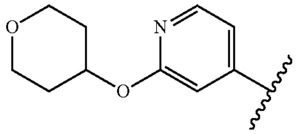 [SMILES: *c1ccnc(OC2CCOCC2)c1] | xlii |
| 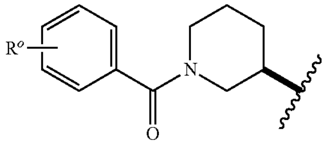 | xliii |
| 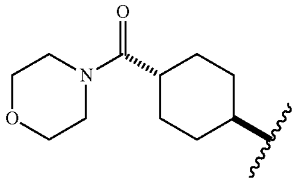 | xliv |
| 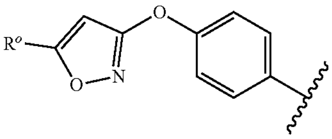 | xlv |
| 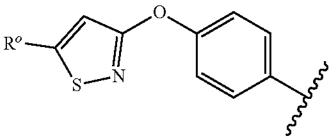 | xlvi |
| 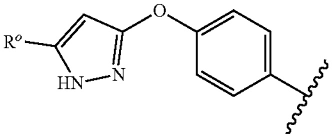 | xlvii |
| 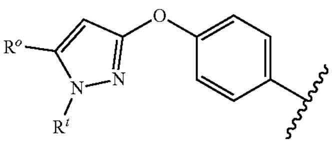 | xlviii |
| 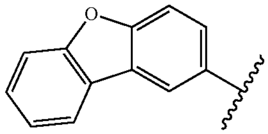 [SMILES: *c1ccc2oc3ccccc3c2c1] | xlix |
TABLE 1-continued
| Exemplary Ring A Groups | |
|---|---|
| 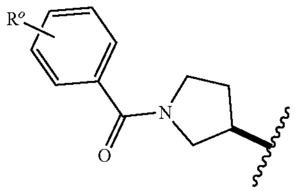 | l |
| 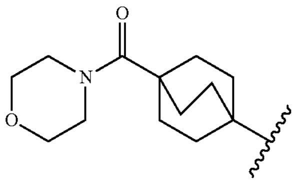 [SMILES: *C12CCC(C(=O)N3CCOCC3)(CC1)CC2] | li |
| 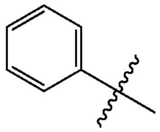 [SMILES: *c1ccccc1] | lii |
| 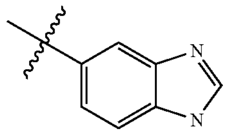 [SMILES: *c1ccc2[nH]cnc2c1] | liii |
| 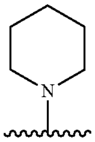 [SMILES: *N1CCCCC1] | liv |
| 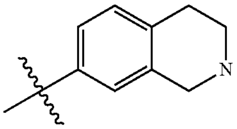 [SMILES: *c1ccc2c(c1)CNCC2] | lv |
| 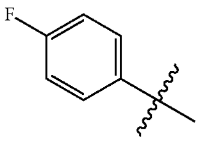 [SMILES: *c1ccc(F)cc1] | lvi |
| 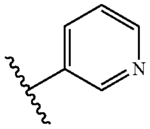 [SMILES: *c1cccnc1] | lvii |
| 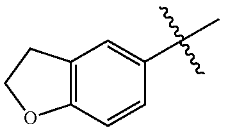 [SMILES: *c1ccc2c(c1)CCO2] | lviii |
| 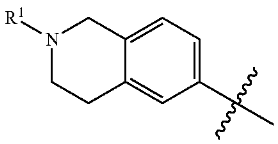 | lix |

TABLE 1-continued
| Exemplary Ring A Groups | |
|---|---|
| 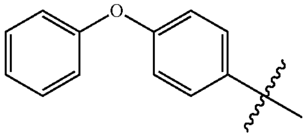 [SMILES: *c1ccc(Oc2ccccc2)cc1] | lx |
| 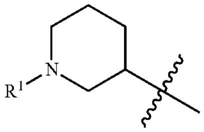 | lxi |
| 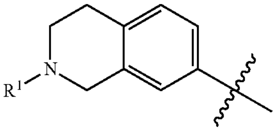 | lxii |
| 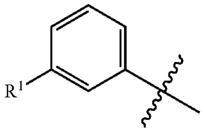 | lxiii |
| 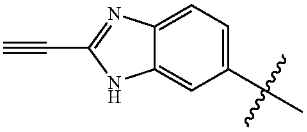 [SMILES: *c1ccc2nc(C#C)[nH]c2c1] | lxiv |
| 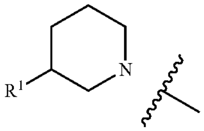 | lxv |
| 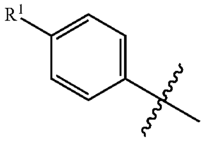 | lxvi |
| 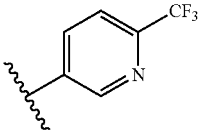 [SMILES: *c1ccc(C(F)(F)F)nc1] | lxvii |
| 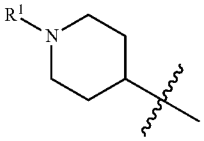 | lxviii |
| 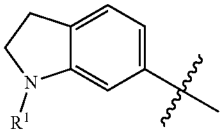 | lxix |
TABLE 1-continued
| Exemplary Ring A Groups | |
|---|---|
| 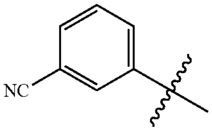 [SMILES: *c1cccc(C#N)c1] | lxx |
| 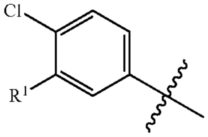 | lxxi |
| 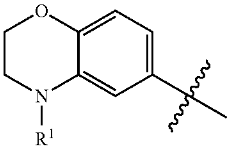 | lxxii |
| 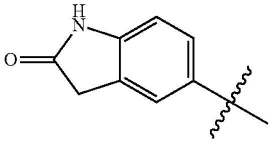 [SMILES: *c1ccc2c(c1)CC(=O)N2] | lxxii |
| 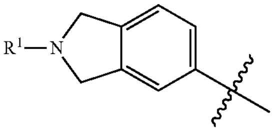 | lxxiv |
| 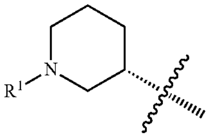 | lxxv |
| 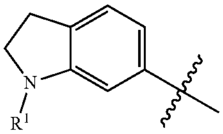 | lxxvi |
| 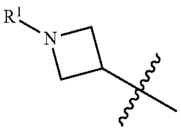 | lxxvii |
| 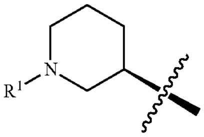 | lxxviii |
| 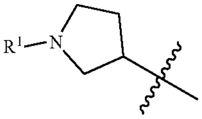 | lxxix |

TABLE 1-continued

| Exemplary Ring A Groups | |
|---|---|
| 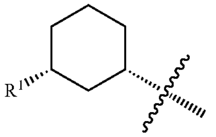 | lxxx |
| 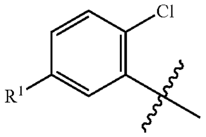 | lxxxi |
| 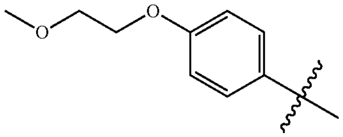 [SMILES: *c1ccc(OCCOC)cc1] | lxxxii |
| 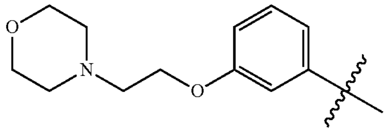 [SMILES: *c1cccc(OCCN2CCOCC2)c1] | lxxxiii |
| 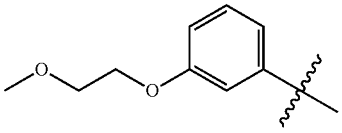 or | lxxxiv |
| 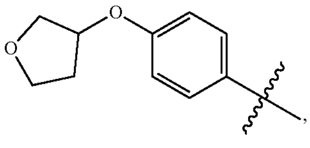 [SMILES: *c1ccc(OC2CCOC2)cc1], | lxxxv |

wherein each R°, R†, and $R^1$ is as defined above and described in classes and subclasses herein.

In certain embodiments, Ring A is selected from i, ii, iv, v, vi, vii, ix, xiv, xvi, lii, lxiii, lxxi, lxxiv, lxxvi, lxxviii, and lxxxi.

As defined generally above, Ring B is an optionally substituted group selected from phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur. In certain embodiments, Ring B is an optionally substituted phenyl group. In some embodiments, Ring B is an optionally substituted naphthyl ring or a bicyclic 8-10 membered heteroaryl ring having 1-4 heteroatoms independently selected from nitrogen, oxygen, or sulfur. In certain other embodiments, Ring B is an optionally substituted 3-7 membered carbocyclic ring. In yet other embodiments, Ring B is an optionally substituted 4-7 membered heterocyclic ring having 1-3 heteroatoms independently selected from nitrogen, oxygen, or sulfur.

In some embodiments, Ring B is phenyl. In some embodiments, Ring B is a 6-membered heteroaryl ring having 1-3 nitrogens. In some embodiments, Ring B is a 5-membered heteroaryl ring having 1 or 2 or 3 heteroatoms independently selected from nitrogen, oxygen, or sulfur.

In some embodiments, Ring B is a 5-6 membered saturated heterocyclic ring having 1 nitrogen. In some embodiments, Ring B is a 9-10 membered bicyclic partially saturated heteroaryl ring having 1-3 nitrogens. In some embodiments, Ring B is a 9-10 membered bicyclic partially saturated heteroaryl ring having 1 nitrogen. In some embodiments, Ring B is a 9-10 membered bicyclic partially saturated heteroaryl ring having 1 nitrogen and 1 oxygen.

In some embodiments, Ring B is an optionally substituted group selected from phenyl, pyridyl, pyrazinyl, pyrimidinyl, imidazolyl, pyrrolidinyl, piperidinyl, indolinyl, indazolyl, and isoindolinyl.

Exemplary Ring B groups are set forth in Table 2.

TABLE 2

| Ring B Groups | |
|---|---|
| 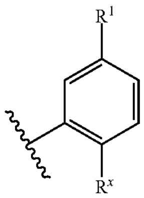 | i |
| 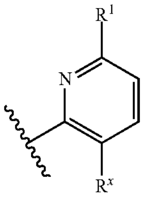 | ii |
| 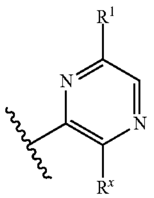 | iii |
| 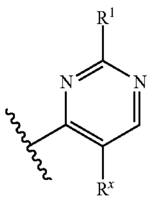 | iv |
| 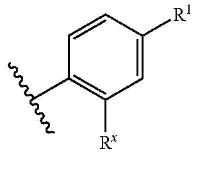 | v |

TABLE 2-continued
| Ring B Groups | |
| --- | --- |
| 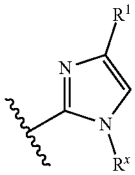 | vi |
| 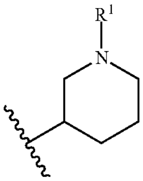 | vii |
| 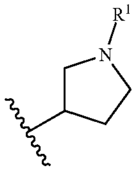 | viii |
| 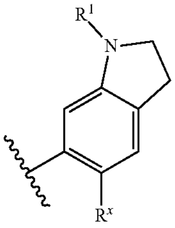 | ix |
| 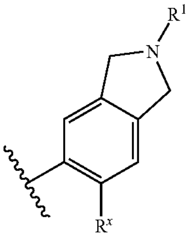 | x |
| 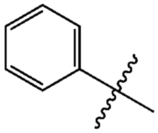 [SMILES: *c1ccccc1] | xi |
| 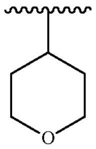 [SMILES: *C1CCOCC1] | xii |
| 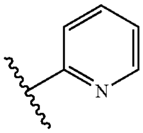 [SMILES: *c1ccccn1] | xiii |
TABLE 2-continued
| Ring B Groups | |
| --- | --- |
| 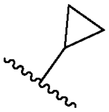 [SMILES: *C1CC1] | xiv |
| 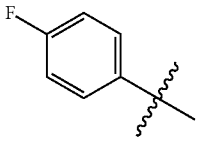 [SMILES: *c1ccc(F)cc1] | xv |
| 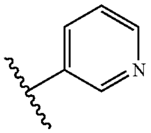 [SMILES: *c1cccnc1] | xvi |
| 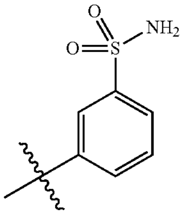 [SMILES: *c1cccc(S(N)(=O)=O)c1] | xvii |
| 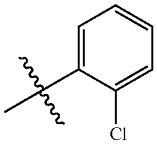 [SMILES: *c1ccccc1Cl] | xviii |
| 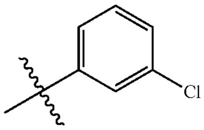 [SMILES: *c1cccc(Cl)c1] | xix |
| 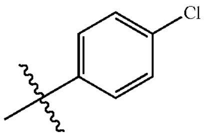 [SMILES: *c1ccc(Cl)cc1] | xx |
| 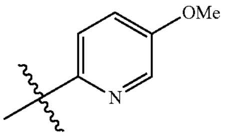 [SMILES: *c1ccc(OC)cn1] | xxi |
| 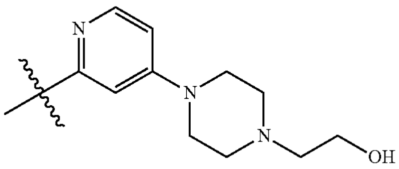 [SMILES: *c1cc(N2CCN(CCO)CC2)ccn1] | xxii |
| 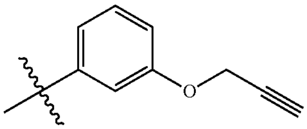 [SMILES: *c1cccc(OCC#C)c1] | xxiii |

TABLE 2-continued
Ring B Groups
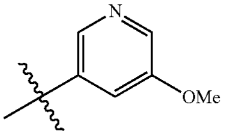 [SMILES: *c1cncc(OC)c1]
xxiv
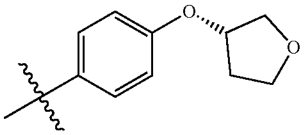
xxv
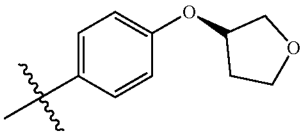
xxvi
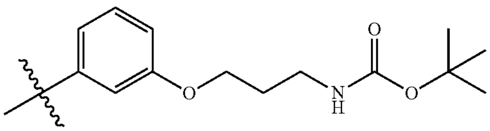 [SMILES: *c1cccc(OCCCNC(=O)OC(C)(C)C)c1]
xxvii
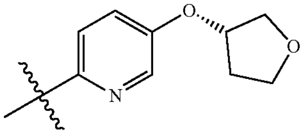
xxviii
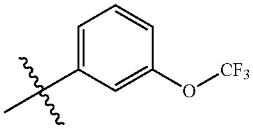 [SMILES: *c1cccc(OC(F)(F)F)c1]
xxix
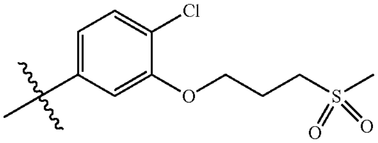 [SMILES: *c1ccc(Cl)c(OCCCS(C)(=O)=O)c1]
xxx
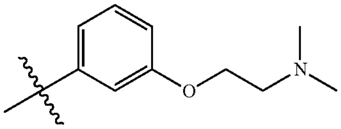 [SMILES: *c1cccc(OCCN(C)C)c1]
xxxi
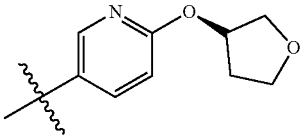
xxxii
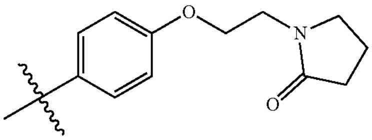 [SMILES: *c1ccc(OCCN2CCCC2=O)cc1]
xxxiii
TABLE 2-continued
Ring B Groups
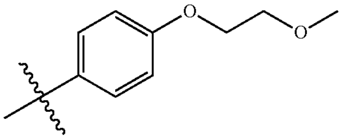 [SMILES: *c1ccc(OCCOC)cc1]
xxxiv
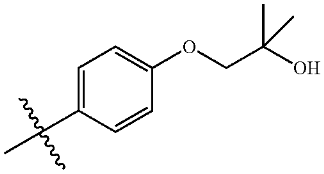 [SMILES: *c1ccc(OCC(C)(C)O)cc1]
xxxv
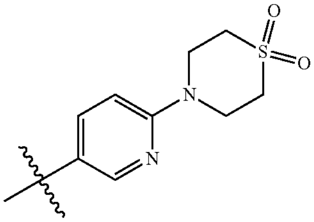 [SMILES: *c1ccc(N2CCS(=O)(=O)CC2)nc1]
xxxvi
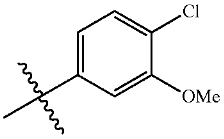 [SMILES: *c1ccc(Cl)c(OC)c1]
xxxvii
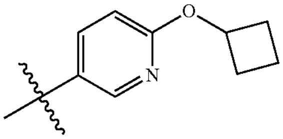 [SMILES: *c1ccc(OC2CCC2)nc1]
xxxviii
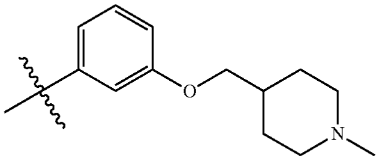 [SMILES: *c1cccc(OCC2CCN(C)CC2)c1]
xxxix
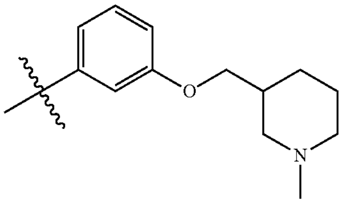 [SMILES: *c1cccc(OCC2CCCN(C)C2)c1]
xl
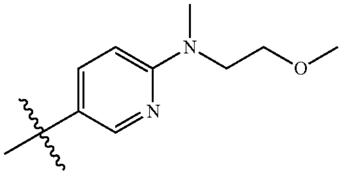 [SMILES: *c1ccc(N(C)CCOC)nc1]
xli TABLE 2-continued
| Ring B Groups |
|---|
| xlii 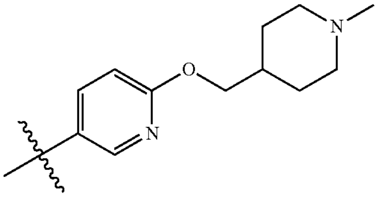 [SMILES: *c1ccc(OCC2CCN(C)CC2)nc1] |
| xliii 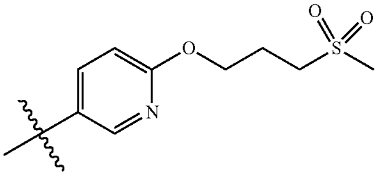 [SMILES: *c1ccc(OCCCS(C)(=O)=O)nc1] |
| xliv 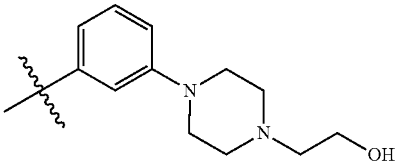 [SMILES: *c1cccc(N2CCN(CCO)CC2)c1] |
| xlv 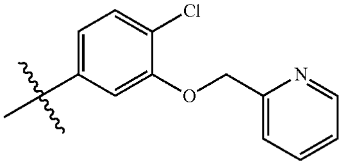 [SMILES: *c1ccc(Cl)c(OCc2ccccn2)c1] |
| xlvi 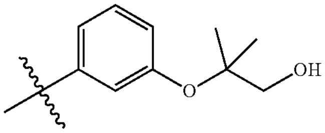 [SMILES: *c1cccc(OC(C)(C)CO)c1] |
| xlvii 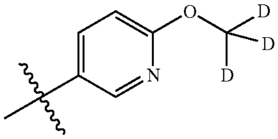 [SMILES: *c1ccc(OC([2H])([2H])[2H])nc1] |
| xlviii 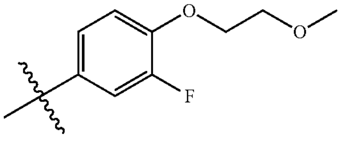 [SMILES: *c1ccc(OCCOC)c(F)c1] |
| xlix 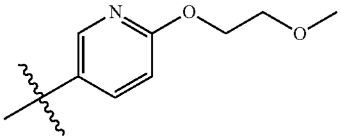 [SMILES: *c1ccc(OCCOC)nc1] |
| l 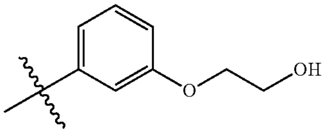 [SMILES: *c1cccc(OCCO)c1] |
TABLE 2-continued
| Ring B Groups |
|---|
| li 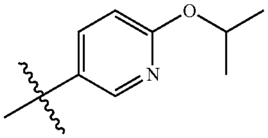 [SMILES: *c1ccc(OC(C)C)nc1] |
| lii 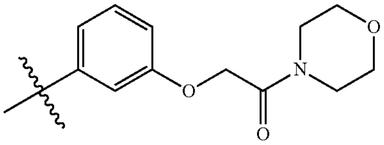 [SMILES: *c1cccc(OCC(=O)N2CCOCC2)c1] |
| liii 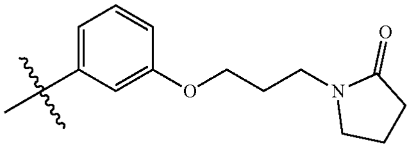 [SMILES: *c1cccc(OCCCN2CCCC2=O)c1] |
| liv 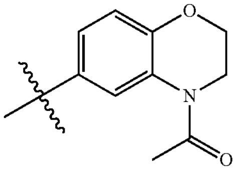 [SMILES: *c1ccc2c(c1)N(C(C)=O)CCO2] |
| lv 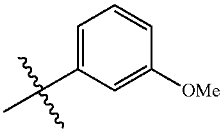 [SMILES: *c1cccc(OC)c1] |
| lvi 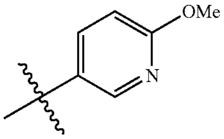 [SMILES: *c1ccc(OC)nc1] |
| lvii 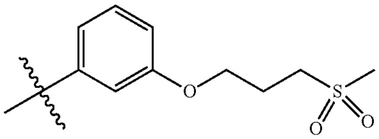 [SMILES: *c1cccc(OCCCS(C)(=O)=O)c1] |
| lviii 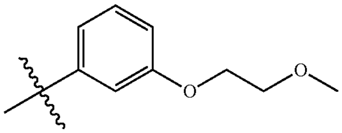 [SMILES: *c1cccc(OCCOC)c1] |
| lix 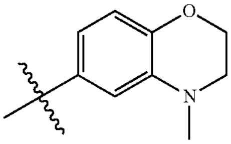 [SMILES: *c1ccc2c(c1)N(C)CCO2] |
| lx 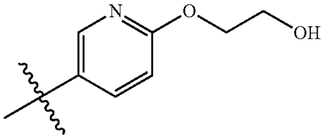 [SMILES: *c1ccc(OCCO)nc1] |

TABLE 2-continued
Ring B Groups
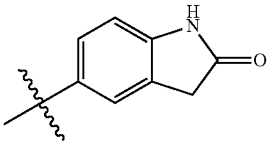 [SMILES: *c1ccc2c(c1)CC(=O)N2]
lxi
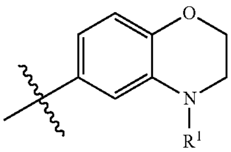
lxii
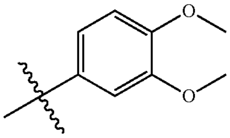 [SMILES: *c1ccc(OC)c(OC)c1]
lxiii
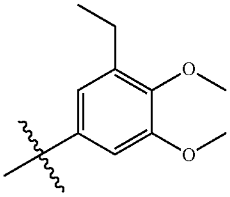 [SMILES: *c1cc(CC)c(OC)c(OC)c1]
lxiv
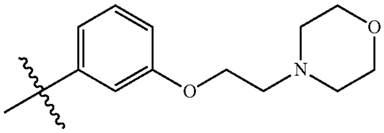 [SMILES: *c1cccc(OCCN2CCOCC2)c1]
lxv
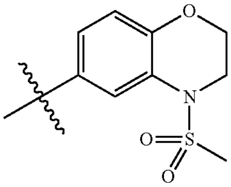 [SMILES: *c1ccc2c(c1)N(S(C)(=O)=O)CCO2]
lxvi
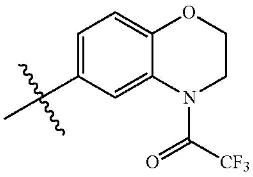 [SMILES: *c1ccc2c(c1)N(C(=O)C(F)(F)F)CCO2]
lxvii
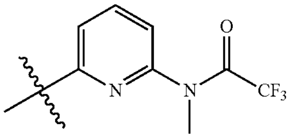 [SMILES: *c1cccc(N(C)C(=O)C(F)(F)F)n1]
lxviii
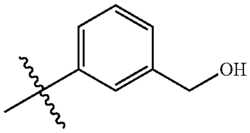 [SMILES: *c1cccc(CO)c1]
lxix
TABLE 2-continued
Ring B Groups
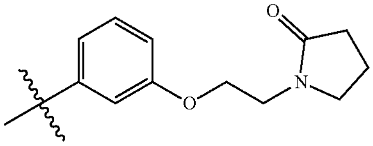 [SMILES: *c1cccc(OCCN2CCCC2=O)c1]
lxx
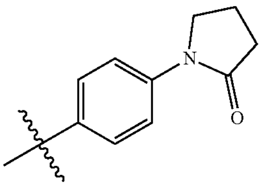 [SMILES: *c1ccc(N2CCCC2=O)cc1]
lxxi
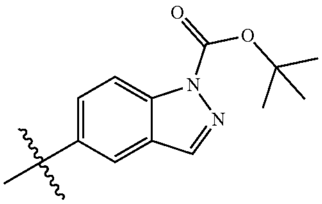 [SMILES: *c1ccc2c(cnn2C(=O)OC(C)(C)C)c1]
lxxii
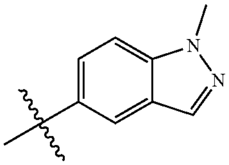 [SMILES: *c1ccc2c(cnn2C)c1]
lxxiii
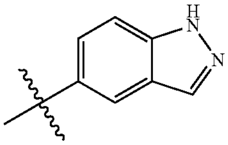 [SMILES: *c1ccc2[nH]ncc2c1]
lxxiv
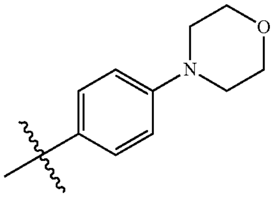 [SMILES: *c1ccc(N2CCOCC2)cc1]
lxxv
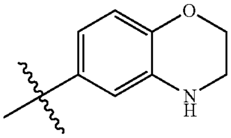 [SMILES: *c1ccc2c(c1)NCCO2]
lxxvi
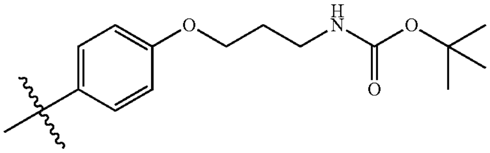 [SMILES: *c1ccc(OCCCNC(=O)OC(C)(C)C)cc1]
lxxvii
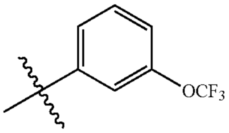 [SMILES: *c1cccc(OC(F)(F)F)c1]
lxxviii TABLE 2-continued
| Ring B Groups | |
|---|---|
| 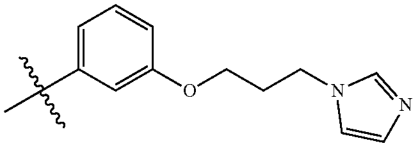 [SMILES: *c1cccc(OCCCn2ccnc2)c1] | lxxix |
| 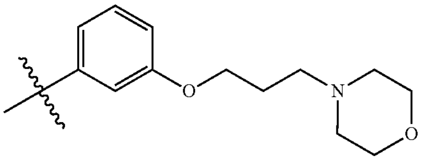 [SMILES: *c1cccc(OCCCN2CCOCC2)c1] | lxxx |
| 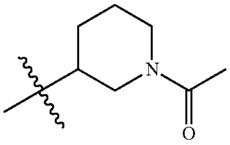 [SMILES: *C1CCCN(C(C)=O)C1] | lxxxi |
| 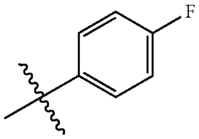 [SMILES: *c1ccc(F)cc1] | lxxxii |
| 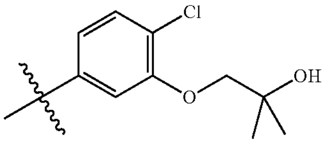 [SMILES: *c1ccc(Cl)c(OCC(C)(C)O)c1] | lxxxiii |
| 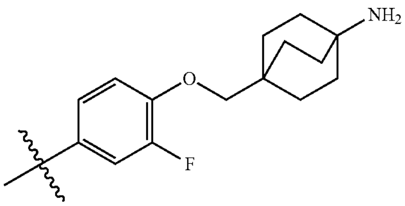 [SMILES: *c1ccc(OCC23CCC(N)(CC2)CC3)c(F)c1] | lxxxiv |
| 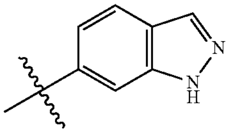 [SMILES: *c1ccc2cn[nH]c2c1] | lxxxv |
| 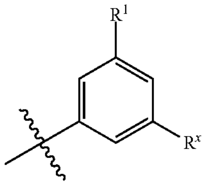 | lxxxvi |
| 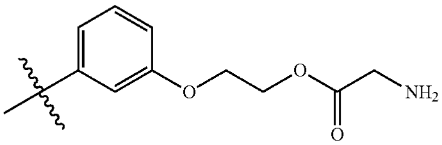 [SMILES: *c1cccc(OCCOC(=O)CN)c1] | lxxxvii |
TABLE 2-continued
| Ring B Groups | |
|---|---|
| 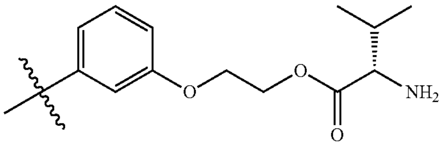 [SMILES: *c1cccc(OCCOC(=O)[C@@H](N)C(C)C)c1] | lxxxviii |
| 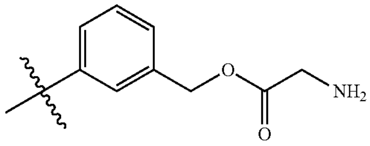 [SMILES: *c1cccc(COC(=O)CN)c1] | lxxxvix |
| 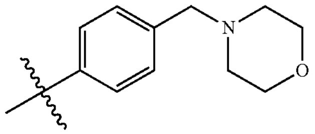 [SMILES: *c1ccc(CN2CCOCC2)cc1] | xc |
| 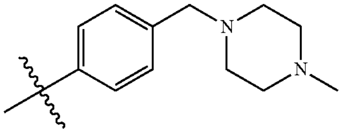 [SMILES: *c1ccc(CN2CCN(C)CC2)cc1] | xci |
| 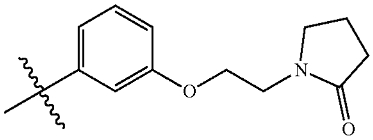 [SMILES: *c1cccc(OCCN2CCCC2=O)c1] | xcii |
| 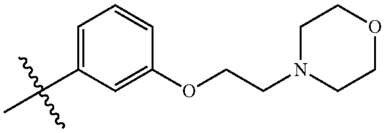 [SMILES: *c1cccc(OCCN2CCOCC2)c1] | xciii |
| 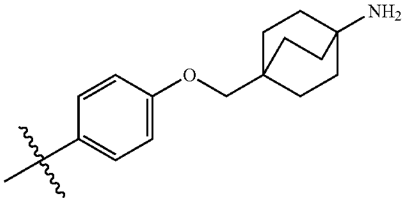 [SMILES: *c1ccc(OCC23CCC(N)(CC2)CC3)cc1] | xciv |
| 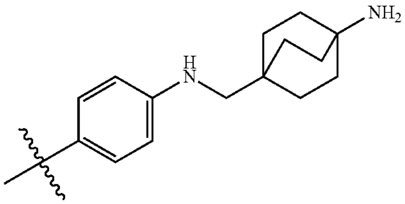 [SMILES: *c1ccc(NCC23CCC(N)(CC2)CC3)cc1] | xcv |
| 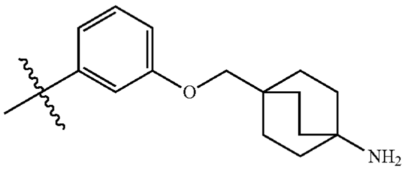 [SMILES: *c1cccc(OCC23CCC(N)(CC2)CC3)c1] | xcvi |

TABLE 2-continued
Ring B Groups
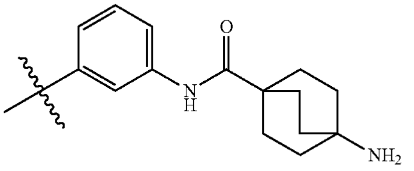 [SMILES: *c1cccc(NC(=O)C23CCC(N)(CC2)CC3)c1]
xcvii
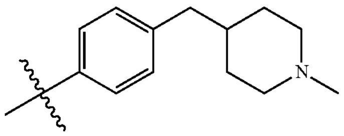 [SMILES: *c1ccc(CC2CCN(C)CC2)cc1]
xcviii
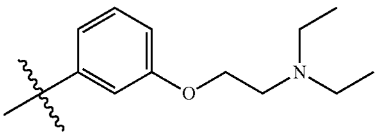 [SMILES: *c1cccc(OCCN(CC)CC)c1]
xcix
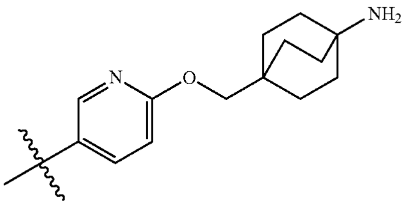 [SMILES: *c1ccc(OCC23CCC(N)(CC2)CC3)nc1]
c
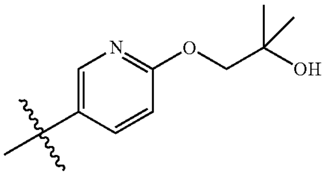 [SMILES: *c1ccc(OCC(C)(C)O)nc1]
ci
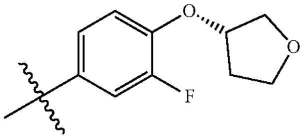
cii
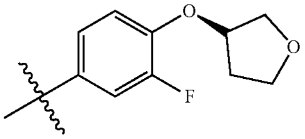
ciii
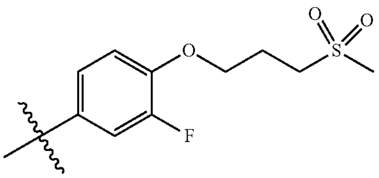 [SMILES: *c1ccc(OCCCS(C)(=O)=O)c(F)c1]
civ
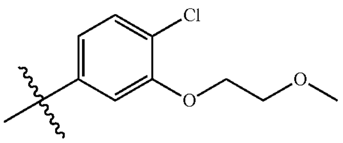 [SMILES: *c1ccc(Cl)c(OCCOC)c1]
cv
TABLE 2-continued
Ring B Groups
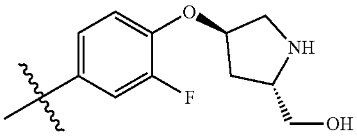 [SMILES: *c1ccc(O[C@H]2CN[C@H](CO)C2)c(F)c1]
cvi
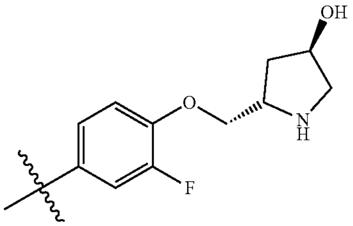
cvii
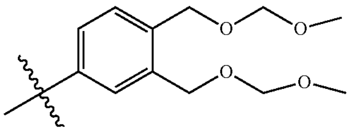 [SMILES: *c1ccc(COCOC)c(COCOC)c1]
cviii
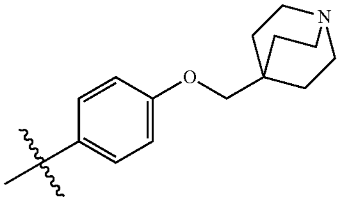 [SMILES: *c1ccc(OCC23CCN(CC2)CC3)cc1]
cix
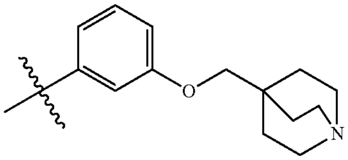 [SMILES: *c1cccc(OCC23CCN(CC2)CC3)c1]
cx
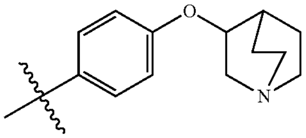 [SMILES: *c1ccc(OC2CN3CCC2CC3)cc1]
cxi
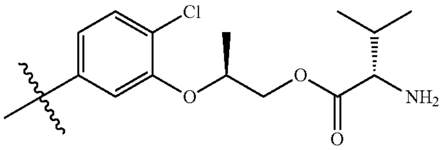 [SMILES: *c1ccc(Cl)c(O[C@@H](C)COC(=O)[C@@H](N)C(C)C)c1]
cxii
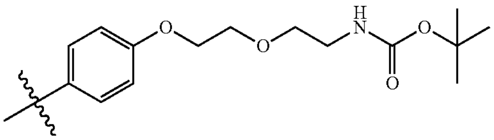 [SMILES: *c1ccc(OCCOCCNC(=O)OC(C)(C)C)cc1]
cxiii
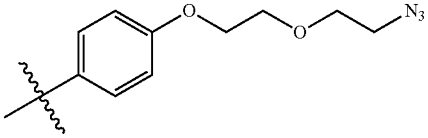 [SMILES: *c1ccc(OCCOCCN=[N+]=[N-])cc1]
cxiv TABLE 2-continued

| Ring B Groups |
| --- |

cxv

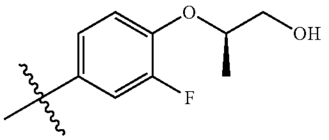 [SMILES: *c1ccc(O[C@H](C)CO)c(F)c1]

cxvi

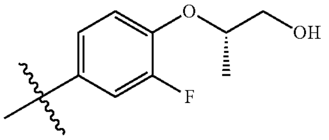 [SMILES: *c1ccc(O[C@@H](C)CO)c(F)c1]

cxvii

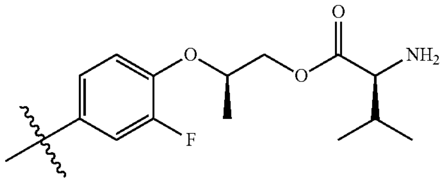 [SMILES: *c1ccc(O[C@H](C)COC(=O)[C@@H](N)C(C)C)c(F)c1]

cxviii

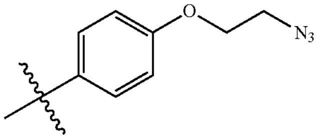 [SMILES: *c1ccc(OCCN=[N+]=[N-])cc1]

cxxix

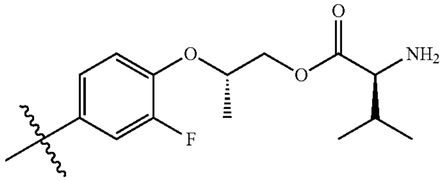 [SMILES: *c1ccc(O[C@@H](C)COC(=O)[C@@H](N)C(C)C)c(F)c1]

cxx

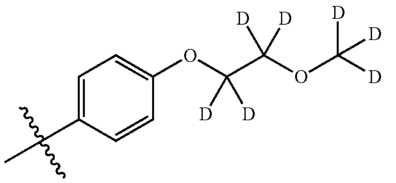 [SMILES: *c1ccc(OC([2H])([2H])C([2H])([2H])OC([2H])([2H])[2H])cc1]

cxxi

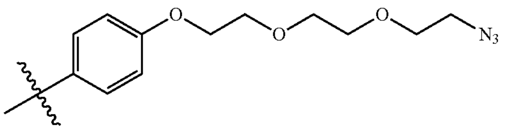

or cxxii

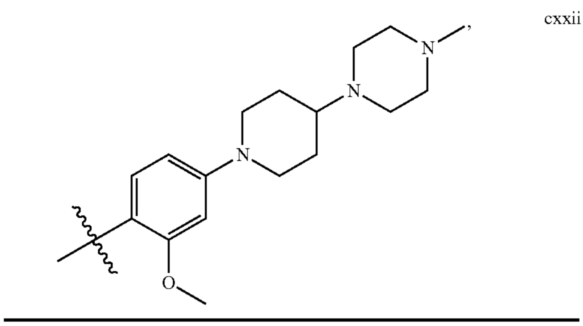

, wherein each $R^1$ and $R^x$ is as defined above and described in classes and subclasses herein.

In certain embodiments, Ring B is selected from i, ii, iii, iv, v, ix, x, xi, xiii, xvi, xvii, xix, xx, xxv, xxvi, xxxii, xxxiv, xxxv, xxxviii, xlii, xlvi, xlviii, l, lviii, lxiv, lxxviii, lxxxiii, lxxxvi, xciv, c, ci, cii, ciii, civ, and cv.

In some embodiments, the m moiety of formula I is 1, 2, 3 or 4. In some embodiments, m is 1. In other embodiments, m is 0.

In some embodiments, the p moiety of formula I is 1, 2, 3 or 4. In some embodiments, p is 1. In other embodiments, p is 0.

As defined generally above, each $R^x$ group of formula I is independently selected from —R, halogen, —OR, —$O(CH_2)_qOR$, —CN, —$NO_2$, —$SO_2R$, —$SO_2N(R)_2$, —SOR, —C(O)R, —$CO_2R$, —$C(O)N(R)_2$, —NRC(O)R, —$NRC(O)NR_2$, —$NRSO_2R$, or —$N(R)_2$, wherein q is 1-4, or $R^x$ and $R^1$ when concurrently present on Ring B are taken together with their intervening atoms to form a 5-7 membered saturated, partially unsaturated, or aryl ring having 0-3 heteroatoms independently selected from nitrogen, oxygen, or sulfur, wherein said ring is substituted with a warhead group and 0-3 groups independently selected from oxo, halogen, CN, or $C_{1-6}$ aliphatic.

In some embodiments, each instance of $R^x$ is independently selected from —R, —OR, —$O(CH_2)_qOR$, or halogen. In certain embodiments, $R^x$ is lower alkyl, lower alkoxy, lower alkoxyalkoxy, or halogen. Exemplary $R^x$ groups include methyl, methoxy, methoxyethoxy and fluoro. In some embodiments, $R^x$ is hydrogen.

As defined generally above, each $R^v$ group of formula I is independently selected from —R, halogen, —OR, —$O(CH_2)_qOR$, —CN, —$NO_2$, —$SO_2R$, —$SO_2N(R)_2$, —SOR, —C(O)R, —$CO_2R$, —$C(O)N(R)_2$, —NRC(O)R, —$NRC(O)NR_2$, —$NRSO_2R$, or —$N(R)_2$, wherein q is 1-4, or $R^v$ and $R^1$ when concurrently present on Ring A are taken together with their intervening atoms to form a 5-7 membered saturated, partially unsaturated, or aryl ring having 0-3 heteroatoms independently selected from nitrogen, oxygen, or sulfur, wherein said ring is substituted with a warhead group and 0-3 groups independently selected from oxo, halogen, CN, or $C_{1-6}$ aliphatic.

In some embodiments, each instance of $R^v$ is independently selected from —R, —OR, —$O(CH_2)_qOR$, or halogen. In certain embodiments, $R^v$ is lower alkyl, lower alkoxy, lower alkoxyalkoxy, or halogen. Exemplary $R^v$ groups include methyl, methoxy, trifluoromethyl, methoxyethoxy, and chloro. In some embodiments, $R^v$ is hydrogen.

In some embodiments, the q moiety is 1, 2, 3, or 4. In certain embodiments, q is 1. In certain other embodiments, q is 2.

As defined generally above, $R^y$ is hydrogen, halogen, —CN, —$CF_3$, $C_{1-4}$ aliphatic, $C_{1-4}$ haloaliphatic, —OR, —C(O)R, or —$C(O)N(R)_2$, where R is as defined above and described herein. In certain embodiments, $R^y$ is hydrogen, halogen, —CN, —$CF_3$, lower alkyl or lower haloalkyl, —C≡CR and cyclopropyl. In other embodiments, $R^y$ is —OR, —C(O)R, or —$C(O)N(R)_2$. In certain embodiments, $R^y$ is —$OCH_3$. In certain other embodiments, $R^y$ is —C(O)$CH_3$. In yet other embodiments, $R^y$ is —C(O)NHR. In some embodiments, $R^y$ is hydrogen. In certain embodiments, $R^y$ is fluorine. In certain other embodiments, $R^y$ is methyl.

As generally defined above, $W^1$ and $W^2$ are each independently a covalent bond or a bivalent $C_{1-3}$ alkylene chain wherein one methylene unit of $W^1$ or $W^2$ is optionally replaced by —$NR^2$—, —$N(R^2)C(O)$—, —$C(O)N(R^2)$—, —$N(R^2)SO_2$—, —$SO_2N(R^2)$—, —O—, —C(O)—, —OC(O)—, —C(O)O—, —S—, —SO— or —$SO_2$—. In certain embodiments, $W^1$ and $W^2$ are the same. In some embodiments, $W^1$ and $W^2$ are different.

In some embodiments, $W^1$ is a covalent bond. In certain embodiments, $W^1$ is a bivalent $C_{1-3}$ alkylene chain wherein one methylene unit of $W^1$ is optionally replaced by $—NR^2—$, $—N(R^2)C(O)—$, $—C(O)N(R^2)—$, $—N(R^2)SO_2—$, $—SO_2N(R^2)—$, —O—, —C(O)—, —OC(O)—, —C(O)O—, —S—, —SO— or $—SO_2—$. In certain embodiments, $W^1$ is —C(=O), $—NR^2—$, —S—, or —O—. In some embodiments, $W^1$ is $—NR^2—$. In other embodiments, $W^1$ is —O—. In certain embodiments, $W^1$ is —NH—, —S—, or —O—. In some embodiments, $W^1$ is $—CH_2O—$, $—CH_2S—$, or $—CH_2NH—$. In some aspects, $W^1$ is $—OCH_2—$, $—SCH_2—$, $—NHCH_2—$, or $—CH_2CH_2—$.

In certain embodiments, $W^2$ is a covalent bond. In some embodiments, $W^2$ is a bivalent $C_{1-3}$ alkylene chain wherein one methylene unit of $W^2$ is optionally replaced by $—NR^2—$, $—N(R^2)C(O)—$, $—C(O)N(R^2)—$, $—N(R^2)SO_2—$, $—SO_2N(R^2)—$, —O—, —C(O)—, —OC(O)—, —C(O)O—, —S—, —SO— or $—SO_2—$. In certain embodiments, $W^2$ is —C(=O), $—NR^2—$, —S—, or —O—. In some embodiments, $W^2$ is $—NR^2—$. In other embodiments, $W^2$ is —O—. In certain embodiments, $W^2$ is —NH—, —S—, or —O—. In some embodiments, $W^2$ is $—CH_2O—$, $—CH_2S—$, or $—CH_2NH—$. In some aspects, $W^2$ is $—OCH_2—$, $—SCH_2—$, $—NHCH_2—$, or $—CH_2CH_2—$.

In some embodiments, Ring B is phenyl, thus forming a compound of formula II-a or II-b:

II-a

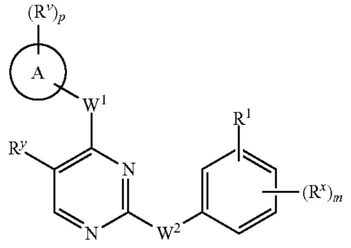

II-b

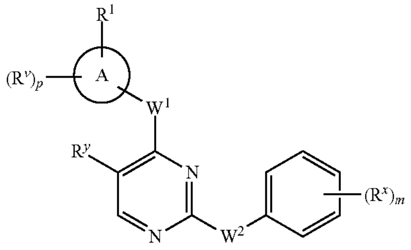

or a pharmaceutically acceptable salt thereof, wherein each of Ring A, m, p, $R^x$, $R^y$, $R^v$, $W^1$, $W^2$, and $R^1$ is as defined above and described in classes and subclasses above and herein.

In certain embodiments, Ring A is phenyl, thus forming a compound of formula III-a or III-b:

III-a

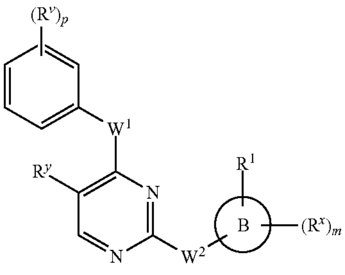

III-b

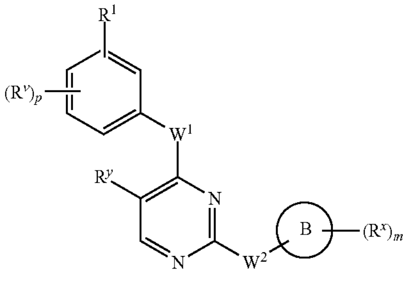

or a pharmaceutically acceptable salt thereof, wherein each of Ring B, m, p, $R^x$, $R^y$, $R^v$, $W^1$, $W^2$, and $R^1$ is as defined above and described in classes and subclasses above and herein.

In certain embodiments, Ring A is phenyl and Ring B is phenyl, thus forming a compound of formula IV-a or IV-b:

IV-a

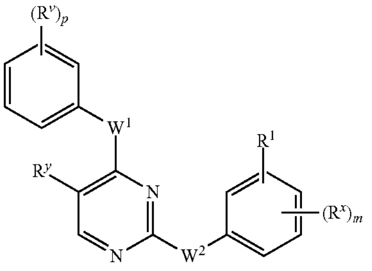

IV-b

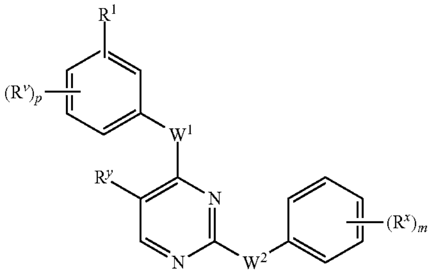

or a pharmaceutically acceptable salt thereof, wherein each of m, p, $R^x$, $R^y$, $R^v$, $W^1$, $W^2$, and $R^1$ is as defined above and described in classes and subclasses above and herein.

As defined generally above, each $R^2$ is independently hydrogen, optionally substituted $C_{1-6}$ aliphatic, or —C(O)R, or $R^2$ and a substituent on Ring A are taken together with their intervening atoms to form a 4-6 membered partially unsaturated or aromatic fused ring, or $R^2$ and $R^y$ are taken together with their intervening atoms to form a 4-6 membered saturated, partially unsaturated, or aromatic fused ring. According to one aspect, $R^2$ is hydrogen. According to another aspect, $R^2$ is —C(O)R, wherein R is an optionally substituted $C_{1-6}$ aliphatic group.

According to some aspects, $R^2$ and a substituent on Ring A are taken together with their intervening atoms to form a 4-7 membered saturated or partially unsaturated ring, thus forming a compound of formula I-a-i or I-b-i:

I-a-i

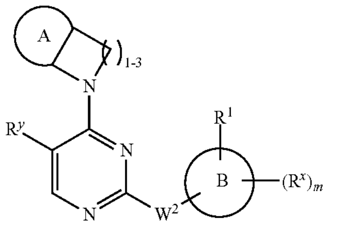

I-b-i

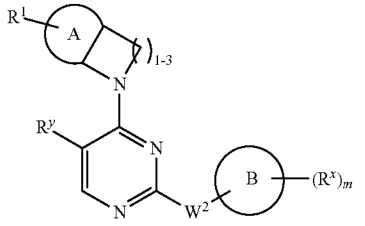

or a pharmaceutically acceptable salt thereof, wherein each of Ring A, $R^1$, $R^x$, and m are as defined above and described in classes and subclasses above and herein.

Similar to the formation of compounds of formulae I-a-i and I-b-i above, it will be understood by one skilled in the art that compounds of formulae II-a, II-b, III-a, III-b, IV-a, and IV-b, will form corresponding compounds II-a-i, II-b-i, III-a-i, III-b-i, IV-a-i, and IV-b-i when $R^2$ and a substituent on Ring A are taken together with their intervening atoms to form a 4-7 membered saturated or partially unsaturated ring.

According to some aspects, $R^2$ and $R^y$ are taken together with their intervening atoms to form a 4-7 partially unsaturated ring, thus forming a compound of formula I-a-ii or I-b-ii:

I-a-ii

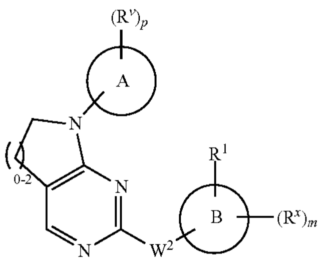

I-b-ii

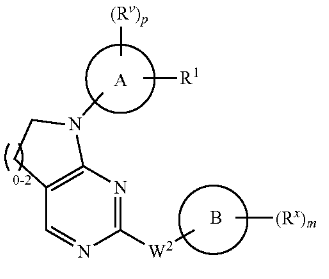

or a pharmaceutically acceptable salt thereof, wherein each of Ring A, $R^1$, $R^x$, and m are as defined above and described in classes and subclasses above and herein.

Similar to the formation of compounds of formulae I-a-ii and I-b-ii above, it will be understood by one skilled in the art that compounds of formulae II-a, II-b, III-a, III-b, IV-a, and IV-b, will form corresponding compounds IV-a-ii, II-b-ii, III-b-ii, IV-a-ii, and IV-b-ii when $R^2$ and $R^y$ are taken together with their intervening atoms to form a 4-7 membered partially unsaturated ring.

As defined generally above, the $R^1$ group of formulae I and II is -L-Y, wherein:

L is a covalent bond or a bivalent $C_{1-8}$ saturated or unsaturated, straight or branched, hydrocarbon chain, wherein one, two, or three methylene units of L are optionally and independently replaced by cyclopropylene, —NR—, —N(R)C(O)—, —C(O)N(R)—, —N(R)$SO_2$—, —$SO_2$N(R)—, —O—, —C(O)—, —OC(O)—, —C(O)O—, —S—, —SO—, —$SO_2$—, —C(═S)—, —C(═NR)—, —N═N—, or —C(═$N_2$)—;

Y is hydrogen, $C_{1-6}$ aliphatic optionally substituted with oxo, halogen, $NO_2$, or CN, or a 3-10 membered monocyclic or bicyclic, saturated, partially unsaturated, or aryl ring having 0-3 heteroatoms independently selected from nitrogen, oxygen, or sulfur, and wherein said ring is substituted with 1-4 $R^e$ groups; and each $R^e$ is independently selected from -Q-Z, oxo, $NO_2$, halogen, CN, a suitable leaving group, or a $C_{1-6}$ aliphatic optionally substituted with oxo, halogen, $NO_2$, or CN, wherein:

Q is a covalent bond or a bivalent $C_{1-6}$ saturated or unsaturated, straight or branched, hydrocarbon chain, wherein one or two methylene units of Q are optionally and independently replaced by —N(R)—, —S—, —O—, —C(O)—, —OC(O)—, —C(O)O—, —SO—, or —$SO_2$—, —N(R)C(O)—, —C(O)N(R)—, —N(R)$SO_2$—, or —$SO_2$N(R)—; and Z is hydrogen or $C_{1-6}$ aliphatic optionally substituted with oxo, halogen, $NO_2$, or CN.

In certain embodiments, L is a covalent bond.

In certain embodiments, L is a bivalent $C_{1-8}$ saturated or unsaturated, straight or branched, hydrocarbon chain. In certain embodiments, L is —$CH_2$—.

In certain embodiments, L is a covalent bond, —$CH_2$—, —NH—, —$CH_2$NH—, —NH$CH_2$—, —NHC(O)—, —NHC(O)$CH_2$OC(O)—, —$CH_2$NHC(O)—, —NH$SO_2$—, —NH$SO_2$$CH_2$—, —NHC(O)$CH_2$OC(O)—, or —$SO_2$NH—.

In some embodiments, L is a bivalent $C_{2-8}$ straight or branched, hydrocarbon chain wherein L has at least one double bond and one or two additional methylene units of L are optionally and independently replaced by —NRC(O)—, —C(O)NR—, —N(R)$SO_2$—, —$SO_2$N(R)—, —S—, —S(O)—, —$SO_2$—, —OC(O)—, —C(O)O—, cyclopropylene, —O—, —N(R)—, or —C(O)—.

In certain embodiments, L is a bivalent $C_{2-8}$ straight or branched, hydrocarbon chain wherein L has at least one double bond and at least one methylene unit of L is replaced by —C(O)—, —NRC(O)—, —C(O)NR—, —N(R)$SO_2$—, —$SO_2$N(R)—, —S—, —S(O)—, —$SO_2$—, —OC(O)—, or —C(O)O—, and one or two additional methylene units of L are optionally and independently replaced by cyclopropylene, —O—, —N(R)—, or —C(O)—.

In some embodiments, L is a bivalent $C_{2-8}$ straight or branched, hydrocarbon chain wherein L has at least one double bond and at least one methylene unit of L is replaced by —C(O)—, and one or two additional methylene units of L are optionally and independently replaced by cyclopropylene, —O—, —N(R)—, or —C(O)—.

As described above, in certain embodiments, L is a bivalent $C_{2-8}$ straight or branched, hydrocarbon chain wherein L has at least one double bond. One of ordinary skill in the art will recognize that such a double bond may exist within the hydrocarbon chain backbone or may be "exo" to the backbone chain and thus forming an alkylidene group. By way of example, such an L group having an alkylidene branched chain includes $—CH_2C(=CH_2)CH_2—$. Thus, in some embodiments, L is a bivalent $C_{2-8}$ straight or branched, hydrocarbon chain wherein L has at least one alkylidenyl double bond. Exemplary L groups include $—NHC(O)C(=CH_2)CH_2—$.

In certain embodiments, L is a bivalent $C_{2-8}$ straight or branched, hydrocarbon chain wherein L has at least one double bond and at least one methylene unit of L is replaced by —C(O)—. In certain embodiments, L is $—C(O)CH=CH(CH_3)—$, $—C(O)CH=CHCH_2NH(CH_3)—$, $—C(O)CH=CH(CH_3)—$, $—C(O)CH=CH—$, $—CH_2C(O)CH=CH—$, $—CH_2C(O)CH=CH(CH_3)—$, $—CH_2CH_2C(O)CH=CH—$, $—CH_2CH_2C(O)CH=CHCH_2—$, $—CH_2CH_2C(O)CH=CHCH_2NH(CH_3)—$, or $—CH_2CH_2C(O)CH=CH(CH_3)—$, or $—CH(CH_3)OC(O)CH=CH—$.

In certain embodiments, L is a bivalent $C_{2-8}$ straight or branched, hydrocarbon chain wherein L has at least one double bond and at least one methylene unit of L is replaced by —OC(O)—.

In some embodiments, L is a bivalent $C_{2-8}$ straight or branched, hydrocarbon chain wherein L has at least one double bond and at least one methylene unit of L is replaced by —NRC(O)—, —C(O)NR—, $—N(R)SO_2—$, $—SO_2N(R)—$, —S—, —S(O)—, $—SO_2—$, —OC(O)—, or —C(O)O—, and one or two additional methylene units of L are optionally and independently replaced by cyclopropylene, —O—, —N(R)—, or —C(O)—. In some embodiments, L is $—CH_2OC(O)CH=CHCH_2—$, $—CH_2—OC(O)CH=CH—$, or $—CH(CH=CH_2)OC(O)CH=CH—$.

In certain embodiments, L is $—NRC(O)CH=CH—$, $—NRC(O)CH=CHCH_2N(CH_3)—$, $—NRC(O)CH=CHCH_2O—$, $—CH_2NRC(O)CH=CH—$, $—NRSO_2CH=CH—$, $—NRSO_2CH=CHCH_2—$, $—NRC(O)(C=N_2)C(O)—$, $—NRC(O)CH=CHCH_2N(CH_3)—$, $—NRSO_2CH=CH—$, $—NRSO_2CH=CHCH_2—$, $—NRC(O)CH=CHCH_2O—$, $—NRC(O)C(=CH_2)CH_2—$, $—CH_2NRC(O)—$, $—CH_2NRC(O)CH=CH—$, $—CH_2CH_2NRC(O)—$, or $—CH_2NRC(O)$cyclopropylene-, wherein each R is independently hydrogen or optionally substituted $C_{1-6}$ aliphatic.

In certain embodiments, L is $—NHC(O)CH=CH—$, $—NHC(O)CH=CHCH_2N(CH_3)—$, $—NHC(O)CH=CHCH_2O—$, $—CH_2NHC(O)CH=CH—$, $—NHSO_2CH=CH—$, $—NHSO_2CH=CHCH_2—$, $—NHC(O)(C=N_2)C(O)—$, $—NHC(O)CH=CHCH_2N(CH_3)—$, $—NHSO_2CH=CH—$, $—NHSO_2CH=CHCH_2—$, $—NHC(O)CH=CHCH_2O—$, $—NHC(O)C(=CH_2)CH_2—$, $—CH_2NHC(O)—$, $—CH_2NHC(O)CH=CH—$, $—CH_2CH_2NHC(O)—$, or $—CH_2NHC(O)$cyclopropylene-.

In some embodiments, L is a bivalent $C_{2-8}$ straight or branched, hydrocarbon chain wherein L has at least one triple bond. In certain embodiments, L is a bivalent $C_{2-8}$ straight or branched, hydrocarbon chain wherein L has at least one triple bond and one or two additional methylene units of L are optionally and independently replaced by —NRC(O)—, —C(O)NR—, —S—, —S(O)—, $—SO_2—$, —C(=S)—, —C(=NR)—, —O—, —N(R)—, or —C(O)—. In some embodiments, L has at least one triple bond and at least one methylene unit of L is replaced by —N(R)—, —N(R)C(O)—, —C(O)—, —C(O)O—, or —OC(O)—, or —O—.

Exemplary L groups include —C≡C—, $—C≡CCH_2N$(isopropyl)-, $—NHC(O)C≡CCH_2CH_2—$, $—CH_2—C≡C—CH_2—$, $—C≡CCH_2O—$, $—CH_2C(O)C≡C—$, —C(O)C≡C—, or $—CH_2OC(=O)C≡C—$.

In certain embodiments, L is a bivalent $C_{2-8}$ straight or branched, hydrocarbon chain wherein one methylene unit of L is replaced by cyclopropylene and one or two additional methylene units of L are independently replaced by —C(O)—, —NRC(O)—, —C(O)NR—, $—N(R)SO_2—$, or $—SO_2N(R)—$. Exemplary L groups include —NHC(O)-cyclopropylene-$SO_2$— and —NHC(O)-cyclopropylene-.

As defined generally above, Y is hydrogen, $C_{1-6}$ aliphatic optionally substituted with oxo, halogen, $NO_2$, or CN, or a 3-10 membered monocyclic or bicyclic, saturated, partially unsaturated, or aryl ring having 0-3 heteroatoms independently selected from nitrogen, oxygen, or sulfur, and wherein said ring is substituted with at 1-4 $R^e$ groups, each $R^e$ is independently selected from -Q-Z, oxo, $NO_2$, halogen, CN, a suitable leaving group, or $C_{1-6}$ aliphatic, wherein Q is a covalent bond or a bivalent $C_{1-6}$ saturated or unsaturated, straight or branched, hydrocarbon chain, wherein one or two methylene units of Q are optionally and independently replaced by —N(R)—, —S—, —O—, —C(O)—, —OC(O)—, —C(O)O—, —SO—, or $—SO_2—$, —N(R)C(O)—, —C(O)N(R)—, $—N(R)SO_2—$, or $—SO_2N(R)—$; and, Z is hydrogen or $C_{1-6}$ aliphatic optionally substituted with oxo, halogen, $NO_2$, or CN.

In certain embodiments, Y is hydrogen.

In certain embodiments, Y is $C_{1-6}$ aliphatic optionally substituted with oxo, halogen, $NO_2$, or CN. In some embodiments, Y is $C_{2-6}$ alkenyl optionally substituted with oxo, halogen, $NO_2$, or CN. In other embodiments, Y is $C_{2-6}$ alkynyl optionally substituted with oxo, halogen, $NO_2$, or CN. In some embodiments, Y is $C_{2-6}$ alkenyl. In other embodiments, Y is $C_{2-4}$ alkynyl.

In other embodiments, Y is $C_{1-6}$ alkyl substituted with oxo, halogen, $NO_2$, or CN. Such Y groups include $—CH_2F$, $—CH_2Cl$, $—CH_2CN$, and $—CH_2NO_2$.

In certain embodiments, Y is a saturated 3-6 membered monocyclic ring having 0-3 heteroatoms independently selected from nitrogen, oxygen, or sulfur, wherein Y is substituted with 1-4 $R^e$ groups, wherein each $R^e$ is as defined above and described herein.

In some embodiments, Y is a saturated 3-4 membered heterocyclic ring having 1 heteroatom selected from oxygen or nitrogen wherein said ring is substituted with 1-2 $R^e$ groups, wherein each $R^e$ is as defined above and described herein. Exemplary such rings are epoxide and oxetane rings, wherein each ring is substituted with 1-2 $R^e$ groups, wherein each $R^e$ is as defined above and described herein.

In other embodiments, Y is a saturated 5-6 membered heterocyclic ring having 1-2 heteroatom selected from oxygen or nitrogen wherein said ring is substituted with 1-4 $R^e$ groups, wherein each $R^e$ is as defined above and described herein. Such rings include piperidine and pyrrolidine, wherein each ring is substituted with 1-4 $R^e$ groups, wherein each $R^e$ is as defined above and described herein. In certain embodiments, Y is

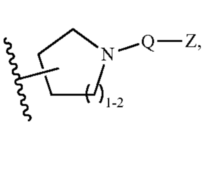 , 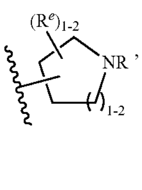 , or 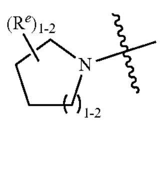 , wherein each R, Q, Z, and $R^e$ is as defined above and described herein.

In some embodiments, Y is a saturated 3-6 membered carbocyclic ring, wherein said ring is substituted with 1-4 $R^e$ groups, wherein each $R^e$ is as defined above and described herein. In certain embodiments, Y is cyclopropyl, cyclobutyl, cyclopentyl, or cyclohexyl, wherein each ring is substituted with 1-4 $R^e$ groups, wherein each $R^e$ is as defined above and described herein. In certain embodiments, Y is

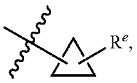

wherein $R^e$ is as defined above and described herein. In certain embodiments, Y is cyclopropyl optionally substituted with halogen, CN or $NO_2$.

In certain embodiments, Y is a partially unsaturated 3-6 membered monocyclic ring having 0-3 heteroatoms independently selected from nitrogen, oxygen, or sulfur, wherein said ring is substituted with 1-4 $R^e$ groups, wherein each $R^e$ is as defined above and described herein.

In some embodiments, Y is a partially unsaturated 3-6 membered carbocyclic ring, wherein said ring is substituted with 1-4 $R^e$ groups, wherein each $R^e$ is as defined above and described herein. In some embodiments, Y is cyclopropenyl, cyclobutenyl, cyclopentenyl, or cyclohexenyl wherein each ring is substituted with 1-4 $R^e$ groups, wherein each $R^e$ is as defined above and described herein. In certain embodiments, Y is

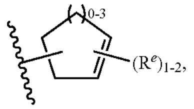

wherein each $R^e$ is as defined above and described herein.

In certain embodiments, Y is a partially unsaturated 4-6 membered heterocyclic ring having 1-2 heteroatoms independently selected from nitrogen, oxygen, or sulfur, wherein said ring is substituted with 1-4 $R^e$ groups, wherein each $R^e$ is as defined above and described herein. In certain embodiments, Y is selected from:

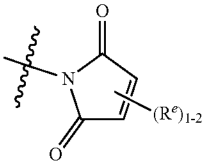
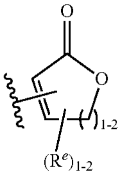
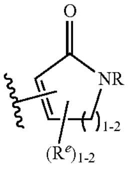
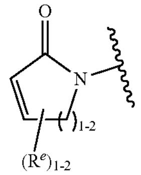

wherein each R and $R^e$ is as defined above and described herein.

In certain embodiments, Y is a 6-membered aromatic ring having 0-2 nitrogens wherein said ring is substituted with 1-4 $R^e$ groups, wherein each $R^e$ group is as defined above and described herein. In certain embodiments, Y is phenyl, pyridyl, or pyrimidinyl, wherein each ring is substituted with 1-4 $R^e$ groups, wherein each $R^e$ is as defined above and described herein.

In some embodiments, Y is selected from:

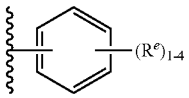
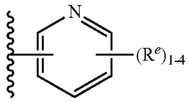
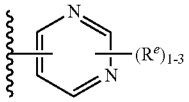
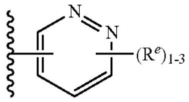
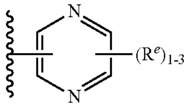

wherein each $R^e$ is as defined above and described herein.

In other embodiments, Y is a 5-membered heteroaryl ring having 1-3 heteroatoms independently selected from nitrogen, oxygen, or sulfur, wherein said ring is substituted with 1-3 $R^e$ groups, wherein each $R^e$ group is as defined above and described herein. In some embodiments, Y is a 5 membered partially unsaturated or aryl ring having 1-3 heteroatoms independently selected from nitrogen, oxygen, and sulfur, wherein said ring is substituted with 1-4 $R^e$ groups, wherein each $R^e$ group is as defined above and described herein. Exemplary such rings are isoxazolyl, oxazolyl, thiazolyl, imidazolyl, pyrazolyl, pyrrolyl, furanyl, thienyl, triazole, thiadiazole, and oxadiazole, wherein each ring is substituted with 1-3 $R^e$ groups, wherein each $R^e$ group is as defined above and described herein. In certain embodiments, Y is selected from:

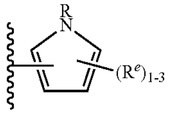
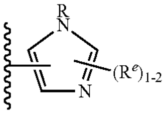
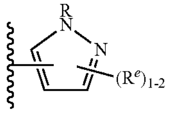
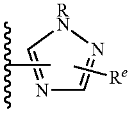
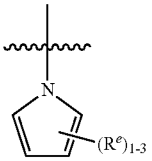
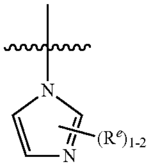
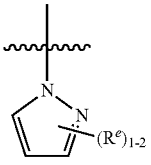
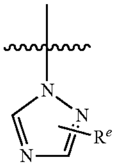
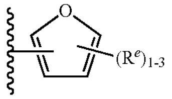
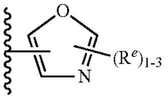
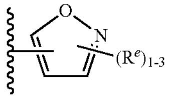
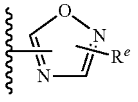
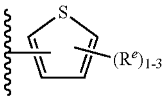

-continued

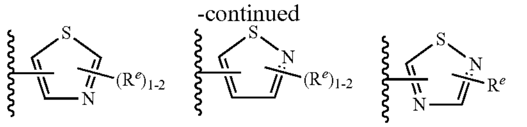

wherein each R and $R^e$ is as defined above and described herein.

In certain embodiments, Y is an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups, wherein $R^e$ is as defined above and described herein. According to another aspect, Y is a 9-10 membered bicyclic, partially unsaturated, or aryl ring having 1-3 heteroatoms independently selected from nitrogen, oxygen, or sulfur, wherein said ring is substituted with 1-4 $R^e$ groups, wherein $R^e$ is as defined above and described herein. Exemplary such bicyclic rings include 2,3-dihydrobenzo[d]isothiazole, wherein said ring is substituted with 1-4 $R^e$ groups, wherein $R^e$ is as defined above and described herein.

As defined generally above, each $R^e$ group is independently selected from -Q-Z, oxo, $NO_2$, halogen, CN, a suitable leaving group, or $C_{1-6}$ aliphatic optionally substituted with oxo, halogen, $NO_2$, or CN, wherein Q is a covalent bond or a bivalent $C_{1-6}$ saturated or unsaturated, straight or branched, hydrocarbon chain, wherein one or two methylene units of Q are optionally and independently replaced by —N(R)—, —S—, —O—, —C(O)—, —OC(O)—, —C(O)O—, —SO—, or —$SO_2$—, —N(R)C(O)—, —C(O)N(R)—, —N(R)$SO_2$—, or —$SO_2$N(R)—; and Z is hydrogen or $C_{1-6}$ aliphatic optionally substituted with oxo, halogen, $NO_2$, or CN.

In certain embodiments, $R^e$ is $C_{1-6}$ aliphatic optionally substituted with oxo, halogen, $NO_2$, or CN. In other embodiments, $R^e$ is oxo, $NO_2$, halogen, or CN.

In some embodiments, $R^e$ is -Q-Z, wherein Q is a covalent bond and Z is hydrogen (i.e., $R^e$ is hydrogen). In other embodiments, $R^e$ is -Q-Z, wherein Q is a bivalent $C_{1-6}$ saturated or unsaturated, straight or branched, hydrocarbon chain, wherein one or two methylene units of Q are optionally and independently replaced by —NR—, —NRC(O)—, —C(O)NR—, —S—, —O—, —C(O)—, —SO—, or —$SO_2$—. In other embodiments, Q is a bivalent $C_{2-6}$ straight or branched, hydrocarbon chain having at least one double bond, wherein one or two methylene units of Q are optionally and independently replaced by —NR—, —NRC(O)—, —C(O)NR—, —S—, —O—, —C(O)—, —SO—, or —$SO_2$—. In certain embodiments, the Z moiety of the $R^e$ group is hydrogen. In some embodiments, -Q-Z is —NHC(O)CH═$CH_2$ or —C(O)CH═$CH_2$.

In certain embodiments, each $R^e$ is independently selected from oxo, $NO_2$, CN, fluoro, chloro, —NHC(O)CH═$CH_2$, —C(O)CH═$CH_2$, —$CH_2$CH═$CH_2$, —C≡CH, —C(O)O$CH_2$Cl, —C(O)O$CH_2$F, —C(O)O$CH_2$CN, —C(O)$CH_2$Cl, —C(O)$CH_2$F, —C(O)$CH_2$CN, or —$CH_2$C(O)$CH_3$.

In certain embodiments, $R^e$ is a suitable leaving group, ie a group that is subject to nucleophilic displacement. A "suitable leaving" is a chemical group that is readily displaced by a desired incoming chemical moiety such as the thiol moiety of a cysteine of interest. Suitable leaving groups are well known in the art, e.g., see, "Advanced Organic Chemistry," Jerry March, 5th Ed., pp. 351-357, John Wiley and Sons, N.Y. Such leaving groups include, but are not limited to, halogen, alkoxy, sulphonyloxy, optionally substituted alkylsulphonyloxy, optionally substituted alkenylsulfonyloxy, optionally substituted arylsulfonyloxy, acyl, and diazonium moieties. Examples of suitable leaving groups include chloro, iodo, bromo, fluoro, acetoxy, methanesulfonyloxy (mesyloxy), tosyloxy, triflyloxy, nitro-phenylsulfonyloxy (nosyloxy), and bromo-phenylsulfonyloxy (brosyloxy).

In certain embodiments, the following embodiments and combinations of -L-Y apply:

(a) L is a bivalent $C_{2-8}$ straight or branched, hydrocarbon chain wherein L has at least one double bond and one or two additional methylene units of L are optionally and independently replaced by —NRC(O)—, —C(O)NR—, —N(R)$SO_2$—, —$SO_2$N(R)—, —S—, —S(O)—, —$SO_2$—, —OC(O)—, —C(O)O—, cyclopropylene, —O—, —N(R)—, or —C(O)—; and Y is hydrogen or $C_{1-6}$ aliphatic optionally substituted with oxo, halogen, $NO_2$, or CN; or (b) L is a bivalent $C_{2-8}$ straight or branched, hydrocarbon chain wherein L has at least one double bond and at least one methylene unit of L is replaced by —C(O)—, —NRC(O)—, —C(O)NR—, —N(R)$SO_2$—, —$SO_2$N(R)—, —S—, —S(O)—, —$SO_2$—, —OC(O)—, or —C(O)O—, and one or two additional methylene units of L are optionally and independently replaced by cyclopropylene, —O—, —N(R)—, or —C(O)—; and Y is hydrogen or $C_{1-6}$ aliphatic optionally substituted with oxo, halogen, $NO_2$, or CN; or (c) L is a bivalent $C_{2-8}$ straight or branched, hydrocarbon chain wherein L has at least one double bond and at least one methylene unit of L is replaced by —C(O)—, and one or two additional methylene units of L are optionally and independently replaced by cyclopropylene, —O—, —N(R)—, or —C(O)—; and Y is hydrogen or $C_{1-6}$ aliphatic optionally substituted with oxo, halogen, $NO_2$, or CN; or (d) L is a bivalent $C_{2-8}$ straight or branched, hydrocarbon chain wherein L has at least one double bond and at least one methylene unit of L is replaced by —C(O)—; and Y is hydrogen or $C_{1-6}$ aliphatic optionally substituted with oxo, halogen, $NO_2$, or CN; or (e) L is a bivalent $C_{2-8}$ straight or branched, hydrocarbon chain wherein L has at least one double bond and at least one methylene unit of L is replaced by —OC(O)—; and Y is hydrogen or $C_{1-6}$ aliphatic optionally substituted with oxo, halogen, $NO_2$, or CN; or (f) L is —NRC(O)CH═CH—, —NRC(O)CH═CH$CH_2$N($CH_3$)—, —NRC(O)CH═CH$CH_2$O—, —$CH_2$NRC(O)CH═CH—, —NR$SO_2$CH═CH—, —NR$SO_2$CH═CH$CH_2$—, —NRC(O)(C═$N_2$)—, —NRC(O)(C═$N_2$)C(O)—, —NRC(O)CH═CH$CH_2$N($CH_3$)—, —NR$SO_2$CH═CH—, —NR$SO_2$CH═CH$CH_2$—, —NRC(O)CH═CH$CH_2$O—, —NRC(O)C(═$CH_2$)$CH_2$—, —$CH_2$NRC(O)—, —$CH_2$NRC(O)CH═CH—, —$CH_2$$CH_2$NRC(O)—, or —$CH_2$NRC(O)cyclopropylene-; wherein R is H or optionally substituted $C_{1-6}$ aliphatic; and Y is hydrogen or $C_{1-6}$ aliphatic optionally substituted with oxo, halogen, $NO_2$, or CN; or (g) L is —NHC(O)CH═CH—, —NHC(O)CH═CH$CH_2$N($CH_3$)—, —NHC(O)CH═CH$CH_2$O—, —$CH_2$NHC(O)CH═CH—, —NH$SO_2$CH═CH—, —NH$SO_2$CH═CH$CH_2$—, —NHC(O)(C═$N_2$)—, —NHC(O)(C═$N_2$)C(O)—, —NHC(O)CH═CH$CH_2$N($CH_3$)—, —NH$SO_2$CH═CH—, —NH$SO_2$CH═CH$CH_2$—, —NHC(O)CH═CH$CH_2$O—, —NHC(O)C(═$CH_2$)

$CH_2$—, —$CH_2NHC(O)$—, —$CH_2NHC(O)CH$═CH—, —$CH_2CH_2NHC(O)$—, or —$CH_2NHC(O)$cyclopropylene-; and Y is hydrogen or $C_{1-6}$ aliphatic optionally substituted with oxo, halogen, $NO_2$, or CN; or (h) L is a bivalent $C_{2-8}$ straight or branched, hydrocarbon chain wherein L has at least one alkylidenyl double bond and at least one methylene unit of L is replaced by —C(O)—, —NRC(O)—, —C(O)NR—, —N(R)$SO_2$—, —$SO_2N(R)$—, —S—, —S(O)—, —$SO_2$—, —OC(O)—, or —C(O)O—, and one or two additional methylene units of L are optionally and independently replaced by cyclopropylene, —O—, —N(R)—, or —C(O)—; and Y is hydrogen or $C_{1-6}$ aliphatic optionally substituted with oxo, halogen, $NO_2$, or CN; or (i) L is a bivalent $C_{2-8}$ straight or branched, hydrocarbon chain wherein L has at least one triple bond and one or two additional methylene units of L are optionally and independently replaced by —NRC(O)—, —C(O)NR—, —N(R)$SO_2$—, —$SO_2N(R)$—, —S—, —S(O)—, —$SO_2$—, —OC(O)—, or —C(O)O—, and Y is hydrogen or $C_{1-6}$ aliphatic optionally substituted with oxo, halogen, $NO_2$, or CN; or (j) L is —C≡C—, —C≡$CCH_2N$(isopropyl)-, —NHC(O)C≡$CH_2CH_2$—, —$CH_2$—C≡$CH_2$—, —C≡$CCH_2O$—, —$CH_2C(O)C$≡C—, —C(O)C≡C—, or —$CH_2OC$(═O)C≡C—; and Y is hydrogen or $C_{1-6}$ aliphatic optionally substituted with oxo, halogen, $NO_2$, or CN; or (k) L is a bivalent $C_{2-8}$ straight or branched, hydrocarbon chain wherein one methylene unit of L is replaced by cyclopropylene and one or two additional methylene units of L are independently replaced by —NRC(O)—, —C(O)NR—, —N(R)$SO_2$—, —$SO_2N(R)$—, —S—, —S(O)—, —$SO_2$—, —OC(O)—, or —C(O)O—; and Y is hydrogen or $C_{1-6}$ aliphatic optionally substituted with oxo, halogen, $NO_2$, or CN; or (l) L is a covalent bond and Y is selected from:

(i) $C_{1-6}$ alkyl substituted with oxo, halogen, $NO_2$, or CN;

(ii) $C_{2-6}$ alkenyl optionally substituted with oxo, halogen, $NO_2$, or CN; or (iii) $C_{2-6}$ alkynyl optionally substituted with oxo, halogen, $NO_2$, or CN; or (iv) a saturated 3-4 membered heterocyclic ring having 1 heteroatom selected from oxygen or nitrogen wherein said ring is substituted with 1-2 $R^e$ groups, wherein each $R^e$ is as defined above and described herein; or (v) a saturated 5-6 membered heterocyclic ring having 1-2 heteroatom selected from oxygen or nitrogen wherein said ring is substituted with 1-4 $R^e$ groups, wherein each $R^e$ is as defined above and described herein; or (vi)

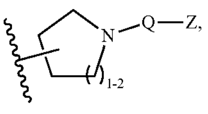

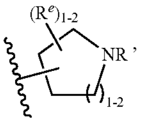

or

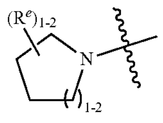

, wherein each R, Q, Z, and $R^e$ is as defined above and described herein; or (vii) a saturated 3-6 membered carbocyclic ring, wherein said ring is substituted with 1-4 $R^e$ groups, wherein each $R^e$ is as defined above and described herein; or (viii) a partially unsaturated 3-6 membered monocyclic ring having 0-3 heteroatoms independently selected from nitrogen, oxygen, or sulfur, wherein said ring is substituted with 1-4 $R^e$ groups, wherein each $R^e$ is as defined above and described herein; or (ix) a partially unsaturated 3-6 membered carbocyclic ring, wherein said ring is substituted with 1-4 $R^e$ groups, wherein each $R^e$ is as defined above and described herein; or (x)

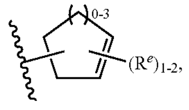

wherein each $R^e$ is as defined above and described herein; or (xi) a partially unsaturated 4-6 membered heterocyclic ring having 1-2 heteroatoms independently selected from nitrogen, oxygen, or sulfur, wherein said ring is substituted with 1-4 $R^e$ groups, wherein each $R^e$ is as defined above and described herein; or (xii)

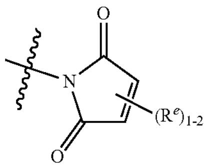

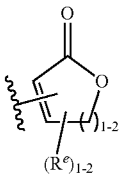

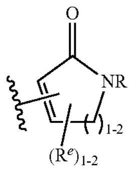

or

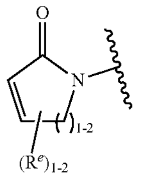

wherein each R and $R^e$ is as defined above and described herein; or (xiii) a 6-membered aromatic ring having 0-2 nitrogens wherein said ring is substituted with 1-4 $R^e$ groups, wherein each $R^e$ group is as defined above and described herein; or (xiv)

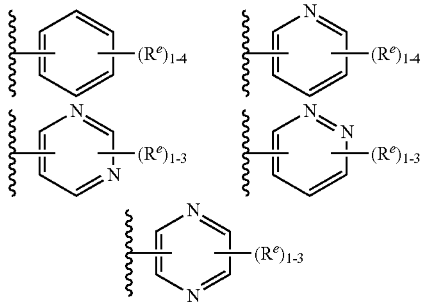

wherein each $R^e$ is as defined above and described herein; or (xv) a 5-membered heteroaryl ring having 1-3 heteroatoms independently selected from nitrogen, oxygen, or sulfur, wherein said ring is substituted with 1-3 $R^e$ groups, wherein each $R^e$ group is as defined above and described herein; or (xvi)

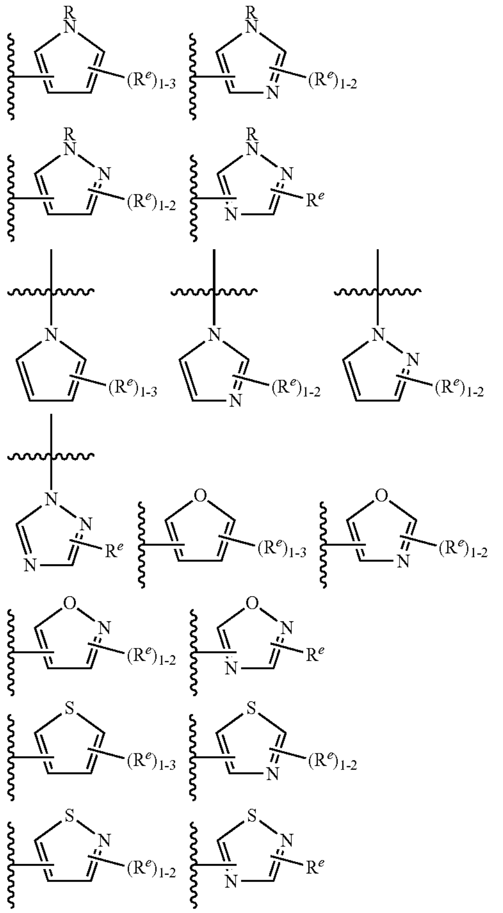

wherein each R and $R^e$ is as defined above and described herein; or (xvii) an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups, wherein $R^e$ is as defined above and described herein;

(m) L is —C(O)— and Y is selected from:

(i) $C_{1-6}$ alkyl substituted with oxo, halogen, $NO_2$, or CN; or (ii) $C_{2-6}$ alkenyl optionally substituted with oxo, halogen, $NO_2$, or CN; or (iii) $C_{2-6}$ alkynyl optionally substituted with oxo, halogen, $NO_2$, or CN; or (iv) a saturated 3-4 membered heterocyclic ring having 1 heteroatom selected from oxygen or nitrogen wherein said ring is substituted with 1-2 $R^e$ groups, wherein each $R^e$ is as defined above and described herein; or (v) a saturated 5-6 membered heterocyclic ring having 1-2 heteroatom selected from oxygen or nitrogen wherein said ring is substituted with 1-4 $R^e$ groups, wherein each $R^e$ is as defined above and described herein; or (vi)

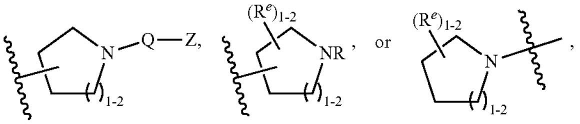

wherein each R, Q, Z, and $R^e$ is as defined above and described herein; or (vii) a saturated 3-6 membered carbocyclic ring, wherein said ring is substituted with 1-4 $R^e$ groups, wherein each $R^e$ is as defined above and described herein; or (viii) a partially unsaturated 3-6 membered monocyclic ring having 0-3 heteroatoms independently selected from nitrogen, oxygen, or sulfur, wherein said ring is substituted with 1-4 $R^e$ groups, wherein each $R^e$ is as defined above and described herein; or (ix) a partially unsaturated 3-6 membered carbocyclic ring, wherein said ring is substituted with 1-4 $R^e$ groups, wherein each $R^e$ is as defined above and described herein; or (x)

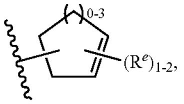

wherein each $R^e$ is as defined above and described herein; or (xi) a partially unsaturated 4-6 membered heterocyclic ring having 1-2 heteroatoms independently selected from nitrogen, oxygen, or sulfur, wherein said ring is substituted with 1-4 $R^e$ groups, wherein each $R^e$ is as defined above and described herein; or (xii)

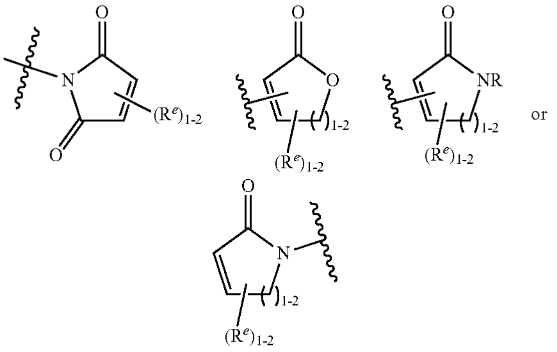

wherein each R and $R^e$ is as defined above and described herein; or (xiii) a 6-membered aromatic ring having 0-2 nitrogens wherein said ring is substituted with 1-4 $R^e$ groups, wherein each $R^e$ group is as defined above and described herein; or (xiv)

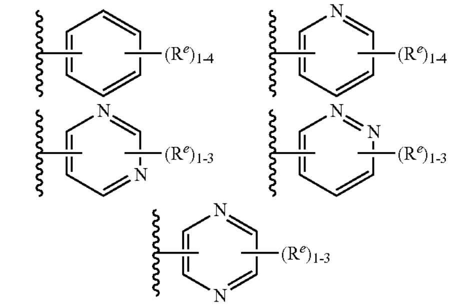

wherein each $R^e$ is as defined above and described herein; or (xv) a 5-membered heteroaryl ring having 1-3 heteroatoms independently selected from nitrogen, oxygen, or sulfur, wherein said ring is substituted with 1-3 $R^e$ groups, wherein each $R^e$ group is as defined above and described herein; or (xvi)

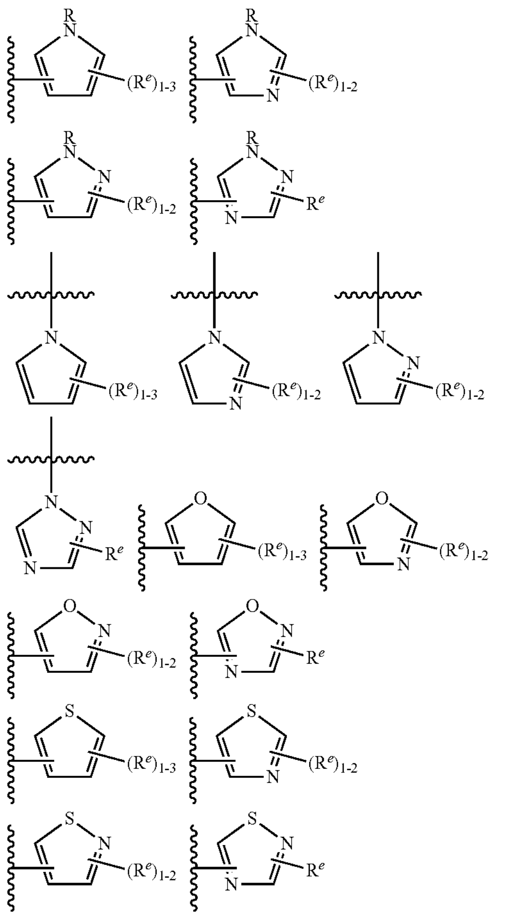

wherein each R and $R^e$ is as defined above and described herein; or (xvii) an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups, wherein $R^e$ is as defined above and described herein;

(n) L is —N(R)C(O)— and Y is selected from:

(i) $C_{1-6}$ alkyl substituted with oxo, halogen, $NO_2$, or CN; or (ii) $C_{2-6}$ alkenyl optionally substituted with oxo, halogen, $NO_2$, or CN; or (iii) $C_{2-6}$ alkynyl optionally substituted with oxo, halogen, $NO_2$, or CN; or (iv) a saturated 3-4 membered heterocyclic ring having 1 heteroatom selected from oxygen or nitrogen wherein said ring is substituted with 1-2 $R^e$ groups, wherein each $R^e$ is as defined above and described herein; or (v) a saturated 5-6 membered heterocyclic ring having 1-2 heteroatom selected from oxygen or nitrogen wherein said ring is substituted with 1-4 $R^e$ groups, wherein each $R^e$ is as defined above and described herein; or (vi)

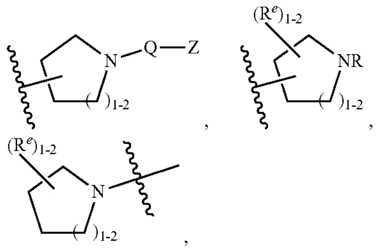

, , or , wherein each R, Q, Z, and $R^e$ is as defined above and described herein; or (vii) a saturated 3-6 membered carbocyclic ring, wherein said ring is substituted with 1-4 $R^e$ groups, wherein each $R^e$ is as defined above and described herein; or (viii) a partially unsaturated 3-6 membered monocyclic ring having 0-3 heteroatoms independently selected from nitrogen, oxygen, or sulfur, wherein said ring is substituted with 1-4 $R^e$ groups, wherein each $R^e$ is as defined above and described herein; or (ix) a partially unsaturated 3-6 membered carbocyclic ring, wherein said ring is substituted with 1-4 $R^e$ groups, wherein each $R^e$ is as defined above and described herein; or (x)

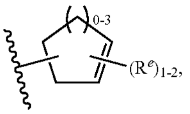

wherein each $R^e$ is as defined above and described herein; or (xi) a partially unsaturated 4-6 membered heterocyclic ring having 1-2 heteroatoms independently selected from nitrogen, oxygen, or sulfur, wherein said ring is substituted with 1-4 $R^e$ groups, wherein each $R^e$ is as defined above and described herein; or (xii)

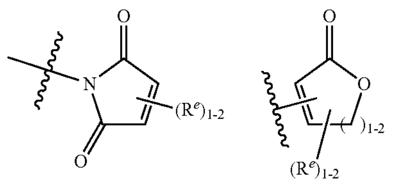

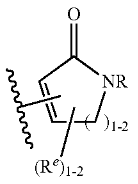

or

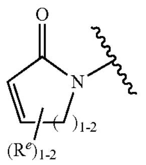

wherein each R and $R^e$ is as defined above and described herein; or (xiii) a 6-membered aromatic ring having 0-2 nitrogens wherein said ring is substituted with 1-4 $R^e$ groups, wherein each $R^e$ group is as defined above and described herein; or (xiv)

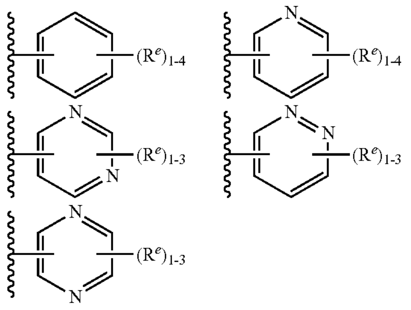

wherein each $R^e$ is as defined above and described herein; or (xv) a 5-membered heteroaryl ring having 1-3 heteroatoms independently selected from nitrogen, oxygen, or sulfur, wherein said ring is substituted with 1-3 $R^e$ groups, wherein each $R^e$ group is as defined above and described herein; or (xvi)

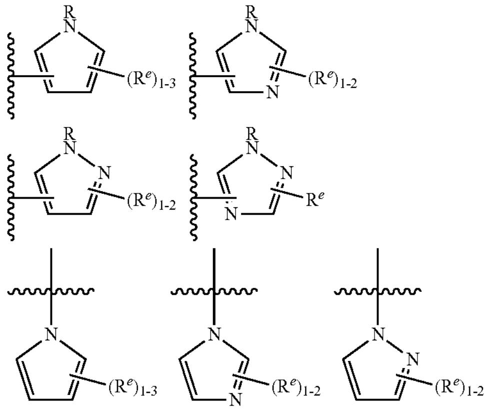

-continued

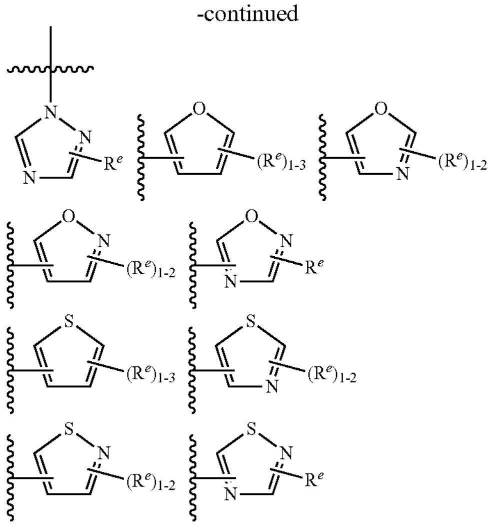

wherein each R and $R^e$ is as defined above and described herein; or (xvii) an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups, wherein $R^e$ is as defined above and described herein;

(o) L is a bivalent $C_{1-8}$ saturated or unsaturated, straight or branched, hydrocarbon chain; and Y is selected from:

(i) $C_{1-6}$ alkyl substituted with oxo, halogen, $NO_2$, or CN;

(ii) $C_{2-6}$ alkenyl optionally substituted with oxo, halogen, $NO_2$, or CN; or (iii) $C_{2-6}$ alkynyl optionally substituted with oxo, halogen, $NO_2$, or CN; or (iv) a saturated 3-4 membered heterocyclic ring having 1 heteroatom selected from oxygen or nitrogen wherein said ring is substituted with 1-2 $R^e$ groups, wherein each $R^e$ is as defined above and described herein; or (v) a saturated 5-6 membered heterocyclic ring having 1-2 heteroatom selected from oxygen or nitrogen wherein said ring is substituted with 1-4 $R^e$ groups, wherein each $R^e$ is as defined above and described herein; or (vi)

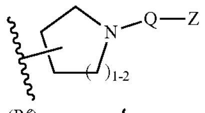

,

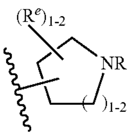

, or

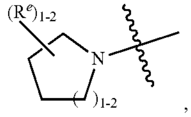

, wherein each R, Q, Z, and $R^e$ is as defined above and described herein; or (vii) a saturated 3-6 membered carbocyclic ring, wherein said ring is substituted with 1-4 $R^e$ groups, wherein each $R^e$ is as defined above and described herein; or (viii) a partially unsaturated 3-6 membered monocyclic ring having 0-3 heteroatoms independently selected from nitrogen, oxygen, or sulfur, wherein said ring is substituted with 1-4 $R^e$ groups, wherein each $R^e$ is as defined above and described herein; or (ix) a partially unsaturated 3-6 membered carbocyclic ring, wherein said ring is substituted with 1-4 $R^e$ groups, wherein each $R^e$ is as defined above and described herein; or (x)

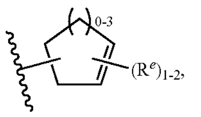

wherein each $R^e$ is as defined above and described herein; or (xi) a partially unsaturated 4-6 membered heterocyclic ring having 1-2 heteroatoms independently selected from nitrogen, oxygen, or sulfur, wherein said ring is substituted with 1-4 $R^e$ groups, wherein each $R^e$ is as defined above and described herein; or (xii)

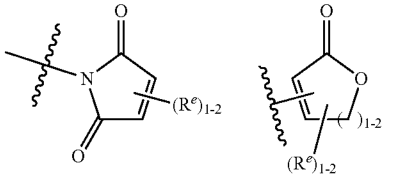

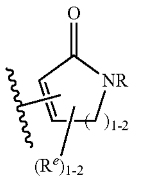

or

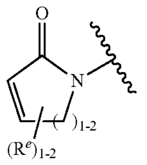

wherein each R and $R^e$ is as defined above and described herein; or (xiii) a 6-membered aromatic ring having 0-2 nitrogens wherein said ring is substituted with 1-4 $R^e$ groups, wherein each $R^e$ group is as defined above and described herein; or (xiv)

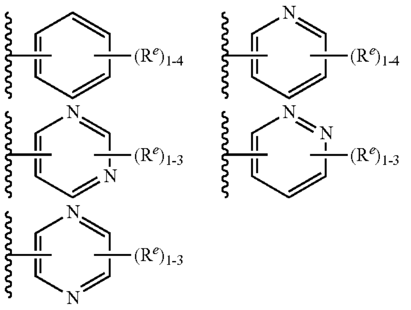

wherein each $R^e$ is as defined above and described herein; or (xv) a 5-membered heteroaryl ring having 1-3 heteroatoms independently selected from nitrogen, oxygen, or sulfur, wherein said ring is substituted with 1-3 $R^e$ groups, wherein each $R^e$ group is as defined above and described herein; or (xvi)

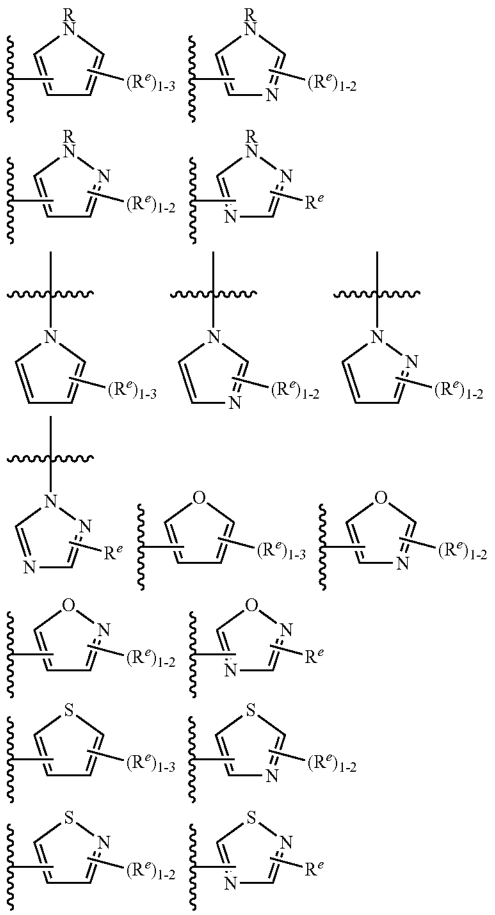

wherein each R and $R^e$ is as defined above and described herein; or (xvii) an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups, wherein $R^e$ is as defined above and described herein;

(p) L is a covalent bond, $—CH_2—$, —NH—, —C(O)—, $—CH_2NH—$, $—NHCH_2—$, —NHC(O)—, $—NHC(O)CH_2OC(O)—$, $—CH_2NHC(O)—$, $—NHSO_2—$, $—NHSO_2CH_2—$, $—NHC(O)CH_2OC(O)—$, or $—SO_2NH—$; and Y is selected from:

(i) $C_{1-6}$ alkyl substituted with oxo, halogen, $NO_2$, or CN; or (ii) $C_{2-6}$ alkenyl optionally substituted with oxo, halogen, $NO_2$, or CN; or (iii) $C_{2-6}$ alkynyl optionally substituted with oxo, halogen, $NO_2$, or CN; or (iv) a saturated 3-4 membered heterocyclic ring having 1 heteroatom selected from oxygen or nitrogen wherein said ring is substituted with 1-2 $R^e$ groups, wherein each $R^e$ is as defined above and described herein; or (v) a saturated 5-6 membered heterocyclic ring having 1-2 heteroatom selected from oxygen or nitrogen wherein said ring is substituted with 1-4 $R^e$ groups, wherein each $R^e$ is as defined above and described herein; or (vi)

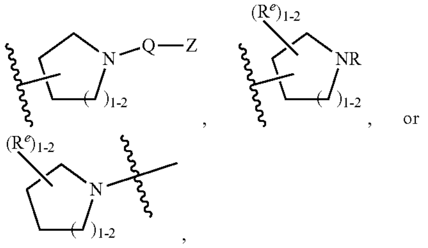

, , or , wherein each R, Q, Z, and $R^e$ is as defined above and described herein; or (vii) a saturated 3-6 membered carbocyclic ring, wherein said ring is substituted with 1-4 $R^e$ groups, wherein each $R^e$ is as defined above and described herein; or (viii) a partially unsaturated 3-6 membered monocyclic ring having 0-3 heteroatoms independently selected from nitrogen, oxygen, or sulfur, wherein said ring is substituted with 1-4 $R^e$ groups, wherein each $R^e$ is as defined above and described herein; or (ix) a partially unsaturated 3-6 membered carbocyclic ring, wherein said ring is substituted with 1-4 $R^e$ groups, wherein each $R^e$ is as defined above and described herein; or (x)

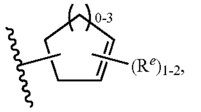

wherein each $R^e$ is as defined above and described herein; or (xi) a partially unsaturated 4-6 membered heterocyclic ring having 1-2 heteroatoms independently selected from nitrogen, oxygen, or sulfur, wherein said ring is substituted with 1-4 $R^e$ groups, wherein each $R^e$ is as defined above and described herein; or (xii)

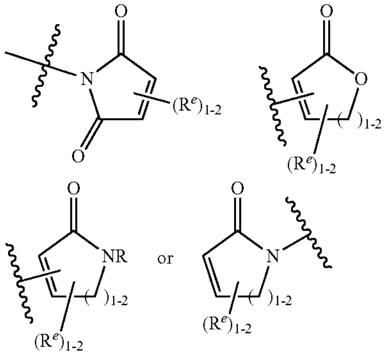

or wherein each R and $R^e$ is as defined above and described herein; or (xiii) a 6-membered aromatic ring having 0-2 nitrogens wherein said ring is substituted with 1-4 $R^e$ groups, wherein each $R^e$ group is as defined above and described herein; or (xiv)

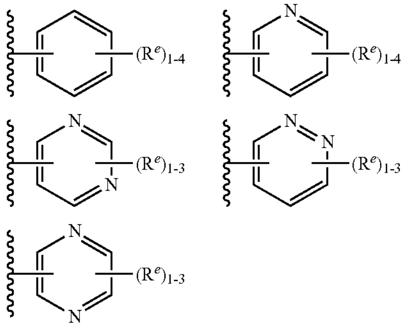

wherein each $R^e$ is as defined above and described herein; or (xv) a 5-membered heteroaryl ring having 1-3 heteroatoms independently selected from nitrogen, oxygen, or sulfur, wherein said ring is substituted with 1-3 $R^e$ groups, wherein each $R^e$ group is as defined above and described herein; or (xvi)

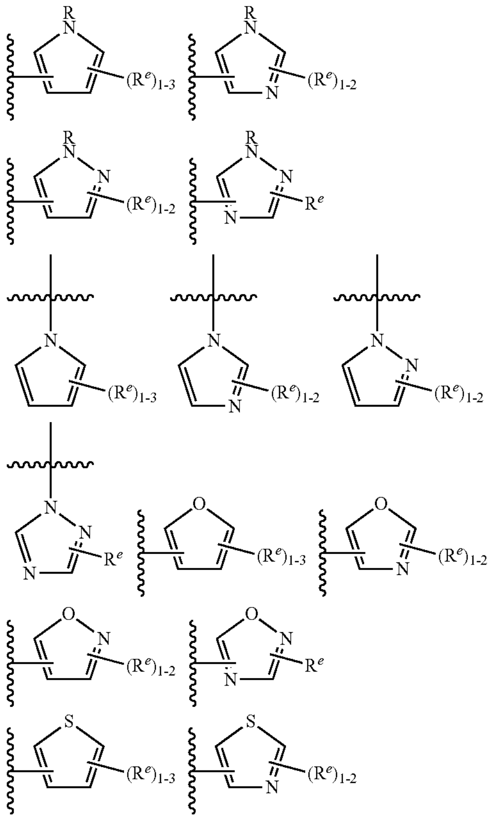

-continued

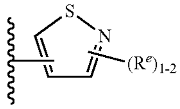 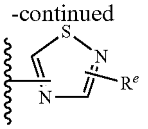

wherein each R and $R^e$ is as defined above and described herein; or (xvii) an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups, wherein $R^e$ is as defined above and described herein.

In certain embodiments, the Y group of formula Ia or Ib is selected from those set forth in Table 3, below, wherein each wavy line indicates the point of attachment to the rest of the molecule.

TABLE 3

| Exemplary Y groups: | |
|---|---|
| 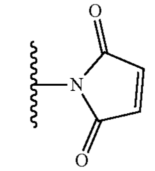 [SMILES: *N1C(=O)C=CC1=O] | a |
| 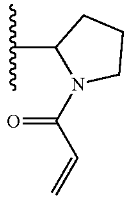 [SMILES: *C1CCCN1C(=O)C=C] | b |
| 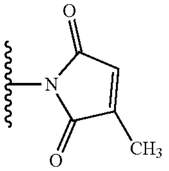 [SMILES: *N1C(=O)C=C(C)C1=O] | c |
| 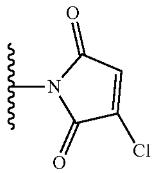 [SMILES: *N1C(=O)C=C(Cl)C1=O] | d |
| 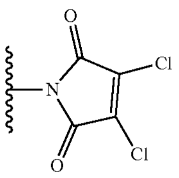 [SMILES: *N1C(=O)C(Cl)=C(Cl)C1=O] | e |
| 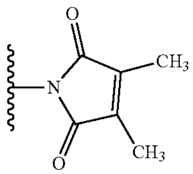 [SMILES: *N1C(=O)C(C)=C(C)C1=O] | f |

TABLE 3-continued

| Exemplary Y groups: | |
|---|---|
| 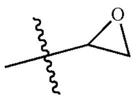 [SMILES: *C1CO1] | g |
| 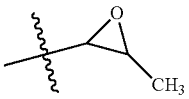 | h |
| 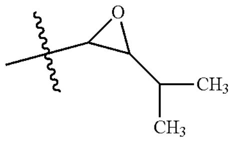 | i |
| 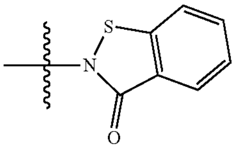 [SMILES: *n1sc2ccccc2c1=O] | j |
| 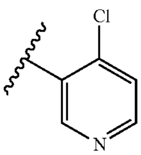 [SMILES: *c1cnccc1Cl] | k |
| 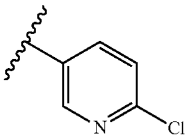 [SMILES: *c1ccc(Cl)nc1] | l |
| 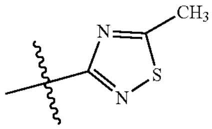 [SMILES: *c1nsc(C)n1] | m |
| 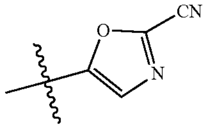 [SMILES: *c1cnc(C#N)o1] | n |
| 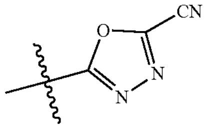 [SMILES: *c1nnc(C#N)o1] | o |
| 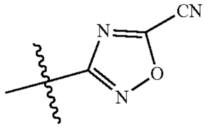 [SMILES: *c1noc(C#N)n1] | p |
| 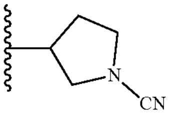 [SMILES: *C1CCN(C#N)C1] | q |

TABLE 3-continued
| Exemplary Y groups: | |
|---|---|
| 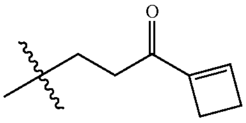 [SMILES: *CCC(=O)C1=CCC1] | r |
| 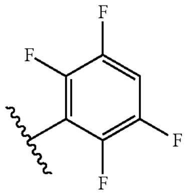 [SMILES: *c1c(F)c(F)cc(F)c1F] | s |
| 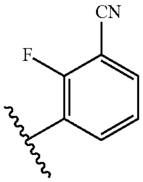 [SMILES: *c1cccc(C#N)c1F] | t |
| 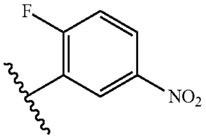 | u |
| 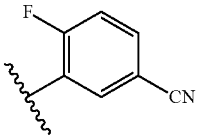 [SMILES: *c1cc(C#N)ccc1F] | v |
| 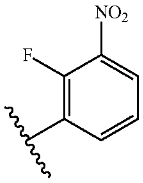 [SMILES: *c1cccc([N+](=O)[O-])c1F] | w |
| 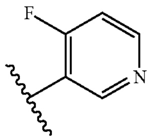 [SMILES: *c1cnccc1F] | x |
| 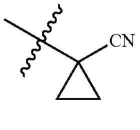 [SMILES: *C1(C#N)CC1] | y |
| 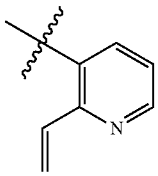 [SMILES: *c1cccnc1C=C] | z |
TABLE 3-continued
| Exemplary Y groups: | |
|---|---|
| 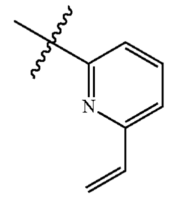 [SMILES: *c1cccc(C=C)n1] | aa |
| 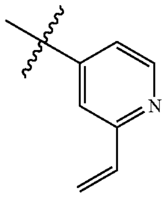 [SMILES: *c1ccnc(C=C)c1] | bb |
| 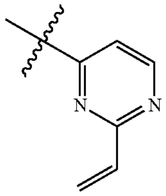 [SMILES: *c1ccnc(C=C)n1] | cc |
| 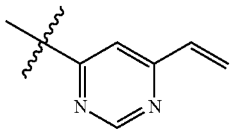 [SMILES: *c1cc(C=C)ncn1] | dd |
| 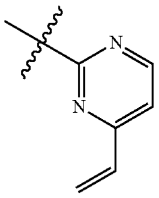 [SMILES: *c1nccc(C=C)n1] | ee |
| 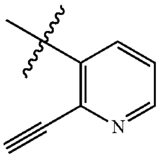 [SMILES: *c1cccnc1C#C] | ff |
| 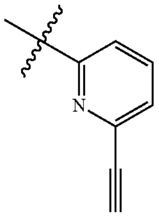 [SMILES: *c1cccc(C#C)n1] | gg |
| 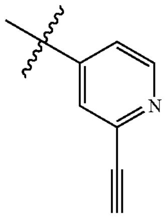 [SMILES: *c1ccnc(C#C)c1] | hh |

TABLE 3-continued
Exemplary Y groups:
ii
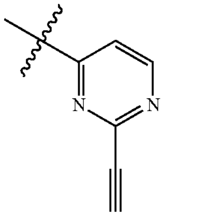 [SMILES: *c1ccnc(C#C)n1]
jj
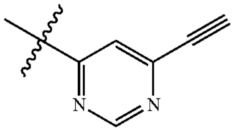 [SMILES: *c1cc(C#C)ncn1]
kk
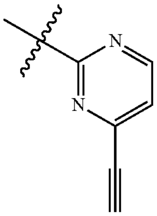 [SMILES: *c1nccc(C#C)n1]
ll
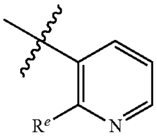
mm
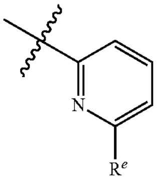
nn
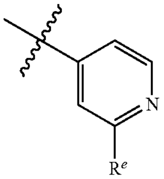
oo
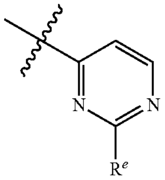
pp
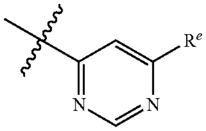
TABLE 3-continued
Exemplary Y groups:
qq
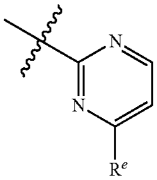
rr
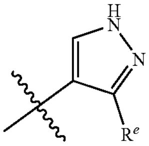
ss
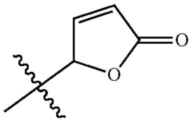
tt
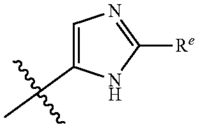
uu
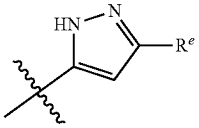
vv
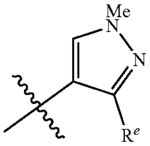
ww
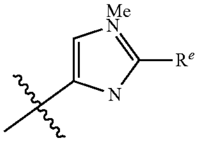
xx
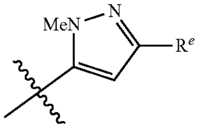
yy
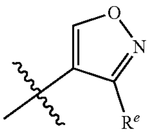
zz
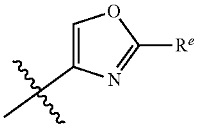

TABLE 3-continued
| Exemplary Y groups: | |
|---|---|
| 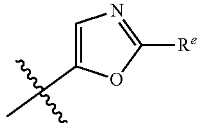 | aaa |
| 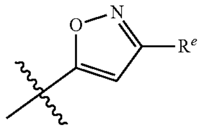 | bbb |
| 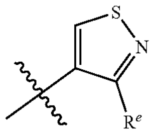 | ccc |
| 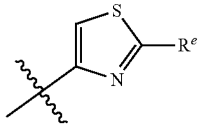 | ddd |
| 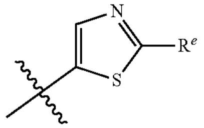 | eee |
| 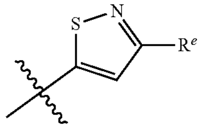 | fff |
| 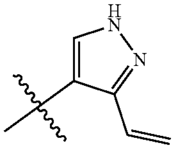 [SMILES: *c1c[nH]nc1C=C] | ggg |
| 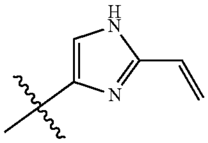 [SMILES: *c1c[nH]c(C=C)n1] | hhh |
| 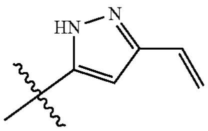 [SMILES: *c1cc(C=C)n[nH]1] | iii |
| 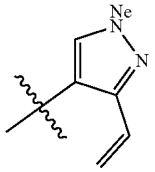 | jjj |
TABLE 3-continued
| Exemplary Y groups: | |
|---|---|
| 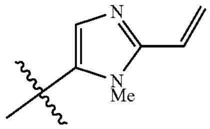 [SMILES: *c1cnc(C=C)n1C] | kkk |
| 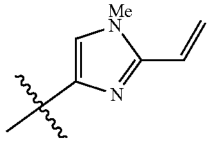 [SMILES: *c1cn(C)c(C=C)n1] | lll |
| 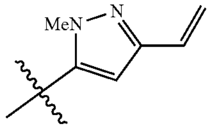 [SMILES: *c1cc(C=C)nn1C] | mmm |
| 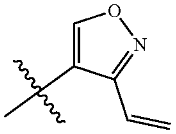 [SMILES: *c1conc1C=C] | nnn |
| 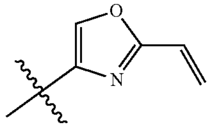 [SMILES: *c1coc(C=C)n1] | ooo |
| 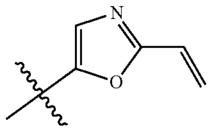 [SMILES: *c1cnc(C=C)o1] | ppp |
| 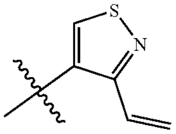 [SMILES: *c1csnc1C=C] | qqq |
| 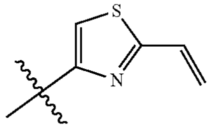 [SMILES: *c1csc(C=C)n1] | rrr |
| 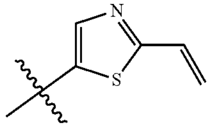 [SMILES: *c1cnc(C=C)s1] | sss |
| 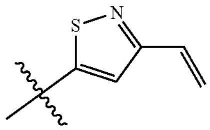 [SMILES: *c1cc(C=C)ns1] | ttt |

TABLE 3-continued
| Exemplary Y groups: | |
|---|---|
| 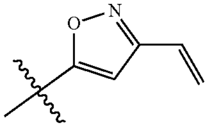 | uuu |
| 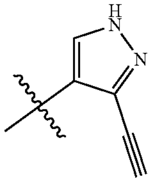 [SMILES: *c1c[nH]nc1C#C] | vvv |
| 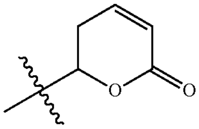 [SMILES: *C1CC=CC(=O)O1] | qqq |
| 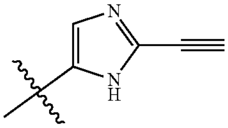 | www |
| 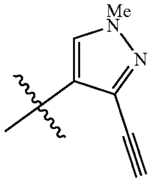 [SMILES: *c1cn(C)nc1C#C] | xxx |
| 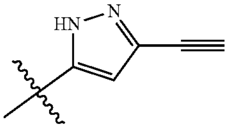 [SMILES: *c1cc(C#C)n[nH]1] | yyy |
| 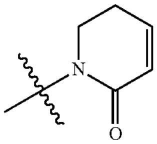 [SMILES: *N1CCC=CC1=O] | zzz |
| 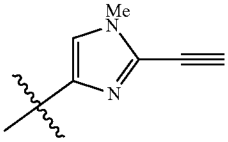 [SMILES: *c1cn(C)c(C#C)n1] | aaaa |
| 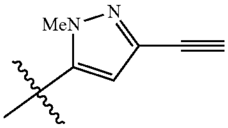 [SMILES: *c1cc(C#C)nn1C] | bbbb |
| 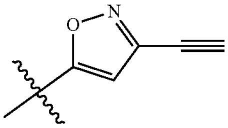 [SMILES: *c1cc(C#C)no1] | cccc |
TABLE 3-continued
| Exemplary Y groups: | |
|---|---|
| 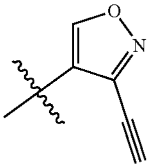 [SMILES: *c1conc1C#C] | dddd |
| 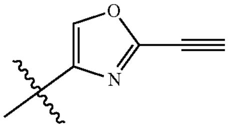 | eeee |
| 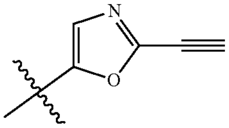 [SMILES: *c1cnc(C#C)o1] | ffff |
| 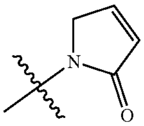 [SMILES: *N1CC=CC1=O] | gggg |
| 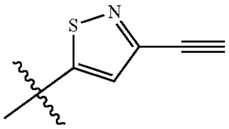 [SMILES: *c1cc(C#C)ns1] | hhhh |
| 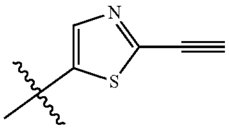 | iiii |
| 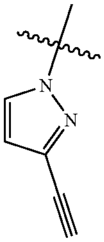 [SMILES: *n1ccc(C#C)n1] | jjjj |
| 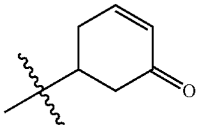 [SMILES: *C1CC=CC(=O)C1] | kkkk |
| 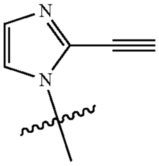 | llll |

TABLE 3-continued

| Exemplary Y groups: | |
|---|---|
| 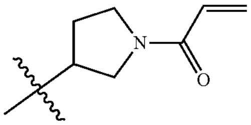 [SMILES: *C1CCN(C(=O)C=C)C1] | mmmmm |
| 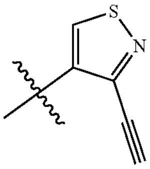 [SMILES: *c1csnc1C#C] | nnnn |
| 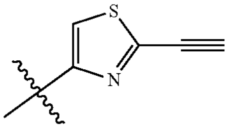 | oooo |
| 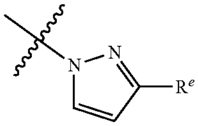 | pppp |
| 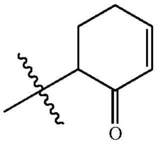 [SMILES: *C1CCC=CC1=O] | qqqq |
| 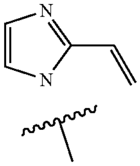 | rrrr |
| 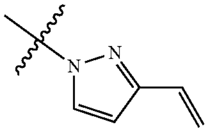 [SMILES: *n1ccc(C=C)n1] | ssss |
| 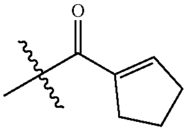 [SMILES: *C(=O)C1=CCCC1] | tttt |
| 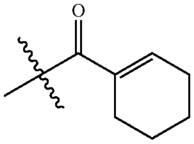 [SMILES: *C(=O)C1=CCCCC1] | uuuu |
| 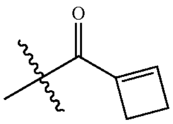 [SMILES: *C(=O)C1=CCC1] | vvvv |
| 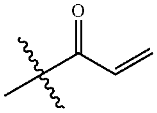 [SMILES: *C(=O)C=C] | wwww |
| 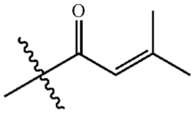 [SMILES: *C(=O)C=C(C)C] | xxxx |
| 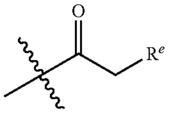 | yyyy |
| 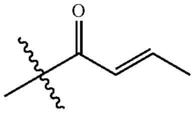 [SMILES: *C(=O)/C=C/C] | zzzz |
| 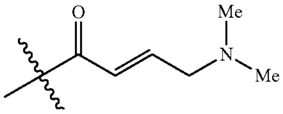 [SMILES: *C(=O)/C=C/CN(C)C] | aaaaa |
| 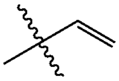 [SMILES: *C=C] | bbbbb |
| 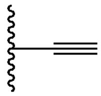 | ccccc |
| 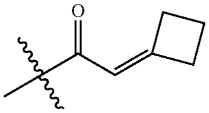 [SMILES: *C(=O)C=C1CCC1] | ddddd |

wherein each $R^e$ is independently a suitable leaving group, $NO_2$, CN, or oxo.

In certain embodiments, $R^1$ is $-C \equiv CH$, $-C \equiv CCH_2NH$(isopropyl), $-NHC(O)C \equiv CCH_2CH_3$, $-CH_2-C \equiv C-CH_3$, $-C \equiv CCH_2OH$, $-CH_2C(O)C \equiv CH$, $-C(O)C \equiv CH$, or $-CH_2OC(=O)C \equiv CH$. In some embodiments, $R^1$ is selected from $-NHC(O)CH=CH_2$, $-NHC(O)CH=CHCH_2N(CH_3)_2$, or $-CH_2NHC(O)CH=CH_2$.

In certain embodiments, $R^1$ is selected from those set forth in Table 4, below, wherein each wavy line indicates the point of attachment to the rest of the molecule.

TABLE 4

| Exemplary $R^1$ Groups | |
|---|---|
| 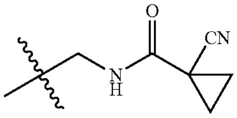 [SMILES: *CNC(=O)C1(C#N)CC1] | a |

TABLE 4-continued
| Exemplary $R^1$ Groups | |
|---|---|
| 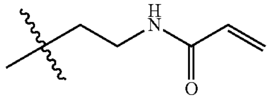 [SMILES: *CCNC(=O)C=C] | b |
| 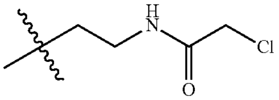 [SMILES: *CCNC(=O)CCl] | c |
| 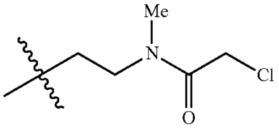 [SMILES: *CCN(C)C(=O)CCl] | d |
| 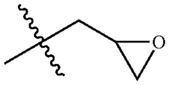 [SMILES: *CC1CO1] | e |
| 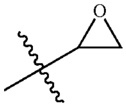 [SMILES: *C1CO1] | f |
| 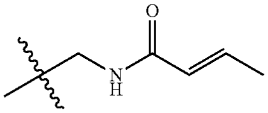 [SMILES: *CNC(=O)/C=C/C] | g |
| 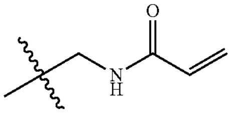 [SMILES: *CNC(=O)C=C] | h |
| 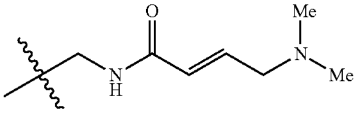 [SMILES: *CNC(=O)/C=C/CN(C)C] | i |
| 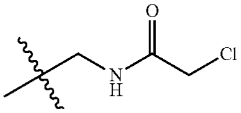 [SMILES: *CNC(=O)CCl] | j |
| 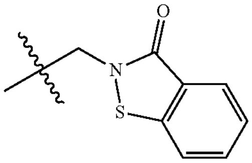 [SMILES: *Cn1sc2ccccc2c1=O] | k |
| 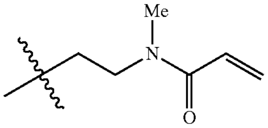 [SMILES: *CCN(C)C(=O)C=C] | l |
| 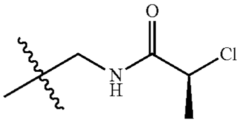 [SMILES: *CNC(=O)[C@H](C)Cl] | m |
TABLE 4-continued
| Exemplary $R^1$ Groups | |
|---|---|
| 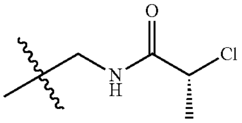 [SMILES: *CNC(=O)[C@@H](C)Cl] | n |
| 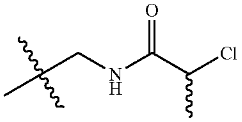 [SMILES: *CNC(=O)C(C)Cl] | o |
| 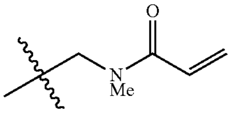 [SMILES: *CN(C)C(=O)C=C] | p |
| 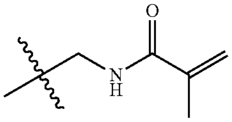 [SMILES: *CNC(=O)C(=C)C] | q |
| 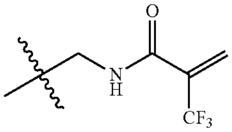 [SMILES: *CNC(=O)C(=C)C(F)(F)F] | r |
| 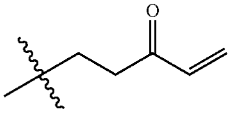 [SMILES: *CCC(=O)C=C] | s |
| 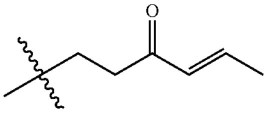 [SMILES: *CCC(=O)/C=C/C] | t |
| 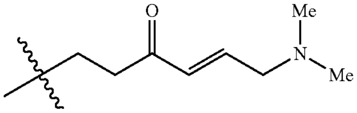 [SMILES: *CCC(=O)/C=C/CN(C)C] | u |
| 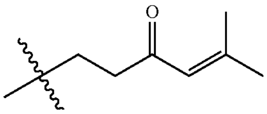 [SMILES: *CCC(=O)C=C(C)C] | v |
| 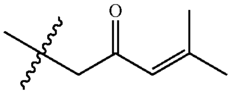 [SMILES: *CC(=O)C=C(C)C] | w |
| 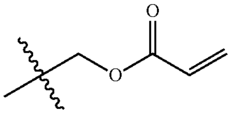 [SMILES: *COC(=O)C=C] | x |
| 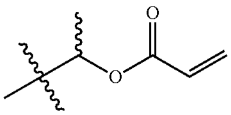 [SMILES: *C(C)OC(=O)C=C] | y |

TABLE 4-continued
Exemplary R[1] Groups
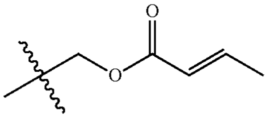 [SMILES: *COC(=O)/C=C/C]
z
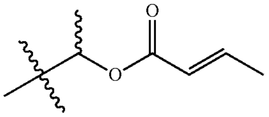 [SMILES: *C(C)OC(=O)/C=C/C]
aa
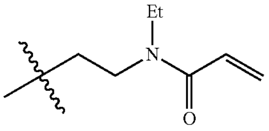 [SMILES: *CCN(CC)C(=O)C=C]
bb
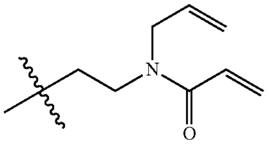 [SMILES: *CCN(CC=C)C(=O)C=C]
cc
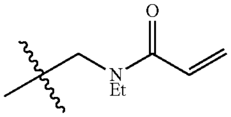
dd
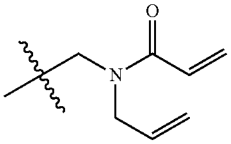 [SMILES: *CN(CC=C)C(=O)C=C]
ee
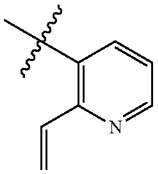 [SMILES: *c1cccnc1C=C]
ff
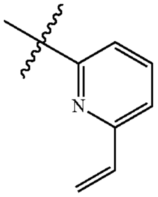 [SMILES: *c1cccc(C=C)n1]
gg
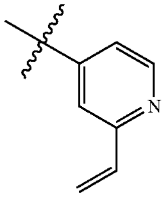 [SMILES: *c1ccnc(C=C)c1]
hh
TABLE 4-continued
Exemplary R[1] Groups
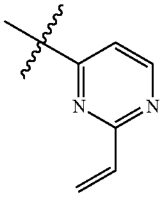 [SMILES: *c1ccnc(C=C)n1]
ii
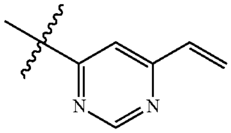 [SMILES: *c1cc(C=C)ncn1]
jj
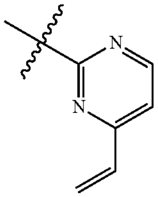 [SMILES: *c1nccc(C=C)n1]
kk
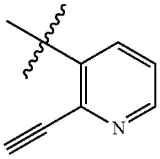 [SMILES: *c1cccnc1C#C]
ll
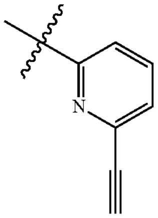 [SMILES: *c1cccc(C#C)n1]
mm
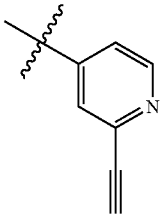 [SMILES: *c1ccnc(C#C)c1]
nn
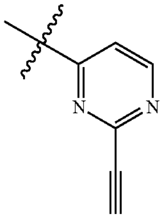 [SMILES: *c1ccnc(C#C)n1]
oo
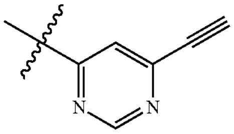 [SMILES: *c1cc(C#C)ncn1]
pp TABLE 4-continued
Exemplary R[1] Groups
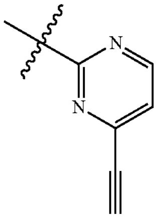 [SMILES: *c1nccc(C#C)n1]
qq
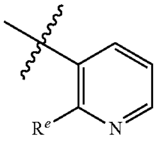
rr
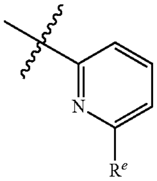
ss
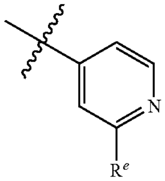
tt
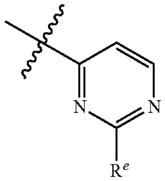
uu
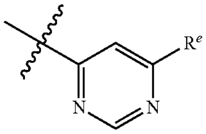
vv
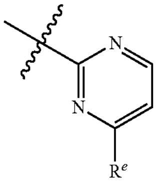
ww
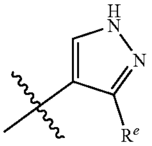
xx
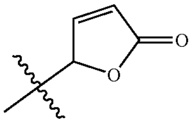 [SMILES: *C1C=CC(=O)O1]
yy
TABLE 4-continued
Exemplary R[1] Groups
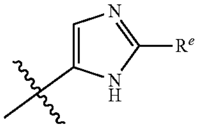
zz
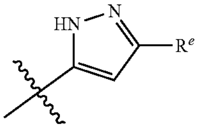
aaa
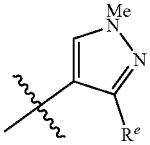
bbb
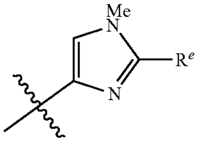
ccc
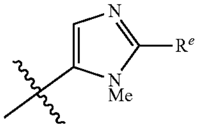
ddd
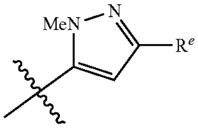
eee
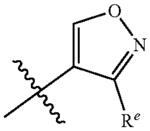
fff
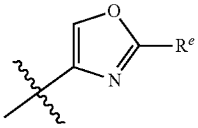
ggg
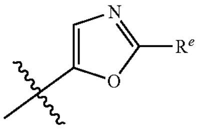
hhh
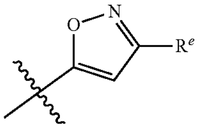
iii TABLE 4-continued
Exemplary R[1] Groups
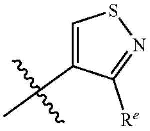
jjj
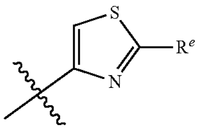
kkk
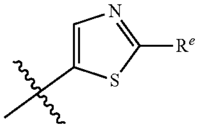
lll
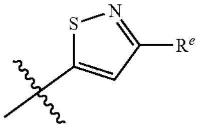
mmm
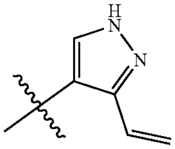 [SMILES: *c1c[nH]nc1C=C]
nnn
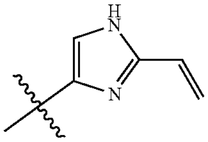 [SMILES: *c1c[nH]c(C=C)n1]
ooo
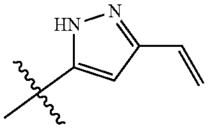
ppp
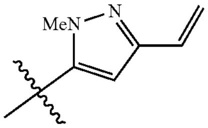 [SMILES: *c1cc(C=C)nn1C]
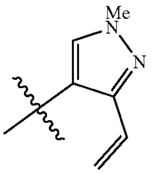 [SMILES: *c1cn(C)nc1C=C]
qqq
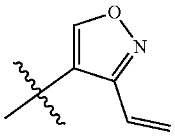 [SMILES: *c1conc1C=C]
rrr
TABLE 4-continued
Exemplary R[1] Groups
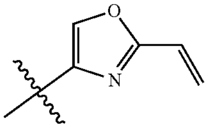 [SMILES: *c1coc(C=C)n1]
sss
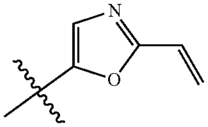
ttt
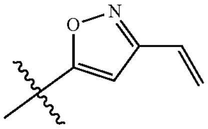
uuu
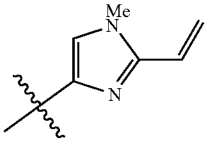 [SMILES: *c1cn(C)c(C=C)n1]
vvv
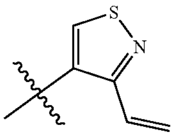 [SMILES: *c1csnc1C=C]
www
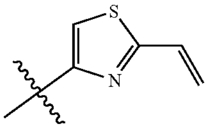 [SMILES: *c1csc(C=C)n1]
xxx
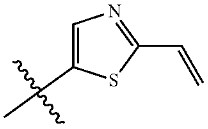
yyy
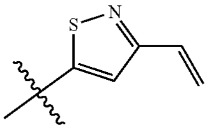 [SMILES: *c1cc(C=C)ns1]
zzz
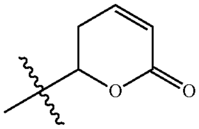 [SMILES: *C1CC=CC(=O)O1]
aaaa
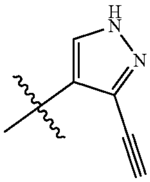 [SMILES: *c1c[nH]nc1C#C]
bbbb TABLE 4-continued
Exemplary R[1] Groups
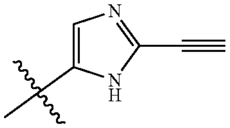
cccc
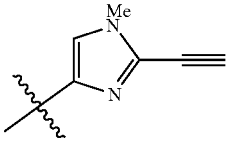 [SMILES: *c1cn(C)c(C#C)n1]
dddd
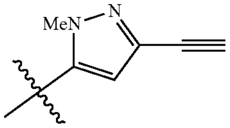
eeee
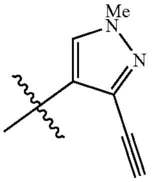 [SMILES: *c1cn(C)nc1C#C]
ffff
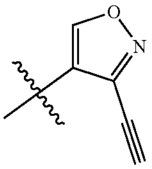 [SMILES: *c1conc1C#C]
gggg
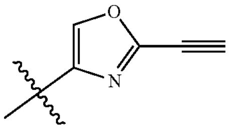
hhhh
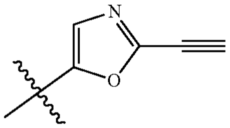
iiii
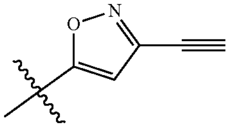
jjjj
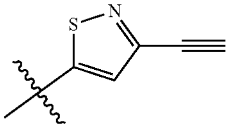
kkkk
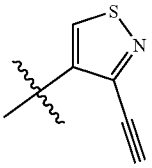 [SMILES: *c1csnc1C#C]
llll
TABLE 4-continued
Exemplary R[1] Groups
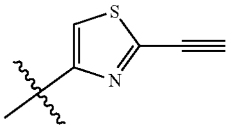 [SMILES: *c1csc(C#C)n1]
mmmm
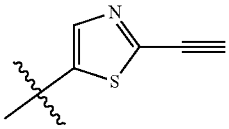
nnnn
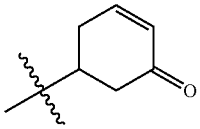 [SMILES: *C1CC=CC(=O)C1]
oooo
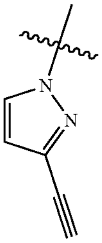 [SMILES: *n1ccc(C#C)n1]
pppp
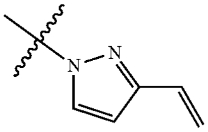 [SMILES: *n1ccc(C=C)n1]
qqqq
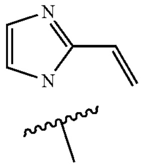
rrrr
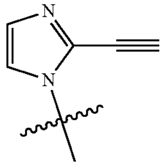 [SMILES: *n1ccnc1C#C]
ssss
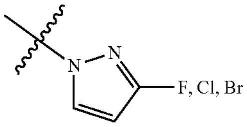
tttt
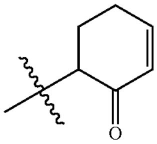 [SMILES: *C1CCC=CC1=O]
uuuu TABLE 4-continued
| Exemplary $R^1$ Groups | |
|---|---|
| 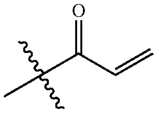 [SMILES: *C(=O)C=C] | vvvv |
| 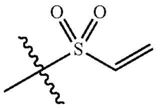 [SMILES: *S(=O)(=O)C=C] | wwww |
| 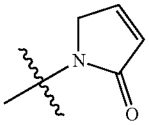 [SMILES: *N1CC=CC1=O] | xxxx |
| 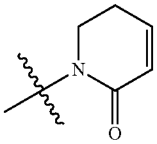 [SMILES: *N1CCC=CC1=O] | yyyy |
| 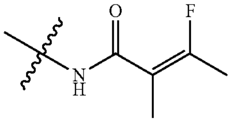 [SMILES: *NC(=O)/C(C)=C(/C)F] | zzzz |
| 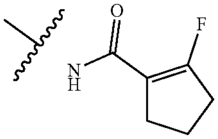 | aaaaa |
| 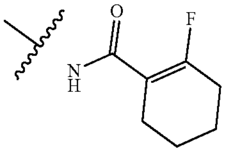 | bbbbb |
| 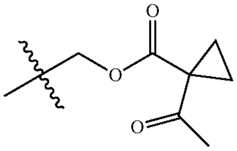 [SMILES: *COC(=O)C1(C(C)=O)CC1] | ccccc |
| 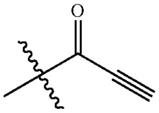 [SMILES: *C(=O)C#C] | ddddd |
| 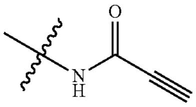 [SMILES: *NC(=O)C#C] | eeeee |
| 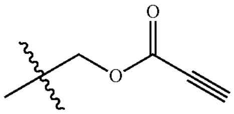 [SMILES: *COC(=O)C#C] | fffff |
TABLE 4-continued
| Exemplary $R^1$ Groups | |
|---|---|
| 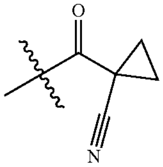 [SMILES: *C(=O)C1(C#N)CC1] | ggggg |
| 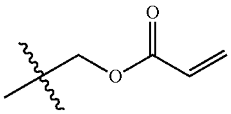 [SMILES: *COC(=O)C=C] | hhhhh |
| 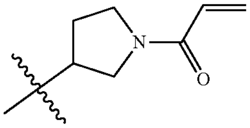 [SMILES: *C1CCN(C(=O)C=C)C1] | iiiii |
| 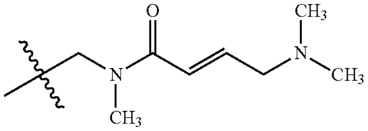 [SMILES: *CN(C)C(=O)/C=C/CN(C)C] | jjjjj |
| 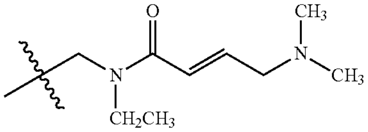 | kkkkk |
| 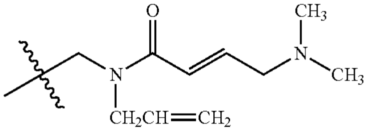 | lllll |
| 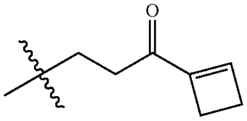 [SMILES: *CCC(=O)C1=CCC1] | mmmmm |
| 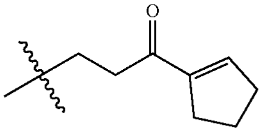 [SMILES: *CCC(=O)C1=CCCC1] | nnnnn |
| 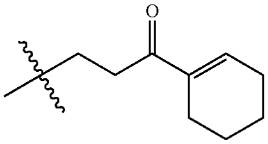 [SMILES: *CCC(=O)C1=CCCCC1] | ooooo |
| 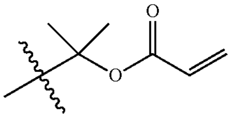 [SMILES: *C(C)(C)OC(=O)C=C] | ppppp |
| 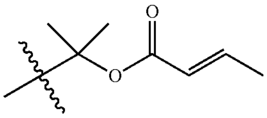 [SMILES: *C(C)(C)OC(=O)/C=C/C] | qqqqq |

TABLE 4-continued
| Exemplary R[1] Groups | |
|---|---|
| 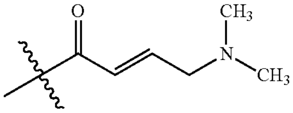 [SMILES: *C(=O)/C=C/CN(C)C] | rrrrr |
| 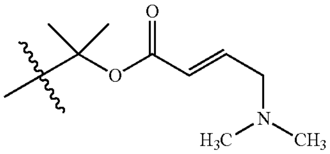 [SMILES: *C(C)(C)OC(=O)/C=C/CN(C)C] | sssss |
| 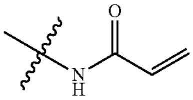 [SMILES: *NC(=O)C=C] | ttttt |
| 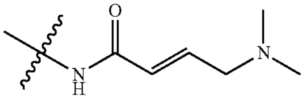 [SMILES: *NC(=O)/C=C/CN(C)C] | uuuuu |
| 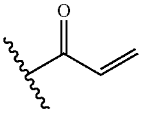 [SMILES: *C(=O)C=C] | vvvvv |
| 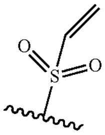 | wwwww |
| 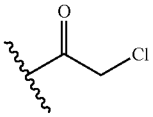 [SMILES: *C(=O)CCl] | xxxxx |
| 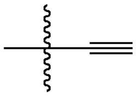 [SMILES: *C#C] | yyyyy |
| 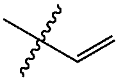 [SMILES: *C=C] | zzzzz |
| 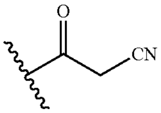 [SMILES: *C(=O)CC#N] | aaaaaa |
| 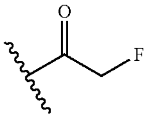 [SMILES: *C(=O)CF] | bbbbbb |
| 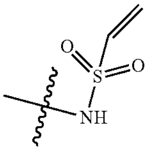 [SMILES: *NS(=O)(=O)C=C] | cccccc |
TABLE 4-continued
| Exemplary R[1] Groups | |
|---|---|
| 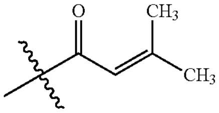 [SMILES: *C(=O)C=C(C)C] | dddddd |
| 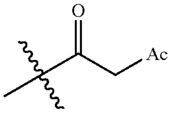 [SMILES: *C(=O)CC(C)=O] | eeeeee |
| 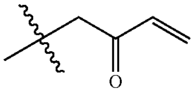 [SMILES: *CC(=O)C=C] | ffffff |
| 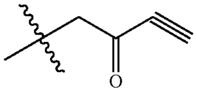 [SMILES: *CC(=O)C#C] | gggggg |
| 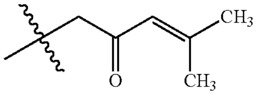 | hhhhhh |
| 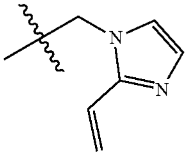 [SMILES: *Cn1ccnc1C=C] | iiiiii |
| 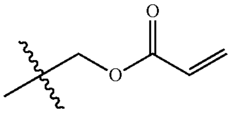 [SMILES: *COC(=O)C=C] | jjjjjj |
| 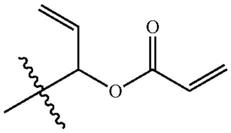 [SMILES: *C(C=C)OC(=O)C=C] | kkkkkk |
| 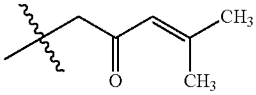 [SMILES: *CC(=O)C=C(C)C] | llllll |
| 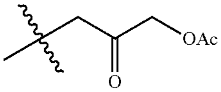 [SMILES: *CC(=O)COC(C)=O] | mmmmmm |
| 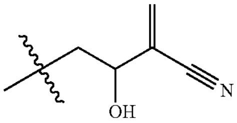 [SMILES: *CC(O)C(=C)C#N] | nnnnnn |
| 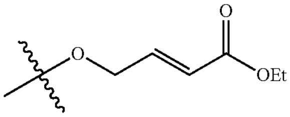 [SMILES: *OC/C=C/C(=O)OCC] | oooooo |

TABLE 4-continued

| Exemplary $R^1$ Groups | |
|---|---|
| 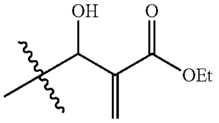 [SMILES: *C(O)C(=C)C(=O)OCC] | pppppp |
| 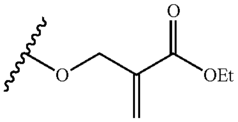 [SMILES: *OCC(=C)C(=O)OCC] | qqqqqq |
| 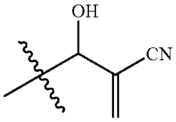 [SMILES: *C(O)C(=C)C#N] | rrrrrr |
| 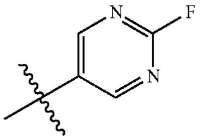 [SMILES: *c1cnc(F)nc1] | ssssss |
| 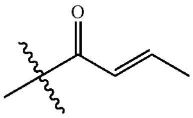 [SMILES: *C(=O)/C=C/C] | tttttt |
| 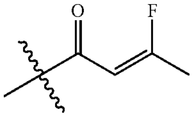 [SMILES: *C(=O)/C=C(/C)F] | uuuuuu |
| 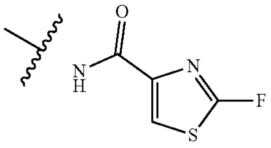 | vvvvvv |
| 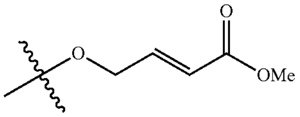 [SMILES: *OC/C=C/C(=O)OC] | wwwwww |
| 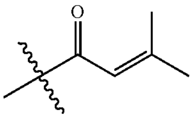 or | xxxxxx |
| 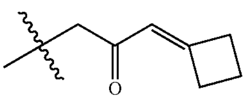 [SMILES: *CC(=O)C=C1CCC1] | yyyyyy |

wherein each $R^e$ is independently a suitable leaving group, $NO_2$, CN, or oxo.

As defined generally above, $R^1$ is a warhead group, or, when $R^1$ and $R^x$ form a ring, then -Q-Z is a warhead group. Without wishing to be bound by any particular theory, it is believed that such $R^1$ groups, i.e. warhead groups, are particularly suitable for covalently binding to a key cysteine residue in the binding domain of certain protein kinases. Protein kinases having a cysteine residue in the binding domain are known to one of ordinary skill in the art and include ErbB1, ErbB2, and ErbB4, or a mutant thereof. In certain embodiments, compounds of the present invention have a warhead group characterized in that inventive compounds target one or more of the following cysteine residues:

| | |
|---|---|
| ERBB 1 | ITQLMPFGCLLDYVREH |
| ERBB 2 | VTQLMPYGCLLDHVREN |
| ERBB 4 | VTQLMPHGCLLEYVHEH |

Thus, in some embodiments, $R^1$ is characterized in that the -L-Y moiety is capable of covalently binding to a cysteine residue thereby irreversibly inhibiting the enzyme. In certain embodiments, the cysteine residue is Cys797 of ErbB1, Cys805 of ErbB2 and Cys803 of ErbB4, or a mutant thereof, where the provided residue numbering is in accordance with Uniprot (code POO533 for ErbB1; code PO4626 for ErbB2, and Q15303 for ErbB4). It will be understood that the Cys of ErbB1 (EGFR) is variably called 773 or 797 depending on whether the parent sequence contains the signal peptide or not. Thus, in accordance with the present invention, the relevant cysteine residue of ErbB1 may be described as Cys 773 or Cys 797 and these terms are used interchangeably.

One of ordinary skill in the art will recognize that a variety of warhead groups, as defined herein, are suitable for such covalent bonding. Such $R^1$ groups include, but are not limited to, those described herein and depicted in Table 4, infra.

As depicted in formulae I-a and I-b supra, the $R^1$ warhead group can be in an ortho-, meta-, or para-position. In certain embodiments, the $R^1$ warhead group is in a meta-position of the phenyl ring relative to the rest of the molecule.

In certain embodiments, $R^1$ is characterized in that the -L-Y moiety is capable of covalently binding to a cysteine residue of TEC, thereby irreversibly inhibiting the enzyme. In some embodiments, the cysteine residue is Cys 449.

In certain embodiments, $R^1$ is characterized in that the -L-Y moiety is capable of covalently binding to a cysteine residue of BTK, thereby irreversibly inhibiting the enzyme. In some embodiments, the cysteine residue is Cys 481.

In certain embodiments, $R^1$ is characterized in that the -L-Y moiety is capable of covalently binding to a cysteine residue of ITK, thereby irreversibly inhibiting the enzyme. In some embodiments, the cysteine residue is Cys 442.

In certain embodiments, $R^1$ is characterized in that the -L-Y moiety is capable of covalently binding to a cysteine residue of BMX, thereby irreversibly inhibiting the enzyme. In some embodiments, the cysteine residue is Cys 496.

In certain embodiments, $R^1$ is characterized in that the -L-Y moiety is capable of covalently binding to a cysteine residue of JAK3, thereby irreversibly inhibiting the enzyme. In some embodiments, the cysteine residue is Cys 909.

In certain embodiments, $R^1$ is characterized in that the -L-Y moiety is capable of covalently binding to a cysteine residue of TXK, thereby irreversibly inhibiting the enzyme. In some embodiments, the cysteine residue is Cys 350.

One of ordinary skill in the art will recognize that a variety of warhead groups, as defined herein, are suitable for such covalent bonding. Such $R^1$ groups include, but are not limited to, those described herein and depicted in Table 3, infra.

Exemplary compounds of the present invention are set forth in Table 5 below.

TABLE 5
| Exemplary Compounds | |
|---|---|
| 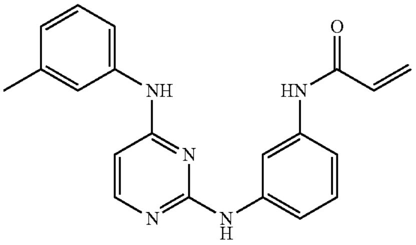 [SMILES: C=CC(=O)Nc1cccc(Nc2nccc(Nc3cccc(C)c3)n2)c1] | I-1 |
| 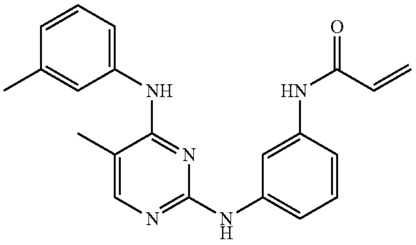 [SMILES: C=CC(=O)Nc1cccc(Nc2ncc(C)c(Nc3cccc(C)c3)n2)c1] | I-2 |
| 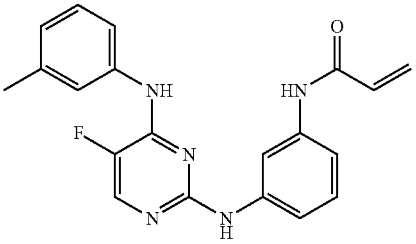 | I-3 |
| 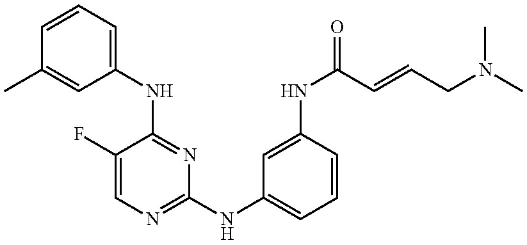 | I-4 |
| 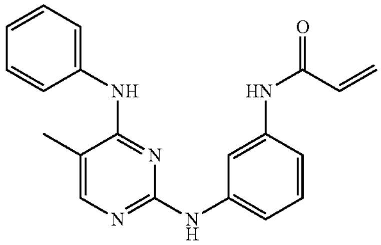 [SMILES: C=CC(=O)Nc1cccc(Nc2ncc(C)c(Nc3ccccc3)n2)c1] | I-5 |
| 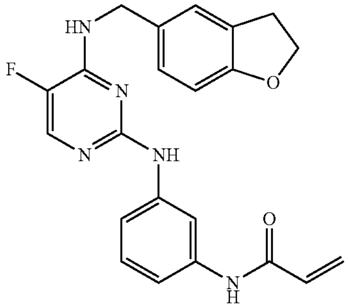 [SMILES: C=CC(=O)Nc1cccc(Nc2ncc(F)c(NCc3ccc4c(c3)CCO4)n2)c1] | I-6 |

TABLE 5-continued
| Exemplary Compounds |
| --- |
| I-7<br>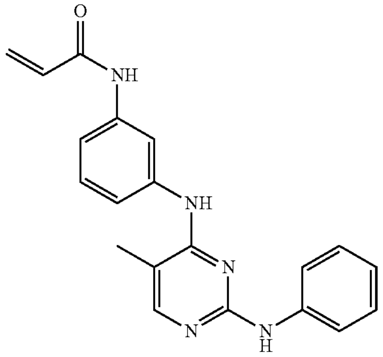 [SMILES: C=CC(=O)Nc1cccc(Nc2nc(Nc3ccccc3)ncc2C)c1] |
| I-8<br>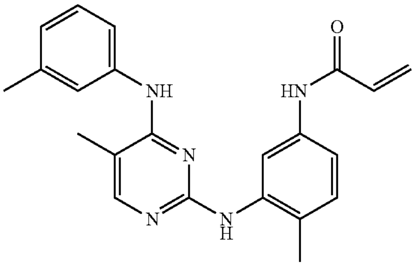 [SMILES: C=CC(=O)Nc1ccc(C)c(Nc2ncc(C)c(Nc3cccc(C)c3)n2)c1] |
| I-9<br>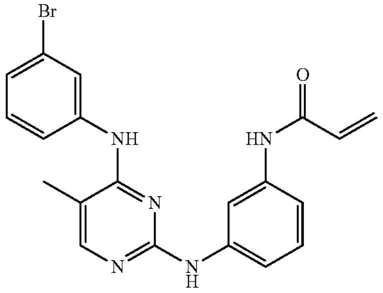 [SMILES: C=CC(=O)Nc1cccc(Nc2ncc(C)c(Nc3cccc(Br)c3)n2)c1] |
| I-10<br>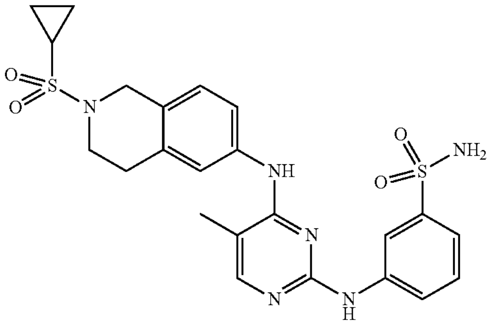 [SMILES: Cc1cnc(Nc2cccc(S(N)(=O)=O)c2)nc1Nc1ccc2c(c1)CCN(S(=O)(=O)C1CC1)C2] |
| I-11<br>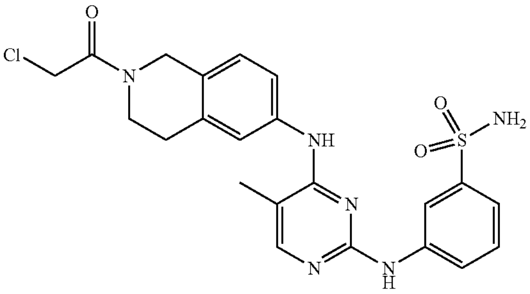 [SMILES: Cc1cnc(Nc2cccc(S(N)(=O)=O)c2)nc1Nc1ccc2c(c1)CCN(C(=O)CCl)C2] |

TABLE 5-continued
| Exemplary Compounds |
| --- |
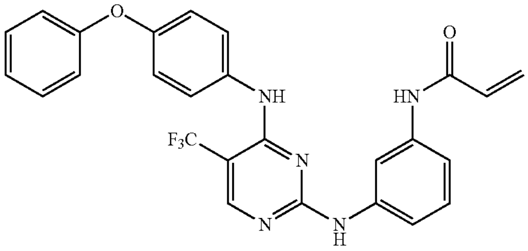 [SMILES: C=CC(=O)Nc1cccc(Nc2ncc(C(F)(F)F)c(Nc3ccc(Oc4ccccc4)cc3)n2)c1]
I-12
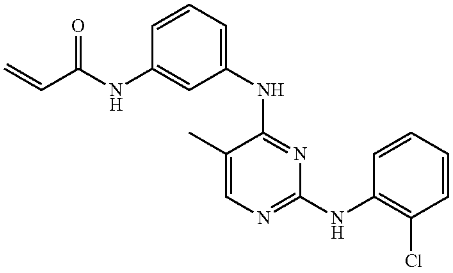 [SMILES: C=CC(=O)Nc1cccc(Nc2nc(Nc3ccccc3Cl)ncc2C)c1]
I-13
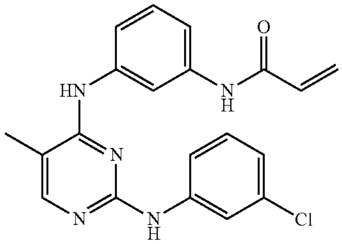 [SMILES: C=CC(=O)Nc1cccc(Nc2nc(Nc3cccc(Cl)c3)ncc2C)c1]
I-14
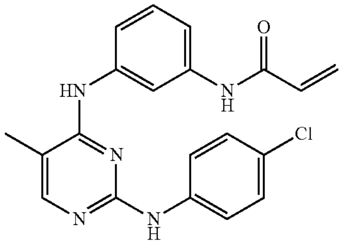 [SMILES: C=CC(=O)Nc1cccc(Nc2nc(Nc3ccc(Cl)cc3)ncc2C)c1]
I-15
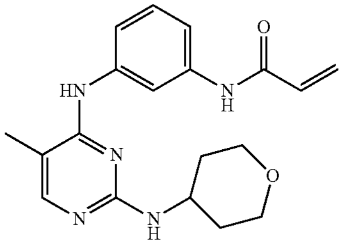 [SMILES: C=CC(=O)Nc1cccc(Nc2nc(NC3CCOCC3)ncc2C)c1]
I-16
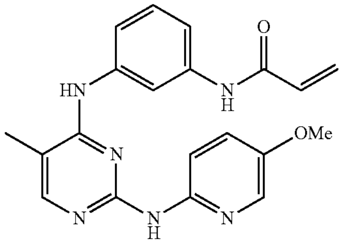 [SMILES: C=CC(=O)Nc1cccc(Nc2nc(Nc3ccc(OC)cn3)ncc2C)c1]
I-17

TABLE 5-continued
| Exemplary Compounds |
| --- |
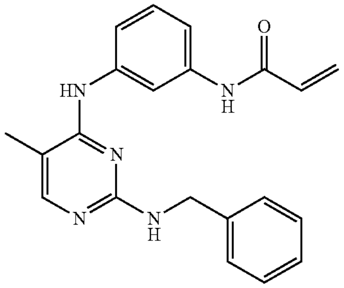 [SMILES: C=CC(=O)Nc1cccc(Nc2nc(NCc3ccccc3)ncc2C)c1]
I-18
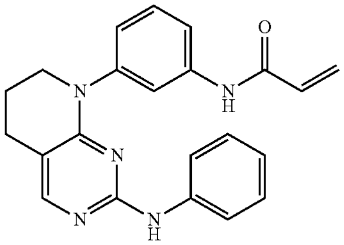 [SMILES: C=CC(=O)Nc1cccc(N2CCCc3cnc(Nc4ccccc4)nc32)c1]
I-19
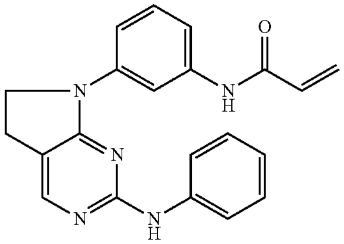 [SMILES: C=CC(=O)Nc1cccc(N2CCc3cnc(Nc4ccccc4)nc32)c1]
I-20
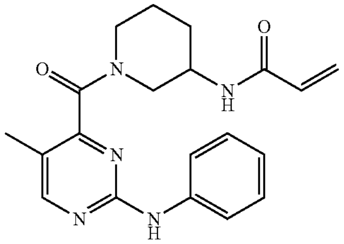 [SMILES: C=CC(=O)NC1CCCN(C(=O)c2nc(Nc3ccccc3)ncc2C)C1]
I-21
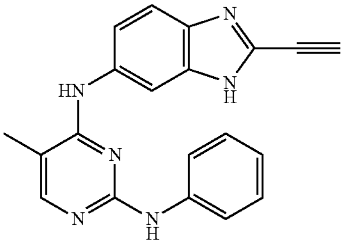 [SMILES: C#Cc1nc2ccc(Nc3nc(Nc4ccccc4)ncc3C)cc2[nH]1]
I-22
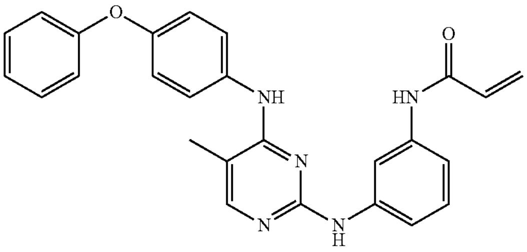 [SMILES: C=CC(=O)Nc1cccc(Nc2ncc(C)c(Nc3ccc(Oc4ccccc4)cc3)n2)c1]
I-23

TABLE 5-continued
| Exemplary Compounds |
|---|
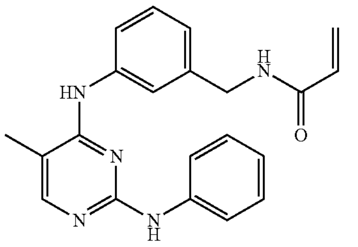 [SMILES: C=CC(=O)NCc1cccc(Nc2nc(Nc3ccccc3)ncc2C)c1]
I-24
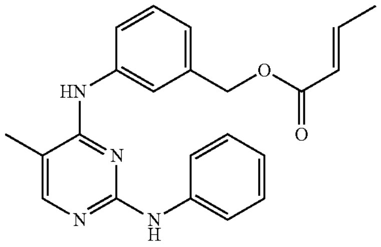 [SMILES: C/C=C/C(=O)OCc1cccc(Nc2nc(Nc3ccccc3)ncc2C)c1]
I-25
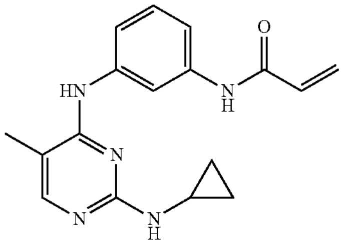 [SMILES: C=CC(=O)Nc1cccc(Nc2nc(NC3CC3)ncc2C)c1]
I-26
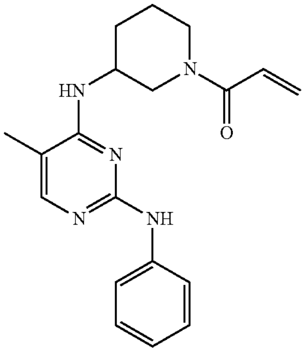 [SMILES: C=CC(=O)N1CCCC(Nc2nc(Nc3ccccc3)ncc2C)C1]
I-27
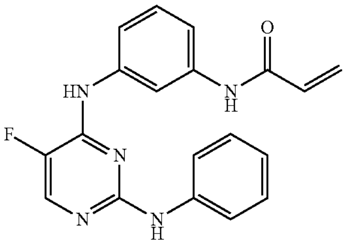 [SMILES: C=CC(=O)Nc1cccc(Nc2nc(Nc3ccccc3)ncc2F)c1]
I-28

TABLE 5-continued
| Exemplary Compounds |
|---|
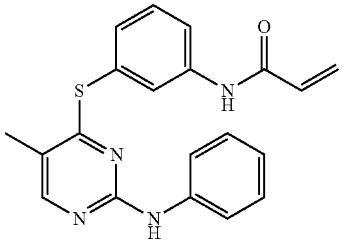 [SMILES: C=CC(=O)Nc1cccc(Sc2nc(Nc3ccccc3)ncc2C)c1]
I-29
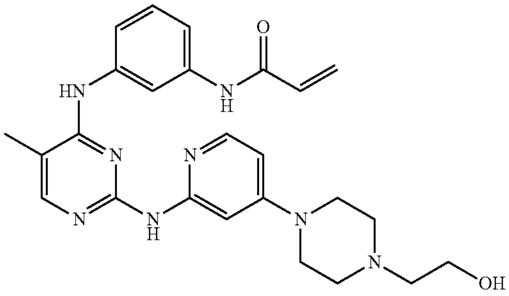 [SMILES: C=CC(=O)Nc1cccc(Nc2nc(Nc3cc(N4CCN(CCO)CC4)ccn3)ncc2C)c1]
I-30
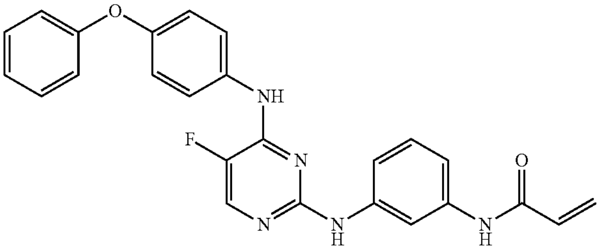 [SMILES: C=CC(=O)Nc1cccc(Nc2ncc(F)c(Nc3ccc(Oc4ccccc4)cc3)n2)c1]
I-31
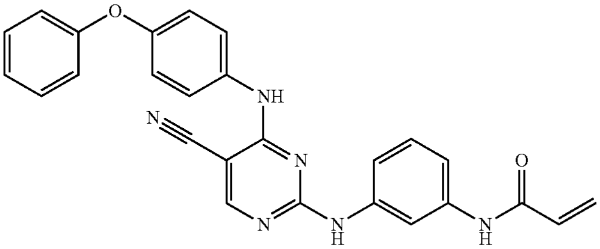 [SMILES: C=CC(=O)Nc1cccc(Nc2ncc(C#N)c(Nc3ccc(Oc4ccccc4)cc3)n2)c1]
I-32
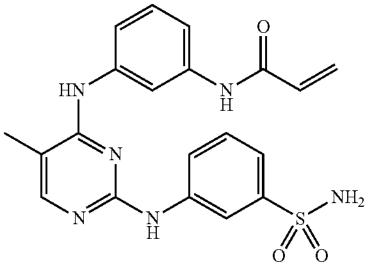 [SMILES: C=CC(=O)Nc1cccc(Nc2nc(Nc3cccc(S(N)(=O)=O)c3)ncc2C)c1]
I-33
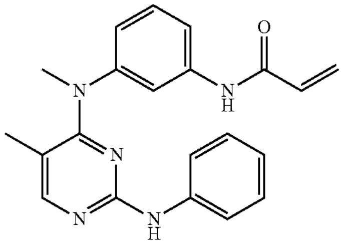 [SMILES: C=CC(=O)Nc1cccc(N(C)c2nc(Nc3ccccc3)ncc2C)c1]
I-34

TABLE 5-continued
Exemplary Compounds
I-35
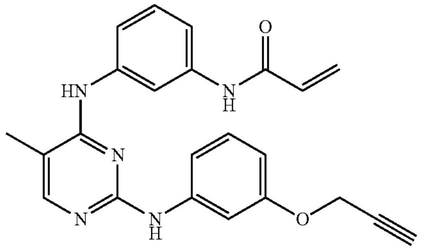 [SMILES: C#CCOc1cccc(Nc2ncc(C)c(Nc3cccc(NC(=O)C=C)c3)n2)c1]
I-36
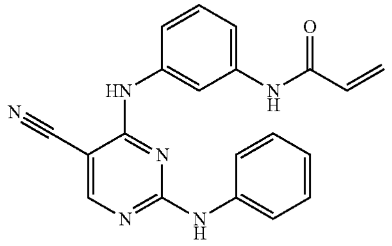 [SMILES: C=CC(=O)Nc1cccc(Nc2nc(Nc3ccccc3)ncc2C#N)c1]
I-37
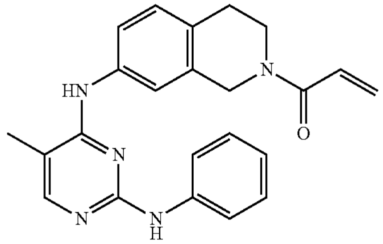 [SMILES: C=CC(=O)N1CCc2ccc(Nc3nc(Nc4ccccc4)ncc3C)cc2C1]
I-38
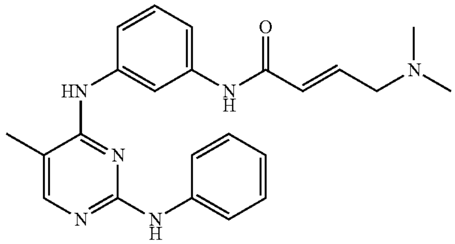
I-39
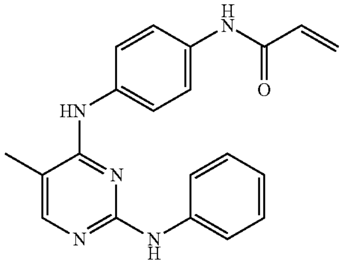 [SMILES: C=CC(=O)Nc1ccc(Nc2nc(Nc3ccccc3)ncc2C)cc1]
I-40
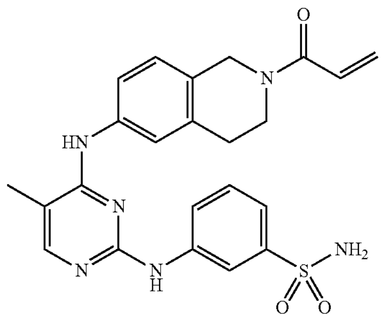 [SMILES: C=CC(=O)N1CCc2cc(Nc3nc(Nc4cccc(S(N)(=O)=O)c4)ncc3C)ccc2C1]

TABLE 5-continued
| Exemplary Compounds |
| --- |
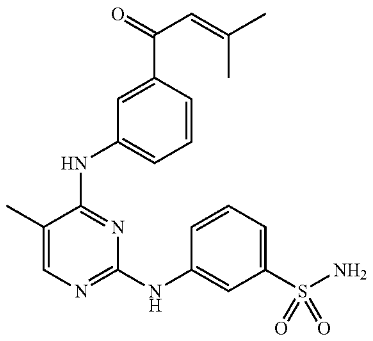 [SMILES: CC(C)=CC(=O)c1cccc(Nc2nc(Nc3cccc(S(N)(=O)=O)c3)ncc2C)c1]
I-41
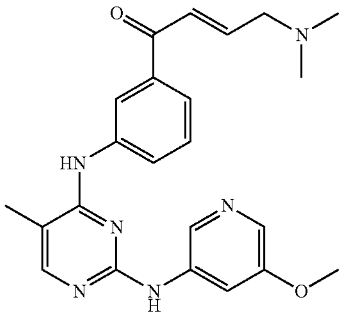
I-42
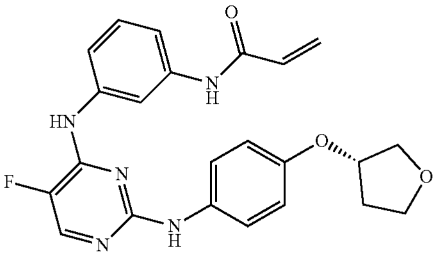 [SMILES: C=CC(=O)Nc1cccc(Nc2nc(Nc3ccc(O[C@H]4CCOC4)cc3)ncc2F)c1]
I-43
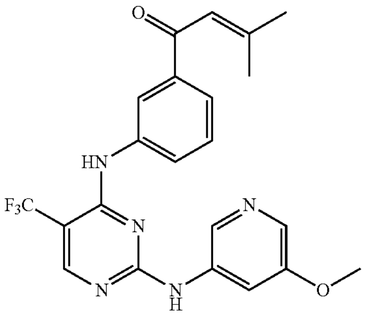 [SMILES: COc1cncc(Nc2ncc(C(F)(F)F)c(Nc3cccc(C(=O)C=C(C)C)c3)n2)c1]
I-44
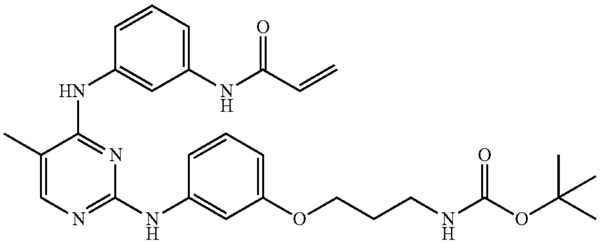 [SMILES: C=CC(=O)Nc1cccc(Nc2nc(Nc3cccc(OCCCNC(=O)OC(C)(C)C)c3)ncc2C)c1]
I-45

TABLE 5-continued
Exemplary Compounds
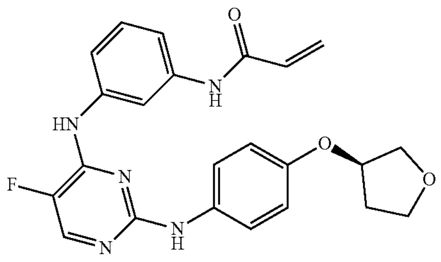
I-46
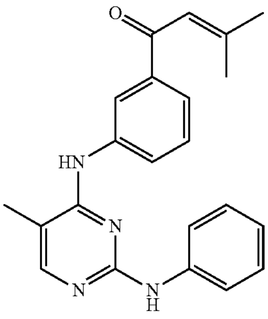 [SMILES: CC(C)=CC(=O)c1cccc(Nc2nc(Nc3ccccc3)ncc2C)c1]
I-47
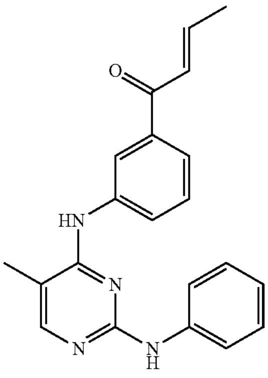 [SMILES: C/C=C/C(=O)c1cccc(Nc2nc(Nc3ccccc3)ncc2C)c1]
I-48
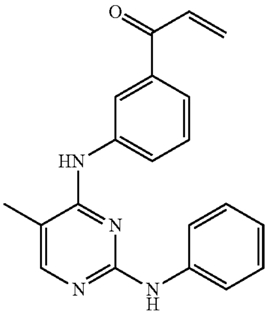 [SMILES: C=CC(=O)c1cccc(Nc2nc(Nc3ccccc3)ncc2C)c1]
I-49
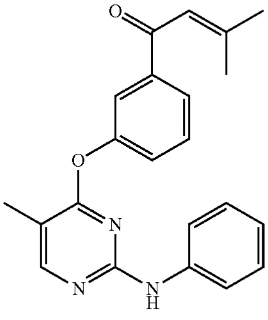 [SMILES: CC(C)=CC(=O)c1cccc(Oc2nc(Nc3ccccc3)ncc2C)c1]
I-50

TABLE 5-continued
| Exemplary Compounds |
|---|
| 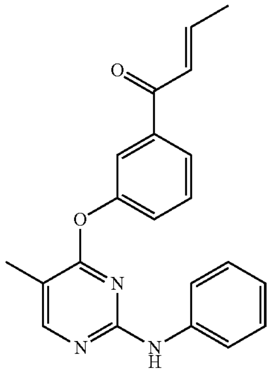 [SMILES: C/C=C/C(=O)c1cccc(Oc2nc(Nc3ccccc3)ncc2C)c1] I-51 |
| 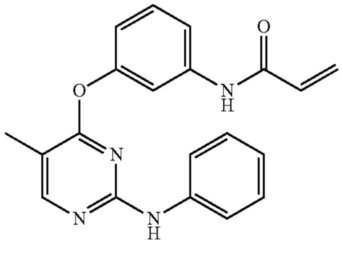 [SMILES: C=CC(=O)Nc1cccc(Oc2nc(Nc3ccccc3)ncc2C)c1] I-52 |
| 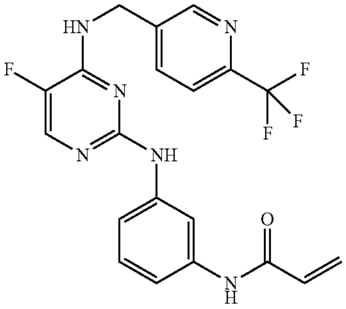 [SMILES: C=CC(=O)Nc1cccc(Nc2ncc(F)c(NCc3ccc(C(F)(F)F)nc3)n2)c1] I-53 |
| 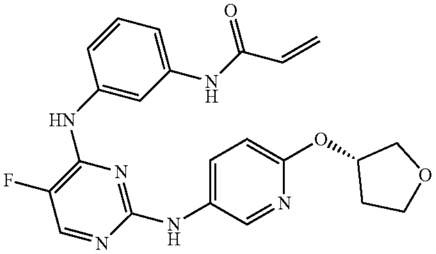 [SMILES: C=CC(=O)Nc1cccc(Nc2nc(Nc3ccc(O[C@H]4CCOC4)nc3)ncc2F)c1] I-54 |
| 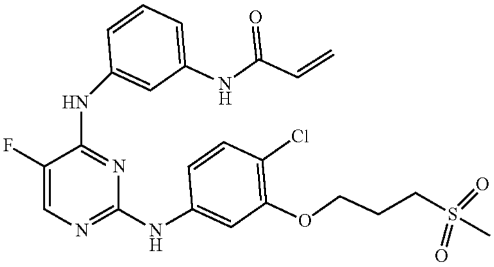 [SMILES: C=CC(=O)Nc1cccc(Nc2nc(Nc3ccc(Cl)c(OCCCS(C)(=O)=O)c3)ncc2F)c1] I-55 |

TABLE 5-continued
Exemplary Compounds
I-56
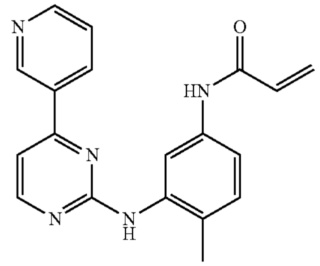 [SMILES: C=CC(=O)Nc1ccc(C)c(Nc2nccc(-c3cccnc3)n2)c1]
I-57
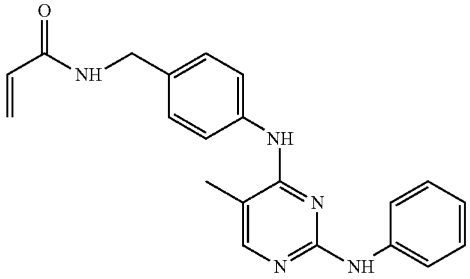
I-58
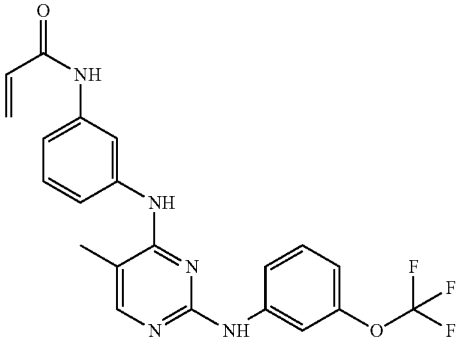 [SMILES: C=CC(=O)Nc1cccc(Nc2nc(Nc3cccc(OC(F)(F)F)c3)ncc2C)c1]
I-59
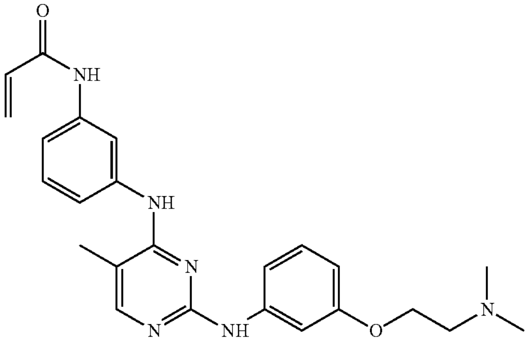 [SMILES: C=CC(=O)Nc1cccc(Nc2nc(Nc3cccc(OCCN(C)C)c3)ncc2C)c1]
I-60
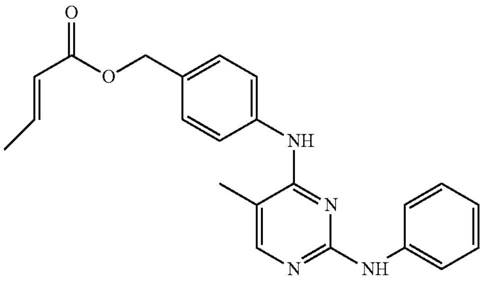 [SMILES: C/C=C/C(=O)OCc1ccc(Nc2nc(Nc3ccccc3)ncc2C)cc1]

TABLE 5-continued
| Exemplary Compounds | |
|---|---|
| 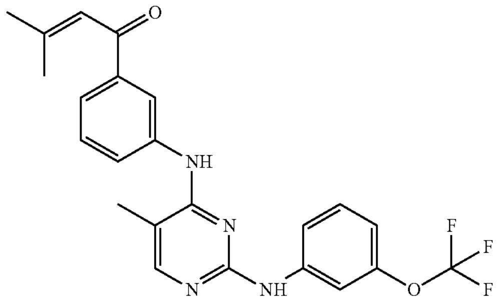 [SMILES: CC(C)=CC(=O)c1cccc(Nc2nc(Nc3cccc(OC(F)(F)F)c3)ncc2C)c1] | I-61 |
| 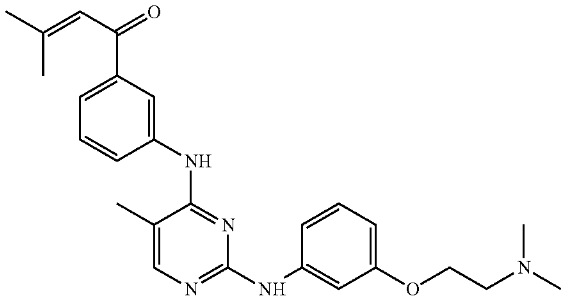 [SMILES: CC(C)=CC(=O)c1cccc(Nc2nc(Nc3cccc(OCCN(C)C)c3)ncc2C)c1] | I-62 |
| 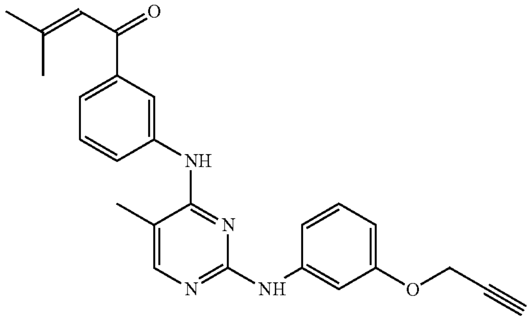 [SMILES: C#CCOc1cccc(Nc2ncc(C)c(Nc3cccc(C(=O)C=C(C)C)c3)n2)c1] | I-63 |
| 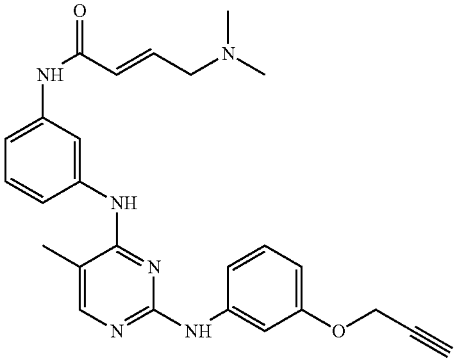 [SMILES: C#CCOc1cccc(Nc2ncc(C)c(Nc3cccc(NC(=O)/C=C/CN(C)C)c3)n2)c1] | I-64 |

TABLE 5-continued
Exemplary Compounds
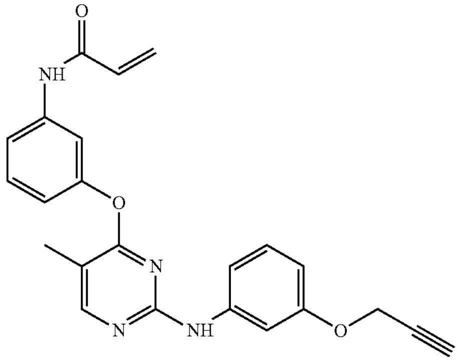 [SMILES: C#CCOc1cccc(Nc2ncc(C)c(Oc3cccc(NC(=O)C=C)c3)n2)c1]
I-65
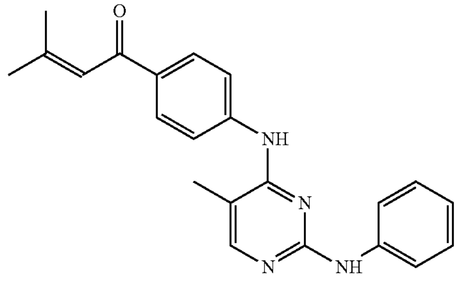 [SMILES: CC(C)=CC(=O)c1ccc(Nc2nc(Nc3ccccc3)ncc2C)cc1]
I-66
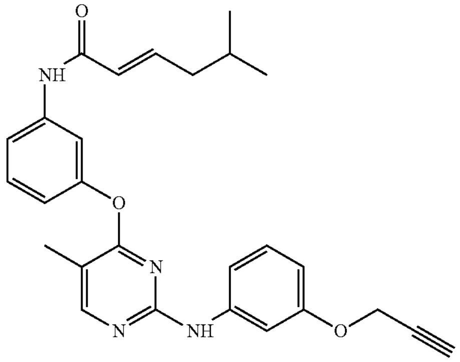 [SMILES: C#CCOc1cccc(Nc2ncc(C)c(Oc3cccc(NC(=O)/C=C/CC(C)C)c3)n2)c1]
I-67
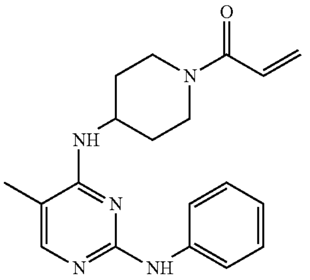 [SMILES: C=CC(=O)N1CCC(Nc2nc(Nc3ccccc3)ncc2C)CC1]
I-68
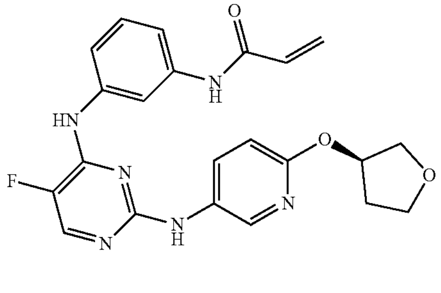 [SMILES: C=CC(=O)Nc1cccc(Nc2nc(Nc3ccc(O[C@@H]4CCOC4)nc3)ncc2F)c1]
I-69

TABLE 5-continued
| Exemplary Compounds |
|---|
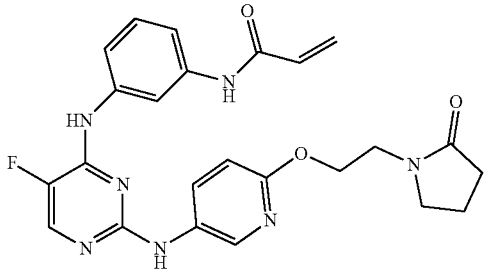 [SMILES: C=CC(=O)Nc1cccc(Nc2nc(Nc3ccc(OCCN4CCCC4=O)nc3)ncc2F)c1]
I-70
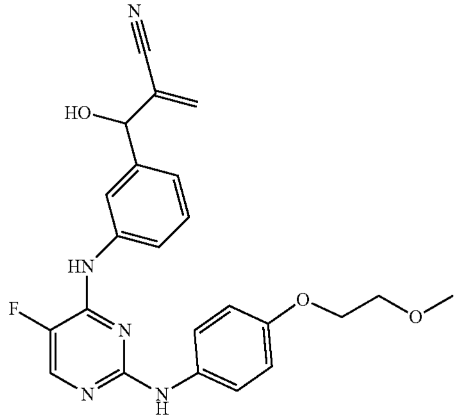 [SMILES: C=C(C#N)C(O)c1cccc(Nc2nc(Nc3ccc(OCCOC)cc3)ncc2F)c1]
I-71
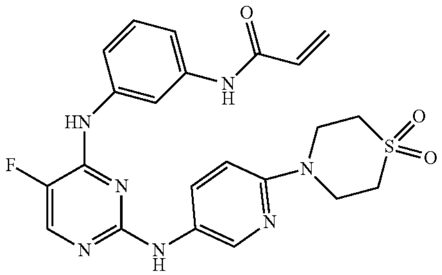 [SMILES: C=CC(=O)Nc1cccc(Nc2nc(Nc3ccc(N4CCS(=O)(=O)CC4)nc3)ncc2F)c1]
I-72
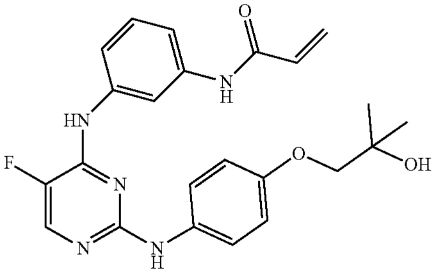 [SMILES: C=CC(=O)Nc1cccc(Nc2nc(Nc3ccc(OCC(C)(C)O)cc3)ncc2F)c1]
I-73
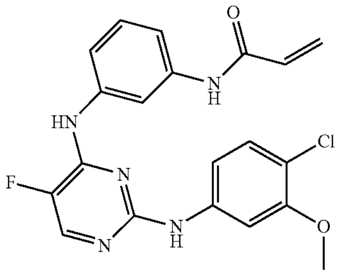 [SMILES: C=CC(=O)Nc1cccc(Nc2nc(Nc3ccc(Cl)c(OC)c3)ncc2F)c1]
I-74

TABLE 5-continued
| Exemplary Compounds |
|---|
I-75
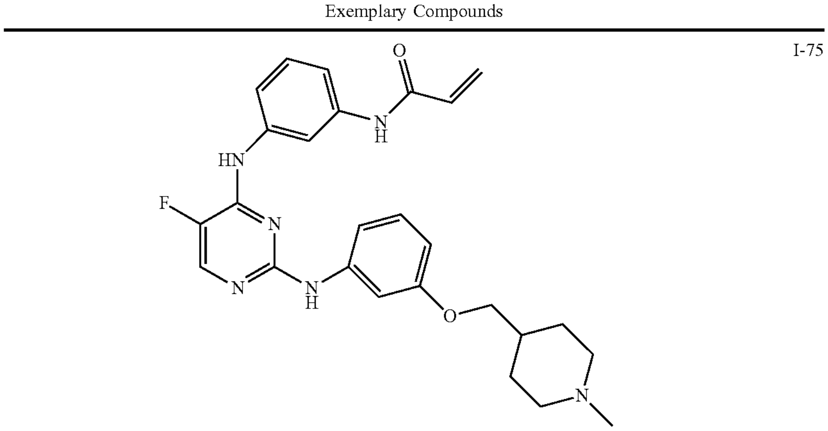
I-76
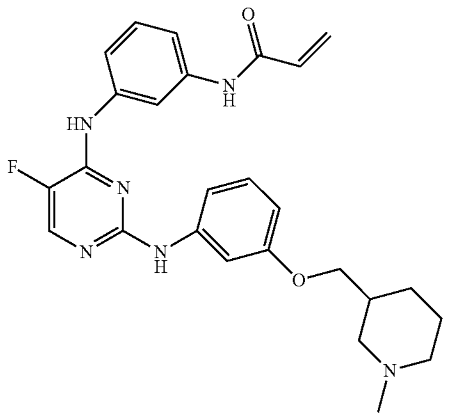 [SMILES: C=CC(=O)Nc1cccc(Nc2nc(Nc3cccc(OCC4CCCN(C)C4)c3)ncc2F)c1]
I-77
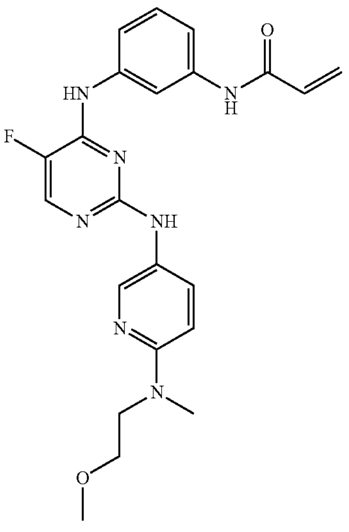 [SMILES: C=CC(=O)Nc1cccc(Nc2nc(Nc3ccc(N(C)CCOC)nc3)ncc2F)c1]
I-78
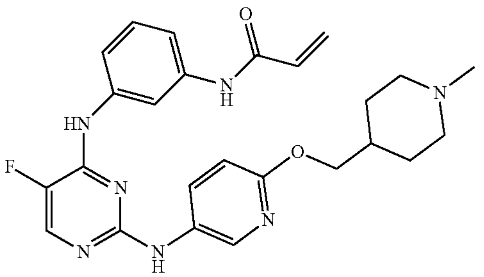 [SMILES: C=CC(=O)Nc1cccc(Nc2nc(Nc3ccc(OCC4CCN(C)CC4)nc3)ncc2F)c1]

TABLE 5-continued
| Exemplary Compounds |
| --- |
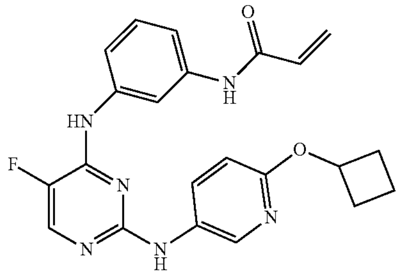 [SMILES: C=CC(=O)Nc1cccc(Nc2nc(Nc3ccc(OC4CCC4)nc3)ncc2F)c1]
I-79
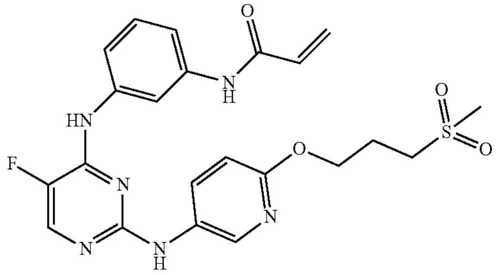 [SMILES: C=CC(=O)Nc1cccc(Nc2nc(Nc3ccc(OCCCS(C)(=O)=O)nc3)ncc2F)c1]
I-80
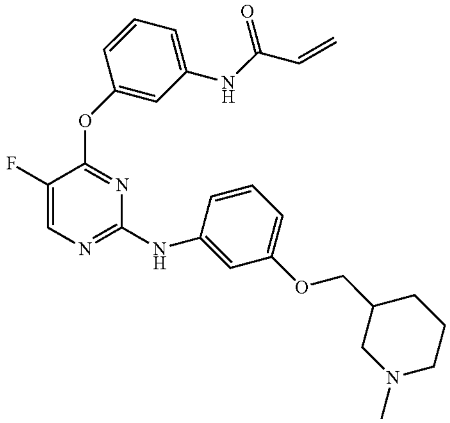 [SMILES: C=CC(=O)Nc1cccc(Oc2nc(Nc3cccc(OCC4CCCN(C)C4)c3)ncc2F)c1]
I-81
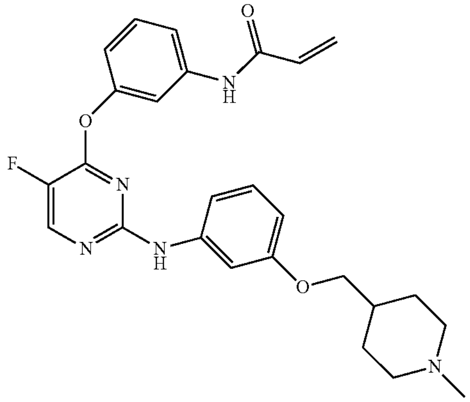 [SMILES: C=CC(=O)Nc1cccc(Oc2nc(Nc3cccc(OCC4CCN(C)CC4)c3)ncc2F)c1]
I-82

TABLE 5-continued
| Exemplary Compounds |
| --- |
| 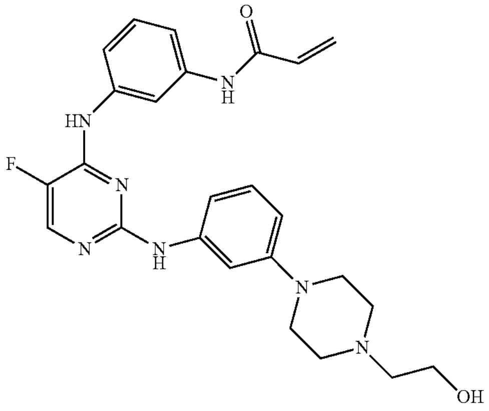 [SMILES: C=CC(=O)Nc1cccc(Nc2nc(Nc3cccc(N4CCN(CCO)CC4)c3)ncc2F)c1] I-83 |
| 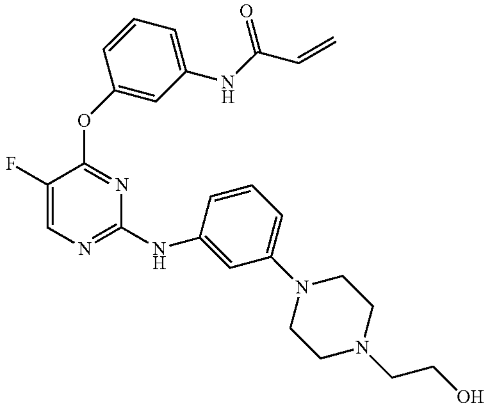 [SMILES: C=CC(=O)Nc1cccc(Oc2nc(Nc3cccc(N4CCN(CCO)CC4)c3)ncc2F)c1] I-84 |
| 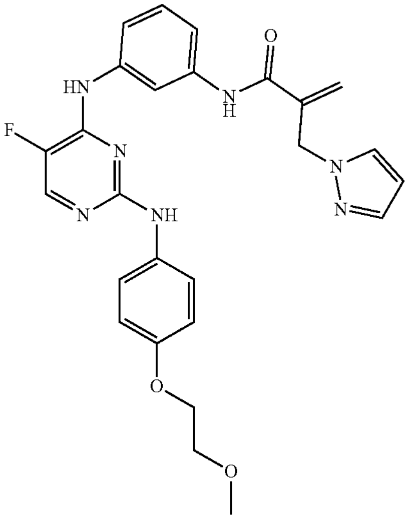 [SMILES: C=C(Cn1cccn1)C(=O)Nc1cccc(Nc2nc(Nc3ccc(OCCOC)cc3)ncc2F)c1] I-85 |

TABLE 5-continued
| Exemplary Compounds |
|---|
| 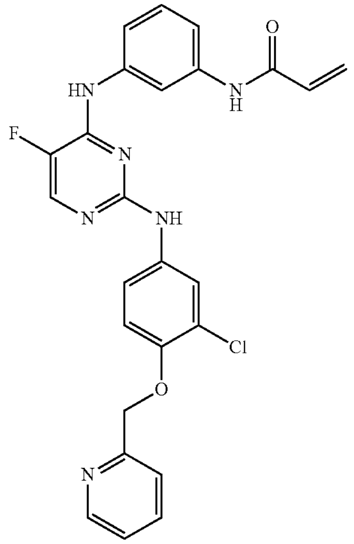 [SMILES: C=CC(=O)Nc1cccc(Nc2nc(Nc3ccc(OCc4ccccn4)c(Cl)c3)ncc2F)c1] I-86 |
| 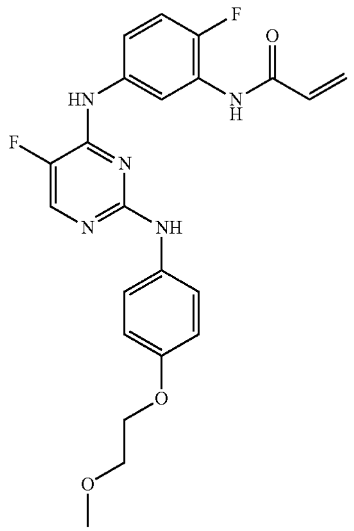 [SMILES: C=CC(=O)Nc1cc(Nc2nc(Nc3ccc(OCCOC)cc3)ncc2F)ccc1F] I-87 |
| 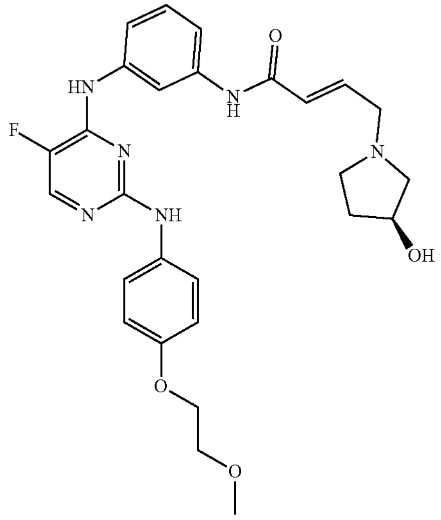 [SMILES: COCCOc1ccc(Nc2ncc(F)c(Nc3cccc(NC(=O)/C=C/CN4CC[C@H](O)C4)c3)n2)cc1] I-88 |

TABLE 5-continued
| Exemplary Compounds |
|---|
I-89
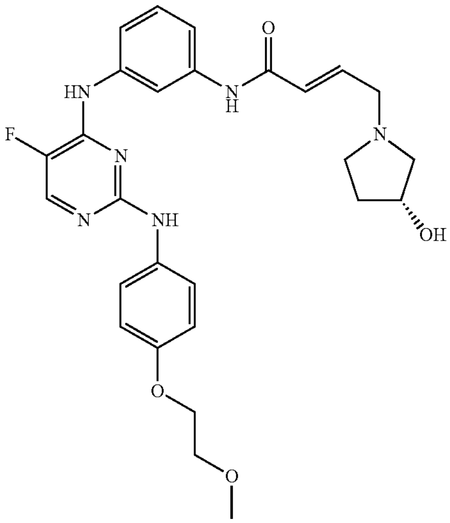 [SMILES: COCCOc1ccc(Nc2ncc(F)c(Nc3cccc(NC(=O)/C=C/CN4CC[C@@H](O)C4)c3)n2)cc1]
I-90
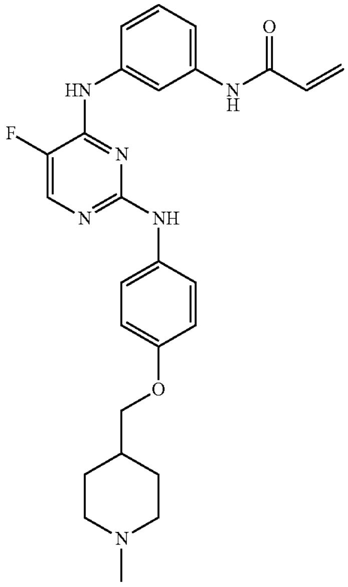 [SMILES: C=CC(=O)Nc1cccc(Nc2nc(Nc3ccc(OCC4CCN(C)CC4)cc3)ncc2F)c1]
I-91
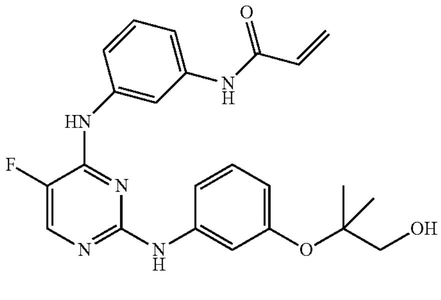 [SMILES: C=CC(=O)Nc1cccc(Nc2nc(Nc3cccc(OC(C)(C)CO)c3)ncc2F)c1]

TABLE 5-continued
Exemplary Compounds
I-92
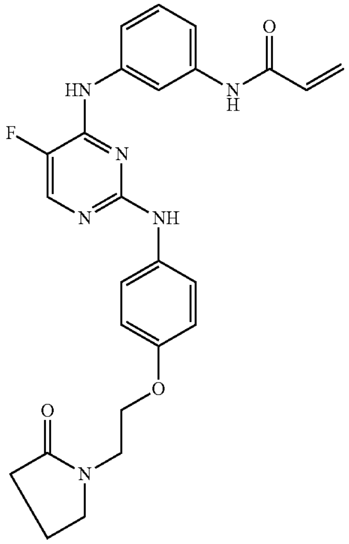 [SMILES: C=CC(=O)Nc1cccc(Nc2nc(Nc3ccc(OCCN4CCCC4=O)cc3)ncc2F)c1]
I-93
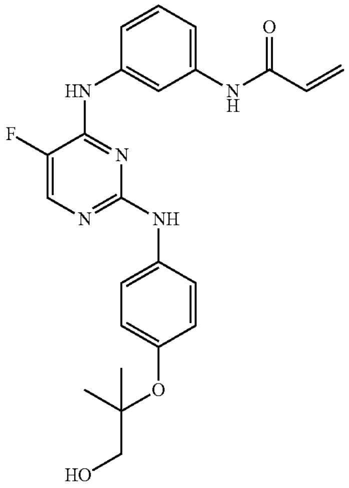 [SMILES: C=CC(=O)Nc1cccc(Nc2nc(Nc3ccc(OC(C)(C)CO)cc3)ncc2F)c1]
I-94
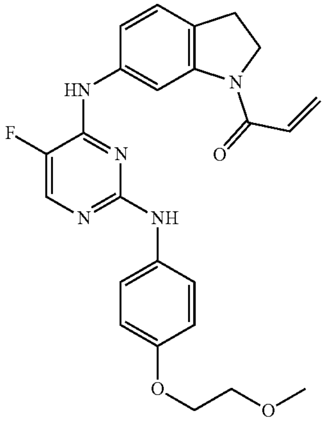 [SMILES: C=CC(=O)N1CCc2ccc(Nc3nc(Nc4ccc(OCCOC)cc4)ncc3F)cc21]

TABLE 5-continued
| Exemplary Compounds | |
|---|---|
| 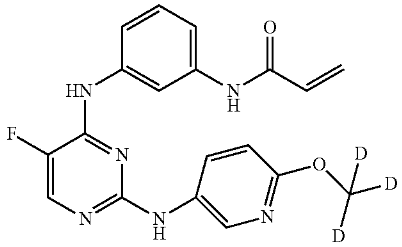 [SMILES: [2H]C([2H])([2H])Oc1ccc(Nc2ncc(F)c(Nc3cccc(NC(=O)C=C)c3)n2)cn1] | I-95 |
| 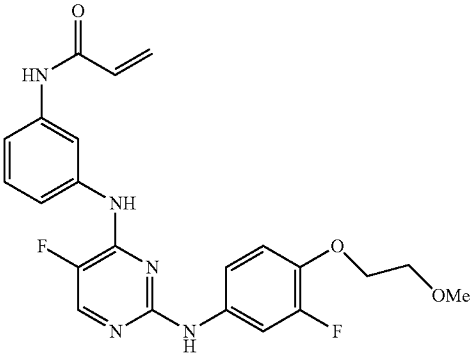 [SMILES: C=CC(=O)Nc1cccc(Nc2nc(Nc3ccc(OCCOC)c(F)c3)ncc2F)c1] | I-96 |
| 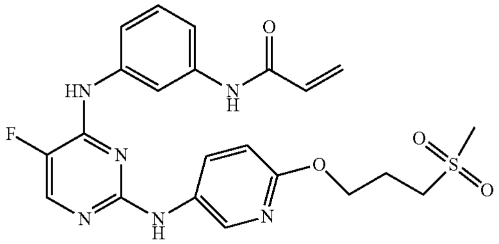 [SMILES: C=CC(=O)Nc1cccc(Nc2nc(Nc3ccc(OCCCS(C)(=O)=O)nc3)ncc2F)c1] | I-97 |
| 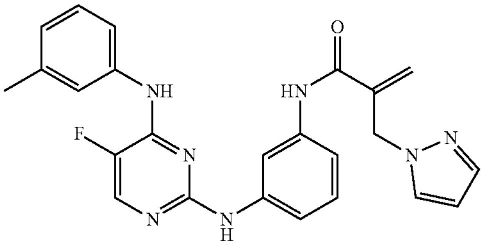 [SMILES: C=C(Cn1cccn1)C(=O)Nc1cccc(Nc2ncc(F)c(Nc3cccc(C)c3)n2)c1] | I-98 |
| 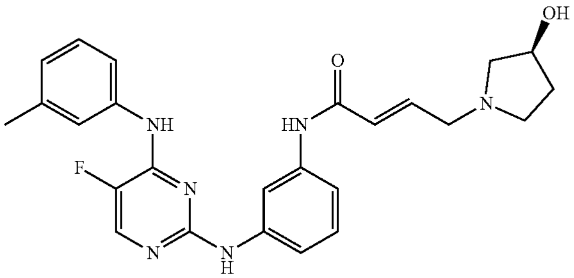 [SMILES: Cc1cccc(Nc2nc(Nc3cccc(NC(=O)/C=C/CN4CC[C@H](O)C4)c3)ncc2F)c1] | I-99 |

TABLE 5-continued
Exemplary Compounds
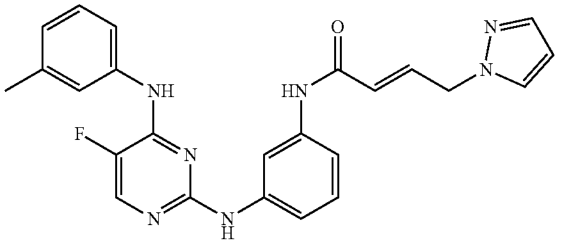 [SMILES: Cc1cccc(Nc2nc(Nc3cccc(NC(=O)/C=C/Cn4cccn4)c3)ncc2F)c1]
I-100
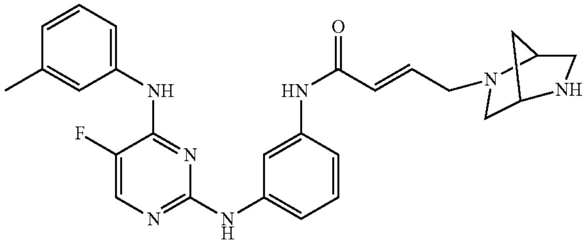 [SMILES: Cc1cccc(Nc2nc(Nc3cccc(NC(=O)/C=C/CN4CC5CC4CN5)c3)ncc2F)c1]
I-101
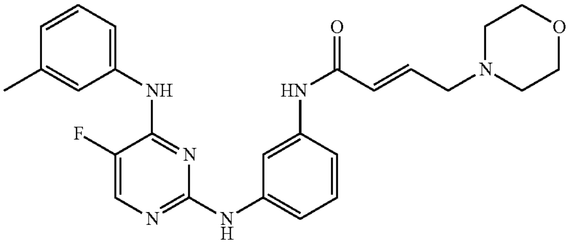 [SMILES: Cc1cccc(Nc2nc(Nc3cccc(NC(=O)/C=C/CN4CCOCC4)c3)ncc2F)c1]
I-102
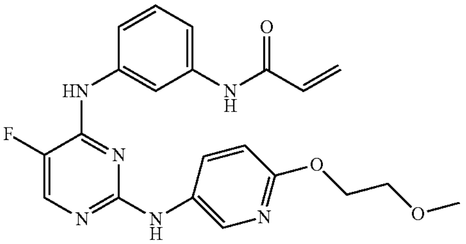 [SMILES: C=CC(=O)Nc1cccc(Nc2nc(Nc3ccc(OCCOC)nc3)ncc2F)c1]
I-103
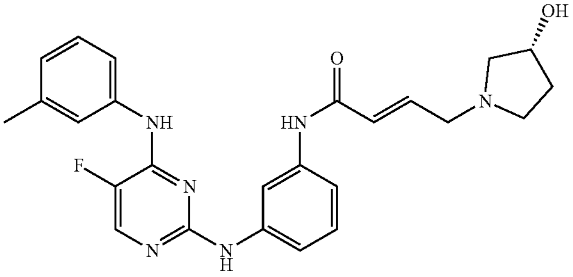 [SMILES: Cc1cccc(Nc2nc(Nc3cccc(NC(=O)/C=C/CN4CC[C@@H](O)C4)c3)ncc2F)c1]
I-104
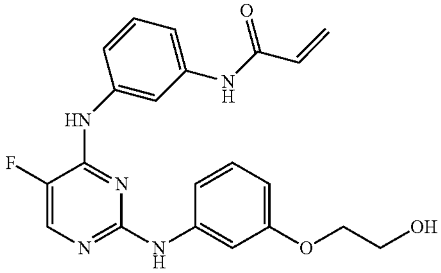 [SMILES: C=CC(=O)Nc1cccc(Nc2nc(Nc3cccc(OCCO)c3)ncc2F)c1]
I-105

TABLE 5-continued
| Exemplary Compounds | |
|---|---|
| 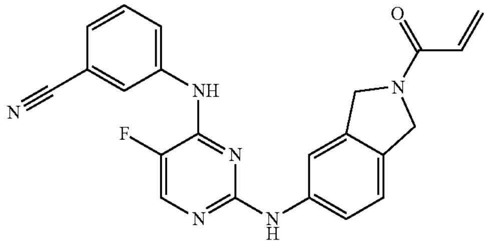 [SMILES: C=CC(=O)N1Cc2ccc(Nc3ncc(F)c(Nc4cccc(C#N)c4)n3)cc2C1] | I-106 |
| 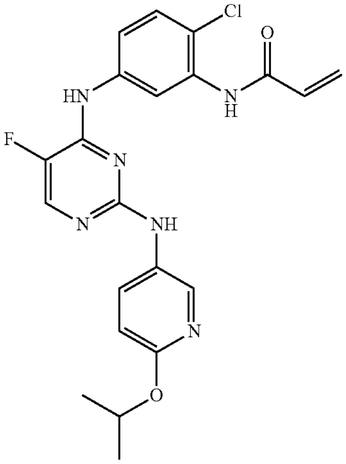 [SMILES: C=CC(=O)Nc1cc(Nc2nc(Nc3ccc(OC(C)C)nc3)ncc2F)ccc1Cl] | I-107 |
| 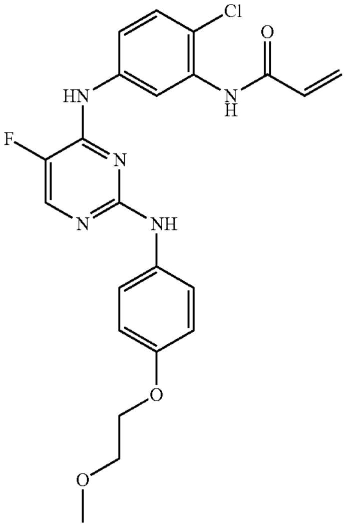 | I-108 |
| 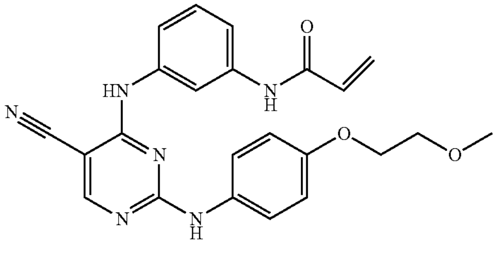 [SMILES: C=CC(=O)Nc1cccc(Nc2nc(Nc3ccc(OCCOC)cc3)ncc2C#N)c1] | I-109 |

TABLE 5-continued
| Exemplary Compounds |
|---|
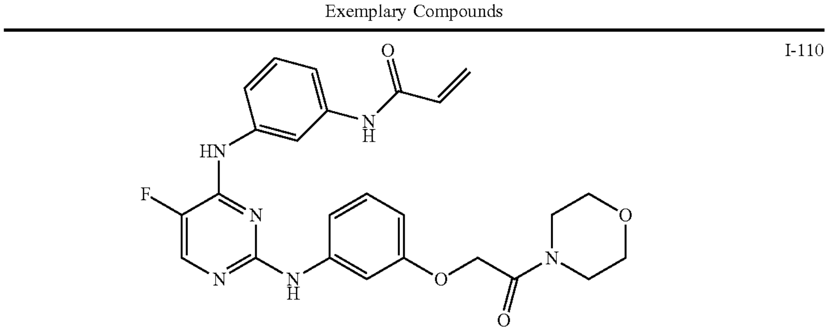
I-110
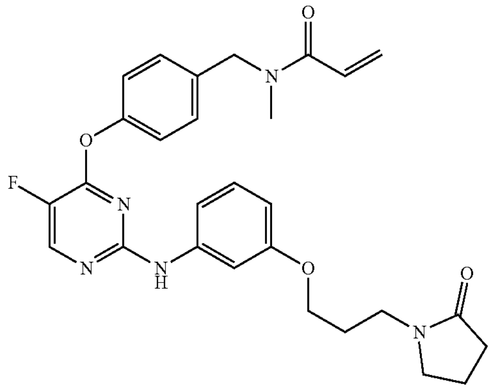 [SMILES: C=CC(=O)N(C)Cc1ccc(Oc2nc(Nc3cccc(OCCCN4CCCC4=O)c3)ncc2F)cc1]
I-111
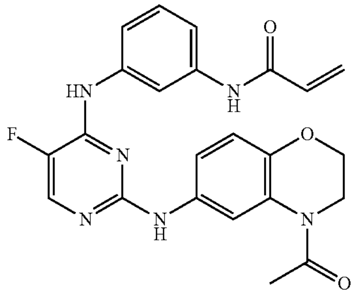 [SMILES: C=CC(=O)Nc1cccc(Nc2nc(Nc3ccc4c(c3)N(C(C)=O)CCO4)ncc2F)c1]
I-112
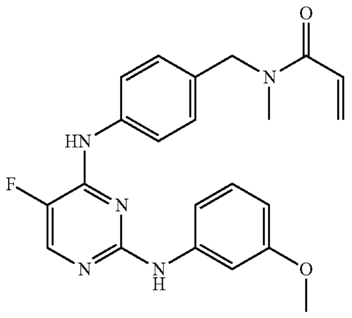 [SMILES: C=CC(=O)N(C)Cc1ccc(Nc2nc(Nc3cccc(OC)c3)ncc2F)cc1]
I-113
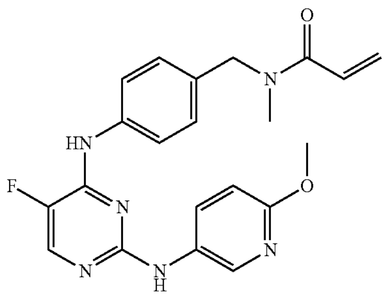 [SMILES: C=CC(=O)N(C)Cc1ccc(Nc2nc(Nc3ccc(OC)nc3)ncc2F)cc1]
I-114

TABLE 5-continued
| Exemplary Compounds |
|---|
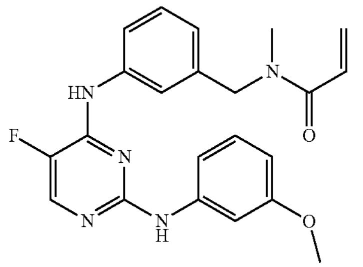 [SMILES: C=CC(=O)N(C)Cc1cccc(Nc2nc(Nc3cccc(OC)c3)ncc2F)c1]
I-115
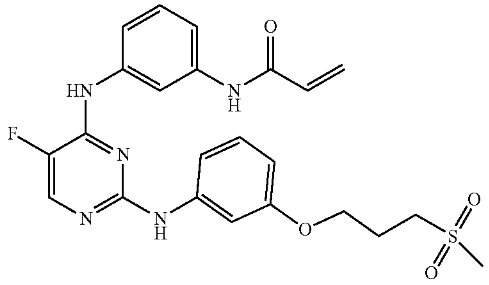 [SMILES: C=CC(=O)Nc1cccc(Nc2nc(Nc3cccc(OCCCS(C)(=O)=O)c3)ncc2F)c1]
I-116
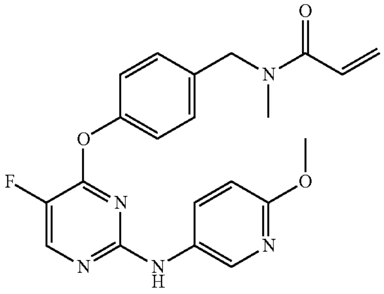 [SMILES: C=CC(=O)N(C)Cc1ccc(Oc2nc(Nc3ccc(OC)nc3)ncc2F)cc1]
I-117
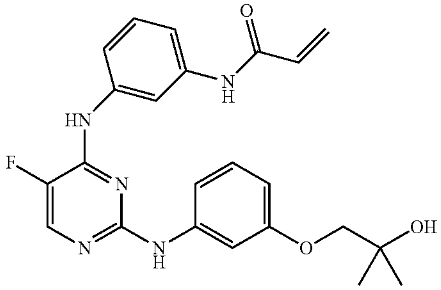 [SMILES: C=CC(=O)Nc1cccc(Nc2nc(Nc3cccc(OCC(C)(C)O)c3)ncc2F)c1]
I-118
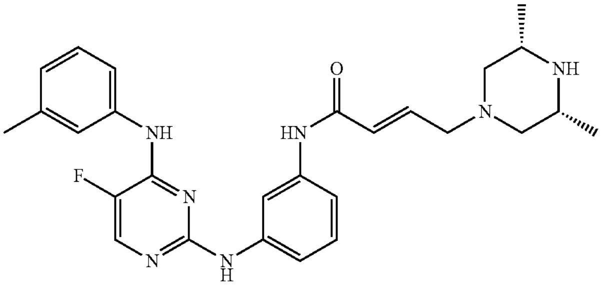
I-119

TABLE 5-continued
Exemplary Compounds
I-120
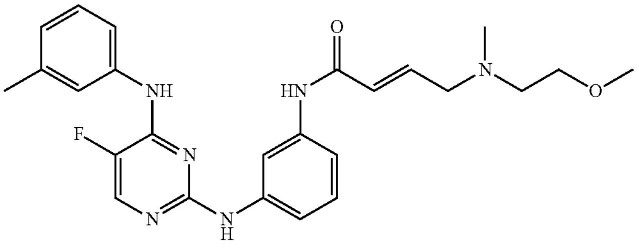
I-121
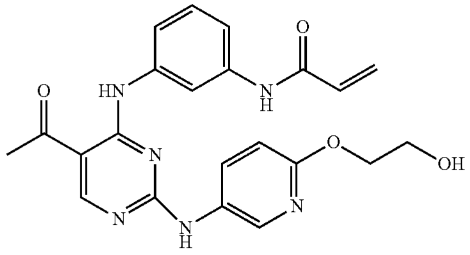 [SMILES: C=CC(=O)Nc1cccc(Nc2nc(Nc3ccc(OCCO)nc3)ncc2C(C)=O)c1]
I-122
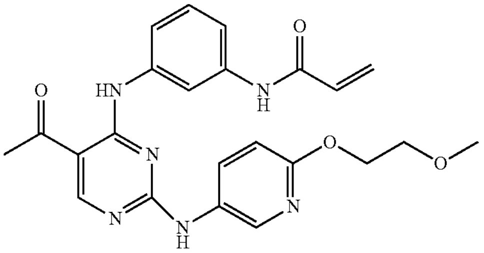 [SMILES: C=CC(=O)Nc1cccc(Nc2nc(Nc3ccc(OCCOC)nc3)ncc2C(C)=O)c1]
I-123
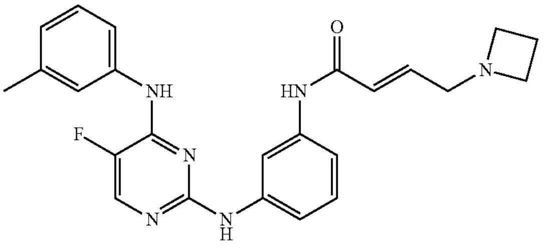 [SMILES: Cc1cccc(Nc2nc(Nc3cccc(NC(=O)/C=C/CN4CCC4)c3)ncc2F)c1]
I-124
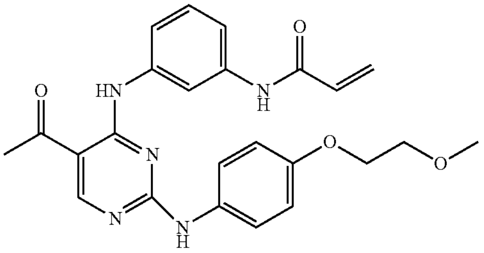 [SMILES: C=CC(=O)Nc1cccc(Nc2nc(Nc3ccc(OCCOC)cc3)ncc2C(C)=O)c1]
I-125
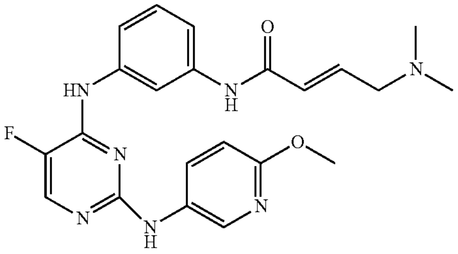 [SMILES: COc1ccc(Nc2ncc(F)c(Nc3cccc(NC(=O)/C=C/CN(C)C)c3)n2)cn1]

TABLE 5-continued
Exemplary Compounds
I-126
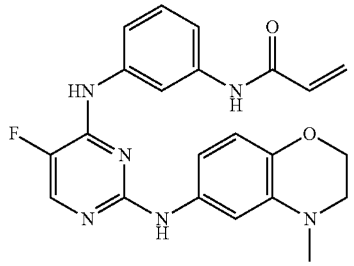 [SMILES: C=CC(=O)Nc1cccc(Nc2nc(Nc3ccc4c(c3)N(C)CCO4)ncc2F)c1]
I-127
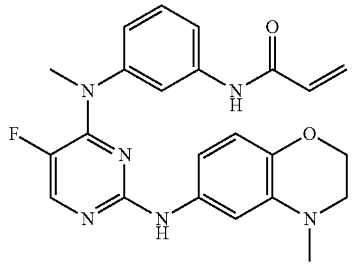 [SMILES: C=CC(=O)Nc1cccc(N(C)c2nc(Nc3ccc4c(c3)N(C)CCO4)ncc2F)c1]
I-128
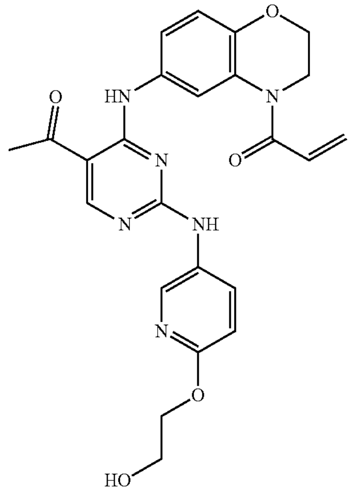 [SMILES: C=CC(=O)N1CCOc2ccc(Nc3nc(Nc4ccc(OCCO)nc4)ncc3C(C)=O)cc21]
I-129
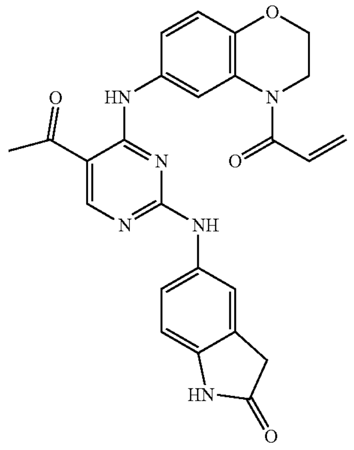 [SMILES: C=CC(=O)N1CCOc2ccc(Nc3nc(Nc4ccc5c(c4)CC(=O)N5)ncc3C(C)=O)cc21]

TABLE 5-continued
| Exemplary Compounds |
| --- |
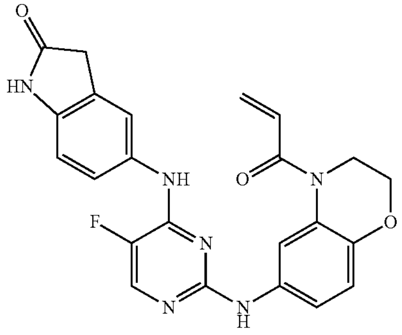 [SMILES: C=CC(=O)N1CCOc2ccc(Nc3ncc(F)c(Nc4ccc5c(c4)CC(=O)N5)n3)cc21]
I-130
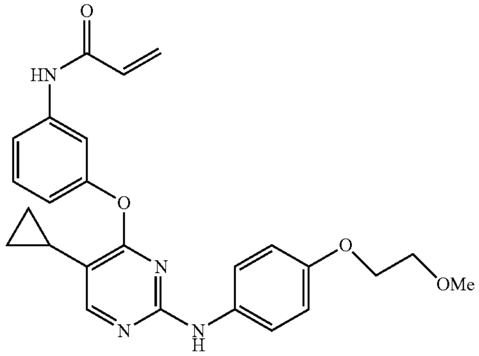 [SMILES: C=CC(=O)Nc1cccc(Oc2nc(Nc3ccc(OCCOC)cc3)ncc2C2CC2)c1]
I-131
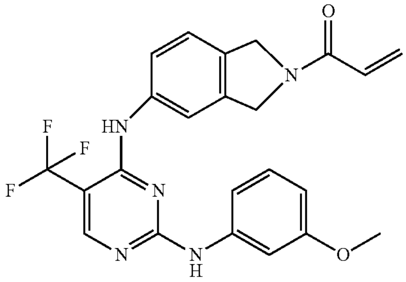 [SMILES: C=CC(=O)N1Cc2ccc(Nc3nc(Nc4cccc(OC)c4)ncc3C(F)(F)F)cc2C1]
I-132
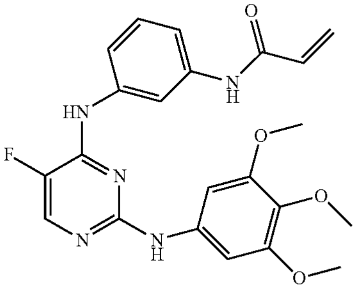 [SMILES: C=CC(=O)Nc1cccc(Nc2nc(Nc3cc(OC)c(OC)c(OC)c3)ncc2F)c1]
I-133
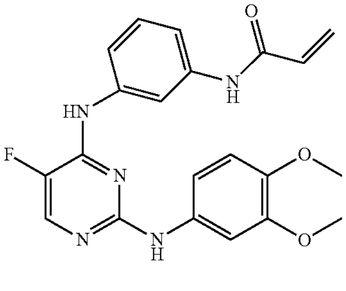 [SMILES: C=CC(=O)Nc1cccc(Nc2nc(Nc3ccc(OC)c(OC)c3)ncc2F)c1]
I-134

TABLE 5-continued
| Exemplary Compounds |
|---|
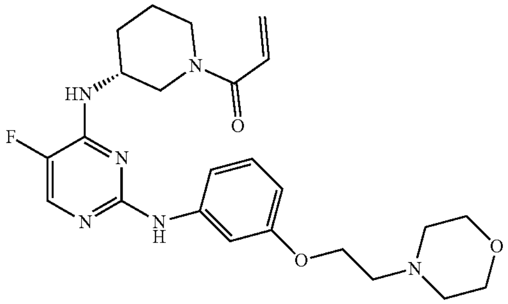
I-135
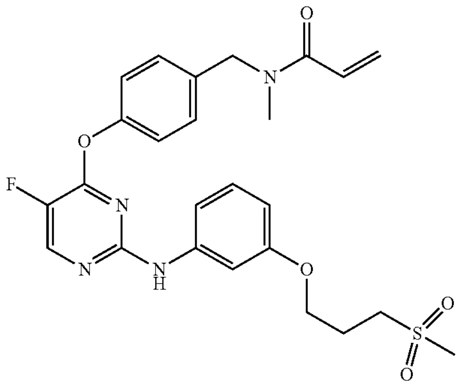 [SMILES: C=CC(=O)N(C)Cc1ccc(Oc2nc(Nc3cccc(OCCCS(C)(=O)=O)c3)ncc2F)cc1]
I-136
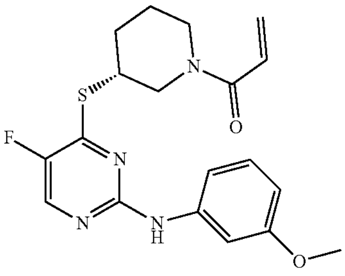 [SMILES: C=CC(=O)N1CCC[C@@H](Sc2nc(Nc3cccc(OC)c3)ncc2F)C1]
I-137
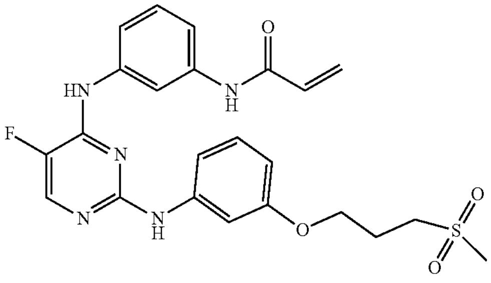 [SMILES: C=CC(=O)Nc1cccc(Nc2nc(Nc3cccc(OCCCS(C)(=O)=O)c3)ncc2F)c1]
I-138

TABLE 5-continued
Exemplary Compounds
I-139
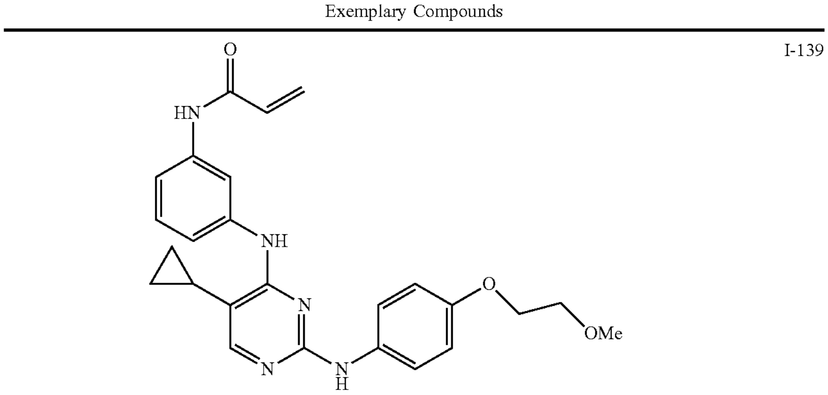
I-140
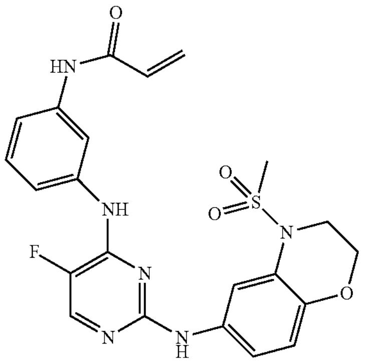 [SMILES: C=CC(=O)Nc1cccc(Nc2nc(Nc3ccc4c(c3)N(S(C)(=O)=O)CCO4)ncc2F)c1]
I-141
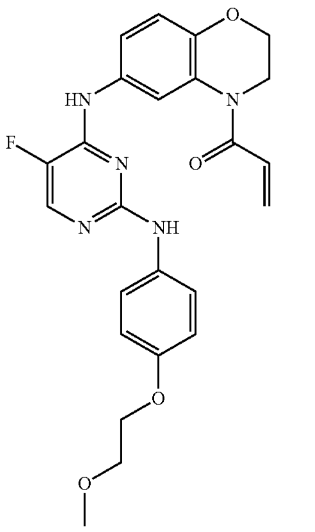 [SMILES: C=CC(=O)N1CCOc2ccc(Nc3nc(Nc4ccc(OCCOC)cc4)ncc3F)cc21]
I-142
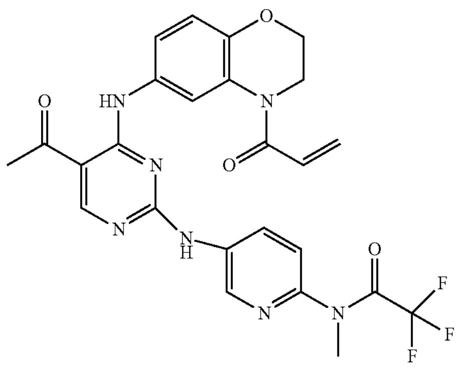 [SMILES: C=CC(=O)N1CCOc2ccc(Nc3nc(Nc4ccc(N(C)C(=O)C(F)(F)F)nc4)ncc3C(C)=O)cc21]

TABLE 5-continued
| Exemplary Compounds |
|---|
I-143
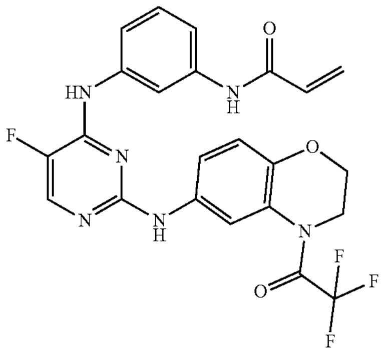 [SMILES: C=CC(=O)Nc1cccc(Nc2nc(Nc3ccc4c(c3)N(C(=O)C(F)(F)F)CCO4)ncc2F)c1]
I-144
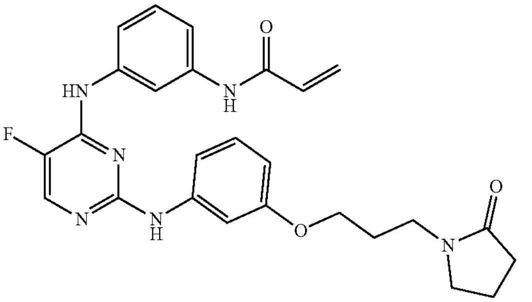 [SMILES: C=CC(=O)Nc1cccc(Nc2nc(Nc3cccc(OCCCN4CCCC4=O)c3)ncc2F)c1]
I-145
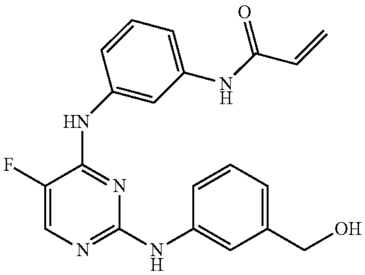 [SMILES: C=CC(=O)Nc1cccc(Nc2nc(Nc3cccc(CO)c3)ncc2F)c1]
I-146
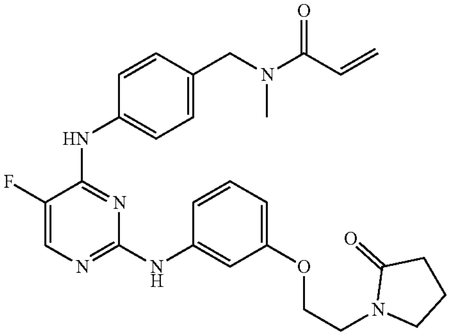 [SMILES: C=CC(=O)N(C)Cc1ccc(Nc2nc(Nc3cccc(OCCN4CCCC4=O)c3)ncc2F)cc1]
I-147
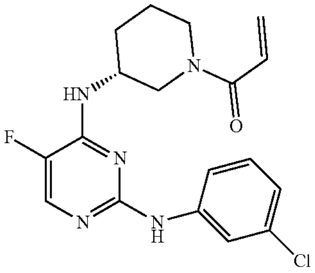 [SMILES: C=CC(=O)N1CCC[C@@H](Nc2nc(Nc3cccc(Cl)c3)ncc2F)C1]

TABLE 5-continued
| Exemplary Compounds | |
|---|---|
| 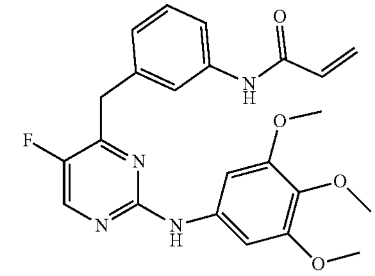 [SMILES: C=CC(=O)Nc1cccc(Cc2nc(Nc3cc(OC)c(OC)c(OC)c3)ncc2F)c1] | I-148 |
| 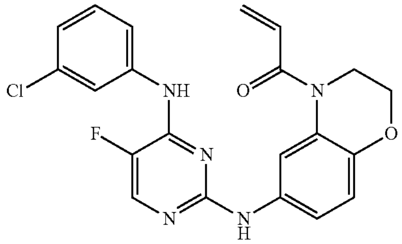 [SMILES: C=CC(=O)N1CCOc2ccc(Nc3ncc(F)c(Nc4cccc(Cl)c4)n3)cc21] | I-149 |
| 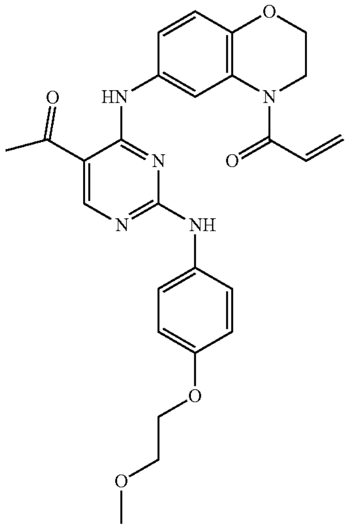 [SMILES: C=CC(=O)N1CCOc2ccc(Nc3nc(Nc4ccc(OCCOC)cc4)ncc3C(C)=O)cc21] | I-150 |
| 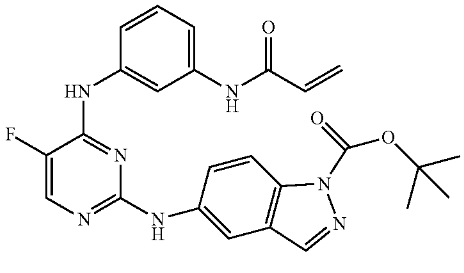 [SMILES: C=CC(=O)Nc1cccc(Nc2nc(Nc3ccc4c(cnn4C(=O)OC(C)(C)C)c3)ncc2F)c1] | I-151 |
| 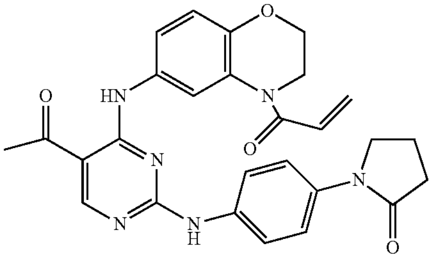 [SMILES: C=CC(=O)N1CCOc2ccc(Nc3nc(Nc4ccc(N5CCCC5=O)cc4)ncc3C(C)=O)cc21] | I-152 |

TABLE 5-continued
| Exemplary Compounds | |
|---|---|
| 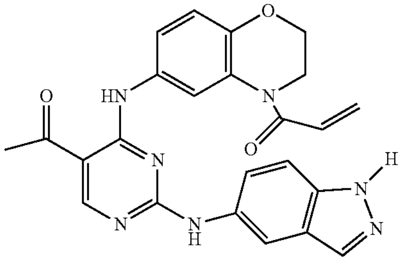 [SMILES: C=CC(=O)N1CCOc2ccc(Nc3nc(Nc4ccc5[nH]ncc5c4)ncc3C(C)=O)cc21] | I-153 |
| 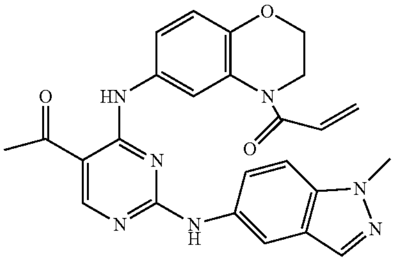 [SMILES: C=CC(=O)N1CCOc2ccc(Nc3nc(Nc4ccc5c(cnn5C)c4)ncc3C(C)=O)cc21] | I-154 |
| 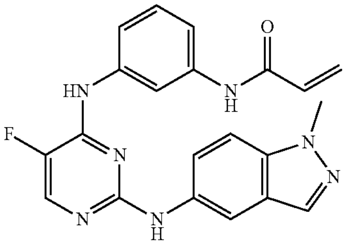 [SMILES: C=CC(=O)Nc1cccc(Nc2nc(Nc3ccc4c(cnn4C)c3)ncc2F)c1] | I-155 |
| 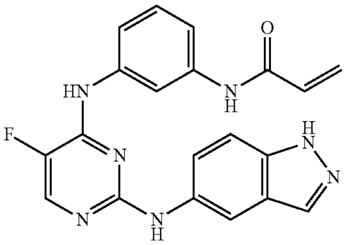 [SMILES: C=CC(=O)Nc1cccc(Nc2nc(Nc3ccc4[nH]ncc4c3)ncc2F)c1] | I-156 |
| 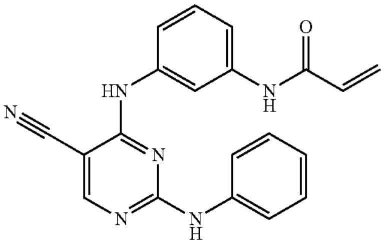 [SMILES: C=CC(=O)Nc1cccc(Nc2nc(Nc3ccccc3)ncc2C#N)c1] | I-157 |
| 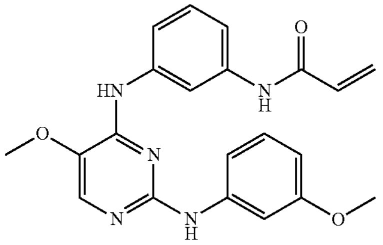 | I-158 |

TABLE 5-continued
Exemplary Compounds
I-159
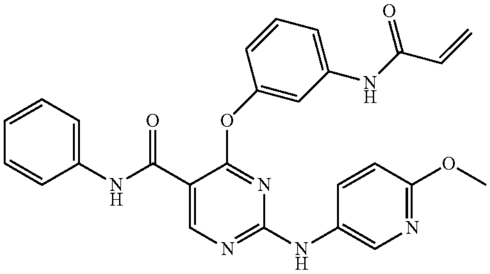 [SMILES: C=CC(=O)Nc1cccc(Oc2nc(Nc3ccc(OC)nc3)ncc2C(=O)Nc2ccccc2)c1]
I-160
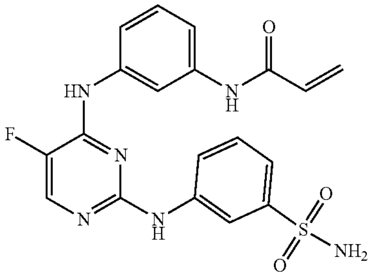 [SMILES: C=CC(=O)Nc1cccc(Nc2nc(Nc3cccc(S(N)(=O)=O)c3)ncc2F)c1]
I-161
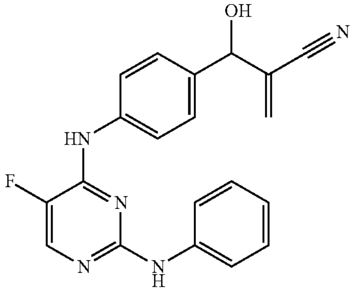 [SMILES: C=C(C#N)C(O)c1ccc(Nc2nc(Nc3ccccc3)ncc2F)cc1]
I-162
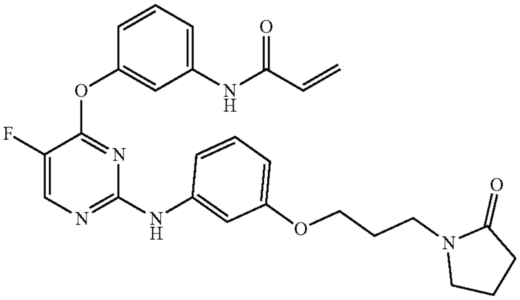 [SMILES: C=CC(=O)Nc1cccc(Oc2nc(Nc3cccc(OCCCN4CCCC4=O)c3)ncc2F)c1]
I-163
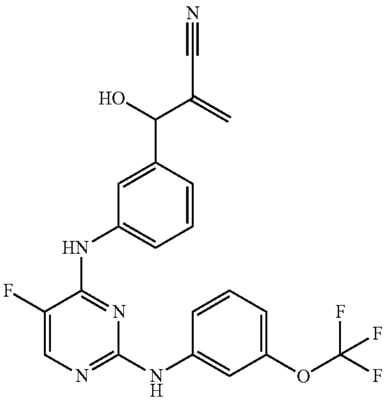 [SMILES: C=C(C#N)C(O)c1cccc(Nc2nc(Nc3cccc(OC(F)(F)F)c3)ncc2F)c1]

TABLE 5-continued
| Exemplary Compounds |
| --- |
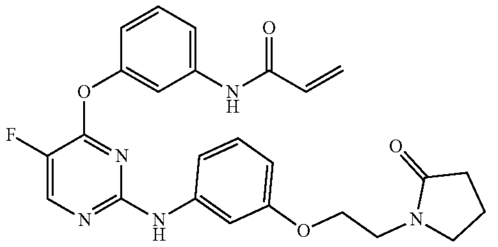 [SMILES: C=CC(=O)Nc1cccc(Oc2nc(Nc3cccc(OCCN4CCCC4=O)c3)ncc2F)c1]
I-164
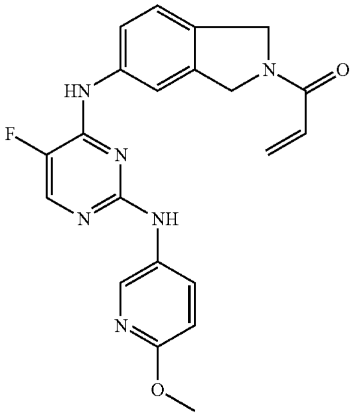 [SMILES: C=CC(=O)N1Cc2ccc(Nc3nc(Nc4ccc(OC)nc4)ncc3F)cc2C1]
I-165
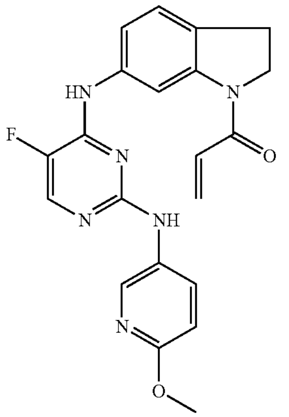 [SMILES: C=CC(=O)N1CCc2ccc(Nc3nc(Nc4ccc(OC)nc4)ncc3F)cc21]
I-166
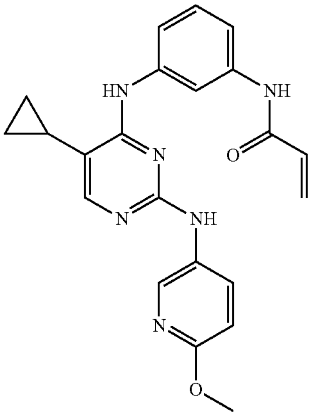 [SMILES: C=CC(=O)Nc1cccc(Nc2nc(Nc3ccc(OC)nc3)ncc2C2CC2)c1]
I-167

TABLE 5-continued
| Exemplary Compounds |
| --- |
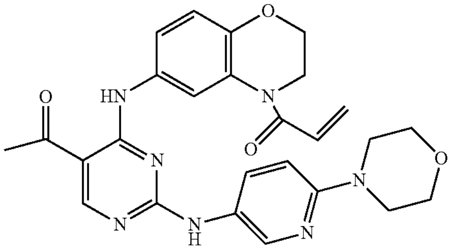 [SMILES: C=CC(=O)N1CCOc2ccc(Nc3nc(Nc4ccc(N5CCOCC5)nc4)ncc3C(C)=O)cc21]
I-168
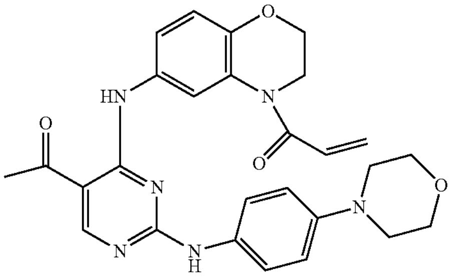 [SMILES: C=CC(=O)N1CCOc2ccc(Nc3nc(Nc4ccc(N5CCOCC5)cc4)ncc3C(C)=O)cc21]
I-169
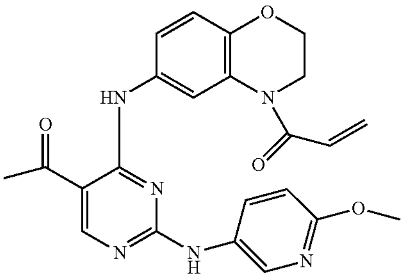 [SMILES: C=CC(=O)N1CCOc2ccc(Nc3nc(Nc4ccc(OC)nc4)ncc3C(C)=O)cc21]
I-170
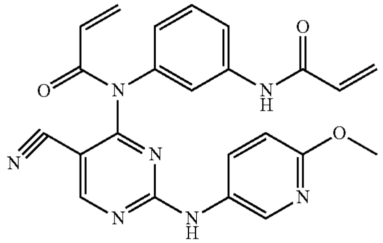 [SMILES: C=CC(=O)Nc1cccc(N(C(=O)C=C)c2nc(Nc3ccc(OC)nc3)ncc2C#N)c1]
I-171
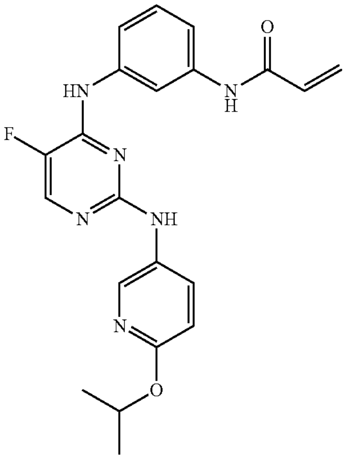 [SMILES: C=CC(=O)Nc1cccc(Nc2nc(Nc3ccc(OC(C)C)nc3)ncc2F)c1]
I-172

TABLE 5-continued
Exemplary Compounds
I-173
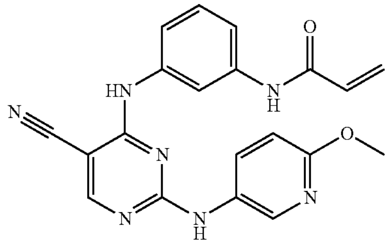 [SMILES: C=CC(=O)Nc1cccc(Nc2nc(Nc3ccc(OC)nc3)ncc2C#N)c1]
I-174
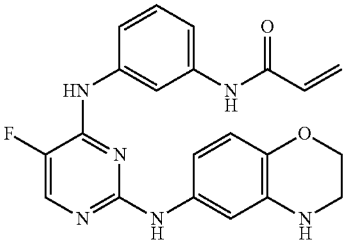 [SMILES: C=CC(=O)Nc1cccc(Nc2nc(Nc3ccc4c(c3)NCCO4)ncc2F)c1]
I-175
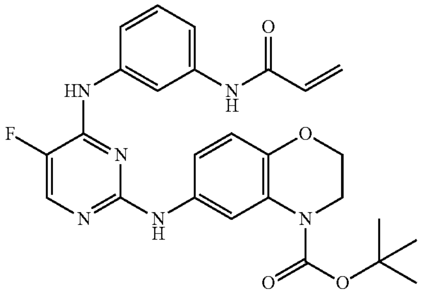 [SMILES: C=CC(=O)Nc1cccc(Nc2nc(Nc3ccc4c(c3)N(C(=O)OC(C)(C)C)CCO4)ncc2F)c1]
I-176
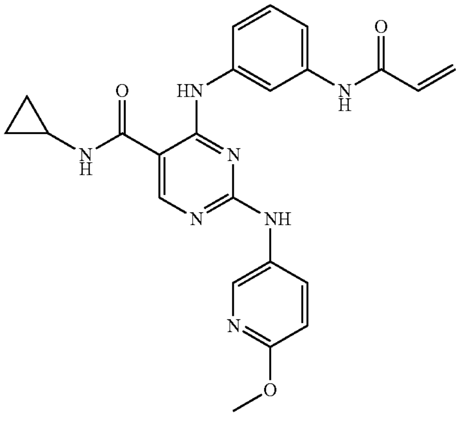 [SMILES: C=CC(=O)Nc1cccc(Nc2nc(Nc3ccc(OC)nc3)ncc2C(=O)NC2CC2)c1]

TABLE 5-continued
| Exemplary Compounds |
|---|
I-177
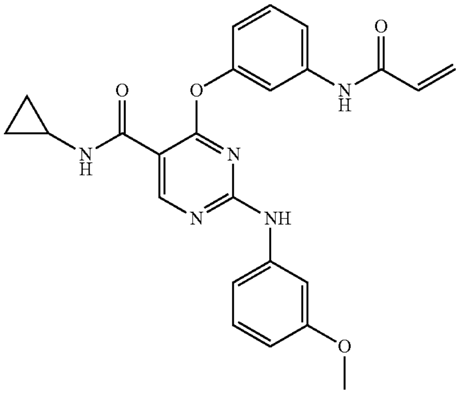 [SMILES: C=CC(=O)Nc1cccc(Oc2nc(Nc3cccc(OC)c3)ncc2C(=O)NC2CC2)c1]
I-178
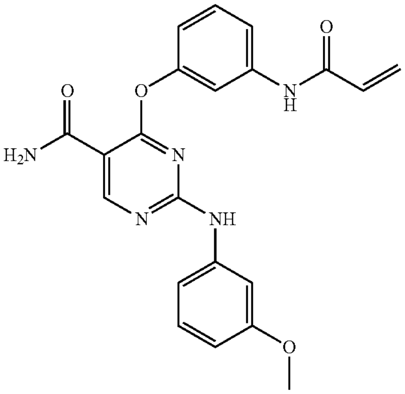 [SMILES: C=CC(=O)Nc1cccc(Oc2nc(Nc3cccc(OC)c3)ncc2C(N)=O)c1]
I-179
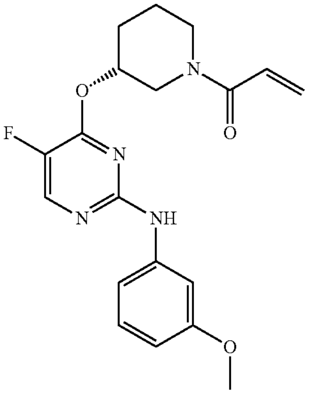
I-180
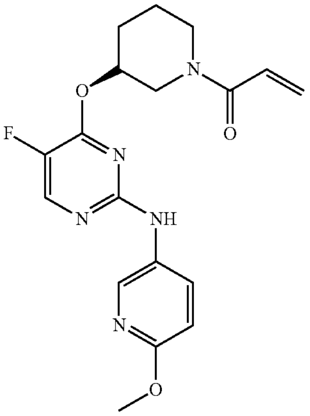

TABLE 5-continued
| Exemplary Compounds |
| --- |
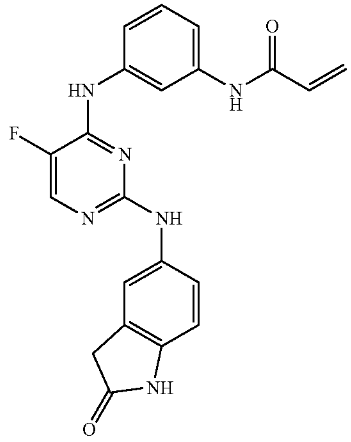 [SMILES: C=CC(=O)Nc1cccc(Nc2nc(Nc3ccc4c(c3)CC(=O)N4)ncc2F)c1]
I-181
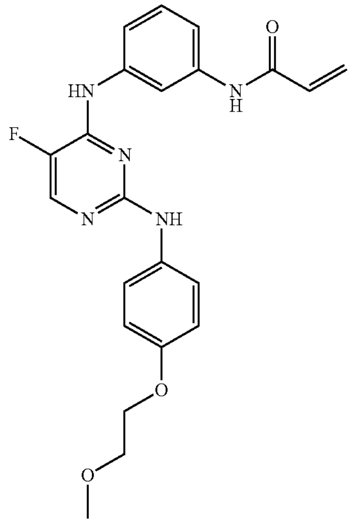 [SMILES: C=CC(=O)Nc1cccc(Nc2nc(Nc3ccc(OCCOC)cc3)ncc2F)c1]
I-182
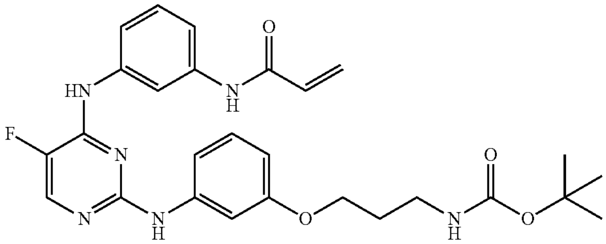 [SMILES: C=CC(=O)Nc1cccc(Nc2nc(Nc3cccc(OCCCNC(=O)OC(C)(C)C)c3)ncc2F)c1]
I-183
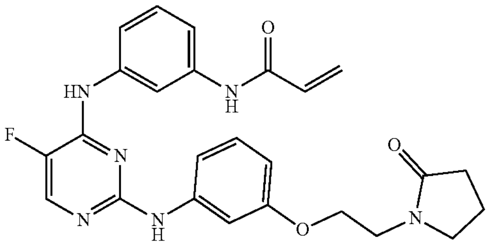 [SMILES: C=CC(=O)Nc1cccc(Nc2nc(Nc3cccc(OCCN4CCCC4=O)c3)ncc2F)c1]
I-184

TABLE 5-continued
| Exemplary Compounds | |
|---|---|
| 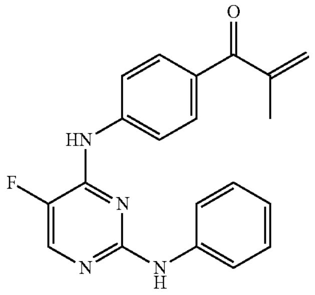 [SMILES: C=C(C)C(=O)c1ccc(Nc2nc(Nc3ccccc3)ncc2F)cc1] | I-185 |
| 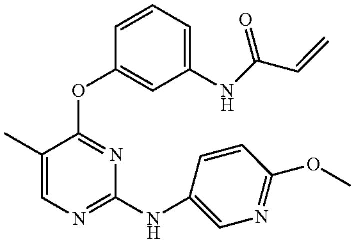 | I-186 |
| 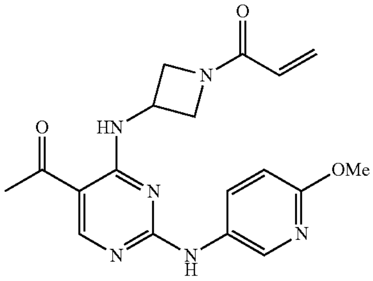 [SMILES: C=CC(=O)N1CC(Nc2nc(Nc3ccc(OC)nc3)ncc2C(C)=O)C1] | I-187 |
| 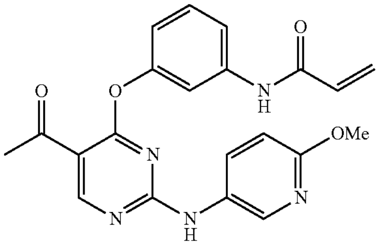 [SMILES: C=CC(=O)Nc1cccc(Oc2nc(Nc3ccc(OC)nc3)ncc2C(C)=O)c1] | I-188 |
| 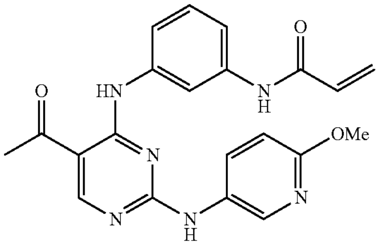 [SMILES: C=CC(=O)Nc1cccc(Nc2nc(Nc3ccc(OC)nc3)ncc2C(C)=O)c1] | I-189 |

TABLE 5-continued
| Exemplary Compounds |
| --- |
I-190
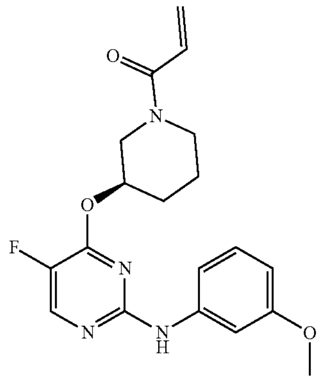 [SMILES: C=CC(=O)N1CCC[C@@H](Oc2nc(Nc3cccc(OC)c3)ncc2F)C1]
I-191
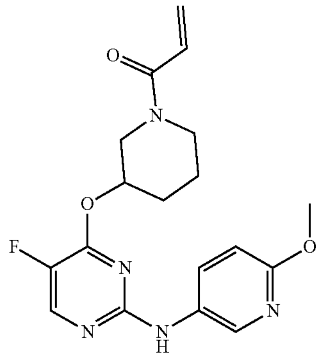 [SMILES: C=CC(=O)N1CCCC(Oc2nc(Nc3ccc(OC)nc3)ncc2F)C1]
I-192
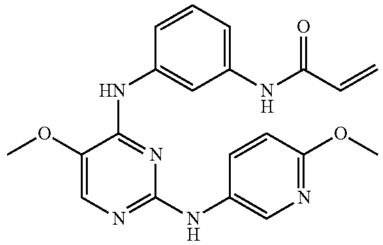
I-193
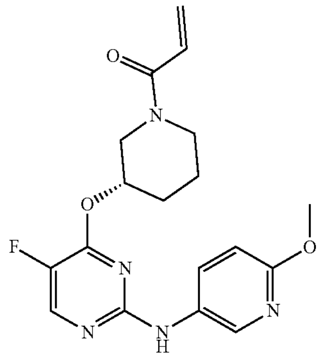

TABLE 5-continued
| Exemplary Compounds |
| --- |
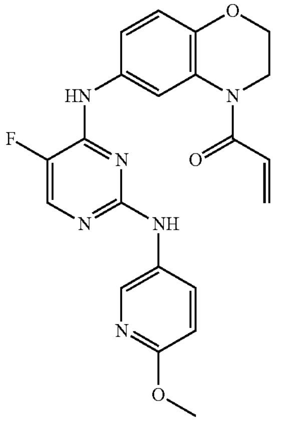 [SMILES: C=CC(=O)N1CCOc2ccc(Nc3nc(Nc4ccc(OC)nc4)ncc3F)cc21]
I-194
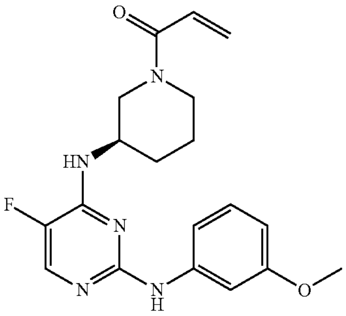 [SMILES: C=CC(=O)N1CCC[C@@H](Nc2nc(Nc3cccc(OC)c3)ncc2F)C1]
I-195
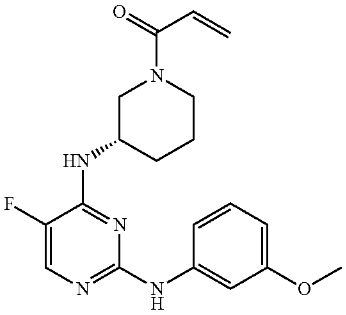 [SMILES: C=CC(=O)N1CCC[C@H](Nc2nc(Nc3cccc(OC)c3)ncc2F)C1]
I-196
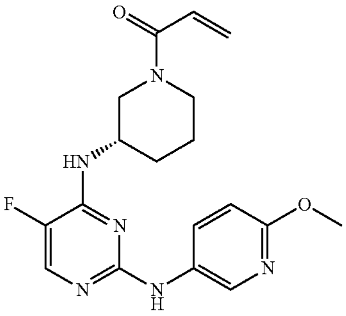 [SMILES: C=CC(=O)N1CCC[C@H](Nc2nc(Nc3ccc(OC)nc3)ncc2F)C1]
I-197

TABLE 5-continued
| Exemplary Compounds |
|---|
I-198
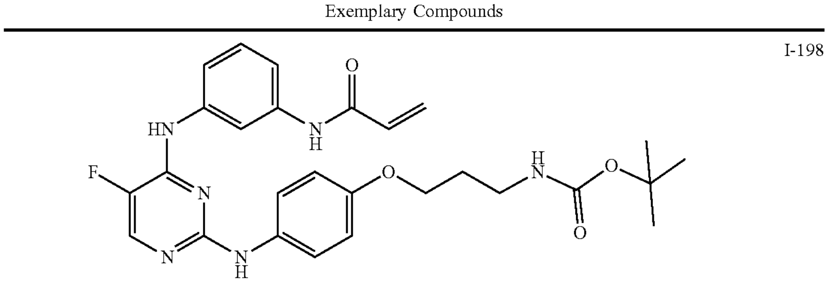
I-199
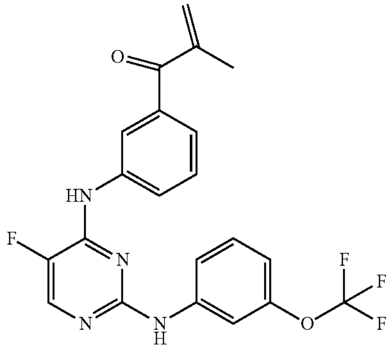 [SMILES: C=C(C)C(=O)c1cccc(Nc2nc(Nc3cccc(OC(F)(F)F)c3)ncc2F)c1]
I-200
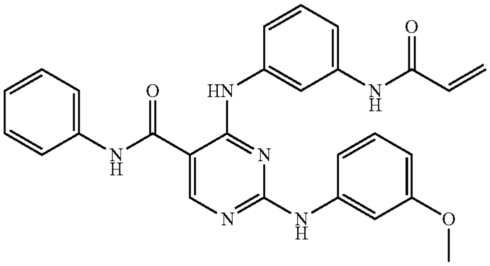 [SMILES: C=CC(=O)Nc1cccc(Nc2nc(Nc3cccc(OC)c3)ncc2C(=O)Nc2ccccc2)c1]
I-201
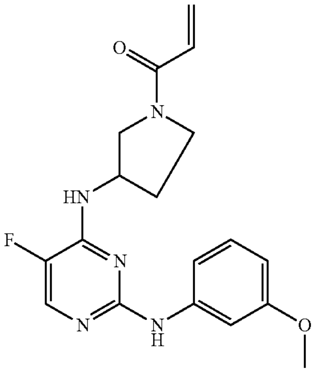 [SMILES: C=CC(=O)N1CCC(Nc2nc(Nc3cccc(OC)c3)ncc2F)C1]
I-202
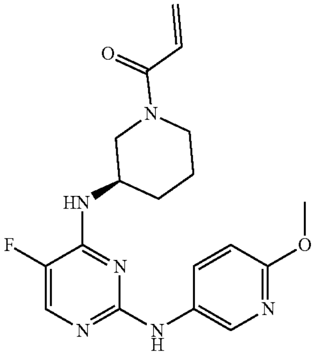 [SMILES: C=CC(=O)N1CCC[C@@H](Nc2nc(Nc3ccc(OC)nc3)ncc2F)C1]

TABLE 5-continued
| Exemplary Compounds |
|---|
| 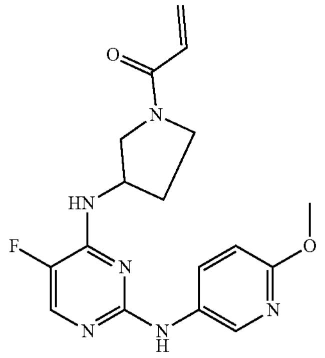 [SMILES: C=CC(=O)N1CCC(Nc2nc(Nc3ccc(OC)nc3)ncc2F)C1] I-203 |
| 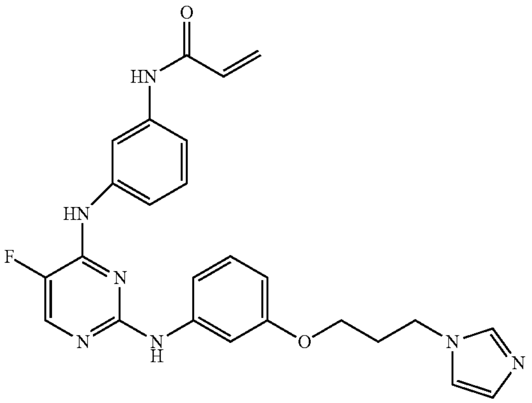 [SMILES: C=CC(=O)Nc1cccc(Nc2nc(Nc3cccc(OCCCn4ccnc4)c3)ncc2F)c1] I-204 |
| 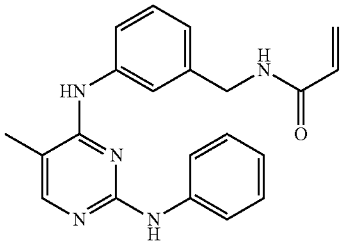 [SMILES: C=CC(=O)NCc1cccc(Nc2nc(Nc3ccccc3)ncc2C)c1] I-205 |
| 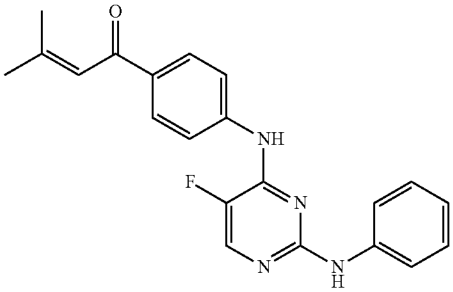 [SMILES: CC(C)=CC(=O)c1ccc(Nc2nc(Nc3ccccc3)ncc2F)cc1] I-206 |

TABLE 5-continued
| Exemplary Compounds |
|---|
| 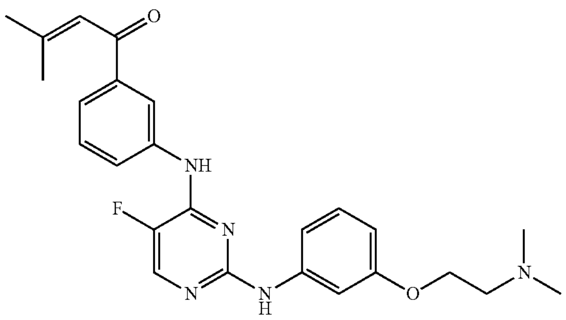 [SMILES: CC(C)=CC(=O)c1cccc(Nc2nc(Nc3cccc(OCCN(C)C)c3)ncc2F)c1] I-207 |
| 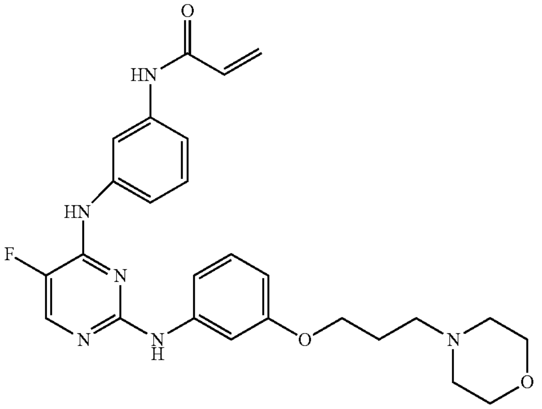 [SMILES: C=CC(=O)Nc1cccc(Nc2nc(Nc3cccc(OCCCN4CCOCC4)c3)ncc2F)c1] I-208 |
| 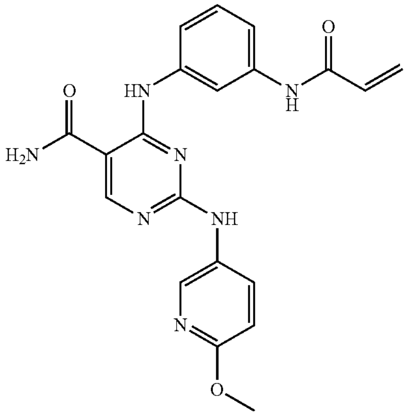 [SMILES: C=CC(=O)Nc1cccc(Nc2nc(Nc3ccc(OC)nc3)ncc2C(N)=O)c1] I-209 |
| 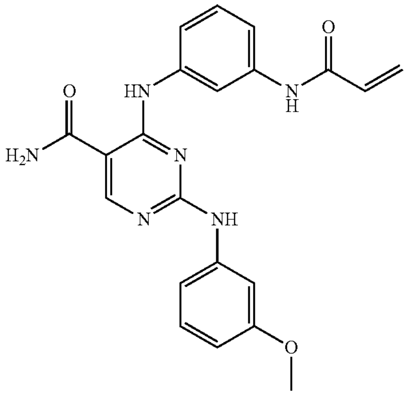 [SMILES: C=CC(=O)Nc1cccc(Nc2nc(Nc3cccc(OC)c3)ncc2C(N)=O)c1] I-210 |

TABLE 5-continued
| Exemplary Compounds | |
|---|---|
| 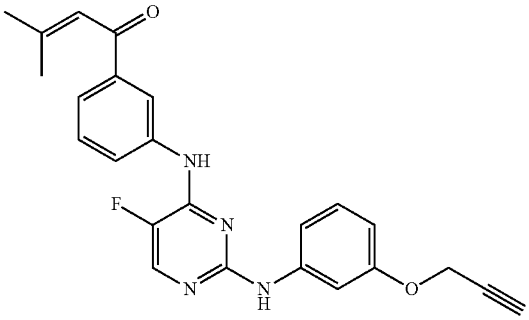 [SMILES: C#CCOc1cccc(Nc2ncc(F)c(Nc3cccc(C(=O)C=C(C)C)c3)n2)c1] | I-211 |
| 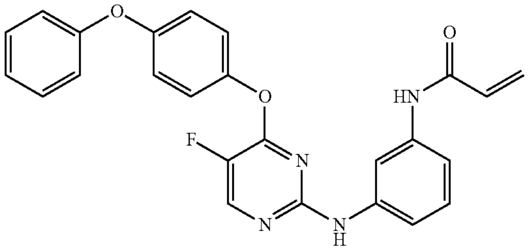 [SMILES: C=CC(=O)Nc1cccc(Nc2ncc(F)c(Oc3ccc(Oc4ccccc4)cc3)n2)c1] | I-212 |
| 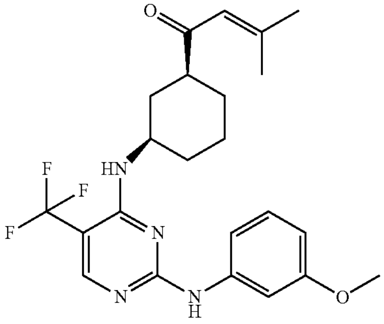 [SMILES: COc1cccc(Nc2ncc(C(F)(F)F)c(N[C@@H]3CCC[C@H](C(=O)C=C(C)C)C3)n2)c1] | I-213 |
| 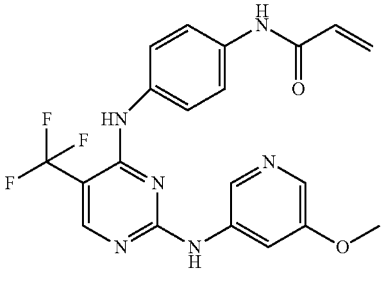 [SMILES: C=CC(=O)Nc1ccc(Nc2nc(Nc3cncc(OC)c3)ncc2C(F)(F)F)cc1] | I-214 |

TABLE 5-continued
| Exemplary Compounds | |
|---|---|
| 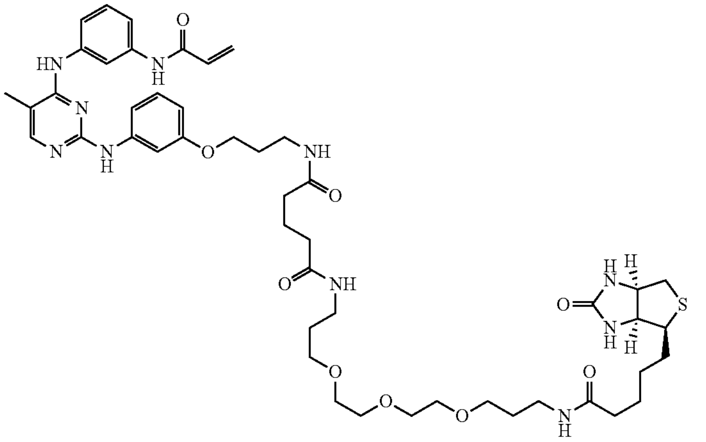 [SMILES: C=CC(=O)Nc1cccc(Nc2nc(Nc3cccc(OCCCNC(=O)CCCC(=O)NCCCOCCOCCOCCCNC(=O)CCCC[C@@H]4SC[C@@H]5NC(=O)N[C@@H]54)c3)ncc2C)c1] | I-215 |
| 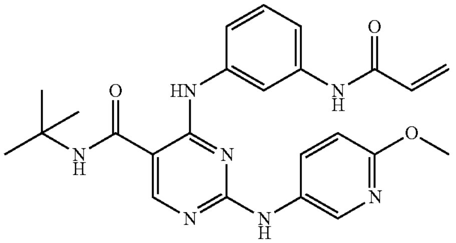 [SMILES: C=CC(=O)Nc1cccc(Nc2nc(Nc3ccc(OC)nc3)ncc2C(=O)NC(C)(C)C)c1] | I-216 |
| 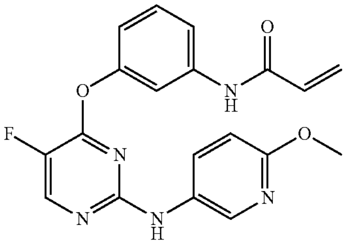 [SMILES: C=CC(=O)Nc1cccc(Oc2nc(Nc3ccc(OC)nc3)ncc2F)c1] | I-217 |
| 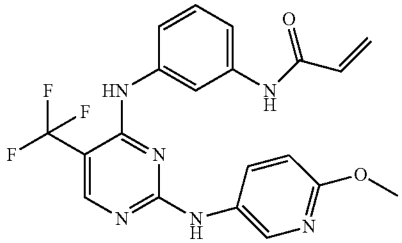 [SMILES: C=CC(=O)Nc1cccc(Nc2nc(Nc3ccc(OC)nc3)ncc2C(F)(F)F)c1] | I-218 |
| 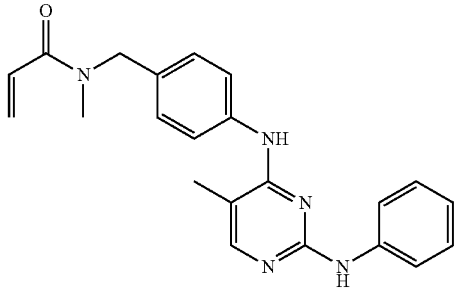 [SMILES: C=CC(=O)N(C)Cc1ccc(Nc2nc(Nc3ccccc3)ncc2C)cc1] | I-219 |

TABLE 5-continued
Exemplary Compounds
I-220
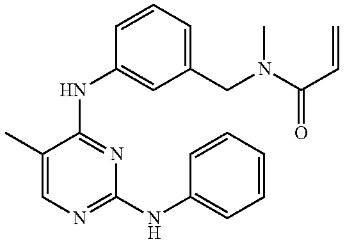 [SMILES: C=CC(=O)N(C)Cc1cccc(Nc2nc(Nc3ccccc3)ncc2C)c1]
I-221
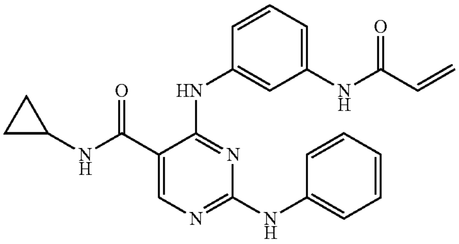 [SMILES: C=CC(=O)Nc1cccc(Nc2nc(Nc3ccccc3)ncc2C(=O)NC2CC2)c1]
I-222
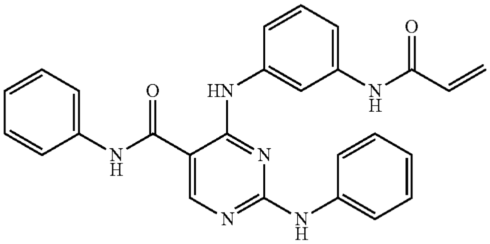 [SMILES: C=CC(=O)Nc1cccc(Nc2nc(Nc3ccccc3)ncc2C(=O)Nc2ccccc2)c1]
I-223
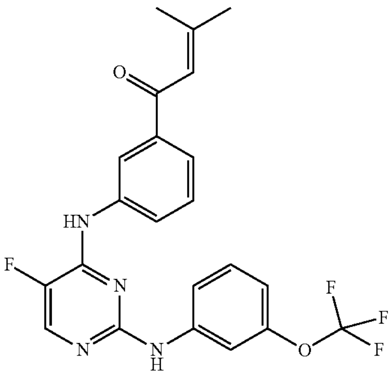 [SMILES: CC(C)=CC(=O)c1cccc(Nc2nc(Nc3cccc(OC(F)(F)F)c3)ncc2F)c1]
I-224
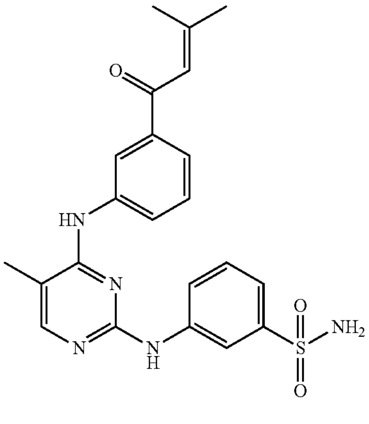 [SMILES: CC(C)=CC(=O)c1cccc(Nc2nc(Nc3cccc(S(N)(=O)=O)c3)ncc2C)c1]

TABLE 5-continued
| Exemplary Compounds | |
| --- | --- |
| 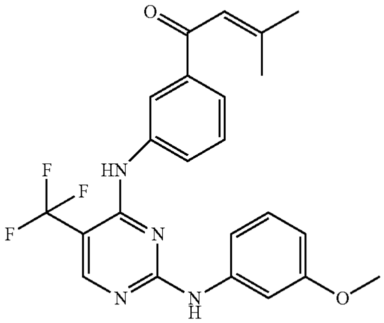 [SMILES: COc1cccc(Nc2ncc(C(F)(F)F)c(Nc3cccc(C(=O)C=C(C)C)c3)n2)c1] | I-225 |
| 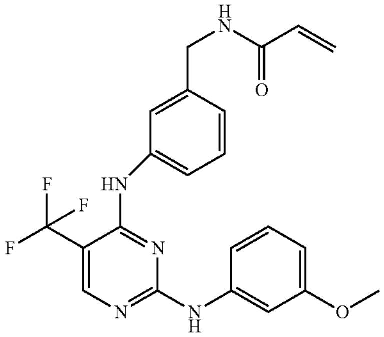 [SMILES: C=CC(=O)NCc1cccc(Nc2nc(Nc3cccc(OC)c3)ncc2C(F)(F)F)c1] | I-226 |
| 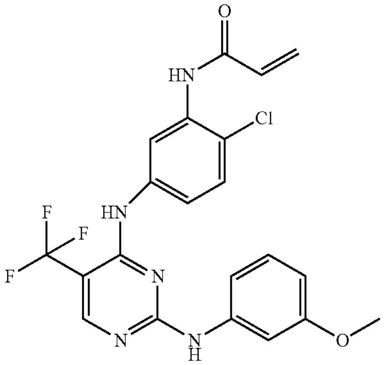 [SMILES: C=CC(=O)Nc1cc(Nc2nc(Nc3cccc(OC)c3)ncc2C(F)(F)F)ccc1Cl] | I-227 |
| 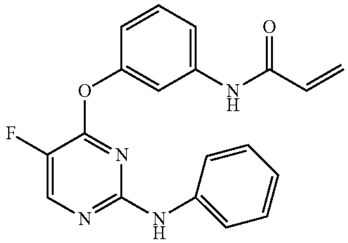 [SMILES: C=CC(=O)Nc1cccc(Oc2nc(Nc3ccccc3)ncc2F)c1] | I-228 |
| 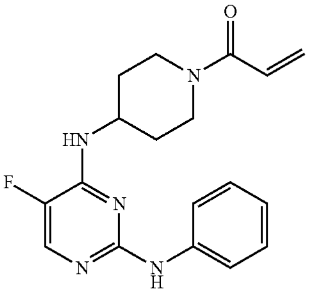 [SMILES: C=CC(=O)N1CCC(Nc2nc(Nc3ccccc3)ncc2F)CC1] | I-229 |

TABLE 5-continued
| Exemplary Compounds |
| --- |
I-230
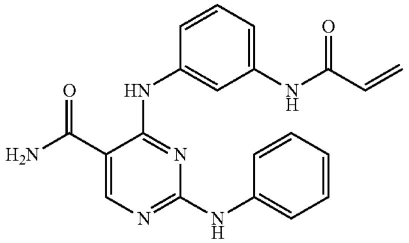 [SMILES: C=CC(=O)Nc1cccc(Nc2nc(Nc3ccccc3)ncc2C(N)=O)c1]
I-231
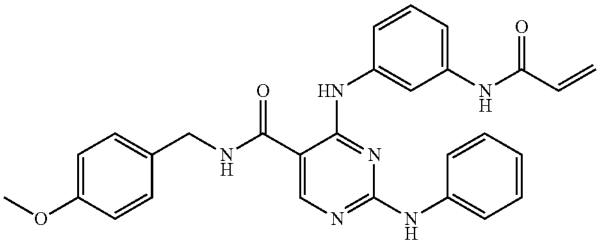 [SMILES: C=CC(=O)Nc1cccc(Nc2nc(Nc3ccccc3)ncc2C(=O)NCc2ccc(OC)cc2)c1]
I-232
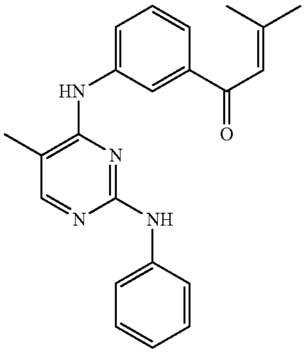 [SMILES: CC(C)=CC(=O)c1cccc(Nc2nc(Nc3ccccc3)ncc2C)c1]
I-233
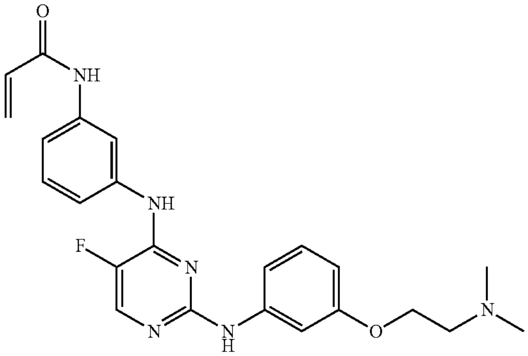 [SMILES: C=CC(=O)Nc1cccc(Nc2nc(Nc3cccc(OCCN(C)C)c3)ncc2F)c1]
I-234
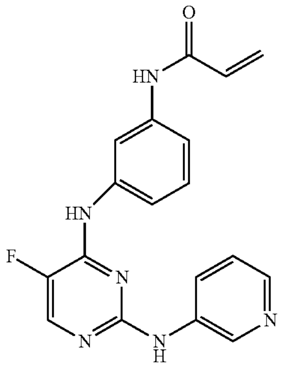 [SMILES: C=CC(=O)Nc1cccc(Nc2nc(Nc3cccnc3)ncc2F)c1]

TABLE 5-continued
| Exemplary Compounds |
| --- |
| 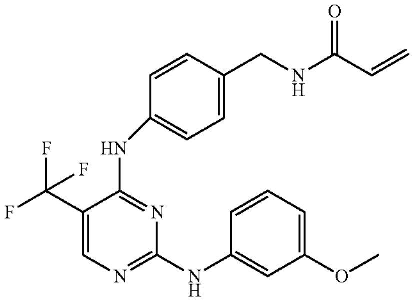 [SMILES: C=CC(=O)NCc1ccc(Nc2nc(Nc3cccc(OC)c3)ncc2C(F)(F)F)cc1] I-235 |
| 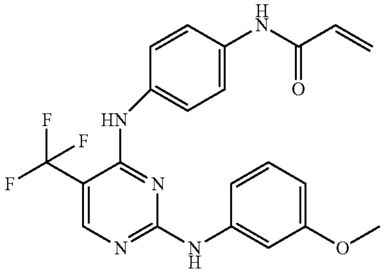 [SMILES: C=CC(=O)Nc1ccc(Nc2nc(Nc3cccc(OC)c3)ncc2C(F)(F)F)cc1] I-236 |
| 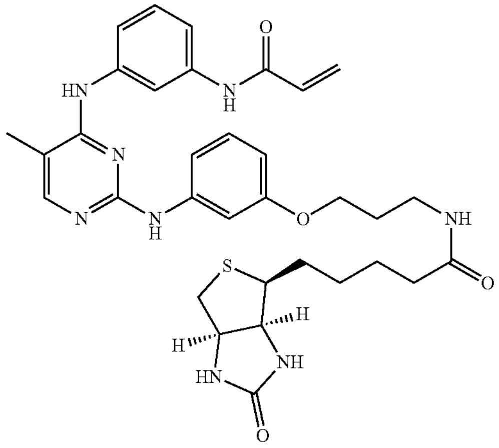 [SMILES: C=CC(=O)Nc1cccc(Nc2nc(Nc3cccc(OCCCNC(=O)CCCC[C@@H]4SC[C@@H]5NC(=O)N[C@@H]54)c3)ncc2C)c1] I-237 |
| 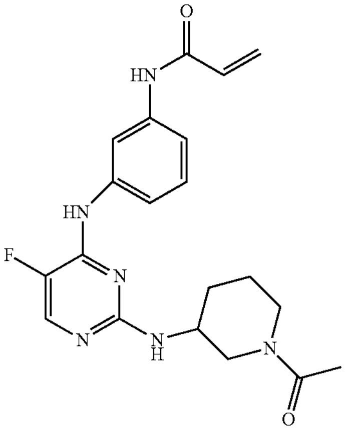 [SMILES: C=CC(=O)Nc1cccc(Nc2nc(NC3CCCN(C(C)=O)C3)ncc2F)c1] I-238 |

TABLE 5-continued
| Exemplary Compounds |
| --- |
| 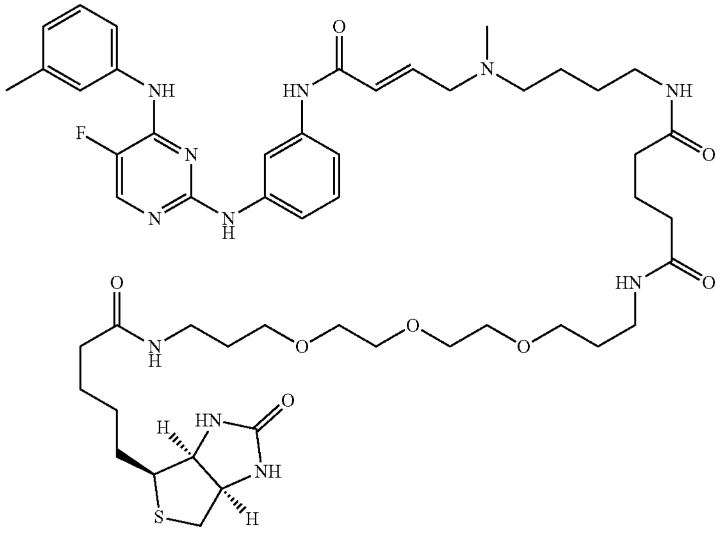 [SMILES: Cc1cccc(Nc2nc(Nc3cccc(NC(=O)/C=C/CN(C)CCCCNC(=O)CCCC(=O)NCCCOCCOCCOCCCNC(=O)CCCC[C@@H]4SC[C@@H]5NC(=O)N[C@@H]54)c3)ncc2F)c1] I-239 |
| 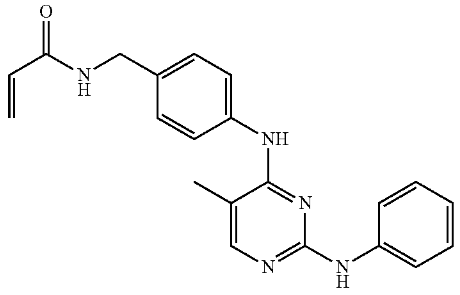 [SMILES: C=CC(=O)NCc1ccc(Nc2nc(Nc3ccccc3)ncc2C)cc1] I-240 |
| 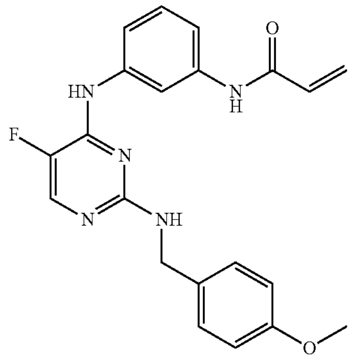 [SMILES: C=CC(=O)Nc1cccc(Nc2nc(NCc3ccc(OC)cc3)ncc2F)c1] I-241 |
| 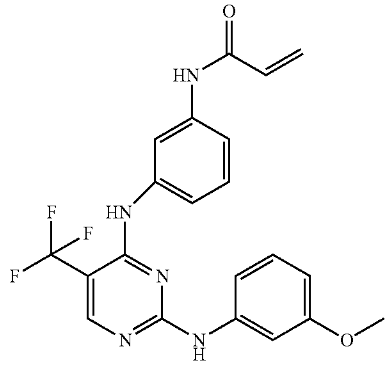 [SMILES: C=CC(=O)Nc1cccc(Nc2nc(Nc3cccc(OC)c3)ncc2C(F)(F)F)c1] I-242 |

TABLE 5-continued
| Exemplary Compounds |
| --- |
| 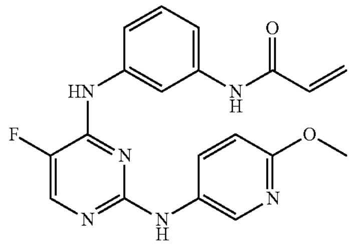 I-243 |
| 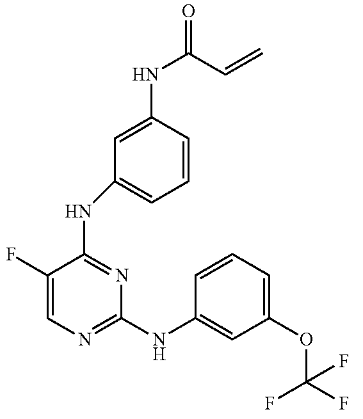 [SMILES: C=CC(=O)Nc1cccc(Nc2nc(Nc3cccc(OC(F)(F)F)c3)ncc2F)c1] I-244 |
| 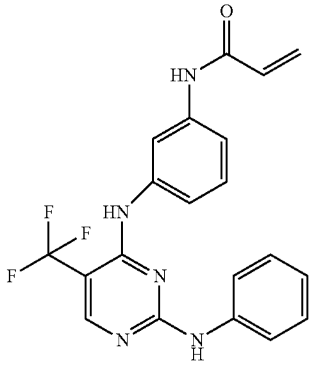 [SMILES: C=CC(=O)Nc1cccc(Nc2nc(Nc3ccccc3)ncc2C(F)(F)F)c1] I-245 |
| 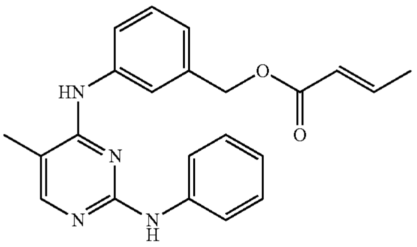 [SMILES: C/C=C/C(=O)OCc1cccc(Nc2nc(Nc3ccccc3)ncc2C)c1] I-246 |

TABLE 5-continued
Exemplary Compounds
I-247
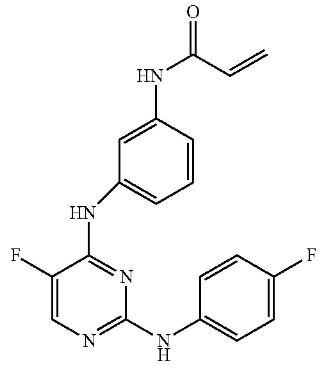 [SMILES: C=CC(=O)Nc1cccc(Nc2nc(Nc3ccc(F)cc3)ncc2F)c1]
I-248
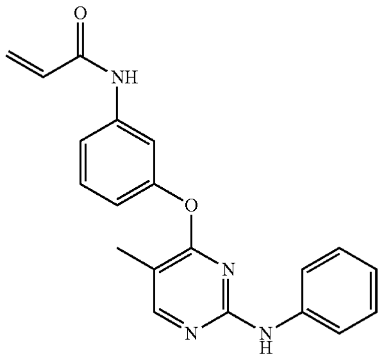 [SMILES: C=CC(=O)Nc1cccc(Oc2nc(Nc3ccccc3)ncc2C)c1]
I-249
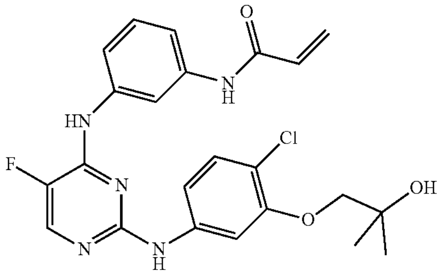 [SMILES: C=CC(=O)Nc1cccc(Nc2nc(Nc3ccc(Cl)c(OCC(C)(C)O)c3)ncc2F)c1]
I-250
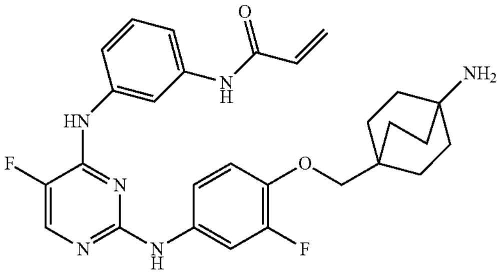 [SMILES: C=CC(=O)Nc1cccc(Nc2nc(Nc3ccc(OCC45CCC(N)(CC4)CC5)c(F)c3)ncc2F)c1]

TABLE 5-continued
| Exemplary Compounds | |
|---|---|
| 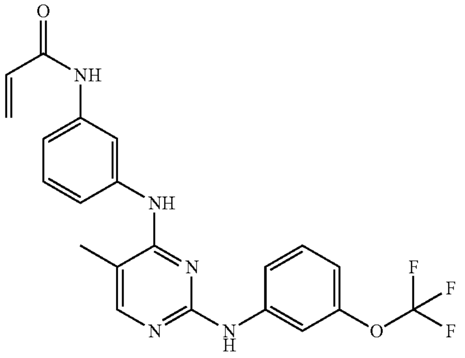 [SMILES: C=CC(=O)Nc1cccc(Nc2nc(Nc3cccc(OC(F)(F)F)c3)ncc2C)c1] | I-251 |
| 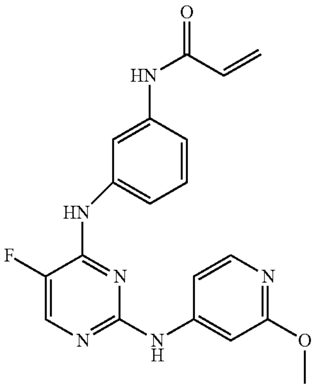 [SMILES: C=CC(=O)Nc1cccc(Nc2nc(Nc3ccnc(OC)c3)ncc2F)c1] | I-252 |
| 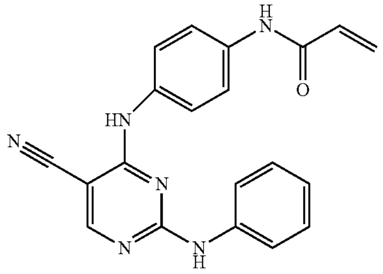 [SMILES: C=CC(=O)Nc1ccc(Nc2nc(Nc3ccccc3)ncc2C#N)cc1] | I-253 |
| 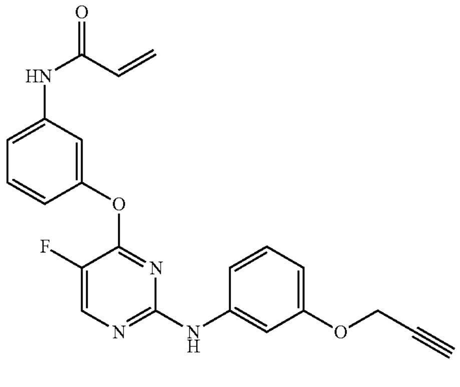 [SMILES: C#CCOc1cccc(Nc2ncc(F)c(Oc3cccc(NC(=O)C=C)c3)n2)c1] | I-254 |

TABLE 5-continued
| Exemplary Compounds | |
|---|---|
| 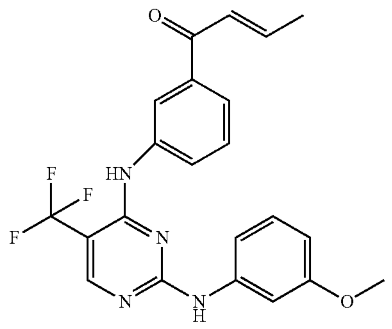 [SMILES: C/C=C/C(=O)c1cccc(Nc2nc(Nc3cccc(OC)c3)ncc2C(F)(F)F)c1] | I-255 |
| 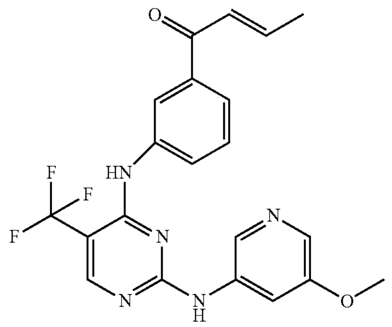 [SMILES: C/C=C/C(=O)c1cccc(Nc2nc(Nc3cncc(OC)c3)ncc2C(F)(F)F)c1] | I-256 |
| 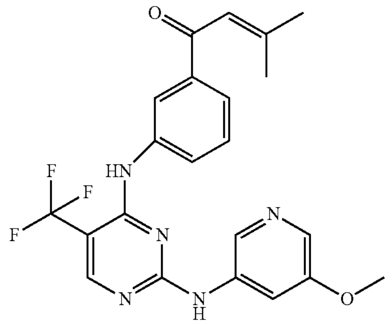 [SMILES: COc1cncc(Nc2ncc(C(F)(F)F)c(Nc3cccc(C(=O)C=C(C)C)c3)n2)c1] | I-257 |
| 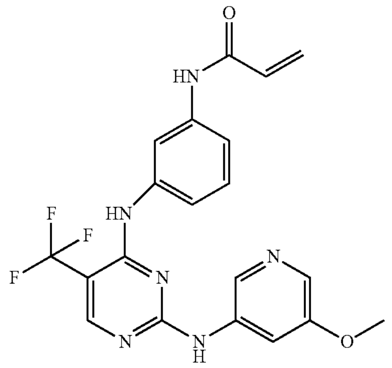 [SMILES: C=CC(=O)Nc1cccc(Nc2nc(Nc3cncc(OC)c3)ncc2C(F)(F)F)c1] | I-258 |

TABLE 5-continued
| Exemplary Compounds |
| --- |
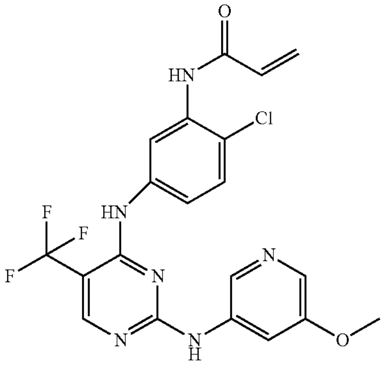 [SMILES: C=CC(=O)Nc1cc(Nc2nc(Nc3cncc(OC)c3)ncc2C(F)(F)F)ccc1Cl]
I-259
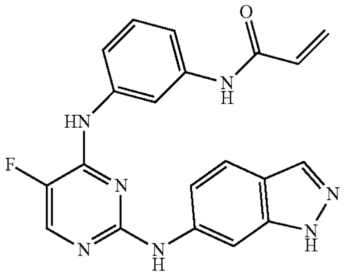 [SMILES: C=CC(=O)Nc1cccc(Nc2nc(Nc3ccc4cn[nH]c4c3)ncc2F)c1]
I-260
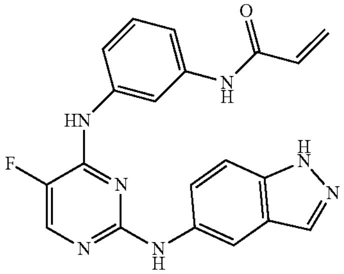 [SMILES: C=CC(=O)Nc1cccc(Nc2nc(Nc3ccc4[nH]ncc4c3)ncc2F)c1]
I-261
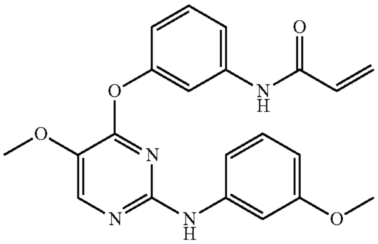 [SMILES: C=CC(=O)Nc1cccc(Oc2nc(Nc3cccc(OC)c3)ncc2OC)c1]
I-262
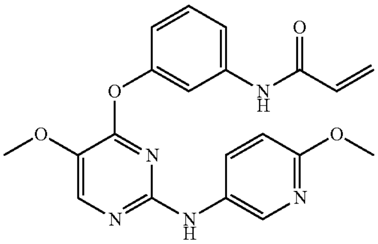
I-263

TABLE 5-continued
Exemplary Compounds
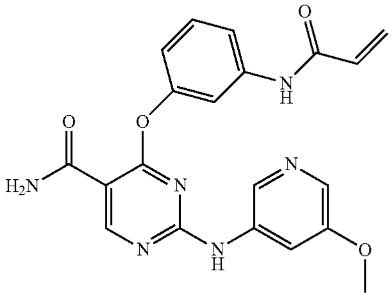 [SMILES: C=CC(=O)Nc1cccc(Oc2nc(Nc3cncc(OC)c3)ncc2C(N)=O)c1]
I-264
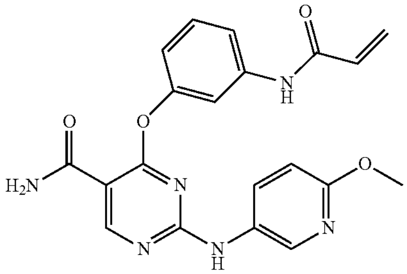 [SMILES: C=CC(=O)Nc1cccc(Oc2nc(Nc3ccc(OC)nc3)ncc2C(N)=O)c1]
I-265
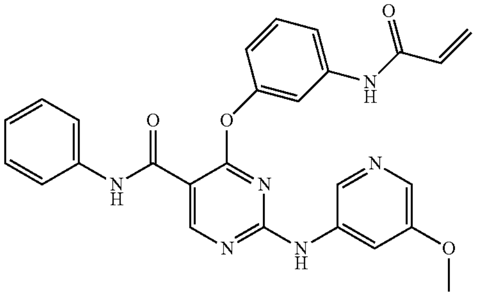 [SMILES: C=CC(=O)Nc1cccc(Oc2nc(Nc3cncc(OC)c3)ncc2C(=O)Nc2ccccc2)c1]
I-266
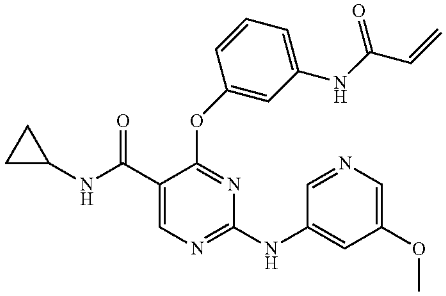 [SMILES: C=CC(=O)Nc1cccc(Oc2nc(Nc3cncc(OC)c3)ncc2C(=O)NC2CC2)c1]
I-267
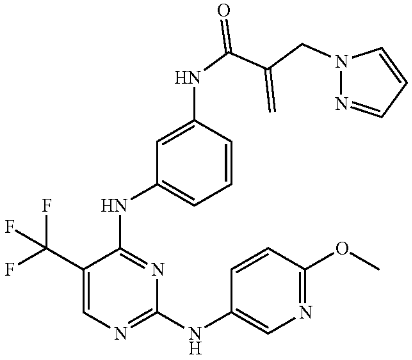 [SMILES: C=C(Cn1cccn1)C(=O)Nc1cccc(Nc2nc(Nc3ccc(OC)nc3)ncc2C(F)(F)F)c1]
I-268

TABLE 5-continued
Exemplary Compounds
I-269
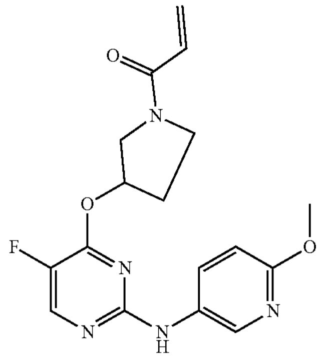 [SMILES: C=CC(=O)N1CCC(Oc2nc(Nc3ccc(OC)nc3)ncc2F)C1]
I-270
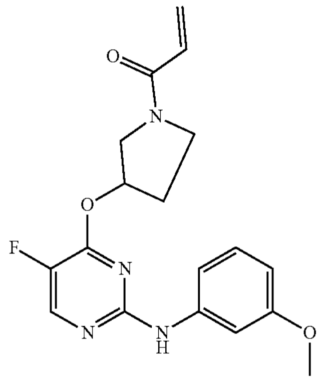 [SMILES: C=CC(=O)N1CCC(Oc2nc(Nc3cccc(OC)c3)ncc2F)C1]
I-271
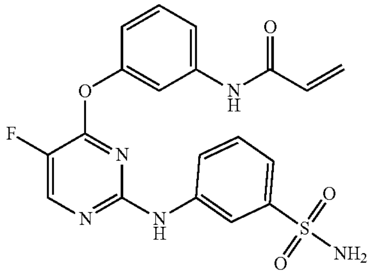 [SMILES: C=CC(=O)Nc1cccc(Oc2nc(Nc3cccc(S(N)(=O)=O)c3)ncc2F)c1]
I-272
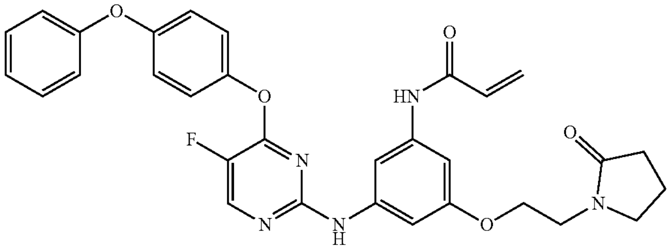 [SMILES: C=CC(=O)Nc1cc(Nc2ncc(F)c(Oc3ccc(Oc4ccccc4)cc3)n2)cc(OCCN2CCCC2=O)c1]
I-273
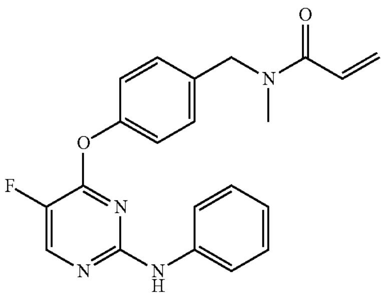 [SMILES: C=CC(=O)N(C)Cc1ccc(Oc2nc(Nc3ccccc3)ncc2F)cc1]

TABLE 5-continued
| Exemplary Compounds | |
|---|---|
| 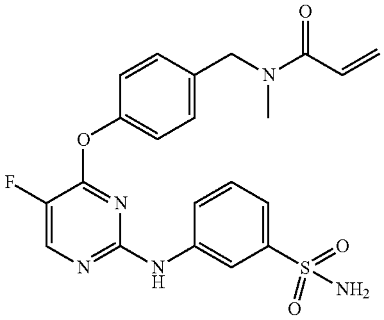 [SMILES: C=CC(=O)N(C)Cc1ccc(Oc2nc(Nc3cccc(S(N)(=O)=O)c3)ncc2F)cc1] | I-274 |
| 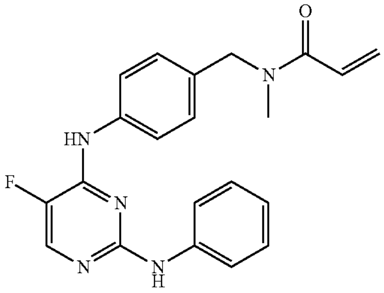 [SMILES: C=CC(=O)N(C)Cc1ccc(Nc2nc(Nc3ccccc3)ncc2F)cc1] | I-275 |
| 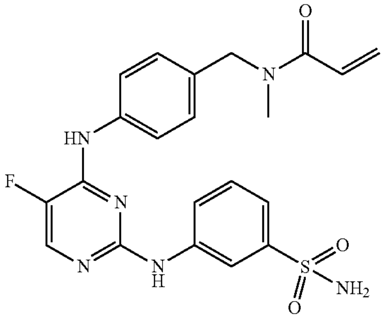 [SMILES: C=CC(=O)N(C)Cc1ccc(Nc2nc(Nc3cccc(S(N)(=O)=O)c3)ncc2F)cc1] | I-276 |
| 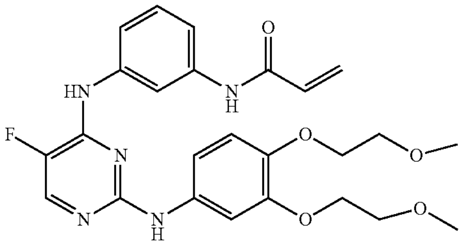 [SMILES: C=CC(=O)Nc1cccc(Nc2nc(Nc3ccc(OCCOC)c(OCCOC)c3)ncc2F)c1] | I-277 |
| 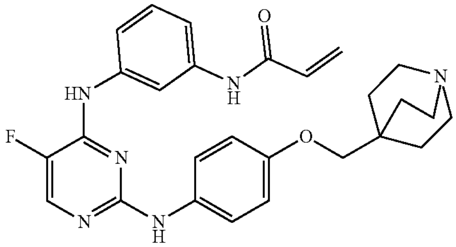 [SMILES: C=CC(=O)Nc1cccc(Nc2nc(Nc3ccc(OCC45CCN(CC4)CC5)cc3)ncc2F)c1] | I-278 |

TABLE 5-continued
| Exemplary Compounds | |
|---|---|
| 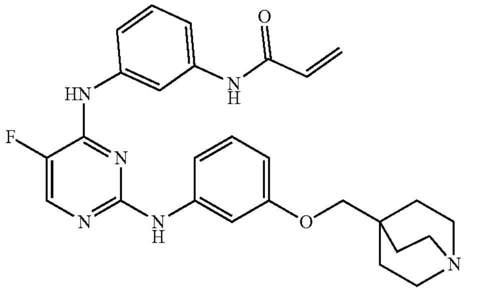 [SMILES: C=CC(=O)Nc1cccc(Nc2nc(Nc3cccc(OCC45CCN(CC4)CC5)c3)ncc2F)c1] | I-279 |
| 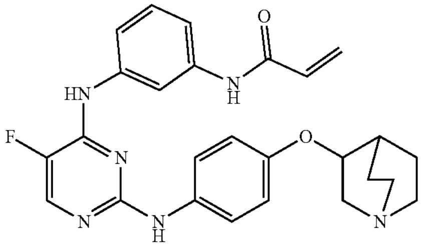 [SMILES: C=CC(=O)Nc1cccc(Nc2nc(Nc3ccc(OC4CN5CCC4CC5)cc3)ncc2F)c1] | I-280 |
| 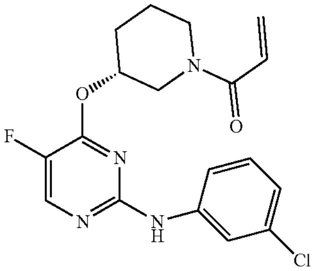 [SMILES: C=CC(=O)N1CCC[C@@H](Oc2nc(Nc3cccc(Cl)c3)ncc2F)C1] | I-281 |
| 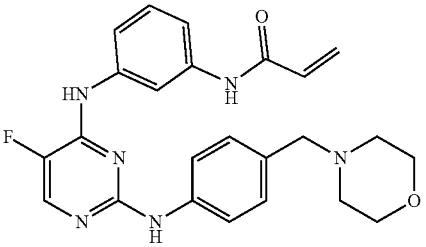 [SMILES: C=CC(=O)Nc1cccc(Nc2nc(Nc3ccc(CN4CCOCC4)cc3)ncc2F)c1] | I-282 |
| 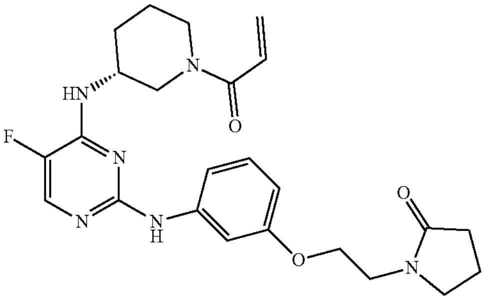 [SMILES: C=CC(=O)N1CCC[C@@H](Nc2nc(Nc3cccc(OCCN4CCCC4=O)c3)ncc2F)C1] | I-283 |

TABLE 5-continued
| Exemplary Compounds | |
|---|---|
| 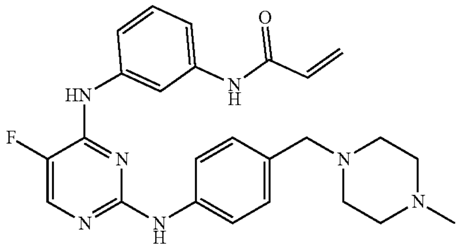 [SMILES: C=CC(=O)Nc1cccc(Nc2nc(Nc3ccc(CN4CCN(C)CC4)cc3)ncc2F)c1] | I-284 |
| 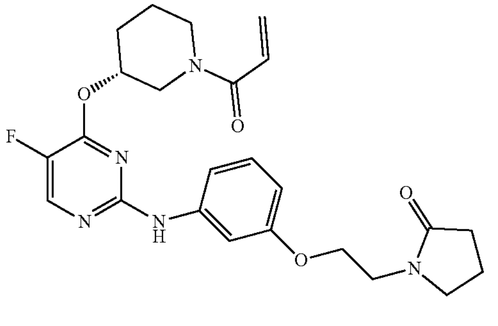 [SMILES: C=CC(=O)N1CCC[C@@H](Oc2nc(Nc3cccc(OCCN4CCCC4=O)c3)ncc2F)C1] | I-285 |
| 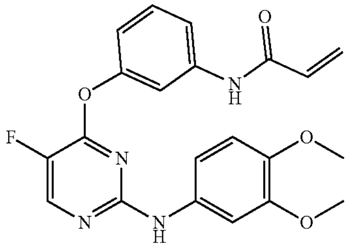 [SMILES: C=CC(=O)Nc1cccc(Oc2nc(Nc3ccc(OC)c(OC)c3)ncc2F)c1] | I-286 |
| 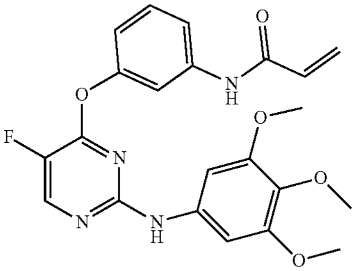 [SMILES: C=CC(=O)Nc1cccc(Oc2nc(Nc3cc(OC)c(OC)c(OC)c3)ncc2F)c1] | I-287 |
| 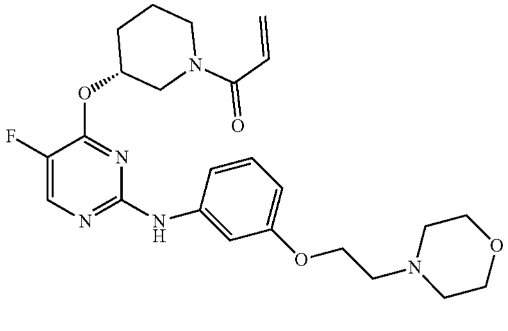 [SMILES: C=CC(=O)N1CCC[C@@H](Oc2nc(Nc3cccc(OCCN4CCOCC4)c3)ncc2F)C1] | I-288 |

TABLE 5-continued
| Exemplary Compounds | |
|---|---|
| 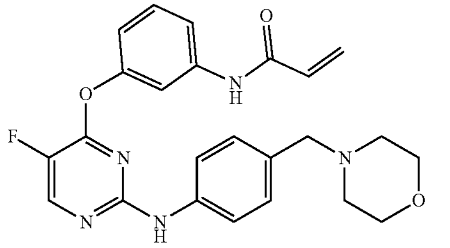 [SMILES: C=CC(=O)Nc1cccc(Oc2nc(Nc3ccc(CN4CCOCC4)cc3)ncc2F)c1] | I-289 |
| 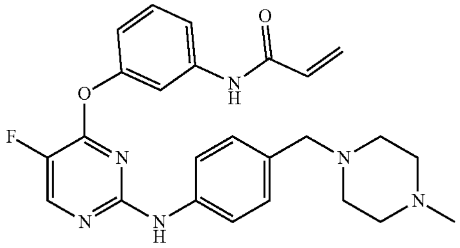 [SMILES: C=CC(=O)Nc1cccc(Oc2nc(Nc3ccc(CN4CCN(C)CC4)cc3)ncc2F)c1] | I-290 |
| 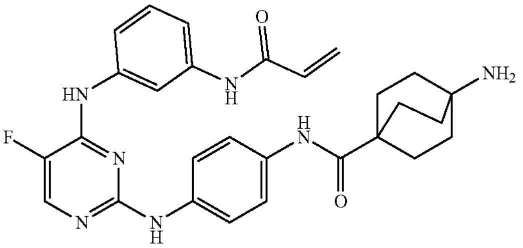 [SMILES: C=CC(=O)Nc1cccc(Nc2nc(Nc3ccc(NC(=O)C45CCC(N)(CC4)CC5)cc3)ncc2F)c1] | I-291 |
| 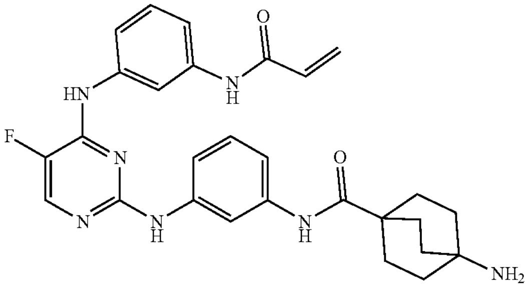 [SMILES: C=CC(=O)Nc1cccc(Nc2nc(Nc3cccc(NC(=O)C45CCC(N)(CC4)CC5)c3)ncc2F)c1] | I-292 |
| 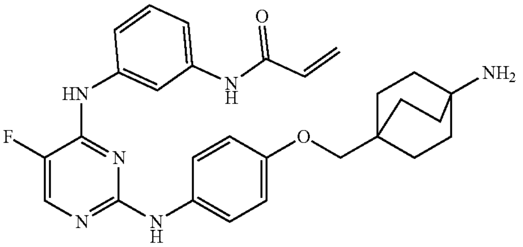 [SMILES: C=CC(=O)Nc1cccc(Nc2nc(Nc3ccc(OCC45CCC(N)(CC4)CC5)cc3)ncc2F)c1] | I-293 |
| 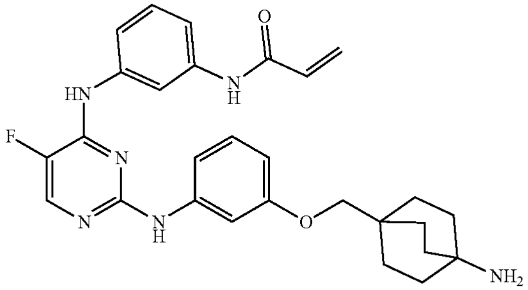 [SMILES: C=CC(=O)Nc1cccc(Nc2nc(Nc3cccc(OCC45CCC(N)(CC4)CC5)c3)ncc2F)c1] | I-294 |

TABLE 5-continued
| Exemplary Compounds |
|---|
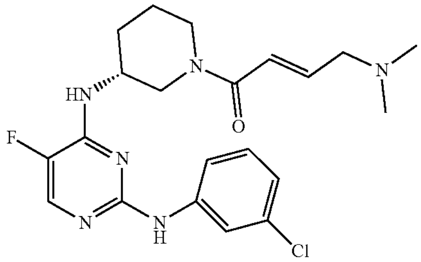 [SMILES: CN(C)C/C=C/C(=O)N1CCC[C@@H](Nc2nc(Nc3cccc(Cl)c3)ncc2F)C1]
I-295
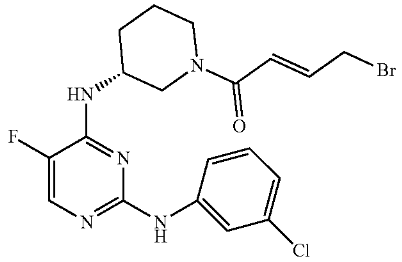 [SMILES: O=C(/C=C/CBr)N1CCC[C@@H](Nc2nc(Nc3cccc(Cl)c3)ncc2F)C1]
I-296
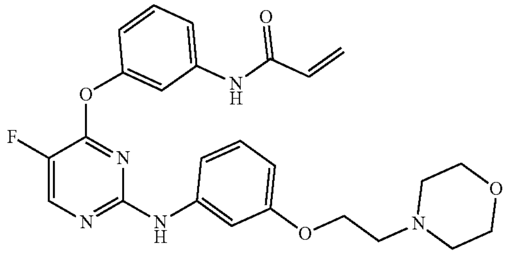 [SMILES: C=CC(=O)Nc1cccc(Oc2nc(Nc3cccc(OCCN4CCOCC4)c3)ncc2F)c1]
I-297
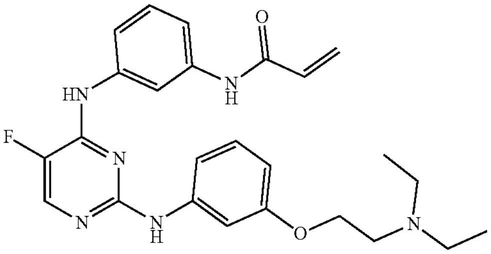 [SMILES: C=CC(=O)Nc1cccc(Nc2nc(Nc3cccc(OCCN(CC)CC)c3)ncc2F)c1]
I-298
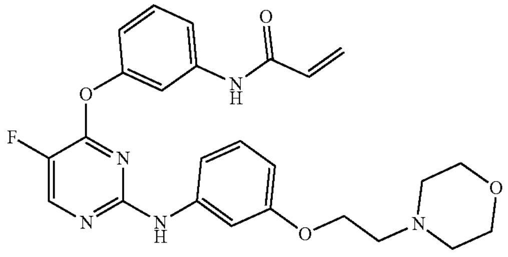 [SMILES: C=CC(=O)Nc1cccc(Oc2nc(Nc3cccc(OCCN4CCOCC4)c3)ncc2F)c1]
I-299
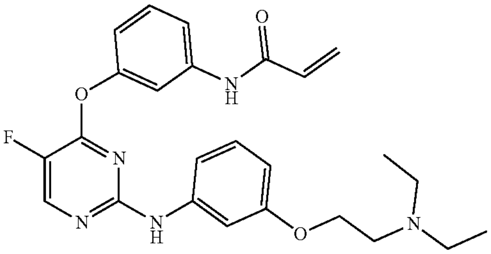 [SMILES: C=CC(=O)Nc1cccc(Oc2nc(Nc3cccc(OCCN(CC)CC)c3)ncc2F)c1]
I-300

TABLE 5-continued
| Exemplary Compounds |
|---|
I-301
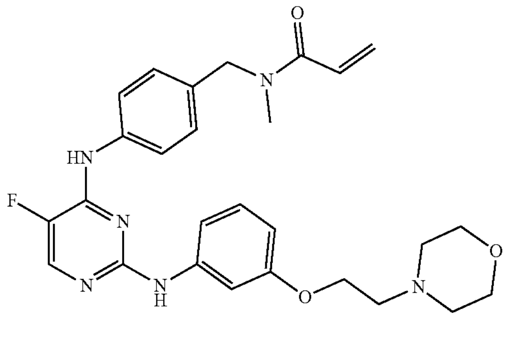 [SMILES: C=CC(=O)N(C)Cc1ccc(Nc2nc(Nc3cccc(OCCN4CCOCC4)c3)ncc2F)cc1]
I-302
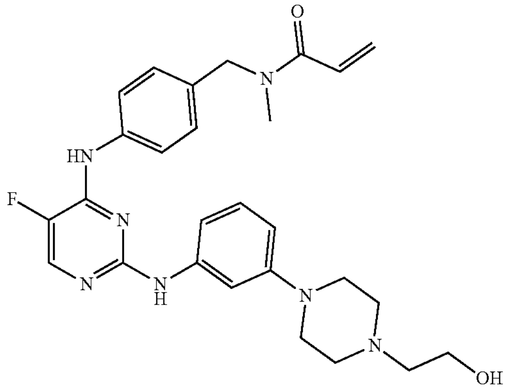 [SMILES: C=CC(=O)N(C)Cc1ccc(Nc2nc(Nc3cccc(N4CCN(CCO)CC4)c3)ncc2F)cc1]
I-303
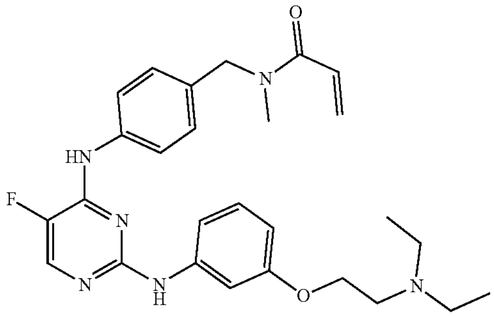 [SMILES: C=CC(=O)N(C)Cc1ccc(Nc2nc(Nc3cccc(OCCN(CC)CC)c3)ncc2F)cc1]
I-304
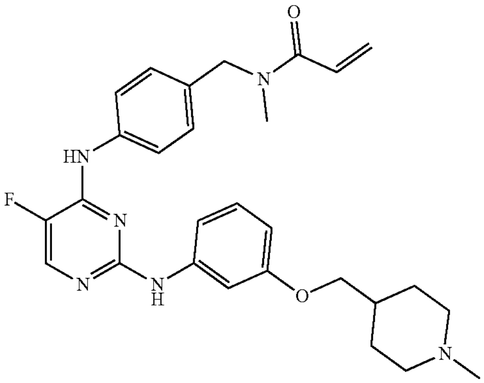 [SMILES: C=CC(=O)N(C)Cc1ccc(Nc2nc(Nc3cccc(OCC4CCN(C)CC4)c3)ncc2F)cc1]

TABLE 5-continued
| Exemplary Compounds | |
|---|---|
| 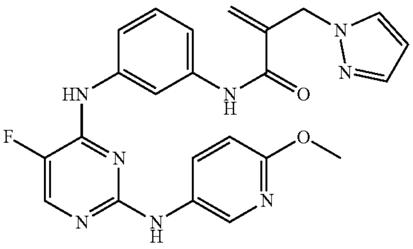 [SMILES: C=C(Cn1cccn1)C(=O)Nc1cccc(Nc2nc(Nc3ccc(OC)nc3)ncc2F)c1] | I-305 |
| 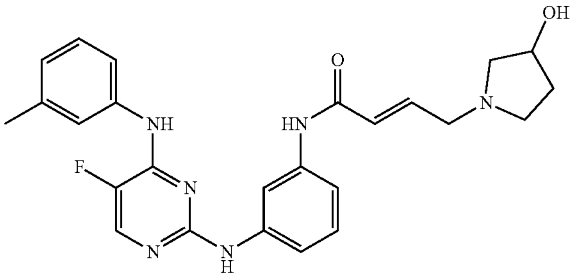 [SMILES: Cc1cccc(Nc2nc(Nc3cccc(NC(=O)/C=C/CN4CCC(O)C4)c3)ncc2F)c1] | I-306 |
| 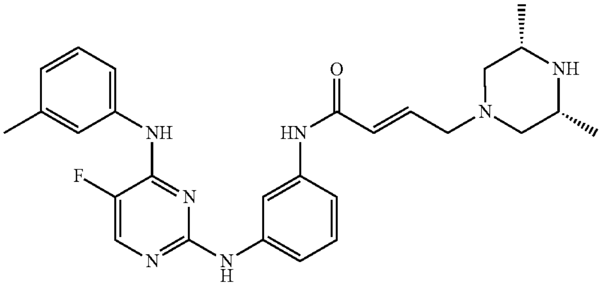 | I-307 |
| 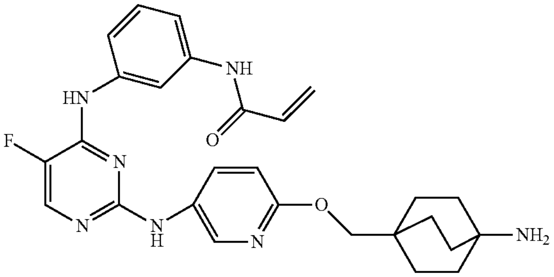 [SMILES: C=CC(=O)Nc1cccc(Nc2nc(Nc3ccc(OCC45CCC(N)(CC4)CC5)nc3)ncc2F)c1] | I-308 |
| 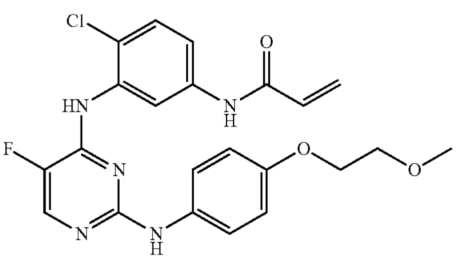 [SMILES: C=CC(=O)Nc1ccc(Cl)c(Nc2nc(Nc3ccc(OCCOC)cc3)ncc2F)c1] | I-309 |

TABLE 5-continued
Exemplary Compounds
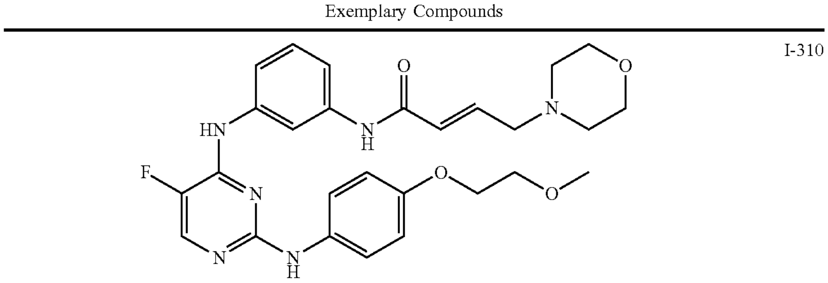
I-310
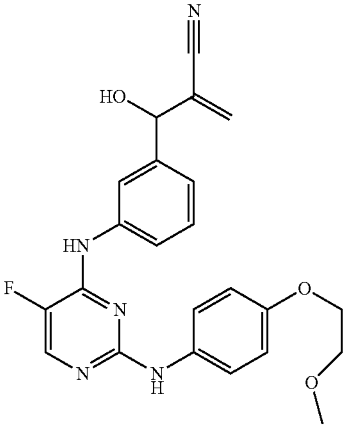 [SMILES: C=C(C#N)C(O)c1cccc(Nc2nc(Nc3ccc(OCCOC)cc3)ncc2F)c1]
I-311
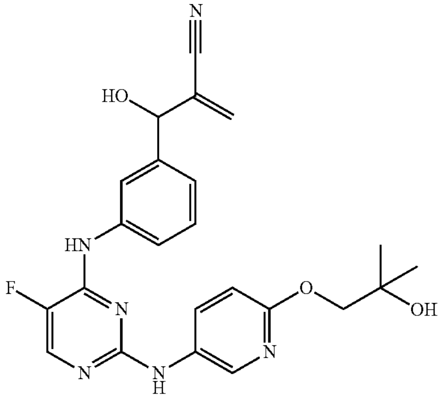 [SMILES: C=C(C#N)C(O)c1cccc(Nc2nc(Nc3ccc(OCC(C)(C)O)nc3)ncc2F)c1]
I-312
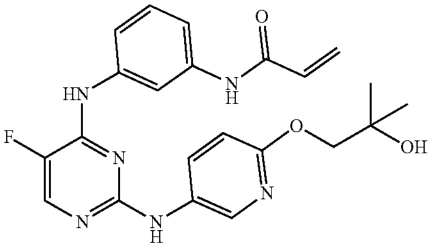 [SMILES: C=CC(=O)Nc1cccc(Nc2nc(Nc3ccc(OCC(C)(C)O)nc3)ncc2F)c1]
I-313
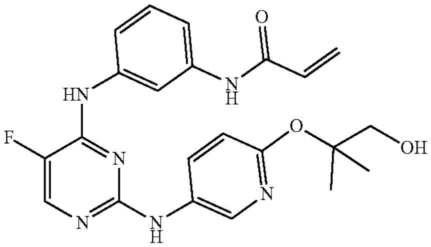 [SMILES: C=CC(=O)Nc1cccc(Nc2nc(Nc3ccc(OC(C)(C)CO)nc3)ncc2F)c1]
I-314

TABLE 5-continued
| Exemplary Compounds |
|---|
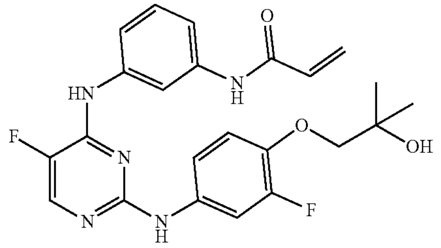 [SMILES: C=CC(=O)Nc1cccc(Nc2nc(Nc3ccc(OCC(C)(C)O)c(F)c3)ncc2F)c1]
I-315
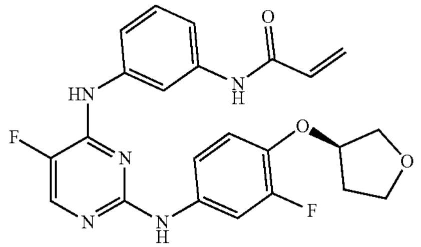 [SMILES: C=CC(=O)Nc1cccc(Nc2nc(Nc3ccc(O[C@@H]4CCOC4)c(F)c3)ncc2F)c1]
I-316
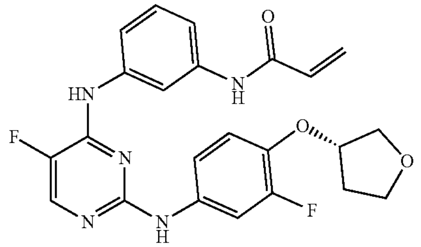 [SMILES: C=CC(=O)Nc1cccc(Nc2nc(Nc3ccc(O[C@H]4CCOC4)c(F)c3)ncc2F)c1]
I-317
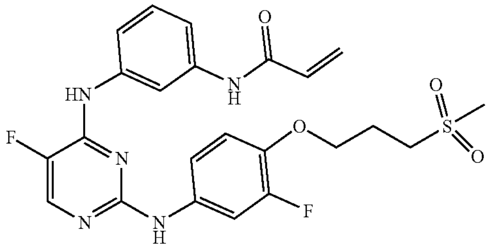 [SMILES: C=CC(=O)Nc1cccc(Nc2nc(Nc3ccc(OCCCS(C)(=O)=O)c(F)c3)ncc2F)c1]
I-318
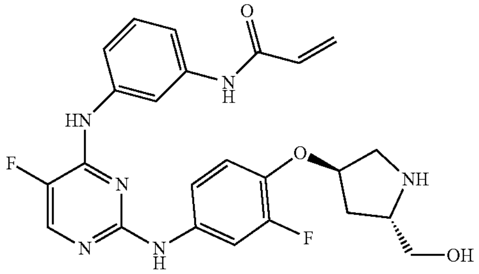 [SMILES: C=CC(=O)Nc1cccc(Nc2nc(Nc3ccc(O[C@H]4CN[C@H](CO)C4)c(F)c3)ncc2F)c1]
I-319
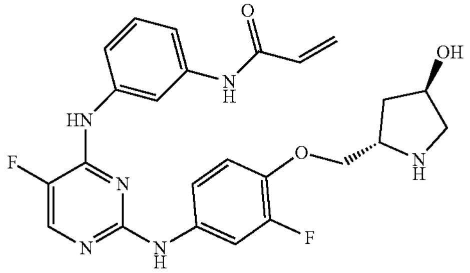 [SMILES: C=CC(=O)Nc1cccc(Nc2nc(Nc3ccc(OC[C@@H]4C[C@@H](O)CN4)c(F)c3)ncc2F)c1]
I-320

TABLE 5-continued
| Exemplary Compounds |
|---|
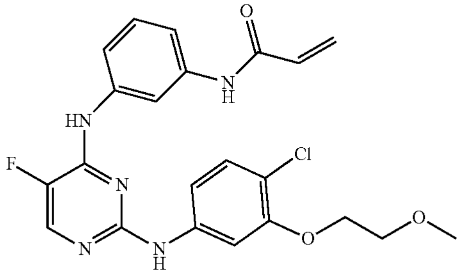 [SMILES: C=CC(=O)Nc1cccc(Nc2nc(Nc3ccc(Cl)c(OCCOC)c3)ncc2F)c1]
I-321
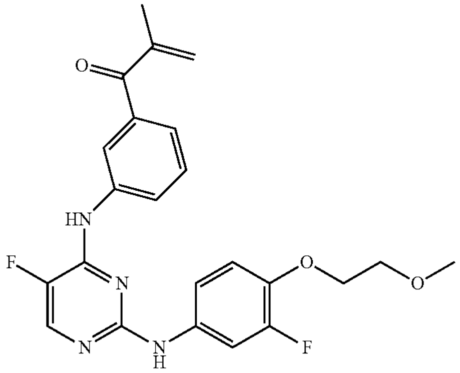 [SMILES: C=C(C)C(=O)c1cccc(Nc2nc(Nc3ccc(OCCOC)c(F)c3)ncc2F)c1]
I-322
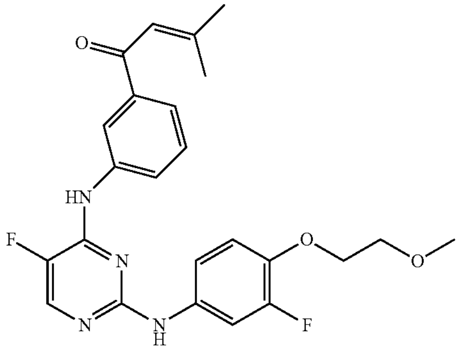 [SMILES: COCCOc1ccc(Nc2ncc(F)c(Nc3cccc(C(=O)C=C(C)C)c3)n2)cc1F]
I-323
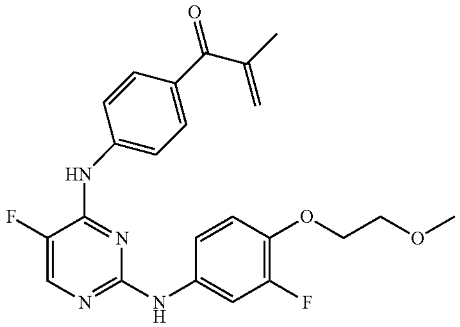 [SMILES: C=C(C)C(=O)c1ccc(Nc2nc(Nc3ccc(OCCOC)c(F)c3)ncc2F)cc1]
I-324

TABLE 5-continued
| Exemplary Compounds |
| --- |
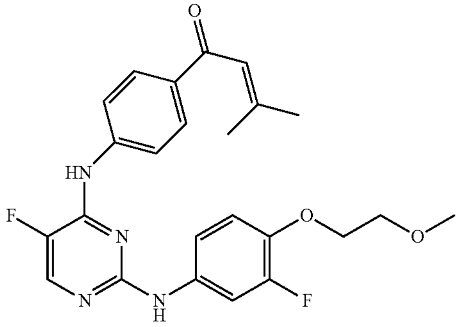 [SMILES: COCCOc1ccc(Nc2ncc(F)c(Nc3ccc(C(=O)C=C(C)C)cc3)n2)cc1F]
I-325
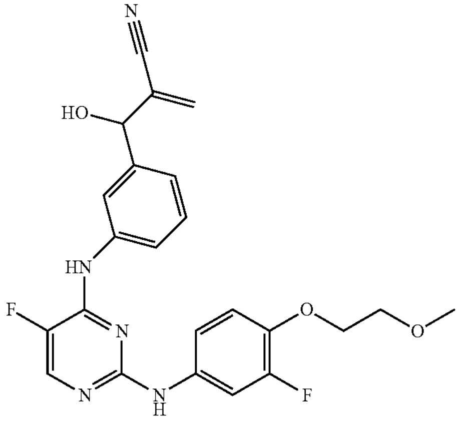 [SMILES: C=C(C#N)C(O)c1cccc(Nc2nc(Nc3ccc(OCCOC)c(F)c3)ncc2F)c1]
I-326
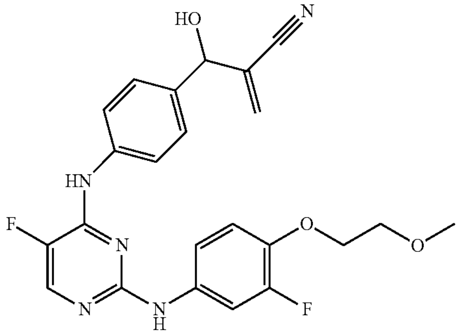 [SMILES: C=C(C#N)C(O)c1ccc(Nc2nc(Nc3ccc(OCCOC)c(F)c3)ncc2F)cc1]
I-327
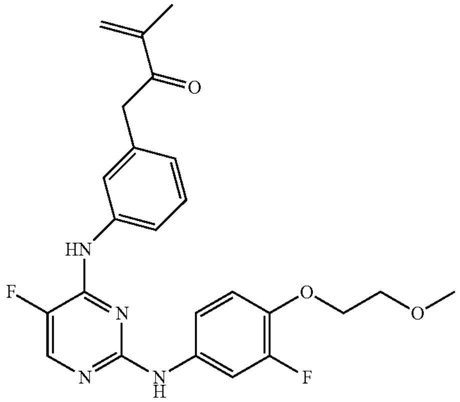 [SMILES: C=C(C)C(=O)Cc1cccc(Nc2nc(Nc3ccc(OCCOC)c(F)c3)ncc2F)c1]
I-328

TABLE 5-continued
| Exemplary Compounds |
|---|
I-329
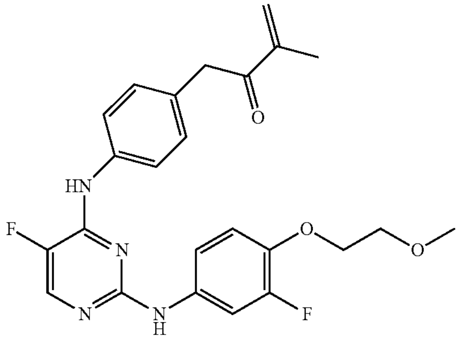 [SMILES: C=C(C)C(=O)Cc1ccc(Nc2nc(Nc3ccc(OCCOC)c(F)c3)ncc2F)cc1]
I-330
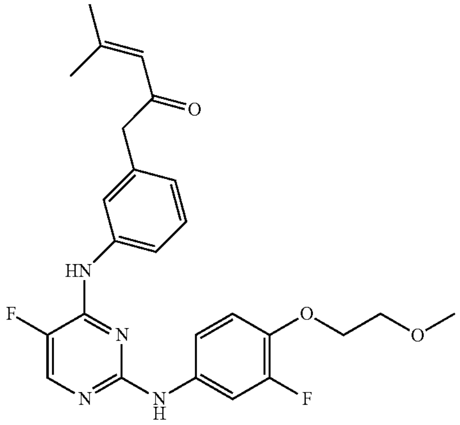 [SMILES: COCCOc1ccc(Nc2ncc(F)c(Nc3cccc(CC(=O)C=C(C)C)c3)n2)cc1F]
I-331
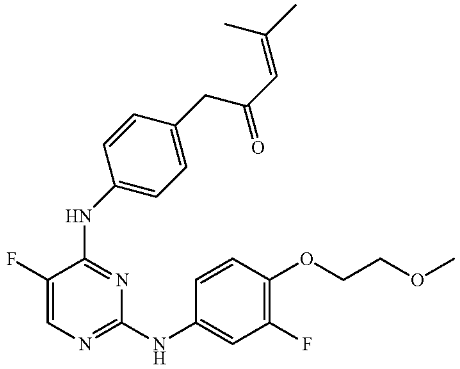 [SMILES: COCCOc1ccc(Nc2ncc(F)c(Nc3ccc(CC(=O)C=C(C)C)cc3)n2)cc1F]
I-332
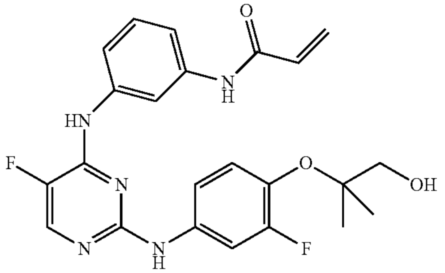 [SMILES: C=CC(=O)Nc1cccc(Nc2nc(Nc3ccc(OC(C)(C)CO)c(F)c3)ncc2F)c1]

TABLE 5-continued
| Exemplary Compounds |
| --- |
| 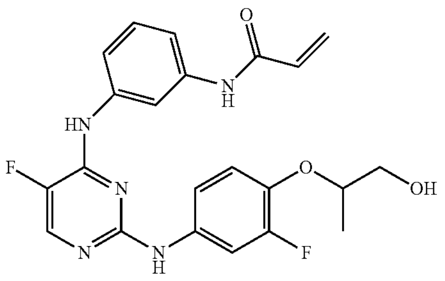 [SMILES: C=CC(=O)Nc1cccc(Nc2nc(Nc3ccc(OC(C)CO)c(F)c3)ncc2F)c1] I-333 |
| 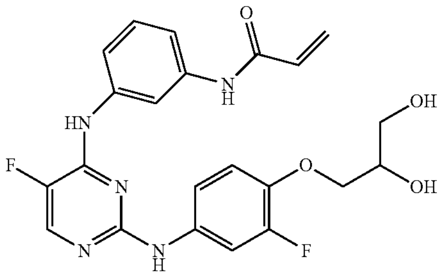 [SMILES: C=CC(=O)Nc1cccc(Nc2nc(Nc3ccc(OCC(O)CO)c(F)c3)ncc2F)c1] I-334 |
| 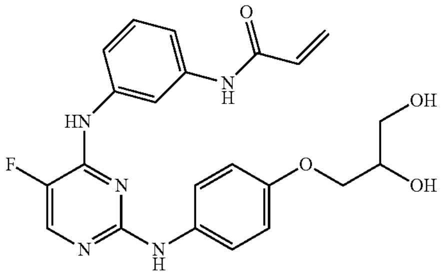 [SMILES: C=CC(=O)Nc1cccc(Nc2nc(Nc3ccc(OCC(O)CO)cc3)ncc2F)c1] I-335 |
| 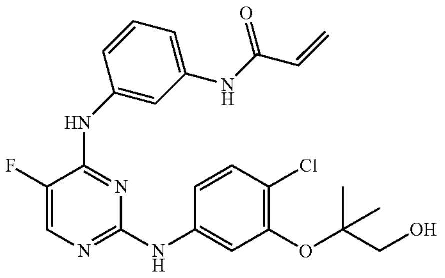 [SMILES: C=CC(=O)Nc1cccc(Nc2nc(Nc3ccc(Cl)c(OC(C)(C)CO)c3)ncc2F)c1] I-336 |
| 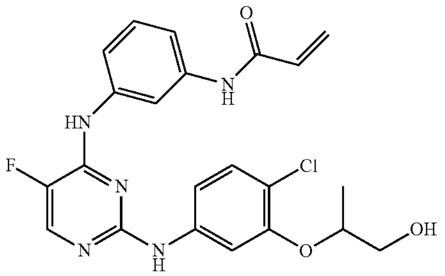 [SMILES: C=CC(=O)Nc1cccc(Nc2nc(Nc3ccc(Cl)c(OC(C)CO)c3)ncc2F)c1] I-337 |

TABLE 5-continued
Exemplary Compounds
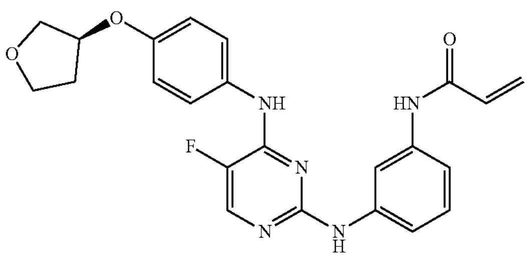 [SMILES: C=CC(=O)Nc1cccc(Nc2ncc(F)c(Nc3ccc(O[C@H]4CCOC4)cc3)n2)c1]
I-338
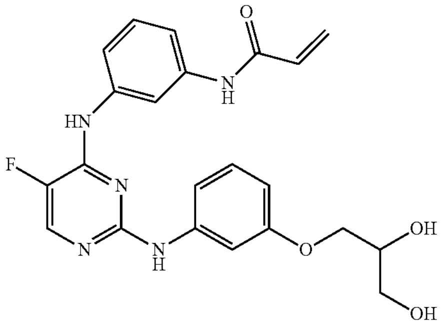 [SMILES: C=CC(=O)Nc1cccc(Nc2nc(Nc3cccc(OCC(O)CO)c3)ncc2F)c1]
I-339
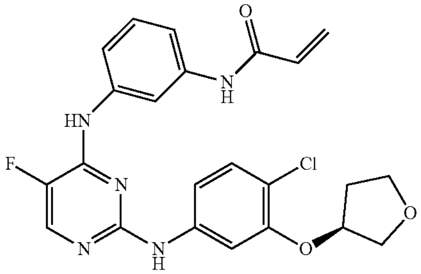 [SMILES: C=CC(=O)Nc1cccc(Nc2nc(Nc3ccc(Cl)c(O[C@H]4CCOC4)c3)ncc2F)c1]
I-340
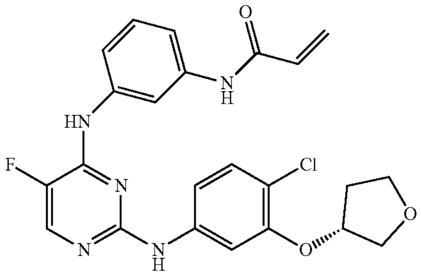 [SMILES: C=CC(=O)Nc1cccc(Nc2nc(Nc3ccc(Cl)c(O[C@@H]4CCOC4)c3)ncc2F)c1]
I-341
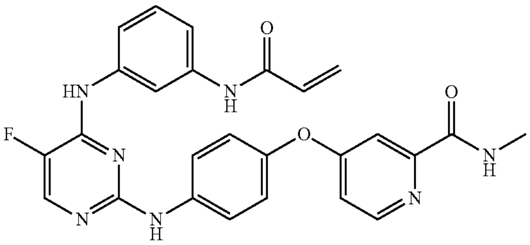 [SMILES: C=CC(=O)Nc1cccc(Nc2nc(Nc3ccc(Oc4ccnc(C(=O)NC)c4)cc3)ncc2F)c1]
I-342

TABLE 5-continued
| Exemplary Compounds |
| --- |
| 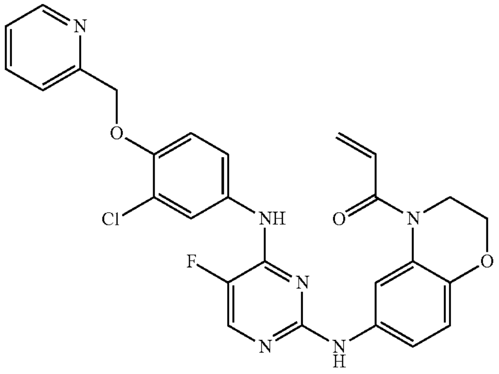 [SMILES: C=CC(=O)N1CCOc2ccc(Nc3ncc(F)c(Nc4ccc(OCc5ccccn5)c(Cl)c4)n3)cc21] I-343 |
| 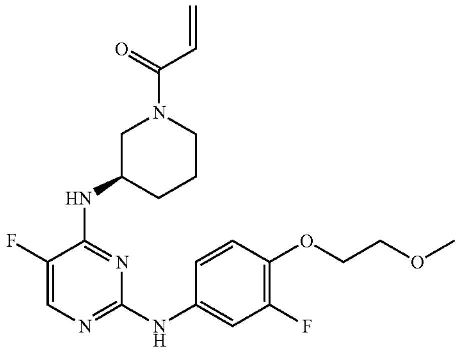 [SMILES: C=CC(=O)N1CCC[C@@H](Nc2nc(Nc3ccc(OCCOC)c(F)c3)ncc2F)C1] I-344 |
| 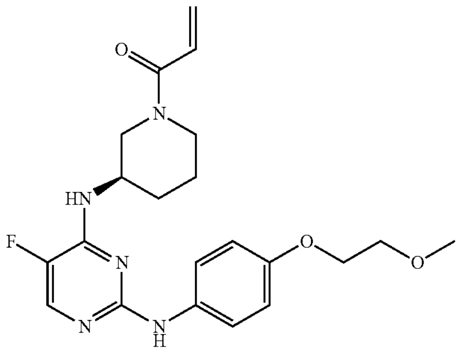 [SMILES: C=CC(=O)N1CCC[C@@H](Nc2nc(Nc3ccc(OCCOC)cc3)ncc2F)C1] I-345 |
| 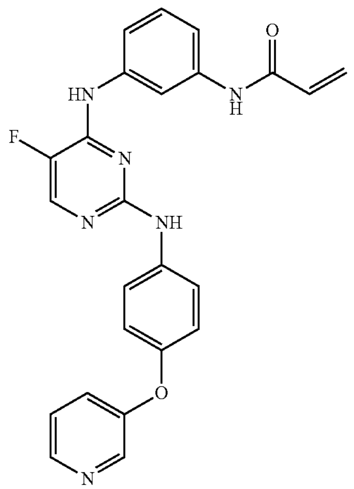 [SMILES: C=CC(=O)Nc1cccc(Nc2nc(Nc3ccc(Oc4cccnc4)cc3)ncc2F)c1] I-346 |

TABLE 5-continued
| Exemplary Compounds |
| --- |
| 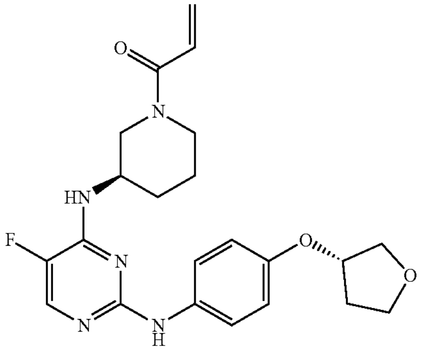 [SMILES: C=CC(=O)N1CCC[C@@H](Nc2nc(Nc3ccc(O[C@H]4CCOC4)cc3)ncc2F)C1] I-347 |
| 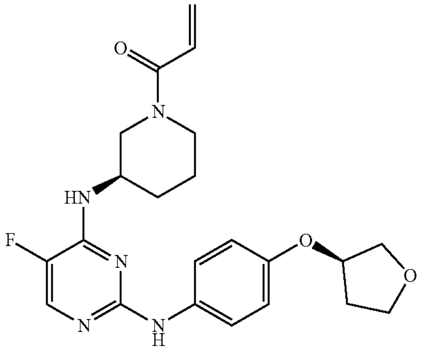 [SMILES: C=CC(=O)N1CCC[C@@H](Nc2nc(Nc3ccc(O[C@@H]4CCOC4)cc3)ncc2F)C1] I-348 |
| 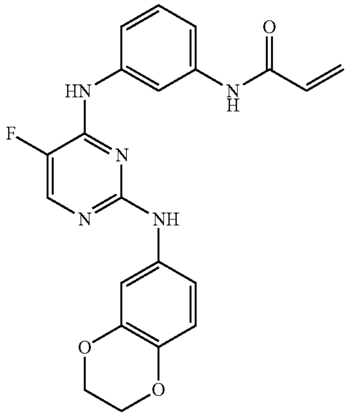 [SMILES: C=CC(=O)Nc1cccc(Nc2nc(Nc3ccc4c(c3)OCCO4)ncc2F)c1] I-349 |

TABLE 5-continued
| Exemplary Compounds |
| --- |
| I-350<br>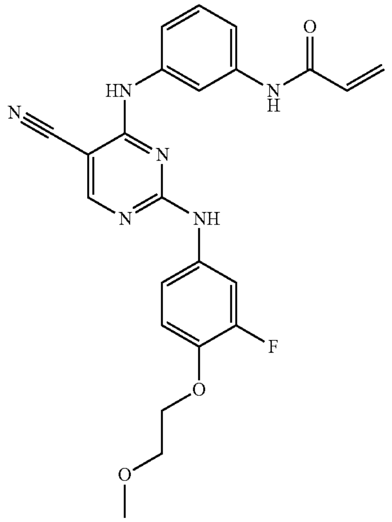 [SMILES: C=CC(=O)Nc1cccc(Nc2nc(Nc3ccc(OCCOC)c(F)c3)ncc2C#N)c1] |
| I-351<br>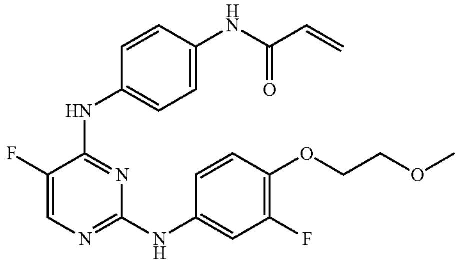 [SMILES: C=CC(=O)Nc1ccc(Nc2nc(Nc3ccc(OCCOC)c(F)c3)ncc2F)cc1] |
| I-352<br>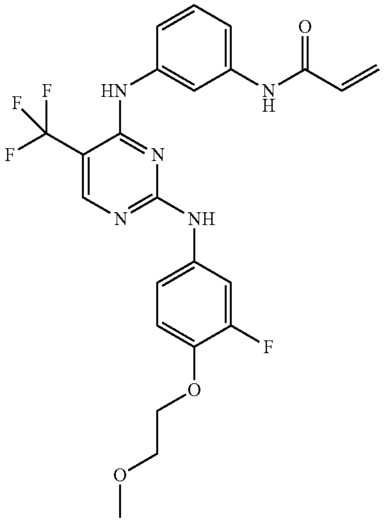 [SMILES: C=CC(=O)Nc1cccc(Nc2nc(Nc3ccc(OCCOC)c(F)c3)ncc2C(F)(F)F)c1] |

TABLE 5-continued
Exemplary Compounds
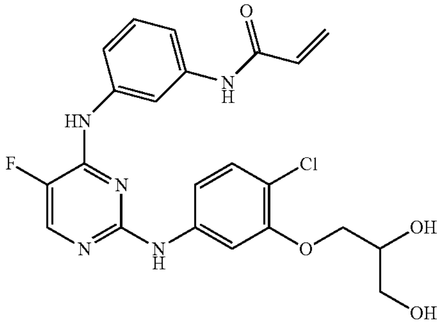 [SMILES: C=CC(=O)Nc1cccc(Nc2nc(Nc3ccc(Cl)c(OCC(O)CO)c3)ncc2F)c1]
I-353
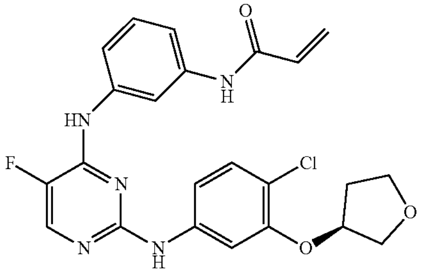 [SMILES: C=CC(=O)Nc1cccc(Nc2nc(Nc3ccc(Cl)c(O[C@H]4CCOC4)c3)ncc2F)c1]
I-354
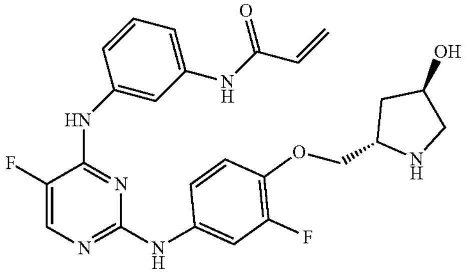 [SMILES: C=CC(=O)Nc1cccc(Nc2nc(Nc3ccc(OC[C@@H]4C[C@@H](O)CN4)c(F)c3)ncc2F)c1]
I-355
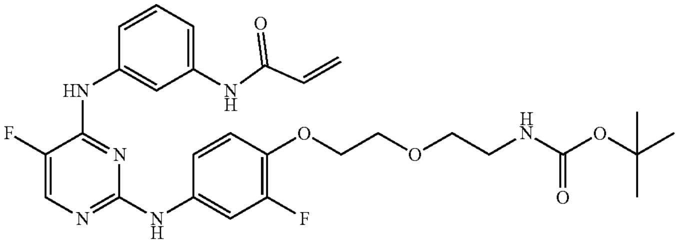 [SMILES: C=CC(=O)Nc1cccc(Nc2nc(Nc3ccc(OCCOCCNC(=O)OC(C)(C)C)c(F)c3)ncc2F)c1]
I-356
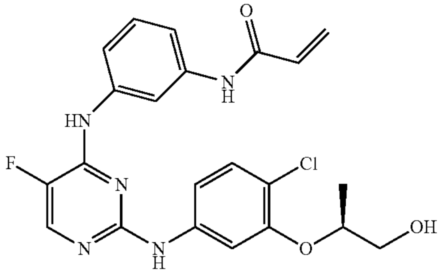 [SMILES: C=CC(=O)Nc1cccc(Nc2nc(Nc3ccc(Cl)c(O[C@@H](C)CO)c3)ncc2F)c1]
I-357

TABLE 5-continued
Exemplary Compounds
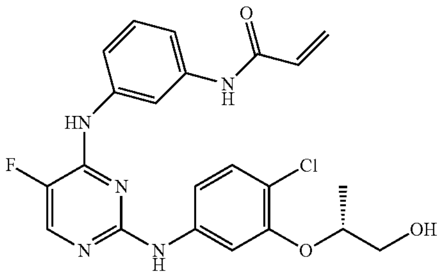 [SMILES: C=CC(=O)Nc1cccc(Nc2nc(Nc3ccc(Cl)c(O[C@H](C)CO)c3)ncc2F)c1]
I-358
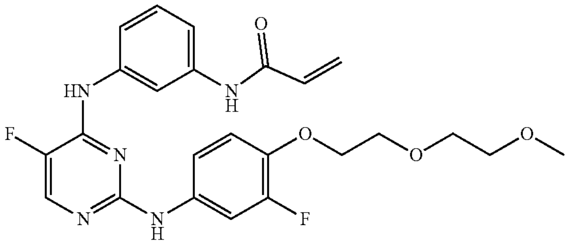 [SMILES: C=CC(=O)Nc1cccc(Nc2nc(Nc3ccc(OCCOCCOC)c(F)c3)ncc2F)c1]
I-359
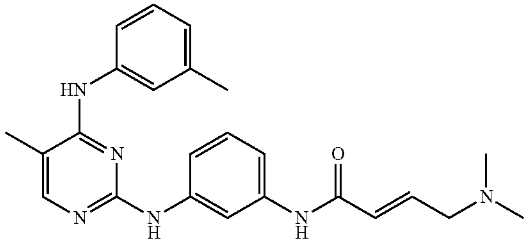
I-360
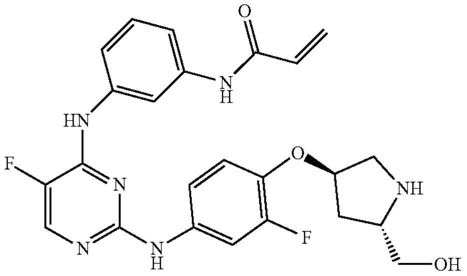 [SMILES: C=CC(=O)Nc1cccc(Nc2nc(Nc3ccc(O[C@H]4CN[C@H](CO)C4)c(F)c3)ncc2F)c1]
I-361
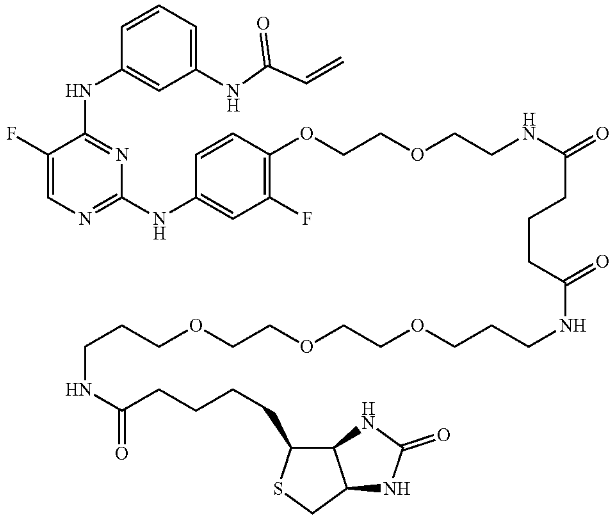 [SMILES: C=CC(=O)Nc1cccc(Nc2nc(Nc3ccc(OCCOCCNC(=O)CCCC(=O)NCCCOCCOCCOCCCNC(=O)CCCC[C@@H]4SC[C@@H]5NC(=O)N[C@@H]54)c(F)c3)ncc2F)c1]
I-362

TABLE 5-continued
| Exemplary Compounds |
| --- |
| I-363 |
| 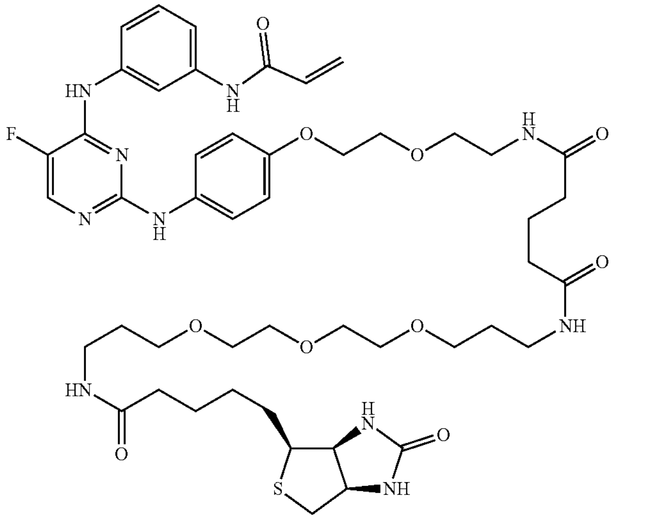 [SMILES: C=CC(=O)Nc1cccc(Nc2nc(Nc3ccc(OCCOCCNC(=O)CCCC(=O)NCCCOCCOCCOCCCNC(=O)CCCC[C@@H]4SC[C@@H]5NC(=O)N[C@@H]54)cc3)ncc2F)c1] |
| I-364 |
| 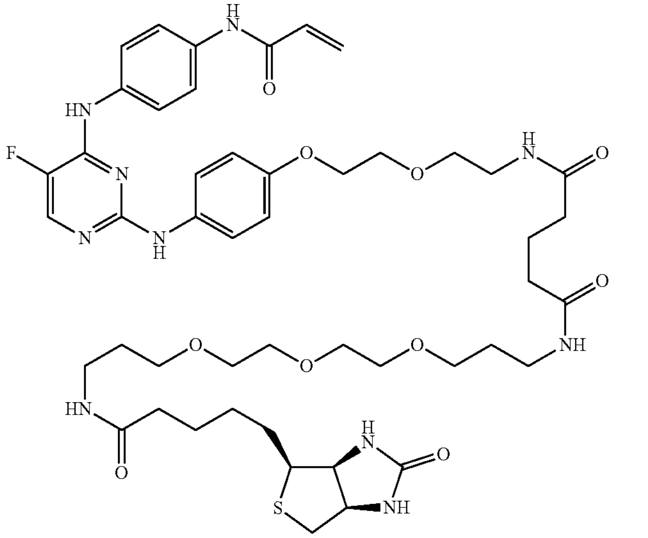 [SMILES: C=CC(=O)Nc1ccc(Nc2nc(Nc3ccc(OCCOCCNC(=O)CCCC(=O)NCCCOCCOCCOCCCNC(=O)CCCC[C@@H]4SC[C@@H]5NC(=O)N[C@@H]54)cc3)ncc2F)cc1] |

TABLE 5-continued
| Exemplary Compounds |
| --- |
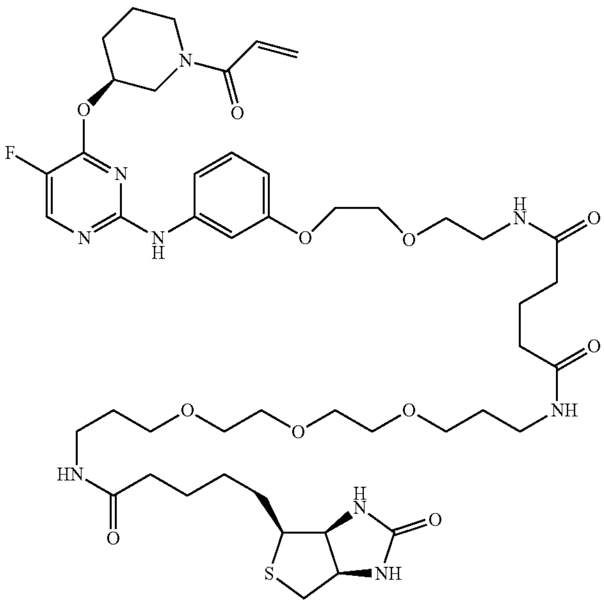 [SMILES: C=CC(=O)N1CCC[C@H](Oc2nc(Nc3cccc(OCCOCCNC(=O)CCCC(=O)NCCCOCCOCCOCCCNC(=O)CCCC[C@@H]4SC[C@@H]5NC(=O)N[C@@H]54)c3)ncc2F)C1]
I-365
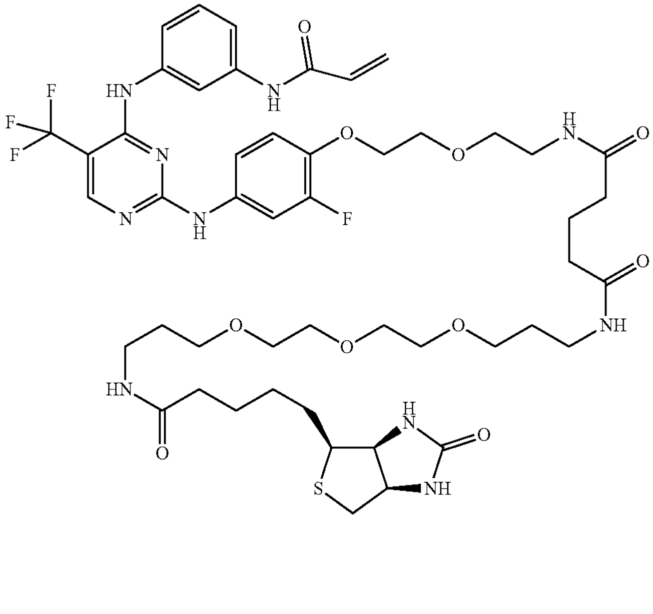 [SMILES: C=CC(=O)Nc1cccc(Nc2nc(Nc3ccc(OCCOCCNC(=O)CCCC(=O)NCCCOCCOCCOCCCNC(=O)CCCC[C@@H]4SC[C@@H]5NC(=O)N[C@@H]54)c(F)c3)ncc2C(F)(F)F)c1]
I-366

TABLE 5-continued
Exemplary Compounds
I-367
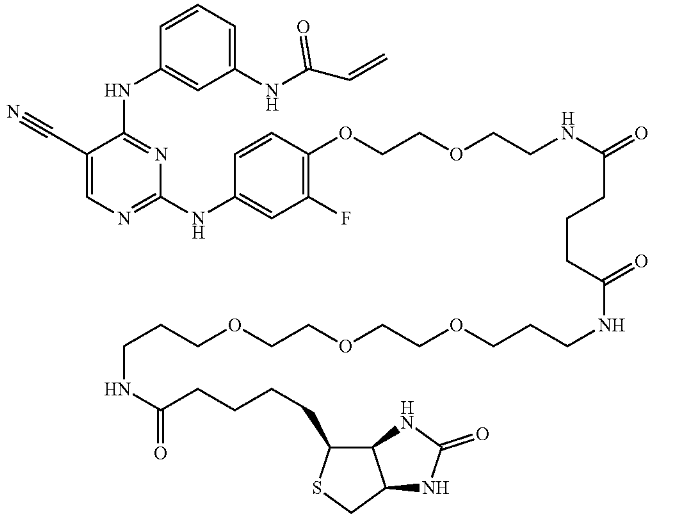 [SMILES: C=CC(=O)Nc1cccc(Nc2nc(Nc3ccc(OCCOCCNC(=O)CCCC(=O)NCCCOCCOCCOCCCNC(=O)CCCC[C@@H]4SC[C@@H]5NC(=O)N[C@@H]54)c(F)c3)ncc2C#N)c1]
I-368
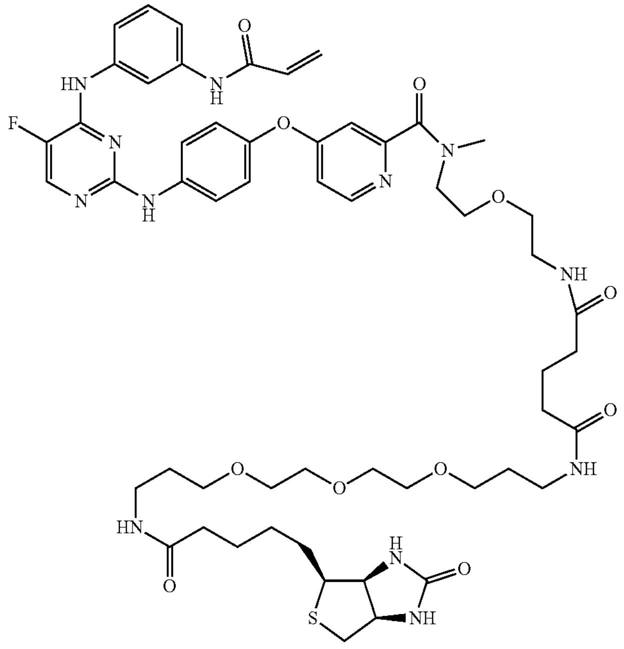 [SMILES: C=CC(=O)Nc1cccc(Nc2nc(Nc3ccc(Oc4ccnc(C(=O)N(C)CCOCCNC(=O)CCCC(=O)NCCCOCCOCCOCCCNC(=O)CCCC[C@@H]5SC[C@@H]6NC(=O)N[C@@H]65)c4)cc3)ncc2F)c1]
I-369
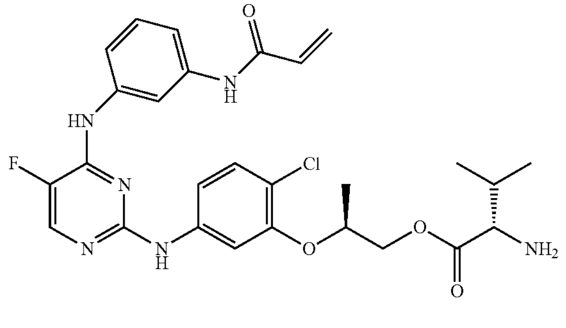 [SMILES: C=CC(=O)Nc1cccc(Nc2nc(Nc3ccc(Cl)c(O[C@@H](C)COC(=O)[C@@H](N)C(C)C)c3)ncc2F)c1]

TABLE 5-continued
| Exemplary Compounds |
| --- |
I-370
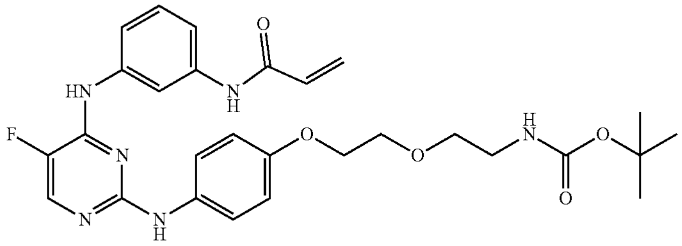 [SMILES: C=CC(=O)Nc1cccc(Nc2nc(Nc3ccc(OCCOCCNC(=O)OC(C)(C)C)cc3)ncc2F)c1]
I-371
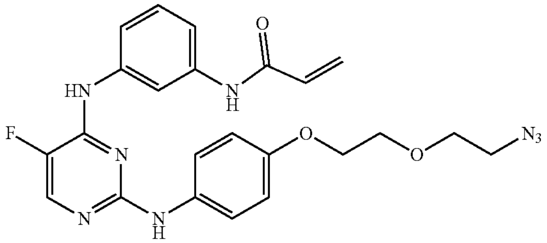 [SMILES: C=CC(=O)Nc1cccc(Nc2nc(Nc3ccc(OCCOCCN=[N+]=[N-])cc3)ncc2F)c1]
I-372
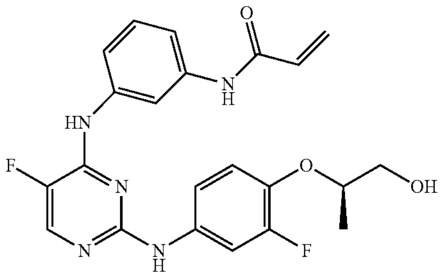 [SMILES: C=CC(=O)Nc1cccc(Nc2nc(Nc3ccc(O[C@H](C)CO)c(F)c3)ncc2F)c1]
I-373
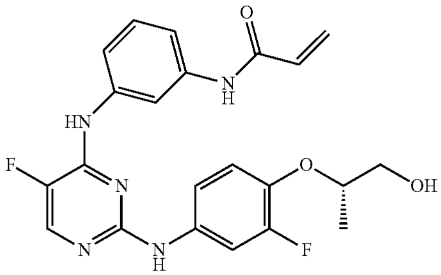 [SMILES: C=CC(=O)Nc1cccc(Nc2nc(Nc3ccc(O[C@@H](C)CO)c(F)c3)ncc2F)c1]
I-374
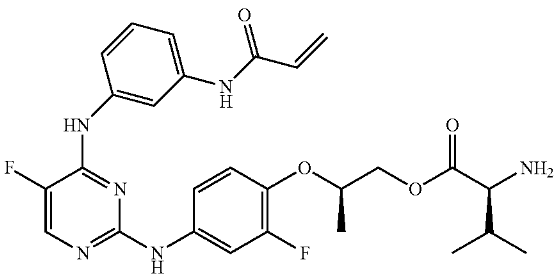 [SMILES: C=CC(=O)Nc1cccc(Nc2nc(Nc3ccc(O[C@H](C)COC(=O)[C@@H](N)C(C)C)c(F)c3)ncc2F)c1]
I-375
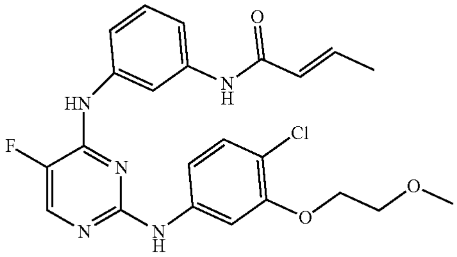 [SMILES: C/C=C/C(=O)Nc1cccc(Nc2nc(Nc3ccc(Cl)c(OCCOC)c3)ncc2F)c1]

TABLE 5-continued
| Exemplary Compounds |
|---|
| 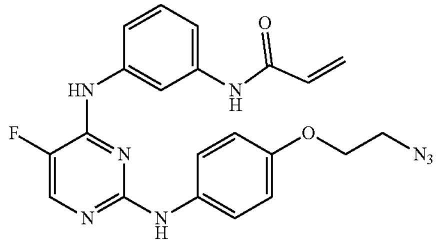 [SMILES: C=CC(=O)Nc1cccc(Nc2nc(Nc3ccc(OCCN=[N+]=[N-])cc3)ncc2F)c1] I-376 |
| 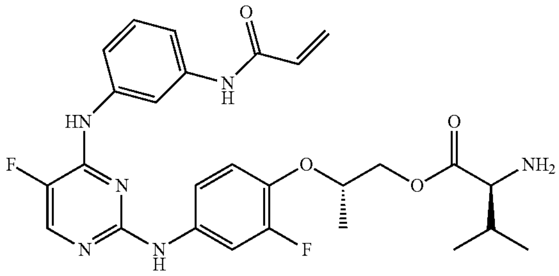 [SMILES: C=CC(=O)Nc1cccc(Nc2nc(Nc3ccc(O[C@@H](C)COC(=O)[C@@H](N)C(C)C)c(F)c3)ncc2F)c1] I-377 |
| 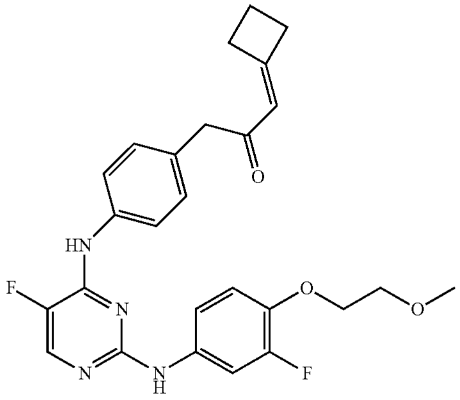 [SMILES: COCCOc1ccc(Nc2ncc(F)c(Nc3ccc(CC(=O)C=C4CCC4)cc3)n2)cc1F] I-378 |
| 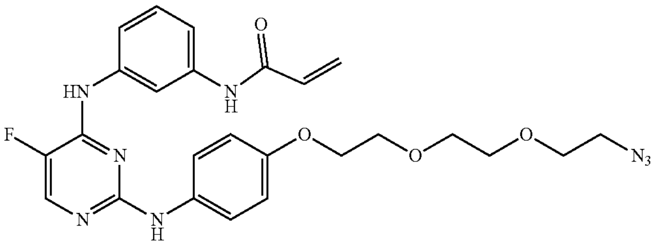 [SMILES: C=CC(=O)Nc1cccc(Nc2nc(Nc3ccc(OCCOCCOCCN=[N+]=[N-])cc3)ncc2F)c1] I-379 |
| 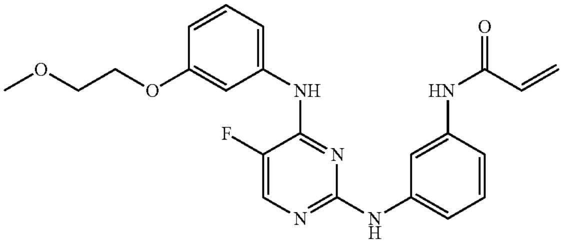 [SMILES: C=CC(=O)Nc1cccc(Nc2ncc(F)c(Nc3cccc(OCCOC)c3)n2)c1] I-380 |

TABLE 5-continued
| Exemplary Compounds |
|---|
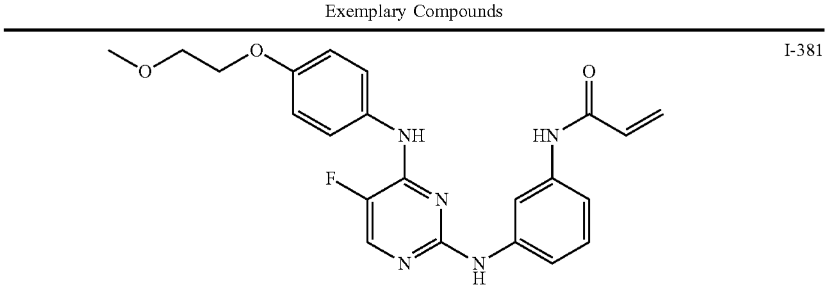
I-381
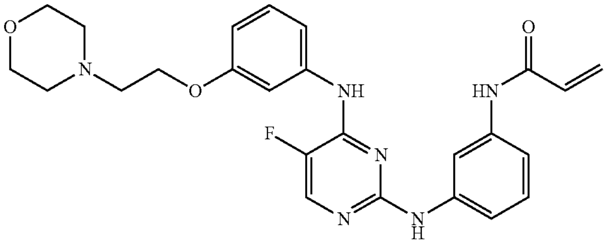 [SMILES: C=CC(=O)Nc1cccc(Nc2ncc(F)c(Nc3cccc(OCCN4CCOCC4)c3)n2)c1]
I-382
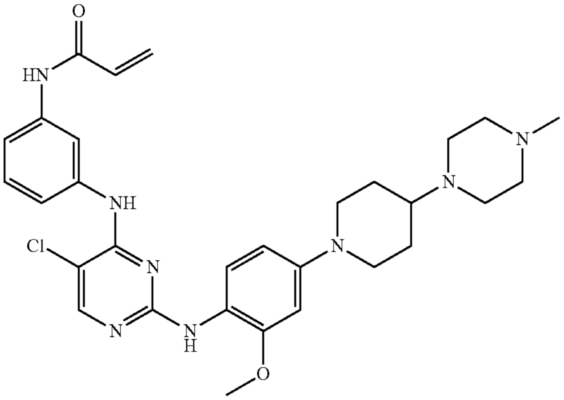 [SMILES: C=CC(=O)Nc1cccc(Nc2nc(Nc3ccc(N4CCC(N5CCN(C)CC5)CC4)cc3OC)ncc2Cl)c1]
I-383
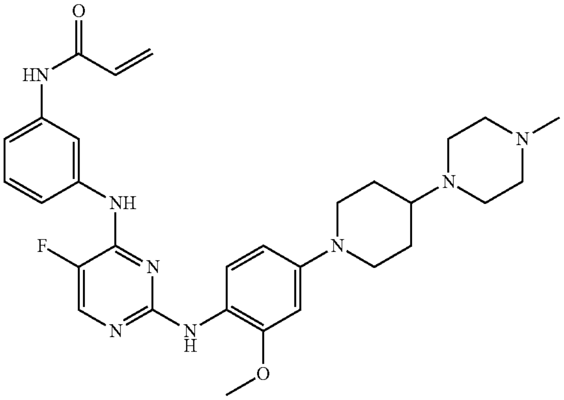 [SMILES: C=CC(=O)Nc1cccc(Nc2nc(Nc3ccc(N4CCC(N5CCN(C)CC5)CC4)cc3OC)ncc2F)c1]
I-384
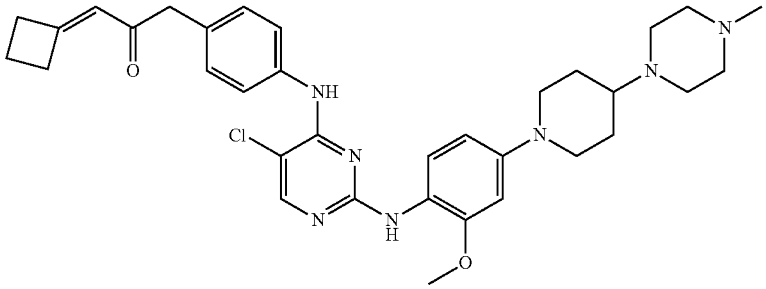 [SMILES: COc1cc(N2CCC(N3CCN(C)CC3)CC2)ccc1Nc1ncc(Cl)c(Nc2ccc(CC(=O)C=C3CCC3)cc2)n1]
I-385

TABLE 5-continued
| Exemplary Compounds |
| --- |
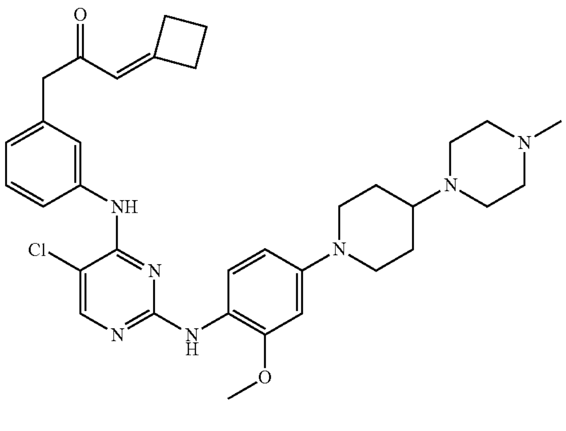 [SMILES: COc1cc(N2CCC(N3CCN(C)CC3)CC2)ccc1Nc1ncc(Cl)c(Nc2cccc(CC(=O)C=C3CCC3)c2)n1]
I-386
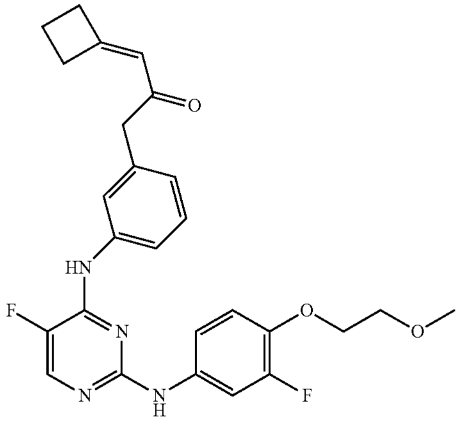 [SMILES: COCCOc1ccc(Nc2ncc(F)c(Nc3cccc(CC(=O)C=C4CCC4)c3)n2)cc1F]
I-387
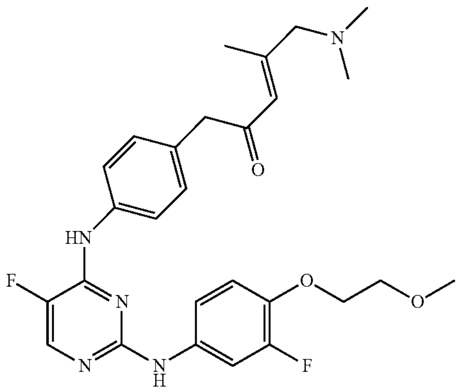 [SMILES: COCCOc1ccc(Nc2ncc(F)c(Nc3ccc(CC(=O)/C=C(\C)CN(C)C)cc3)n2)cc1F]
I-388

TABLE 5-continued
Exemplary Compounds
I-389
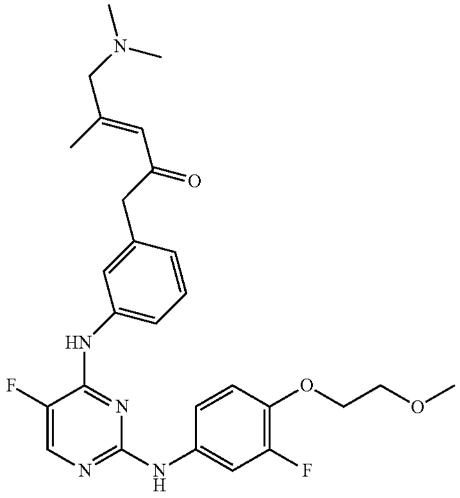 [SMILES: COCCOc1ccc(Nc2ncc(F)c(Nc3cccc(CC(=O)/C=C(\C)CN(C)C)c3)n2)cc1F]
I-390
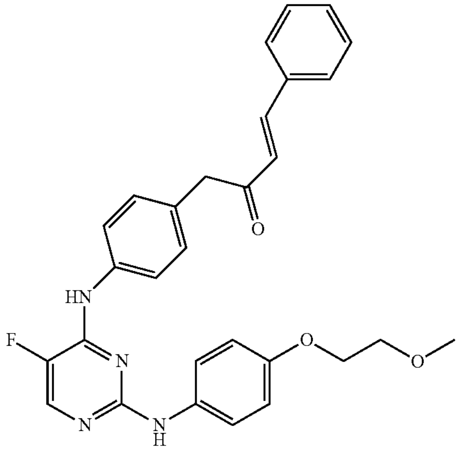 [SMILES: COCCOc1ccc(Nc2ncc(F)c(Nc3ccc(CC(=O)/C=C/c4ccccc4)cc3)n2)cc1]
I-391
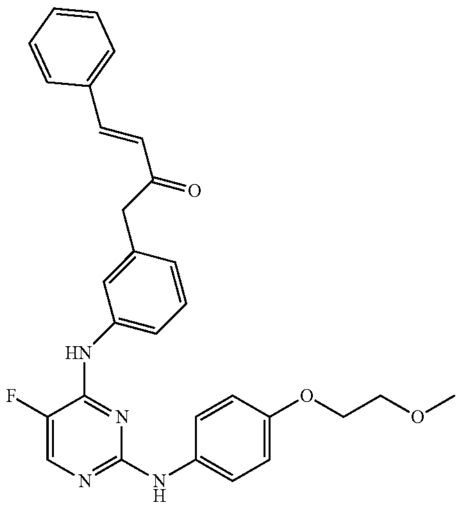 [SMILES: COCCOc1ccc(Nc2ncc(F)c(Nc3cccc(CC(=O)/C=C/c4ccccc4)c3)n2)cc1]

TABLE 5-continued
| Exemplary Compounds |
| --- |
| 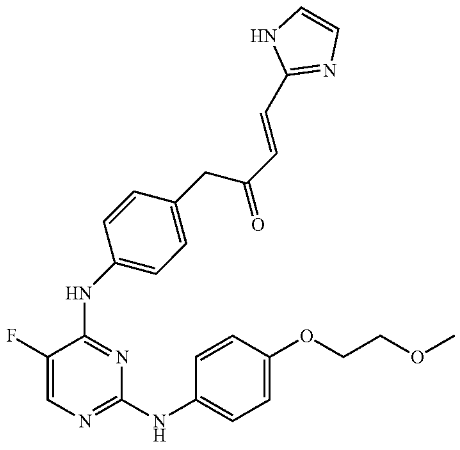 [SMILES: COCCOc1ccc(Nc2ncc(F)c(Nc3ccc(CC(=O)/C=C/c4ncc[nH]4)cc3)n2)cc1] I-392 |
| 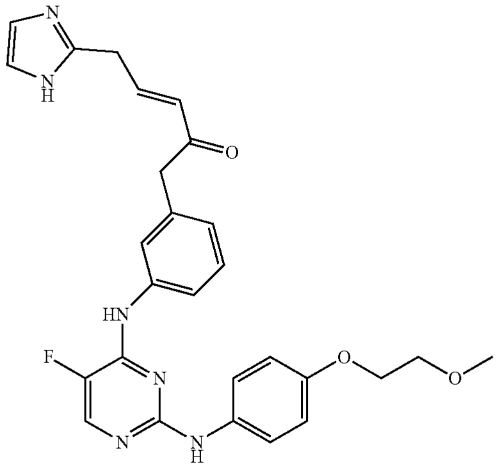 [SMILES: COCCOc1ccc(Nc2ncc(F)c(Nc3cccc(CC(=O)/C=C/Cc4ncc[nH]4)c3)n2)cc1] I-393 |
In certain embodiments, the present invention provides any compound depicted in Table 5, above, or a pharmaceutically acceptable salt thereof.
In certain embodiments, the present invention provides a compound selected from:
I-7
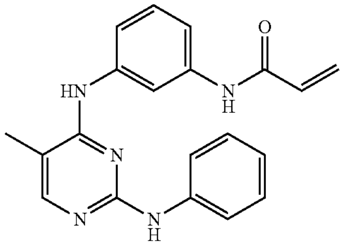
-continued
I-4
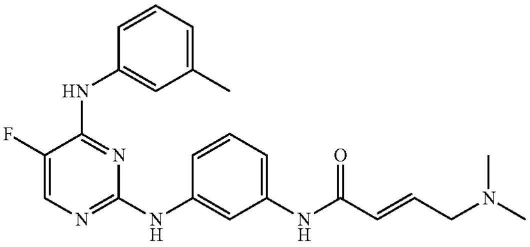

-continued

I-96

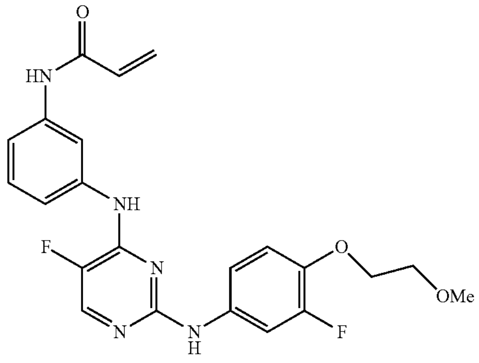

I-182

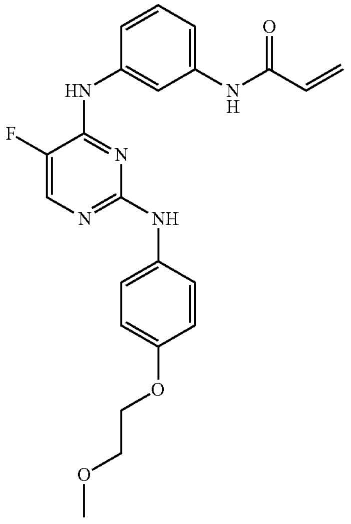

I-190

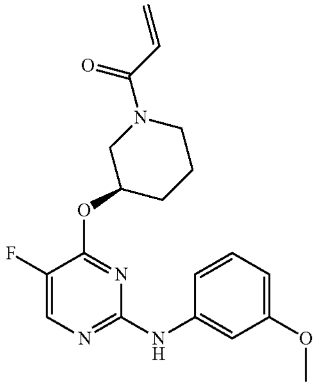

I-249

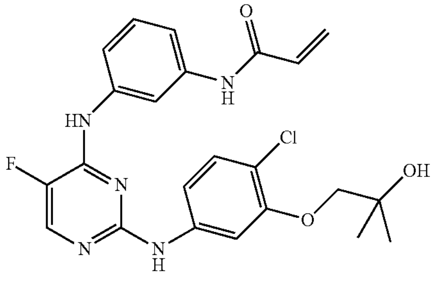

-continued

I-342

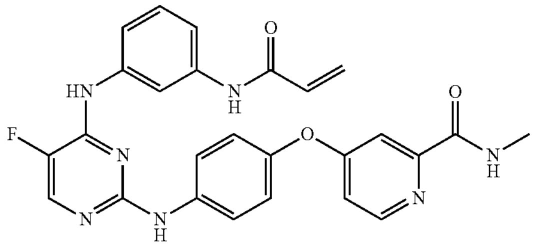

or a pharmaceutically acceptable salt thereof.

As described herein, compounds of the present invention are irreversible inhibitors of at least one of ErbB1, ErbB2, ErbB3 and ErbB4, or a mutant thereof. In some embodiments, provided compounds are irreversible inhibitors of a TEC-kinase (e.g. BTK) and JAK3. One of ordinary skill in the art will recognize that certain compounds of the present invention are reversible inhibitors. In certain embodiments, such compounds are useful as assay comparator compounds. In other embodiments, such reversible compounds are useful as inhibitors of ErbB1, ErbB2, ErbB3, ErbB4, a TEC-kinase, and/or JAK3, or a mutant thereof, and therefore useful for treating one or disorders as described herein. An exemplary reversible compound of the present invention has the following structure.

$I^R$-7

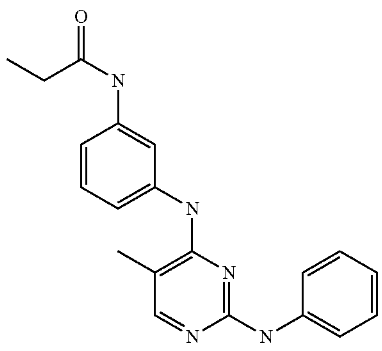

or a pharmaceutically acceptable salt thereof.

4. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit a protein kinase, particularly at least one of ErbB1, ErbB2, ErbB3, ErbB4, a TEC-kinase, and/or JAK3, or a mutant thereof, in a biological sample or in a patient. In certain embodiments, the amount of compound in compositions of this invention is such that is effective to measurably inhibit at least one of ErbB1, ErbB2, ErbB3, ErbB4, a TEC-kinase, and/or JAK3, or a mutant thereof, in a biological sample or in a patient. In certain embodiments, a composition of this invention is formulated for administration to a patient in need of such composition. In some embodiments, a composition of this invention is formulated for oral administration to a patient.

The term "patient", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of at least one of ErbB1, ErbB2, ErbB3, ErbB4, a TEC-kinase, and/or JAK3, or a mutant thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the inhibition of protein kinase activity of one or more enzymes.

Drug resistance is emerging as a significant challenge for targeted therapies. For example, drug resistance has been reported for Gleevec® and Iressa®, as well as several other kinase inhibitors in development. In addition, drug resistance has been reported for the cKit and PDGFR receptors. It has been reported that irreversible inhibitors may be effective against drug resistant forms of protein kinases (Kwak, E. L., R. Sordella, et al. (2005). "Irreversible inhibitors of the EGF receptor may circumvent acquired resistance to gefitinib." *PNAS* 102(21): 7665-7670.) Without wishing to be bound by any particular theory, it is believed that compounds of the present invention may be effective inhibitors of drug resistant forms of protein kinases.

As used herein, the term "clinical drug resistance" refers to the loss of susceptibility of a drug target to drug treatment as a consequence of mutations in the drug target.

As used herein, the term "resistance" refers to changes in the wild-type nucleic acid sequence coding a target protein, and/or the protein sequence of the target, which changes decrease or abolish the inhibitory effect of the inhibitor on the target protein.

Examples of kinases that are inhibited by the compounds and compositions described herein and against which the methods described herein are useful include ErbB1, ErbB2, ErbB3, ErbB4, a TEC-kinase (including BTK, ITK, TEC, BMX and RLK), and/or JAK3, or a mutant thereof.

The activity of a compound utilized in this invention as an inhibitor of ErbB1, ErbB2, ErbB3, ErbB4, a TEC-kinase, and/or JAK3, or a mutant thereof, may be assayed in vitro, in vivo or in a cell line. In vitro assays include assays that determine inhibition of either the phosphorylation activity and/or the subsequent functional consequences, or ATPase activity of activated ErbB1, ErbB2, ErbB3, ErbB4, a TEC-kinase, and/or JAK3, or a mutant thereof. Alternate in vitro assays quantitate the ability of the inhibitor to bind to ErbB1, ErbB2, ErbB3, ErbB4, a TEC-kinase, and/or JAK3. Inhibitor binding may be measured by radiolabeling the inhibitor prior to binding, isolating the inhibitor/ErbB1, inhibitor/ErbB2, inhibitor/ErbB3, inhibitor/ErbB4, inhibitor/TEC-kinase (i.e., TEC, BTK, ITK, RLK and BMX), or inhibitor/JAK3 complex and determining the amount of radiolabel bound. Alternatively, inhibitor binding may be determined by running a competition experiment where new inhibitors are incubated with ErbB1, ErbB2, ErbB3, ErbB4, a TEC-kinase, and/or JAK3 bound to known radioligands. Detailed conditions for assaying a compound utilized in this invention as an inhibitor of ErbB1, ErbB2, ErbB3, ErbB4, a TEC-kinase, and/or JAK3, or a mutant thereof, are set forth in the Examples below.

Protein tyrosine kinases are a class of enzymes that catalyze the transfer of a phosphate group from ATP or GTP to a tyrosine residue located on a protein substrate. Receptor tyrosine kinases act to transmit signals from the outside of a cell to the inside by activating secondary messaging effectors via a phosphorylation event. A variety of cellular processes are promoted by these signals, including proliferation, carbohydrate utilization, protein synthesis, angiogenesis, cell growth, and cell survival.

(a) ErbB Family

ErbB receptors, a major family of receptor tyrosine kinases, are composed of an extracellular ligand binding domain, a single transmembrane domain, and an intracellular domain with tyrosine kinase activity. The ErbB family comprises ErbB1 (commonly known as EGFR), ErbB2 (commonly known as HER2 or neu), ErbB3 (commonly known as HER3), and ErbB4 (commonly known as HER4). More than 10 ligands (including EGF, TGFα, AR, BTC, EPR, HB-EGF, NRG-1, NRG-2, NRG-3, NRG-4) have been identified for the various receptor family members. Upon ligand binding the extracellular domain undergoes conformational change, allowing the formation of homodimers or heterodimers with other members of the ErbB family. Dimerization induces tyrosine phosphorylation of specific residues in the intracellular domain that serve as docking sites for adaptor proteins and downstream effectors. In some contexts, activation of phosphatidyl-inositol 3-kinase (PI3K) and mitogen-activated protein kinase pathways occur, leading to cell proliferation and survival (Lin, N. U.; Winer, E. P., Breast Cancer Res 6: 204-210, 2004).

Interaction between family members is necessitated by deficiencies in ErbB2, which has no known ligand, and ErbB3, which is kinase dead. EGFR, ErbB3, and ErbB4 bind ligand to induce ErbB receptor homodimerization or heterodimerization, whereas ErbB2 functions as the preferred dimerization partner. The composition of the pairwise combinations is important for signal diversification, as dimer identity determines which downstream pathways are activated. Representative downstream gene products in the ErbB signal transduction pathway include Shc, Grb2, SOS1, Ras, Raf1, Mek, ERK1, ERK2, ERα, Akt, mTOR, FKHR, p27, Cyclin D1, FasL, GSK-3, Bad, and STAT3.

There is strong precedent for involvement of the EGFR and other members of the ErbB family in human cancer because over 60% of all solid tumors overexpress at least one of these proteins or their ligands. Constitutively active, tumorigenic EGFR vIII, a mutant possessing a truncated extracellular domain, has been reported to be present in up to 78% of breast carcinomas and has also been found in glioblastomas. Overexpression of EGFR is commonly found in breast, lung, head and neck, bladder tumors, while ErbB2 expression is frequently elevated in human tumors of epithelial origin. Activating mutations in the tyrosine kinase domain have been identified in patients with non-small cell lung cancer (Lin, N. U.; Winer, E. P., Breast Cancer Res 6: 204-210, 2004). ErbB1 and/or ErbB2 amplification has also been implicated in squamous cell carcinomas, salivary gland carcinomas, ovarian carcinomas, and pancreatic cancers (Cooper, G. C. Oncogenes. 2$^{nd}$ ed. Sudbury: Jones and Barlett, 1995; Zhang, Y., et al., Cancer Res 66: 1025-32, 2006). Overexpression of ErbB2 has potent transforming activity, likely due to its ability to cooperate with other ErbB receptors (Sherman, L., et al., Oncogene 18: 6692-99, 1999). In fact, some human cancers that overexpress both EGFR and ErbB2 have a poorer prognosis than cancers that overexpress either receptor alone.

The ErbB signaling network is often a key component in the pathogenesis of breast cancer. Amplification of ErbB2 is associated with an aggressive tumor phenotype that is characterized by relatively rapid tumor growth, metastatic spread to visceral sites, and drug resistance. ErbB2 has been shown to be amplified in 20% of axillary node-negative ("ANN") breast cancer cases, and this amplification has been identified as an independent prognostic factor for risk of recurrence in ANN breast cancer. (Andrulis, I. L., et al., J Clin Oncol 16: 1340-9, 1998).

Targeted blockade of ErbB signaling with trastuzumab (Herceptin), a monoclonal antibody directed at ErbB2, has been shown to improve survival in women with ErbB2-positive, advanced breast cancer. Other monoclonal antibodies directed against ErbB receptors include cetuximab (Erbitux) and panitumumab (Vectibix).

Several small molecule tyrosine kinase inhibitors (TKIs) have been found to act selectively upon ErbB family members. Notable examples include gefitinib (Iressa) and erlotinib (Tarceva), both of which target the EGFR. These small molecules compete with ATP for binding to the kinase domain of the receptor. Compared to monoclonal antibodies, TKIs have several advantages in that they are orally bioavailable, well-tolerated, and appear to be active against truncated forms of ErbB2 and EGFR receptors (e.g., EGFR vIII) in vitro. In addition, the small size of small molecule TKIs may allow them to penetrate sanctuary sites such as the central nervous system. Finally, the homology between kinase domains of ErbB receptors allows for development of TKIs that target more than one member of the ErbB family simultaneously, the advantages of which are described herein.

Although certain malignancies have been linked to the overexpression of individual receptors, efficient signal transduction relies on the coexpression of ErbB receptor family members. This cooperation of ErbB receptor family members in signal transduction and malignant transformation may limit the success of agents that target individual receptors in the treatment of cancer; a potential mechanism of resistance to agents targeting a single ErbB receptor is upregulation of other members of the receptor family (Britten, C. D., Mol Cancer Ther 3: 1335-42, 2004).

Agents that target two or more ErbB receptors are called pan-ErbB regulators. ERRP is a pan-ErbB negative regulator that is expressed in most benign pancreatic ductal epithelium and islet cells. Tumors have been found to experience a progressive loss in ERRP expression. That Erbitux and Herceptin show success in a limited patient base (tumors having increased expression of EGFR or ErbB2) could be partly due to coexpression of multiple ErbB family members.

In both in vitro and in vivo models, strategies that employ a dual ErbB approach seem to have greater antitumor activity than agents targeting a single ErbB receptor. Thus, agents that target multiple members of ErbB family are likely to provide therapeutic benefit to a broader patient population (Zhang, Y., et al., Cancer Res 66: 1025-32, 2006). In certain embodiments, provided compounds inhibit one or more of ErbB1, ErbB2, ErbB3, and ErbB4. In some embodiments, provided compounds inhibit two or more of ErbB1, ErbB2, ErbB3, and ErbB4, or a mutant thereof, and are therefore pan-ErbB inhibitors.

Clearly, there is growing evidence to support the concurrent inhibition of two or more ErbB (i.e., pan-ErbB) receptors in cancer therapy. Possible pan-ErbB approaches with small molecules include using combinations of agents that target individual ErbB receptors, using single agents that target multiple ErbB receptors, or using agents that interfere with ErbB receptor interactions (e.g., dimerization). Additional strategies include therapies utilizing a small molecule in combination with antibodies, or chemoprevention therapies (Lin, N. U.; Winer, E. P., Breast Cancer Res 6: 204-210, 2004).

An example of small molecule pan-ErbB inhibition is CI-1033, an irreversible pan-ErbB inhibitor that covalently binds to the ATP binding site of the intracellular kinase domain. Another irreversible pan-ErbB receptor tyrosine kinase inhibitor is HKI-272, which inhibits the growth of tumor cells that express ErbB-1 (EGFR) and ErbB-2 (HER-2) in culture and xenografts, and has antitumor activity in HER-2-positive breast cancer (Andrulis, I. L., et al., J Clin Oncol 16: 1340-9, 1998). Irreversible inhibitors have demonstrated superior antitumor activity in comparison with reversible inhibitors.

Neurofibromatosis type I (NF1) is a dominantly inherited human disease affecting one in 2500-3500 individuals. Several organ systems are affected, including bones, skin, iris, and the central nervous system, as manifested in learning disabilities and gliomas. A hallmark of NF1 is the development of benign tumors of the peripheral nervous system (neurofibromas), which vary greatly in both number and size among patients. Neurofibromas are heterogeneous tumors composed of Schwann cells, neurons, fibroblasts and other cells, w/ Schwann cells being the major (60-80%) cell type.

Aberrant expression of the EGFR is associated with tumor development in NF1 and in animal models of NF1, suggesting a role in pathogenesis and representing a novel potential therapeutic target. EGFR expression affects the growth of tumor cell lines derived from NF1 patients under conditions where EGF is not the primary factor driving growth of the cells. These data suggest that EGFR may play an important role in NF1 tumorigenesis and Schwann cell transformation (DeClue, J. E., et al., J Clin Invest 105: 1233-41, 2000).

Patients with NF1 develop aggressive Schwann cell neoplasmas known as malignant peripheral nerve sheath tumors (MPNSTs). Schwann cells are the major supportive cell population in the peripheral nervous system. Neoplastic Schwann cells within these neoplasms variably express the ErbB tyrosine kinases mediating NRG-1 responses (ErbB2, ErbB3, ErbB4). Neuregulin-1 (NRG-1) proteins promote the differentiation, survival, and/or proliferation of many cell types in the developing nervous system, and overexpression of NRG-1 in myelinating Schwann cells induces the formation of malignant peripheral nerve sheath tumors (MPNSTs) (Fallon, K. B., et al., J Neuro Oncol 66: 273-84, 2004).

Deregulation of Schwann cell growth is a primary defect driving the development of both benign neurofibromas and MPNST in neurofibromatosis type I (NF1) patients. Growth of MPNSTs and transformed mouse Schwann cells in vitro is highly EGF-dependent and can be blocked by EGFR inhibitors under conditions where EGF is the primary growth factor. Some human MPNST cell lines have been found to demonstrate constitutive ErbB phosphorylation. While treatment with ErbB inhibitors abolishes ErbB phosphorylation and reduces DNA synthesis in these lines, effective chemotherapeutic regimens for MPNST remain elusive (Stonecypher, M. S., et al., Oncogene 24: 5589-5605, 2005).

Schwannomas are peripheral nerve tumors comprised almost entirely of Schwann-like cells, and typically have mutations in the neurofibromatosis type II (NF2) tumor suppressor gene. Ninety percent of NF2 patients develop bilateral vestibular schwannomas and/or spinal schwannomas. Enlarging schwannomas can compress adjacent structures, resulting in deafness and other neurologic problems. Surgical removal of these tumors is difficult, often resulting in increased patient morbidity.

Both normal human Schwann cells and schwannoma cells express neuregulin receptors (i.e., ErbB receptors), and schwannoma cells proliferate in response to neuregulin. It is possible that aberrant neuregulin production or response contributes to aberrant schwannoma cell proliferation (Pelton, P. D., et al., Oncogene 17: 2195-2209, 1998).

The NF2 tumor suppressor, Merlin, is a membrane/cytoskeleton-associated protein implicated in the regulation of tyrosine kinase activity. Genetic interactions between a Merlin mutation and EGFR pathway mutations have been documented in Drosophila (LaJeunesse, D. R., et al., Genetics 158: 667-79, 2001). Other evidence suggests Merlin can inhibit EGFR internalization and signaling upon cell-cell contact by restraining the EGFR into a membrane compartment from which it can neither signal nor be internalized (McClatchey, A. I., et al., Genes and Development 19: 2265-77, 2005; Curto, M. C., et al., J Cell Biol 177: 893-903, 2007).

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Provided compounds are inhibitors of one or more of ErbB1, ErbB2, ErbB3, and ErbB4 and are therefore useful for treating one or more disorders associated with activity of one of more of ErbB1, ErbB2, ErbB3, and ErbB4. Thus, in certain embodiments, the present invention provides a method for treating an ErbB1-mediated, an ErbB2-mediated, an ErbB3-mediated, and/or ErbB4-mediated disorder comprising the step of administering to a patient in need thereof a compound of the present invention, or pharmaceutically acceptable composition thereof.

As used herein, the terms "ErbB1-mediated", "ErbB2-mediated," "ErbB3-mediated," and/or "ErbB4-mediated" disorders or conditions as used herein means any disease or other deleterious condition in which one or more of ErbB1, ErbB2, ErbB3, and/or ErbB4, or a mutant thereof, are known to play a role. Accordingly, another embodiment of the present invention relates to treating or lessening the severity of one or more diseases in which one or more of ErbB1, ErbB2, ErbB3, and/or ErbB4, or a mutant thereof, are known to play a role. Specifically, the present invention relates to a method of treating or lessening the severity of a disease or condition selected from a proliferative disorder, wherein said method comprises administering to a patient in need thereof a compound or composition according to the present invention.

In some embodiments, the present invention provides a method for treating or lessening the severity of one or more disorders selected from a cancer. In some embodiments, the cancer is associated with a solid tumor. In certain embodiments, the cancer is breast cancer, glioblastoma, lung cancer, cancer of the head and neck, colorectal cancer, bladder cancer, or non-small cell lung cancer. In some embodiments, the present invention provides a method for treating or lessening the severity of one or more disorders selected from squamous cell carcinoma, salivary gland carcinoma, ovarian carcinoma, or pancreatic cancer.

In certain embodiments, the present invention provides a method for treating or lessening the severity of neurofibromatosis type I (NF1), neurofibromatosis type II (NF2) Schwann cell neoplasms (e.g. MPNST's), or Schwannomas.

(b) TEC Family

The TEC family of non-receptor tyrosine kinases, referred to herein as "TEC-kinases," plays a central role in signaling through antigen-receptors such as the TCR, BCR and Fc receptors (reviewed in Miller A, et al. Current Opinion in Immunology 14; 331-340 (2002). TEC-kinases are essential for T cell activation. Three members of the family, Itk, Rlk and, are activated downstream of antigen receptor engagement in T cells and transmit signals to downstream effectors, including PLC-γ. Combined deletion of Itk and Rlk in mice leads to a profound inhibition of TCR responses including proliferation, cytokine production and immune responses to an intracellular parasite (*Toxoplasma gondii*) (Schaeffer et al., Science 284; 638-641 (1999)). Intracellular signalling following TCR engagement is effected in ITK/RLK deficient T cells; inositol triphosphate production, calcium mobilization and MAP kinase activation are all reduced. Tec-kinases are also essential for B cell development and activation.

TEC-kinases include five family members, which are expressed primarily in hematopoietic cells: TEC, BTK, ITK (also known as TSK and EMT), RLK (also known as TXK), and BMX (also known as ETK). Additional related TEC-kinases have been found in Drosophila melanogaster, zebrafish (*Danio rerió*), skate (*Raja eglanteria*), and sea urchin (*Anthocidaris crassispina*).

Provided compounds are inhibitors of one of more TEC-kinases and are therefore useful for treating one or more disorders associated with activity of one or more TEC-kinases. Thus, in certain embodiments, the present invention provides a method for treating a TEC-mediated disorder comprising the step of administering to a patient in need thereof a compound of the present invention, or pharmaceutically acceptable composition thereof.

The term "TEC-mediated condition", as used herein means any disease or other deleterious condition in which TEC-kinases are known to play a role. Such conditions include those described herein and in Melcher, M et al., "The Role of TEC Family Kinases in Inflammatory Processes", *Anti-Inflammatory & Anti Allergy Agents in Medicinal Chemistry*, Vol. 6, No. 1, pp. 61-69 (February 2007). Accordingly, another embodiment of the present invention relates to treating or lessening the severity of one or more diseases in which TEC-kinases are known to play a role. Specifically, the present invention relates to a method of treating or lessening the severity of a disease or condition selected from autoimmune, inflammatory, proliferative, and hyperproliferative diseases and immunologically-mediated diseases including rejection of transplanted organs or tissues and Acquired Immunodeficiency Syndrome (AIDS)(also known as HIV), wherein said method comprises administering to a patient in need thereof a composition of the present invention.

In some embodiments, the present invention provides a method for treating or lessening the severity of one or more diseases and conditions associated with TEC-kinases including diseases of the respiratory tract including, without limitation, reversible obstructive airways diseases including asthma, such as bronchial, allergic, intrinsic, extrinsic and dust asthma, particularly chronic or inveterate asthma (e.g., late asthma airways hyper-responsiveness) and bronchitis. In some embodiments, the present invention provides a method for treating or lessening the severity of one or more diseases and conditions associated with TEC-kinases including those conditions characterized by inflammation of the nasal mucus membrane, including acute rhinitis, allergic, atrophic rhinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofoulous rhinitis, seasonal rhinitis including rhinitis nervosa (hay fever) and vasomotor rhinitis, sarcoidosis, farmer's lung and related diseases, fibroid lung, and idiopathic interstitial pneumonia.

In some embodiments, the present invention provides a method for treating or lessening the severity of one or more diseases and conditions associated with TEC-kinases including diseases of the bone and joints including, without limitation, rheumatoid arthritis, seronegative spondyloarthropathies (including ankylosing spondylitis, psoriatic arthritis and Reiter's disease), Behcet's disease, Sjogren's syndrome, systemic sclerosis, osteoporosis, bone cancer, and bone metastasis.

In some embodiments, the present invention provides a method for treating or lessening the severity of one or more diseases and conditions associated with TEC-kinases including diseases and disorders of the skin, including, without limitation, psoriasis, systemic sclerosis, atopical dermatitis, contact dermatitis and other eczematous dermatitis, seborrhoetic dermatitis, Lichen planus, pemphigus, bullous pemphigus, epidermolysis bullosa, urticaria, angiodermas, vasculitides, erythemas, cutaneous eosinophilias, uveitis, alopecia, areata and vernal conjunctivitis.

In some embodiments, the present invention provides a method for treating or lessening the severity of one or more diseases and conditions associated with TEC-kinases including diseases and disorders of the gastrointestinal tract, including, without limitation, celiac disease, proctitis, eosinophilic gastro-enteritis, mastocytosis, pancreatitis, Crohn's disease, ulcerative colitis, food-related allergies which have effects remote from the gut, e. g. migraine, rhinitis and eczema.

In some embodiments, the present invention provides a method for treating or lessening the severity of one or more diseases and conditions associated with TEC-kinases including those diseases and disorders of other tissues and systemic disease, including, without limitation, multiple sclerosis, artherosclerosis, lupus erythematosus, systemic lupus erythematosus, Hashimoto's thyroiditis, myasthenia gravis, diabetes, nephrotic syndrome, eosinophilia fascitis, hyper IgE syndrome, lepromatous leprosy, sezary syndrome and idiopathic thrombocytopenia purpura, restenosis following angioplasty, tumours (for example leukemia, lymphomas, and prostate cancers), and artherosclerosis. In certain embodiments, the diabetes is type I diabetes.

In some embodiments, the present invention provides a method for treating or lessening the severity of one or more diseases and conditions associated with TEC-kinases including allograft rejection including, without limitation, acute and chronic allograft rejection following for example transplantation of kidney, heart, liver, lung, bone marrow, skin and cornea; and chronic graft versus host disease.

In some embodiments, the present invention relates to a method of treating or lessening the severity of one or more of the diseases or conditions associated with TEC-kinases, as recited above, wherein said method comprises administering to a patient in need thereof a compound or composition according to the present invention.

(c) Bruton's Tyrosine Kinase (BTK)

Bruton's tyrosine kinase ("BTK"), a member of TEC-kinases, is a key signaling enzyme expressed in all hematopoietic cell types except T lymphocytes and natural killer cells. BTK plays an essential role in the B-cell signaling pathway linking cell surface B-cell receptor (BCR) stimulation to downstream intracellular responses.

BTK is a key regulator of B-cell development, activation, signaling, and survival (Kurosaki, Curr Op Imm, 2000, 276-281; Schaeffer and Schwartzberg, Curr Op Imm 2000, 282-288). In addition, BTK plays a role in a number of other hematopoietic cell signaling pathways, e.g., Toll like receptor (TLR) and cytokine receptor-mediated TNF-α production in macrophages, IgE receptor (Fc_epsilon_RI) signaling in mast cells, inhibition of Fas/APO-1 apoptotic signaling in B-lineage lymphoid cells, and collagen-stimulated platelet aggregation. See, e.g., C. A. Jeffries, et al., (2003), Journal of Biological Chemistry 278:26258-26264; N. J. Horwood, et al., (2003), The Journal of Experimental Medicine 197: 1603-1611; Iwaki et al. (2005), Journal of Biological Chemistry 280(48):40261-40270; Vassilev et al. (1999), Journal of Biological Chemistry 274(3): 1646-1656, and Quek et al. (1998), Current Biology 8(20): 1137-1140.

Patients with mutations in BTK have a profound block in B cell development, resulting in the almost complete absence of mature B lymphocytes and plasma cells, severely reduced Ig levels and a profound inhibition of humoral response to recall antigens (reviewed in Vihinen et al Frontiers in Bioscience 5: d917-928). Mice deficient in BTK also have a reduced number of peripheral B cells and greatly decreased serum levels of IgM and IgG3. BTK deletion in mice has a profound effect on B cell proliferation induced by anti-IgM, and inhibits immune responses to thymus-independent type II antigens (Ellmeier et al, J Exp Med 192: 1611-1623 (2000)). BTK also plays a crucial role in mast cell activation through the high-affinity IgE receptor (Fc_epsilon_RI). BTK deficient murine mast cells have reduced degranulation and decreased production of proinflammatory cytokines following Fc_epsilon_RI cross-linking (Kawakami et al. Journal of Leukocyte Biology 65: 286-290).

BTK has been implicated in diabetes. BTK deficiency in non-obese diabetic mice dramatically protects against diabetes and improves B cell-related tolerance, as indicated by failure to generate autoantibodies to insulin (Kendall, et al. J. Immunol. 183: 6403-6412 (2009)). Modulation of BTK and improvement of B cell-related tolerance can therefore be used in treatment of diabetes, particularly T cell-mediated autoimmune diabetes, e.g. type I diabetes.

BTK is also implicated in various cancers. For example, BTK is upregulated in pancreatic cancer cells compared with normal pancreas cells, and BTK is also upregulated in chronic pancreatitis cells, which is sometimes a precursor to pancreatic cancer (Crnogorac-Jurcevic, et al. Gastroenterology 129: 1454-1463 (2005)). Due to the key role of BTK in regulation of B-cell development, activation, signaling, and survival, BTK is involved in many B cell-related cancers.

Provided compounds are inhibitors of BTK and are therefore useful for treating one or more disorders associated with activity of BTK. Thus, in some embodiments, the present invention provides a method for treating a BTK-mediated disorder comprising the step of administering to a patient in need thereof a compound of the present invention, or pharmaceutically acceptable composition thereof.

As used herein, the term "BTK-mediated" disorders or conditions as used herein means any disease or other deleterious condition in which BTK, or a mutant thereof, is known to play a role. Accordingly, another embodiment of the present invention relates to treating or lessening the severity of one or more diseases in which BTK, or a mutant thereof, is known to play a role. Specifically, the present invention relates to a method of treating or lessening the severity of a disease or condition selected from a proliferative disorder or an autoimmune disorder, wherein said method comprises administering to a patient in need thereof a compound or composition according to the present invention.

In some embodiments, the present invention provides a method for treating or lessening the severity of one or more diseases and conditions associated with BTK. In some embodiments, the disease or condition is an autoimmune disease, e.g., inflammatory bowel disease, arthritis, systemic lupus erythematosus (SLE), vasculitis, idiopathic thrombocytopenic purpura (ITP), rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, autoimmune thyroiditis, Sjogren's syndrome, multiple sclerosis, systemic sclerosis, Lyme neuroborreliosis, Guillain-Barre syndrome, acute disseminated encephalomyelitis, Addison's disease, opsoclonus-myoclonus syndrome, ankylosing spondylosis, antiphospholipid antibody syndrome, aplastic anemia, autoimmune hepatitis, autoimmune gastritis, pernicious anemia, celiac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, membranous glomerulonephropathy, endometriosis, interstitial cystitis, pemphigus vulgaris, bullous pemphigoid, neuromyotonia, scleroderma, or vulvodynia. In some embodiments, the disease or condition is a hyperproliferative disease or immunologically-mediated diseases including rejection of transplanted organs or tissues and Acquired Immunodeficiency Syndrome (AIDS, also known as HIV). In certain embodiments, the diabetes is type I diabetes.

In some embodiments, the present invention provides a method for treating or lessening the severity of one or more diseases and conditions associated with BTK, wherein the disease or condition is selected from heteroimmune conditions or diseases, which include, but are not limited to graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis.

In some embodiments, the present invention provides a method for treating or lessening the severity of one or more diseases and conditions associated with BTK, wherein the disease or condition is selected from an inflammatory disease, e.g., asthma, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis.

In some embodiments, the present invention provides a method for treating or lessening the severity of one or more diseases and conditions associated with BTK, wherein the disease or condition is selected from a cancer. In one embodiment, the cancer is a B-cell proliferative disorder, e.g., diffuse large B cell lymphoma, follicular lymphoma, chronic lymphocytic lymphoma, chronic lymphocytic leukemia, acute lymphocytic leukemia, B-cell prolymphocytic leukemia, lymphoplasmacytic lymphoma/Waldenstrom macroglobulinemia, splenic marginal zone lymphoma, multiple myeloma (also known as plasma cell myeloma), non-Hodgkin's lymphoma, Hodgkin's lymphoma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, Burkitt lymphoma/leukemia, or lymphomatoid granulomatosis. In some embodiments, the cancer is breast cancer, prostate cancer, or cancer of the mast cells (e.g., mastocytoma, mast cell leukemia, mast cell sarcoma, systemic mastocytosis). In one embodiment, the cancer is bone cancer. In another embodiment, the cancer is of other primary origin and metastasizes to the bone. In certain embodiments, the cancer is colorectal cancer or pancreatic cancer.

In some embodiments, the present invention provides a method for treating or lessening the severity of one or more diseases or conditions associated with BTK including diseases of the bone and joints including, without limitation, rheumatoid arthritis, seronegative spondyloarthropathies (including ankylosing spondylitis, psoriatic arthritis and Reiter's disease), Behcet's disease, Sjogren's syndrome, systemic sclerosis, osteoporosis, bone cancer, and bone metastasis.

In some embodiments, the present invention provides a method for treating or lessening the severity of one or more diseases and conditions associated with BTK, wherein the disease or condition is selected from a thromboembolic disorder, e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, or deep venous thrombosis.

In some embodiments, the present invention provides a method for treating or lessening the severity of one or more diseases and conditions associated with BTK, including infectious and noninfectious inflammatory events and autoimmune and other inflammatory diseases. These autoimmune and inflammatory diseases, disorders, and syndromes include inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, scleraderma, mycosis fungoides, acute inflammatory responses (such as acute respiratory distress syndrome and ischemia/reperfusion injury), and Graves' disease. In certain embodiments, the diabetes is type I diabetes.

In some embodiments, the present invention provides a method for treating or lessening the severity of one or more diseases and conditions associated with BTK, selected from rheumatoid arthritis, multiple sclerosis, B-cell chronic lymphocytic leukemia, acute lymphocytic leukemia, hairy cell leukemia, non-Hodgkin's lymphoma, Hodgkin's lymphoma, multiple myeloma, bone cancer, bone metastasis, osteoporosis, diabetes (e.g. type I diabetes), irritable bowel syndrome, Crohn's disease, lupus and renal transplant.

(d) ITK

Interleukin-2 inducible T-cell kinase ("ITK") is expressed in T cells, mast cells and natural killer cells. It is activated in T cells upon stimulation of the T cell receptor (TCR), and in mast cells upon activation of the high affinity IgE receptor. Following receptor stimulation in T cells, Lck, a Src tyrosine kinase family member, phosphorylates Y511 in the kinase domain activation loop of ITK (S. D. Heyeck et al., 1997, J. Biol. Chem, 272, 25401-25408). Activated ITK, together with Zap-70 is required for phosphorylation and activation of PLC-gamma (S. C. Bunnell et al., 2000, J. Biol. Chem., 275, 2219-2230). PLC-gamma catalyzes the formation of inositol 1,4,5-triphosphate and diacylglycerol, leading to calcium mobilization and PKC activation, respectively. These events activate numerous downstream pathways and lead ultimately to degranulation (mast cells) and cytokine gene expression (T cells) (Y. Kawakami et al., 1999, J. Leukocyte Biol., 65, 286-290).

The role of ITK in T cell activation has been confirmed in ITK knockout mice. $CD4^+$ T cells from ITK knockout mice have a diminished proliferative response in a mixed lymphocyte reaction or upon Con A or anti-CD3 stimulation. (X. C. Liao and D. R. Littman, 1995, Immunity, 3, 757-769). Also, T cells from ITK knockout mice produced little IL-2 upon TCR stimulation resulting in reduced proliferation of these cells. In another study, ITK deficient $CD4^+$ T cells produced reduced levels of cytokines including IL-4, IL-5 and IL-13 upon stimulation of the TCR, even after priming with inducing conditions (D. J. Fowell, 1999, Immunity, 11, 399-409).

The role of ITK in PLC-gamma activation and in calcium mobilization was also confirmed in the T cells of these knockout mice, which had severely impaired $IP_3$ generation and no extracellular calcium influx upon TCR stimulation (K. Liu et al., 1998, J. Exp. Med. 187, 1721-1727). Such studies support a key role for ITK in activation of T cells and mast cells. Thus an inhibitor of ITK would be of therapeutic benefit in diseases mediated by inappropriate activation of these cells.

It has been well established that T cells play an important role in regulating the immune response (Powrie and Coffman, 1993, Immunology Today, 14, 270-274). Indeed, activation of T cells is often the initiating event in immunological disorders. Following activation of the TCR, there is an influx of calcium that is required for T cell activation. Upon activation, T cells produce cytokines, including IL-2, 4, 5, 9, 10, and 13 leading to T cell proliferation, differentiation, and effector function. Clinical studies with inhibitors of IL-2 have shown that interference with T cell activation and proliferation effectively suppresses immune response in vivo (Waldmann, 1993, Immunology Today, 14, 264-270). Accordingly, agents that inhibit T lymphocyte activation and subsequent cytokine production, are therapeutically useful for selectively suppressing the immune response in a patient in need of such immunosuppression.

Mast cells play a critical roll in asthma and allergic disorders by releasing proinflammatory mediators and cytokines. Antigen-mediated aggregation of Fc.epsilon.RI, the high-affinity receptor for IgE, results in activation of mast cells (D. B. Corry et al., 1999, Nature, 402, B18-23). This triggers a series of signaling events resulting in the release of mediators, including histamine, proteases, leukotrienes and cytokines (J. R. Gordon et al., 1990, Immunology Today, 11, 458-464.) These mediators cause increased vascular permeability, mucus production, bronchoconstriction, tissue degradation and inflammation thus playing key roles in the etiology and symptoms of asthma and allergic disorders.

Published data using ITK knockout mice suggests that in the absence of ITK function, increased numbers of memory T cells are generated (A. T. Miller et al., 2002 The Journal of Immunology, 168, 2163-2172). One strategy to improve vaccination methods is to increase the number of memory T cells generated (S. M. Kaech et al., Nature Reviews Immunology, 2, 251-262). In addition, deletion of ITK in mice results in reduced T cell receptor (TCR)-induced proliferation and secretion of the cytokines IL-2, IL-4, IL-5, IL-10 and IFN-y (Schaeffer et al, Science 284; 638-641 (1999)), Fowell et al, Immunity 11, 399-409 (1999), Schaeffer et al, Nature Immunology 2 (12): 1183-1188 (2001))). The immunological symptoms of allergic asthma are attenuated in ITK−/−mice. Lung inflammation, eosinophil infiltration and mucus production are drastically reduced in ITK−/−mice in response to challenge with the allergen OVA (Mueller et al, Journal of Immunology 170: 5056-5063 (2003)). ITK has also been implicated in atopic dermatitis. This gene has been reported to be more highly expressed in peripheral blood T cells from patients with moderate and/or severe atopic dermatitis than in controls or patients with mild atopic dermatitis (Matsumoto et al, International Archives of Allergy and Immunology 129: 327-340 (2002)).

Splenocytes from RLK−/−mice secrete half the IL-2 produced by wild type animals in response to TCR engagement (Schaeffer et al, Science 284: 638-641 (1999)), while combined deletion of ITK and RLK in mice leads to a profound inhibition of TCR-induced responses including proliferation and production of the cytokines IL-2, IL-4, IL-5 and IFN-y (Schaeffer et al, Nature Immunology 2 (12): 1183-1188 (2001), Schaeffer et al, Science 284: 638-641 (1999)). Intracellular signalling following TCR engagement is effected in ITK/RLK deficient T cells; inositol triphosphate production, calcium mobilization, MAP kinase activation, and activation of the transcription factors NFAT and AP-1 are all reduced (Schaeffer et al, Science 284: 638-641 (1999), Schaeffer et al, Nature Immunology 2 (12): 1183-1188 (2001)).

Provided compounds are inhibitors of ITK and are therefore useful for treating one or more disorders associated with activity of ITK. Thus, in some embodiments, the present invention provides a method for treating an ITK-mediated disorder comprising the step of administering to a patient in need thereof a compound of the present invention, or pharmaceutically acceptable composition thereof.

As used herein, the term "ITK-mediated" disorders or conditions as used herein means any disease or other deleterious condition in which ITK, or a mutant thereof, is known to play a role. Accordingly, another embodiment of the present invention relates to treating or lessening the severity of one or more diseases in which ITK, or a mutant thereof, is known to play a role. Specifically, the present invention relates to a method of treating or lessening the severity of a disease or condition selected from a mast cell-mediated condition, a basophil-mediated disorder, an immune or allergic disorder, wherein said method comprises administering to a patient in need thereof a compound or composition according to the present invention.

In some embodiments, the present invention provides a method for treating or lessening the severity of one or more diseases and conditions associated with ITK, wherein the disease or condition is an immune disorder, including inflammatory diseases, autoimmune diseases, organ and bone marrow transplant rejection and other disorders associated with T cell-mediated immune response or mast cell-mediated immune response.

In certain embodiments, the present invention provides a method for treating or lessening the severity of one or more diseases and conditions associated with ITK, wherein the disease or condition is acute or chronic inflammation, an allergy, contact dermatitis, psoriasis, rheumatoid arthritis, multiple sclerosis, diabetes (e.g. type 1 diabetes), inflammatory bowel disease, Guillain-Barre syndrome, Crohn's disease, ulcerative colitis, cancer, graft versus host disease (and other forms of organ or bone marrow transplant rejection) or lupus erythematosus.

In certain embodiments, the present invention provides a method for treating or lessening the severity of one or more diseases and conditions associated with ITK, wherein the disease or condition is a mast cell driven conditions, a basophil-mediated disorder, reversible obstructive airway disease, asthma, rhinitis, chronic obstructive pulmonary disease (COPD), peripheral T-cell lymphomas or HIV [also known as Acquired Immunodeficiency Syndrome (AIDS)]. Such conditions include those described in Readinger, et al., PNAS 105: 6684-6689 (2008).

(e) JAK Family

The Janus kinases (JAK) are a family of tyrosine kinases consisting of JAK1, JAK2, JAK3 and TYK2. The JAKs play a critical role in cytokine signaling. The down-stream substrates of the JAK family of kinases include the signal transducer and activator of transcription (STAT) proteins. JAK/STAT signaling has been implicated in the mediation of many abnormal immune responses such as allergies, asthma, autoimmune diseases such as transplant rejection, rheumatoid arthritis, amyotrophic lateral sclerosis and multiple sclerosis as well as in solid and hematologic malignancies such as leukemias and lymphomas. The pharmaceutical intervention in the JAK/STAT pathway has been reviewed [Frank, Mol. Med. 5: 432-456 (1999) & Seidel, et al, Oncogene 19: 2645-2656 (2000)].

JAK1, JAK2, and TYK2 are ubiquitously expressed, while JAK3 is predominantly expressed in hematopoietic cells. JAK3 binds exclusively to the common cytokine receptor gamma chain (γc) and is activated by IL-2, IL-4, IL-7, IL-9, and IL-15.

The proliferation and survival of murine mast cells induced by IL-4 and IL-9 have, in fact, been shown to be dependent on JAK3- and γc-signaling [Suzuki et al, Blood 96: 2172-2180 (2000)].

Cross-linking of the high-affinity immunoglobulin (Ig) E receptors of sensitized mast cells leads to a release of proinflammatory mediators, including a number of vasoactive cytokines resulting in acute allergic, or immediate (type I) hypersensitivity reactions [Gordon et al, Nature 346: 274-276 (1990) & Galli, N. Engl. J. Med., 328: 257-265 (1993)]. A crucial role for JAK3 in IgE receptor-mediated mast cell responses in vitro and in vivo has been established [Malaviya, et al, Biochem. Biophys. Res. Commun. 257: 807-813 (1999)]. In addition, the prevention of type I hypersensitivity reactions, including anaphylaxis, mediated by mast cell-activation through inhibition of JAK3 has also been reported [Malaviya et al, J. Biol. Chem. 274: 27028-27038 (1999)]. Targeting mast cells with JAK3 inhibitors modulated mast cell degranulation in vitro and prevented IgE receptor/antigen-mediated anaphylactic reactions in vivo.

A recent study described the successful targeting of JAK3 for immune suppression and allograft acceptance. The study demonstrated a dose-dependent survival of buffalo heart allograft in Wistar Furth recipients upon administration of inhibitors of JAK3 indicating the possibility of regulating unwanted immune responses in graft versus host disease [Kirken, Transpl. Proc. 33: 3268-3270 (2001)].

IL-4-mediated STAT-phosphorylation has been implicated as the mechanism involved in early and late stages of rheumatoid arthritis (RA). Up-regulation of proinflammatory cytokines in RA synovium and synovial fluid is a characteristic of the disease. It has been demonstrated that IL-4-mediated activation of IL-4/STAT pathway is mediated through the Janus kinases (JAK 1 & 3) and that IL-4-associated JAK kinases are expressed in the RA synovium [Muller-Ladner, et al, J. Immunol. 164: 3894-3901 (2000)].

Familial amyotrophic lateral sclerosis (FALS) is a fatal neurodegenerative disorder affecting about 10% of ALS patients. The survival rates of FALS mice were increased upon treatment with a JAK3 specific inhibitor. This confirmed that JAK3 plays a role in FALS [Trieu, et al, Biochem. Biophys. Res. Commun. 267: 22-25 (2000)].

Signal transducer and activator of transcription (STAT) proteins are activated by, among others, the JAK family kinases. Results form a recent study suggested the possibility of intervention in the JAK/STAT signaling pathway by targeting JAK family kinases with specific inhibitors for the treatment of leukemia [Sudbeck, et al., Clin. Cancer Res. 5: 1569-1582 (1999)]. JAK3 specific compounds were shown to inhibit the clonogenic growth of JAK3-expressing cell lines DAUDI, RAMOS, LC1; 19, NALM-6, MOLT-3 and HL-60. Inhibition of JAK3 and TYK 2 abrogated tyrosine phosphorylation of STAT3, and inhibited cell growth of mycosis fungoides, a form of cutaneous T cell lymphoma.

JAK3 has also been implicated in diabetes. A JAK3 inhibitor exhibited potent immunomodulatory activity and delayed the onset of diabetes in the NOD mouse model of autoimmune type 1 diabetes (Cetkovic-Cvrlje, et al. Clin. Immunol. 106: 213-225 (2003)).

According to another embodiment, the invention provides a method for treating or lessening the severity of a JAK3- mediated disease or condition in a patient comprising the step of administering to said patient a composition according to the present invention.

The term "JAK3-mediated disease", as used herein means any disease or other deleterious condition in which a JAK3 kinase is known to play a role. Accordingly, another embodiment of the present invention relates to treating or lessening the severity of one or more diseases in which JAK3 is known to play a role. Specifically, the present invention relates to a method of treating or lessening the severity of a disease or condition selected from immune responses such as allergic or type I hypersensitivity reactions, asthma, autoimmune diseases such as transplant rejection, graft versus host disease, rheumatoid arthritis, diabetes (e.g. type I diabetes), amyotrophic lateral sclerosis, and multiple sclerosis, neurodegenerative disorders such as familial amyotrophic lateral sclerosis (FALS), as well as in solid and hematologic malignancies such as leukemias and lymphomas, wherein said method comprises administering to a patient in need thereof a composition according to the present invention.

The compounds and compositions, according to the method of the present invention, may be administered using any amount and any route of administration effective for treating or lessening the severity of cancer, an autoimmune disorder, a neurodegenerative or neurological disorder, schizophrenia, a bone-related disorder, liver disease, or a cardiac disorder. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting protein kinase activity in a biological sample comprising the step of contacting said biological sample with a compound of this invention, or a composition comprising said compound.

According to another embodiment, the invention relates to a method of inhibiting ErbB1, ErbB2, ErbB3, ErbB4, a TEC-kinase, and/or JAK3, or a mutant thereof, activity in a biological sample comprising the step of contacting said biological sample with a compound of this invention, or a composition comprising said compound. In certain embodiments, the invention relates to a method of irreversibly inhibiting ErbB1, ErbB2, ErbB3, ErbB4, a TEC-kinase, and/or JAK3, or a mutant thereof, activity in a biological sample comprising the step of contacting said biological sample with a compound of this invention, or a composition comprising said compound.

The term “biological sample”, as used herein, includes, without limitation, cell cultures or extracts thereof; biopsied material obtained from a mammal or extracts thereof; and blood, saliva, urine, feces, semen, tears, or other body fluids or extracts thereof.

Inhibition of protein kinase, or a protein kinase selected from ErbB1, ErbB2, ErbB3, ErbB4, a TEC-kinase, and/or JAK3, or a mutant thereof, activity in a biological sample is useful for a variety of purposes that are known to one of skill in the art. Examples of such purposes include, but are not limited to, blood transfusion, organ transplantation, biological specimen storage, and biological assays.

Another embodiment of the present invention relates to a method of inhibiting protein kinase activity in a patient comprising the step of administering to said patient a compound of the present invention, or a composition comprising said compound.

According to another embodiment, the invention relates to a method of inhibiting one or more of ErbB1, ErbB2, ErbB3, ErbB4, a TEC-kinase, and/or JAK3, or a mutant thereof, activity in a patient comprising the step of administering to said patient a compound of the present invention, or a composition comprising said compound. According to certain embodiments, the invention relates to a method of irreversibly inhibiting one or more of ErbB1, ErbB2, ErbB3, ErbB4, a TEC-kinase, and/or JAK3, or a mutant thereof, activity in a patient comprising the step of administering to said patient a compound of the present invention, or a composition comprising said compound. In other embodiments, the present invention provides a method for treating a disorder mediated by one or more of ErbB1, ErbB2, ErbB3, ErbB4, a TEC-kinase, and/or JAK3, or a mutant thereof, in a patient in need thereof, comprising the step of administering to said patient a compound according to the present invention or pharmaceutically acceptable composition thereof. Such disorders are described in detail herein.

Depending upon the particular condition, or disease, to be treated, additional therapeutic agents, which are normally administered to treat that condition, may also be present in the compositions of this invention. As used herein, additional therapeutic agents that are normally administered to treat a particular disease, or condition, are known as “appropriate for the disease, or condition, being treated.”

For example, compounds of the present invention, or a pharmaceutically acceptable composition thereof, are administered in combination with chemotherapeutic agents to treat proliferative diseases and cancer. Examples of known chemotherapeutic agents include, but are not limited to, Adriamycin, dexamethasone, vincristine, cyclophosphamide, fluorouracil, topotecan, taxol, interferons, platinum derivatives, taxane (e.g., paclitaxel), vinca alkaloids (e.g., vinblastine), anthracyclines (e.g., doxorubicin), epipodophyllotoxins (e.g., etoposide), cisplatin, an mTOR inhibitor (e.g., a rapamycin), methotrexate, actinomycin D, dolastatin 10, colchicine, emetine, trimetrexate, metoprine, cyclosporine, daunorubicin, teniposide, amphotericin, alkylating agents (e.g., chlorambucil), 5-fluorouracil, campthothecin, cisplatin, metronidazole, and Gleevec™, among others. In other embodiments, a compound of the present invention is administered in combination with a biologic agent, such as Avastin or VECTIBIX.

In certain embodiments, compounds of the present invention, or a pharmaceutically acceptable composition thereof, are administered in combination with an antiproliferative or chemotherapeutic agent selected from any one or more of abarelix, aldesleukin, alemtuzumab, alitretinoin, allopurinol, altretamine, amifostine, anastrozole, arsenic trioxide, asparaginase, azacitidine, BCG Live, bevacuzimab, fluorouracil, bexarotene, bleomycin, bortezomib, busulfan, calusterone, capecitabine, camptothecin, carboplatin, carmustine, celecoxib, cetuximab, chlorambucil, cladribine, clofarabine, cyclophosphamide, cytarabine, dactinomycin, darbepoetin alfa, daunorubicin, denileukin, dexrazoxane, docetaxel, doxorubicin (neutral), doxorubicin hydrochloride, dromostanolone propionate, epirubicin, epoetin alfa, erlotinib, estramustine, etoposide phosphate, etoposide, exemestane, filgrastim, floxuridine fludarabine, fulvestrant, gefitinib, gemcitabine, gemtuzumab, goserelin acetate, histrelin acetate, hydroxyurea, ibritumomab, idarubicin, ifosfamide, imatinib mesylate, interferon alfa-2a, interferon alfa-2b, irinotecan, lenalidomide, letrozole, leucovorin, leuprolide acetate, levamisole, lomustine, megestrol acetate, melphalan, mercaptopurine, 6-MP, mesna, methotrexate, methoxsalen, mitomycin C, mitotane, mitoxantrone, nandrolone, nelarabine, nofetumomab, oprelvekin, oxaliplatin, paclitaxel, palifermin, pamidronate, pegademase, pegaspargase, pegfilgrastim, pemetrexed disodium, pentostatin, pipobroman, plicamycin, porfimer sodium, procarbazine, quinacrine, rasburicase, rituximab, sargramostim, sorafenib, streptozocin, sunitinib maleate, talc, tamoxifen, temozolomide, teniposide, VM-26, testolactone, thioguanine, 6-TG, thiotepa, topotecan, toremifene, tositumomab, trastuzumab, tretinoin, ATRA, uracil mustard, valrubicin, vinblastine, vincristine, vinorelbine, zoledronate, or zoledronic acid.

Other examples of agents the inhibitors of this invention may also be combined with include, without limitation: treatments for Alzheimer's Disease such as donepezil hydrochloride) (Aricept®) and rivastigmine (Exelon®); treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), glatiramer acetate (Copaxone®), and mitoxantrone; treatments for asthma such as albuterol and montelukast (Singulair®); agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

In certain embodiments, compounds of the present invention, or a pharmaceutically acceptable composition thereof, are administered in combination with a monoclonal antibody or an siRNA therapeutic.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a provided compound, an additional therapeutic agent, and a pharmaceutically acceptable carrier, adjuvant, or vehicle.

The amount of both, an inventive compound and additional therapeutic agent (in those compositions which comprise an additional therapeutic agent as described above)) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 μg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by precoating the device with a pharmaceutically acceptable composition comprising a kinase inhibitor. Implantable devices coated with a compound of this invention are another embodiment of the present invention.

5. Probe Compounds

In certain aspects, a compound of the present invention may be tethered to a detectable moiety to form a probe compound. In one aspect, a probe compound of the invention comprises an irreversible protein kinase inhibitor of formula I-a or I-b, as described herein, a detectable moiety, and a tethering moiety that attaches the inhibitor to the detectable moiety.

In some embodiments, such probe compounds of the present invention comprise a provided compound of formula I-a or I-b tethered to a detectable moiety, $R^t$, by a bivalent tethering moiety, -T-. The tethering moiety may be attached to a compound of formula I-a or I-b via Ring A, Ring B, or $R^1$. One of ordinary skill in the art will appreciate that when a tethering moiety is attached to $R^1$, $R^1$ is a bivalent warhead group denoted as $R^{1'}$. In certain embodiments, a provided probe compound is selected from any of formula V-a, V-b, VI-a, VI-b, VII-a, or VII-b:

V-a

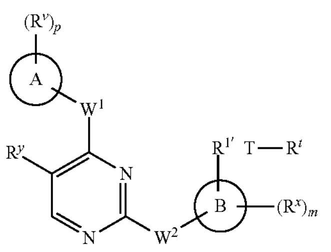

V-b

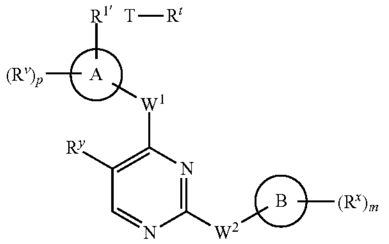

VI-a

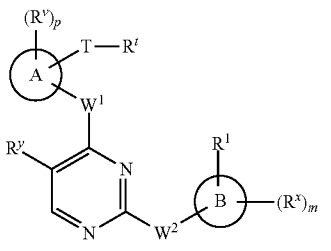

VI-b

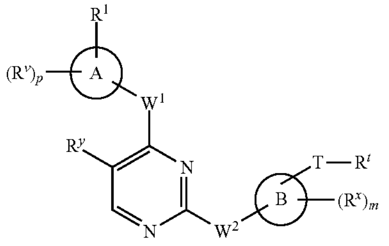

-continued

VII-a

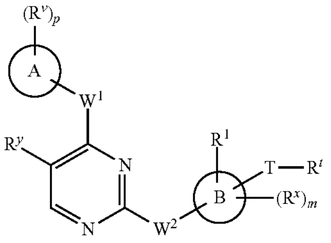

VII-b

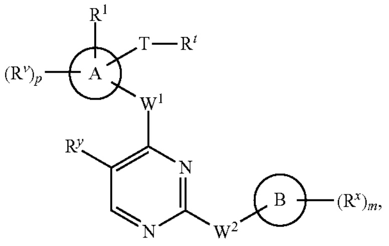

wherein each of Ring A, Ring B, m, p, $R^x$, $R^y$, $R^v$, $W^1$, and $W^2$ is as defined above with respect to formulae I-a and I-b, and described in classes and subclasses herein, $R^{1'}$ is a bivalent warhead group, T is a bivalent tethering moiety; and $R^t$ is a detectable moiety.

In some embodiments, $R^t$ is a detectable moiety selected from a primary label or a secondary label. In certain embodiments, $R^t$ is a detectable moiety selected from a fluorescent label (e.g., a fluorescent dye or a fluorophore), a mass-tag, a chemiluminescent group, a chromophore, an electron dense group, or an energy transfer agent.

As used herein, the term "detectable moiety" is used interchangeably with the term "label" and "reporter" and relates to any moiety capable of being detected, e.g., primary labels and secondary labels. A presence of a detectable moiety can be measured using methods for quantifying (in absolute, approximate or relative terms) the detectable moiety in a system under study. In some embodiments, such methods are well known to one of ordinary skill in the art and include any methods that quantify a reporter moiety (e.g., a label, a dye, a photocrosslinker, a cytotoxic compound, a drug, an affinity label, a photoaffinity label, a reactive compound, an antibody or antibody fragment, a biomaterial, a nanoparticle, a spin label, a fluorophore, a metal-containing moiety, a radioactive moiety, quantum dot(s), a novel functional group, a group that covalently or noncovalently interacts with other molecules, a photocaged moiety, an actinic radiation excitable moiety, a ligand, a photoisomerizable moiety, biotin, a biotin analog (e.g., biotin sulfoxide), a moiety incorporating a heavy atom, a chemically cleavable group, a photocleavable group, a redox-active agent, an isotopically labeled moiety, a biophysical probe, a phosphorescent group, a chemiluminescent group, an electron dense group, a magnetic group, an intercalating group, a chromophore, an energy transfer agent, a biologically active agent, a detectable label, and any combination of the above).

Primary labels, such as radioisotopes (e.g., tritium, $^{32}P$, $^{33}P$, $^{35}S$, $^{14}C$, $^{123}I$, $^{124}I$, $^{125}I$, or $^{131}I$), mass-tags including, but not limited to, stable isotopes (e.g., $^{13}C$, $^{2}H$, $^{17}O$, $^{18}O$, $^{15}N$, $^{19}F$, and $^{127}I$), positron emitting isotopes (e.g., $^{11}C$, $^{18}F$, $^{13}N$, $^{124}I$, and $^{15}O$), and fluorescent labels are signal generating reporter groups which can be detected without further modifications. Detectable moities may be analyzed by methods including, but not limited to fluorescence, positron emission tomography, SPECT medical imaging, chemiluminescence, electron-spin resonance, ultraviolet/visible absorbance spectroscopy, mass spectrometry, nuclear magnetic resonance, magnetic resonance, flow cytometry, autoradiography, scintillation counting, phosphoimaging, and electrochemical methods.

The term "secondary label" as used herein refers to moieties such as biotin and various protein antigens that require the presence of a second intermediate for production of a detectable signal. For biotin, the secondary intermediate may include streptavidin-enzyme conjugates. For antigen labels, secondary intermediates may include antibody-enzyme conjugates. Some fluorescent groups act as secondary labels because they transfer energy to another group in the process of nonradiative fluorescent resonance energy transfer (FRET), and the second group produces the detected signal.

The terms "fluorescent label", "fluorescent dye", and "fluorophore" as used herein refer to moieties that absorb light energy at a defined excitation wavelength and emit light energy at a different wavelength. Examples of fluorescent labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 493/503, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethylrhodamine (TAMRA), Texas Red, Texas Red-X, 5(6)-Carboxyfluorescein, 2,7-Dichlorofluorescein, N,N-Bis(2,4,6-trimethylphenyl)-3,4:9,10-perylenebis(dicarboximide, HPTS, Ethyl Eosin, DY-490XL MegaStokes, DY-485XL MegaStokes, Adirondack Green 520, ATTO 465, ATTO 488, ATTO 495, YOYO-1,5-FAM, BCECF, dichlorofluorescein, rhodamine 110, rhodamine 123, YO-PRO-1, SYTOX Green, Sodium Green, SYBR Green I, Alexa Fluor 500, FITC, Fluo-3, Fluo-4, fluoro-emerald, YoYo-1 ssDNA, YoYo-1 dsDNA, YoYo-1, SYTO RNASelect, Diversa Green-FP, Dragon Green, EvaGreen, Surf Green EX, Spectrum Green, NeuroTrace 500525, NBD-X, MitoTracker Green FM, LysoTracker Green DND-26, CBQCA, PA-GFP (post-activation), WEGFP (post-activation), FlASH-CCXXCC, Azami Green monomeric, Azami Green, green fluorescent protein (GFP), EGFP (Campbell Tsien 2003), EGFP (Patterson 2001), Kaede Green, 7-Benzylamino-4-Nitrobenz-2-Oxa-1,3-Diazole, Bexl, Doxorubicin, Lumio Green, and SuperGlo GFP.

The term "mass-tag" as used herein refers to any moiety that is capable of being uniquely detected by virtue of its mass using mass spectrometry (MS) detection techniques. Examples of mass-tags include electrophore release tags such as N-[3-[4'-[(p-Methoxytetrafluorobenzyl)oxy]phenyl]-3-methylglyceronyl]isonipecotic Acid, 4'-[2,3,5,6-Tetrafluoro-4-(pentafluorophenoxyl)]methyl acetophenone, and their derivatives. The synthesis and utility of these mass-tags is described in U.S. Pat. Nos. 4,650,750, 4,709,016, 5,360,8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) may also be used as mass-tags. Stable isotopes (e.g., $^{13}C$, $^{2}H$, $^{17}O$, $^{18}O$, and $^{15}N$) may also be used as mass-tags.

The term "chemiluminescent group," as used herein, refers to a group which emits light as a result of a chemical reaction without the addition of heat. By way of example, luminol (5-amino-2,3-dihydro-1,4-phthalazinedione) reacts with oxidants like hydrogen peroxide ($H_2O_2$) in the presence of a base and a metal catalyst to produce an excited state product (3-aminophthalate, 3-APA).

The term "chromophore," as used herein, refers to a molecule which absorbs light of visible wavelengths, UV wavelengths or IR wavelengths.

The term "dye," as used herein, refers to a soluble, coloring substance which contains a chromophore.

The term "electron dense group," as used herein, refers to a group which scatters electrons when irradiated with an electron beam. Such groups include, but are not limited to, ammonium molybdate, bismuth subnitrate, cadmium iodide, carbohydrazide, ferric chloride hexahydrate, hexamethylene tetramine, indium trichloride anhydrous, lanthanum nitrate, lead acetate trihydrate, lead citrate trihydrate, lead nitrate, periodic acid, phosphomolybdic acid, phosphotungstic acid, potassium ferricyanide, potassium ferrocyanide, ruthenium red, silver nitrate, silver proteinate (Ag Assay: 8.0-8.5%) "Strong", silver tetraphenylporphin (S-TPPS), sodium chloroaurate, sodium tungstate, thallium nitrate, thiosemicarbazide (TSC), uranyl acetate, uranyl nitrate, and vanadyl sulfate.

The term "energy transfer agent," as used herein, refers to a molecule which either donates or accepts energy from another molecule. By way of example only, fluorescence resonance energy transfer (FRET) is a dipole-dipole coupling process by which the excited-state energy of a fluorescence donor molecule is non-radiatively transferred to an unexcited acceptor molecule which then fluorescently emits the donated energy at a longer wavelength.

The term "moiety incorporating a heavy atom," as used herein, refers to a group which incorporates an ion of atom which is usually heavier than carbon. In some embodiments, such ions or atoms include, but are not limited to, silicon, tungsten, gold, lead, and uranium.

The term "photoaffinity label," as used herein, refers to a label with a group, which, upon exposure to light, forms a linkage with a molecule for which the label has an affinity.

The term "photocaged moiety," as used herein, refers to a group which, upon illumination at certain wavelengths, covalently or non-covalently binds other ions or molecules.

The term "photoisomerizable moiety," as used herein, refers to a group wherein upon illumination with light changes from one isomeric form to another.

The term "radioactive moiety," as used herein, refers to a group whose nuclei spontaneously give off nuclear radiation, such as alpha, beta, or gamma particles; wherein, alpha particles are helium nuclei, beta particles are electrons, and gamma particles are high energy photons.

The term "spin label," as used herein, refers to molecules which contain an atom or a group of atoms exhibiting an unpaired electron spin (i.e. a stable paramagnetic group) that in some embodiments are detected by electron spin resonance spectroscopy and in other embodiments are attached to another molecule. Such spin-label molecules include, but are not limited to, nitryl radicals and nitroxides, and in some embodiments are single spin-labels or double spin-labels.

The term "quantum dots," as used herein, refers to colloidal semiconductor nanocrystals that in some embodiments are detected in the near-infrared and have extremely high quantum yields (i.e., very bright upon modest illumination).

One of ordinary skill in the art will recognize that a detectable moiety may be attached to a provided compound via a suitable substituent. As used herein, the term "suitable substituent" refers to a moiety that is capable of covalent attachment to a detectable moiety. Such moieties are well known to one of ordinary skill in the art and include groups containing, e.g., a carboxylate moiety, an amino moiety, a thiol moiety, or a hydroxyl moiety, to name but a few. It will be appreciated that such moieties may be directly attached to a provided compound or via a tethering moiety, such as a bivalent saturated or unsaturated hydrocarbon chain.

In some embodiments, detectable moieties are attached to a provided compound via click chemistry. In some embodiments, such moieties are attached via a 1,3-cycloaddition of an azide with an alkyne, optionally in the presence of a copper catalyst. Methods of using click chemistry are known in the art and include those described by Rostovtsev et al., Angew. Chem. Int. Ed. 2002, 41, 2596-99 and Sun et al., Bioconjugate Chem., 2006, 17, 52-57. In some embodiments, a click ready inhibitor moiety is provided and reacted with a click ready -T-$R^t$ moiety. As used herein, "click ready" refers to a moiety containing an azide or alkyne for use in a click chemistry reaction. In some embodiments, the click ready inhibitor moiety comprises an azide. In certain embodiments, the click ready -T-$R^t$ moiety comprises a strained cyclooctyne for use in a copper-free click chemistry reaction (for example, using methods described in Baskin et al., Proc. Natl. Acad. Sci. USA 2007, 104, 16793-16797).

In certain embodiments, the click ready inhibitor moiety is of one of the following formulae:

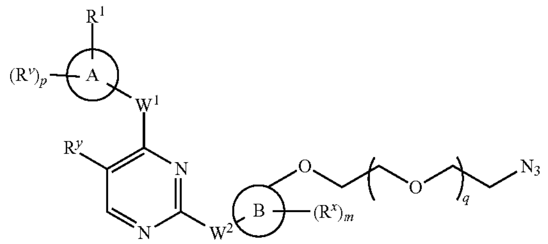

-continued

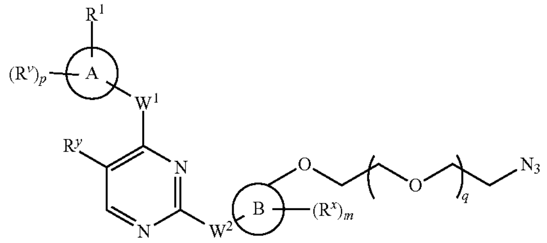

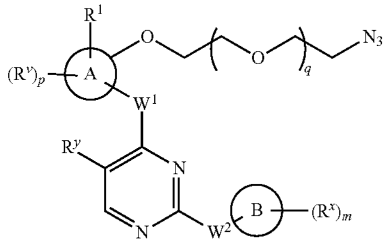

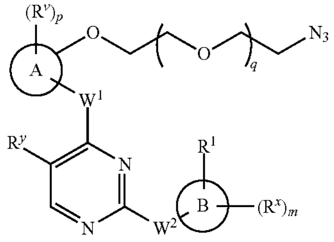

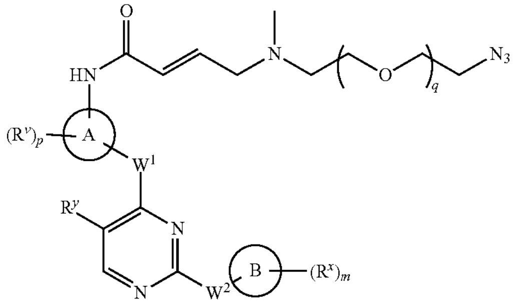

or

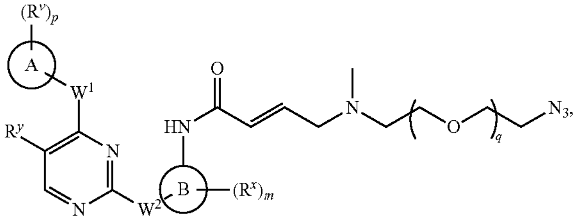

wherein Ring A, Ring B, $W^1$, $W^2$, $R^y$, $R^v$, p, $R^x$, and m are as defined above with respect to Formula I and described herein, and q is 1, 2, or 3.

Exemplary click ready inhibitors include:

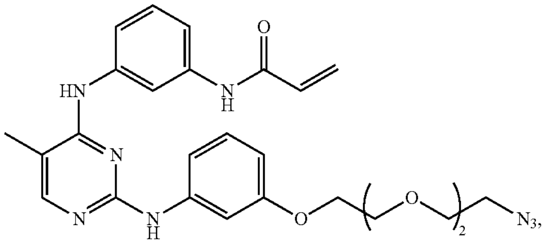

-continued
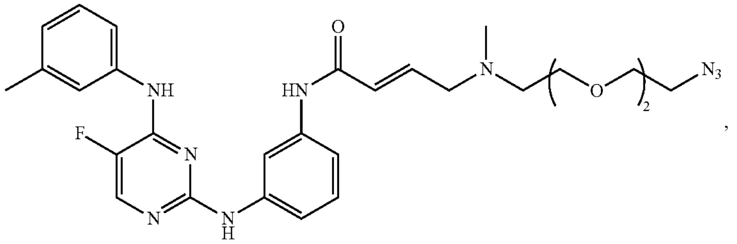
, and
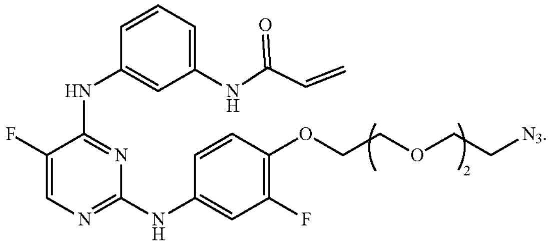
In some embodiments, the click ready -T-R$^t$ moiety is of formula:
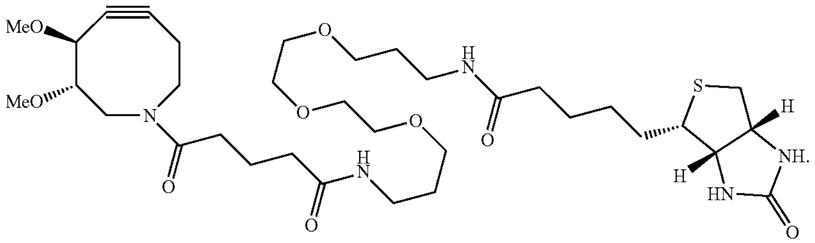 [SMILES: CO[C@H]1C#CCCN(C(=O)CCCC(=O)NCCCOCCOCCOCCCNC(=O)CCCC[C@@H]2SC[C@@H]3NC(=O)N[C@@H]32)C[C@@H]1OC]
An exemplary reaction in which a click ready inhibitor moiety and a click ready -T-R$^t$ moiety are joined through a [2+3]-cycloaddition is as follows:
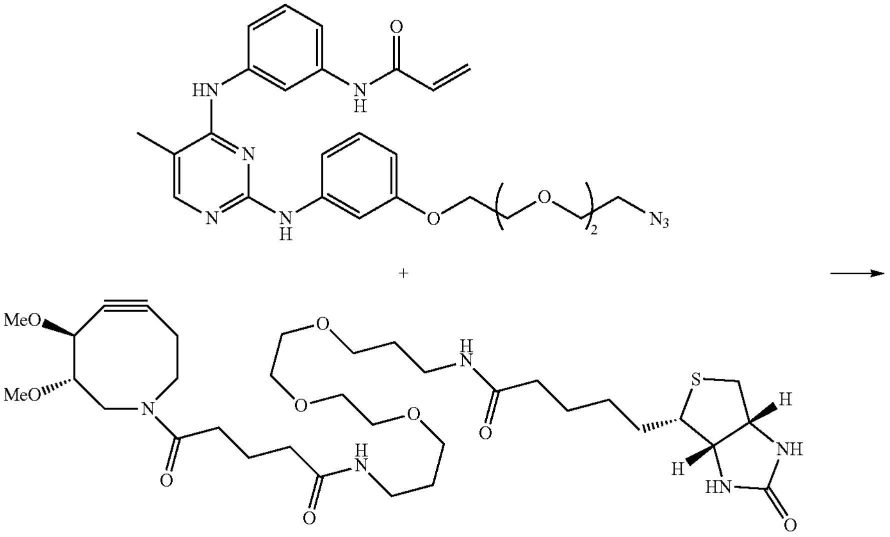

-continued

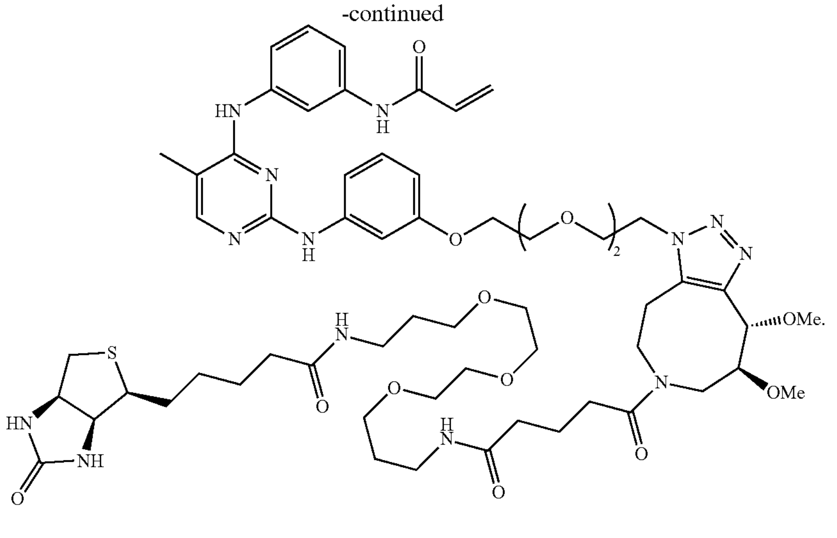

In some embodiments, the detectable moiety, R', is selected from a label, a dye, a photocrosslinker, a cytotoxic compound, a drug, an affinity label, a photoaffinity label, a reactive compound, an antibody or antibody fragment, a biomaterial, a nanoparticle, a spin label, a fluorophore, a metal-containing moiety, a radioactive moiety, quantum dot(s), a novel functional group, a group that covalently or noncovalently interacts with other molecules, a photocaged moiety, an actinic radiation excitable moiety, a ligand, a photoisomerizable moiety, biotin, a biotin analog (e.g., biotin sulfoxide), a moiety incorporating a heavy atom, a chemically cleavable group, a photocleavable group, a redox-active agent, an isotopically labeled moiety, a biophysical probe, a phosphorescent group, a chemiluminescent group, an electron dense group, a magnetic group, an intercalating group, a chromophore, an energy transfer agent, a biologically active agent, a detectable label, or a combination thereof.

In some embodiments, R' is biotin or an analog thereof. In certain embodiments, R' is biotin. In certain other embodiments, R' is biotin sulfoxide.

In another embodiment, R' is a fluorophore. In a further embodiment, the fluorophore is selected from Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 493/503, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxy-coumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethylrhodamine (TAMRA), Texas Red, Texas Red-X, 5(6)-Carboxyfluorescein, 2,7-Dichlorofluorescein, N,N-Bis(2,4,6-trimethylphenyl)-3,4:9,10-perylenebis(dicarboximide, HPTS, Ethyl Eosin, DY-490XL MegaStokes, DY-485XL MegaStokes, Adirondack Green 520, ATTO 465, ATTO 488, ATTO 495, YOYO-1,5-FAM, BCECF, dichlorofluorescein, rhodamine 110, rhodamine 123, YO-PRO-1, SYTOX Green, Sodium Green, SYBR Green I, Alexa Fluor 500, FITC, Fluo-3, Fluo-4, fluoro-emerald, YoYo-1 ssDNA, YoYo-1 dsDNA, YoYo-1, SYTO RNASelect, Diversa Green-FP, Dragon Green, EvaGreen, Surf Green EX, Spectrum Green, NeuroTrace 500525, NBD-X, MitoTracker Green FM, LysoTracker Green DND-26, CBQCA, PA-GFP (post-activation), WEGFP (post-activation), FlASH-CCXXCC, Azami Green monomeric, Azami Green, green fluorescent protein (GFP), EGFP (Campbell Tsien 2003), EGFP (Patterson 2001), Kaede Green, 7-Benzylamino-4-Nitrobenz-2-Oxa-1,3-Diazole, Bexl, Doxorubicin, Lumio Green, or SuperGlo GFP.

As described generally above, a provided probe compound comprises a tethering moiety, -T-, that attaches the irreversible inhibitor to the detectable moiety. As used herein, the term "tether" or "tethering moiety" refers to any bivalent chemical spacer including, but not limited to, a covalent bond, a polymer, a water soluble polymer, optionally substituted alkyl, optionally substituted heteroalkyl, optionally substituted heterocycloalkyl, optionally substituted cycloalkyl, optionally substituted heterocyclyl, optionally substituted heterocycloalkylalkyl, optionally substituted heterocycloalkylalkenyl, optionally substituted aryl, optionally substituted heteroaryl, optionally substituted heterocycloalkylalkenylalkyl, an optionally substituted amide moiety, an ether moiety, an ketone moiety, an ester moiety, an optionally substituted carbamate moiety, an optionally substituted hydrazone moiety, an optionally substituted hydrazine moiety, an optionally substituted oxime moiety, a disulfide moiety, an optionally substituted imine moiety, an optionally substituted sulfonamide moiety, a sulfone moiety, a sulfoxide moiety, a thioether moiety, or any combination thereof.

In some embodiments, the tethering moiety, -T-, is selected from a covalent bond, a polymer, a water soluble polymer, optionally substituted alkyl, optionally substituted heteroalkyl, optionally substituted heterocycloalkyl, optionally substituted cycloalkyl, optionally substituted heterocycloalkylalkyl, optionally substituted heterocycloalkylalkenyl, optionally substituted aryl, optionally substituted heteroaryl, and optionally substituted heterocycloalkylalkenylalkyl. In some embodiments, the tethering moiety is an optionally substituted heterocycle. In other embodiments, the heterocycle is selected from aziridine, oxirane, episulfide, azetidine, oxetane, pyrroline, tetrahydrofuran, tetrahydrothiophene, pyrrolidine, pyrazole, pyrrole, imidazole, triazole, tetrazole, oxazole, isoxazole, oxirene, thiazole, isothiazole, dithiolane, furan, thiophene, piperidine, tetrahydropyran, thiane, pyridine, pyran, thiapyrane, pyridazine, pyrimidine, pyrazine, piperazine, oxazine, thiazine, dithiane, and dioxane. In some embodiments, the heterocycle is piperazine. In further embodiments, the tethering moiety is optionally substituted with halogen, —CN, —OH, $—NO_2$, alkyl, S(O), and $S(O)_2$. In other embodiments, the water soluble polymer is a PEG group.

In other embodiments, the tethering moiety provides sufficient spatial separation between the detectable moiety and the protein kinase inhibitor moiety. In further embodiments, the tethering moiety is stable. In yet a further embodiment, the tethering moiety does not substantially affect the response of the detectable moiety. In other embodiments, the tethering moiety provides chemical stability to the probe compound. In further embodiments, the tethering moiety provides sufficient solubility to the probe compound.

In some embodiments, a tethering moiety, -T-, such as a water soluble polymer is coupled at one end to a provided irreversible inhibitor and to a detectable moiety, $R^t$, at the other end. In other embodiments, a water soluble polymer is coupled via a functional group or substituent of the provided irreversible inhibitor. In further embodiments, a water soluble polymer is coupled via a functional group or substituent of the reporter moiety.

In some embodiments, examples of hydrophilic polymers, for use in tethering moiety -T-, include, but are not limited to: polyalkyl ethers and alkoxy-capped analogs thereof (e.g., polyoxyethylene glycol, polyoxyethylene/propylene glycol, and methoxy or ethoxy-capped analogs thereof, polyoxyethylene glycol, the latter is also known as polyethylene glycol or PEG); polyvinylpyrrolidones; polyvinylalkyl ethers; polyoxazolines, polyalkyl oxazolines and polyhydroxyalkyl oxazolines; polyacrylamides, polyalkyl acrylamides, and polyhydroxyalkyl acrylamides (e.g., polyhydroxypropylmethacrylamide and derivatives thereof); polyhydroxyalkyl acrylates; polysialic acids and analogs thereof, hydrophilic peptide sequences; polysaccharides and their derivatives, including dextran and dextran derivatives, e.g., carboxymethyldextran, dextran sulfates, aminodextran; cellulose and its derivatives, e.g., carboxymethyl cellulose, hydroxyalkyl celluloses; chitin and its derivatives, e.g., chitosan, succinyl chitosan, carboxymethylchitin, carboxymethylchitosan; hyaluronic acid and its derivatives; starches; alginates; chondroitin sulfate; albumin; pullulan and carboxymethyl pullulan; polyaminoacids and derivatives thereof, e.g., polyglutamic acids, polylysines, polyaspartic acids, polyaspartamides; maleic anhydride copolymers such as: styrene maleic anhydride copolymer, divinylethyl ether maleic anhydride copolymer; polyvinyl alcohols; copolymers thereof, terpolymers thereof, mixtures thereof, and derivatives of the foregoing. In other embodiments, a water soluble polymer is any structural form including but not limited to linear, forked or branched. In further embodiments, multifunctional polymer derivatives include, but are not limited to, linear polymers having two termini, each terminus being bonded to a functional group which is the same or different.

In some embodiments, a water polymer comprises a poly(ethylene glycol) moiety. In further embodiments, the molecular weight of the polymer is of a wide range, including but not limited to, between about 100 Da and about 100,000 Da or more. In yet further embodiments, the molecular weight of the polymer is between about 100 Da and about 100,000 Da, including but not limited to, about 100,000 Da, about 95,000 Da, about 90,000 Da, about 85,000 Da, about 80,000 Da, about 75,000 Da, about 70,000 Da, about 65,000 Da, about 60,000 Da, about 55,000 Da, about 50,000 Da, about 45,000 Da, about 40,000 Da, about 35,000 Da, 30,000 Da, about 25,000 Da, about 20,000 Da, about 15,000 Da, about 10,000 Da, about 9,000 Da, about 8,000 Da, about 7,000 Da, about 6,000 Da, about 5,000 Da, about 4,000 Da, about 3,000 Da, about 2,000 Da, about 1,000 Da, about 900 Da, about 800 Da, about 700 Da, about 600 Da, about 500 Da, about 400 Da, about 300 Da, about 200 Da, and about 100 Da. In some embodiments, the molecular weight of the polymer is between about 100 Da and 50,000 Da. In some embodiments, the molecular weight of the polymer is between about 100 Da and 40,000 Da. In some embodiments, the molecular weight of the polymer is between about 1,000 Da and 40,000 Da. In some embodiments, the molecular weight of the polymer is between about 5,000 Da and 40,000 Da. In some embodiments, the molecular weight of the polymer is between about 10,000 Da and 40,000 Da. In some embodiments, the poly(ethylene glycol) molecule is a branched polymer. In further embodiments, the molecular weight of the branched chain PEG is between about 1,000 Da and about 100,000 Da, including but not limited to, about 100,000 Da, about 95,000 Da, about 90,000 Da, about 85,000 Da, about 80,000 Da, about 75,000 Da, about 70,000 Da, about 65,000 Da, about 60,000 Da, about 55,000 Da, about 50,000 Da, about 45,000 Da, about 40,000 Da, about 35,000 Da, about 30,000 Da, about 25,000 Da, about 20,000 Da, about 15,000 Da, about 10,000 Da, about 9,000 Da, about 8,000 Da, about 7,000 Da, about 6,000 Da, about 5,000 Da, about 4,000 Da, about 3,000 Da, about 2,000 Da, and about 1,000 Da. In some embodiments, the molecular weight of a branched chain PEG is between about 1,000 Da and about 50,000 Da. In some embodiments, the molecular weight of a branched chain PEG is between about 1,000 Da and about 40,000 Da. In some embodiments, the molecular weight of a branched chain PEG is between about 5,000 Da and about 40,000 Da. In some embodiments, the molecular weight of a branched chain PEG is between about 5,000 Da and about 20,000 Da. The foregoing list for substantially water soluble backbones is by no means exhaustive and is merely illustrative, and in some embodiments, polymeric materials having the qualities described above are suitable for use in methods and compositions described herein.

One of ordinary skill in the art will appreciate that when $-T-R^t$ is attached to a compound of formula I-a or I-b via the $R^1$ warhead group, then the resulting tethering moiety comprises the $R^1$ warhead group. As used herein, the phrase "comprises a warhead group" means that the tethering moiety formed by $—R^{1'}$-T- of formula V-a or V-b is either substituted with a warhead group or has such a warhead group incorporated within the tethering moiety. For example, the tethering moiety formed by $—R^{1'}$-T- may be substituted with an -L-Y warhead group, wherein such groups are as described herein. Alternatively, the tethering moiety formed by $—R^{1'}$-T- has the appropriate features of a warhead group incorporated within the tethering moiety. For example, the tethering moiety formed by $—R^{1'}$-T- may include one or more units of unsaturation and optional substituents and/or heteroatoms which, in combination, result in a moiety that is capable of covalently modifying a protein kinase in accordance with the present invention. Such tethering moiety are depicted below.

In some embodiments, a methylene unit of an —$R^{1'}$-T- tethering moiety is replaced by a bivalent -L-Y'— moiety to provide a compound of formula V-a-iii or V-b-iii:

V-a-iii

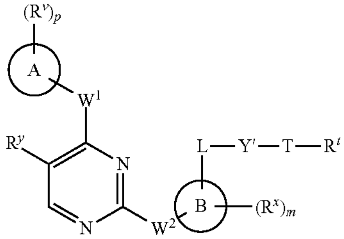

V-b-iii

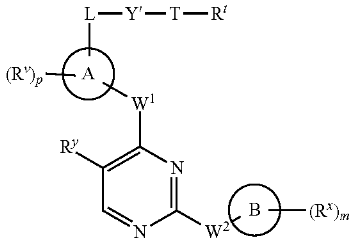

wherein each of Ring A, Ring B, m, p, $R^x$, $R^y$, $R^v$, $W^1$, $W^2$, T, L, Y', and $R^t$ is as defined above and described in classes and subclasses herein and Y' is a bivalent version of the Y group defined above and described in classes and subclasses herein.

In some embodiments, a methylene unit of an —$R^{1'}$-T- tethering moiety is replaced by an -L(Y)— moiety to provide a compound of formula V-a-iv or V-b-iv:

V-a-iv

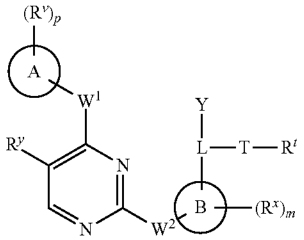

-continued

V-b-iv

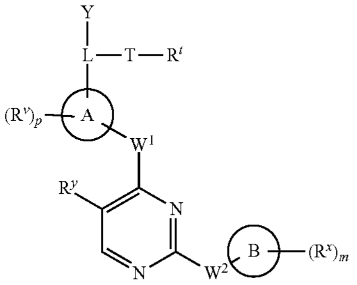

wherein each of Ring A, Ring B, m, p, $R^x$, $R^y$, $R^v$, $W^1$, $W^2$, T, L, Y, and $R^t$ is as defined above and described in classes and subclasses herein.

In some embodiments, a tethering moiety is substituted with an L-Y moiety to provide a compound of formula V-a-v or V-b-v:

V-a-v

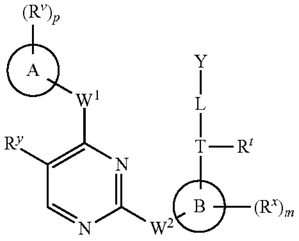

V-b-v

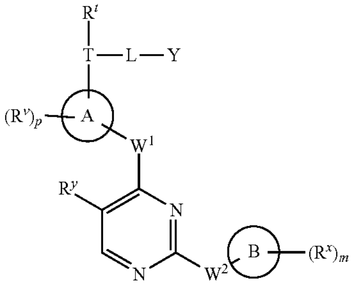

wherein each of Ring A, Ring B, m, p, $R^x$, $R^y$, $R^v$, $W^1$, $W^2$, T, L, Y, and $R^t$ is as defined above and described in classes and subclasses herein.

In certain embodiments, the tethering moiety, -T-, has one of the following structures:

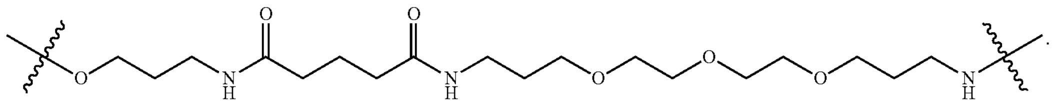 [SMILES: *NCCCOCCOCCOCCCNC(=O)CCCC(=O)NCCCO*]

In some embodiments, the tethering moiety, -T-, has the following structure:

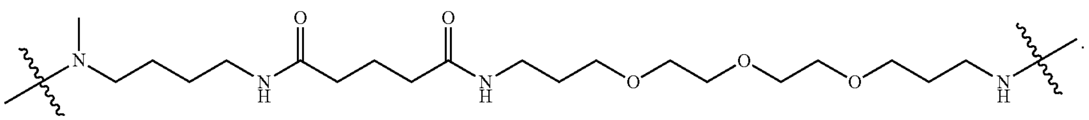 [SMILES: *NCCCOCCOCCOCCCNC(=O)CCCC(=O)NCCCCN(*)C]

In other embodiments, the tethering moiety, -T-, has the following structure:

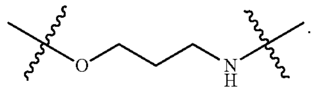 [SMILES: *NCCCO*]

In certain other embodiments, the tethering moiety, -T-, has the following structure:

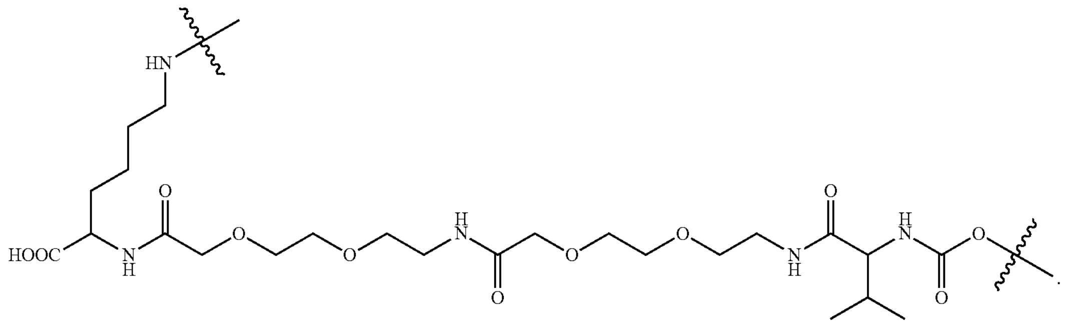 [SMILES: *NCCCCC(NC(=O)COCCOCCNC(=O)COCCOCCNC(=O)C(NC(=O)O*)C(C)C)C(=O)O]

In yet other embodiments, the tethering moiety, -T-, has the following structure:

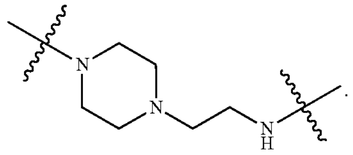 [SMILES: *NCCN1CCN(*)CC1]

In some embodiments, the tethering moiety, -T-, has the following structure:

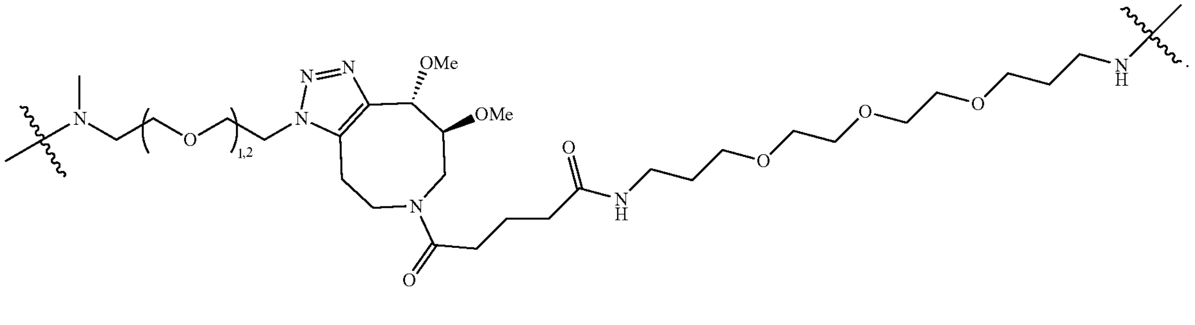

In some embodiments, -T-$R^t$ is of the following structure:

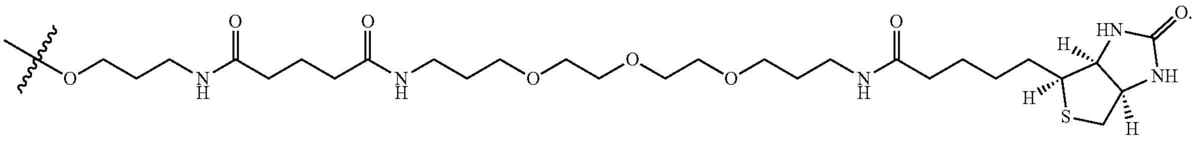 [SMILES: *OCCCNC(=O)CCCC(=O)NCCCOCCOCCOCCCNC(=O)CCCC[C@@H]1SC[C@@H]2NC(=O)N[C@@H]21]

In other embodiments, -T-R' is of the following structure:
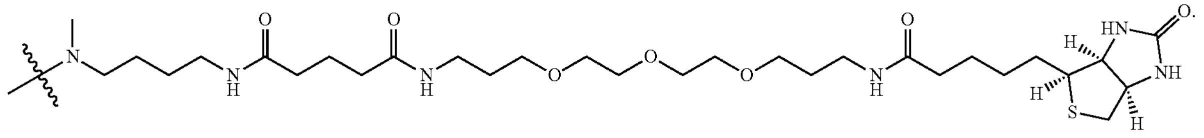 [SMILES: *N(C)CCCCNC(=O)CCCC(=O)NCCCOCCOCCOCCCNC(=O)CCCC[C@@H]1SC[C@@H]2NC(=O)N[C@@H]21]
In certain embodiments, -T-R' is of the following structure:
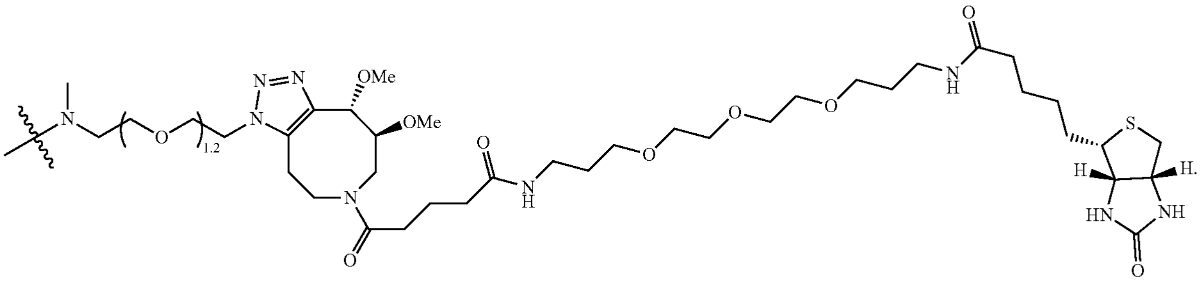
In some embodiments, a probe compound of formula V-a, V-b, VI-a, VI-b, VII-a, or VII-b is derived from any compound of Table 5.
In certain embodiments, the probe compound is one of the following structures:
I-215
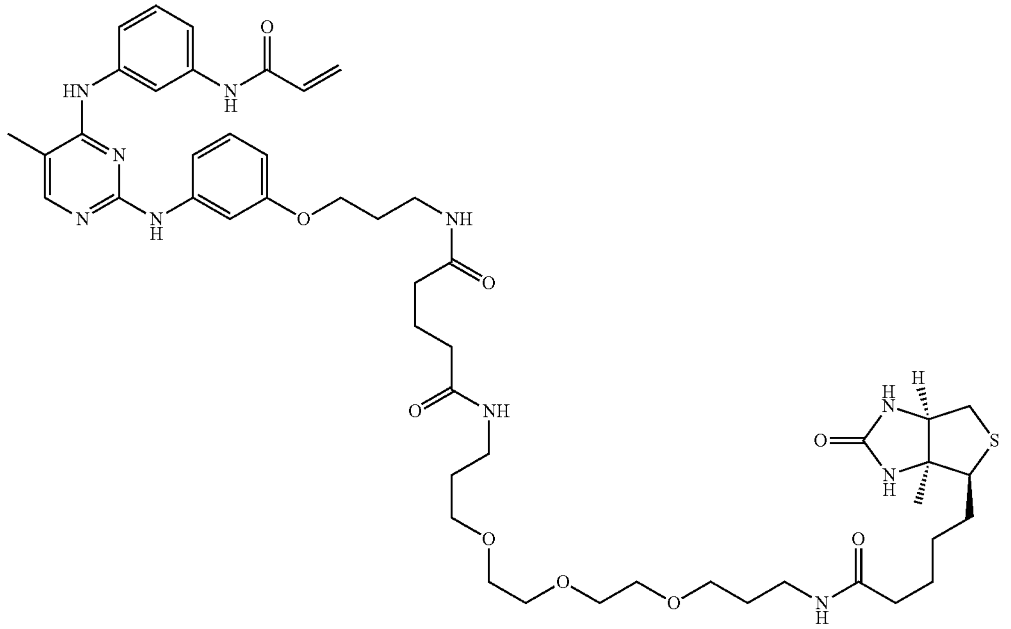

-continued
I-239
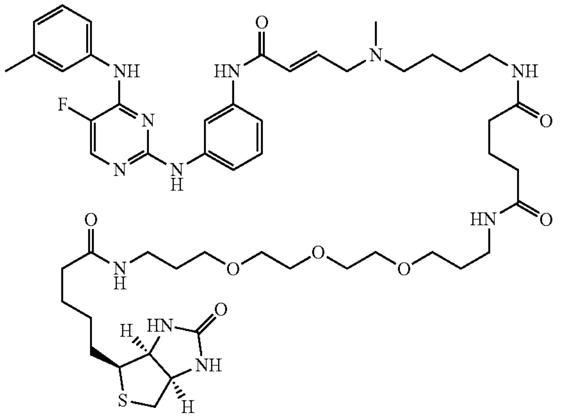
I-362
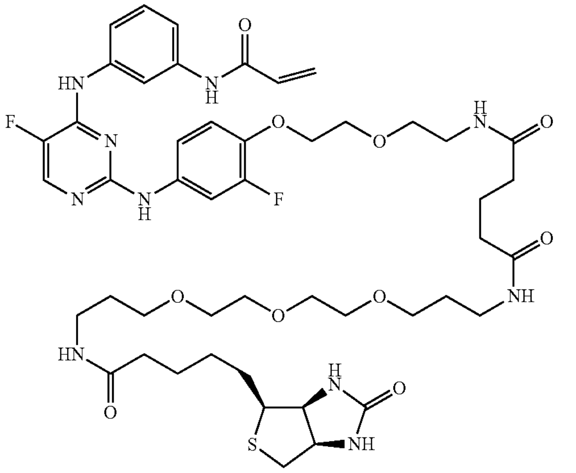
I-363
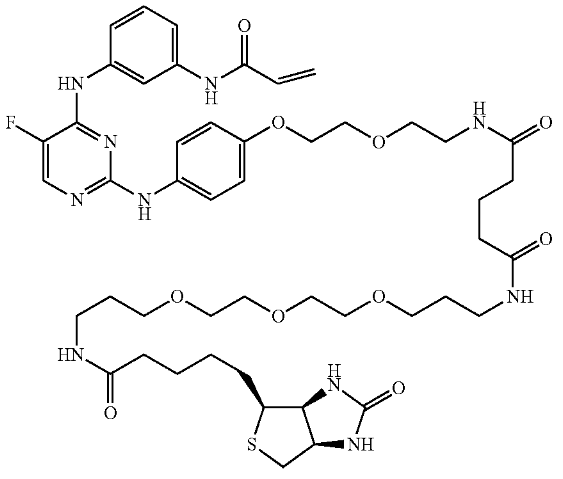
I-364
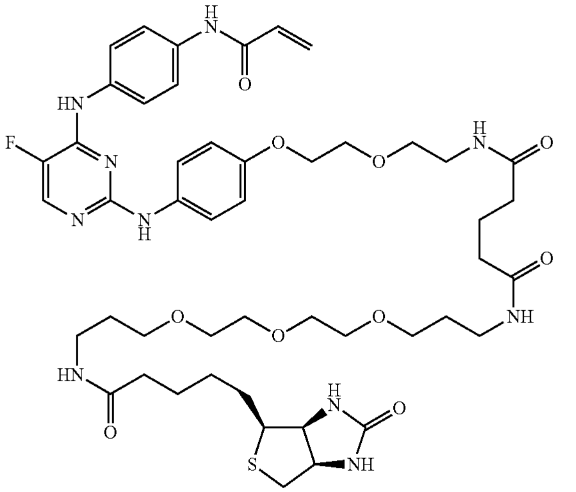
I-365
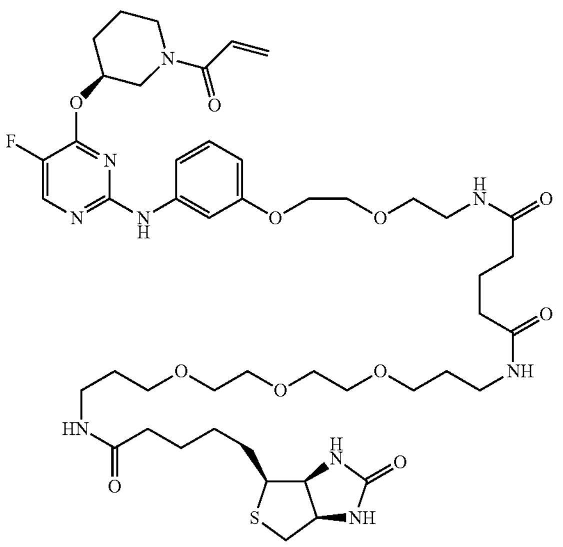
I-366
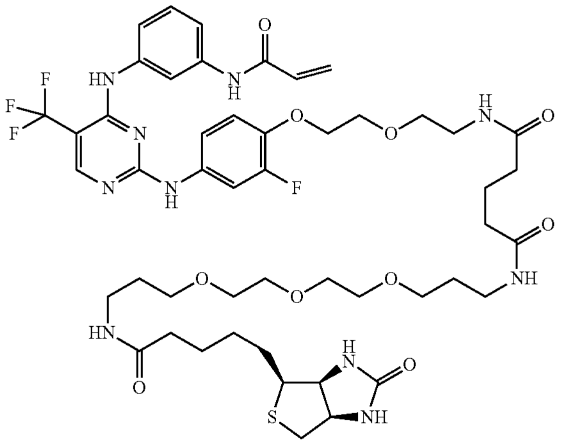

-continued

I-367

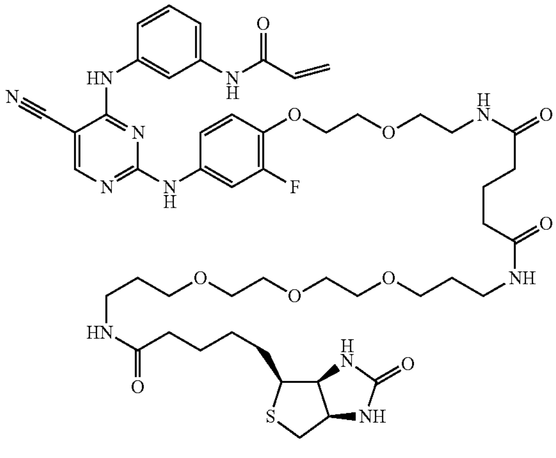

I-368

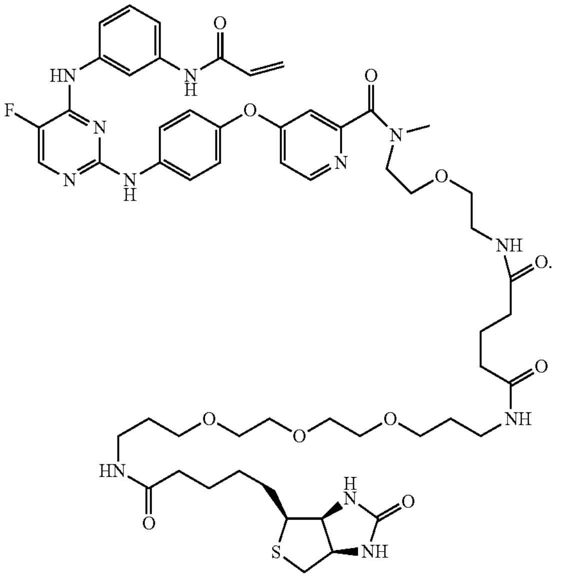

It will be appreciated that many -T-$R^t$ reagents are commercially available. For example, numerous biotinylating reagents are available from, e.g., Thermo Scientific having varying tether lengths. Such reagents include NHS-$PEG_4$-Biotin and NHS-$PEG_{12}$-Biotin.

In some embodiments, analogous probe structures to the ones exemplified above are prepared using click-ready inhibitor moieties and click-ready -T-$R^t$ moieties, as described herein.

In some embodiments, a provided probe compound covalently modifies a phosphorylated conformation of a protein kinase. In one aspect, the phosphorylated conformation of the protein kinase is either an active or inactive form of the protein kinase. In certain embodiments, the phosphorylated conformation of the protein kinase is an active form of said kinase. In certain embodiments, the probe compound is cell permeable.

In some embodiments, the present invention provides a method for determining occupancy of a protein kinase by a provided irreversible inhibitor (i.e., a compound of formula I-a or I-b) in a patient, comprising providing one or more tissues, cell types, or a lysate thereof, obtained from a patient administered at least one dose of a compound of said irreversible inhibitor, contacting said tissue, cell type or lysate thereof with a probe compound (i.e., a compound of formula V-a, V-b, VI-a, VI-b, VII-a, or VII-b) to covalent modify at least one protein kinase present in said lysate, and measuring the amount of said protein kinase covalently modified by the probe compound to determine occupancy of said protein kinase by said compound of formula I-a or I-b as compared to occupancy of said protein kinase by said probe compound. In certain embodiments, the method further comprises the step of adjusting the dose of the compound of formula I-a or I-b to increase occupancy of the protein kinase. In certain other embodiments, the method further comprises the step of adjusting the dose of the compound of formula I-a or I-b to decrease occupancy of the protein kinase.

As used herein, the terms "occupancy" or "occupy" refer to the extent to which a protein kinase is modified by a provided covalent inhibitor compound. One of ordinary skill in the art would appreciate that it is desirable to administer the lowest dose possible to achieve the desired efficacious occupancy of the protein kinase.

In some embodiments, the protein kinase to be modified is BTK. In other embodiments, the protein kinase to be modified is EGFR. In certain embodiments, the protein kinase is JAK. In certain other embodiments, the protein kinase is one or more of ErbB1, ErbB2, or ErbB4. In yet other embodiments, the protein kinase is TEC, ITK, or BMX.

In some embodiments, the probe compound comprises the irreversible inhibitor for which occupancy is being determined.

In some embodiments, the present invention provides a method for assessing the efficacy of a provided irreversible inhibitor in a mammal, comprising administering a provided irreversible inhibitor to the mammal, administering a provided probe compound to tissues or cells isolated from the mammal, or a lysate thereof, measuring the activity of the detectable moiety of the probe compound, and comparing the activity of the detectable moiety to a standard.

In other embodiments, the present invention provides a method for assessing the pharmacodynamics of a provided irreversible inhibitor in a mammal, comprising administering a provided irreversible inhibitor to the mammal, administering a probe compound presented herein to one or more cell types, or a lysate thereof, isolated from the mammal, and measuring the activity of the detectable moiety of the probe compound at different time points following the administration of the inhibitor.

In yet other embodiments, the present invention provides a method for in vitro labeling of a protein kinase comprising contacting said protein kinase with a probe compound described herein. In one embodiment, the contacting step comprises incubating the protein kinase with a probe compound presented herein.

In certain embodiments, the present invention provides a method for in vitro labeling of a protein kinase comprising contacting one or more cells or tissues, or a lysate thereof, expressing the protein kinase with a probe compound described herein.

In certain other embodiments, the present invention provides a method for detecting a labeled protein kinase comprising separating proteins, the proteins comprising a protein kinase labeled by probe compound described herein, by electrophoresis and detecting the probe compound by fluorescence.

In some embodiments, the present invention provides a method for assessing the pharmacodynamics of a provided irreversible inhibitor in vitro, comprising incubating the provided irreversible inhibitor with the target protein kinase, adding the probe compound presented herein to the target protein kinase, and determining the amount of target modified by the probe compound.

In certain embodiments, the probe compound is detected by binding to avidin, streptavidin, neutravidin, or captavidin.

In some embodiments, the probe is detected by Western blot. In other embodiments, the probe is detected by ELISA. In certain embodiments, the probe is detected by flow cytometry.

In other embodiments, the present invention provides a method for probing the kinome with irreversible inhibitors comprising incubating one or more cell types, or a lysate thereof, with a biotinylated probe compound to generate proteins modified with a biotin moiety, digesting the proteins, capturing with avidin or an analog thereof, and performing multi-dimensional LC-MS-MS to identify protein kinases modified by the probe compound and the adduction sites of said kinases.

In certain embodiments, the present invention provides a method for measuring protein synthesis in cells comprising incubating cells with an irreversible inhibitor of the target protein, forming lysates of the cells at specific time points, and incubating said cell lysates with an inventive probe compound to measure the appearance of free protein over an extended period of time.

In other embodiments, the present invention provides a method for determining a dosing schedule in a mammal for maximizing occupancy of a target protein kinase comprising assaying a one or more cell types, or a lysate thereof, isolated from the mammal, (derived from, e.g., splenocytes, peripheral B cells, whole blood, lymph nodes, intestinal tissue, or other tissues) from a mammal administered a provided irreversible inhibitor of formula I-a or I-b, wherein the assaying step comprises contacting said one or more tissues, cell types, or a lysate thereof, with a provided probe compound and measuring the amount of protein kinase covalently modified by the probe compound.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Compound numbers utilized in the Examples below correspond to compound numbers set forth in Table 5, supra.

Example 1

Preparation of N-(3-(5-methyl-2-(phenylamino)pyrimidin-4-ylamino)phenyl)acrylamide I-7

I-7

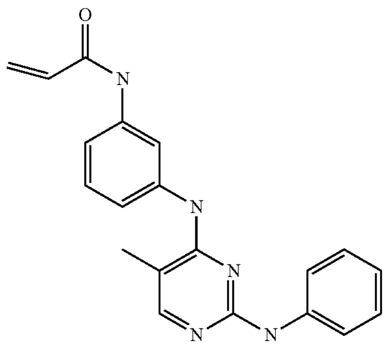

The title compound was prepared according to the schemes, steps and intermediates described below.

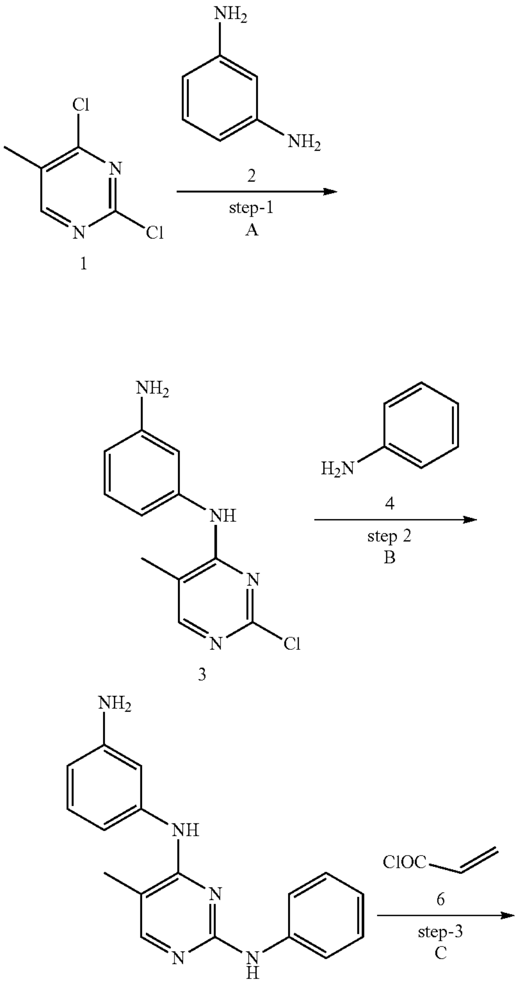

1

3

5

-continued

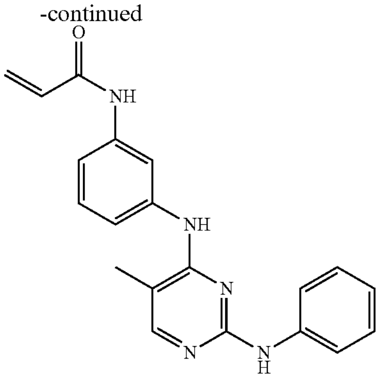

I-7

A) DIPEA, n-BuOH, 120° C., 30 min, MW; B) NMP, 200° C., 10 min, MW; C) NMP, 0° C.-30 min, rt-30 min.

Step-1

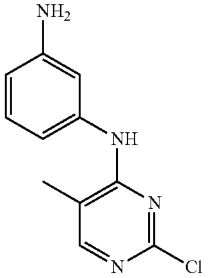

3

A solution of 1 (2.0 g, 0.012 mol), 1,3-phenylenediamine (2.0 g, 0.018 mmol), DIPEA (2.33 g, 0.018 mol) in n-BuOH (20 mL) was subjected to microwave irradiation at 120° C. for 30 min. The reaction mixture was then quenched with water (100 mL), extracted with EtOAc (3×100 mL). The combined EtOAc extract was washed with water (100 mL), brine (100 mL), dried over $Na_2SO_4$ and concentrated under reduced pressure. The residue obtained was further purified column chromatography ($SiO_2$, 60-120 mesh, EtOAc/$CHCl_3$: 15/85) gave 3 (1.3 g, 45%) as a dark brown solid.

Step-2

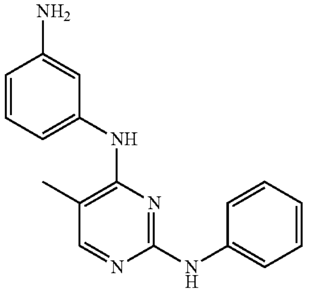

5

A solution of 3 (1.0 g, 4.27 mmol), 4 (1.5 g, 16.12 mmol) in NMP (10.0 mL) was subjected to microwave irradiation (200° C., 10 min). The reaction mixture was cooled, diluted with water (100 mL) and extracted with EtOAc (3×100 mL). The combined ethyl acetate extract was washed with water (100 mL), brine (100 mL), dried over $Na_2SO_4$ and concentrated under reduced pressure gave a residue. The crude residue was further purified by column chromatography ($SiO_2$, $CHCl_3$/MeOH: 98/2) gave 5 (0.5 g, 40.3%) as a light brown solid.

Step-3

I-7

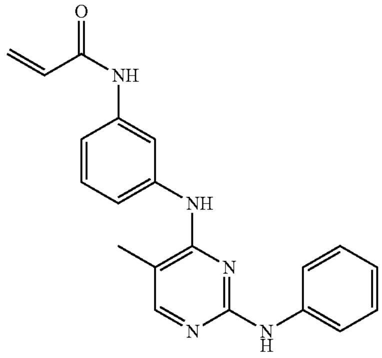

To a stirred solution of 5 (200 mg, 0.68 mmol) in NMP (2.0 mL) at 0° C. was added acryloyl chloride (248 mg, 0.2.74 mmol) and the reaction mixture was stirred at 0° C. for 60 min. The reaction mixture was then stirred with hexane for ½ h and then hexane was removed by decantation from the mixture and the residue was quenched with water (10 mL). The aqueous solution was basified with sat. $NaHCO_3$ solution and then extracted with EtOAc (3×10 mL). The combined EtOAc extract was washed with water (10 mL), brine (10 mL), dried over $Na_2SO_4$ and concentrated under reduced pressure. The residue obtained was further purified column chromatography ($SiO_2$, 230-400, MeOH/$CHCl_3$: 10/90) gave I-7 (110 mg, 46.4%) as a brown solid. $^1H$ NMR (DMSO-$d_6$) δ ppm: 2.10 (s, 3H), 5.73 (dd, 1.88 & 10.42 Hz, 1H), 6.24 (dd, J=1.88 & 17 Hz, 1H), 6.44 (dd, J=10.08 & 16.92 Hz, 1H), 6.78 (t, J=7.36 Hz, 1H), 7.06-7.11 (m, 2H), 7.26 (t, J=8.08 Hz, 1H), 7.38-7.40 (bm, 2H), 7.65 (d, J=8.52 Hz, 2H), 7.88 (s, 1H), 7.92 (s, 1H), 8.37 (s, 1H), 8.91 (s, 1H), 10.09 (s, 1H); LCMS: m/e 346.8 (M+1).

Example 2

Preparation of N-(3-(4-(m-tolylamino)pyrimidin-2-ylamino)phenyl)acrylamide I-1

I-1

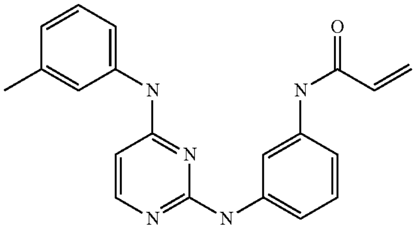

The title compound was prepared according to the schemes, steps and intermediates described below.

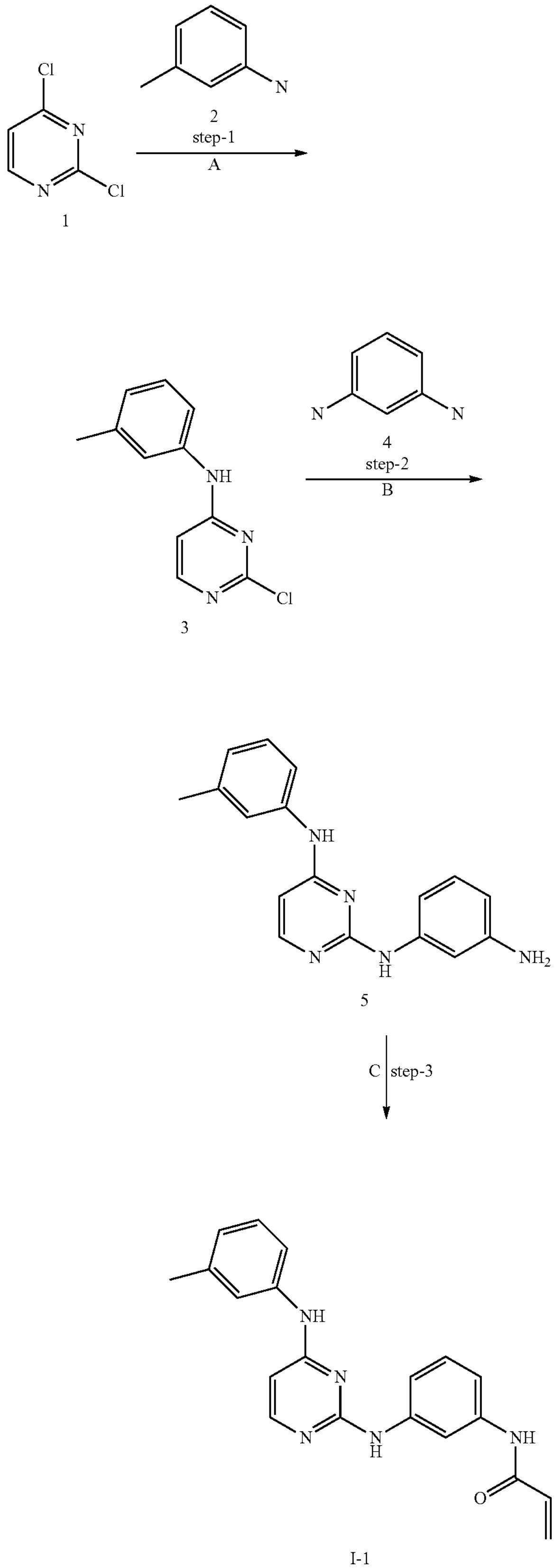

I-1

A) DIEA, n-BuOH, 110° C., 30 min, microwave; B) NMP, 200° C., 10 min, microwave; C) acryloyl chloride, NMP, 0° C.-30 min, rt-30 min.

Step-1

3

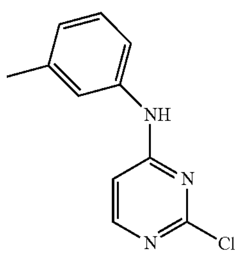

A solution of 1 (0.5 g, 3.35 mmol), m-toluidine (0.36 g, 3.35 mmol), DIEA (0.65 g, 5.0 mmol) in n-BuOH (2.0 mL) was subjected to microwave irradiation at 110° C. for 30 min. The reaction mixture was then concentrated under reduced pressure, quenched with water (5 mL), extracted with EtOAc (3×20 mL). The combined EtOAc extract was washed with water (5 mL), brine (5 mL), dried over $Na_2SO_4$ and concentrated under reduced pressure. The residue obtained was further purified column chromatography ($SiO_2$, 60-120 mesh, $CHCl_3$/MeOH: 99/1) gave 3 (0.4 g, 54.2%) as a yellow solid.

Step-2

5

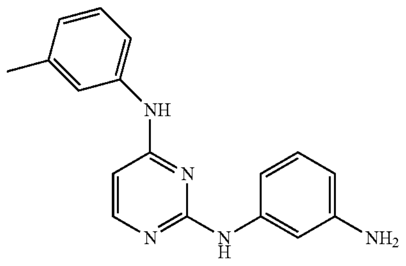

A solution of 3 (0.2 g, 0.91 mmol), 4 (0.2 g, 1.8 mmol) in NMP (2.0 mL) was subjected to microwave irradiation (200° C., 10 min). Then the reaction mixture was cooled, diluted with water (10 mL) and extracted with $CH_2Cl_2$ (3×15 mL). The combined $CH_2Cl_2$ extract was washed with water (5 mL), brine (5 mL), dried over $Na_2SO_4$ and concentrated under reduced pressure to get a residue. The crude residue was further purified by column chromatography ($SiO_2$, $CHCl_3$/MeOH: 98/2) and gave 5 (0.14 g, 53%) as a light yellow solid.

Step-3

I-1

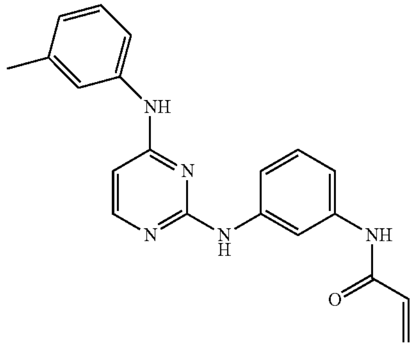

To a stirred solution of 5 (0.075 g, 0.25 mmol) in NMP (1.0 mL) at 0° C. was added acryloyl chloride (0.19 g, 2.0 mmoL) and the reaction mixture was stirred at 0° C. for 30 min followed by stirring at rt for 30 min. The neat reaction mixture was subjected to purification by column chromatography (neutral $Al_2O_3$, $CHCl_3$/MeOH: 98/2) gave I-1 (0.04 g, 45%) as a white solid. $^1$H NMR (DMSO-d6) δ ppm: 2.56 (s, 3H), 5.71 (dd, J=2.0 & 10.08 Hz, 1H), 6.20-6.25 (m, 2H), 6.45 (dd, J=10.12 & 17.00 Hz, 1H), 6.78 (d, J=7.52 Hz, 1H), 7.12-7.19 (m, 2H), 7.31 (d, J=8.44 Hz, 1H), 7.46-7.53 (m, 3H), 7.87 (s, 1H), 7.99 (d, J=5.76 Hz, 1H), 9.15 (s, 1H), 9.24 (s, 1H), 10.03 (s, 1H); LCMS: m/e 346.4 (M+1).

Example 3

Preparation of N-(3-(5-methyl-4-(m-tolylamino)pyrimidin-2-ylamino)phenyl)acrylamide I-2

I-2

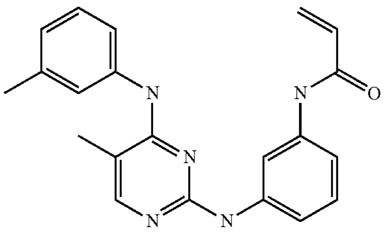

The title compound was prepared according to the schemes, steps and intermediates described below.

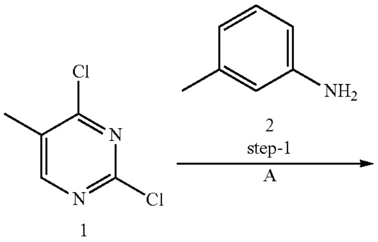

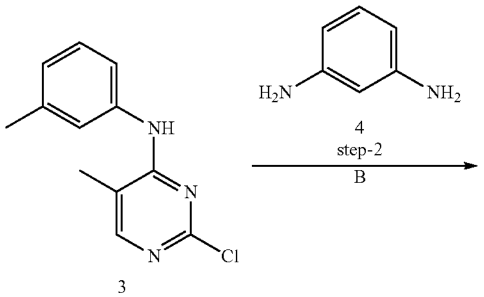

-continued

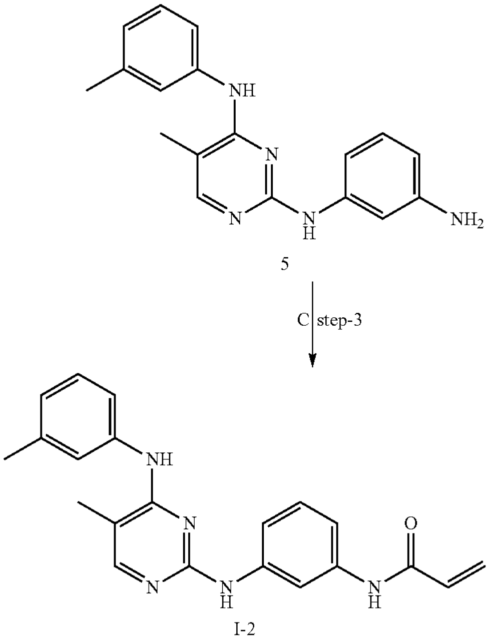

A) DIPEA, n-BuOH, 110° C., 30 min, MW; B) NMP, 200° C., 15 min, MW; C) acryloyl chloride, NMP, 0° C.-30 min, rt-30 min.

Step-1

3

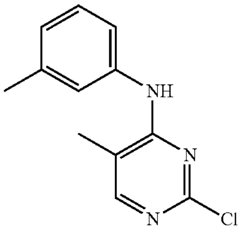

A solution of 1 (0.1 g, 0.613 mmol), 2 (0.066 g, 0.613 mmol), DIPEA (0.118 g, 0.919 mmol) in n-BuOH (2.0 mL) was subjected to microwave irradiation at 110° C. for 90 min. The reaction mixture was cooled, concentrated under reduced pressure and the residue obtained was further purified by column chromatography ($SiO_2$, Methanol/chloroform mixtures) gave 3 (0.05 g, 34%) as an off white solid.

Step-2

5

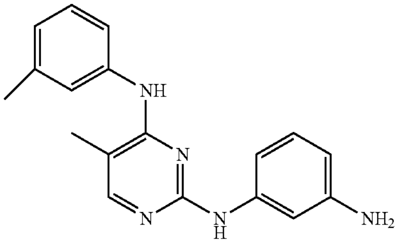

A solution of 3 (0.05 g, 0.213 mmol), 4 (0.046 g, 0.427 mmol) in NMP (2.0 mL) was subjected to microwave irradiation (200° C., 15 min). Then the reaction mixture was cooled, diluted with water (15 mL) and extracted with EtOAc (3×15 mL). The combined EtOAc extract was washed with water (10 mL), brine (10 mL), dried over $Na_2SO_4$ and concentrated under reduced pressure gave a residue. The crude residue was further purified by column chromatography ($SiO_2$, $CHCl_3$/MeOH: 98/2) gave 5 (0.03 g, 46%) as a grey solid.

Step-3

I-2

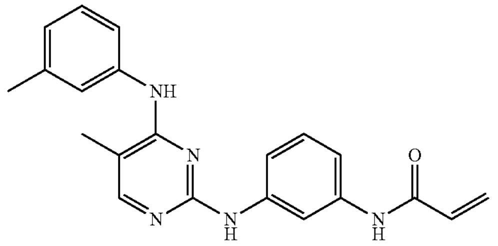

To a stirred solution of 5 (0.025 g, 0.082 mmol) in NMP (0.5 mL) at 0° C. was added acryloyl chloride (0.073 g, 0.821 mmol) and the reaction mixture was stirred at 0° C. for 30 min followed by stirring at rt for 30 min. The crude reaction mixture was passed through an alumina column (neutral $Al_2O_3$, chloroform/methanol mixtures) gave I-2 (0.012 g, 41%) as a pale brown solid. $^1H$ NMR (DMSO-$d_6$) δ ppm: 2.10 (s, 3H), 2.27 (s, 3H), 5.72 (dd, J=2 & 10.04 Hz, 1H), 6.22 (dd, J=1.96 & 16.92 Hz, 1H), 6.45 (dd, J=10.08 & 16.92 Hz, 1H), 6.83 (d, J=7.36 Hz, 1H), 7.09 (t, J=8.06 Hz, 1H), 7.17 (t, J=7.78 Hz, 1H), 7.26 (d, J=7.80 Hz, 1H), 7.47 (d, J=1.08 Hz, 1H), 7.53 (s, 1H), 7.58 (d, J=8.60 Hz, 1H), 7.78 (s, 1H), 7.88 (s, 1H), 8.15 (s, 1H), 9.01 (s, 1H), 9.99 (s, 1H); LCMS: m/e 360.1 (M+1).

Example 4

Preparation of N-(3-(5-fluoro-4-(m-tolylamino)pyrimidin-2-ylamino)phenyl)acrylamide I-3

I-3

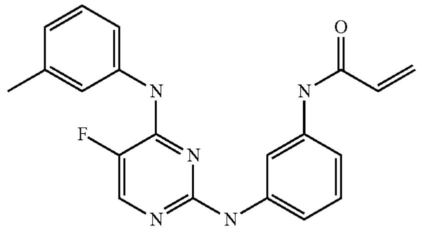

The title compound was prepared according to the schemes, steps and intermediates described below.

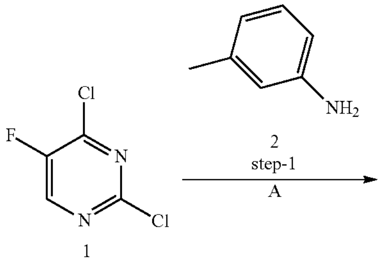

-continued

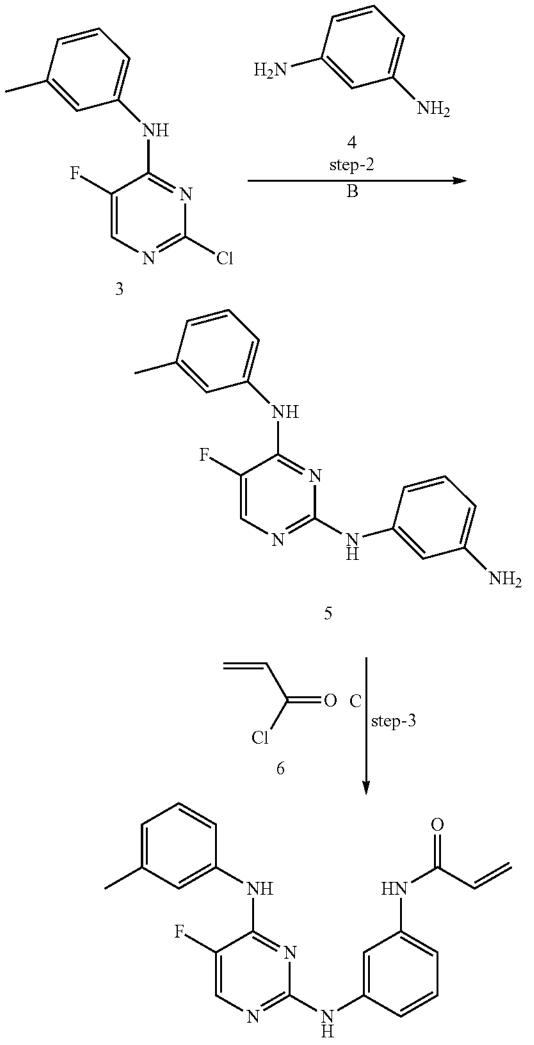

I-3

A) n-butanol, DIPEA, 110° C., 45 min, MW; B) NMP, 200° C., 10 min, MW; C) NMP, DMAP, 0° C., 30 min.

Step-1

3

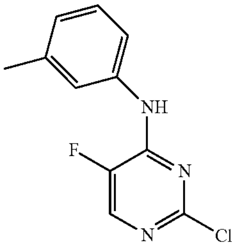

To a solution of 1 (0.5 g, 3 mmol) in n-butanol (5.0 mL) was added 2 (0.64 g, 0.6 mmol), DIPEA (0.116 g, 0.8 mmol) and the reaction mixture was irradiated under microwave at 110° C. for 45 min. It was cooled, quenched with water (50 mL) and extracted with EtOAc (2×25 mL). The combined EtOAc extract was washed with water (25 mL), brine (25 mL), dried over $Na_2SO_4$ and concentrated under reduced pressure gave 3 (0.45 g, 63%) which was taken for the next step without further purification.

Step-2

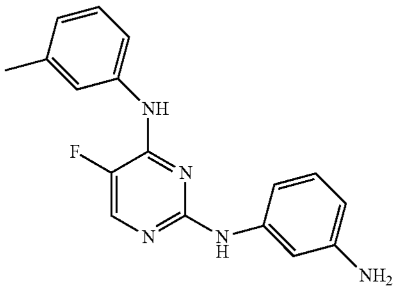

A solution of 3 (0.45 g, 1.8 mmol) and 4 (0.41 g, 3.7 mmol) in NMP (4.5 mL) was subjected to microwave irradiation at 200° C. for 10 min. It was cooled, diluted with water (25 mL) and extracted with EtOAc (3×25 mL). The combined EtOAc extract was washed with water (2×25 mL), brine (25 mL), dried over $Na_2SO_4$ and concentrated under reduced pressure. The residue obtained was further purified by column chromatography ($SiO_2$, 60-120, Chloroform/Ethyl acetate: 90/10) gave 5 (0.23 g, 41%) as a light yellow solid.

Step-3

I-3

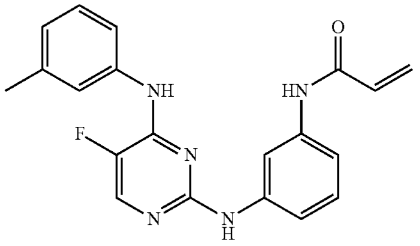

To a stirred solution of 5 (0.075 g, 0.24 mmol), in NMP (1.5 mL) at 0° C. under N2 atmosphere was added DMAP (0.059 g, 0.48 mmol) and Acryloyl chloride (0.064 g, 0.725 mmol) and the reaction mixture was kept at this temperature for 30 min. It was quenched with water (7.5 mL) and extracted with EtOAc (3×25 mL). The combined EtOAc extract was washed with 5% Citric acid (10 mL), water (2×10 mL), brine (10 mL), dried over $Na_2SO_4$ and concentrated under reduced pressure. The crude residue was further purified by column chromatography ($Al_2O_3$, Chloroform/Methanol: 98/2) gave I-3 (0.01 g, 11.3%) as an off white solid. $^1H$ NMR (DMSO-$d_6$) δ ppm: 2.27 (s, 3H), 5.72 (d, J=9.84 Hz, 1H), 6.22 (d, J=16.92 Hz, 1H), 6.44 (dd, J=10.2 & 17.02 Hz, 1H), 6.85 (d, J=7.12 Hz, 1H), 7.12-7.19 (m, 2H), 7.29 (d, J=7.68 Hz, 1H), 7.43 (d, J=7.92 Hz, 1H), 7.61-7.63 (m, 2H), 7.82 (s, 1H), 8.08 (s, 1H), 9.23 (bs, 2H), 10.03 (s, 1H); LCMS: m/e 364.2 (M+1).

Example 5

Preparation of (E)-4-(dimethylamino)-N-(3-(5-fluoro-4-(m-tolylamino)pyrimidin-2-ylamino)phenyl)but-2-enamide I-4

I-4

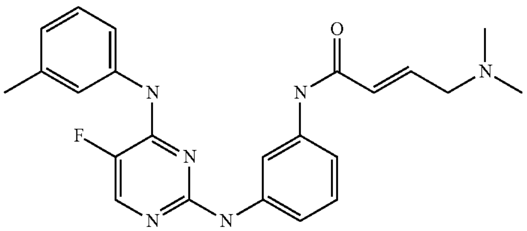

The title compound was prepared according to the schemes, steps and intermediates described below.

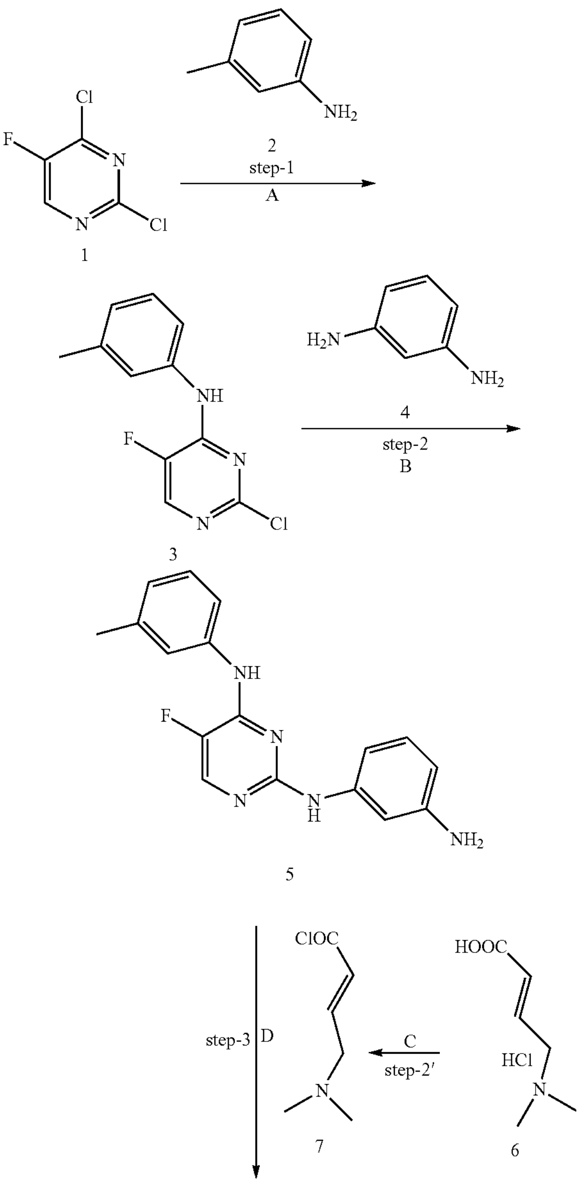

-continued

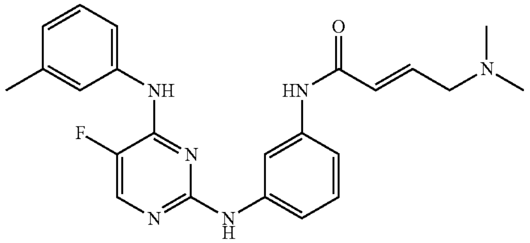

I-4

A) n-butanol, DIPEA, 110° C., 45 min, MW; B) NMP, 200° C., 10 min, MW; C) oxalyl chloride, $CH_3CN$, ½ h at 25° C., 5 min at 45° C.; D) NMP, 0° C. to 10° C., 30 min.

Step-1

3

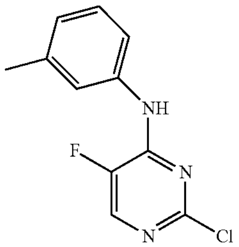

A solution of 1 (0.5 g, 3.0 mmol), 2 (0.32 g, 3.0 mmol) in n-butanol (5.0 mL) was subjected to microwave irradiation (110° C., 45 min). It was cooled, quenched with water (50 mL) and extracted with EtOAc (2×25 mL). The combined EtOAc extract was washed with water (25 mL), brine (25 mL), dried over $Na_2SO_4$ and concentrated under reduced pressure gave 3 (0.45 g, 63%) which was taken for next step without further purification.

Step-2

5

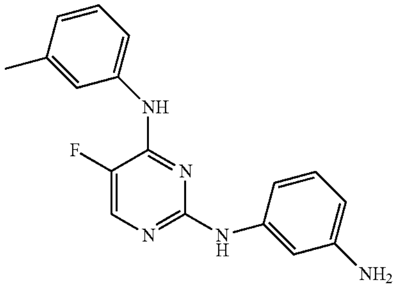

A solution of 3 (0.45 g, 1.8 mmol), 4 (0.41 g, 3.7 mmol) in NMP (4.5 mL) was subjected to microwave irradiation (200° C., 10 min). It was cooled, diluted with water (25 mL) and extracted with EtOAc (3×25 mL). The combined ethyl acetate extract was washed with water (2×25 mL), brine (25 mL), dried over $Na_2SO_4$ and concentrated under reduced pressure. The residue was further purified by column chromatography ($SiO_2$, Chloroform/Ethyl acetate: 90/10) gave 5 (0.23 g, 41%) as a light yellow solid.

Step-3a

7

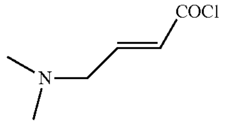

To a stirred solution of 6 (0.13 g, 0.80 mmol) in $CH_3CN$ (1.0 mL) was added oxalyl chloride (0.122 g, 0.96 mmol) at 0° C. The reaction mixture was allowed to stir at 0° C. for ½ h and then at RT for 2 h. Finally it was heated at 45° C. for 5 min, cooled and the reaction mixture was taken for next step without further purification.

Step-3

I-4

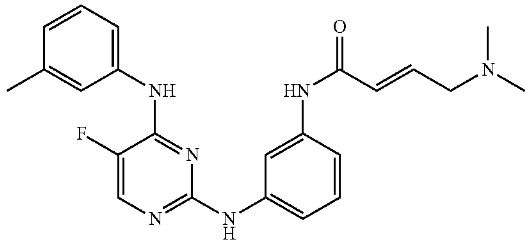

To a stirred solution of 5 (0.05 g, 0.16 mmol) in NMP (1.0 mL) was added 7 at 0° C. The reaction mixture was stirred at 0° C. for 30 min and at 10° C. for 30 min. It was quenched with sat. Sodium bicarbonate soln. (5 mL) and extracted with $CH_2Cl_2$ (3×5 mL). The combined organic extract was washed with water (1 mL), brine (1 mL) and dried over $Na_2SO_4$. Concentration under reduced pressure followed by purification by column chromatography ($SiO_2$, 230-400, $CHCl_3$/MeOH, 95/5) gave I-4 (0.02 g, 29.4%) as a white solid. $^1H$ NMR (DMSO-$d_6$) δ ppm: 2.21 (s, 6H), 2.28 (s, 3H), 3.08 (bd, J=5.6 Hz, 2H), 6.29 (d, J=15.60 Hz, 1H), 6.67-6.74 (m, 1H), 6.86 (d, J=7.20 Hz, 1H), 7.12-7.20 (m, 2H), 7.27 (d, J=8.00 Hz, 1H), 7.43 (d, J=8.00 Hz, 1H), 7.62-7.64 (m, 2H), 7.82 (s, 1H), 8.08 (d, J=3.6 Hz, 1H), 9.23 (s, 1H), 9.24 (s, 1H), 9.96 (s, 1H); LCMS: m/e 421.2 (M+1).

Example 6

Preparation of N-(3-(5-methyl-4-(phenylamino)pyrimidin-2-ylamino)phenyl) acrylamide I-5

I-5

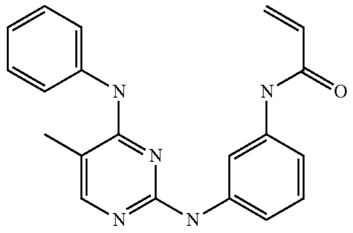

The title compound was prepared according to the schemes, steps and intermediates described below.

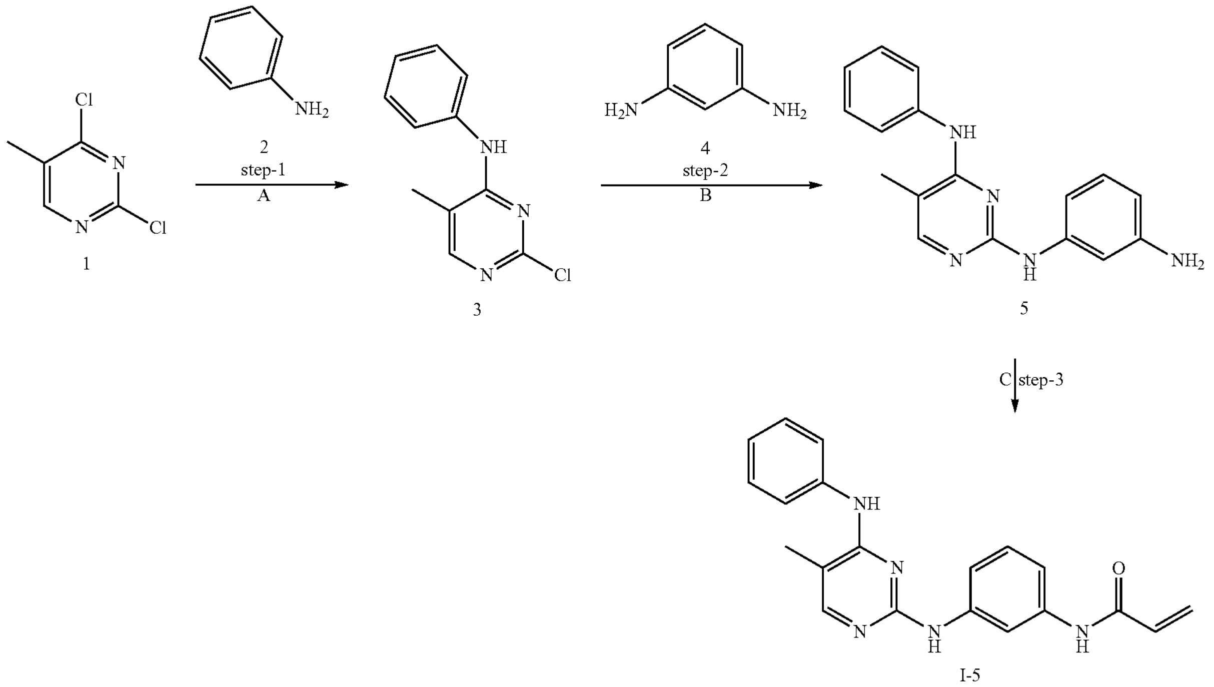

A) DIPEA, n-BuOH, 110° C., 30 min, MW; B) NMP, 200° C., 15 min, MW; C) acryloyl chloride, NMP, 0° C. - 30 min, rt-30 min.

Step-1

3

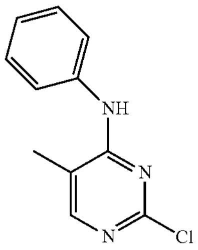

A solution of 1 (0.1 g, 0.613 mmol), 2 (0.114 g, 1.226 mmol), DIPEA (0.118 g, 0.919 mmol) in n-BuOH (2.0 mL) was subjected to microwave irradiation at 110° C. for 90 min. The reaction mixture was cooled, concentrated under reduced pressure and the residue was further purified by column chromatography ($SiO_2$, 60-120, Methanol/chloroform: 1/9) gave 3 (0.08 g, 59%) as a white solid Step-2

5

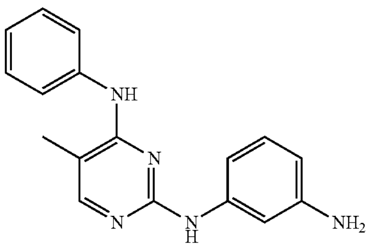

A solution of 3 (0.08 g, 0.364 mmol), 4 (0.059 g, 0.546 mmol) in NMP (2.0 ml) was subjected to microwave irradiation (200° C., 15 min). The reaction mixture was cooled, diluted with water (15 mL) and extracted with EtOAc (3×15 mL). The combined ethyl acetate extract was washed with water (10 mL), brine (10 mL), dried over $Na_2SO_4$ and concentrated under reduced pressure gave a residue. The crude residue was further purified by column chromatography ($SiO_2$, 60-120, $CHCl_3$/MeOH: 98/2) gave 5 (0.06 g, 60%) as a light grey solid. $^1H$ NMR (DMSO-$d_6$) δ ppm: 2.09 (s, 3H), 4.74 (s, 2H), 6.09-6.11 (m, 1H), 6.77-6.85 (m, 2H), 6.91 (t, J=1.72 Hz, 1H), 7.02 (t, J=7.36 Hz, 1H), 7.31 (t, J=7.52 Hz, 2H), 7.75 (d, J=7.68 Hz, 2H), 7.84 (s, 1H), 8.18 (s, 1H), 8.65 (s, 1H); LCMS: m/e 293.2 (M+1).

Step-3

I-5

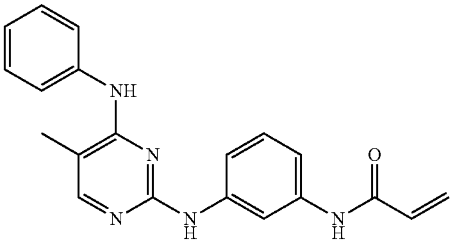

To a stirred solution of 5 (60 mg, 0.205 mmol) in NMP (2.0 mL) at 0° C. was added acryloyl chloride (0.148 g, 1.64 mmol) and the reaction mixture was stirred at 0° C. for 30 min. The neat reaction mixture was passed through an alumina column (neutral $Al_2O_3$, chloroform/methanol, 99/1) gave I-5 (0.013 g, 18.5%) as an off-white solid. $^1H$ NMR (DMSO-$d_6$) δ ppm: 2.11 (s, 3H), 5.72 (dd, J=1.92 & 10.04 Hz, 1H), 6.22 (dd, J=1.92 & 16.92 Hz, 1H), 6.45 (dd, J=9.32

& 16.92 Hz, 1H), 7.00 (t, J=7.28 Hz, 1H), 7.09 (t, J=8.04 Hz, 1H), 7.23-7.30 (m, 3H), 7.43 (d, J=8.04 Hz, 1H), 7.75-7.77 (m, 2H), 7.83 (s, 1H), 7.88 (s, 1H), 8.22 (s, 1H), 9.00 (s, 1H), 9.99 (s, 1H); LCMS: m/e 346 (M+1).

Example 7

Preparation of N-(4-methyl-3-(5-methyl-4-(m-tolylamino)pyrimidin-2-ylamino) phenyl)acrylamide I-8

I-8

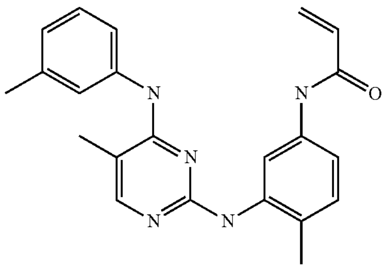

The title compound was prepared according to the schemes, steps and intermediates described below Step 1'

4

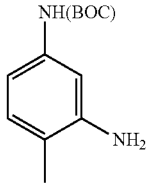

To a stirred solution of A (5 g, 0.04 mmol) in MeOH (75 mL) was added $(BOC)_2O$ (11.59 g, 0.050 mmol), slowly at −10° C. The reaction was stirred at this temperature for 4 h and then reaction mixture was concentrated under reduced pressure. The residue obtained was taken in EtOAc (300 mL). It was washed with water (25 mL), brine (25 mL) and dried over $Na_2SO_4$. Filtration followed by concentration under reduced pressure offered 4 (2.5 g, 27%) as an off-white solid.

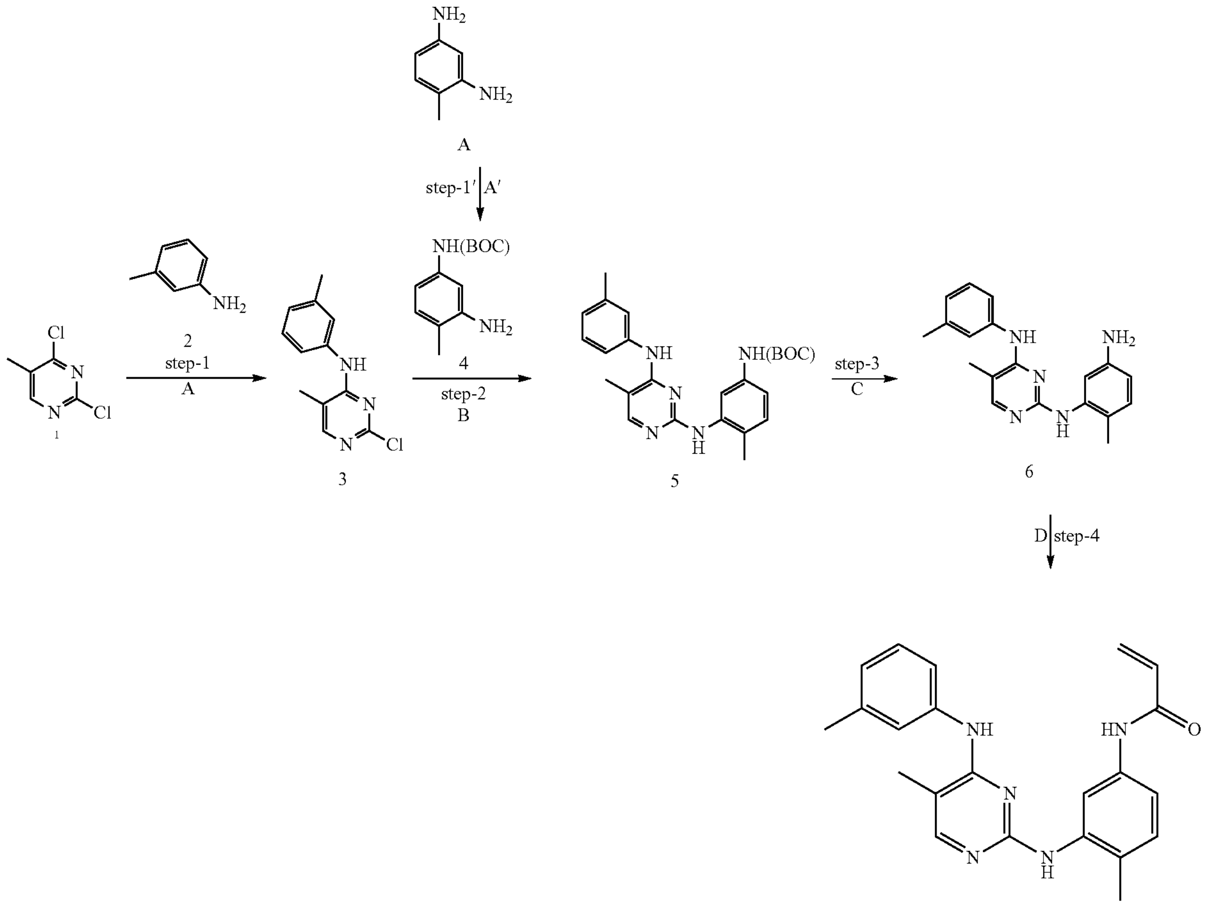

I-8

A) DIPEA, n-BuOH, 120° C., 60 min., MW; A') $(BOC)_2O$, MeOH, -10° C., 4 h; B) $Pd(OAc)_2$, BINAP, $Cs_2CO_3$, toluene, 110° C., 12 h; C) TFA, $CH_2Cl_2$, 0° C. - 30 min, rt-2 h; D) acryloyl chloride, NMP, 0° C. - 30 min, rt - 30 min.

Step 1

3

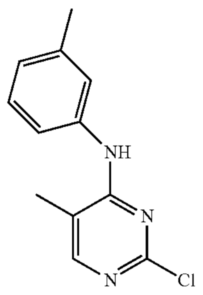

A solution of 1 (0.5 g, 3.06 mmol), 2 (0.39 g, 3.06 mmol), DIPEA (0.59 g, 4.5 mmol) in n-BuOH (5 mL) was subjected to microwave irradiation (120° C., 30 min). The reaction mixture was cooled, solvents removed under reduced pressure and the residue obtained was quenched with water (5 mL). It was extracted with EtOAc (3×20 mL) and the combined EtOAc layer was washed with water (5 mL), brine (5 mL) and dried over $Na_2SO_4$. Filtration followed by concentration under reduced pressure offered a residue which was further purified by column chromatography ($SiO_2$, 60-120, $CHCl_3$/MeOH: 9/1) gave 3 (0.35 g, 49%) as an off-white solid.

Step 2

5

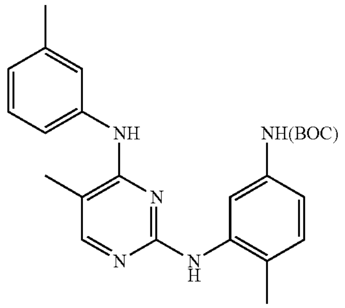

A solution of 3 (0.1 g, 0.43 mmol), 4 (0.14 g, 0.64 mmol), $Pd(OAc)_2$ (10 mg, 0.043 mmol), BINAP (0.013 g, 0.021 mmol) and $Cs_2CO_3$ (0.2 g, 1.06 mmol) in degassed toluene (toluene was purged with $N_2$ for 15 min) was refluxed for 12 h under $N_2$ atmosphere. The reaction mixture was cooled and passed through a short bed of Celite®. The filtrate was diluted with EtOAc (25 mL) and washed with water (5 mL), brine (5 mL) and dried over $Na_2SO_4$. Filtration followed by concentration under reduced pressure offered a residue which was further purified by column chromatography ($SiO_2$, 60-120, $CHCl_3$/MeOH: 9/1) gave 5 (40 mg, 22%) as an off-white solid.

Step-3

6

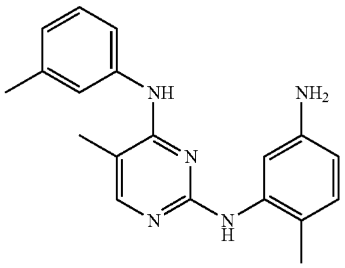

To a stirred solution of 5 (0.04 g, 0.095 mmol) in dry $CH_2Cl_2$ (2 mL) at 0° C. was added $CF_3COOH$ (0.2 mL, 5 vol) and the reaction mixture was kept at this temperature for 30 min. It was allowed to come to rt and stir at this temperature for 2 h. It was quenched with ice-cooled water (2 mL), basified with sodium carbonate solution and extracted with EtOAc (2×10 mL). The combined EtOAc extract was washed with water (2 mL), brine (2 mL) and dried over $Na_2SO_4$. Filtration followed by concentration under reduced pressure offered 6 (22 mg, 73%) as a light brown solid.

Step-4

I-8

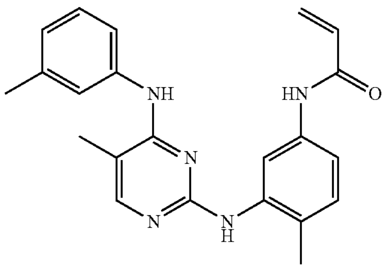

To a stirred solution of 6 (0.2 g, 0.63 mmol) in NMP (4 mL) at 0° C. was added acryloyl chloride (0.12 g, 1.25 mmol). The reaction was kept at this temperature for 30 min and then at rt for 30 min. It was quenched with ice-cooled water (2 mL) and extracted with EtOAc (2×10 mL). The combined EtOAc extract was washed with water (2 mL), brine (2 mL) and dried over $Na_2SO_4$. Filtration followed by concentration under reduced pressure offered a residue which was further purified by column chromatography ($SiO_2$, 230-400, $CHCl_3$/MeOH: 9/1) gave I-8 (10 mg, 4%) as a white solid. $^1$H NMR (DMSO-$d_6$) δ ppm: 2.07 (s, 3H), 2.13 (s, 6H), 5.70 (dd, J=1.92 & 10.08 Hz, 1H), 6.20 (dd, J=1.96 & 16.88 Hz, 1H), 6.41 (dd, J=10.16 & 16.96 Hz, 1H), 6.69 (d, J=7.36 Hz, 1H), 6.98 (t, J=7.76 Hz, 1H), 7.11 (d, J=8.24 Hz, 1H), 7.41 (q, J=9.92 Hz, 1H), 7.49-7.51 (m, 2H), 7.73 (s, 1H), 7.80 (s, 1H), 7.97 (s, 1H), 8.16 (s, 1H), 10.00 (s, 1H); LCMS: m/e 374 (M+1).

Example 8

Preparation of N-(3-(4-(3-bromophenylamino)-5-methylpyrimidin-2-ylamino)phenyl) acrylamide I-9

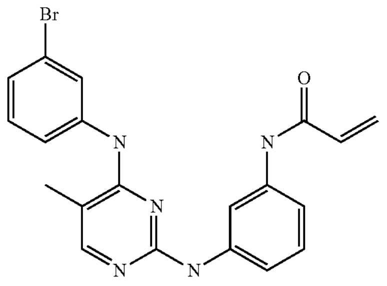

I-9

The title compound was prepared according to the schemes, steps and intermediates described below.

Step 1

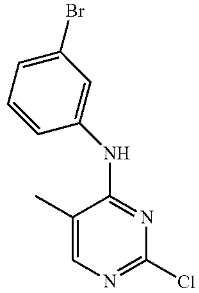

3

A solution of 1 (0.5 g, 3.06 mmol), 2 (0.53 g, 3.06 mmol) and DIPEA (0.80 mL, 4.06 mmol) in n-butanol (5 mL) was subjected to microwave irradiation (110° C., 1 h). The reaction mixture was cooled and concentrated under reduced pressure gave a residue. The residue taken in EtOAc (5 mL) and washed with $NaHCO_3$ solution (2 mL), water (2 mL) and with brine solution (2 mL). Drying over $Na_2SO_4$ followed by concentration under reduced pressure offered crude 3 which was further purified by column chromatography ($SiO_2$, 60-120, chloroform/methanol, 9/1) gave 3 (0.125 g, 13%) as a brown solid.

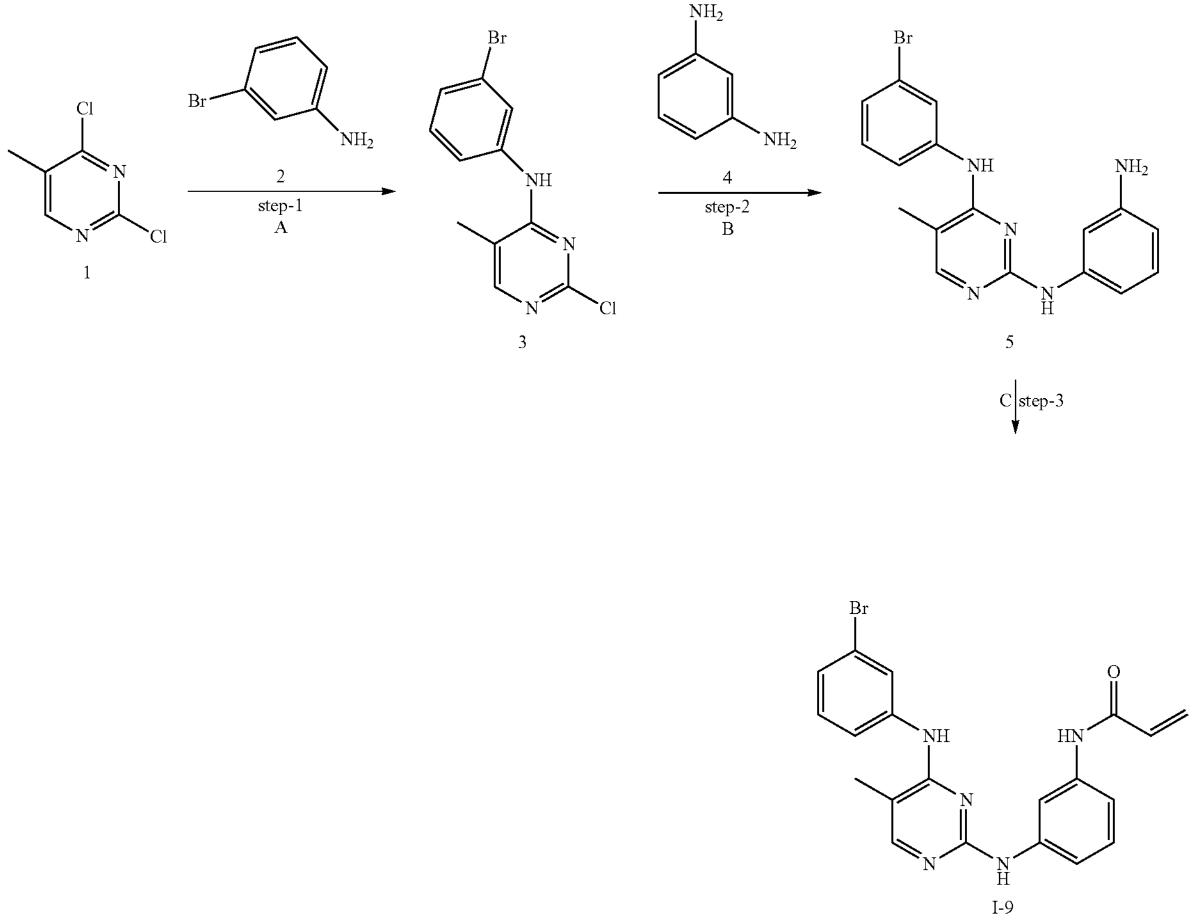

A) DIPEA, n-butanol, 110° C., 1 h, MW; B) 1.5 N HCl, ethanol, 90° C., 30 min., MW; C) acryloyl chloride, NMP, 0° C., 30 min.

Step 2

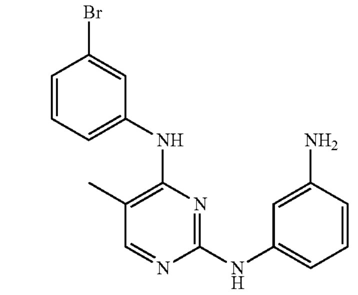

To a solution of 3 (0.15 g, 0.5 mmol) in EtOH (3 mL) was added 4 (0.081 g, 0.75 mmol) followed by 1.5 N HCl (0.055 g, 1.5 mmol). The reaction mixture was subjected to microwave irradiation (90° C., 30 min), cooled and concentrated under reduced pressure. The residue obtained was taken in EtOAc (5 mL) and washed with $NaHCO_3$ solution (2 mL), water (2 mL), and brine (2 mL). It was dried over $Na_2SO_4$, filtered and concentrated under reduced pressure gave crude 5. It was further purified by column chromatography ($SiO_2$, 60-120, chloroform/methanol, 9/1) gave 5 (0.06 g, 32%) as a light brown solid.

Step 3

I-9

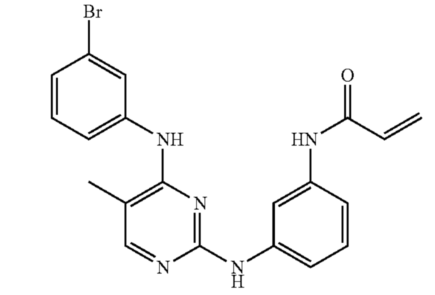

To a stirred solution of 5 (0.06 g, 0.16 mmol) in NMP (1 mL) was added acryloyl chloride (0.117 g, 1.29 mmol) at 0° C. The reaction mixture was allowed to stir at this temperature for 30 min and then taken in dichloromethane (2 mL). It was washed with $NaHCO_3$ solution (1 mL), water (1 mL) and with brine solution (1 mL). It was dried over $Na_2SO_4$, filtered and concentrated under reduced pressure. The residue was further purified by column chromatography ($SiO_2$, 60-120, chloroform/methanol, 9/1) gave I-9 (0.016 g, 23%) as a pale brown solid. $^1H$ NMR (DMSO-$d_6$) δ ppm: 2.16 (s, 3H), 5.75 (dd, J=1.72 & 10 Hz, 1H), 6.23 (dd, J=1.76 & 16.88, Hz, 1H), 6.45 (dd, J=10.08 & 16.92 Hz, 1H), 7.22-7.34 (m, 4H), 7.38 (d, J=8.00 Hz, 1H), 7.63 (d, J=8.08 Hz, 1H), 7.77 (s, 1H), 7.82 (s, 1H), 7.93 (s, 1H), 9.68 (s, 1H), 10.26 (s, 1H), 10.34 (s, 1H); LCMS: m/e 426 (M+1).

Example 9

Preparation of 3-(4-(2-(cyclopropylsulfonyl)-1,2,3,4-tetrahydroisoquinolin-6-ylamino)-5-methylpyrimidin-2-ylamino)benzenesulfonamide I-10

I-10

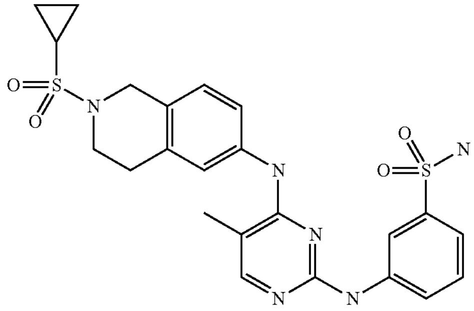

The title compound was prepared according to the schemes, steps and intermediates described below.

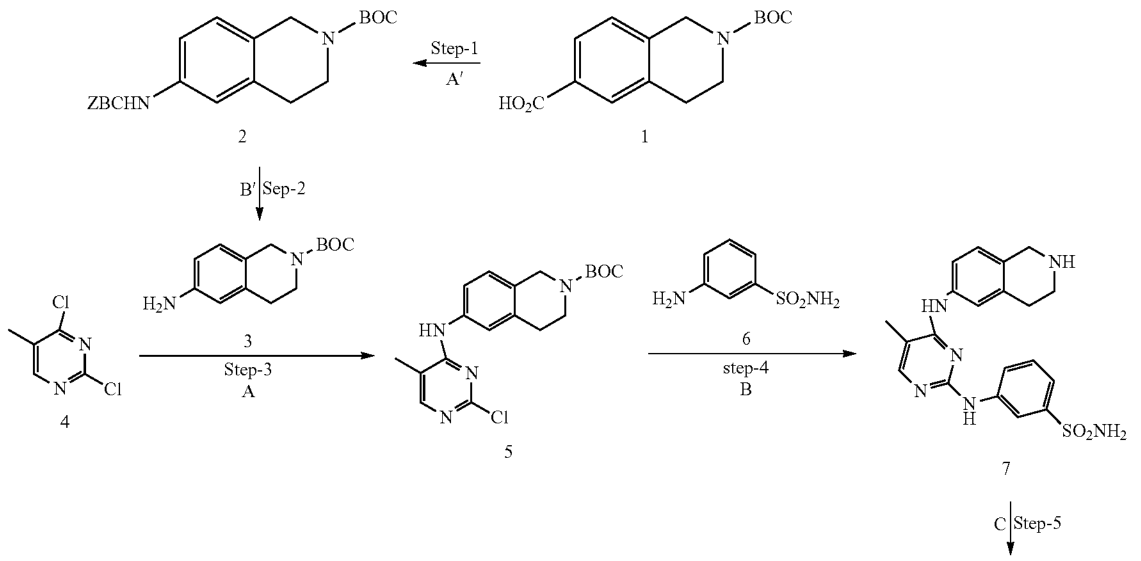

-continued

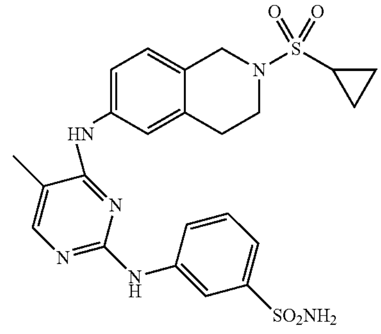

I-10

A') DPPA, Benzyl alcohol, $Et_3N$, toluene, 110° C., 12 h; B') $Pd(OH)_2$, Ammonium formate, EtOH, reflux, 6 h; A) DIPEA, n-BuOH, 120° C., 1 h., MW: B) 1.5 N HCl, EtOH, reflux 12 h.; C) Cyclopropylsulphonyl chloride, DIPEA, THF, rt, 12 h.

Steps 1-4

The procedure for synthesizing scaffold 7 is described in the experimental for Compound I-11 herein.

Step 5

I-10

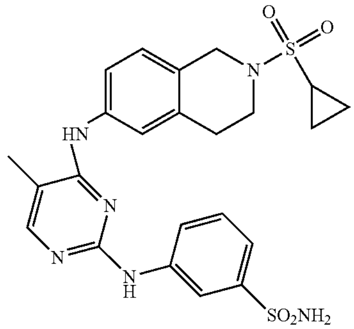

To a stirred solution of 7 (0.05 g, 0.0121 mmol) in THF (4 mL) at 0° C., was added DIPEA (0.023 g, 0.182 mmol) followed by cyclopropylsulphonyl chloride (0.031 g, 0.182 mmol) under $N_2$ atmosphere. The reaction mixture was allowed to come to rt and maintained at this temperature for 12 h. It was taken in EtOAc (10 mL), washed with water (5 mL), brine (5 mL) and dried over $Na_2SO_4$. Filtration followed by concentration under reduced pressure offered a residue which was further purified by column chromatography ($SiO_2$, 60-120, pet ether/ethyl acetate, 6/4) gave I-10 (0.035 g, 56%) as a yellow solid. $^1H$ NMR (DMSO-$d_6$) δ ppm: 0.97-0.1.00 (m, 4H), 2.12 (s, 3H), 2.60-2.66 (m, 1H), 2.90 (t, J=5.2 Hz, 2H), 3.52 (t, J=6 Hz, 2H), 4.42 (s, 2H), 7.16 (d, J=8.4 Hz, 1H), 7.27 (s, 2H), 7.31-7.35 (m, 2H), 7.53 (s, 1H), 7.59 (d, J=8.4 Hz, 1H), 7.92 (s, 1H), 8.03-8.04 (m, 2H), 8.45 (s, 1H), 9.40 (s, 1H); LCMS: m/e 515 (M+1).

Example 10

Preparation of 3-(4-(2-(2-chloroacetyl)-1,2,3,4-tetrahydroisoquinolin-6-ylamino)-5-methylpyrimidin-2-ylamino)benzenesulfonamide

I-11

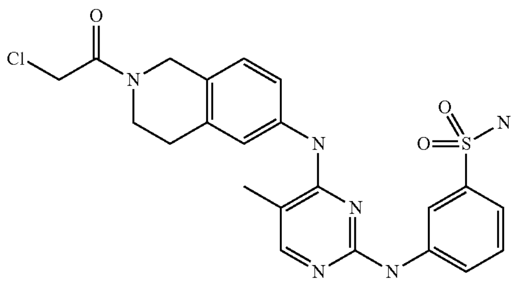

The title compound was prepared according to the schemes, steps and intermediates described below.

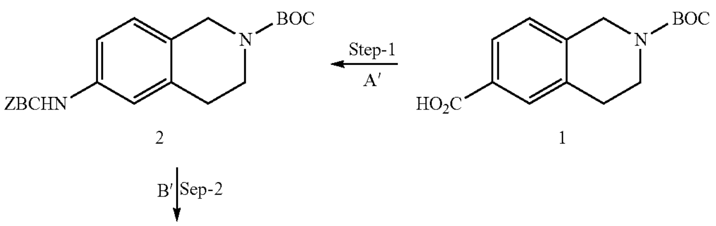

2

1

-continued

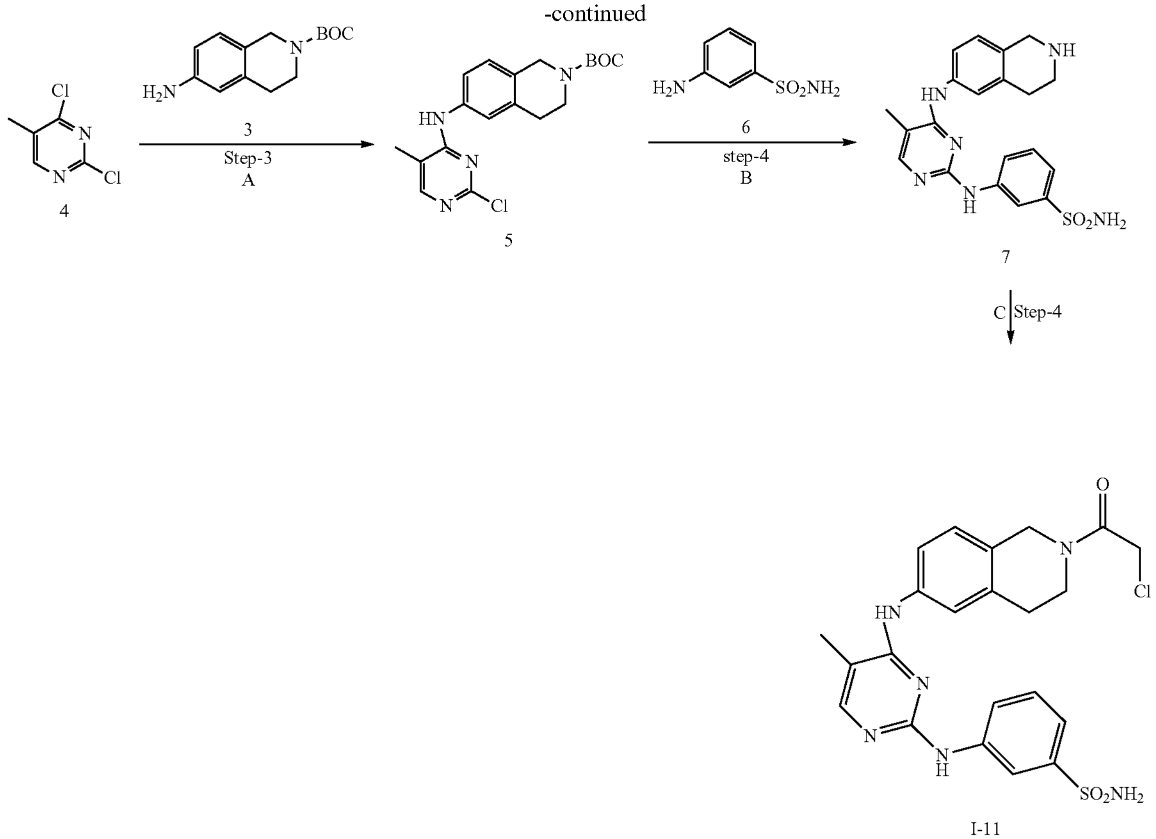

A′) DPPA, Benzyl alcohol, $Et_3N$, toluene, 110° C., 12 h; B′) $Pd(OH)_2$, Ammonium formate, EtOH, reflux, 6 h; A) DIPEA, n-BuOH, 120° C., 1 h., MW: B) 1.5 N HC. EtOH, reflux 12 h.; C) $Cl—CH_2—COCl$, $Et_3N$, THF, rt, 12 h.

Step-1

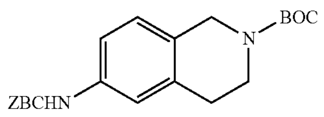

2

To a stirred solution of 1 (1.5 g, 5.4 mmol) in toluene (15 mL) was added DPPA (2.17 g, 8.11 mmol), $Et_3N$ (1.05 mL, 8.11 mmol) and benzyl alcohol (0.876 g, 8.11 mmol) under $N_2$. The reaction mixture was allowed to reflux for 12 h, cooled and diluted with ethyl acetate (100 mL). It was washed with water (5 mL), brine solution (5 mL) and dried over $Na_2SO4$. It was filtered and concentrated under reduced pressure and the residue was purified by column chromatography ($SiO_2$, 60-120, chloroform/methanol, 9/1) gave 2 (2.0 g, 97%) as a white solid.

Step-2

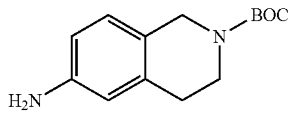

3

To a stirred solution of 2 (2.2 g, 5.75 mmol) in EtOH (25 mL) was added ammonium formate (3.68 g, 57.5 mmol) and the reaction mixture was refluxed for 6 h. It was cooled, filtered though a Celite® bed and filtrate was concentrated under reduced pressure gave 3 (1.3 g, 91%) as a dark brown oil which was used without further purification.

Step-3

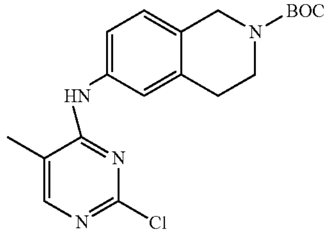

5

A solution of 3 (1.4 g, 5.56 mmol), 4 (0.912 g, 5.56 mmol) and DIPEA (1.077 g, 8.3 mmol) in n-BuOH (15 mL) was subjected to microwave irradiation at 120° C. for 45 min. The reaction mixture was cooled and concentrated under reduced pressure. The residue was taken in ethyl acetate (20 mL) and washed with water (5 mL) and brine (5 mL). Drying over $Na_2SO_4$ followed by concentration under reduced pressure offered a residue which was purified by column chromatography ($SiO_2$, 60-120, chloroform/methanol, 9/1) gave 5 (1.1 g, 52%) as a cream colored solid.

Step-4

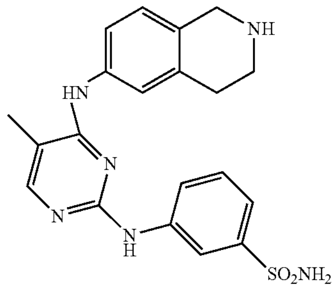

7

To a stirred solution of 5 (0.25 g, 0.66 mmol) in ethanol (5 mL) was added 6 (0.126 g, 0.73 mmol) and catalytic amount of aq.HCl and the reaction mixture was refluxed for 12 h at 100° C. It was cooled, the solid precipitated was filtered and washed with diethyl ether and dried under high vacuum gave 7 (0.24 g, 82%) as a light yellow solid.

Step-5

I-11

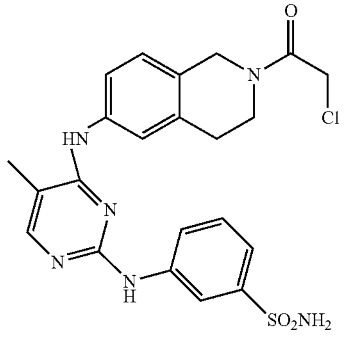

To a stirred solution of 7 (0.2 g, 0.487 mmol) in NMP (5 mL) was added $Et_3N$ (0.094 g, 0.731 mmol). The solution was cooled to 0° C. and chloroacetylchloride (0.082 g, 0.731 mmol) was added to it. The reaction mixture was allowed to come to rt and stir at this temperature for 12 h. It was quenched with ice cooled water (2 mL) and extracted with ethyl acetate (3×5 mL). The combined ethyl acetate extract was washed with brine solution (2 mL), dried over anhydrous $Na_2SO_4$, filtered and concentrated under reduced pressure. The residue obtained was further purified by column chromatography ($SiO_2$, 60-120, chloroform/methanol, 9/1) gave I-11 (0.038 g, 16%) as a light yellow solid. $^1H$ NMR (DMSO-$d_6$) δ ppm: 2.11 (s, 3H), 2.77-2.89 (m, 2H), 3.70-3.72 (m, 2H), 4.49 (d, J=2.92 Hz, 2H), 4.63 (d, J=23.56 Hz, 2H), 7.15-7.17 (m, 1H), 7.24 (s, 2H), 7.30-7.32 (m, 2H), 7.50-7.65 (m, 2H), 7.91 (s, 1H), 8.04-8.05 (m, 2H), 8.27 (s, 1H), 9.31 (s, 1H), LCMS: m/e 486.8 ($MH^+$).

Example 11

Preparation of N-(3-(5-methyl-4-(4-phenoxyphenylamino)pyrimidin-2-ylamino) phenyl)acrylamide I-23

I-23

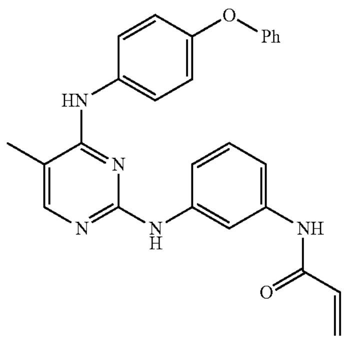

The title compound was prepared according to the schemes, steps and intermediates described below.

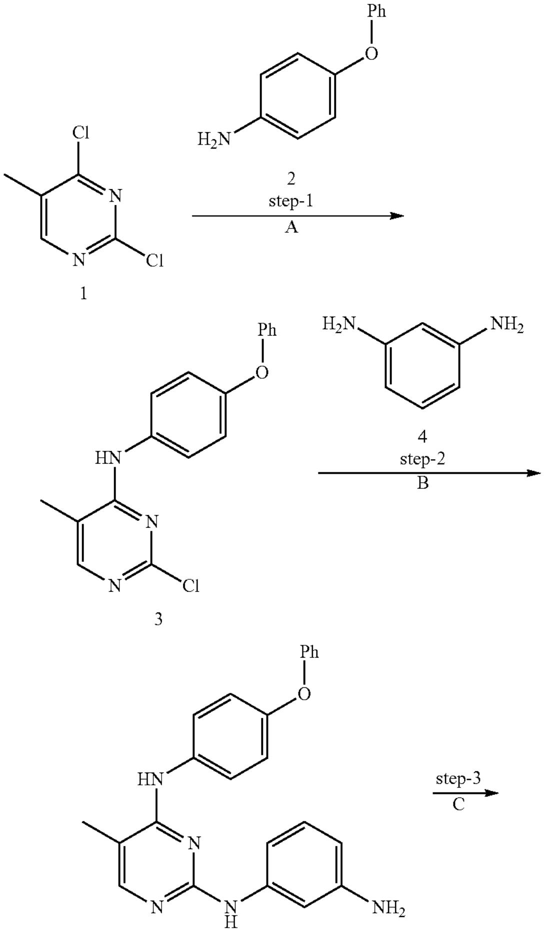

-continued

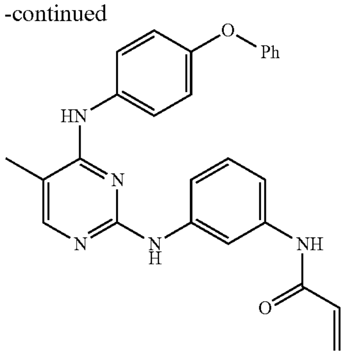

I-23

A) DIPEA, n-butanol, 100° C., 1 h, MW; B) conc. HCl, n-BuOH, 160° C., 20 min, MW; C) Acryloyl chloride 0° C., rt, 1 h.

Step-1

3

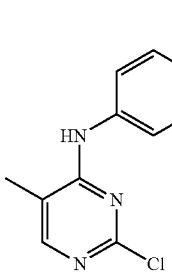

A solution of 1 (0.2 g, 1.2 mmol), 2 (0.12 g, 0.95 mmol) and DIPEA (0.23 g, 1.78 mmol) in n-BuOH (2 mL) was subjected to microwave irradiation (100° C. for 1 h). Then the reaction mixture was cooled, concentrated under reduced pressure and the residue was taken in EtOAc (5 mL). It was washed with $NaHCO_3$ solution (2 mL), water (2 mL), brine (2 mL) and then dried over anhydrous $Na_2SO_4$. Concentrated under reduced pressure followed with purification by column chromatography ($SiO_2$, 60-120, chloroform/methanol, 9/1) gave 3 (0.11 g, 28.9%) as a light brown solid.

Step-2

5

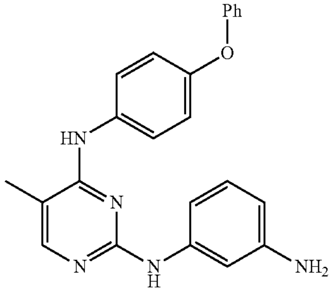

To a solution 3 (0.11 g, 0.3 mmol), 4 (0.114 g, 1.05 mmol) in n-butanol (1 mL) was added conc. HCl (1 drop) and the mixture was subjected to microwave irradiation (165° C. for 10 min). The reaction mixture was cooled, concentrated under reduced pressure and the residue was taken in EtOAc (5 mL). It was washed with $NaHCO_3$ solution (2 mL), water (2 mL) and brine (2 mL). Drying over $Na_2SO_4$ followed by concentration under reduced pressure offered residue which was purified by column chromatography ($SiO_2$, 60-120, chloroform/methanol, 9/1) gave 5 (0.08 g, 65%) as a brown solid.

Step-3

I-23

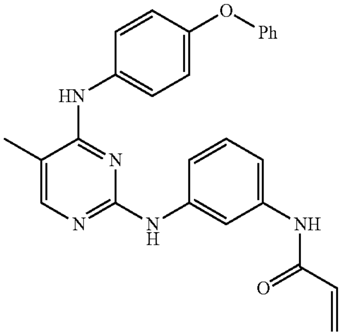

To a stirred solution 5 (0.015 g, 0.03 mmol) in NMP (1 mL) was added acryloyl chloride (0.005 g, 0.05 mmol) at 0° C. The reaction mixture was allowed to come to rt and kept at this temperature for 1 h. It was diluted with dichloromethane (2 mL) and washed with $NaHCO_3$ solution (1 mL), water (1 mL) and brine (1 mL). Drying over $Na_2SO_4$ followed by concentration under reduced pressure offered a residue which was further purified by column chromatography ($SiO_2$, 60-120, chloroform/methanol, 9/1) gave I-23 (0.004 g, 23%) as a brown solid. 400 MHz, MeOD: δ 2.14 (s, 3H), 5.71 (d, J=11.20 Hz, 1H), 6.30-6.44 (m, 2H), 6.94-6.99 (m, 4H), 7.07-7.15 (m, 2H), 7.22 (d, J=7.2 Hz, 1H), 7.34-7.36 (m, 3H), 7.63 (d, J=8.8 Hz, 2H), 7.79 (s, 2H); LCMS: m/e 437 (M+1).

Example 12

Preparation of N-(3-(5-methyl-2-(3-sulfamoylphenylamino)pyrimidin-4-ylamino)phenyl)acrylamide I-33

I-33

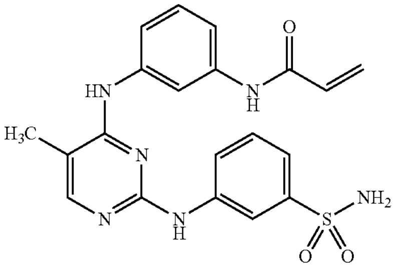

The title compound was prepared according to the schemes, steps and intermediates described below.

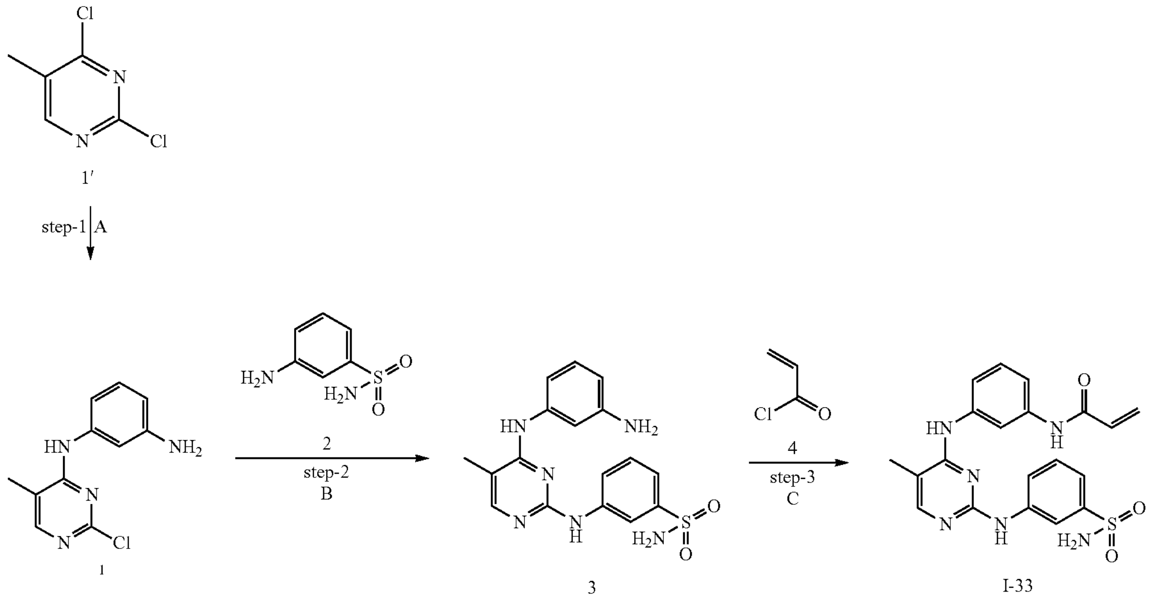

3

I-33

A) DIPEA, n-BuOH, 120° C., 30 min., MW; B) 1.5 N HCl, Ethanol, 100° C., 12 h; C) NMP, 0° C. to rt, 1 h.

Step-1

1

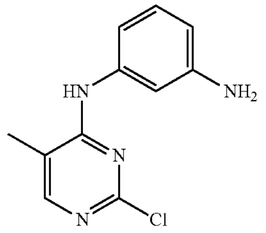

A solution of 1 (0.5 g, 3.06 mmol), 1 (0.49 g, 4.59 mmol) and DIPEA (0.59 g, 4.59 mmol) in n-butanol (8 mL) was subjected to microwave irradiation (120° C., 30 min). It was cooled, quenched with water (5 mL) and extracted with ethyl acetate (3×20 mL). The combined ethyl acetate layer was washed with brine solution (5 mL), dried over $Na_2SO_4$, filtered and concentrated under reduced pressure. The residue was further purified by column chromatography ($SiO_2$, 60-120, chloroform/ethyl acetate, 9/1) gave 1 (0.25 g, 34.77%) as a light brown solid.

Step-2

3

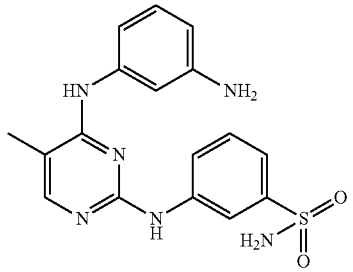

To a stirred solution of 3 (0.1 g, 0.48 mmol), in ethanol (2 mL) was added 4 (0.070 g, 0.42 mmol) and catalytic amount of 1.5 N HCl (3 drops), then heated to 100° C., for 12 h. Reaction mixture then cooled, solid separated, which was filtered and washed with ether 5 (0.1 g as crude), which was taken to next step as such.

Step-3

I-33

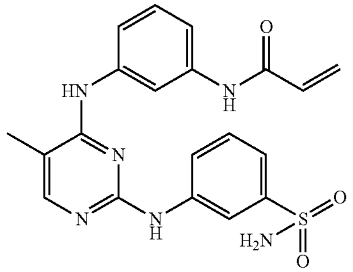

To a stirred solution of 5 (0.1 g, 0.27 mmol) in NMP (2 mL) was added acryloyl chloride (0.037 g, 0.425 mmol) at 0° C., this was then stirred at room temperature for 1 h, then the reaction mixture was quenched with water (4 mL) and basified with NaHCO3, this was then extracted with ethyl acetate (5 mL), combined organic layer washed with brine solution (1 mL), dried over anhydrous $Na_2SO_4$, filtered then concentrated, Crude then purified using preparative HPLC yields I-33 (0.07 g, 6%) as an off white solid. $^1$H NMR (MeOD) δ ppm: 2.17 (s, 3H), 5.78 (dd, J=2.36 & 9.52 Hz, 1H), 6.34-6.48 (m, 2H), 7.26-7.43 (m, 5H), 7.87 (s, 1H), 7.96-8.03 (m, 3H); LCMS: m/e 425 (M+1).

Example 13

Preparation of N-(3-(methyl(5-methyl-2-(phenylamino)pyrimidin-4-yl)amino)phenyl)acrylamide I-34

I-34

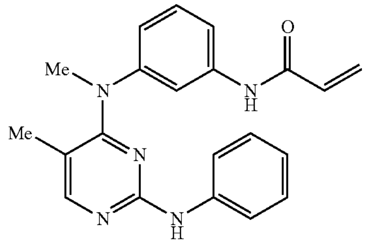

The title compound was prepared according to the schemes, steps and intermediates described below.

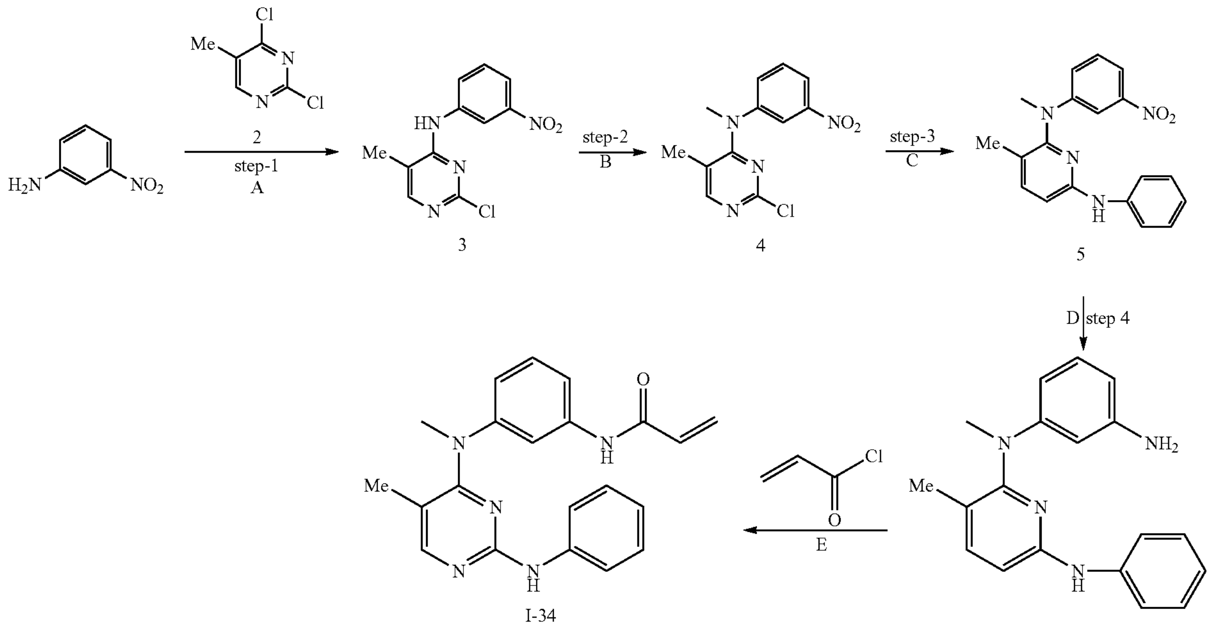

A) Pd(OAC)$_2$, BINAP, Cs$_2$CO$_3$, Toluene, 100° C., 16 h; B) NaH, CH$_3$I,THF, 0° C. - 30 min, rt-16 h.; C) Aniline, conc. HCl, Ethanol, 90° C., 60 min; D) H$_2$, Pd/C, Ethanol, 16 h; E) acryloyl chloride, NMP, 0° C., 1 h.

Step-1

3

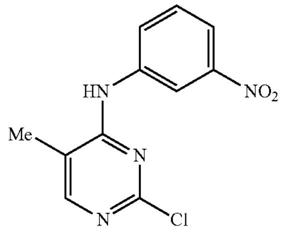

To a stirred solution of 2 (1.0 g, 6.0 mmol), in Toluene (30.0 mL) was added 1 (0.84 g, 6.0 mmol), BINAP (0.186 g, 0.3 mmol), $Cs_2CO_3$ (4.87 g, 15.0 mmol). The reaction mixture was degassed by purging $N_2$ for 15 min. $Pd(OAc)_2$ (0.134 g, 0.6 mmol) was then added to the reaction mixture and the reaction mixture was heated at 100° C. for 16 h under $N_2$ atmosphere. It was then cooled, diluted with Ethyl acetate (30 mL) and filtered through Celite®. Filtrate was washed with water (2×25 mL), brine (25 mL), dried over $Na_2SO_4$ and concentrated under reduced pressure. The residue obtained was further purified column chromatography ($SiO_2$, 60-120 mesh, Ethylacetete/hexane: 10/90) gave a solid which was washed with ether gave 3 (0.6 g, 37%) as a light yellow solid.

Step-2

4

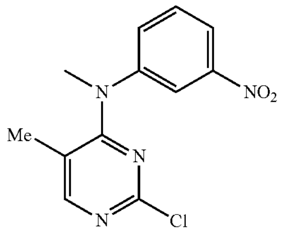

To a stirred mixture of NaH (0.1 g, 2.5 mmol, 60% dispersion in paraffin oil) in dry THF (10.0 mL) was added 3 (0.5 g, 1.89 mmol) at 0° C., and the reaction mixture was stirred at this temperature for 30 min. $CH_3I$ (0.305 g, 2.15 mmol) was added to it and the reaction was allowed to come to rt and stir at this temperature for 16 h. The reaction mixture was diluted with water (25 mL) and extracted with EtOAc (3×25 mL). The combined EtOAc extract was washed with water (25 mL), brine (25 mL), dried over $Na_2SO_4$ and concentrated under reduced pressure gave a residue. The crude residue was further purified by column chromatography ($SiO_2$, $CHCl_3$/MeOH: 99/1) gave 4 (0.12 g, 22.7%) as a light yellow solid.

Step-3

5

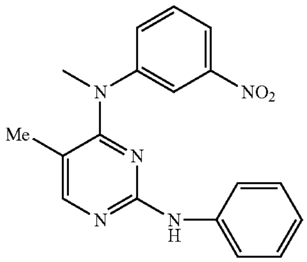

To a solution of 4 (120 mg, 0.431 mmol) in EtOH (2 mL) was added Conc.HCl (0.044 g, 1.2 mmol) and Aniline (0.16 g, 1.72 mmol) and the reaction mixture was heated in a sealed pressure tube at 90° C. for 1 h. The reaction mixture was cooled, solvents removed by concentration under reduced pressure and the residue obtained was diluted with 10% $NaHCO_3$ (10.0 mL). It was extracted with EtOAc (3×15 mL) and the combined EtOAc extract was washed with water (15 mL), brine (15 mL), dried over $Na_2SO_4$. Concentration under reduced pressure offered a residue which was further purified by column chromatography ($SiO_2$, $CHCl_3$/MeOH: 99/1) gave 5 (0.11 g, 76%) as a light yellow solid.

Step-4

6

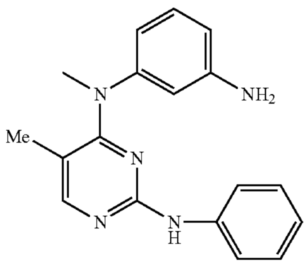

A solution of 5 (0.110 g, 0.328 mmol), in Ethanol (50 mL)) was added 10% Palladium on charcoal (0.022 g) and the reaction mixture was stirred under H2 atmosphere (1.5 Kg) at rt for 16 h. It was filtered through Celite® and concentrated under reduced pressure gave a residue. The residue was purified by column chromatography ($SiO_2$, 60-120, methanol/chloroform: 1/99) gave 6 (0.07 g, 69.9%) as a colorless viscous liquid.

Step-5

I-34

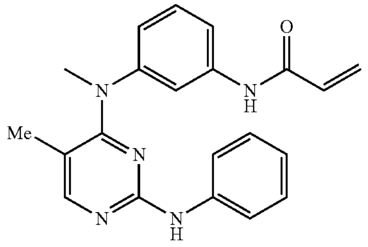

To a stirred solution of 6 (0.070 g, 0.23 mmol) in NMP (1.5 mL) at 0° C. was added acryloyl chloride (0.083 g, 0.916 mmol) and the reaction mixture was stirred at 0° C. for 1 h. It was quenched with 10% sodium bicarbonate solution (15 mL) and the solid precipitated out was filtered, washed with cold water (5 mL), hexane (5 mL). The solid was dried for 2 h under reduced pressure gave I-34 (0.033 g, 40%) as a pale yellow sold. $^1H$ NMR (DMSO-$d_6$) δ ppm: δ 1.47 (s, 3H), 3.45 (s, 3H), 5.74 (dd, J=Hz, 1H), 6.22 (dd, J=2.0 & 16.98 Hz, 1H), 6.38 (dd, J=10 & 16.94 Hz, 1H), 6.85-6.91 (m, 2H), 7.21-7.25 (m, 2H), 7.32 (t, J=8.02 Hz, 1H), 7.43-7.47 (m, 2H), 7.77-7.79 (m, 2H), 7.90 (s, 1H), 9.22 (s, 1H), 10.18 (s, 1H); LCMS: m/e 360.8 (M+1).

Example 14

Preparation of N-(3-(5-methyl-2-(3-(prop-2-yny-loxy)phenylamino)pyrimidin-4-ylamino)phenyl) acrylamide I-35

I-35

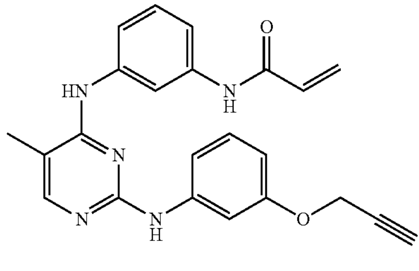

The title compound was prepared according to the schemes, steps and intermediates described below.

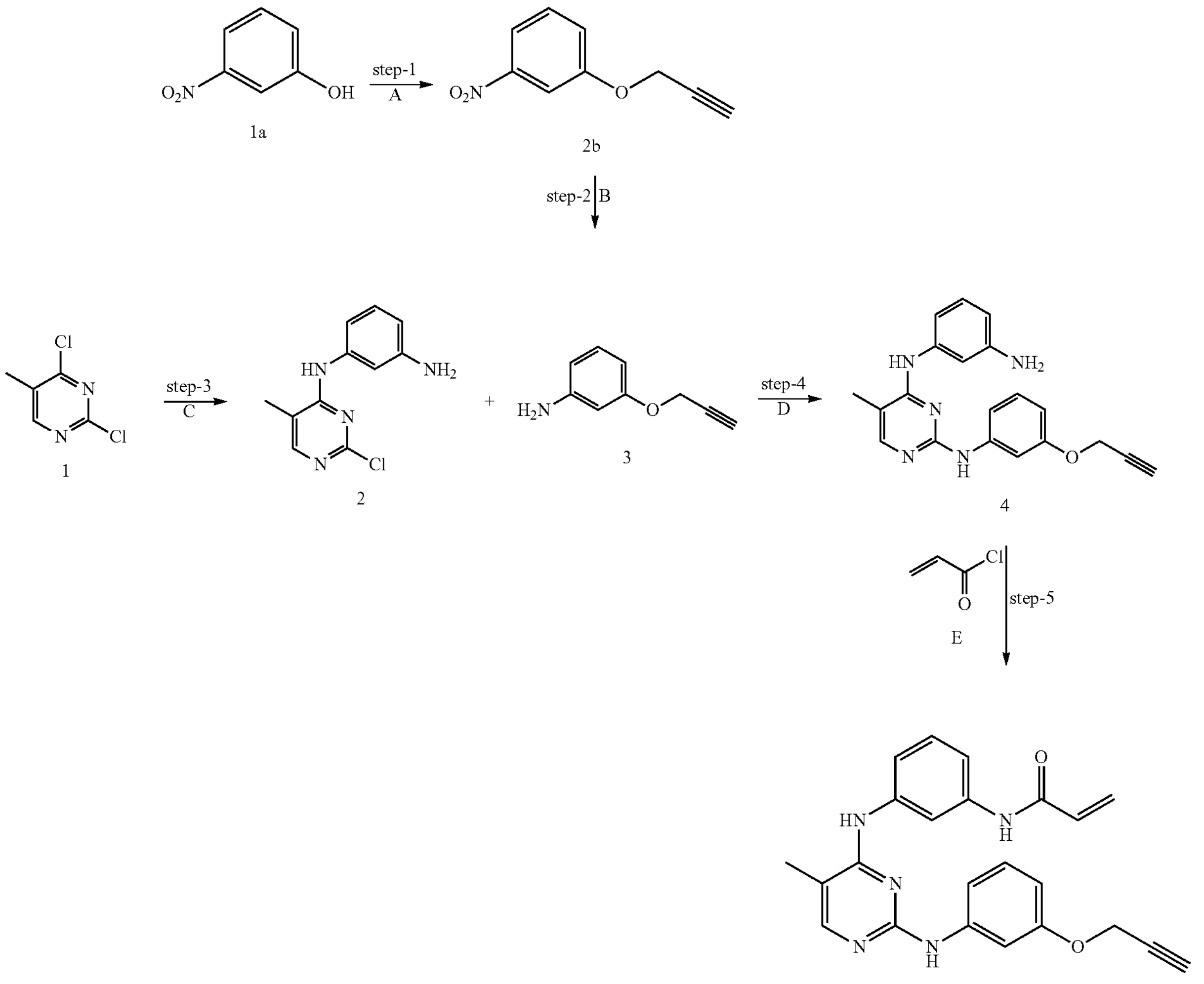

A) $K_2CO_3$, $CH_3CN$, 65°C., 8 h; B) Fe powder, $NH_4Cl$, MeOH, $H_2O$, 80° C., 4 h; C) 1,3-pheneylendiamine, DIPEA, n-BuOH, 120° C., 30 min, MW: D) Con•HCl, absolute ethanol, 110° C., 2 h; E) NMP, 0° C., 1 h.

Step-1

2b

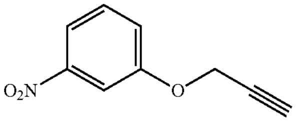

To a stirred solution of 1a (4 g, 0.0287 mol) and $K_2CO_3$ (5.6 g, 0.0574 mol) in $CH_3CN$ (15 mL) was added propargyl bromide (4.1 g, 0.0345 mol) and the resulting mixture was allowed to reflux for 8 h. The reaction mixture was then cooled, quenched with water and extracted with EtOAc (3×50 mL). The combined EtOAc extract was washed with water (20 mL), brine (20 mL) and dried over $Na_2SO_4$. Filtration followed by concentration under reduced pressure furnished 2b as a brownish solid which was used without further purification.

Step-2

3

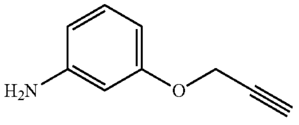

To a stirred solution of 2b in a mixture of methanol (30 mL) and water (30 mL) was added, $NH_4Cl$ (10.3 g, 0.194 mol) and iron powder (6.8 g, 0.121 mol) respectively. Resulting mixture was refluxed at 80° C. for 4 h. Reaction mixture was cooled, diluted with methanol and filtered through a pad of Celite®. The filtrate was concentrated under reduced pressure and the residue was taken in EtOAc. It was washed with water, brine, dried over $Na_2SO_4$ and concentrated under reduced pressure gave a residue. The residue was further purified by column chromatography (SiO2, 60-120, gravity column chromatography, the expected product was eluted with $CHCl_3$/MeOH: 96/4) gave 3 (3.2 g, 91%) as a brownish solid.

Step-3

2

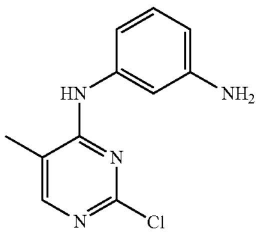

A solution of 2, 4-dichloro-5-methyl pyrimidine 1 (0.3 g, 0.0018 mol), 1,3-phenylene diamine (0.24 g, 0022 mol), DIPEA (0.35 g, 0.0027 mol) in n-BuOH (3 mL) was subjected to microwave irradiation (120° C., 30 min). The reaction mixture was cooled, quenched with water (15 mL) and extracted with EtOAc (3×15 mL). The combined EtOAc extract was washed with water (20 mL), brine (20 mL), dried over $Na_2SO_4$ and concentrated under reduced pressure. The residue obtained was further purified column chromatography (SiO2, 60-120) gave 2 (0.15 g, 35%) as a brownish solid.

Step-4

4

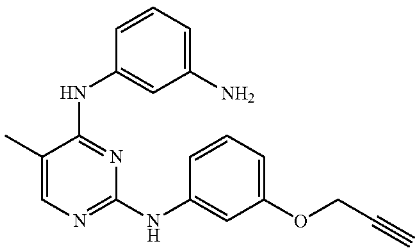

2 (0.15 g, 0.006 mol) and 3 (0.37 g, 0.0025 mol) were taken in a pressure tube and to it were added abs. EtOH (3 mL) followed by conc. HCl (0.04 g, 0.0012 mol). The tube was tightly screw fitted and was heated at 120° C. for 2 h. The reaction mixture was then cooled, solvents removed under reduced pressure and residue obtained was taken in EtOAc (10 mL). It was washed with water (4 mL), $NaHCO_3$ (4 mL) and brine (5 mL). Drying over Na2SO4 followed by concentration under reduced pressure offered a residue which was further purified by column chromatography ($SiO_2$, 60-120, gravity column chromatography, expected compound getting eluted in $CHCl_3$/MeOH: 94/6) gave 4 (125 mg, 56%) as a light brown solid.

Step-5

I-35

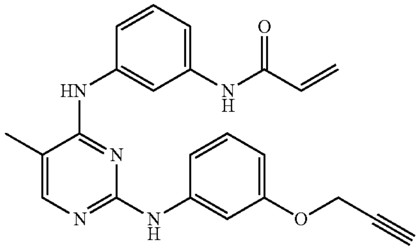

To a stirred solution of 4 (0.1 g, 0.002 mol) in NMP (8 mL) was added acryloyl chloride (0.1 g, 0.001 mol) drop wise at 0° C. The reaction was kept at this temperature for 10 min and then allowed to come to rt and stir at this temperature for 1.5 h. It was then quenched with 10% sodium bicarbonate solution (8 mL) and extracted with EtOAc (2×15 mL). The combined EtOAc extract was washed with water (10 mL), brine (10 mL) dried over $Na_2SO_4$ and concentrated under reduced pressure. The residue obtained was purified by column chromatography (SiO2, 60-120, gravity column chromatography, expected compound getting eluted in $CHCl_3$/MeOH: 90/10) gave I-35 (20 mg, 18%) as an off-white solid. $^1$H NMR (DMSO-$d_6$) δ ppm: 2.11 (s, 3H), 3.51 (s, 1H), 4.61 (s, 2H), 5.74 (d, J=9.08 Hz, 1H), 6.25 (d, J=15.84 Hz, 1H), 6.45 (s, 2H), 7.02 (s, 1H), 7.27-7.45 (m, 5H), 7.91 (d, J=8.84 Hz, 2H), 8.36 (s, 1H), 8.93 (s, 1H), 10.09 (s, 1H), LCMS: m/e 400 (M+1).

Example 15

Preparation of (E)-4-(dimethylamino)-N-(3-(5-methyl-2-(phenylamino)pyrimidin-4-ylamino)phenyl)but-2-enamide I-38

I-38

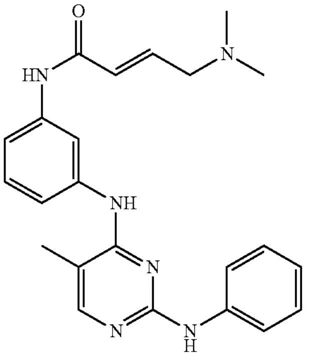

The title compound was prepared according to the schemes, steps and intermediates described below.

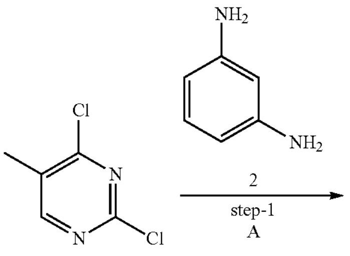

1

-continued

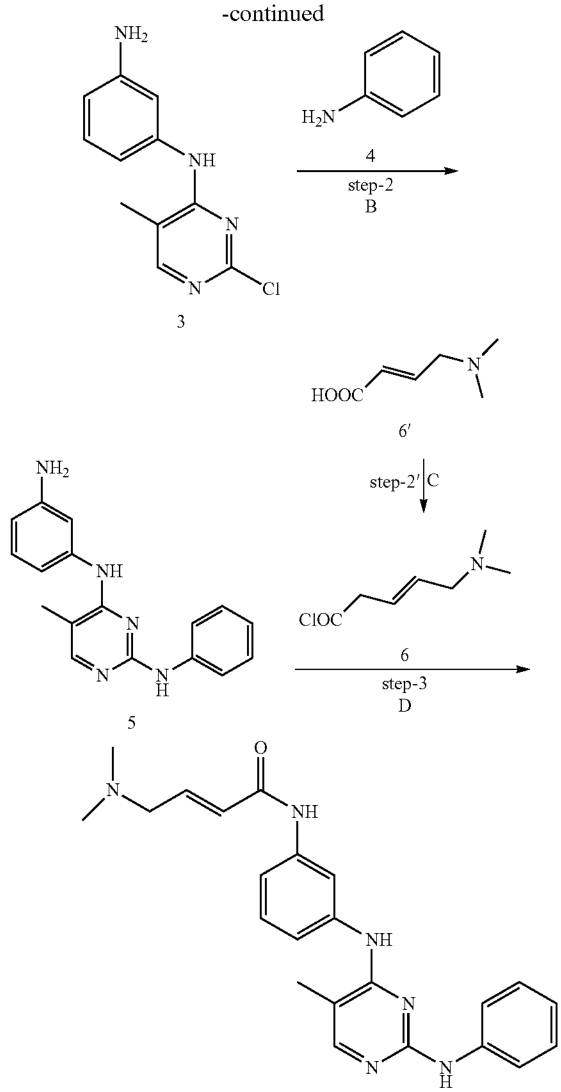

I-38

A) DIEA, n-BuOH, 120° C., 30 min, MW; B) NMP, 200° C., 10 min, MW; C)) oxaldyl chloride, $CH_3CN$, 30 min at 0° C., 2 h at 25° C., 5 min at 45° C., D) NMP, 0° C., 1 h.

Step-1

3

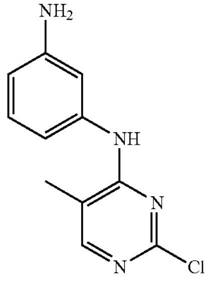

A solution of 1 (2.0 g, 12 mmol), 2 (2.0 g, 18 mmol), DIPEA (2.33 g, 18 mmol) in n-BuOH (20.0 mL) was subjected to microwave irradiation at 120° C. for 30 min. The reaction mixture was then quenched with water (100 mL), extracted with EtOAc (3×100 mL). The combined EtOAc extract was washed with water (100 mL), brine (100 mL), dried over $Na_2SO_4$ and concentrated under reduced pressure. The residue obtained was further purified column chromatography ($SiO_2$, 60-120 mesh, EtOAc/$CHCl_3$: 15/85) gave 3 (1.3 g, 45%) as a dark brown solid.

Step-2

5

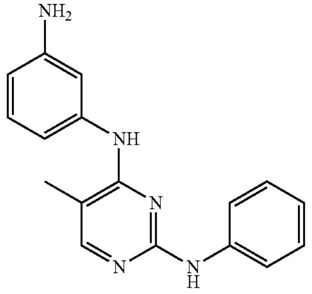

A solution of 3 (1.0 g, 4.27 mmol), 4 (1.5 g, 16.12 mmol) in NMP (10 mL) was subjected to microwave irradiation (200° C., 10 min). Then the reaction mixture was cooled, diluted with water (100 mL) and extracted with EtOAc (3×100 mL). The combined EtOAc extract was washed with water (100 mL), brine (100 mL), dried over $Na_2SO_4$ and concentrated under reduced pressure gave a residue. The crude residue was further purified by column chromatography ($SiO_2$, 60-120, $CHCl_3$/MeOH: 98/2) gave 5 (0.5 g, 40.3%) as a light brown solid.

Step-2'

6

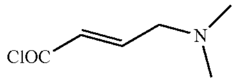

To a stirred solution of 6' (70 mg, 0.42 mmol) in $CH_3CN$ (1.0 mL) was added oxalyl chloride (80 mg, 0.62 mmol) at 0° C. The reaction mixture was allowed to stir at 0° C. for ½ h and then at rt for 2 h. Finally it was heated at 45° C. for 5 min, cooled and the reaction mixture was taken for the next step without further purification.

Step-3

I-38

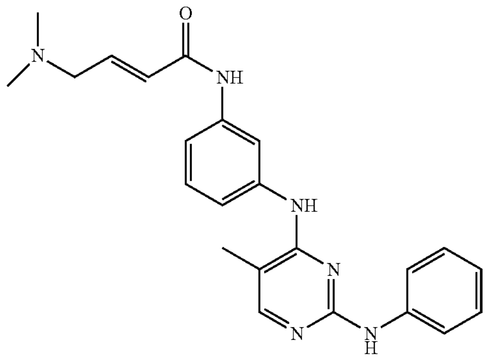

To a stirred solution of 5 (75 mg, 0.12 mmol) in NMP (1 mL) was added 6 at 0° C. The reaction mixture was stirred at 0° C. for 1 h, quenched with cold water (5 mL), basified with $Et_3N$ and extracted with $CH_2Cl_2$ (3×10 mL). The combined organic extract was washed with water (5 mL), brine (5 mL) and dried over $Na_2SO_4$. Concentration under reduced pressure followed by purification over silica gel (60-120) using 5% methanol in chloroform gave crude compound (20 mg) as a brown gummy solid, which was again taken into dichloromethane and stirred with 10% bicarbonate solution for 30 min, dichloromethane layer separated, dried over $Na_2SO_4$ and concentrated to give I-38 (8 mg, 17%) as a brown solid. $^1H$ NMR (DMSO-$d_6$) δ ppm: 2.15 (s, 3H), 2.32 (s, 6H), 3.21 (d, J=5.76 Hz, 2H), 6.27 (d, J=15.36 Hz, 1H), 6.84-6.93 (m, 2H), 7.14 (t, J=7.52 Hz, 2H), 7.27-7.33 (m, 2H), 7.44 (dd, J=2.04 Hz & 5.08 Hz, 1H), 7.53 (d, J=7.72 Hz, 2H), 7.80 (s, 1H), 8.00 (s, 1H); LCMS: m/e 402.8 (M+1).

Example 16

Preparation of N-(4-(5-methyl-2-(phenylamino)pyrimidin-4-ylamino)phenyl) acrylamide I-39

I-39

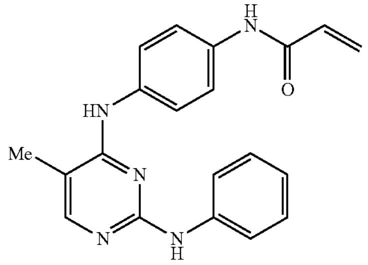

The title compound was prepared according to the schemes, steps and intermediates described below.

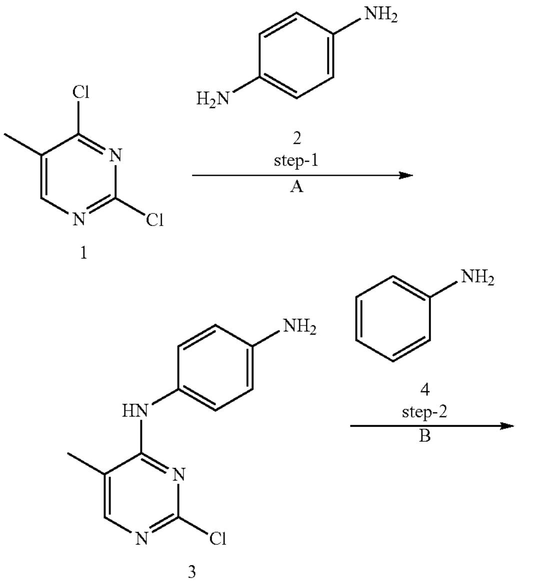

-continued

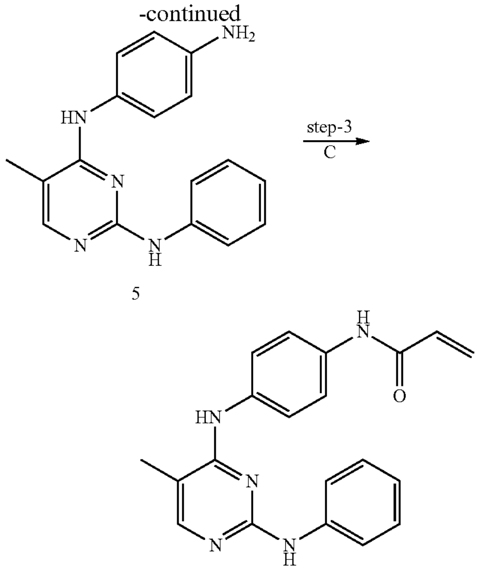

A) DIPEA, n-BuOH, 110° C., 45 min, MW; B) Conc.HCl, n-BuOH, 150° C., 10 min, MW; C) Acryloyl chloride, NMP, 0° C. -30 min, rt-2 h.

Step-1

3

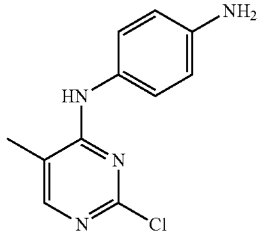

A solution of 1 (0.4 g, 2.4 mmol), 2 (0.3 g, 2.6 mmol), DIPEA (0.46 g, 3.6 mmol) in n-BuOH (10 mL) was subjected to microwave irradiation (110° C., 45 min). The reaction mixture was cooled, quenched with water (20 mL) and extracted with EtOAc (3×15 mL). The combined EtOAc extract was washed with water (20 mL), brine (20 mL), dried over $Na_2SO_4$ and concentrated under reduced pressure. The residue was purified by column chromatography ($SiO_2$, 60-120, $CHCl_3$/MeOH: 99/1) gave 3 (350 mg, 62%) as an off-white solid.

Step-2

5

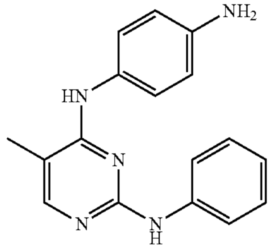

A solution of 3 (0.2 g, 0.8 mmol), 4 (0.63 g, 6.8 mmol) and con.HCl (0.03 g, 0.8 mmol) in n-BuOH (10 mL) was subjected to microwave irradiation (150° C., 10 min). Then the reaction mixture was cooled, diluted with water (10 mL), basified with 10% sodium bicarbonate solution and extracted with EtOAc (3×15 mL). The combined EtOAc extract was washed with water (15 mL), brine (15 mL), dried over $Na_2SO_4$ and concentrated under reduced pressure. The crude residue was purified by column chromatography ($SiO_2$, 60-120, $CHCl_3$/MeOH: 97/3) gave 5 (110 mg, 47%) as a brown colored gummy solid.

Step-3

I-39

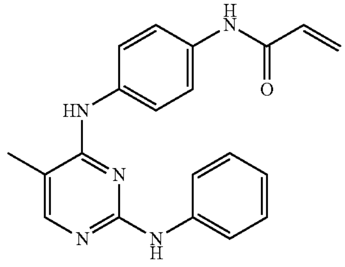

To a stirred solution of 5 (0.06 g, 0.2 mmol) in NMP (2 mL) was added acryloyl chloride (0.03 g, 0.3 mmol) at 0° C. It was allowed to stir at the same temperature for 20 min and then at rt for 2 h. The reaction mixture was quenched with water, basified with 10% sodium bicarbonate solution and extracted with EtOAc (3×10 mL). The combined EtOAc layer was washed with water (10 mL), brine (10 mL), dried over $Na_2SO_4$ and concentrated under reduced pressure. The residue was purified by column chromatography ($SiO_2$, 60-120) and finally by preparative HPLC gave I-39 (10 mg, 16%) as an off-white solid. $^1$H NMR (DMSO-$d_6$) δ ppm: 2.10 (s, 3H), 5.71-5.76 (m, 1H), 6.25 (dd, J=2.04 & 16.96 Hz, 1H), 6.45 (dd, J=10.08 & 16.92 Hz, 1H), 6.84 (t, J=7.30 Hz, 1H), 7.14-7.18 (m, 2H), 7.62-7.68 (m, 6H), 7.86 (s, 1H), 8.26 (s, 1H), 8.94 (s, 1H), 10.11 (s, 1H), LCMS: m/e 346 (M+1).

Example 17

Preparation of N-(3-(5-methyl-2-(phenylamino)pyrimidin-4-ylamino)phenyl) propionamide $I^R$-7

$I^R$-7

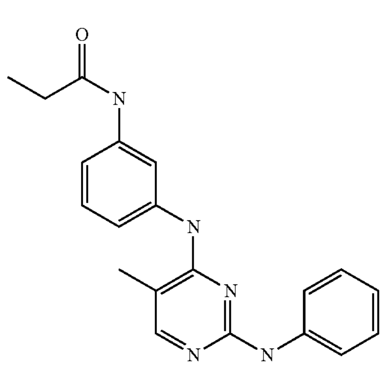

The title compound was prepared according to the schemes, steps and intermediates described below.

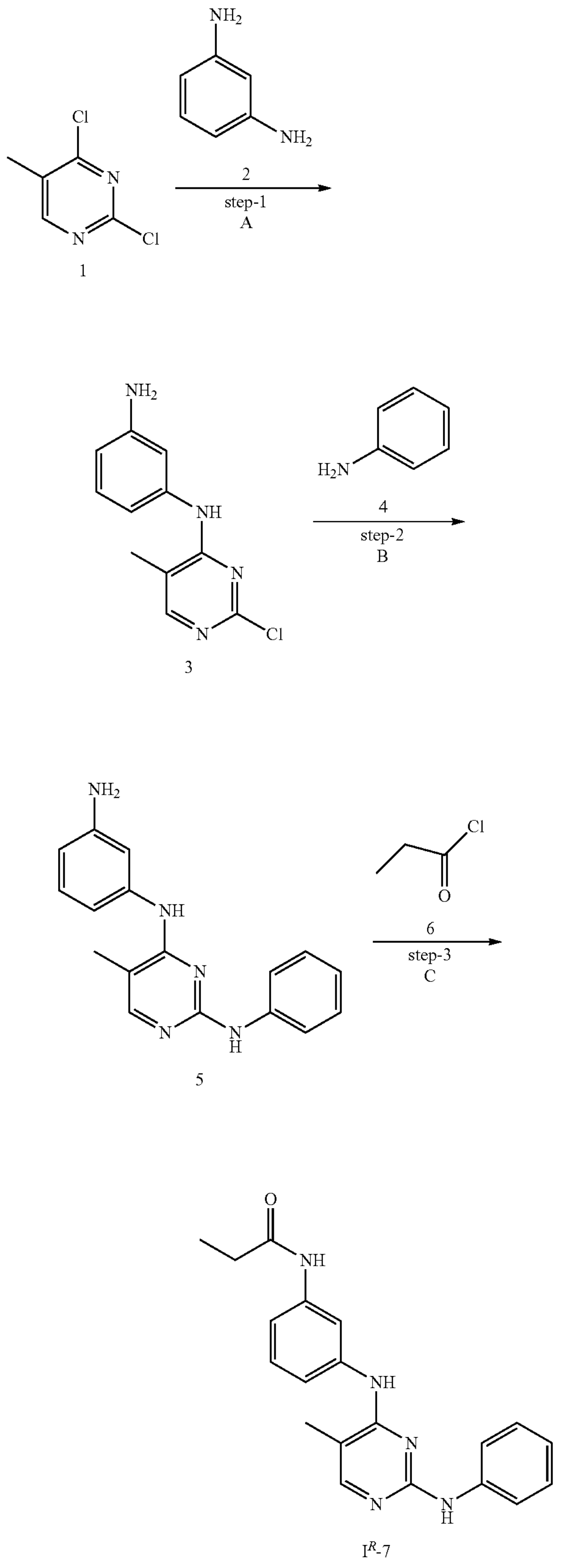

A) DIPEA, n-BuOH, 120° C., 30 min, MW; B) NMP, 200° C., 10 min, MW: C) 6, NMP, 0° C., 60 min.

Step-1

3

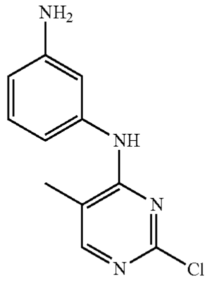

A solution of 1 (2.0 g, 12 mmol), 2 (2.0 g, 18 mmol), DIPEA (2.33 g, 18 mmol) in n-BuOH (20.0 mL) was subjected to microwave irradiation at 120° C. for 30 min. The reaction mixture was then quenched with water (100 mL), extracted with EtOAc (3×100 mL). The combined EtOAc extract was washed with water (100 mL), brine (100 mL), dried over $Na_2SO_4$ and concentrated under reduced pressure. The residue obtained was further purified column chromatography ($SiO_2$, 60-120 mesh, EtOAc/$CHCl_3$: 15/85) gave 3 (1.3 g, 45%) as a dark brown solid.

Step-2

5

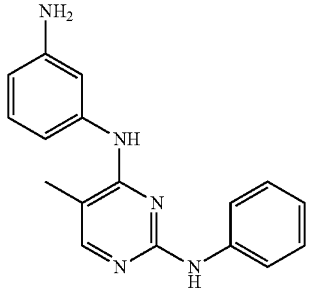

A solution of 3 (1.0 g, 4.27 mmol), 4 (1.5 g, 16.12 mmol) in NMP (10 mL) was subjected to microwave irradiation (200° C., 10 min). Then the reaction mixture was cooled, diluted with water (100 mL) and extracted with EtOAc (3×100 mL). The combined EtOAc extract was washed with water (100 mL), brine (100 mL), dried over $Na_2SO_4$ and concentrated under reduced pressure gave a residue. The crude residue was further purified by column chromatography ($SiO_2$, $CHCl_3$/MeOH: 98/2) gave 5 (0.5 g, 40.3%) as a light brown solid.

Step-3

$I^R$-7

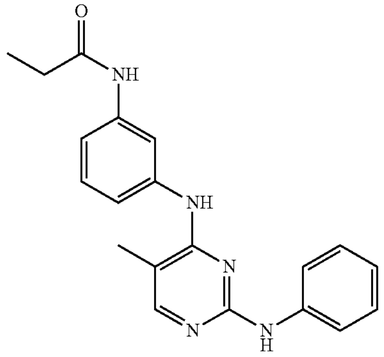

To a stirred solution of 5 (75 mg, 0.25 mmol) in NMP (1.0 mL) at 0° C. was added propanoyl chloride (6) (72 mg, 0.75 mmol) and the reaction mixture was stirred at 0° C. for 60 min. The reaction mixture was then quenched with water (5 mL), basified with $Et_3N$ and extracted with EtOAc (3×10 mL). The combined EtOAc extract was washed with water (10 mL), brine (10 mL), dried over $Na_2SO_4$ and concentrated under reduced pressure. The residue obtained was further purified column chromatography ($SiO_2$, 230-400, methanol/chloroform: 2/98) gave $I^R$-7 (0.025 g, 28.73%) as an off white solid. $^1$H NMR (DMSO-$d_6$) δ ppm: 1.08 (t, J=7.6 Hz, 3H), 2.11 (s, 3H), 2.31 (q, J=7.6 Hz, 2H), 6.81 (t, J=7.2 Hz, 1H), 7.11 (t, J=8 Hz, 2H), 7.21-7.25 (m, 1H), 7.31 (d, J=8.40 Hz, 1H), 7.36 (d, J=8.00 Hz, 1H), 7.66 (d, J=8.40 Hz, 2H), 7.86 (s, 1H), 7.89 (s, 1H), 8.35 (s, 1H), 8.93 (s, 1H), 9.81 (s, 1H); LCMS: m/e 348.3 (M+1).

Example 18

Preparation of N-(4-methyl-3-(4-(pyridin-3-yl)pyrimidin-2-ylamino)phenyl)acrylamide I-56

I-56

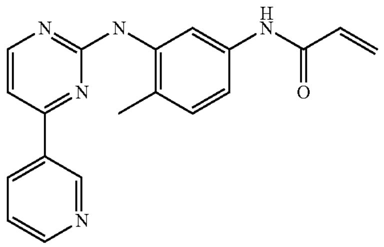

The title compound was prepared according to the schemes, steps and intermediates described below.

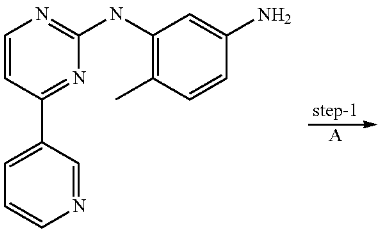

1

-continued

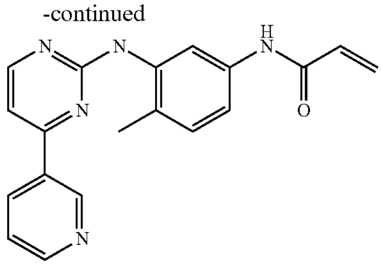

I-56

A) acryloyl chloride, $Et_3N$, DMF, rt, 12 h
Step-1

I-56

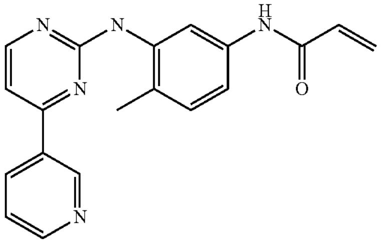

To a stirred solution of 1 (0.15 g, 0.54 mmol) and $Et_3N$ (0.11 g, 1.08 mmol) in DMF (1 mL) at 0° C. was added acryloyl chloride (0.09 g, 1.08 mmol), drop-wise, under $N_2$ atmosphere. The reaction mixture was allowed to come to rt and stirred further 12 h. It was then quenched with ice-cold water (2 mL) and extracted with EtOAc (2×15 mL). The combined EtOAc extract was washed with brine (2 mL), dried over $Na_2SO_4$ and concentrated under reduced pressure to get a crude residue. The residue was further purified by preparative HPLC and gave I-56 (0.060 g, 33%) as a pale yellow solid. $^1H$ NMR (DMSO-$d_6$) δ ppm: 2.19 (s, 3H), 5.72 (dd, J=2 & 10.08 Hz, 1H), 6.22 (dd, J=2 & 16.92 Hz, 1H), 6.45 (dd, J=10 & 17 Hz, 1H), 7.16 (d, J=8.36 Hz, 1H), 7.32 (dd, J=1.92 & 8.16 Hz, 1H), 7.42 (d, J=5.12 Hz, 1H), 7.50-7.53 (m, 1H), 7.95 (d, J=1.68 Hz, 1H), 8.45 (dd, J=6.16 & 8.16 Hz, 1H), 8.49 (d, J=5.16 Hz, 1H), 8.68 (dd, J=1.56 & 4.76 Hz, 1H), 8.95 (s, 1H), 9.25 (d, J=1.56 Hz, 1H), 10.08 (s, 1H); LCMS: m/e 332.4 (M+1).

Example 19

General Method for Preparing Compounds Having an Enone-Containing Warhead, e.g., 3-methyl-1-(3-(5-methyl-2-(phenylamino)pyrimidin-4-ylamino)phenyl)but-2-en-1-one I-47

I-47

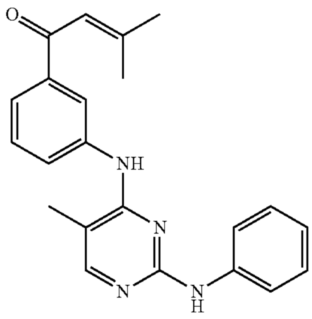

The title compound is prepared according to the schemes, steps and intermediates described below. It is also appreciated by one skilled in the art that I-47 is an exemplary compounds having enone-containing warheads, and that other compounds having enone-containing warheads can be synthesized in a substantially similar manner according to the schemes, steps and corresponding intermediates described below.

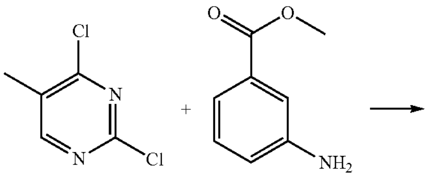

1 2

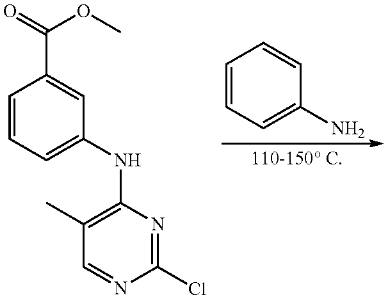

3

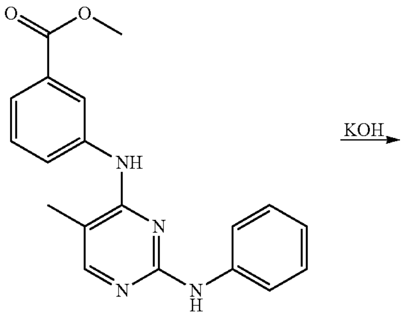

4

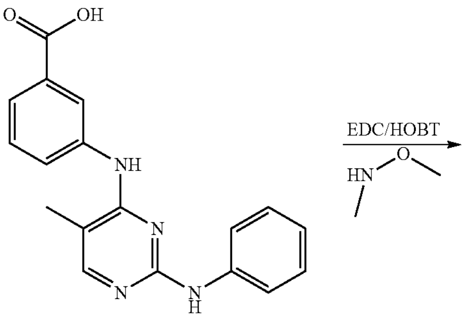

5

-continued

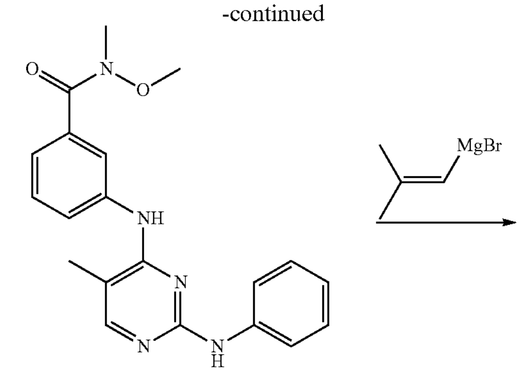

6

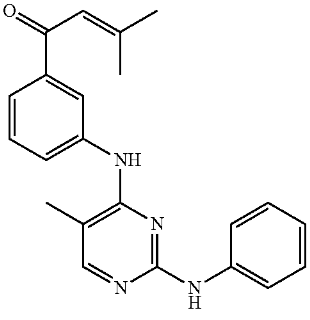

I-47

Compounds 1 and 2 are coupled in the presence of triethylamine to yield compound 3. Compound 3 is treated with analine at elevated temperature to yield compound 4. Saponification of Compound 4 with potassium hydroxide yields acid compound 5, which is coupled to N—O-dimethylhydroxylamine using EDC to yield compound 6. Treatment of Compound 6 at low temperature yields exemplary compound I-47.

Example 20

Preparation of N-(3-(5-fluoro-2-(4-(2-methoxyethoxy)phenylamino)pyrimidin-4-ylamino)phenyl) acrylamide I-182

I-182

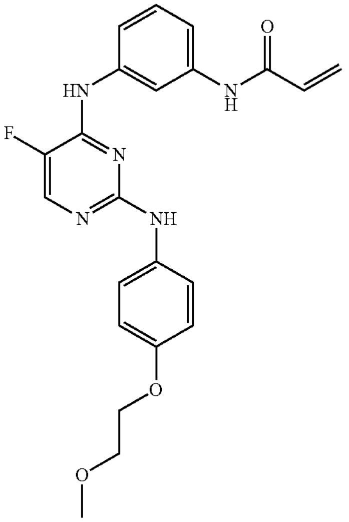

The title compound was prepared according to the schemes, steps and intermediates described below.

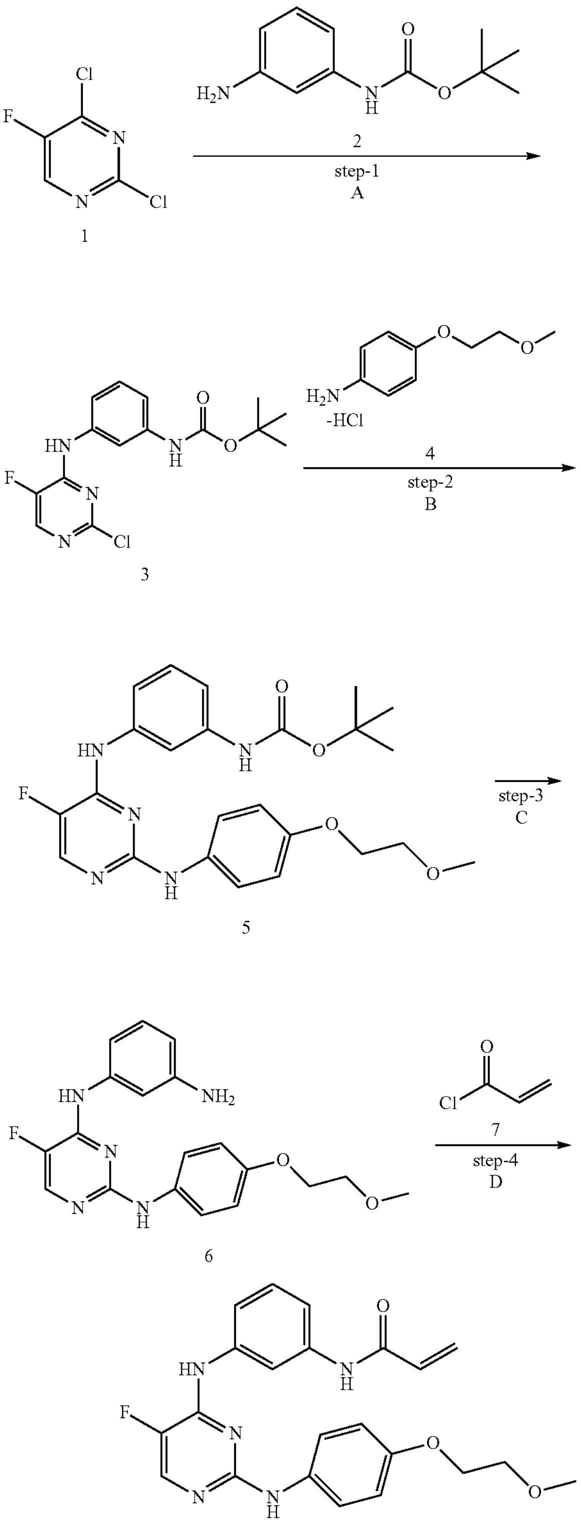

I-182

A) 2, DIPEA, THF, reflux; B) 4, t-amyl alcohol, HOAc, reflux; C) TFA, DCM; D) 7, DIPEA, THF, -10° C.

Step-1

3

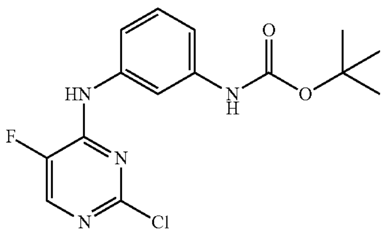

1 (800 mg, 4.8 mmoL), 2 (996 mg, 4.8 mmoL) and Hunig's base (948 uL, 5.75 mmoL) were dissolved in THF (20 mL). The reaction mixture was heated at reflux overnight. After cooling, partitioned between water/brine (10 mL), agitated and separated the layers. Dried organic phase over sodium sulfate, and the solvent was removed via rotary evaporation. Titration with EtOAc and Heptane gave after filtration a white solid, lg. LC/MS (RT=2.03/(M+1)) 339.1.

Step-2

5

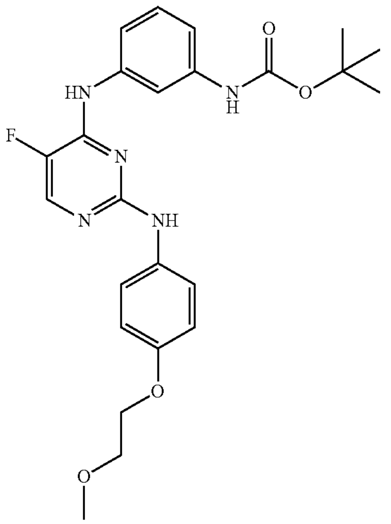

3 (800 mg, 2.37 mmoL) and 4 (576 mg, 2.84 mmoL) were suspended in tert-amyl alcohol (14 mL) and acetic acid (5 drops). Heated to reflux for 4 h. After cooling, solvent was removed via rotary evaporation. The dark oil was partitioned between water/brine and THF (10 mL each), agitated, and separated layers and dried organic phase over sodium sulfate. The solvent was removed via rotary evaporation to afford a purple solid, 0.55 g. LC/MS (RT=2.997/(M+1)) 470.2. Additional 150 mg of product minus the (BOC) protecting group crystallized from the aqueous layer.

Step-3

6

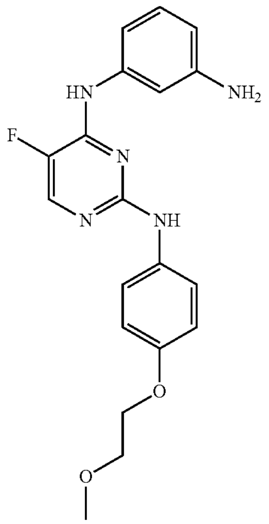

To a solution of 6 (550 mg, 1.17 mmol) in DCM (20 mL) was added TFA (2 mL). Stirred for 30 min at rt for 4 h; removed solvent via rotary evaporation and partitioned oil with cold (0° C.) saturated sodium bicarbonate (10 mL) and EtOAc (10 mL), agitated and separated layers. Organic phase was dried over sodium sulfate and the solvent was removed via rotary evaporation to give a dark oil. Flash chromatography using 20%-100% Heptane/EtOAc gradient using combiflash system gave 309 mg of a light pink solid. LC/MS (RT=2.78/(M+1)) 370.2.

Step-4

I-182

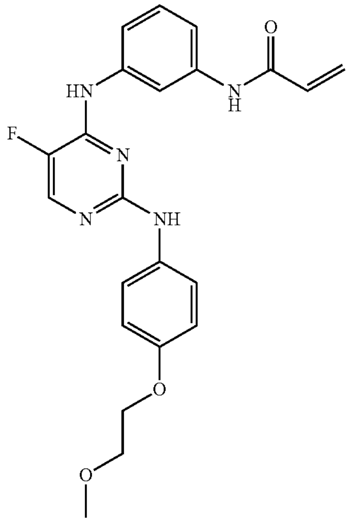

A solution of 6 (309 mg, 0.84 mmol) in THF (10 mL) was cooled in a water/ice-MeOH bath (−10° C.). To this was added 7 (71 μL, 0.88 mmoL), stirred for 10 min, then added Hunig's base (145 uL, 0.88 mmoL), and stirred for 10 min. Partitioned between water/brine (10 mL), agitated and separated the layers. Dried organic phase over sodium sulfate. The solvent was removed via rotary evaporation and triturated with diethyl ether to afford after filtration 285 mg (80%) of an off-white solid. LC/MS (RT=2.79/(M+H)) 424.2.

Example 21

Preparation of N-(3-(2-(3-chloro-4-(pyridin-2-yl-methoxy)phenylamino)-5-fluoropyrimidin-4-ylamino)phenyl)acrylamide I-86

I-86

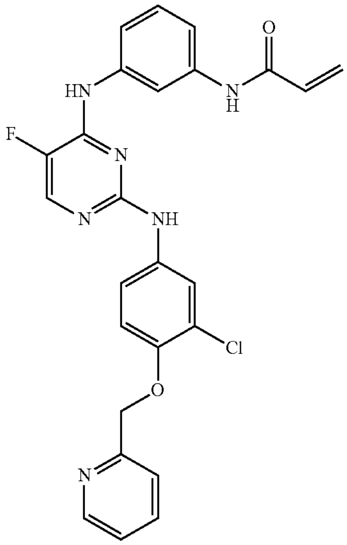

The title compound was prepared according to the schemes, steps and intermediates described in Example 20, by using 3-chloro-4-(pyridine-2-ylmethoxy)aniline in the place of 4 in Step 2. LC/MS (RT=2.87/(M+H)) 491.1.

Example 22

Preparation of N-(3-(5-fluoro-2-(4-(2-(2-oxopyrrolidin-1-yl)ethoxy)phenylamino)pyrimidin-4-ylamino)phenyl)acrylamide I-92

I-92

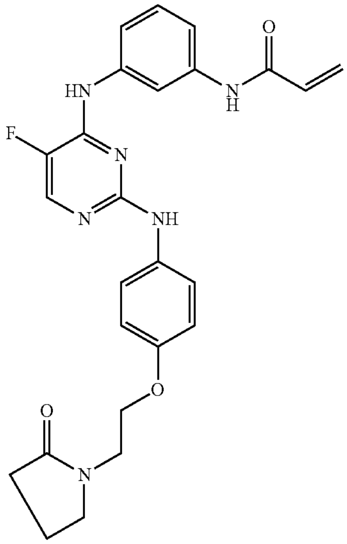

The title compound was prepared according to the schemes, steps and intermediates described in Example 20, by using 1-(2-(4-aminophenoxy)ethyl)pyrrolidin-2-one in the place of 4 in Step 2. LC/MS (RT=2.718/(M+H)) 477.1.

Example 23

Preparation of N-(3-(5-fluoro-2-(4-(1-hydroxy-2-methylpropan-2-yloxy)phenylamino)pyrimidin-4-ylamino)phenyl)acrylamide I-93

I-93

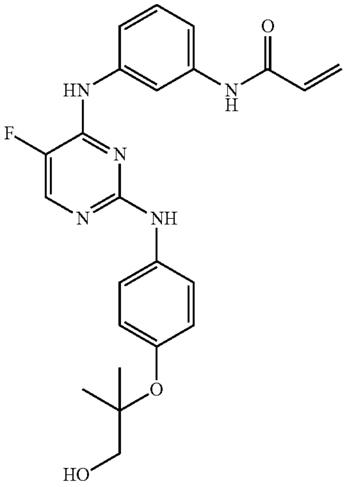

The title compound was prepared according to the schemes, steps and intermediates described in Example 20, by using 2-(4-aminophenoxy)-2-methylpropan-1-ol in the place of 4 in Step 2. LC/MS (RT=2.724/(M+H)) 438.1.

Example 24

Preparation of N-(3-(5-fluoro-2-(6-isopropoxypyridin-3-ylamino)pyrimidin-4-ylamino)phenyl)acrylamide I-172

I-172

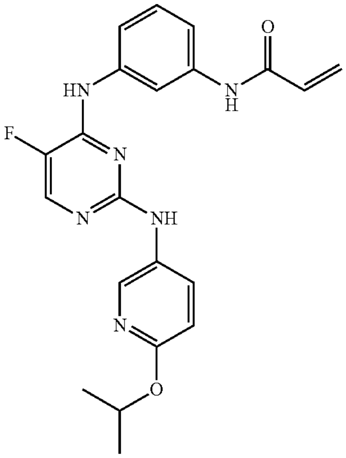

The title compound was prepared according to the schemes, steps and intermediates described in Example 20, by using 6-isopropoxypyridin-3-amine in the place of 4 in Step 2. LC/MS (RT=2.878/(M+H)) 409.2.

Example 25

Preparation of N-(3-(5-fluoro-2-(2-oxoindolin-5-ylamino)pyrimidin-4-ylamino)phenyl)acrylamide I-181

I-181

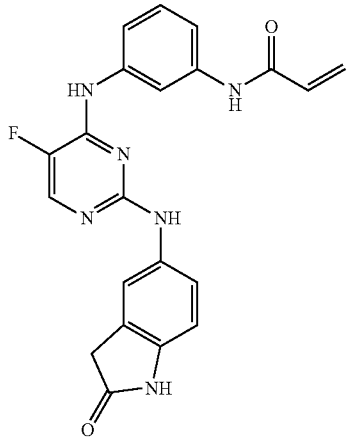

The title compound was prepared according to the schemes, steps and intermediates described in Example 20, by using 5-aminoindolin-2-one in the place of 4 in Step 2. LC/MS (RT=2.617/(M+H)) 405.1.

Example 26

Preparation of N-(2-chloro-5-(5-fluoro-2-(4-(2-methoxyethoxy)phenylamino)pyrimidin-4-ylamino)phenyl)acrylamide I-108

I-108

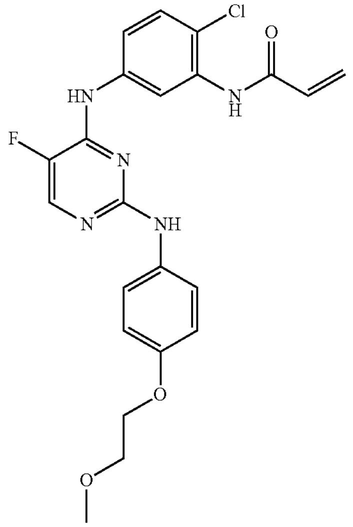

The title compound was prepared according to the schemes, steps and intermediates described in Example 20, by using tert-butyl 5-amino-2-chlorophenylcarbamate in the place of 2 in Step 1. LC/MS (RT=2.852/(M+H)) 458.1.

Example 27

Preparation of N-(2-chloro-5-(5-fluoro-2-(6-isopropoxypyridin-3-ylamino)pyrimidin-4-ylamino)phenyl)acrylamide I-107

I-107

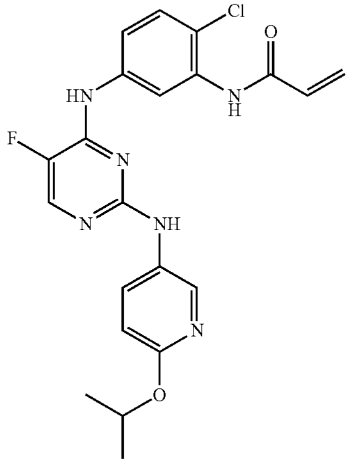

The title compound was prepared according to the schemes, steps and intermediates described in Example 20, by using tert-butyl 5-amino-2-fluorophenylcarbamate in the place of 2 in Step 1 and 6-isopropoxypyridin-3-amine in the place of 4 in Step 2. LC/MS (RT=2.938/(M+H)) 443.1.

Example 28

Preparation of N-(2-fluoro-5-(5-fluoro-2-(4-(2-methoxyethoxy)phenylamino)pyrimidin-4-ylamino)phenyl)acrylamide I-87

I-87

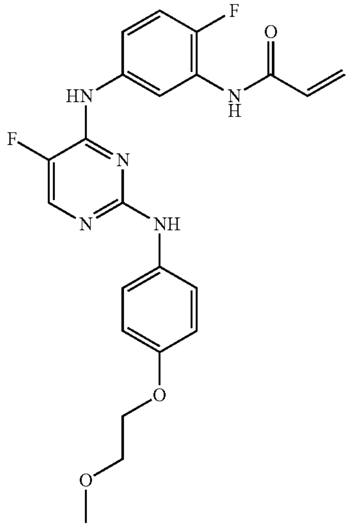

The title compound was prepared according to the schemes, steps and intermediates described in Example 20, by using tert-butyl 5-amino-2-fluorophenylcarbamate in the place of 2 in Step 1. LC/MS (RT=2.797/(M+H)) 442.0.

Example 29

Preparation of N-(3-(5-fluoro-2-(4-((1-methylpiperidin-4-yl)methoxy)phenylamino)pyrimidin-4-ylamino)phenyl)acrylamide I-90

I-90

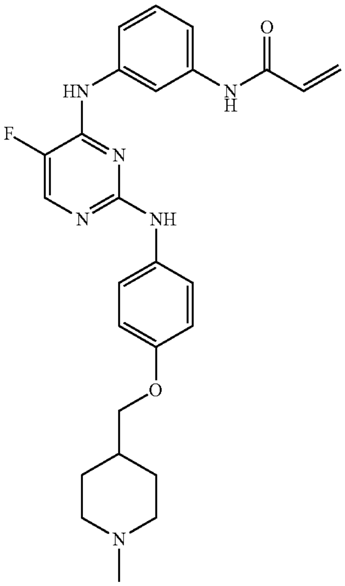

The title compound was prepared according to the schemes, steps and intermediates described below.

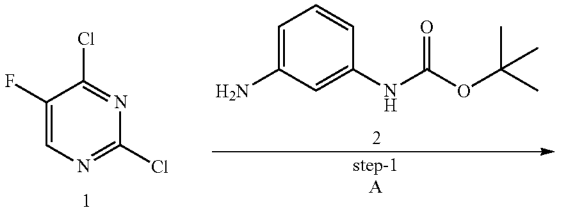

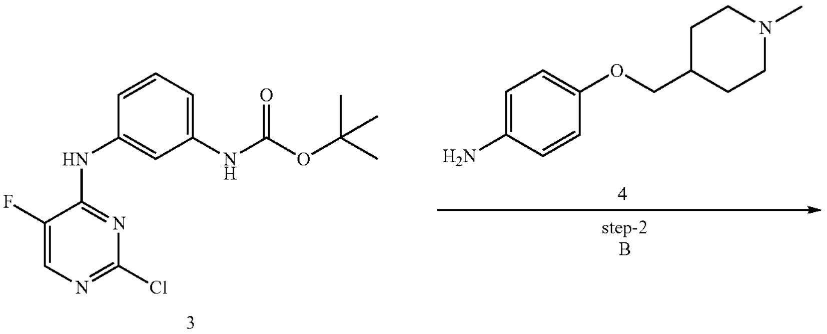

-continued

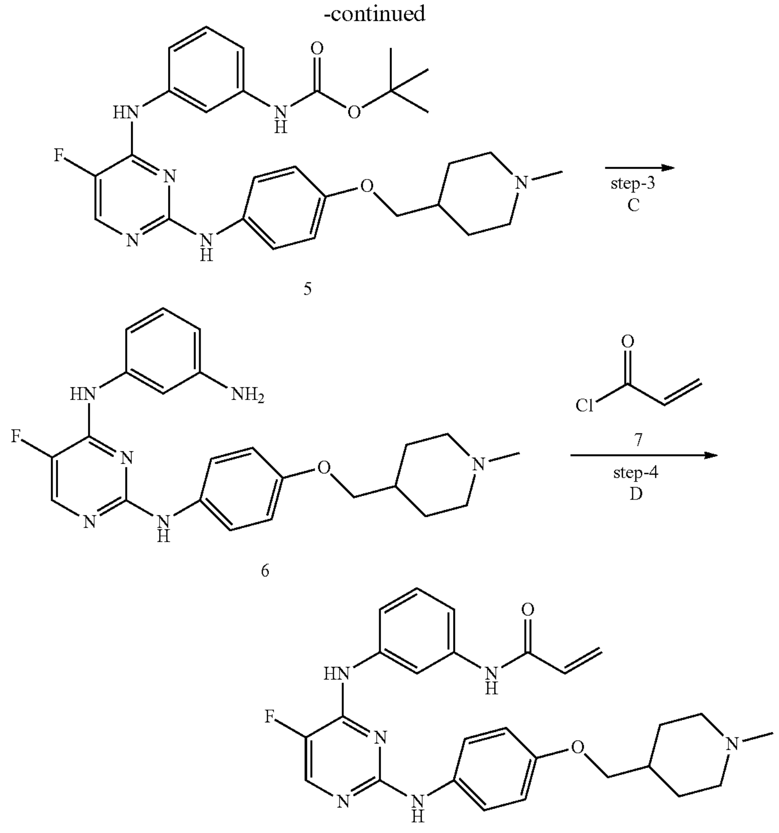

5

7

6

I-90

A) 2, DIPEA, THF, reflux; B) 4, Pd(OAc)$_2$, X-Phos, CsCO$_3$, dioxane, reflux, 12 h; C) TFA, DCM; D) 7, DIPEA, THF, -10° C.

Step-1

3

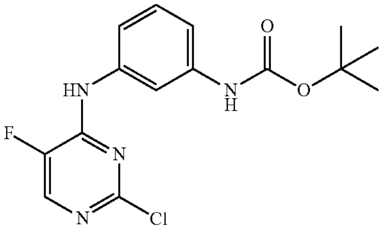

1 (800 mg, 4.8 mmoL), 2 (996 mg, 4.8 mmoL) and Hunig's base (948 uL, 5.75 mmoL) were dissolved in THF (20 mL). The reaction mixture was heated at reflux overnight. After cooling, partitioned with water/brine (10 mL), agitated and separated the layers. Dried organic phase over sodium sulfate and the solvent was removed via rotary evaporation. Titration with EtOAc and Heptane gave after filtration a white solid, 1 g. LC/MS (RT=2.03/(M+1)) 339.1.

Step-2

5

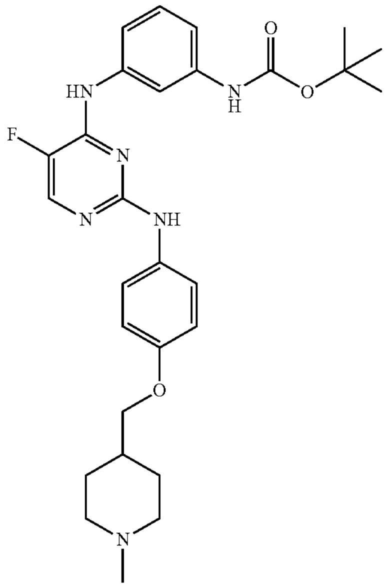

3 (205 mg, 0.61 mmoL) and 4 (150 mg, 0.73 mmoL) was dissolved in dioxane (4 mL). Degassed the solution for 1 min. Palladium acetate (20 mg, 5 moL %), X-Phos ligand (35 mg, 10 moL %) and $CsCO_3$ (325 mg, 1.2 mmoL) were added in that order. Degassed the suspension for 1 min and under argon atmosphere the mixture was heated to reflux for 12 h. After cooling, solvent was removed via rotary evaporation. The dark oil was partitioned between water/brine and EtOAc (5 mL each), agitated, filtered off precipitate and separated layers of the filtrate. Dried organic phase over sodium sulfate. The solvent was removed via rotary evaporation to give a dark oil. Flash chromatography using 0-30% gradient of Heptane/EtOAc afforded light yellow oil. LC/MS (RT=3.043/(M+1)) 523.2.

Step-3

6

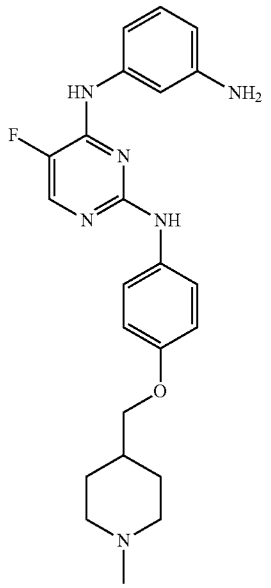

To a solution of 5 (144 mg, 0.27 mmol) in DCM (10 mL) was added TFA (1 mL). Stirred for 30 min at rt for 12 h; removed solvent via rotary evaporation and partitioned oil with cold (0° C.) saturated sodium bicarbonate (5 mL) and EtOAc (5 mL), agitated and separated layers. Organic phase was dried over sodium sulfate and the solvent was removed via rotary evaporation to give light yellow foam. LC/MS (RT=2.723/(M+1)) 423.1.

Step-4

I-90

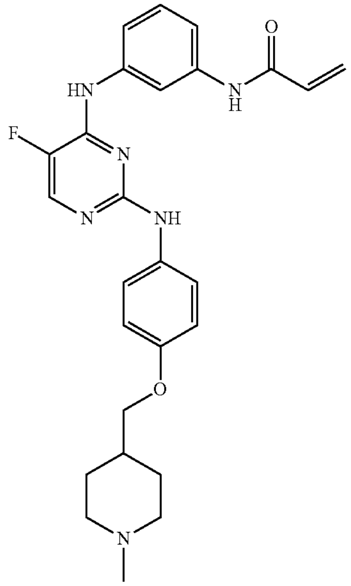

A solution of 6 (105 mg, 0.25 mmol) in THF (3 mL) was cooled in water/ice-MeOH bath (−10° C.). To this was added 7 (21 μL, 0.26 mmoL), stirred for 10 min, then added Hunig's base (51 μL, 0.26 mmoL), and stirred for 10 min. Partitioned with water/brine (5 mL), agitated and separated the layers. Dried organic phase over sodium sulfate. The solvent was removed via rotary evaporation afford a light yellow foam. LC/MS (RT=2.726/(M+H)) 477.1.

Example 30

Preparation of N-(3-(5-fluoro-2-(6-((2-methoxyethyl)(methyl)amino)pyridin-3-ylamino)pyrimidin-4-ylamino)phenyl)acrylamide I-77

I-77

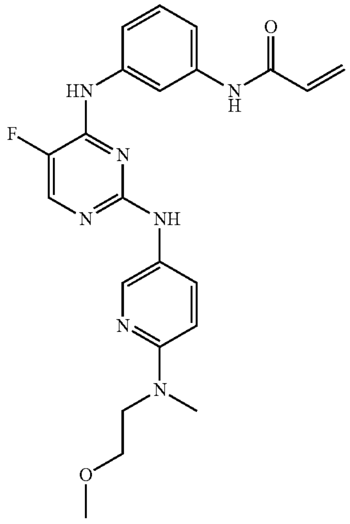

The title compound was prepared according to the schemes, steps and intermediates described in Example 29, by using $N^2$-(2-methoxyethyl)-$N^2$-methylpyridine-2,5-diamine in the place of 4 in Step 2. LC/MS (RT=2.739/(M+H)) 438.1.

Example 31

Preparation of 1-(6-(5-fluoro-2-(6-methoxypyridin-3-ylamino)pyrimidin-4-ylamino)-2H-benzo[b][1,4]oxazin-4(3H)-yl)prop-2-en-1-one I-194

I-194

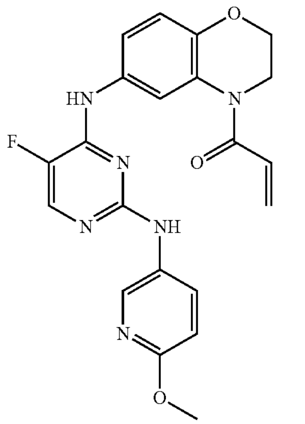

The title compound was prepared according to the schemes, steps and intermediates described below.

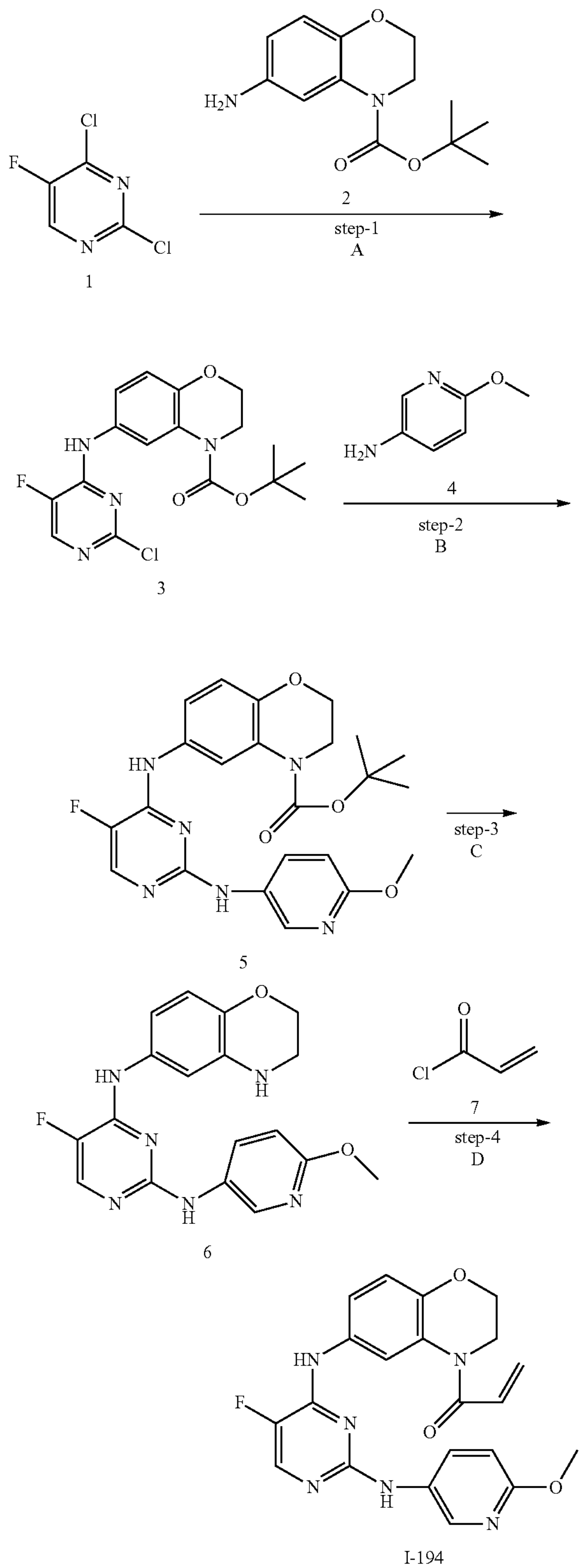

A) 2, DIPEA, THF, reflux; B) 4, HOAc, tert-amyl alcohol, reflux, 12 h; C) TFA, DCM; D) 7, DIPEA, DCM, NMP, -10° C.

Step-1

3

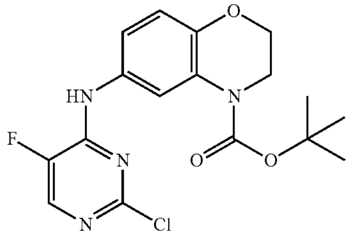

1 (186 mg, 1.1 mmoL), 2 (280 mg, 1.1 mmoL) and Hunig's base (220 μL, 1.3 mmoL) were dissolved in THF (6 mL). The reaction mixture was heated at reflux overnight. After cooling, partitioned with water/brine (6 mL), agitated and separated the layers. Dried organic phase over sodium sulfate and the solvent was removed via rotary evaporation to give a tan solid. LC/MS (RT=3.008/(M+1)) 381.1.

Step-2

5

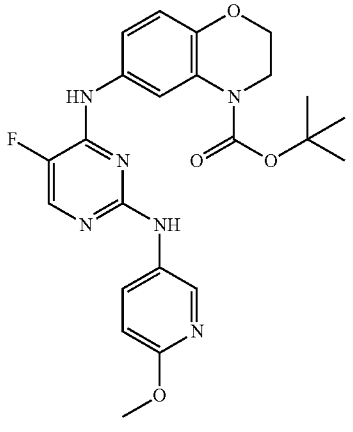

3 (215 mg, 0.56 mmoL) and 4 (83 mg, 0.66 mmoL) was suspended in tert-amyl alcohol (6 mL) and acetic acid (3 drops). Heated to reflux for 12 h. After cooling, solvent was removed via rotary evaporation. The dark oil was partitioned between water/brine and EtOAc (5 mL each), agitated, and separated layers and dried organic phase over sodium sulfate. The solvent was removed via rotary evaporation to afford an oil. Flash chromatography using 30-70% gradient of heptane/ethyl acetate on combiflash system gave a tan solid. LC/MS (RT=2.011/(M+1)) 469.2.

Step-3

6

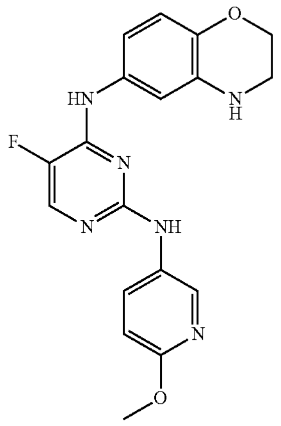

To a solution of 5 (200 mg, 0.43 mmol) in DCM (10 mL) was added TFA (1 mL). Stir for 30 min at rt for 12 h; removed solvent via rotary evaporation and partitioned oil between cold (0° C.) saturated sodium bicarbonate (5 mL) and EtOAc (5 mL), agitated and separated layers. Organic phase was dried over sodium sulfate and the solvent was removed via rotary evaporation to give a pink solid. LC/MS (RT=2.782/(M+1)) 369.1.

Step-4

I-194

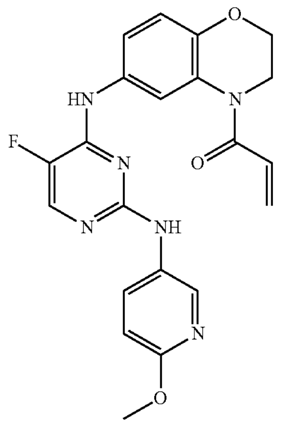

A solution of 6 (150 mg, 0.41 mmol) in DCM (2 mL) and NMP (0.5 mL) was cooled in water/ice-MeOH bath (=10° C.). To this was added 7 (34 μL, 0.43 mmoL), stirred for 10 min, then added Hunig's base (70 μL, 0.43 mmoL), and stirred for 10 min. Partitioned between water/brine (5 mL), agitated and separated the layers. Dried organic phase over sodium sulfate. Purified directly via flash chromatography using 20-80% gradient of heptane/ethyl acetate to give a pink solid. LC/MS (RT=2.8/(M+H)) 423.1.

Example 32

Preparation of 1-(6-(5-fluoro-2-(4-(2-methoxy-ethoxy)phenylamino)pyrimidin-4-ylamino)-2H-benzo[b][1,4]oxazin-4(3H)-yl)prop-2-en-1-one I-141

I-141

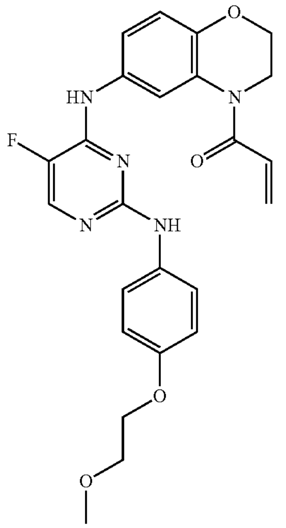

The title compound was prepared according to the schemes, steps and intermediates described in Example 31, by using 4-(2-methoxyethoxy)aniline in the place of 4 in Step 2. LC/MS (RT=2.845/(M+H)) 466.2.

Example 33

Preparation of 1-(6-(5-fluoro-2-(6-methoxypyridin-3-ylamino)pyrimidin-4-ylamino)indolin-1-yl)prop-2-en-1-one I-166

I-166

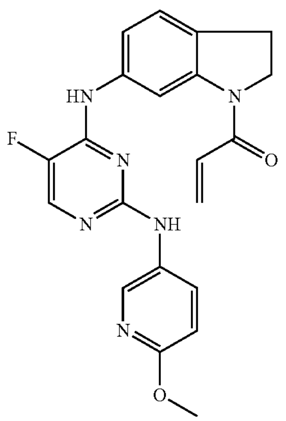

The title compound was prepared according to the schemes, steps and intermediates described in Example 31, by using tert-butyl 6-aminoindoline-1-carboxylate in the place of 2 in Step 1. LC/MS (RT=2.825/(M+H)) 407.1.

Example 34

Preparation of 1-(5-(5-fluoro-2-(6-methoxypyridin-3-ylamino)pyrimidin-4-ylamino)isoindolin-2-yl)prop-2-en-1-one I-165

I-165

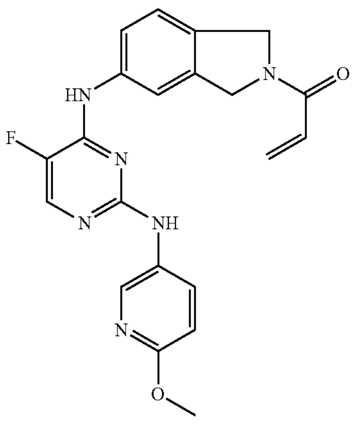

The title compound was prepared according to the schemes, steps and intermediates described in Example 31, by using tert-butyl 5-aminoisoindoline-1-carboxylate in the place of 2 in Step 1. LC/MS (RT=2.751/(M+H)) 407.1.

Example 35

Preparation of 1-(6-(4-(3-chlorophenylamino)-5-fluoropyrimidin-2-ylamino)-2H-benzo[b][1,4]oxazin-4(3H)-yl)prop-2-en-1-one I-149

I-149

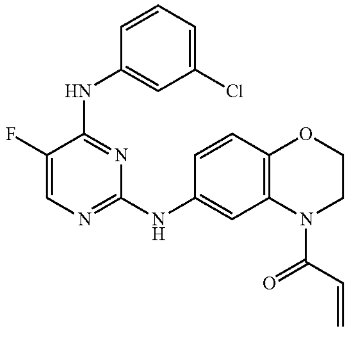

The title compound was prepared according to the schemes, steps and intermediates described below.

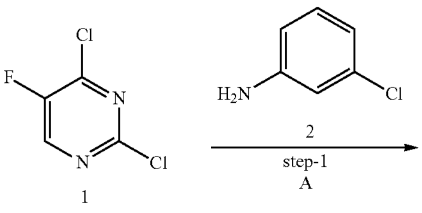

-continued

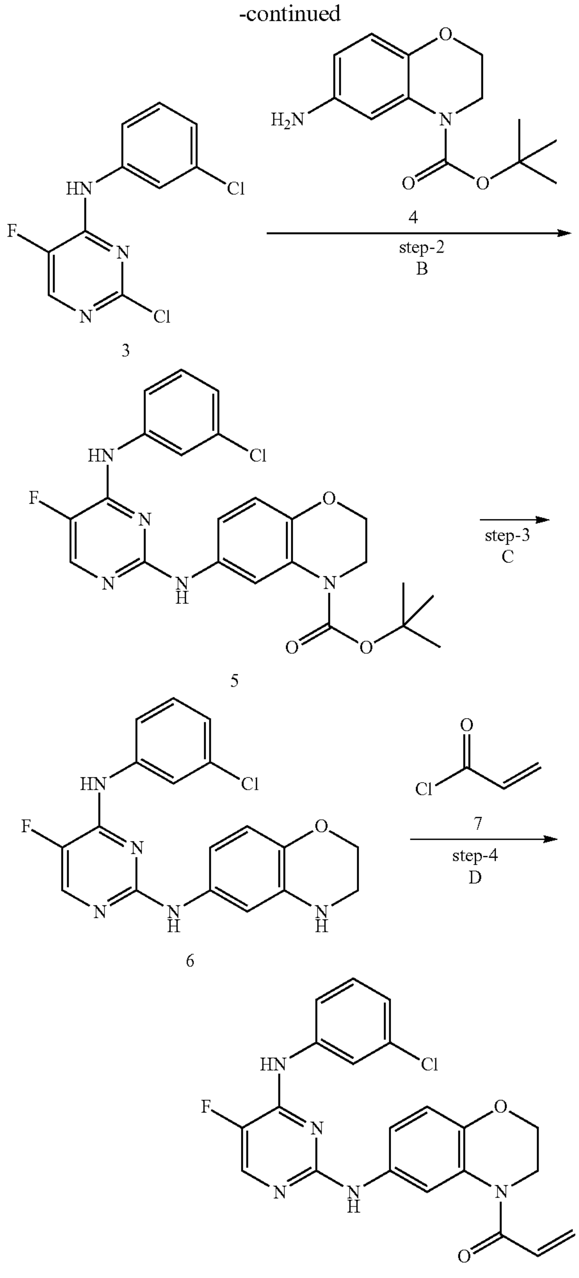

I-149

A) 2, DIPEA, THF, reflux; B) 4, HOAc, tert-amyl alcohol, reflux, 12 h; C) TFA, DCM; D) 7, DIPEA, THF, -10° C.

Step-1

3

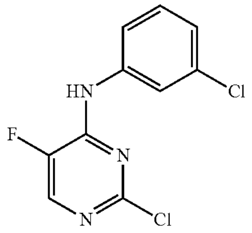

1 (484 mg, 2.9 mmoL), 2 (305 mg, 2.9 mmoL) and Hunig's base (526 μL, 3.5 mmoL) were dissolved in THF (10 mL). The reaction mixture was heated at reflux overnight. After cooling, partitioned between water/brine (10 mL), agitated and separated the layers. Dried organic phase over sodium sulfate and the solvent was removed via rotary evaporation. Flash chromatography using a gradient of 0-30% heptane/ethyl acetate on combiflash system gave a white solid. LC/MS (RT=2.03/(M+1)) 339.1.

Step-2

5

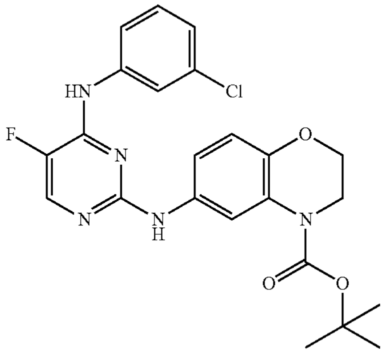

3 (150 mg, 0.58 mmoL) and 4 (175 mg, 0.7 mmoL) were suspended in tert-amyl alcohol (8 mL) and acetic acid (3 drops). Heated to reflux for 12 h. After cooling, solvent was removed via rotary evaporation. The dark oil was partitioned between water/brine and EtOAC (5 mL each), agitated, and separated layers and dried organic phase over sodium sulfate. The solvent was removed via rotary evaporation to afford a dark oil. Flash chromatography using a gradient of 0-25% heptane/ethyl acetate on combiflash system gave a white solid. LC/MS (RT=2.997/(M+1)) 470.2.

Step-3

6

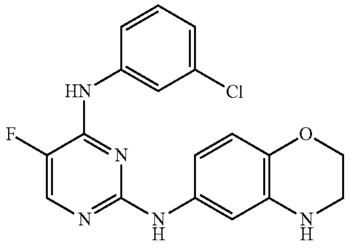

To a solution of 5 (180 mg, 0.38 mmol) in DCM (10 mL) was added TFA (1 mL). Stirred for 30 min at rt for 4 h; removed solvent via rotary evaporation and partitioned oil between cold (0° C.) saturated sodium bicarbonate (5 mL) and EtOAc (5 mL), agitated and separated layers. Organic phase was dried over sodium sulfate and the solvent was removed via rotary evaporation to give light yellow solid. LC/MS (RT=2.723/(M+1)) 423.1.

Step-4

I-149

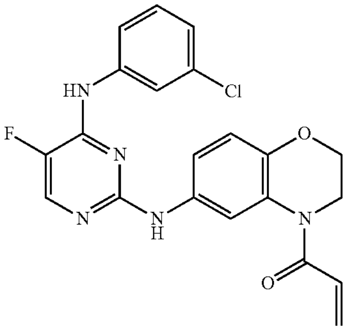

A solution of 6 (150 mg, 0.4 mmol) in THF (3 mL) was cooled in water/ice-MeOH bath (−10° C.). To this was added 7 (34 μL, 0.42 mmoL), stirred for 10 min, then added Hunig's base (70 μL, 0.42 mmoL), and stirred for 10 min. Partitioned between water/brine (5 mL), agitated and separated the layers. Dried organic phase over sodium sulfate. The solvent was removed via rotary evaporation to afford a light yellow solid. Flash chromatography using gradient of 10-50% heptane/ethyl acetate on combiflash system gave a white solid. LC/MS (RT=2.945/(M+H)) 426.

Example 36

Preparation of 5-(2-(4-acryloyl-3,4-dihydro-2H-benzo[b][1,4]oxazin-6-ylamino)-5-fluoropyrimidin-4-ylamino)indolin-2-one I-130

I-130

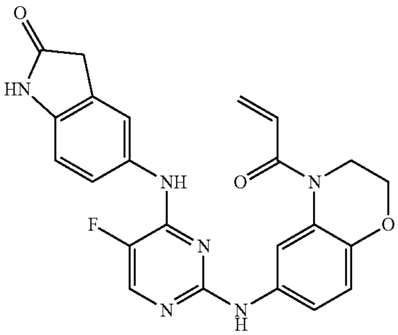

The title compound was prepared according to the schemes, steps and intermediates described in Example 35, by using 5-aminoindolin-2-one in the place of 2 in Step 1. LC/MS (RT=2.673/(M+H)) 447.1.

Example 37
Preparation of 4-(3-acrylamidophenylamino)-2-(phenylamino)pyrimidine-5-carboxamide I-230
I-230
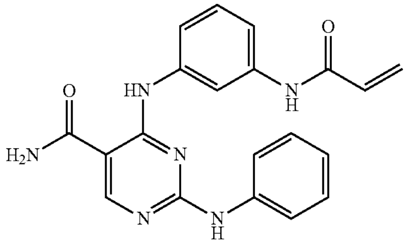
The title compound was prepared according to the schemes, steps and intermediates described below.
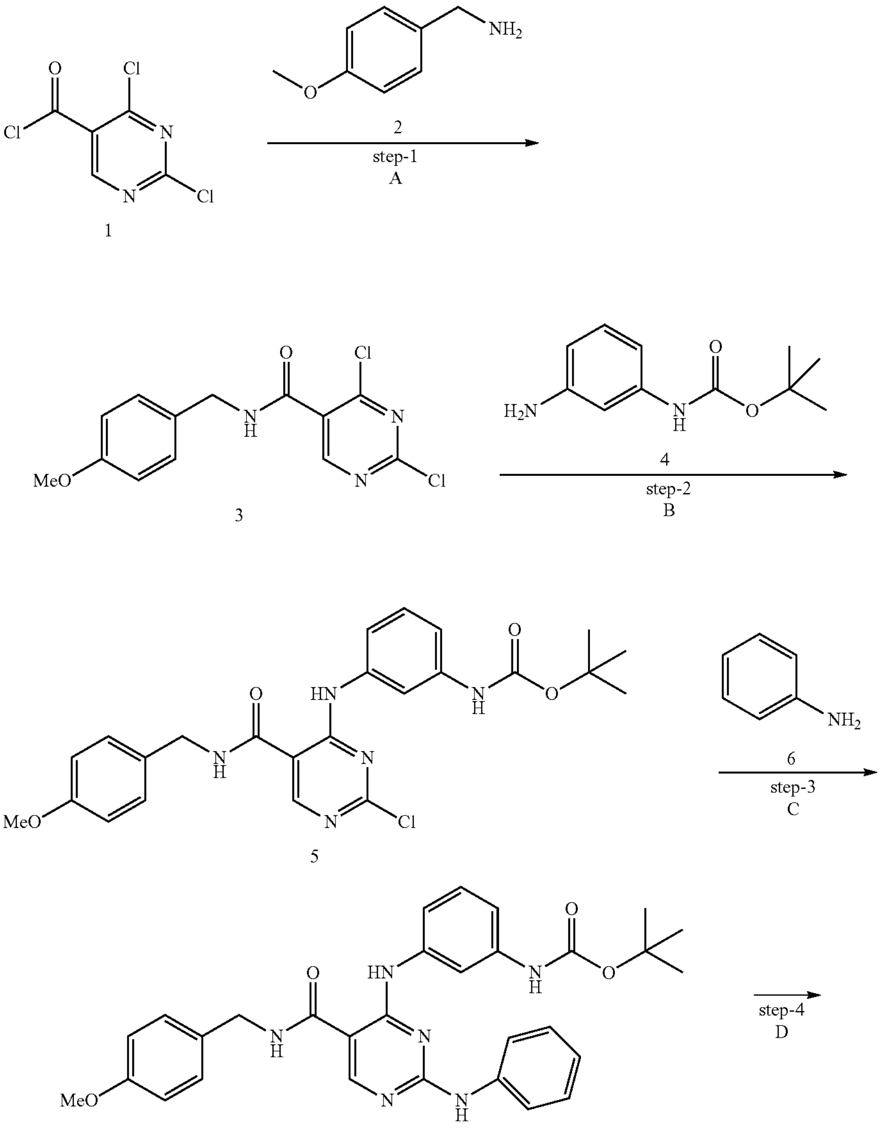
7

-continued

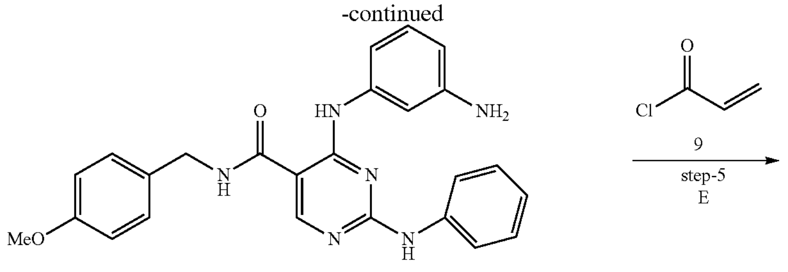

8

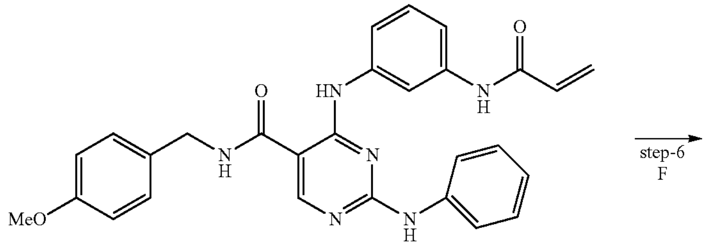

I-231

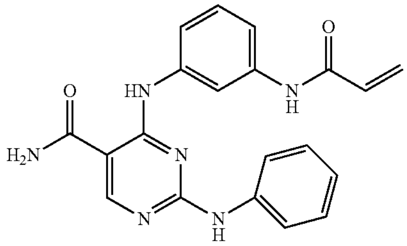

I-230

A) 2, $NEt_3$ DCM, 0° C. to rt; B) 4, DIPEA, THF, rt, 12 h; C) 6, DIPEA, t-amyl alcohol, reflux, 4 h; D) TFA, DCM, rt; E) 7, $NEt_3$, THF, 0° C.; F)TFA, TfOH, DCM, rt.

Step-1

3

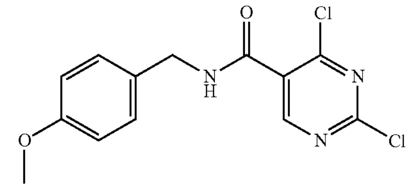

1 (500 mg, 2.4 mmoL, prepared from 2,4-dihydroxypyrimidine-5-carboxylic acid according to *J. Med. Chem.* 50: 591 (2007) and US 2007/0072851) was dissolved in DCM (10 mL) and chilled in an ice/water bath (0° C.). 2 (309 μL, 2.4 mmoL) was added and the mixture stirred for 10 min. Triethylamine (365 μL, 2.6 mmol) was added and the mixture was allowed to warm to rt and stir for 30 min. The solvent was reduced in volume via rotary evaporation and directly purified by flash chromatography using a gradient of 0-30% heptane/ethyl acetate on combiflash system to give a white solid. LC/MS (RT=2.789/(M+1)) 312.

Step-2

5

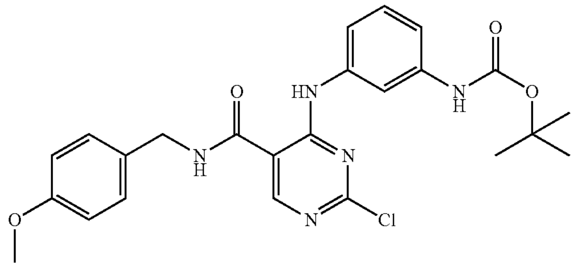

3 (170 mg, 0.55 mmoL), 4 (113 mg, 0.55 mmoL) and Hunig's base (108 μL, 0.65 mmoL) were dissolved in THF (6 mL). Stirred at rt for 12 h. Partitioned between water/brine, agitated, and separated layers and dried organic phase over sodium sulfate. The solvent was removed via rotary evaporation to afford after titration with EtOAc a white solid. LC/MS (RT=3.123/(M+1)) 484.

Step-3

7

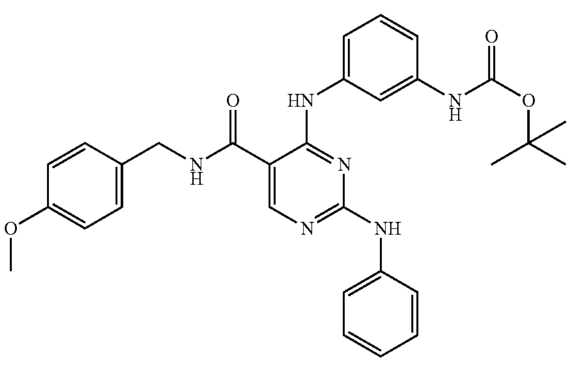

5 (230 mg, 0.48 mmol), 6 (126 μL, 1.4 mmoL) and Hunig's base (94 μL, 0.57 mmoL) is dissolved in t-amyl alcohol (6 mL). Heat to reflux for 4 h, cool and water was added to the solid mass. Agitated, filtered and dried to give a white solid. LC/MS (RT=3.182/(M+1)) 541.2.

Step-4

8

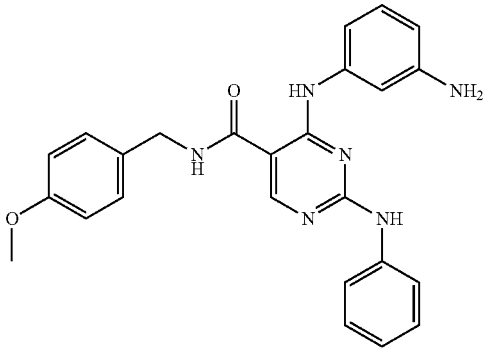

7 (180 mg, 0.33 mmol) was suspended in DCM (10 mL) and treated with TFA (1 mL). Stirred overnight at rt. Diluted with DCM (40 mL) and washed with NaOH (1N, 25 mL). Agitated, precipitate formed, filtered and dry to give a white solid. LC/MS (RT=2.934/(M+1)) 441.1.

Step-5

I-231

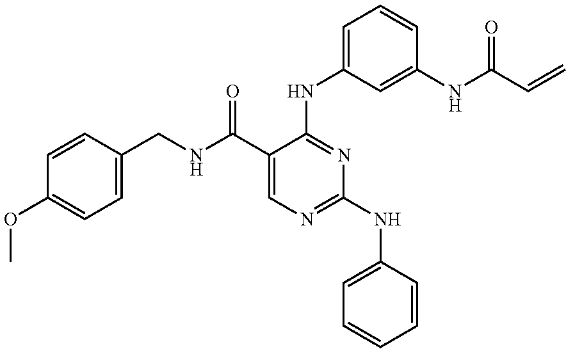

A suspension of 8 (130 mg, 0.29 mmol) in THF (6 mL) was cooled in water/ice (0° C.). To this was added 9 (25 μL (plus additional 5 μL), 0.38 mmoL (total)), then added triethyl amine (43 μL (plus additional 11 μL), 0.38 mmoL (total)), and stirred for a total time of 1 h. Water was added, agitated, filtered off remaining precipitate and discarded. The filtrate was dried over sodium sulfate. The solvent was removed via rotary evaporation to afford a yellow solid. Flash chromatography using a gradient of 0-25% heptane/ethyl acetate on combiflash system gave a white solid. LC/MS (RT=2.964/(M+H)) 495.1.

Step-6

I-230

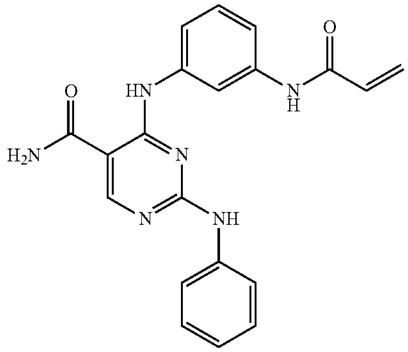

To a suspension of I-231 (30 mg, 0.061 mmol) in DCM (4 mL) was added TFA (200 μL) and triflic acid (68 μL, 0.61 mmoL). Stirred at rt 1 h. Removed solvent under reduce pressure via rotary evaporation and partitioned with cold (0° C.) saturated sodium bicarbonate (10 mL) and EtOAc (10 mL), agitated and separated layers. Dried organic layer over sodium sulfate and the solvent was removed via rotary evaporation to afford after titration with diethyl ether a white solid. LC/MS (RT=2.715/(M+H)) 375.1.

Example 38

Preparation of 4-(3-acrylamidophenylamino)-N-phenyl-2-(phenylamino)pyrimidine-5-carboxamide I-222

I-222

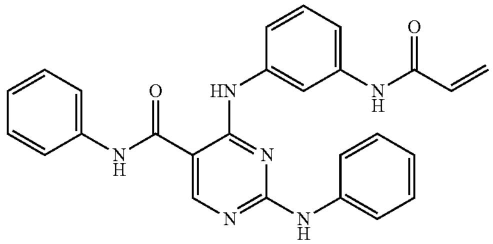

The title compound was prepared according to the schemes, steps and intermediates described in Example 37, by using aniline in the place of 2 in Step 1 and omitting Step 6. LC/MS (RT=2.991/(M+H)) 451.2.

Example 39

Preparation of 4-(3-acrylamidophenylamino)-N-cyclopropyl-2-(phenylamino)pyrimidine-5-carboxamide I-221

I-221

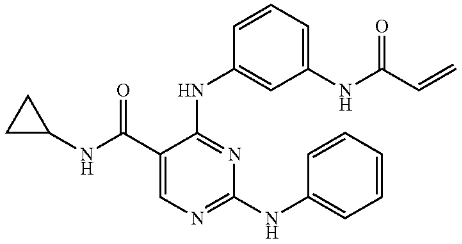

The title compound was prepared according to the schemes, steps and intermediates described in Example 37, by using cyclopropylamine in the place of 2 in Step 1 and omitting Step 6. LC/MS (RT=2.838/(M+H)) 415.2.

Example 40

Preparation of 4-(3-acrylamidophenylamino)-2-(3-methoxyphenylamino)pyrimidine-5-carboxamide I-210

I-210

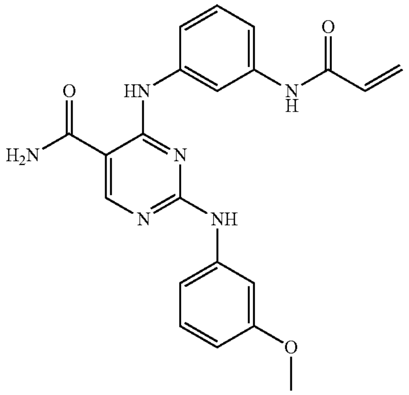

The title compound was prepared according to the schemes, steps and intermediates described in Example 37, by using 3-methoxyaniline in the place of 6 in Step 3. LC/MS (RT=2.743/(M+H)) 405.1.

Example 41

Preparation of 4-(3-acrylamidophenylamino)-2-(6-methoxypyridin-3-ylamino)pyrimidine-5-carboxamide I-209

I-209

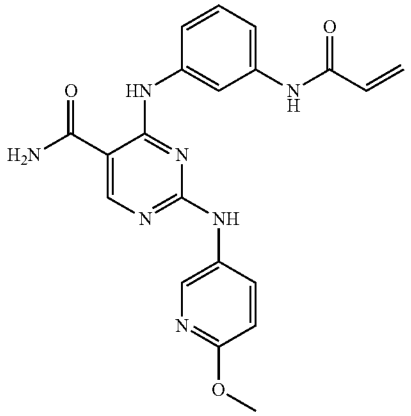

The title compound was prepared according to the schemes, steps and intermediates described in Example 37, by using 6-methoxypyridin-3-amine in the place of 6 in Step 3. LC/MS (RT=2.657/(M+H)) 406.2.

Example 42

Preparation of 1-{6-[5-Acetyl-2-(6-methoxy-pyridin-3-ylamino)-pyrimidin-4-ylamino]-2,3-dihydro-benzo[1,4]oxazin-4-yl}-propenone I-170

I-170

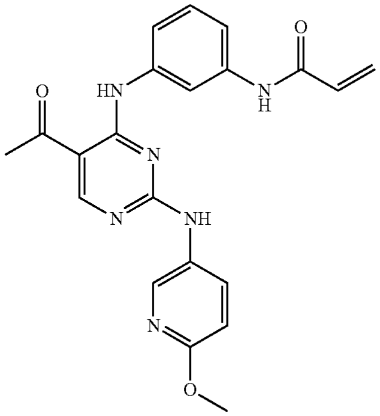

The title compound was prepared according to the schemes, steps and intermediates described below.

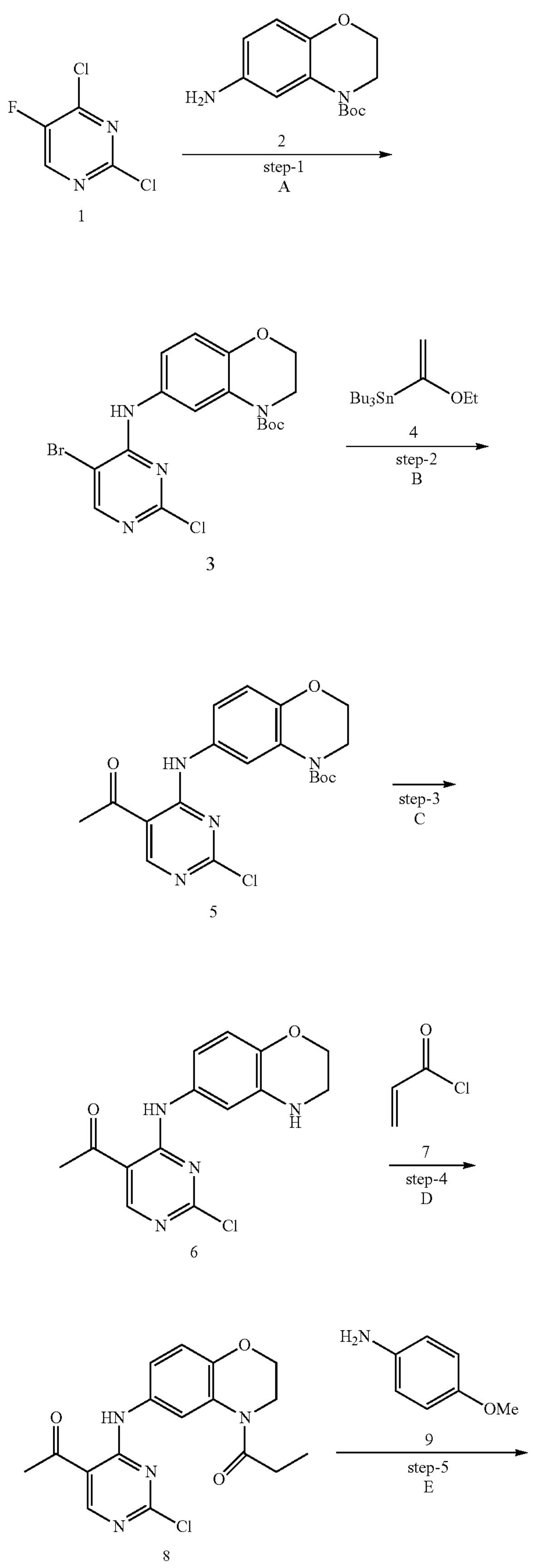

-continued

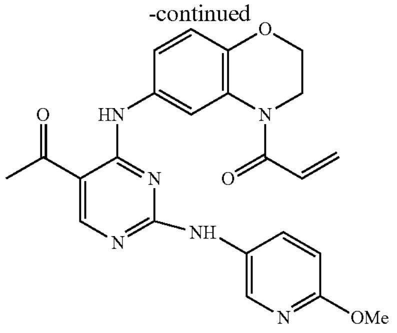

I-170

A) 2, DIPEA, THF, 70° C., 16 h; B) (a) 4, $PdCl_2(PPh_3)_2$, DMF, 70° C.; (b) 1N HCl, acetone, 60° C., 15 min; C) HCl/dioxane, DCM; D) 7, DIPEA, NMP, DCM, -20° C., to rt; E) 9, pTsOH, dioxane, 100° C., 15 min.

Step-1

3

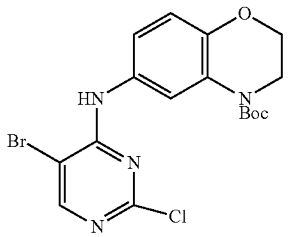

A mixture of 499 mg of 1 (2.19 mmol), 547 mg of 2 (2.19 mmol), and 500 uL of N,N-diisopropylethylamine in 20 mL of anhydrous tetrahydrofuran was heated at 70° C. overnight. After cooling down, the reaction mixture was concentrated, and subject to aqueous workup with 50 mL of EtOAc, 20 mL of sodium bicarbonate solution, brine, and dried over anhydrous sodium sulfate. After filtration and concentration, the residue was passed through a short silica cartridge, eluted with heptanes/EtOAc (v/v 3/1), giving 815 mg of a slight yellow solid (84%). LC-MS: m/z 441.0 (ES+), 439.0 (ES−).

Step-2

5

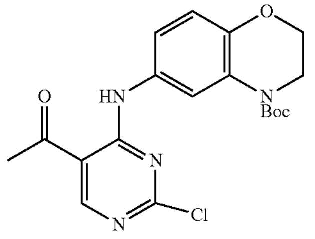

A mixture of intermediate 3 (815 mg, 1.85 mmol), 4 (740 mg, 1.1 equiv.), 27 mg of dichlorobis(triphenylphosphine) palladium (II) (2% mol) in 6 mL of anhydrous DMF was purged with nitrogen for 30 min. The reaction mixture was then heated at 70° C. overnight. LC-MS showed 70% conversion. After cooling down, 30 mL of ethyl acetate and 760 mg of potassium fluoride in 5 mL of water was added, and the mixture was stirred at rt for at least 2 hr. The white precipitate was filtered out, and the organic layer was separated, washed with water, brine, and dried over anhydrous sodium sulfate.

After filtration and concentration, the residue was dissolved in 20 mL of acetone, followed by addition of 3 mL of 1.0 N aqueous HCl solution. The mixture was heated at 60° C. for 15 min, and concentrated under reduced pressure. Normal workup was done using 50 mL of EtOAc, 10 mL of saturated sodium bicarbonate solution, brine, anhydrous sodium sulfate. After concentration, the residue was purified by flash column chromatography on silica gel, giving 405 mg of yellow solid (70% based on consumed starting material), also recovering intermediate 3 183 mg. LC-MS: m/z 405.1 (ES+), 403.1 (ES−).

Step-3

6

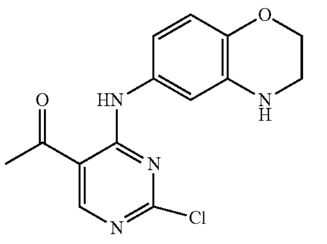

To a mixture of 1.28 g of intermediate I-2 in 10 mL of dichloromethane, was added 10 mL of 4.0 N HCl in dioxane. After stirring at rt overnight, the solvent was removed, and the residue was dried in vacuum. LC-MS: m/z 305.1 (ES+), 303.1 (ES−).

Step-4

8

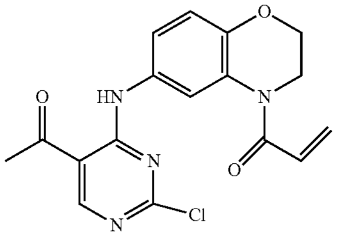

Under $N_2$, to a mixture of the intermediate 6 obtained above, 1 mL of DIPEA in 10 mL of NMP and 10 mL of dichloromethane at −20° C., was added 275 uL of 7 (1.1 equiv). The reaction was continued for 5 min, then quenched with 1 mL of isopropyl alcohol. The reaction mixture was warmed up to rt, and extracted with 100 mL of EtOAc, washed with water 10 mL×2, brine, dried over sodium sulfate. After filtration and concentration, the residue was purified by flash column chromatography with eluent heptanes/EtOAc (v/v 2/3), giving yellow solid I-3 450 mg (40%). LC-MS: m/z 359.1 (ES+), 357.1 (ES−).

Step-5

I-170

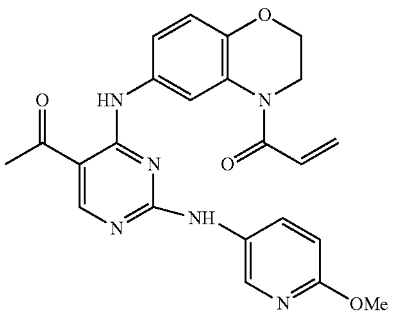

The mixture of 30 mg intermediate 8 (84 μmol) and 13 mg of 9 (1.2 equiv) in 1 mL of 0.08 M p-TsOH dioxane solution was heated at 100° C. for 15 min. After cooling down, the reaction mixture was subject to regular work up with 50 mL of EtOAc, aqueous sodium bicarbonate, brine, and dried over anhydrous sodium sulfate. After concentration, the residue was purified by column chromatography on silica gel with heptane/EtOAc (v/v 1/4) as eluent, giving 22.8 mg pale white solid (61%). LC-MS: m/z=447.1 (ES+), 445.2 (ES−).

Example 43

Preparation of 1-{6-[5-Acetyl-2-(4-morpholin-4-yl-phenylamino)-pyrimidin-4-ylamino]-2,3-dihydro-benzo[1,4]oxazin-4-yl}-propenone I-169

I-169

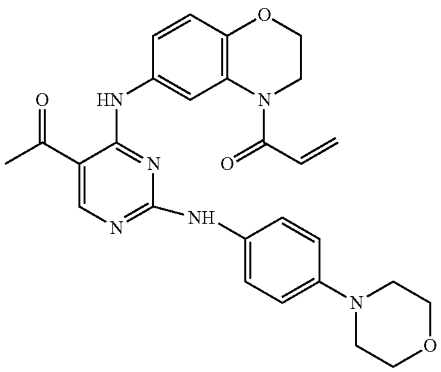

The title compound was prepared according to the schemes, steps and intermediates described in Example 42, by using 4-morpholin-4-yl-phenylamine in the place of 9 in Step 5. LC-MS: m/z 501.1 (ES+), 499.2 (ES−).

Example 44

Preparation of 1-{6-[5-Acetyl-2-(6-morpholin-4-yl-pyridin-3-ylamino)-pyrimidin-4-ylamino]-2,3-dihydro-benzo[1,4]oxazin-4-yl}-propenone I-168

I-168

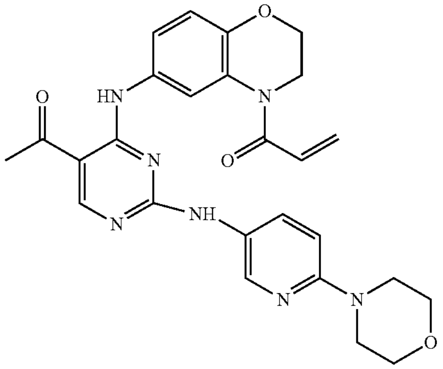

The title compound was prepared according to the schemes, steps and intermediates described in Example 42, by using 3-amino-[6-morpholin-4-yl]-pyridine in the place of 9 in Step 5. LC-MS: m/z 502.2 (ES+), 500.3 (ES−).

Example 45

Preparation of 1-{6-[5-Acetyl-2-(1-methyl-1H-indazol-6-ylamino)-pyrimidin-4-ylamino]-2,3-dihydro-benzo[1,4]oxazin-4-yl}-propenone I-154

I-154

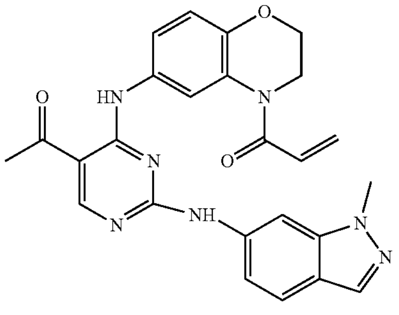

The title compound was prepared according to the schemes, steps and intermediates described in Example 42, by using 1-methyl-1H-indazol-6-ylamine in the place of 9 in Step 5. LC-MS: m/z 470.1 (ES+), 468.1 (ES−).

Example 46

Preparation of 1-{6-[5-Acetyl-2-(1H-indazol-6-ylamino)-pyrimidin-4-ylamino]-2,3-dihydro-benzo[1,4]oxazin-4-yl}-propenone I-153

I-153

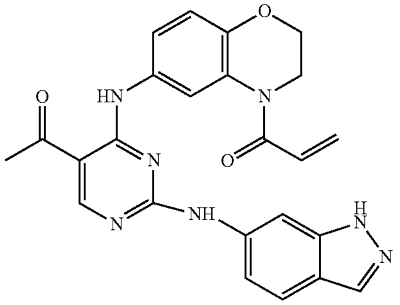

The title compound was prepared according to the schemes, steps and intermediates described in Example 42, by using 1H-indazole-6-ylamine in the place of 9 in Step 5. LC-MS: m/z 456.1 (ES+), 454.2 (ES−).

Example 47

Preparation of 1-{4-[5-Acetyl-4-(4-acryloyl-3,4-dihydro-2H-benzo[1,4]oxazin-6-ylamino)-pyrimidin-2-ylamino]-phenyl}-pyrrolidin-2-one I-152

I-152

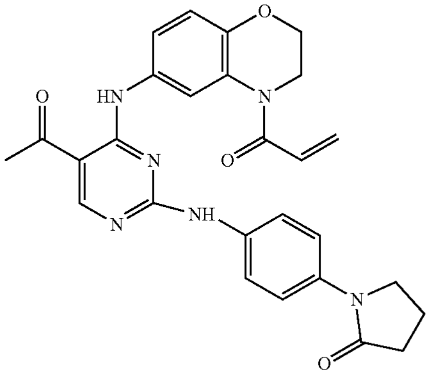

The title compound was prepared according to the schemes, steps and intermediates described in Example 42, by using 1-(4-amino-phenyl)-pyrrolidin-2-one in the place of 9 in Step 5. LC-MS: m/z 456.1 (ES+), 454.2 (ES−).

Example 48

Preparation of 1-(6-{5-Acetyl-2-[4-(2-methoxy-ethoxy)-phenylamino]-pyrimidin-4-ylamino}-2,3-dihydro-benzo[1,4]oxazin-4-yl)-propenone I-150

I-150

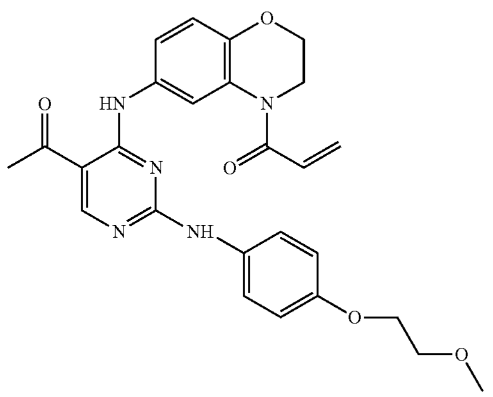

The title compound was prepared according to the schemes, steps and intermediates described in Example 42, by using 4-(2-methoxy-ethoxy)-phenylamine in the place of 9 in Step 5. LC-MS: m/z 490.2 (ES+), 488.3 (ES−).

Example 49

Preparation of 5-[5-Acetyl-4-(4-acryloyl-3,4-dihydro-2H-benzo[1,4]oxazin-6-ylamino)-pyrimidin-2-ylamino]-1,3-dihydro-indol-2-one I-129

I-129

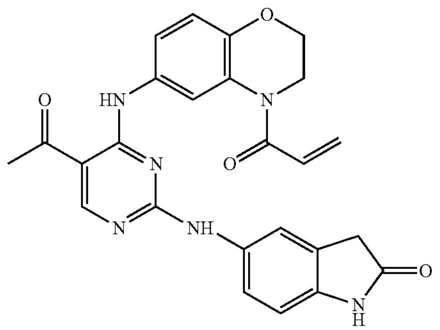

The title compound was prepared according to the schemes, steps and intermediates described in Example 42, by using 5-amino-1,3-dihydro-indol-2-one in the place of 9 in Step 5. LC-MS: m/z 471.1 (ES+), 469.2 (ES−).

Example 50

Preparation of 1-(6-{5-Acetyl-2-[6-(2-hydroxy-ethoxy)-pyridin-3-ylamino]-pyrimidin-4-ylamino}-2,3-dihydro-benzo[1,4]oxazin-4-yl)-propenone I-128

I-128

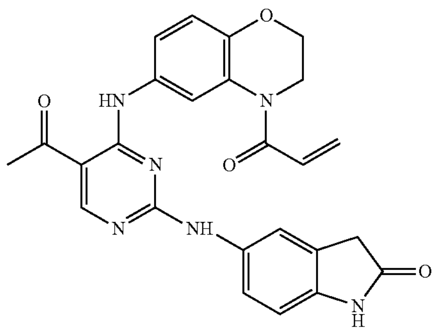

The title compound was prepared according to the schemes, steps and intermediates described in Example 42, by using 2-(5-amino-pyridin-2-yloxy)-ethanol in the place of 9 in Step 5. LC-MS: m/z 477.1 (ES+), 475.2 (ES−).

Example 51

Preparation of N-{3-[5-Acetyl-2-(6-methoxy-pyridin-3-ylamino)-pyrimidin-4-ylamino]-phenyl}-acrylamide I-189

I-189

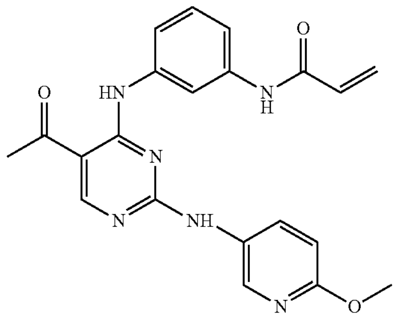

The title compound was prepared according to the schemes, steps and intermediates described in Example 42, by using tert-butyl 3-aminophenylcarbamate in the place of 2 in Step 1 and 5-amino-2-methoxypyridine in the place of 9 in Step 5. LC-MS: m/z 405.1 (ES+), 403.2 (ES−).

Example 52

Preparation of N-{3-[5-Acetyl-2-(6-methoxy-pyridin-3-ylamino)-pyrimidin-4-yloxy]-phenyl}-acrylamide I-188

I-188

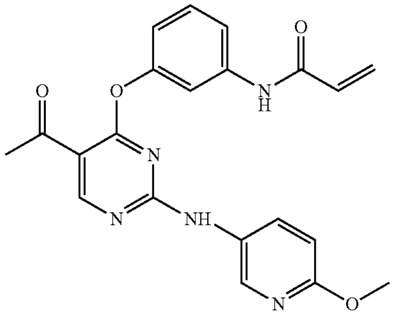

The title compound was prepared according to the schemes, steps and intermediates described in Example 42, by using tert-butyl 3-hydroxyphenylcarbamate in the place of 2 in Step 1 and 5-amino-2-methoxypyridine in the place of 9 in Step 5. LC-MS: m/z 406.2 (ES+), 404.1 (ES−).

Example 53

Preparation of 1-{3-[5-Acetyl-2-(6-methoxy-pyridin-3-ylamino)-pyrimidin-4-ylamino]-azetidin-1-yl}-propenone I-187

I-187

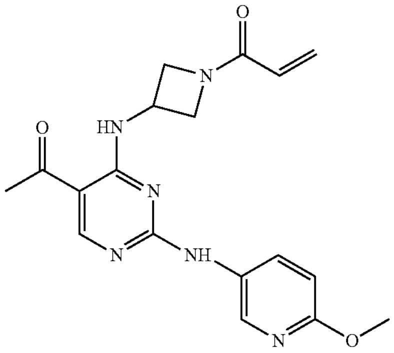

The title compound was prepared according to the schemes, steps and intermediates described in Example 42, by using 3-amino-N-Boc-azetidine in the place of 2 in Step 1 and 5-amino-2-methoxypyridine in the place of 9 in Step 5. LC-MS: m/z 369.1 (ES+), 367.2 (ES−).

Example 54

Preparation of N-(3-{5-Acetyl-2-[4-(2-methoxy-ethoxy)-phenylamino]-pyrimidin-4-ylamino}-phenyl)-acrylamide I-124

I-124

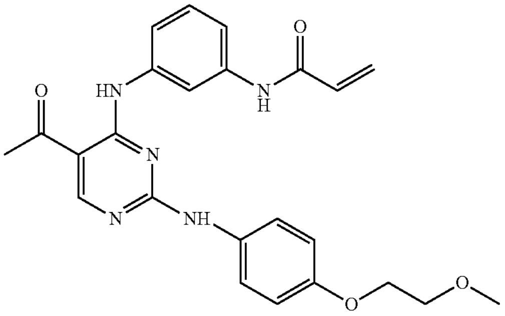

The title compound was prepared according to the schemes, steps and intermediates described in Example 42, by using tert-butyl 3-aminophenylcarbamate in the place of 2 in Step 1 and 4-(2-methoxy-ethoxy)-phenylamine in the place of 9 in Step 5. LC-MS: m/z 448.2 (ES+), 446.3 (ES−).

Example 55

Preparation of N-(3-{5-Acetyl-2-[6-(2-methoxy-ethoxy)-pyridin-3-ylamino]-pyrimidin-4-ylamino}-phenyl)-acrylamide I-122

I-122

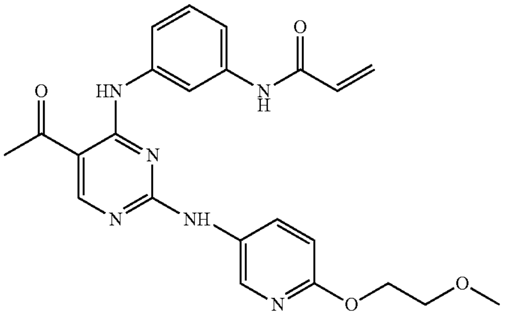

The title compound was prepared according to the schemes, steps and intermediates described in Example 42, by using tert-butyl 3-aminophenylcarbamate in the place of 2 in Step 1 and 6-(2-Methoxy-ethoxy)-pyridin-3-ylamine in the place of 9 in Step 5. LC-MS: m/z 449.2 (ES+), 447.1 (ES−).

Example 56

Preparation of N-(3-{5-Acetyl-2-[6-(2-hydroxy-ethoxy)-pyridin-3-ylamino]-pyrimidin-4-ylamino}-phenyl)-acrylamide I-121

I-121

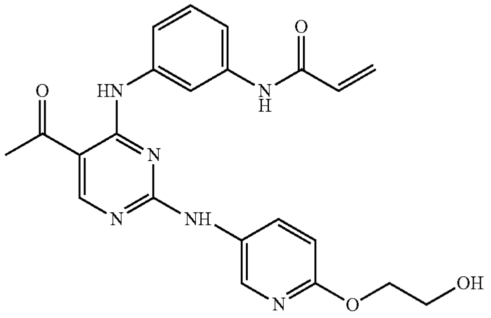

The title compound was prepared according to the schemes, steps and intermediates described in Example 42, by using tert-butyl 3-aminophenylcarbamate in the place of 2 in Step 1 and 2-(5-Amino-pyridin-2-yloxy)-ethanol in the place of 9 in Step 5. LC-MS: m/z 435.1 (ES+), 433.2 (ES−).

Example 57

Preparation of 4-(3-acrylamidophenoxy)-2-(3-methoxyphenylamino)-pyrimidine-5-carboxylic acid phenylamide I-200

I-200

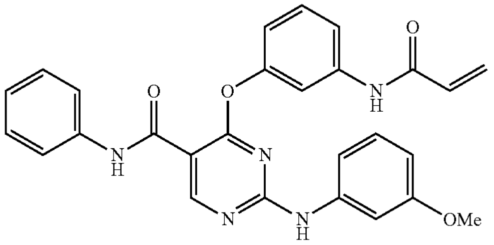

The title compound was prepared according to the schemes, steps and intermediates described below.

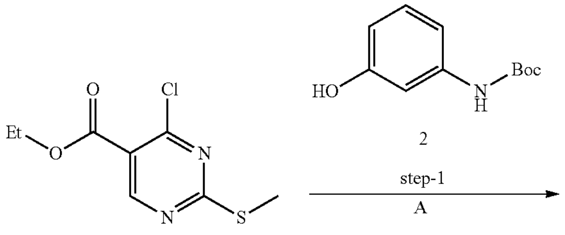

1 2

-continued

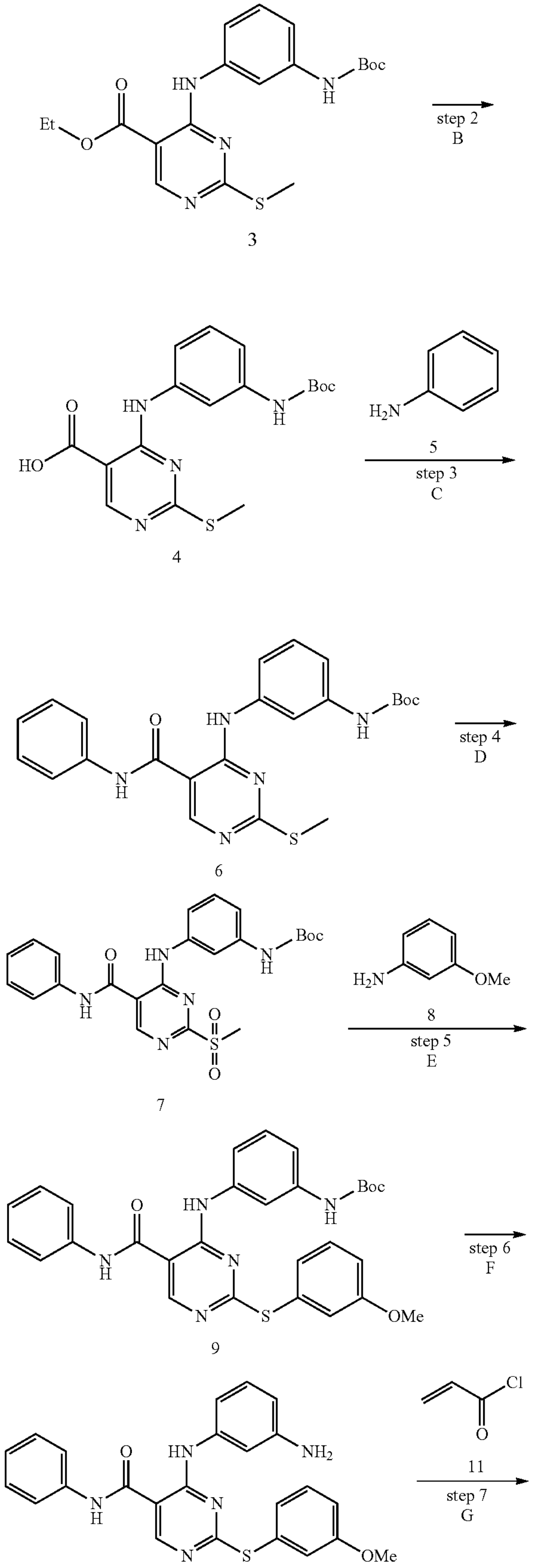

3 4 6 7 9 9

-continued

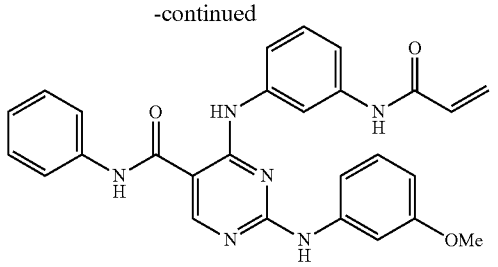

I-200

A) 2, NaH, THF, 0° C; B) NaOH, THF, MeOH; C) 5, TBTU, DIPEA, $CH_3CN$, 0° C.; D) MCPBA, $CH_2Cl_2$, 0° C.; E) 8, 50° C., 3 h; F) TFA, $CH_2Cl_2$; G) 11, DIPEA, $CH_2Cl_2$

Step 1

3

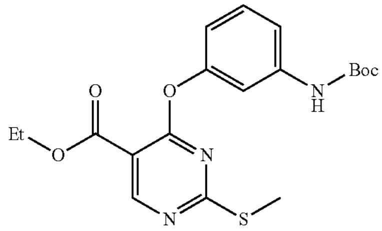

To a stirred solution of (3-hydroxyphenyl)carbamic acid tert-butyl ester 2 (1.79 g, 8.59 mmol) at 0° C. was added a suspension of sodium hydride (60% dispersion in mineral oil) (0.34 g, 8.9 mmol) in anhydrous THF (30 mL). The mixture was stirred at 0° C. for 20 minutes. The phenoxide solution was then added dropwise at 0° C. to a solution of 4-chloro-(2-methylsulfanyl)pyrimidine-5-carboxylic acid ethyl ester 1 (2 g, 8.59 mmol) in THF (20 mL). The reaction mixture was stirred at 0° C. for 2 hours. The reaction mixture was diluted with ethyl acetate (150 mL) and washed with water (50 mL) and then brine (50 mL). The organic layer was dried over sodium sulphate, filtered and concentrated in vacuo. The crude product was washed with $CH_2Cl_2$:hexane (1:9) to afford the title compound 3 as a white solid (2.43 g, 70%).

Step-2

4

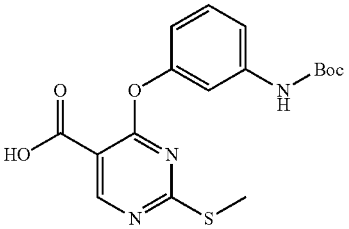

To a stirred solution of 4-(3-tert-butoxycarbonylamino-phenoxy)-2-(methylsulfanyl-pyrimidine)-5-carboxylic acid ethyl ester 3 (2 g, 4.93 mmol) in THF (60 mL), was added methanol (60 mL) at −10° C., followed by aqueous sodium hydroxide (0.3 g, 30 mL water, 7.5 mmol). The reaction mixture was allowed warm to room temperature and was stirred for 1 hour. The reaction mixture was diluted with water (50 mL), acidified with citric acid and the resulting solid was collected by filtration and washed with ice cold water (50 mL) to yield 4 as a white solid. (1.52 g, 82%).

Step-3

6

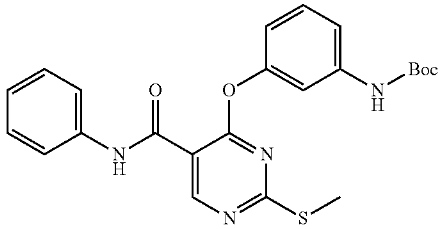

To a stirred solution of 4-(3-tert-butoxycarbonylamino-phenoxy)-2-(methylsulfanyl)pyrimidine-5-carboxylic acid 4 (2.0 g, 5.29 mmol) and TBTU (2.55 g, 7.94 mmol) in acetonitrile (30 mL) at 0° C. was added DIPEA (1.36 g, 10.6 mmol) followed by aniline 5 (0.60 g, 6.35 mmol). The reaction was stirred at room temperature for 2 hours. After completion of the reaction the reaction mixture was poured into ice cold water (100 mL) and the white solid obtained was collected by filtration and washed with ice cold water (20 mL), dried under in vacuo to afford the title compound 6 (1.79 g, 75%).

Step-4

7

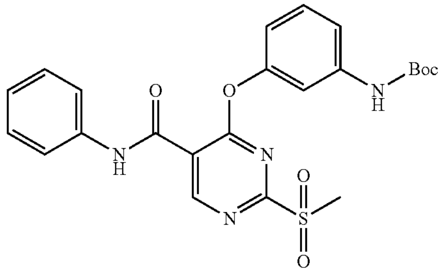

To a stirred solution of [3-(2-methylsulfanyl-5-phenylcarbamoylpyrimidin-4-yloxy)-phenyl]-carbamic acid tert-butyl ester 6 (1.5 g, 3.31 mmol) in $CH_2Cl_2$ at 0° C. was added a solution m-CPBA (70%, 1.62 g, 2 eq) in $CH_2Cl_2$ (10 mL). The reaction mixture was allowed to warm to room temperature and was stirred for 12 h. The reaction was quenched with saturated aqueous $NaHCO_3$ and the whole was extracted with EtOAc. The organic layer was washed with brine, dried over $Na_2SO_4$, filtered, and concentrated in vacuo. The crude product was washed with $CH_2Cl_2$:hexane (1:9) to afford the title compound 7 as a white solid (1.16 g, 73%).

Step-5

9

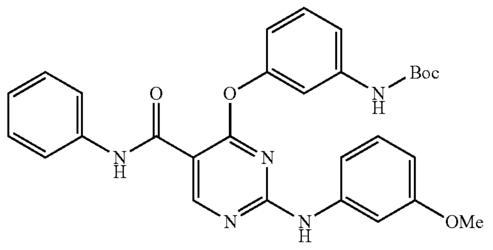

Excess 3-methoxyaniline (8) (2 mL) was added to solid [3-(2-methanesulfonyl-5-phenylcarbamoyl-pyrimidin-4-yloxy)-phenyl]-carbamic acid tert-butyl ester 7 (0.5 g, 1.03 mmol) and the resulting mixture was heated to 50° C. under an argon atmosphere for 3 hours. The reaction mixture was cooled to room temperature and diluted with ethyl acetate/hexane (1:1, 20 mL) and the resulting precipitate filtered and washed with ethyl acetate/hexane (1:1, 10 mL) to afford the desired product 9 as a white solid (0.40 g, 75% yield).

Step-6

10

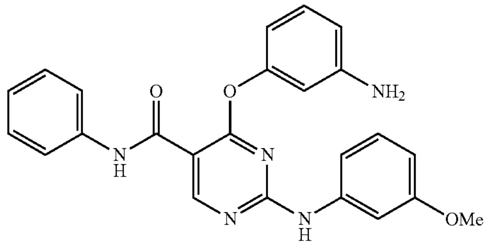

To a solution of {3-[2-(3-methoxy-phenylamino)-5-phenylcarbamoyl-pyrimidin-4-yloxy]-phenyl}-carbamic acid tert-butyl ester 9 (0.3 g, 0.56 mmol) in $CH_2Cl_2$ (10 mL) was added trifluoroacetic acid (2 mL) and the mixture was stirred at room temperature for 1 hour. Solvents were removed under reduced pressure and the residue was dissolved in $CH_2Cl_2$, washed with 10% aqueous $NaHCO_3$ solution, dried ($Na_2SO_4$), filtered, and evaporated under reduced pressure to provide the free amine 10 as white solid.

Step-7

I-200

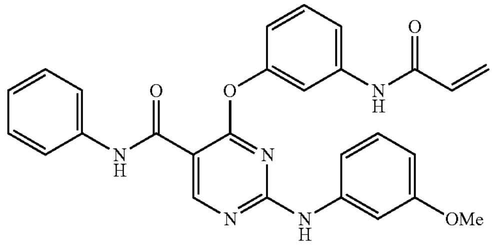

To a stirred solution of amine 10 (0.24 g, 0.56 mmol) in dichloromethane (20 mL) under argon atmosphere cooled to −70° C. was added DIPEA (0.072 g, 0.56 mmol) followed by drop wise addition of acryloyl chloride (0.050 g, 0.56 mmol). The resulting mixture was stirred at −70° C. for 5 minutes, and the reaction mixture diluted with $CH_2Cl_2$ (50 mL) and then was washed with saturated aqueous NaCl solution (10 mL). The organic layer was dried ($Na_2SO_4$), filtered and evaporated under reduced pressure. The residue was purified by flash chromatography on silica gel using (MeOH—$CHCl_3$ 5:95) as eluent to provide the target compound 11 (0.094 g, 35%) as white solid: $^1$H NMR (200 MHz, DMF-d7) δ 8.9 (s, 1H), 8.10-7.70 (m, 6H), 7.60-7.10 (m, 6H), 6.60 (m, 2H) 6.40 (dd, 1H, J=8.0, 2.0 Hz), 5.80 (m, 2H), 3.70 (s, 3H).

Example 58

Preparation of 4-(3-acrylamidophenoxy)-2-(6-methoxypyridin-3-ylamino)-pyrimidine-5-carboxylic acid phenylamide I-159

I-159

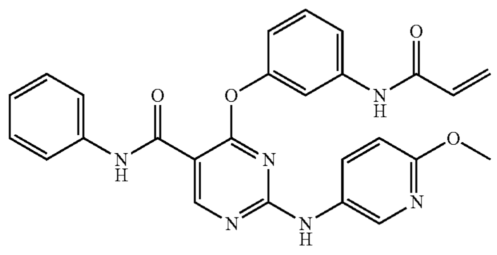

The title compound was prepared according to the schemes, steps and intermediates described in Example 57 by using 6-methoxy-3-aminopyridine in place of 8 in Step 5. $^1$H NMR (200 MHz, DMSO-$d_6$ δ 8.90 (s, 1H), 8.20 (brs, 1H), 7.90-7.60 (m, 4H), 7.45 (m, 4H), 7.10 (m, 2H), 6.50 (m, 1H), 6.20 (m, 2H), 5.90 (dd, J=8.0, 2.0 Hz, 1H), 3.90 (s, 3H).

Example 59

Preparation of 4-(3-acrylamidophenoxy)-2-(3-methoxyphenylamino)-pyrimidine-5-carboxylic Acid Cyclopropylamide I-177

I-177

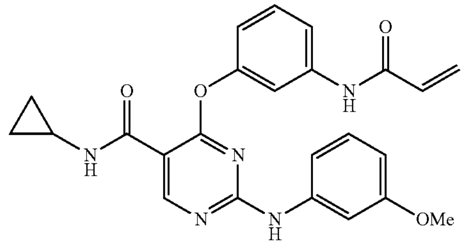

The title compound was prepared according to the schemes, steps and intermediates described in Example 57 by using cyclopropylamine in place of 5 in Step 3. $^1$H NMR (200 MHz, $CD_3OD$) δ 9.0 (s, 1H), 7.90 (brs, 1H), 7.50 (m, 3H), 7.0 (m, 4H), 6.50 (m, 1H), 6.40 (d, J=8.0 Hz, 2H), 5.80 (dd, J=8.2, 3.0 Hz, 1H), 3.60 (s, 3H), 0.90 (m, 2H), 0.62 (m, 2H).

Example 60

Preparation of 4-(3-acrylamidophenoxy)-2-(6-methoxypyridin-3-ylamino)-pyrimidine-5-carboxylic Acid Cyclopropylamide I-176

I-176

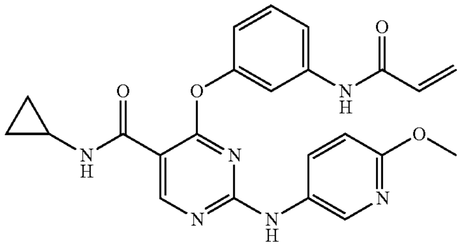

The title compound was prepared according to the schemes, steps and intermediates described in Example 57 by using cyclopropylamine in place of 5 in Step 3 and 6-methoxy-3-aminopyridine in place of 8 in Step 5. $^{1}$H NMR (200 MHz, $CD_3OD$) δ 8.90 (s, 1H), 7.95 (brs, 1H), 7.90-7.82 (m, 3H), 7.40 (m, 3H), 6.98 (d, J=6.0 Hz, 1H), 6.42 (m, 2H), 5.90 (dd, J=8.0, 2.0 Hz, 1H), 3.90 (s, 3H), 0.95 (m, 2H), 0.83 (m, 2H).

Example 61

Preparation of 4-(3-acrylamidophenoxy)-2-(3-methoxyphenylamino)pyrimidine-5-carboxylic Acid Amide I-178

I-178

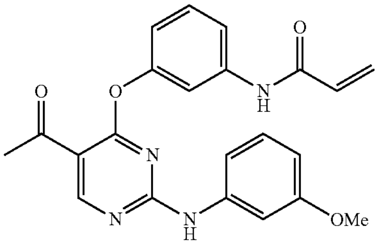

The title compound was prepared according to the schemes, steps and intermediates described below.

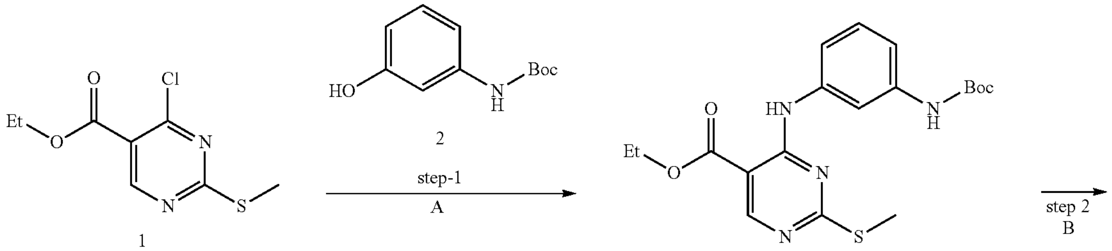

1 2 3

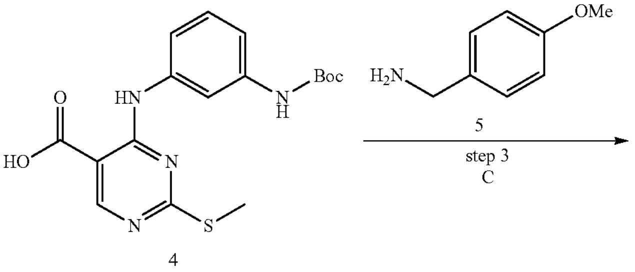

4 5

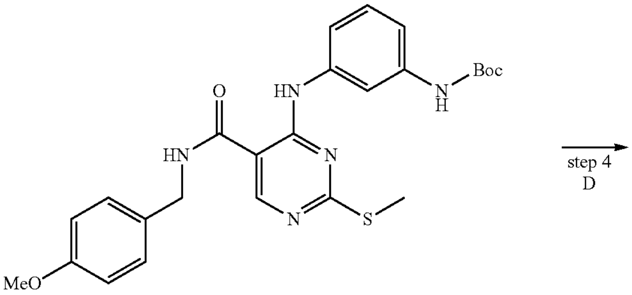

6

-continued
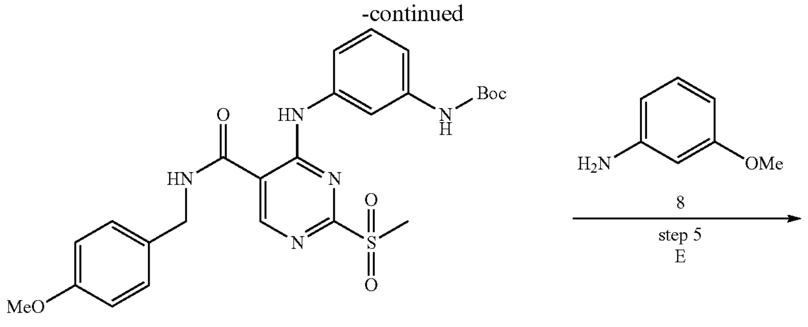
7
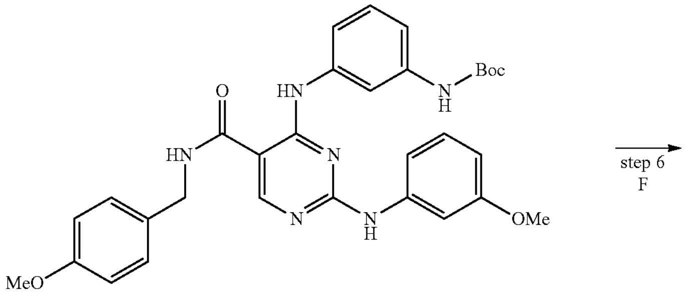
9
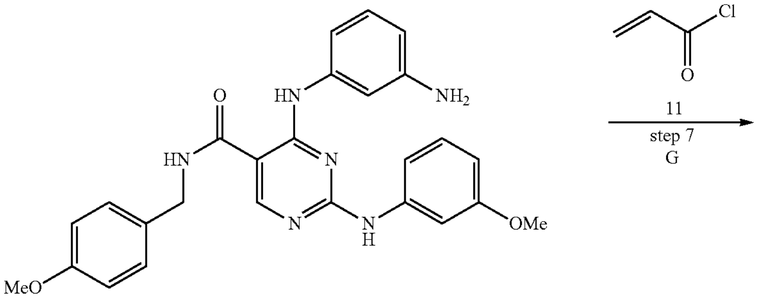
10
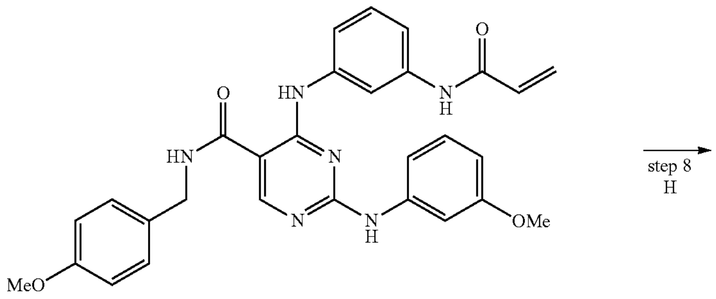
11
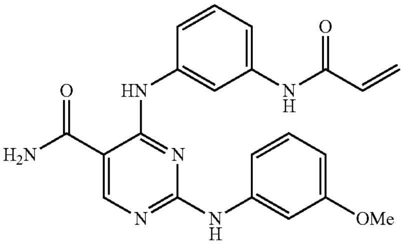
I-178
A) 2, NaH, THF, 0° C.; B) LiOH, THF, $H_2O$; C) 5, TBTU, DIPEA, $CH_3CN$; D) MCPBA, $CHCl_3$. 0° C.; E) 8, DMA, 90° C., 24 h; F) 4N HCl, dioxane; G) 11, $CH_2Cl_2$; H) triflic acid, TFA, $CH_2Cl_2$ Step-1

3

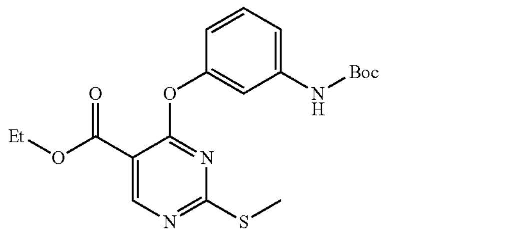

Step 1 was carried out in a manner similar to Step 1 in Example 57.

Step-2

4

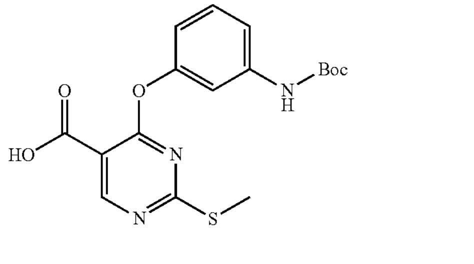

Saponification of 3 (4.58 g, 11.3 mmol) by LiOH (500 mg, 20 mmol) in 80 mL THF/H2O (1:1) and usual workup with 1 N HCl gave free acid 4.

Step-3

6

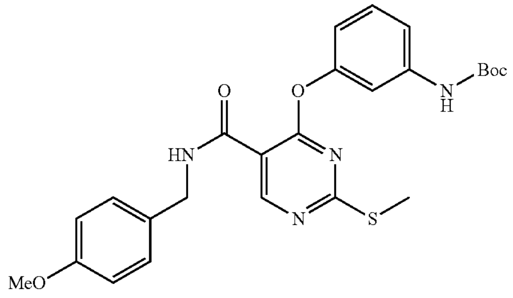

Acid 4 was directly mixed with 4-methoxybenzylamine (1.55 g, 11.3 mmol), TBTU (5.4 g, 16.8 mmol) and DIEA (2.4 mL, 13.4 mmol) in 100 mL MeCN at room temperature. The reaction mixture was run overnight to give 6 as a white solid (4.2 g, 8.5 mmol) after flash chromatography (EtOAc-hexane).

Step-4

7

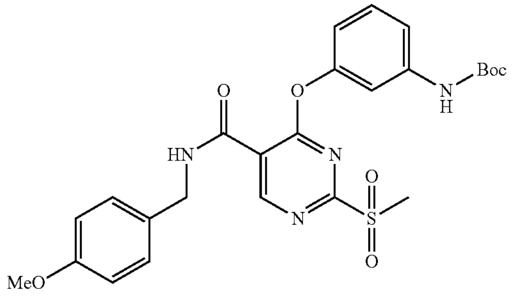

Step 4 was run in a manner similar to Step 4 in Example 57 with $CHCl_3$ being substituted for $CH_2Cl_2$ as the solvent.

Step-5

9

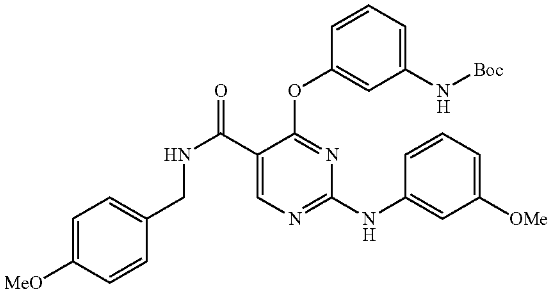

The 2-methylsulfone of 7 (1.0 g, 1.9 mmol) was mixed with 3-methoxyaniline (420 mg, 3.4 mmol) in DMA and the mixture was heated at 90° C. for 24 hours. Workup was done in a manner similar to that for Step-5 in Example 57 to give 9 (300 mg, 0.52 mmol).

Steps-6, 7, and 8

I-178

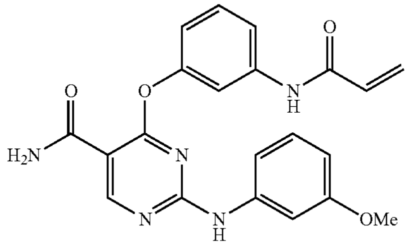

The Boc group was removed from 9 by treatment with 4 N HCl in dioxane. The product (300 mg, 0.52 mmol) was treated immediately with acryloyl chloride (43 μL, 0.52 mmol) in 15 mL DCM at −40° C. This intermediate was purified by flash chromatography (MeOH-DCM) and was reacted with triflic acid and TFA in DCM to provide the crude benzylamine 11 (120 mg, 0.228 mmol). This intermediate (120 mg, 0.228 mmol) was converted to I-178 using triflic acid (305 μL, 3.44 mmol) in TFA/DCM (5 mL, 1:1) at room temperature to provide ~35 mg final compound I-178 as grey powder after purification via column chromatography (16% yield for three steps). MS: m/z=405.

Example 62
Preparation of tert-butyl 3-(3-(4-(3-acrylamidophenylamino)-5-methylpyrimidin-2-ylamino)phenoxy)propylcarbamate I-45
I-45
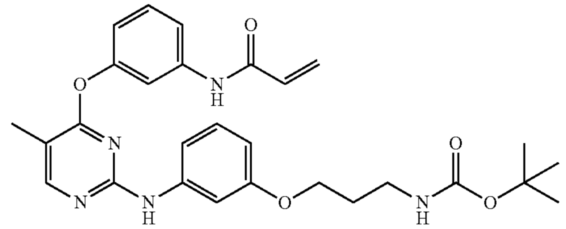
The title compound was prepared according to the schemes, steps and intermediates described below.
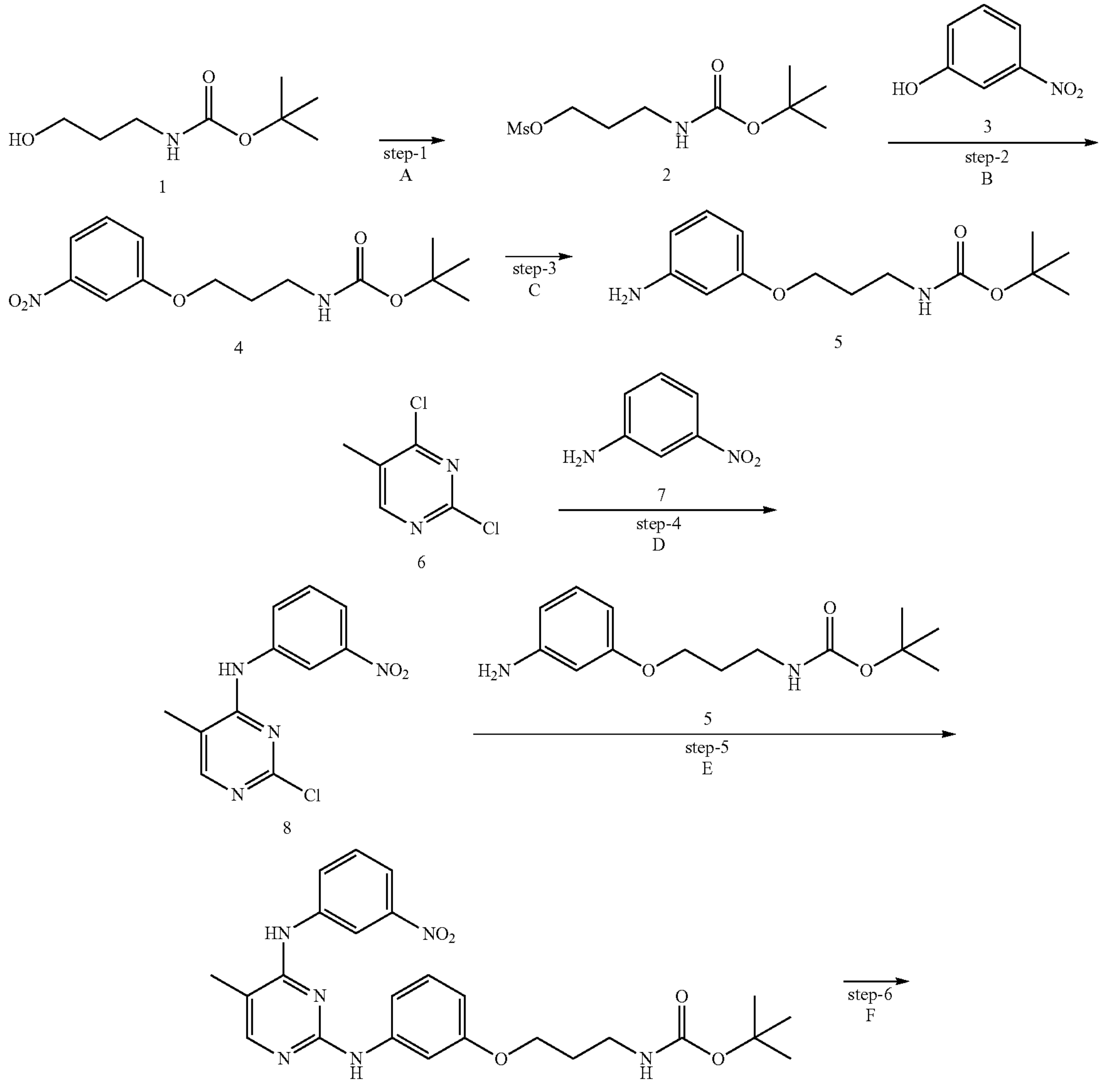
9

-continued

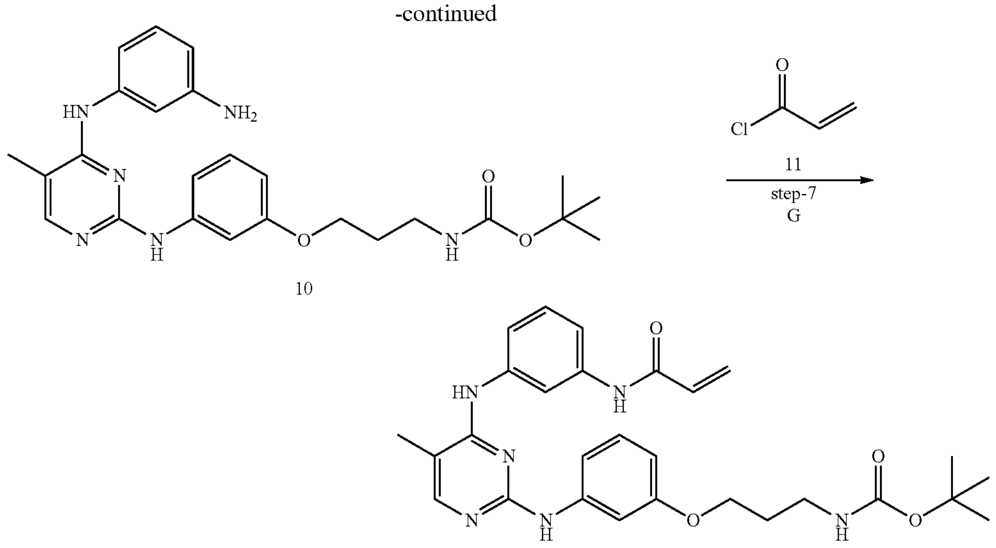

10

I-45

A) 1, methanesulfonyl chloride, $CH_2Cl_2$, Et3N, rt, 1 h; B) 3, $K_2CO_3$, DMF, 60° C; C) $H_2$, Pd/C, EtOH, rt, 16 hr; D) 6, 7, $Pd(OAc)_2$, BINAP, $Cs_2CO_3$, toluene, 100° C., 16 hr; E) 5, AcOH, EtOH, 90° C., 16 hr; F) $H_2$, Pd/C, EtOH, rt, 16 hr; G) 11, NMP, 0° C., 15 min Step-1

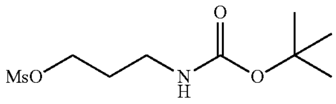

2

To a stirring solution of 1 (1.0 g, 5.7 mmol) in dichloromethane (20.0 mL) was added $Et_3N$ (1.15 g, 11.41 mmol) and methanesulfonyl chloride (0.98 g, 8.56 mmol). The reaction mixture was stirred under nitrogen atmosphere at rt for 60 min. It was quenched with water (20 mL) and extracted with EtOAc (2×50 mL). The combined EtOAc extract was washed with 10% $NaHCO_3$ soln. (25 mL), water (25 mL), brine (25 mL), dried over $Na_2SO_4$ and concentrated under reduced pressure to get 2 (1.36 g, 94%) as a colorless viscous liquid. It was used in the next step without further purification.

Step-2

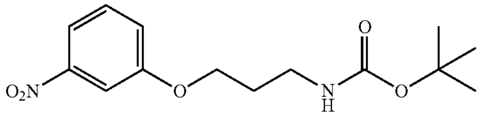

4

To a stirring solution of 2 (0.749 g, 5.39 mmol) and $K_2CO_3$ (0.99 g, 7.19 mmol) in dry DMF (20 mL) was added 3 (1.36 g, 5.39 mmol) and the reaction mixture was heated at 60° C. for 16 h under nitrogen atmosphere. It was cooled, concentrated under reduced pressure and the residue was taken in ethyl acetate (25 mL). The ethyl acetate soln. was washed with water (2×10 mL), brine (10 mL), dried over $Na_2SO_4$ and concentrated under reduced pressure to get 4 (1.2 g, 75%) as a yellowish viscous liquid. It was used in the next step without further purification.

Step-3

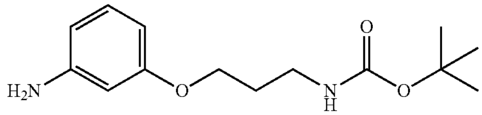

5

To a solution of 4 (1.20 g, 4.05 mmol) in ethanol (25 mL)) was added Pd/C (0.12 g, 10% w/w) and the reaction mixture was allowed to stir under $H_2$ atmosphere (1.5 Kg hydrogen pressure) at rt for 16 h. The reaction mixture was filtered through a pad of Celite® and concentrated under reduced pressure to get 5 (0.95 g, 88%) as a brownish viscous oil. It was used in the next step without further purification.

Step-4

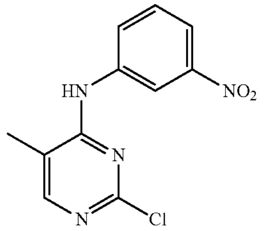

8

To a solution of 6 (1.69 g, 12.26 mmol), in toluene (50.0 mL) was added 7 (2.0 g, 12.26 mmol), BINAP (0.3 g, 0.49 mmol), cesium carbonate (7.9 g, 24.5 mmol). The solution was degassed (by purging $N_2$ for 15 min) and to it was added $Pd(OAc)_2$ (0.054 g, 0.25 mmol). The reaction mixture was stirred at 100° C. for 16 h under nitrogen atmosphere. It was cooled, diluted with ethyl acetate (100 mL) and filtered through Celite®. The filtrate was washed with water (2×25 mL), brine (25 mL), dried over $Na_2SO_4$ and concentrated under reduced pressure. The residue obtained was further purified by column chromatography ($SiO_2$, 60-120 mesh, Ethylacetete/hexane: 15/85). The solid obtained after evaporating the required fractions was washed with diethyl ether and dried under high vacuum to get 8 (1.2 g, 37%) as a light yellow solid.

Step-5

9

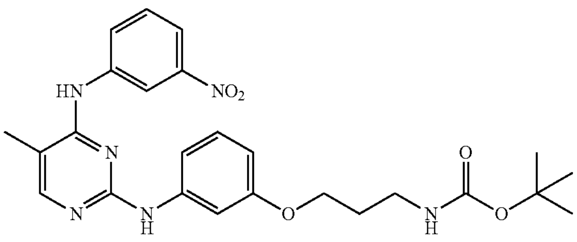

To a solution of 8 (0.5 g, 1.89 mmol) and 5 (0.805 g, 3.0 mmol) in ethanol (10.0 mL) was added glacial acetic acid (0.056 g, 0.95 mmol), and the reaction mixture was stirred in a sealed tube for 16 h at 90° C. The reaction mixture was cooled, concentrated under reduced pressure. The residue was quenched with 10% sodium bicarbonate soln. (10.0 mL) and extracted with ethyl acetate (3×15 mL). The combined ethyl acetate extract was washed with water (15 mL), brine (15 mL), dried over $Na_2SO_4$ and concentrated under reduced pressure to get a residue. The crude residue was further purified by column chromatography ($SiO_2$, EtOAc/Hexane: 50/50) to get 9 (0.57 g, 61%) as a light yellow solid.

Step-6

10

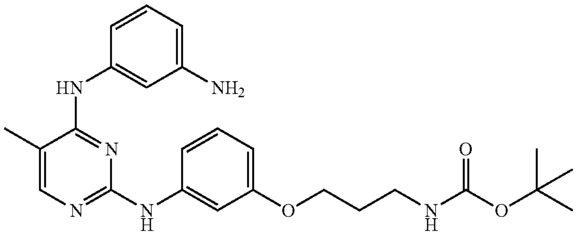

To a solution of 9 (0.56 g, 1.13 mmol) in ethanol (25 mL)) was added 10% Pd/C (0.068 g) and the reaction mixture was allowed to stir under $H_2$ atmosphere (1.5 Kg hydrogen pressure) at rt for 16 h. The reaction mixture was filtered through a pad of Celite® and concentrated under reduced pressure to get 10 (0.45 g, 85%) as a brownish solid. It was used in the next step without further purification.

Step-7

I-45

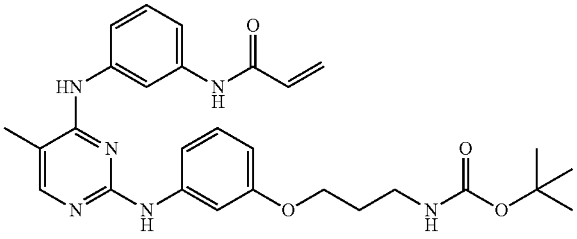

To a stirred solution of 10 (0.25 g, 0.5382 mmol) in NMP (2.5 mL) at 0° C. was added acryloyl chloride (0.073 g, 0.807 mmol) and the reaction mixture was stirred at 0° C. for 15 min The reaction mixture was added drop wise to a cold, stirring solution of 10% $NaHCO_3$. After complete addition the solution was stirred for another 30 min at 0° C., and then filtered through a Buchner funnel to isolate the precipitated solid. The solid was washed with cold water and hexane. It was dissolved in methanol:dichloromethane (50:50, 10 mL) and concentrated under reduced pressure. The residue obtained was suspended in cold water (50 mL), $Et_3N$ was added to it and it was extracted with ethyl acetate (2×100 mL). The combined ethyl acetate extract was washed with water (50 mL), brine (50 mL), dried over $Na_2SO_4$ and concentrated under reduced pressure to get I-45 (0.100 g, 35.8%) as an off-white solid. $^1$H NMR (DMSO-$d_6$) δ ppm: 1.37 (s, 9H), 1.70-1.80 (m, 2H), 2.10 (s, 3H), 3.00-3.06 (m, 2H), 3.79 (t, J=6.24 Hz, 2H), 5.74 (d, J=11.92 Hz, 1H), 6.24 (dd, J=1.84 & 15.16 Hz, 1H), 6.35-6.47 (m, 2H), 6.80-6.90 (bs, 1H), 6.97 (t, J=8.28 Hz, 1H), 7.23-7.27 (m, 2H), 7.31 (s, 1H), 7.37 (d, J=8.2 Hz, 1H), 7.46 (d, J=7.48 Hz, 1H), 7.90-7.90-7.91 (m, 2H), 8.36 (s, 1H), 8.87 (s, 1H), 10.07 (s, 1H); LCMS: m/e 519 (M+1).

Example 63

Preparation of tert-butyl 3-(3-(4-(3-acrylamidophenylamino)-5-fluoropyrimidin-2-ylamino)phenoxy) propylcarbamate I-183

I-183

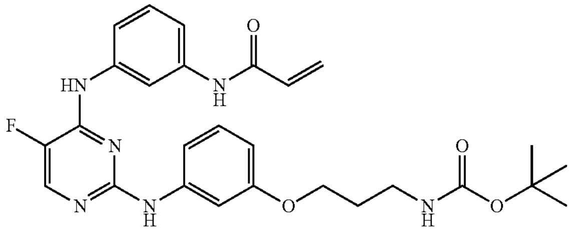

The title compound was prepared according to the schemes, steps and intermediates described below.

2'

1

2

3

4

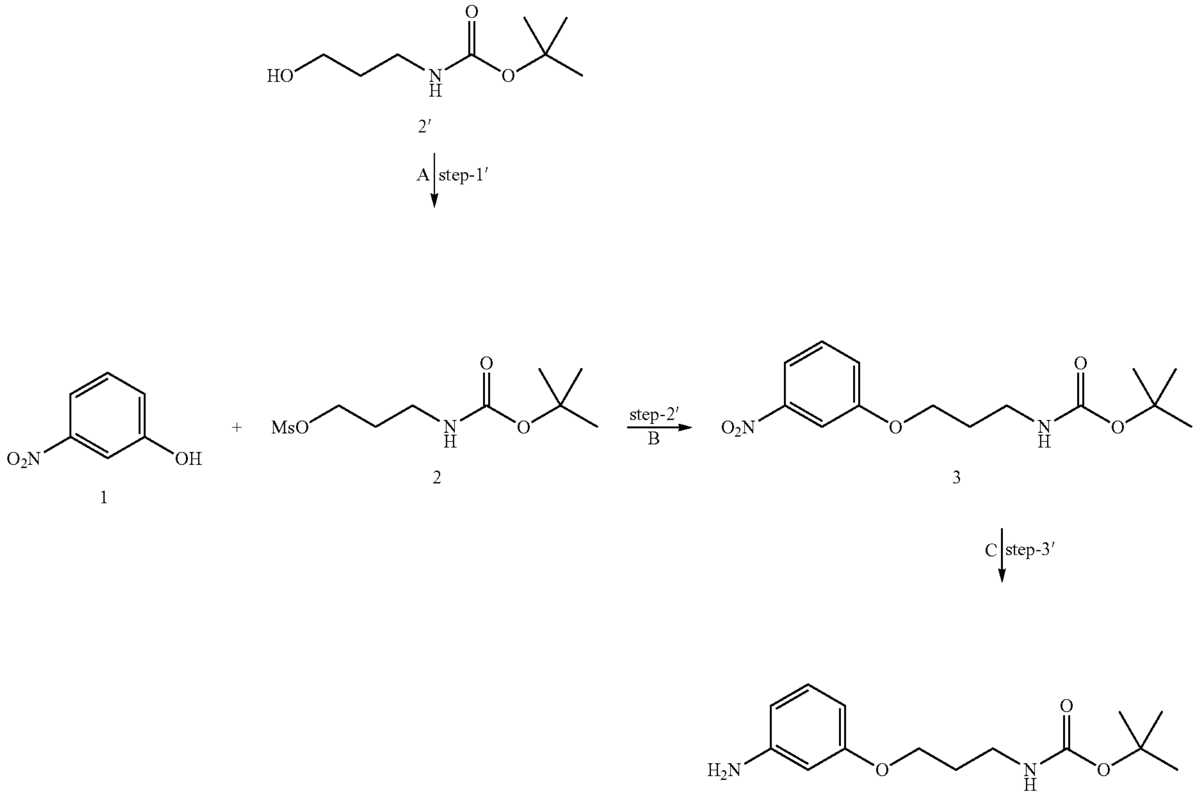

A) methanesulfonyl chloride, $CH_2Cl_2$, $Et_3N$, rt, 1 h; B) $K_2CO_3$, DMF, 60° C., 16 h; C) Pd—C, $H_2$, ethanol, rt, 16 h.

Step 1'

2

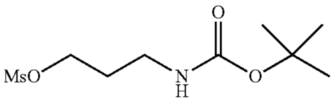

To a stirred solution of 2' (4.0 g, 22.8 mmol) in dichloromethane (80.0 mL) was added $Et_3N$ (4.6 g, 45.5 mmol) and methanesulfonyl chloride (3.92 g, 34.2 mmol), and the reaction mixture was stirred under nitrogen atmosphere at RT for 60 min. The reaction was quenched with water (50 mL) and extracted with EtOAc (2×100 mL). The combined extracts were washed with 10% $NaHCO_3$ solution (50 mL), water (50 mL), and brine (50 mL), dried over $Na_2SO_4$, and concentrated under reduced pressure to give 2 (5.5 g, 95.2%) as a light yellow viscous liquid. Compound 2 was used in the next step without further purification.

Step 2'

3

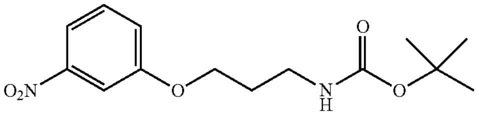

To a stirred solution of 1 (2.3 g, 16.5 mmol) and $K_2CO_3$ (4.6 g, 33.3 mmol) in dry DMF (100 mL) was added 2 (5.5 g, 21.7 mmol), and the reaction mixture was heated at 60° C. for 16 h under nitrogen atmosphere. The reaction was cooled, quenched with water (250 ml), and extracted with EtOAc (2×100 mL). The combined extracts were washed with 10% $NaHCO_3$ solution (100 mL), water (3×100 mL), and brine (100 mL), dried over $Na_2SO_4$, and concentrated under reduced pressure to give 3 (4.0 g, 81.6%) as a light yellow viscous liquid. Compound 3 was used in the next step without further purification.

Step 3'

4

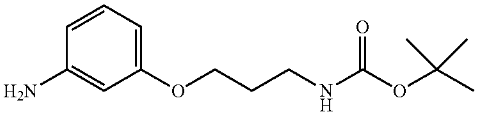

To a solution of 3 (4.0 g, 13.4 mmol) in ethanol (50 mL) was added Pd/C (0.8 g, 10% w/w), and the reaction mixture was allowed to stir under $H_2$ atmosphere (1.5 Kg hydrogen pressure) at rt for 16 h. The reaction mixture was filtered through a pad of Celite® and concentrated under reduced pressure to give 4 (3.3 g, 91.9%) as a brownish viscous oil. Compound 4 was used in the next step without further purification.

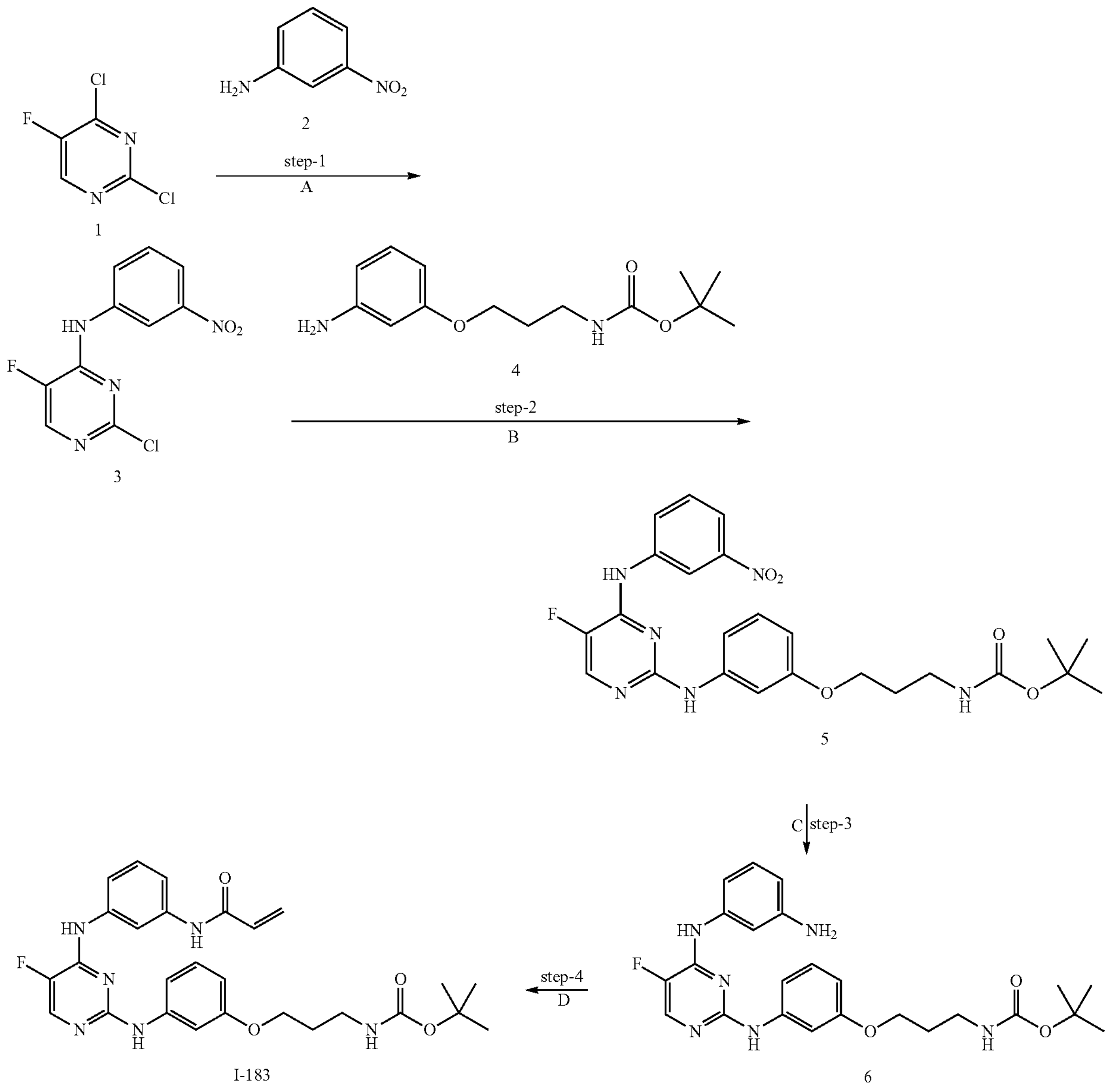

Step 1

3

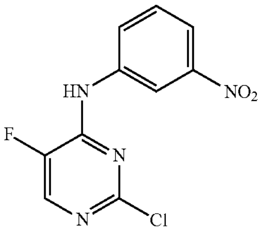

A pressure tube was charged with 2 (10.0 g, 0.072 mol), 1 (24.1 g, 0.145 mol), n-BuOH (100 mL) and DIPEA (13.9 g, 0.108 mol), and the contents were stirred at 120° C. for 2 h. The reaction mixture was cooled, and the precipitated solid was isolated by filtration through a Buchner funnel, washed with cold hexane and dried to give 3 (12.5 g, 64%) as a yellow solid. Compound 3 was used in the next step without further purifications.

Step 2

5

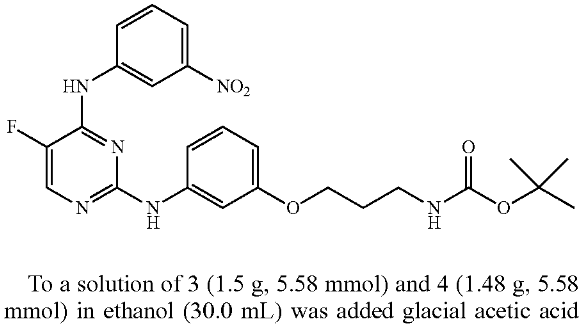

To a solution of 3 (1.5 g, 5.58 mmol) and 4 (1.48 g, 5.58 mmol) in ethanol (30.0 mL) was added glacial acetic acid (0.167 g, 2.79 mmol), and the reaction mixture was stirred in a pressure tube at 90° C. for 48 h. The reaction mixture was cooled and concentrated under reduced pressure; the residue was quenched with 10% sodium bicarbonate solution (20.0 mL) and extracted with ethyl acetate (2×50 mL). The combined extracts were washed with water (25 mL) and brine (25 mL), dried over $Na_2SO_4$, and concentrated under reduced pressure to give crude 5. The crude residue was purified by column chromatography (neutral $Al_2O_3$, MeOH/Chloroform: 0.5/99.5) to give 5 (1.4 g, 50.3%) as a brown solid.

Step 3

6

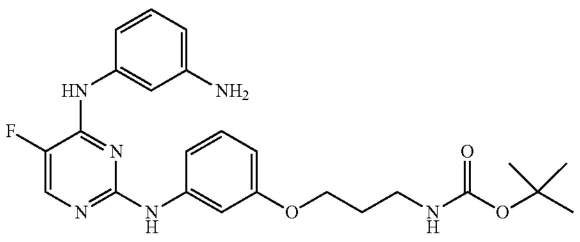

To a solution of 5 (1.4 g, 2.8 mmol) in ethanol (50 mL)) was added 10% Pd/C (0.28 g, 10% w/w) and the reaction mixture was allowed to stir under $H_2$ atmosphere (1.5 Kg hydrogen pressure) at rt for 16 h. The reaction mixture was filtered through a pad of Celite® and concentrated under reduced pressure to give a residue. The crude residue was further purified by column chromatography (neutral $Al_2O_3$, MeOH/Chloroform: 0.5/99.5) to give a solid which was washed with dichloromethane/hexane mixtures to give 6 (0.7 g, 53.4%) as a pale brown solid.

Step 4

I-183

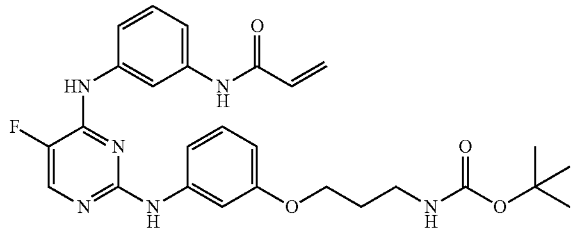

tert-Butyl 3-(3-(4-(3-acrylamidophenylamino)-5-fluoropyrimidin-2-ylamino)phenoxy)propylcarbamate To a stirred solution of 6 (0.25 g, 0.533 mmol) and potassium carbonate (0.138 g, 1.02 mmol) in NMP (2.5 mL) at 0° C. was added acryloyl chloride (0.060 g, 0.665 mmol), and the reaction mixture was stirred at 0° C. for 30 min. The reaction mixture was added dropwise to a cold, stirring solution of 10% $NaHCO_3$ and stirred at the same temperature (0° C.) for 30 min. A white solid precipitated out and was isolated by filtration through a Buchner funnel. The solid was washed with cold water and hexane and dissolved in mixture of methanol/dichloromethane (50:50, 10 mL) and concentrated under reduced pressure. The residue obtained was suspended in cold water (25 mL), $Et_3N$ was added, and it was extracted with ethyl acetate (2×50 mL). The combined extracts were washed with water (50 mL), brine (50 mL), dried over $Na_2SO_4$ and concentrated under reduced pressure to give I-183 (0.255 g, 91.4%) as light yellow solid. $^1$H NMR (DMSO-$d_6$) δ ppm: 1.36 (s, 9H), 1.78 (quin, J=6.4 Hz, 2H), 3.01-3.06 (m, 2H), 3.83 (t, J=6.12 Hz, 2H), 5.74 (dd, J=1.4 & 10.04 Hz, 1H), 6.24 (d, J=16.84 Hz, 1H), 6.41-6.48 (m, 2H), 6.88 (s, 1H), 7.03 (t, J=8.24 Hz, 1H), 7.23-7.31 (m, 3H), 7.41 (d, J=8.28 Hz, 1H), 7.56 (d, J=7.96 Hz, 1H), 7.90 (s, 1H), 8.11 (d, J=3.56 Hz, 1H), 9.11 (s, 1H), 9.43 (s, 1H), 10.10 (s, 1H); LCMS: m/e 523.1 (M+1).

Example 64

Preparation of tert-butyl 3-(4-(4-(3-acrylamidophenylamino)-5-fluoropyrimidin-2-ylamino)phenoxy)propylcarbamate I-198

I-198

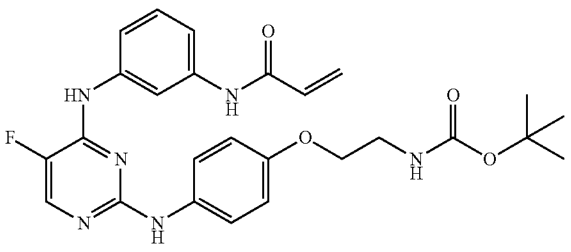

The title compound was prepared according to the schemes, steps and intermediates described in Example 63 by using tert-butyl 3-(4aminophenoxy)propylcarbamate in place of 4 in Step-2. $^1$H NMR (DMSO-$d_6$) δ ppm: 1.37 (s, 9H), 1.78 (quin, J=6.36 Hz, 2H), 3.05 (q, J=6.24 Hz, 2H), 3.86 (t, J=6.2 Hz, 2H), 5.75 (dd, J=1.92 & 10.04 Hz, 1H), 6.24 (dd, J=1.92 & 16.92 Hz, 1H), 6.45 (dd, J=10.08 & 16.92 Hz, 1H), 6.72 (d, J=9 Hz, 2H), 6.89 (t, J=5.4 Hz, 1H), 7.26 (t, J=8.08 Hz, 1H), 7.40 (d, J=8.12 Hz, 1H), 7.48-7.52 (m, 3H), 7.92 (s, 1H), 8.05 (d, J=3.72 Hz, 1H), 8.95 (s, 1H), 9.36 (s, 1H), 10.12 (s, 1H); LCMS: m/e 523.2 (M+1).

The intermediate tert-butyl 3-(4aminophenoxy)propylcarbamate was prepared by the scheme shown below.

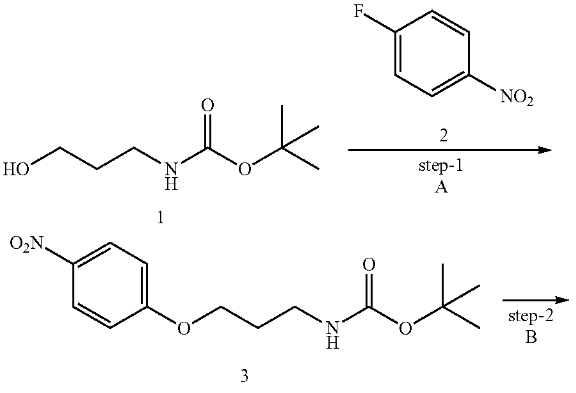

-continued

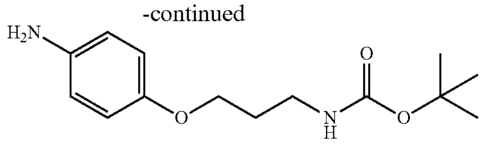

4

A) NaH, THF, rt, 16 h; B) $H_2$, Pd/C, EtOH, rt, 16 hr

Step-1

To a stirring solution of 1 (1.7 g, 9.7 mmol) in dry THF (40 mL) was added NaH (0.72 g, 18.0 mmol, 60% dispersion in paraffin oil) at 0° C. and the reaction mixture was stirred at rt for 15 min under nitrogen atmosphere. To it was added 2 (2.0 g, 13.87 mmol) and the reaction mixture was stirred at rt for 16 h. It was quenched with cold water (20 mL), and extracted with ethyl acetate (25 mL). The ethyl acetate extract was washed with water (2×10 mL), brine (10 mL), dried over $Na_2SO_4$ and concentrated under reduced pressure to get an oily liquid which was triturated with hexane to get 3 (2.0 g, 69.5%) as a yellow crystalline solid.

Step-2

To a solution of 3 (2.0 g, 6.749 mmol) in ethanol (30 mL)) was added 10% Pd/C (0.4 g, 20% w/w) and the reaction mixture was allowed to stir under $H_2$ atmosphere (1.5 Kg hydrogen pressure) at rt for 16 h. The reaction mixture was filtered through a pad of Celite® and concentrated under reduced pressure to get 4 (1.6 g, 89.3%) as a pinkish viscous oil. It was used in the next step without further purification.

Example 65

Preparation of 4-(3acrylamidophenylamino)-5-fluoro-2-(3,4-dimethoxyphenylamino)-pyrimidine I-134

I-134

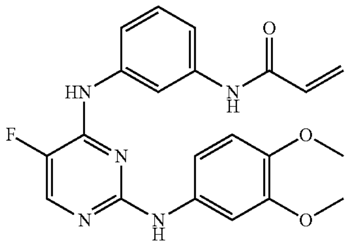

The title compound was prepared according to the schemes, steps and intermediates described in Example 20 by using 3,4-dimethoxyaniline in place of 4 in Step-2. $^1$H NMR (200 MHz, $CD_3OD$) δ 8.50 (s, 1H), 7.80 (d, J=6.5 Hz, 1H), 7.70-7.66 (m, 2H), 7.20 (m, 1H), 7.0 (m, 2H), 6.41 (m, 2H), 5.92 (dd, J=8.0, 2.0 Hz, 1H), 3.89 (s, 6H).

Example 66

Preparation of 4-(3-acrylamidophenylamino)-5-fluoro-2-(3,4,5-trimethoxyphenylamino)-pyrimidine I-133

I-133

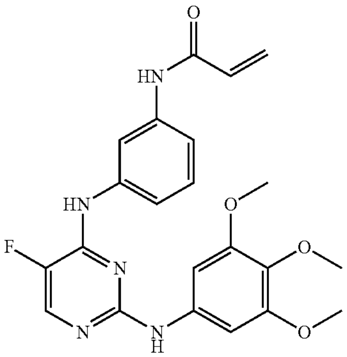

The title compound was prepared according to the schemes, steps and intermediates described in Example 20 by using 3,4,5-trimethoxyaniline in place of 4 in Step-2. $^1$H NMR (200 MHz, $CD_3OD$) δ 8.10 (s, 1H), 8.0 (d, J=6.0 Hz, 1H), 7.50 (m, 2H), 7.30 (m, 1H), 7.0 (m, 2H), 6.45 (m, 2H), 5.90 (dd, J=8.0, 2.0 Hz, 1H), 3.90 (s, 3H), 3.89 (s, 9H).

Example 67

Preparation of 4-(3-acrylamidophenylamino)-5-fluoro-2-(3-(hydroxymethyl)phenylamino)-pyrimidine I-145

I-145

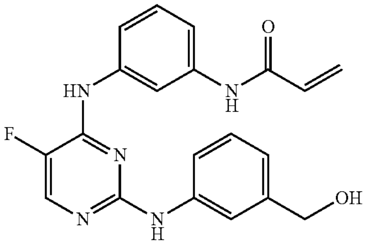

The title compound was prepared according to the schemes, steps and intermediates described in Example 20 by using 3-hydroxymethylaniline in place of 4 in Step-2. $^1$H NMR (DMSO-$d_6$) δ ppm: 4.38 (d, J=5.6 Hz, 2H), 5.07 (t, J=5.68 Hz, 1H), 5.75 (d, J=10.84 Hz, 1H), 6.24 (dd, J=16.96 Hz, 1H), 6.44 (dt, J=10.04 & 17.0 Hz, 1H), 6.83 (d, J=7.4 Hz, 1H), 7.10 (t, J=7.72 Hz, 1H), 7.28 (t, J=8.16 Hz, 1H), 7.40 (d, J=8.08 Hz, 1H), 7.55-7.59 (m, 3H), 7.92 (s, 1H), 8.09 (d, J=3.6 Hz, 1H), 9.11 (s, 1H), 9.40 (s, 1H), 10.1 (s, 1H); LCMS: m/e 378.0 (M+1).

Example 68

Preparation of 4-(3-acrylamidophenylamino)-5-fluoro-2-(3-(3-(2-oxopyrrolidin-1-yl)propoxy)phenylamino)-pyrimidine I-144

I-144

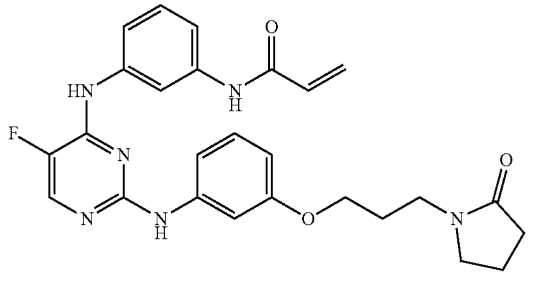

The title compound was prepared according to the schemes, steps and intermediates described in Example 20 by using 3-(2-oxopyrrolidin-1-yl)propoxyaniline in place of 4 in Step-2. $^1$H NMR (DMSO-$d_6$) δ ppm: 1.8-1.94 (m, 4H), 2.18 (q, J=8.08 Hz, 2H), 3.26-3.40 (m, 4H), 3.80 (t, J=6 Hz, 2H), 5.74 (d, J=10.72 Hz, 1H), 6.24 (d, J=15.64 Hz, 1H), 6.41-6.80 (m, 2H), 7.04 (t, J=8.16 Hz, 1H), 7.22-7.29 (m, 2H), 7.33 (s, 1H), 7.42 (d, J=8.08 Hz, 1H), 7.55 (d, J=7.52 Hz, 1H), 7.91 (s, 1H), 8.11 (d, J=3.48 Hz, 1H), 9.13 (s, 1H), 9.43 (s, 1H), 10.11 (s, 1H); LCMS: m/e 491 (M+1).

Example 69

Preparation of 4-(3-acrylamidophenylamino)-5-fluoro-2-(3-(3-(methylsulfonyl)propoxy)phenylamino)-pyrimidine I-138

I-138

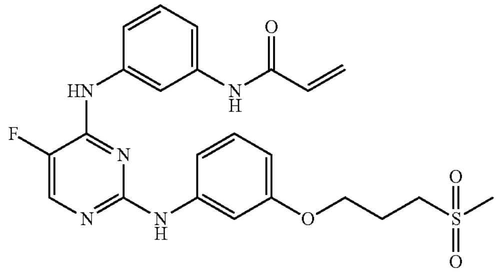

The title compound was prepared according to the schemes, steps and intermediates described in Example 20 by using 3-(3-(methylsulfonyl)propoxyaniline in place of 4 in Step-2. $^1$H NMR (DMSO-$d_6$) δ ppm: 2.05-2.15 (m, 2H), 3.0 (s, 3H), 3.22 (t, J=7.76 Hz, 2H), 3.93 (t, J=6.08 Hz, 2H), 5.74 (dd, J=1.88 & 10 Hz, 1H), 6.25 (dd, J=1.8 & 16.88 Hz, 1H), 6.44 (dd, J=10.16 & 16.84 Hz, 2H), 7.05 (t, J=8.16 Hz, 1H), 7.24-7.30 (m, 2H), 7.35 (s, 1H), 7.42 (d, J=8.2 Hz, 1H), 7.55 (d, J=8 Hz, 1H), 7.90 (s, 1H), 8.11 (d, J=3.6 Hz, 1H), 9.14 (s, 1H), 9.43 (s, 1H), 10.10 (s, 1H); LCMS: m/e 484 (M+1).

The intermediate 3-(3-(methylsulfonyl)propoxyaniline was prepared by the scheme shown below.

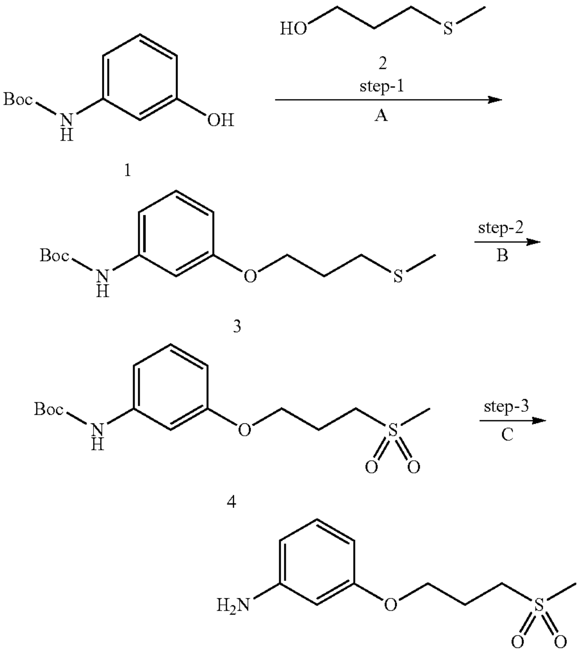

A) DEAD, $Ph_3P$, $Et_3N$, THF, rt, 1 hr; B) MCPBA, $CH_2Cl_2$, rt, 30 min; C) TFA, $CH_2Cl_2$, rt, 1 hr Step-1

3

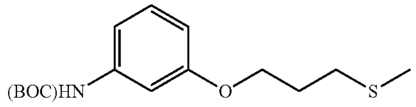

To a stirred solution of 2 (1.1 g, 10.3 mmol) in THF (20 mL) were added 1 (2.18 g, 10.3 mmol), $PPh_3$ (2.98 g, 11.3 mmol) and $Et_3N$ (1.68 g, 15 mmol) under $N_2$ atmosphere. The reaction mixture was cooled to 0° C. and to it was added DEAD (1.98 g, 11.3 mmol). The reaction mixture was allowed to come to rt and stirred for 1 h. It was quenched with water, extracted with ethyl acetate (3×25 mL) and the combined EtOAc extract was washed with water and brine solution (5 mL each). The residue obtained after concentration under reduced pressure was purified by column chromatography ($SiO_2$, 60-120, pet ether/ethyl acetate, 8/2) to get 3 (2 g 60.6%) as a white solid.

Step-2

4

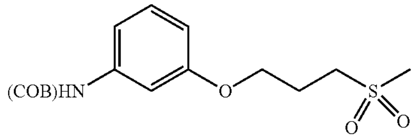

To a stirred solution of 3 (2 g, 6.7 mmol) in $CH_2Cl_2$ (25 mL) was added m-CPBA (4.13 g, 26.7 mmol) at −10° C. The reaction mixture was allowed to come to rt and stirred for 30 min. It was quenched with $Na_2CO_3$ solution (10 mL), extracted with $CH_2Cl_2$ (10 mL), dried over $Na_2SO_4$, filtered and concentrated under reduced pressure. The residue was further purified by column chromatography ($SiO_2$, 60-120, chloroform/methanol 9/1) to get 4 (1.05 g, 68.8%) as a yellow oil.

Step-3

5

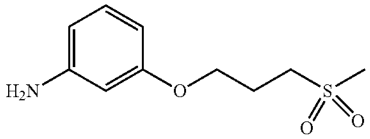

To a stirred solution of 4 (0.75 g, 2.2 mmol) in $CH_2Cl_2$ (7.5 mL) was added TFA (3 vol.) at 0° C. The reaction mixture was allowed to come to rt and stirred further at it for 1 h. It was concentrated under reduced pressure, basified with $NaHCO_3$ solution (5 mL) and extracted with $CH_2Cl_2$ (3×10 mL). The combined organic extract was washed with water (2 mL) and brine solution (2 mL). Drying over $Na_2SO_4$ followed by filtration and concentration under reduced pressure offered 5 (500 mg, 96%) as brown solid.

Example 70

Preparation of N-(3-(5-fluoro-2-(3-(2-hydroxy-ethoxy)phenylamino)pyrimidin-4-ylamino)phenyl) acrylamide I-105

I-105

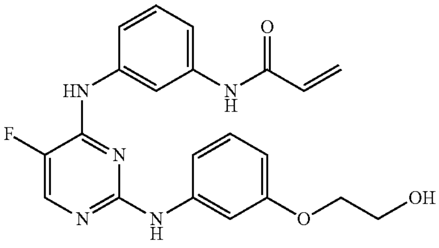

The title compound was prepared according to the schemes, steps and intermediates described in Example 20 by using 3-(2-hydroxy)ethoxyaniline in place of 4 in Step-2. $^1$H NMR (DMSO-$d_6$) δ ppm: 3.67 (dd, J=4.5 & 10 Hz, 2H), 3.85-3.87 (m, 2H), 4.83 (t, J=5.6 Hz, 1H), 5.75 (bd, J=10 Hz, 1H), 6.25 (d, J=15.6 Hz, 1H), 6.42-6.46 (m, 2H), 7.05 (t, J=8.4 Hz, 1H), 7.26 (d, J=8 Hz, 1H), 7.30 (d, J=8 Hz, 1H), 7.33 (s, 1H), 7.41 (d, J=8 Hz, 1H), 7.57 (d, J=8 Hz, 1H), 7.92 (s, 1H), 8.11 (d, J=3.6 Hz, 1H), 9.11 (s, 1H), 9.42 (s, 1H), 10.11 (s, 1H); LCMS: m/e 409.9 (M+1).

The intermediate 3-(2-hydroxy)ethoxyaniline was prepared by the scheme shown below.

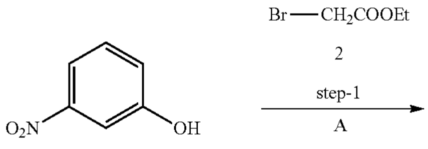

1

-continued

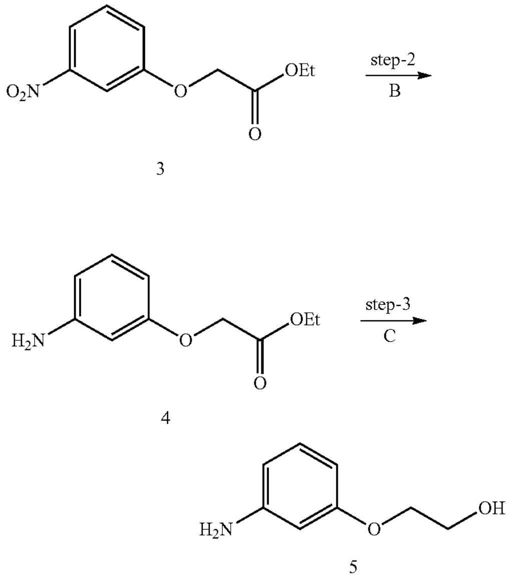

A) $K_2CO_3$, DMF, 70° C., 12 h; B) Pd—C, $H_2$, ethanol, rt, 10 h; C) 1M LAH solution, THF, -15° C., 45 min.

Step-1

3

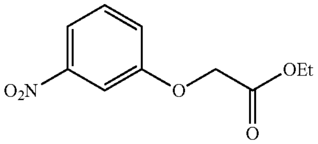

To a stirring solution of 1 (2.0 g, 14.37 mmol) and $K_2CO_3$ (3.95 g, 28.6 mmol) in dry DMF (15 mL) was added 2 (2.88 g, 17.25 mmol) and the reaction was stirred at rt 70° C. for 12 h under nitrogen atmosphere. The reaction mixture was cooled, concentrated under reduced pressure and the residue was diluted with ethyl acetate (50 mL). It was washed with water (2×10 mL), brine (10 mL), dried over $Na_2SO_4$ and concentrated under reduced pressure to get 3 (2.5 g, 78%) as a light brown liquid. It was used in the next step without further purification.

Step-2

4

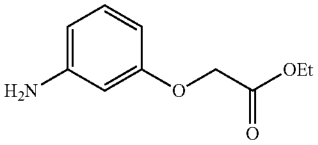

To a solution of 3 (2.0 g, 8.88 mmol) in ethanol (20 mL)) was added Pd/C (0.2 g, 10% w/w) and the reaction mixture was allowed to stir under $H_2$ atmosphere (1.0 Kg hydrogen pressure) at rt for 10 h. The reaction mixture was filtered through a pad of Celite® and concentrated under reduced pressure to get 4 (1.6 g, 94%) as a light brown liquid. It was used in the next step without further purification.

Step-3

5

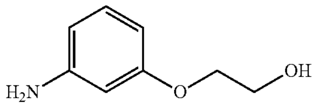

To a stirring solution of 4 (1.2 g, 6.14 mmol) in dry THF (12 mL)) was added lithium aluminum hydride (9.2 mL, 9.20 mmol, 1.0 M soln. in THF) at −15° C., under $N_2$ atmosphere. The reaction mixture was allowed to come to rt and stirred at it for 45 min. The reaction mixture was quenched with saturated ammonium chloride solution and was filtered through a pad of Celite® and extracted with EtOAc (2×20 mL). The combined organic layer was washed with brine (10 mL) and concentrated under reduced pressure to get A (0.9 g, 95%) as a dark brown liquid. It was used in the next step without further purification.

Example 71

Preparation of N-(3-(5-fluoro-2-(3-(2-hydroxy-2-methylpropoxy)phenylamino)pyrimidin-4-ylamino)phenyl)acrylamide I-118

I-118

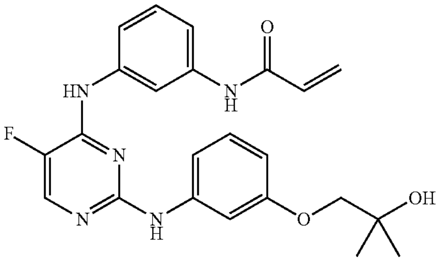

The title compound was prepared according to the schemes, steps and intermediates described below.

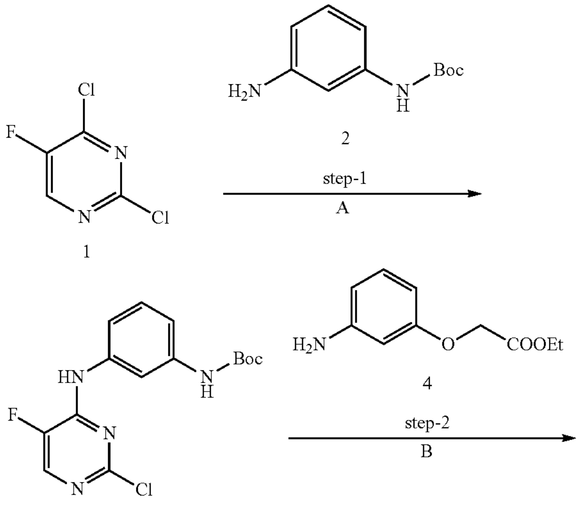

1, 2, 3, 4

-continued

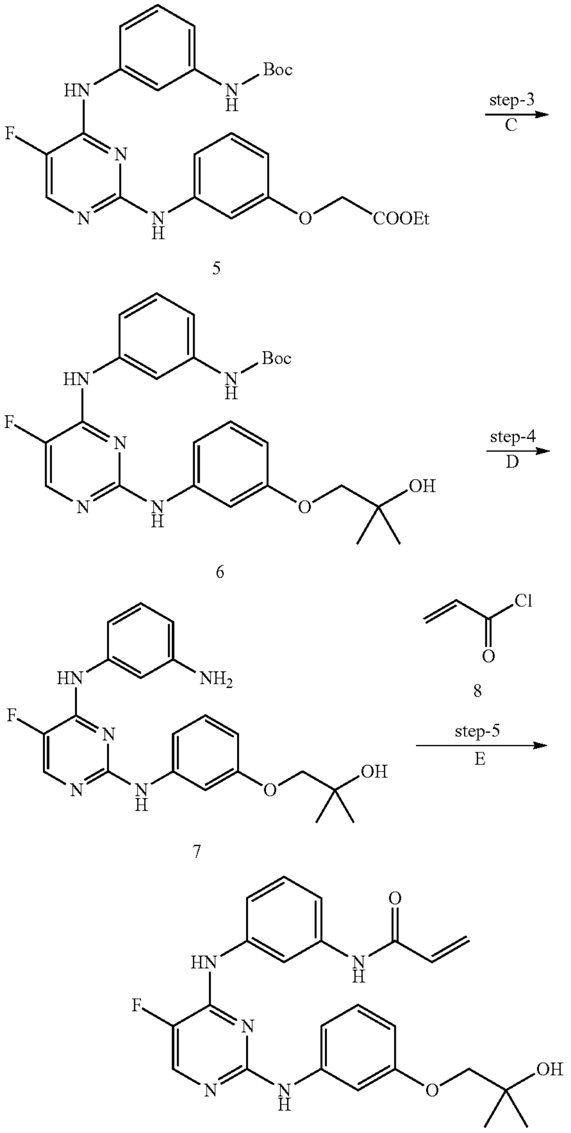

5, 6, 7, 8

I-118

A) DIPEA, n-BuOH, 110° C., 16 h; B) Pd(OAc)$_2$, BINAP, CsCO$_3$, toluene, 100° C., 16 h; C) MeMgBr (3M solution in ether), THF, -78° C., 3 h; D) TFA, $CH_2Cl_2$, rt, 3 h.
E) $K_2CO_3$, NMP, rt, 45 min.

Step-1

3

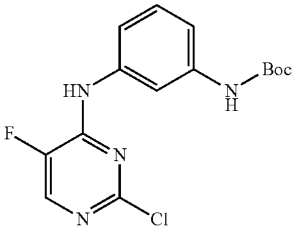

Compound 3 was prepared according to the schemes, steps and intermediates described in Example 20.

Step-2

5

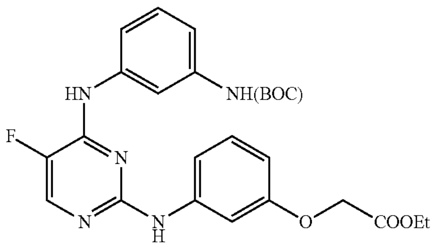

A solution of 4 (0.7 g, 3.5 mmol), 3 (1.45 g, 4.3 mmol), $Pd(OAc)_2$ (0.03 g, 0.14 mmol), BINAP (0.13 g, 0.21 mmol) and $Cs_2CO_3$ (2.8 g, 8.7 mmol) in degassed toluene (30 mL) (toluene was purged with $N_2$ for 30 min) was heated at 100° C. for 16 h under $N_2$ atmosphere. The reaction mixture was cooled, diluted with EtOAc (15 mL) and washed with water (10 mL), brine (10 mL) and dried over $Na_2SO_4$. Filtration followed by concentration under reduced pressure offered a residue which was further purified by column chromatography ($SiO_2$, 60-120, pet ether/ethyl acetate, 6/4) to get 5 (700 mg, 40%) as a white solid.

Step-3

6

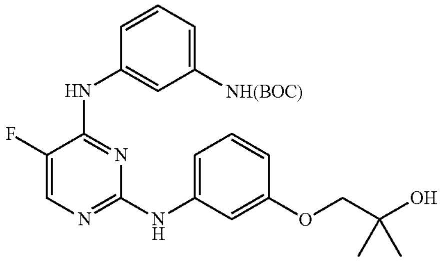

To a stirred solution of 5 (0.4 g, 0.8 mmol) in THF (10 mL) was added Methyl magnesium bromide ((3 M solution in ether, 1.6 mL, 4.8 mmol) at −78° C. The reaction mixture was allowed to warm to −30° C. over 3 h, cooled again to −78° C. and quenched with saturated ammonium chloride solution (5 mL). The mixture was filtered through Celite® and filtrate was concentrated under reduced pressure to afford 6 as a pale yellow solid (300 mg, 78%) which was taken for next step without further purification.

Step-4

7

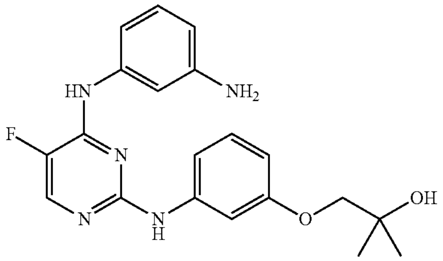

To a stirred solution of 6 (0.2 g, 0.4 mmol) in $CH_2Cl_2$ (7.5 mL) was added TFA (3 vol.) at 0° C. The reaction mixture was allowed to come to rt and stirred further at it for 3 h. It was concentrated under reduced pressure, basified with $NaHCO_3$ solution (5 mL) and extracted with $CH_2Cl_2$ (3×10 mL). The combined organic extract was washed with water (2 mL) and brine solution (2 mL). Drying over $Na_2SO_4$ followed by filtration and concentration under reduced pressure afforded a residue which was further purified by column chromatography ($SiO_2$, 60-120, pet ether/ethyl acetate, 6/4) to get 7 (130 mg, 86%) as a white solid.

Step-5

I-118

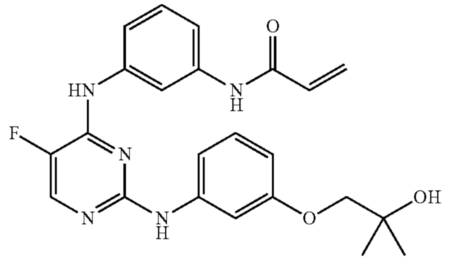

To a stirred solution of 7 (0.08 g, 0.2 mmol) and potassium carbonate (0.11 g, 0.8 mmol) in NMP (1 mL) at 0° C. was added 8 (0.023 g, 0.22 mmol) and the reaction mixture was stirred at 0° C. for 45 min The reaction mixture was added drop wise to a cold, stirring solution of 10% $NaHCO_3$ and stirred at the same temperature (0° C.) for 30 min. A solid precipitated out which was isolated by filtration through a Buchner funnel. The solid was washed with cold water, hexane and dissolved in a mixture of methanol/dichloromethane (50:50, 5 mL) and concentrated under reduced pressure. The residue obtained was suspended in cold water (10 mL), $Et_3N$ was added to it and it was extracted with ethyl acetate (2×5 mL). The combined ethyl acetate extract was washed with water (2 mL), brine (2 mL), dried over $Na_2SO_4$ and concentrated under reduced pressure. The residue obtained was further purified by column chromatography ($SiO_2$, 60-120, pet ether/ethyl acetate, 5/5) to get I-118 (35 mg, 38%) as a white solid. $^1H$ NMR ($CD_3OD$) δ ppm: 1.27 (s, 6H), 3.67 (s, 2H), 5.76 (dd, J=2.4 & 9.6 Hz, 1H), 6.34 (dd, J=2 & 16.8 Hz, 1H), 6.42 (dd, J=9.6 & 16.8 Hz, 1H), 6.54 (td, J=2 & 7.2 Hz, 1H), 7.07-7.12 (m, 2H), 7.27-7.31 (m, 2H), 7.40 (d, J=8 Hz, 1H), 7.45 (d, J=8 Hz, 1H), 7.92 (d, J=4 Hz, 1H), 8.07 (d, J=2 Hz, 1H); LCMS: m/e 436.2 (M−1).

Example 72

Preparation of N-(3-(5-fluoro-2-(3-(2-morpholino-2-oxoethoxy)phenylamino)pyrimidin-4-ylamino)phenyl)acrylamide I-110

I-110

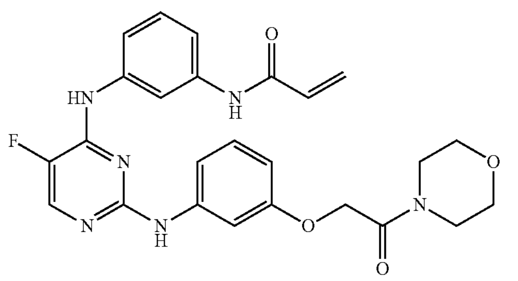

The title compound was prepared according to the schemes, steps and intermediates described in Example 20 by using 4-[(3-aminophenoxy)acetyl]-morpholine in place of 4 in Step-2. $^1$H NMR (DMSO-$d_6$) δ ppm: 3.4-3.5 (bm, 4H), 3.5-3.6 (bm, 4H), 4.69 (s, 2H), 5.75 (dd, J=2 & 10 Hz, 1H), 6.25 (dd, J=2 & 17.2 Hz, 1H), 6.42-6.49 (m, 2H), 7.05 (t, J=8 Hz, 1H), 7.29 (t, J=8 Hz, 3H), 7.41 (d, J=8 Hz, 1H), 7.57 (d, J=8.8 Hz, 1H), 7.91 (s, 1H), 8.12 (d, J=3.6 Hz, 1H), 9.15 (s, 1H), 9.45 (s, 1H), 10.12 (s, 1H); LCMS: m/e 491.0 (M-2).

The intermediate 4-[(3-aminophenoxy)acetyl]-morpholine was prepared by the scheme shown below.

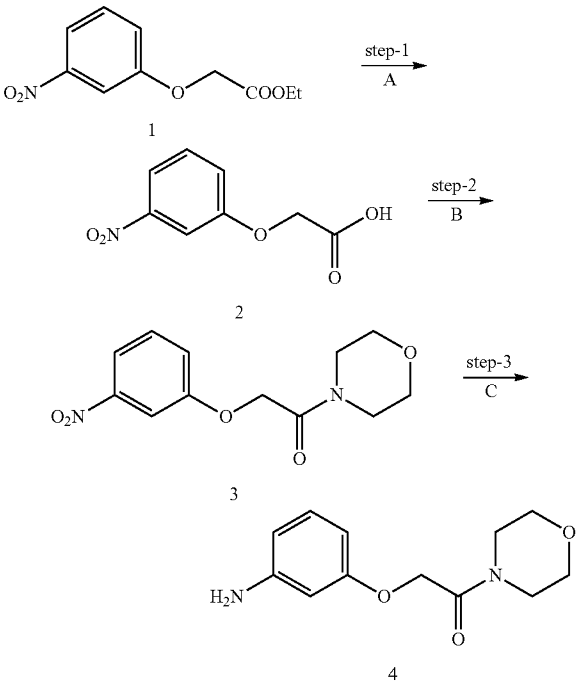

A) LiOH, THF, MeOH, $H_2O$, $H_2O$, rt, 4 h; B) $SOCl_2$, 85° C., morpholine, 0° C., 30 min; C) Pd—C, $H_2$, ethyl acetate, rt, 2 h.

Step-1

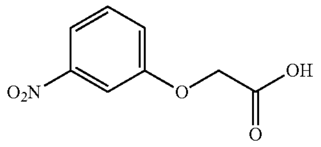

2

To a stirred solution of 1 (1.0 g, 4.44 mmol) in methanol/THF/water: 5 mL/5 mL/5 mL was added LiOH monohydrate (0.75 g, 17.76 mmol) and the reaction mixture was stirred at rt for 4 h. It was concentrated under reduced pressure, the residue was diluted with water (10 mL), acidified with 1.0 N HCl (PH~5-6) and extracted with ether (2×20 mL). The combined ether extract was washed with water (20 mL), brine (20 mL), dried over $Na_2SO_4$ and concentrated under reduced pressure to get 2 (0.8 g, 91.43%) as an off-white solid.

Step-2

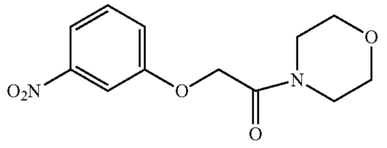

3

Thionyl chloride (2.0 ml, 27.56 mmol) was added to 2 (0.2 g, 1.014 mmol) under nitrogen atmosphere. A drop of N,N Dimethylformamide was added to the mixture and the contents were stirred at 85° C. for 2 h. After cooling to rt thionyl chloride was removed by concentration under reduced pressure. The residue was cooled to 0° C., morpholine (0.5 g, 5.74 mmol) was added to it in small portions and the reaction mixture was stirred at 0° C. for 30 min. The reaction mixture was allowed to come to rt and stirred at it for 30 min, cooled and quenched with water (10 mL). The contents were extracted with ether (2×10 mL) and the combined ether extract was washed with water (5 mL), brine (5 mL), dried over $Na_2SO_4$ and concentrated under reduced pressure to get 3 (0.180 g, 66.67%) as a yellow solid.

Step-3

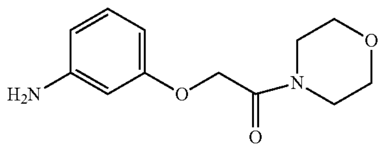

4

To a solution of 3 (0.180 g, 0.676 mmol) in ethyl acetate (10 mL)) was added Pd/C (0.036 g, 20% w/w) and the reaction mixture was allowed to stir under $H_2$ atmosphere (1.0 Kg hydrogen pressure) at rt for 2 h. The reaction mixture was filtered through a pad of Celite® and concentrated under reduced pressure to get A (0.14 g, 87.67%) as an off-white solid. It was used in the next step without further purifications.

Example 73

Preparation of N-(3-(5-fluoro-2-(3-(1-hydroxy-2-methylpropan-2-yloxy)phenylamino)pyrimidin-4-ylamino)phenyl)acrylamide I-91

I-91

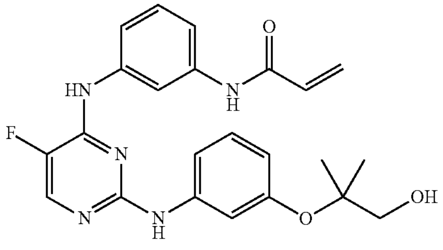

The title compound was prepared according to the schemes, steps and intermediates described in Example 20 by using 3-(1-hydroxy-2-methylpropan-2-yloxy)aniline in place of 4 in Step-2. $^1H$ NMR (DMSO-$d_6$) δ ppm: 1.16 (s, 6H), 3.32-3.35 (m, 2H), 4.81 (t, J=5.74 Hz, 1H), 5.74 (dd, J=1.84 & 10.04 Hz, 1H), 6.24 (dd, J=1.88 & 16.96 Hz, 1H), 6.44 (dd, J=10.12 & 16.96 Hz, 1H), 6.50 (dd, J=2.12 & 7.96 Hz, 1H), 7.02 (t, J=8.12 Hz, 1H), 7.26-7.30 (m, 2H), 7.41 (d, J=8.16 Hz, 1H), 7.48 (d, J=8.24 Hz, 1H), 7.57 (d, J=8.12 Hz, 1H), 7.92 (s, 1H), 8.09 (d, J=3.6 Hz, 1H), 9.07 (s, 1H), 9.41 (s, 1H), 10.09 (s, 1H); LCMS: m/e 438.0 (M+1).

The intermediate 3-(1-hydroxy-2-methylpropan-2-yloxy) aniline was prepared by the scheme shown below.

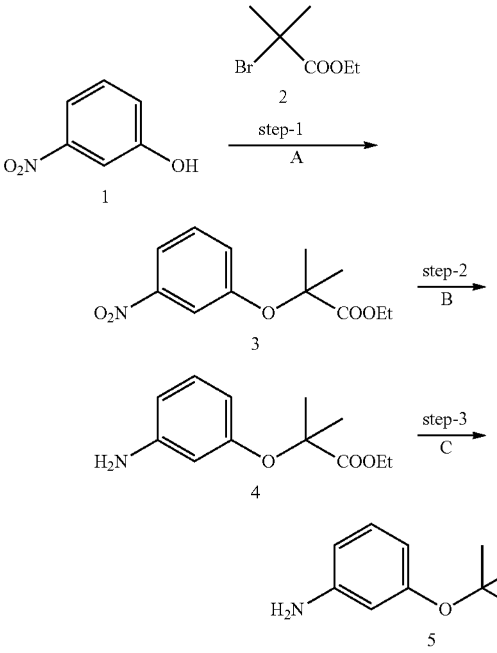

A) $K_2CO_3$, DMF, 16 h, rt;
B) Pd/C, ethanol, 5 h, rt;
C) LAH (1M in THF solution), 0° C. to rt, 2 h.

Step-1

3

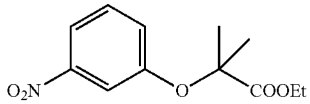

To a solution of 1 (0.5 g 3.59 mmol) and 2 (0.84 g 4.316 mmol) in DMF was added $K_2CO_3$ (0.99 g, 7.194 mmol). After stirring at rt for 16 h, reaction mixture was concentrated under reduced pressure. The residue was diluted with ethyl acetate (10 mL) and washed with 10% NaOH solution (5 mL), water (5 mL) and brine solution (5 mL). Drying over $Na_2SO_4$, followed by concentration under reduced pressure gave 3 as red brown liquid (0.5 g, 52%).

Step-2

4

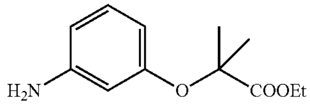

To a stirred solution of 3 (0.45 g, 1.77 mmol) in ethanol (5 mL) was added Pd/C (45 mg) and the reaction mixture was hydrogenated (bladder pressure, ~1.5 Kg) for 5 h. The reaction mixture was passed through a Celite® bed and concentrated under vacuum to get 4 (0.35 g, 88%) as a colorless liquid.

Step-3

5

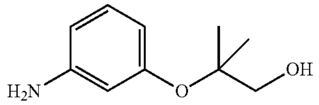

To a stirred solution of 4 (0.25 g, 1.15 mmol) in THF (5 mL) under $N_2$ was added LAH (3.45 mL, 3.35 mmol, 1M solution in THF,) at 0° C. The reaction mixture was allowed to come to rt and stirred at it for 2 h. It was carefully quenched with saturated $Na_2SO_4$ solution (2 mL), filtered and concentrated. The residue was further purified by column chromatography ($SiO_2$, 60-120, pet ether/ethyl acetate, 6/4) to give 5 as a light brown liquid (0.15 g, 71%).

Example 74

Preparation of N-(3-(5-fluoro-2-(3-(2-(2-oxopyrrolidin-1-yl)ethoxy)phenylamino)pyrimidin-4-ylamino)phenyl)acrylamide I-164

I-164

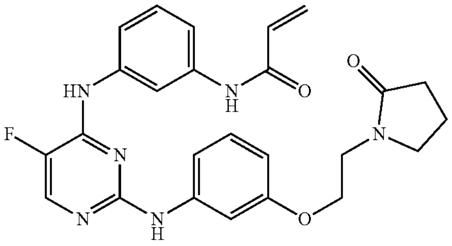

The title compound was prepared according to the schemes, steps and intermediates described in Example 20 by using 3-(2-(2-oxopyrrolidin-1-yl)ethoxy)aniline in place of 4 in Step-2. $^1$H NMR (DMSO-$d_6$) δ ppm: 1.89 (quin, J=7.6 Hz, 2H), 2.21 (t, J=8 Hz, 2H), 3.40 (t, J=6.8 Hz, 2H), 3.50 (t, J=5.6 Hz, 2H), 3.93 (t, J=5.2 Hz, 2H), 5.75 (dd, J=2 & 10 Hz, 1H), 6.25 (dd, J=2 & 16.84 Hz, 1H), 6.42-6.49 (m, 2H), 7.05 (t, J=8.4 Hz, 1H), 7.28 (t, J=8 Hz, 2H), 7.33 (s, 1H), 7.43 (d, J=8 Hz, 1H), 7.57 (d, J=8 Hz, 1H), 7.92 (s, 1H), 8.12 (d, J=3.6 Hz, 1H), 9.15 (s, 1H), 9.45 (s, 1H), 10.13 (s, 1H); LCMS: m/e 475 (M-2).

Example 75

Preparation of N-(3-(5-fluoro-2-(6-(3-(methylsulfonyl)propoxy)pyridin-3-ylamino)pyrimidin-4-ylamino)phenyl)acrylamide I-80

I-80

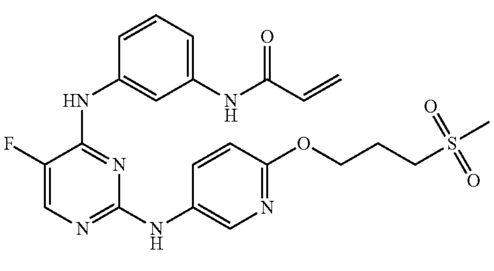

The title compound was prepared according to the schemes, steps and intermediates described in Example 20 by using 3-amino-6-(3-(methylsulfonyl)propoxy)pyridine in place of 4 in Step-2. $^1$H NMR (DMSO-$d_6$) δ ppm: 2.05-2.20 (m, 2H), 3.00 (s, 3H), 3.24 (t, J=7.46 Hz, 2H), 4.27 (t, J=6.32 Hz, 2H), 5.75 (dd, J=1.76 & 10 Hz, 1H), 6.25 (dd, J=1.8 & 16.96 Hz, 1H), 6.45 (dd, J=10.04 & 16.92 Hz, 1H), 6.65 (d, J=8.88 Hz, 1H), 7.27 (t, J=8.08 Hz, 1H), 7.39 (d, J=8.08 Hz, 1H), 7.49 (d, J=8 Hz, 1H), 7.92 (s, 1H), 7.99 (dd, J=2.6 & 8.76 Hz, 1H), 8.07 (d, J=3.64 Hz, 1H), 8.31 (d, J=2.28 Hz, 1H), 9.10 (s, 1H), 10.11 (s, 1H); LCMS: m/e 486.9 (M+1).

Example 76

Preparation of N-(3-(2-(6-cyclobutoxypyridin-3-ylamino)-5-fluoropyrimidin-4-ylamino)phenyl)acrylamide I-79

I-79

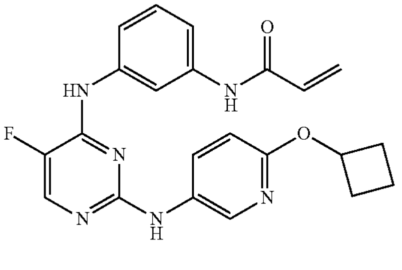

The title compound was prepared according to the schemes, steps and intermediates described in Example 20 by using 3-amino-6-cyclobutoxypyridine in place of 4 in Step-2. $^1$H NMR (DMSO-$d_6$) δ ppm: 1.57-1.66 (m, 1H), 1.71-1.78 (m, 1H), 1.94-2.04 (m, 2H), 2.32-2.38 (m, 2H), 4.95-5.05 (m, 1H), 5.73-5.76 (m, 1H), 6.25 (dd, J=1.92 & 16.92 Hz, 1H), 6.45 (dd, J=10.08 & 16.92 Hz, 1H), 6.58 (d, J=8.84 Hz, 1H), 7.25 (t, J=8.04 Hz, 1H), 7.39 (d, J=7.84 Hz, 1H), 7.45-7.55 (m, 1H), 7.90 (s, 1H), 7.94 (dd, J=2.72 & 8.88 Hz, 1H), 8.06 (d, J=3.68 Hz, 1H), 8.27 (d, J=2.6 Hz, 1H), 9.04 (s, 1H), 9.41 (s, 1H), 10.1 (s, 1H); LCMS: m/e 421.2 (M+1).

Example 77

Preparation of N-(3-(5-fluoro-2-(6-((1-methylpiperidin-4-yl)methoxy)pyridin-3-ylamino)pyrimidin-4-ylamino)phenyl)acrylamide I-78

I-78

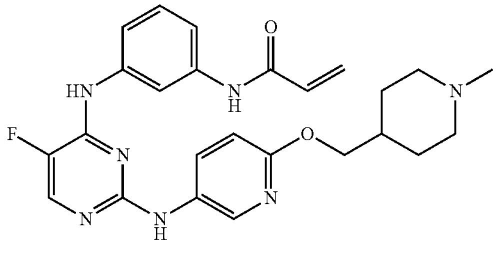

The title compound was prepared according to the schemes, steps and intermediates described in Example 20 by using 3-amino-6-(1-methylpiperidin-4-yl)methoxypyridine in place of 4 in Step-2. $^1$H NMR (DMSO-$d_6$) δ ppm: 1.23-1.27 (m, 3H), 1.65-1.69 (m, 2H), 1.83 (t, J=11.72 Hz, 2H), 2.14 (s, 3H), 2.75 (d, J=11.24 Hz, 2H), 4.0 (d, J=6.2 Hz, 2H), 5.74 (dd, J=2 & 10.04 Hz, 1H), 6.24 (dd, J=1.96 & 16.92 Hz, 1H), 6.45 (dd, J=10.08 & 16.92 Hz, 1H), 6.62 (d, J=8.88 Hz, 1H), 7.27 (t, J=8.08 Hz, 1H), 7.40 (d, J=8.88 Hz, 1H), 7.47 (d, J=7.6 Hz, 1H), 7.92 (s, 1H), 7.97 (dd, J=2.76 & 8.92 Hz, 1H), 8.07 (d, J=3.72 Hz, 1H), 8.28 (d, J=2.64 Hz, 1H), 9.07 (s, 1H), 9.41 (s, 1H), 10.11 (s, 1H); LCMS: m/e 478.0 (M+1).

Example 77

Preparation of N-(3-(5-fluoro-2-(4-chloro-3-methoxyphenylamino)pyrimidin-4-ylamino)phenyl) acrylamide I-74

I-74

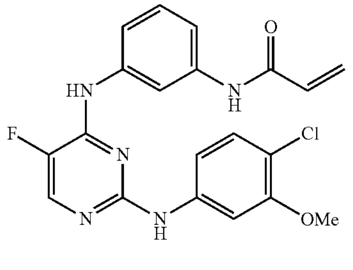

The title compound was prepared according to the schemes, steps and intermediates described in Example 20 by using 4-chloro-3-methoxyaniline in place of 4 in Step-2.

$^{1}$H NMR (DMSO-$d_6$) δ ppm: 3.64 (s, 3H), 5.74 (dd, J=2.12 & 9.96 Hz, 1H), 6.24 (dd, J=1.84 & 17 Hz, 1H), 6.44 (dd, J=10 & 16.84 Hz, 1H), 7.13 (s, 1H), 7.28 (t, J=8.08 Hz, 1H), 7.36 (dd, J=2.12 & 8.68 Hz, 1H), 7.40 (d, J=7.64 Hz, 1H), 7.45 (d, J=2.04 Hz, 1H), 7.50 (d, J=8.12 Hz, 1H), 7.91 (s, 1H), 8.13 (d, J=3.52 Hz, 1H), 9.28 (s, 1H), 9.48 (s, 1H), 10.12 (s, 1H); LCMS: m/e 414.0 (M+1).

Example 78

Preparation of N-(3-(5-fluoro-2-(4-(2-hydroxy-2-methylpropoxy)phenylamino)pyrimidin-4-ylamino) phenyl)acrylamide I-73

I-73

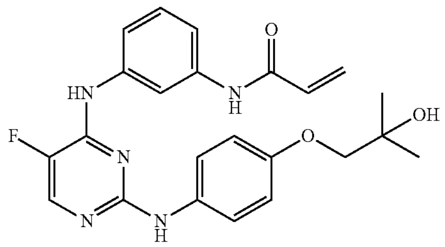

The title compound was prepared according to the schemes, steps and intermediates described in Example 20 by using 4-(2-hydroxy-2-methylpropoxy)aniline in place of 4 in Step-2. $^{1}$H NMR (MeOD) δ ppm: 1.33 (s, 6H), 3.75 (s, 2H), 5.80 (dd, J=3.28 & 10.64 Hz, 1H), 6.39 (dd, J=2.24 & 16.96 Hz, 1H), 6.47 (dd, J=9.6 & 16.96 Hz, 1H), 6.84 (td, J=3.48 & 9.0 Hz, 2H), 7.30 (t, J=7.72 Hz, 1H), 7.41-7.50 (m, 4H), 7.89 (d, J=3.88 Hz, 1H), 8.09 (s, 1H); LCMS: m/e 438 (M+1).

Example 79

Preparation of N-(3-(5-fluoro-2-(6-(1,1-dioxidothiomorpholin-4-yl) pyridin-3-ylamino)pyrimidin-4-ylamino)phenyl)acrylamide I-72

I-72

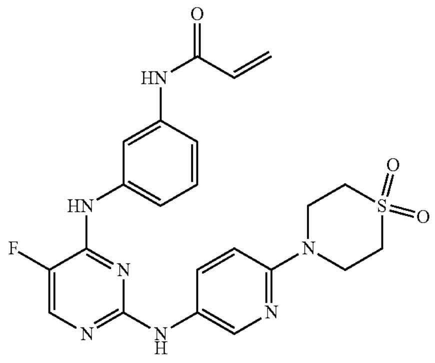

The title compound was prepared according to the schemes, steps and intermediates described in Example 20 by using 3-amino-6-(1,1-dioxidothiomorpholin-4-yl) pyridine in place of 4 in Step-2. $^{1}$H NMR (DMSO-$d_6$) δ ppm: 3.00-3.15 (bm, 4H), 3.90-4.10 (bm, 4H), 5.76 (dd, J=1.64 & 10.04 Hz, 1H), 6.26 (dd, J=1.72 & 16.92 Hz, 1H), 6.46 (dd, J=10.04 & 16.88 Hz, 1H), 6.87 (d, J=9.04 Hz, 1H), 7.20 (t, J=8.04 Hz, 1H), 7.39 (d, J=8.24 Hz, 1H), 7.50 (d, J=7.68 Hz, 1H), 7.90-7.93 (m, 2H), 8.06 (d, J=3.6 Hz, 1H), 8.35 (d, J=2.4 Hz, 1H), 9.0 (s, 1H), 9.40 (s, 1H), 10.12 (s, 1H); LCMS: m/e 484 (M+1).

Example 80

Preparation of N-(3-(5-fluoro-2-(6-(2-(2-oxopyrrolidin-1-yl)ethoxy)pyridin-3-ylamino)pyrimidin-4-ylamino)phenyl)acrylamide I-70

I-70

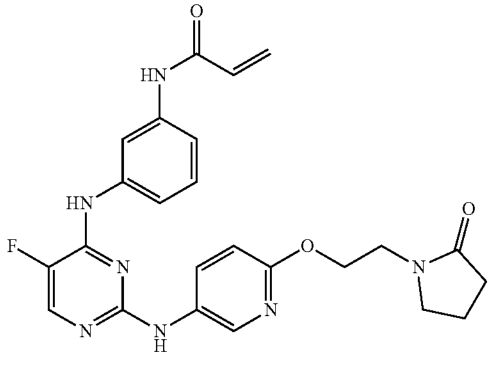

The title compound was prepared according to the schemes, steps and intermediates described in Example 20 by using 3-amino-6-(2-(2-oxopyrrolidin-1-yl)ethoxy)pyridine in place of 4 in Step-2. $^{1}$H NMR (DMSO-$d_6$) δ ppm: 1.90 (quintet, J=7.6 Hz, 2H), 2.19 (t, J=8.04 Hz, 2H), 3.41 (t, J=6.88 Hz, 2H), 3.50 (t, J=5.36 Hz, 2H), 4.27 (t, J=5.48 Hz, 2H), 5.75 (d, J=10.92 Hz, 1H), 6.25 (d, J=17.04 Hz, 1H), 6.45 (dd, J=10.12 & 16.84 Hz, 1H), 6.63 (d, J=8.96 Hz, 1H), 7.27 (t, J=8.04 Hz, 1H), 7.39 (d, J=7.56 Hz, 1H), 7.47 (d, J=7.32 Hz, 1H), 7.92 (s, 1H), 7.98 (dd, J=2.36 & 8.84 Hz, 1H), 8.08 (d, J=3.3 Hz, 1H), 8.31 (d, J=2.24 Hz, 1H), 9.10 (s, 1H), 9.44 (s, 1H), 10.11 (s, 1H); LCMS: m/e 478.0 (M+1).

Example 81

Preparation of (R)—N-(3-(5-fluoro-2-(6-(tetrahydrofuran-3-yloxy)pyridin-3-ylamino)pyrimidin-4-ylamino)phenyl)acrylamide I-69

I-69

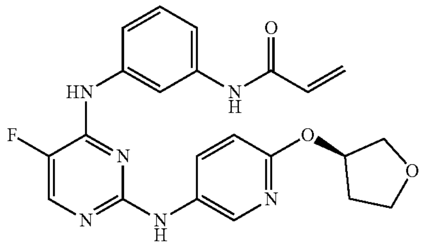

The title compound was prepared according to the schemes, steps and intermediates described in Example 20 by using (R)-3-amino-6-(tetrahydrofuran-3-yloxy)pyridine in place of 4 in Step-2. $^1$H NMR (DMSO-$d_6$) δ ppm: 1.91-1.99 (m, 1H), 2.14-2.23 (m, 1H), 3.70-3.77 (m, 2H), 3.81 (dd, J=7.90 & 15.48 Hz, 1H), 3.88 (dd, J=4.76 & 10.16 Hz, 1H), 5.38 (t, J=4.68 Hz, 1H), 5.75 (dd, J=1.72 & 10.08 Hz, 1H), 6.24 (d, J=16.92 Hz, 1H), 6.45 (dd, J=10.16 & 16.88 Hz, 1H), 6.63 (d, J=8.84 Hz, 1H), 7.26 (d, J=7.64 Hz, 1H), 7.39 (d, J=7.92 Hz, 1H), 7.46 (d, J=7.64 Hz, 1H), 7.92 (s, 1H), 7.97 (dd, J=2.6 & 8.83 Hz, 1H), 8.07 (d, J=3.6 Hz, 1H), 8.32 (d, J=2.48 Hz, 1H), 9.08 (s, 1H), 9.42 (s, 1H), 10.10 (s, 1H); LCMS: m/e 437.2 (M+1).

Example 82

Preparation of N-(3-(2-(4-chloro-3-(3-(methylsulfonyl)propoxy)phenylamino)-5-fluoropyrimidin-4-ylamino)phenyl)acrylamide I-55

I-55

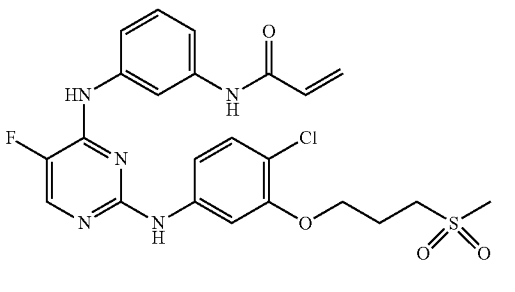

The title compound was prepared according to the schemes, steps and intermediates described in Example 20 by using 4-chloro-3-(3-(methylsulfonyl)propoxy)aniline in place of 4 in Step-2. $^1$H NMR (DMSO-$d_6$) δ ppm: 2.07-2.14 (m, 2H), 3.0 (s, 3H), 3.22 (t, J=7.72 Hz, 2H), 3.90 (t, J=6.08 Hz, 2H), 5.75 (dd, J=1.88 & 10.08 Hz, 1H), 6.24 (dd, J=1.84 & 16.92 Hz, 1H), 6.44 (dd, J=10.12 & 16.96 Hz, 1H), 7.15 (d, J=8.72 Hz, 1H), 7.30 (t, J=8.08 Hz, 1H), 7.35 (dd, J=2.2 & 8.8 Hz, 1H), 7.43 (d, J=8 Hz, 1H), 7.45-7.55 (m, 2H), 7.91 (s, 1H), 8.14 (d, J=3.56 Hz, 1H), 9.31 (s, 1H), 9.49 (s, 1H), 10.14 (s, 1H); LCMS: m/e 520.0 (M+1).

Example 83

Preparation of N-(3-(2-(3-fluoro-4-(2-methoxyethoxy)phenylamino)-5-fluoropyrimidin-4-ylamino)phenyl)acrylamide I-96

I-96

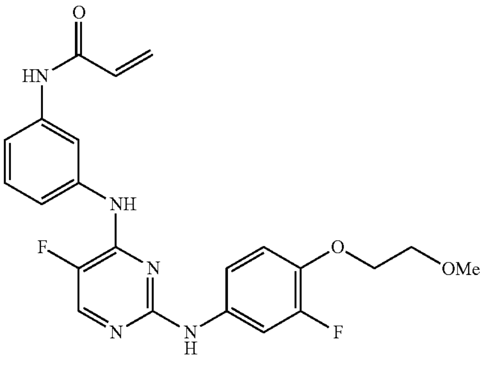

The title compound was prepared according to the schemes, steps and intermediates described in Example 20 by using 3-fluoro-4-(2-methoxyethoxy)aniline in place of 4 in Step-2. $^1$H NMR (DMSO, 400 MHz) δ 10.13 (s, 1H), 9.43 (s, 1H), 9.18 (s, 1H), 8.09 (d, 1H, J=3.68 Hz), 7.92 (s, 1H), 7.65 (dd, 1H, J=2.3, 14.2 Hz), 7.47 (d, 1H, J=8.24 Hz), 7.41 (d, 1H, J=8.28 Hz), 7.27 (t, 2H, J=8.0 Hz), 6.94 (t, 1H, J=9.4 Hz), 6.44 (dd, 1H, J=16.96, 10.1 Hz), 6.23 (dd, 1H, J=1.84, 16.96 Hz), 5.73 (dd, 1H, J=1.4, 10.1 Hz), 4.04 (m, 2H), 3.61 (m, 2H), 3.29 (s, 3H). MS m/z: 442.0 (M+H$^+$).

Example 84

Preparation of N-(3-(2-(4-tert-butoxycarbonyl-2,3-dihydrobenzo[1,4]oxazin-6-yl)amino-5-fluoropyrimidin-4-ylamino)phenyl)acrylamide I-175

I-175

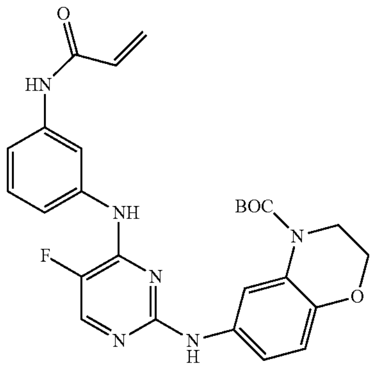

The title compound was prepared according to the schemes, steps and intermediates described in Example 20 by using 6-amino-4-tert-butoxycarbonyl-2,3-dihydrobenzo[1,4]oxaxine in place of 4 in Step-2. MS m/z: 507.1 (M+H$^+$).

Example 85

Preparation of N-(3-(2-(4-tert-butoxycarbonyl-2,3-dihydrobenzo[1,4]oxazin-6-yl)amino-5-fluoropyrimidin-4-ylamino)phenyl)acrylamide I-174

I-174

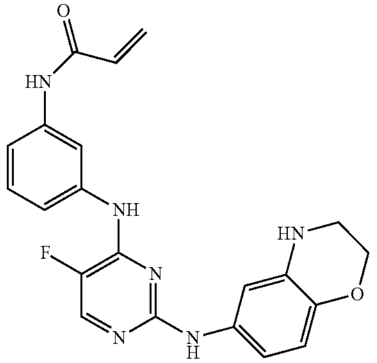

The title compound was prepared by treating the product of Example 84 with 4N HCl in dioxane at rt for 1 hr followed by removal of solvents in vacuo. MS m/z: 407.1 (M+H$^+$).

Example 86

Preparation of N-(3-(2-(4-trifluoroacetyl-2,3-dihydrobenzo[1,4]oxazin-6-yl)amino-5-fluoropyrimidin-4-ylamino)phenyl)acrylamide I-143

I-143

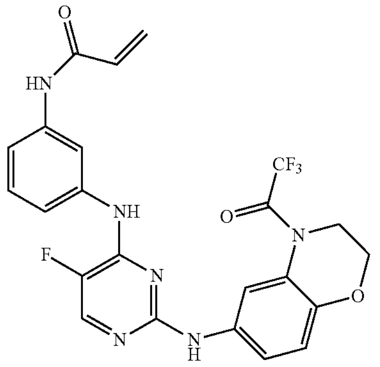

The title compound was prepared by treating the product of Example 85 with trifluoroacetic anhydride at rt for 1 hr followed by removal of solvents in vacuo. MS m/z: 503.1 ($M+H^+$).

Example 87

Preparation of N-(3-(2-(4-methylsulfonyl-2,3-dihydrobenzo[1,4]oxazin-6-yl)amino-5-fluoropyrimidin-4-ylamino)phenyl)acrylamide I-140

I-140

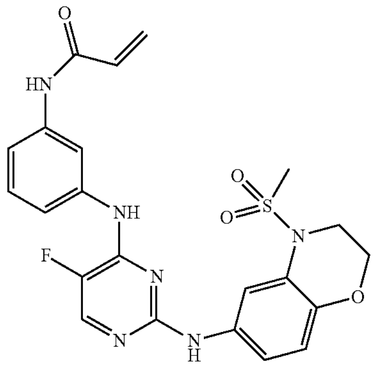

The title compound was prepared by treating the product of Example 85 with mesyl chloride $Et_3N$ in $CH_2Cl_2$ at 0° C. for 30 min, followed by washing with aqueous $NaHCO_3$, drying over $Na_2SO_4$ and removal of solvents in vacuo. MS m/z: 485.1 ($M+H^-$).

Example 88

Preparation of N-(3-(2-(4-methyl-2,3-dihydrobenzo[1,4]oxazin-6-yl)amino-5-fluoropyrimidin-4-ylamino)phenyl)acrylamide I-126

I-126

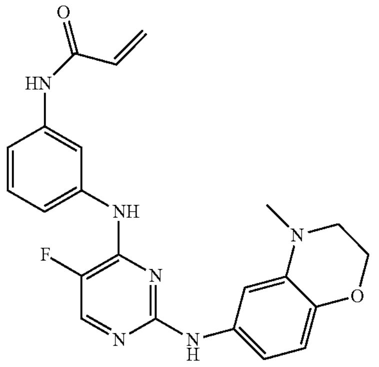

The title compound was prepared according to the schemes, steps and intermediates described in Example 20 by using 6-amino-4-methyl-2,3-dihydrobenzo[1,4]oxazine in place of 4 in Step-2. MS m/z: 421.1 ($M+H^+$).

Example 89

Preparation of N-(3-(2-(4-acetyl-2,3-dihydrobenzo[1,4]oxazin-6-yl)amino-5-fluoropyrimidin-4-ylamino)phenyl)acrylamide I-112

I-112

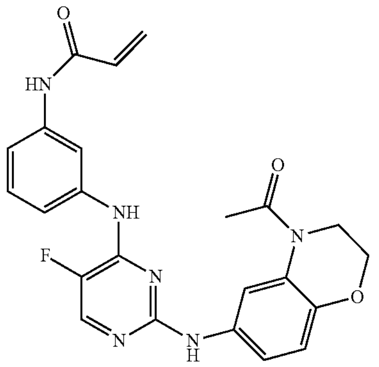

The title compound was prepared by treating the product of Example 85 with acetic anhydride and pyridine in $CH_2Cl_2$ at rt for 1 hr, followed by washing with 1N HCl, then with aqueous $NaHCO_3$, drying over $Na_2SO_4$ and removal of solvents in vacuo. MS m/z: 449.1 ($M+H^+$).

Example 90

Preparation of N-(3-(2-(1-tert-butoxycarbonyl-1H-indazol-5-yl)amino)-5-fluoropyrimidin-4-ylamino)phenyl)acrylamide I-151

I-151

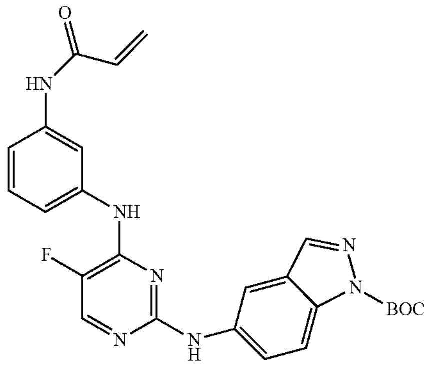

The title compound was prepared according to the schemes, steps and intermediates described in Example 20 by using 5-amino-N-(tert-butoxycarbonyl)-1H-indazole in place of 4 in Step-2. MS m/z: 490.2 $(M+H^+)$.

Example 91

Preparation of N-(3-(2-(1H-indazol-5-yl)amino)-5-fluoropyrimidin-4-ylamino)phenyl)acrylamide I-156

I-156

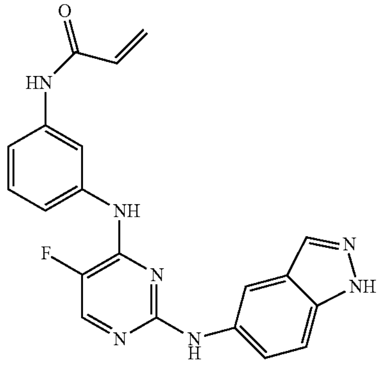

The title compound was prepared by treating the product of Example 90 with 4N HCl in dioxane at rt for 1 hr followed by removal of solvents in vacuo. MS m/z: 390.1 $(M+H^+)$.

Example 92

Preparation of N-(3-(2-(1-methyl-1H-indazol-5-yl)amino)-5-fluoropyrimidin-4-ylamino)phenyl)acrylamide I-155

I-155

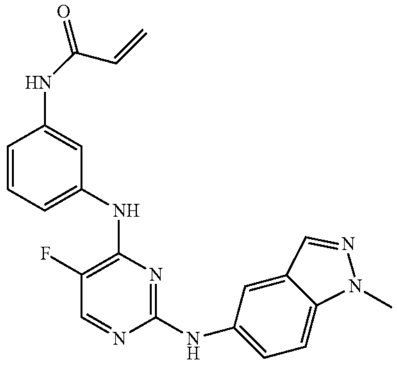

The title compound was prepared according to the schemes, steps and intermediates described in Example 20 by using 5-amino-1-methyl-1H-indazole in place of 4 in Step-2. MS m/z: 404.2 $(M+H^+)$.

Example 93

Preparation of N-(3-(5-fluoro-2-(3-sulfamoylphenylamino)pyrimidin-4-ylamino)phenyl)acrylamide I-160

I-160

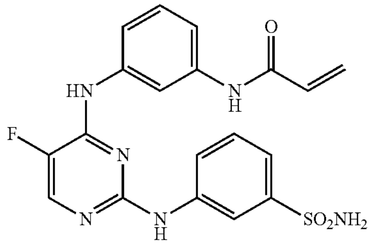

The title compound was prepared according to the schemes, steps and intermediates described below.

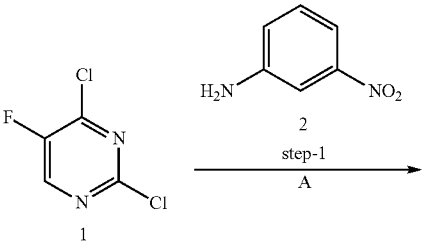

-continued

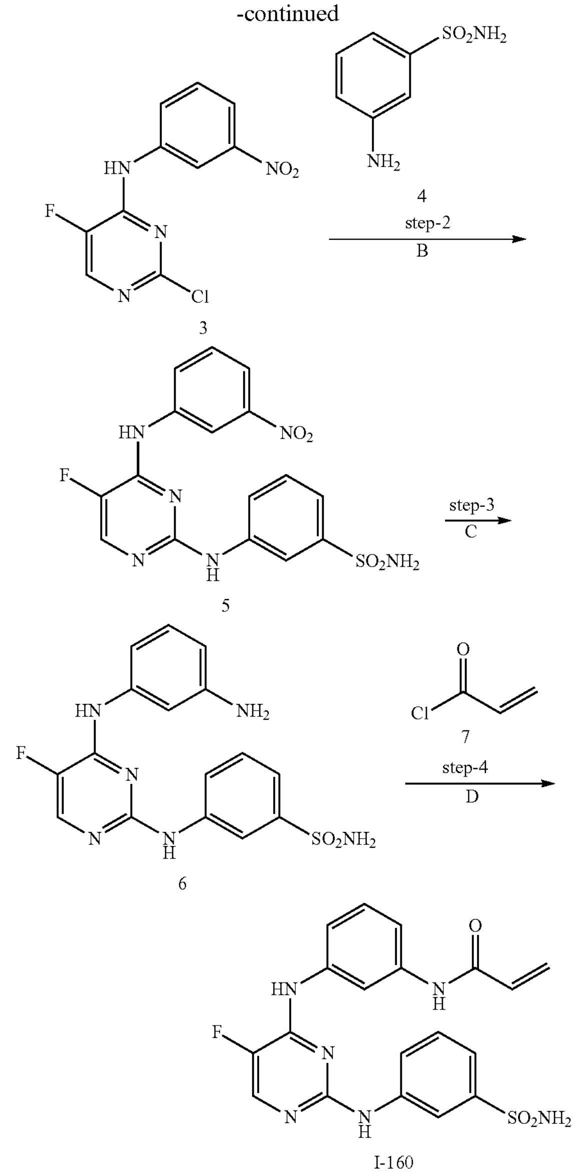

A) DIPEA, n-butanol, 120° C., 2 h, pressure tube;
B) AcOH, ethanol, 90° C., 16 h;
C) Pd-C, $H_2$, ethanol, rt, 3 h;
D) acryloyl chloride, $K_2CO_3$, 0° C., 60 min.

Step-1

3

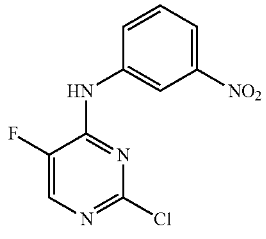

A pressure tube was charged with 2 (10.0 g, 0.072 mol), 1 (24.1 g, 0.145 mol), n-BuOH (100 mL) and DIPEA (13.9 g, 0.108 mol) and the contents were stirred at 120° C. for 2 h. The reaction mixture was cooled, the precipitated solid was isolated by filtration through a Buchner funnel, washed with cold hexane and dried to get 3 (12.5 g, 64%) as a yellow solid. It was used in the next step without further purification.

Step-2

5

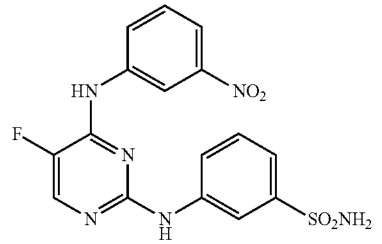

To a solution of 3 (0.25 g, 0.93 mmol) and 4 (0.16 g, 0.93 mmol) in ethanol (2.5 mL) was added glacial acetic acid (0.083 g, 1.39 mmol), and the reaction mixture was stirred in a pressure tube at 90° C. for 16 h. It was cooled, the precipitated solid was isolated by filtration through a Buchner funnel, washed with cold ether and dried to get 5 (0.245 g, 65%) as brown solid. It was used in the next step without further purification.

Step-3

6

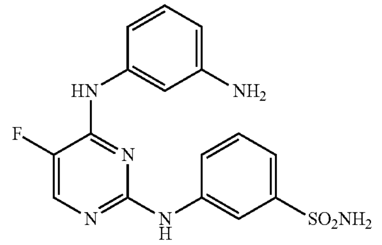

To a solution of 5 (0.1 g, 0.24 mmol in methanol (4 mL)) was added 10% Pd/C (0.2 g, 20% w/w) and the reaction mixture was allowed to stir under $H_2$ atmosphere (1.5 Kg hydrogen pressure) at rt for 3 h. The reaction mixture was filtered through a pad of Celite® and concentrated under reduced pressure to get 6 (0.076 g, 82%) as a brown solid. It was used in the next step without further purification.

Step-4

I-160

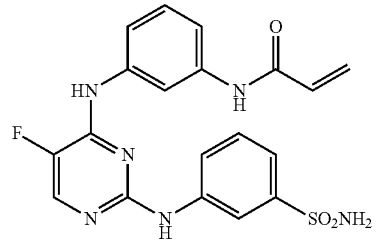

To a stirred solution of 6 (0.07 g, 0.18 mmol) and potassium carbonate (0.051 g, 0.37 mmol) in NMP (0.7 mL) at 0° C. was added acryloyl chloride (0.021 g, 0.23 mmol) and the reaction mixture was stirred at 0° C. for 60 min The reaction mixture was added drop wise to a cold, stirring solution of 10% $NaHCO_3$ and kept at the same temperature (0° C.) for 30 min. A solid precipitated out which was isolated by filtration through a Buchner funnel. The solid was washed with cold water and hexane and dissolved in mixture of methanol/dichloromethane (50:50, 5 mL) and concentrated under reduced pressure. The residue obtained was suspended in cold water (10 mL), $Et_3N$ was added to it and it was extracted with ethyl acetate (2×10 mL). The combined ethyl acetate extract was washed with water (5 mL), brine (5 mL), dried over $Na_2SO_4$ and concentrated under reduced pressure get a residue. The crude residue was further purified by column chromatography (neutral $Al_2O_3$, MeOH/chloroform: 3/97) to get I-160 (0.028 g, 35%) as light brown solid. $^1H$ NMR (DMSO-$d_6$) δ ppm: 5.75 (dd, J=1.68 & 10.24 Hz, 1H), 6.25 (dd, J=1.8 & 17 Hz, 1H), 6.43 (dd, J=10 & 16.92 Hz, 1H), 7.27-7.35 (m, 5H), 7.40 (d, J=8 Hz, 1H), 7.60 (d, J=8.16 Hz, 1H), 7.92 (s, 1H), 7.95-8.05 (m, 1H), 8.07 (s, 1H), 8.14 (d, J=3.52 Hz, 1H), 9.50 (s, 2H), 10.12 (s, 1H); LCMS: m/e 428.9 (M+1).

Example 94

Preparation of N-(3-(5-cyano-2-(4-(2-methoxyethoxy)phenylamino)pyrimidin-4-ylamino)phenyl) acrylamide I-109

I-109

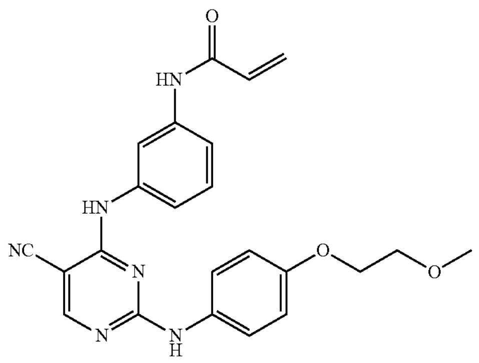

The title compound was prepared according to the steps and intermediates as described below.

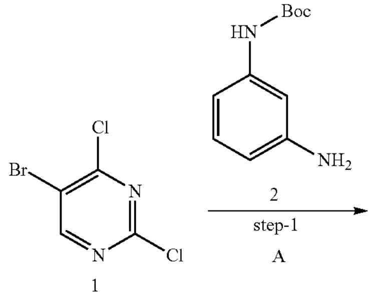

-continued

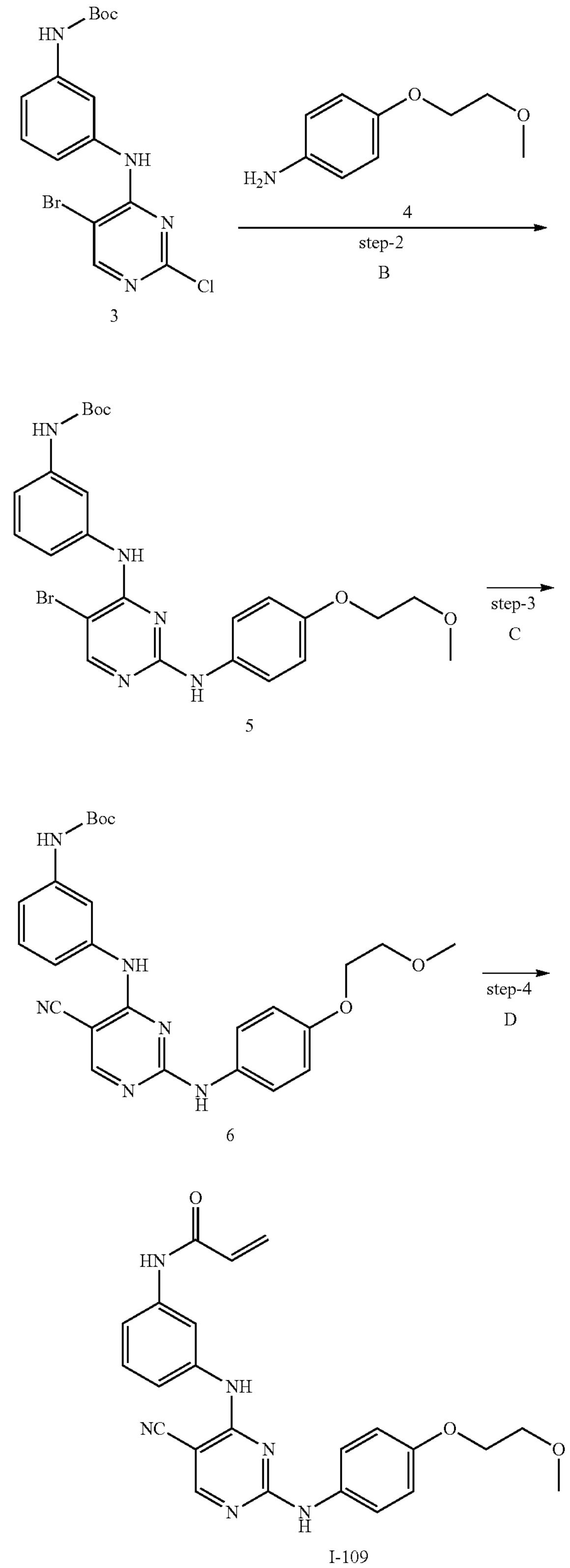

A) DMA, $K_2CO_3$, rt, 10 h, pressure tube;
B) PTSA, dioxane, 100° C., 2 h;
C) $Zn(CN)_2$, $Ph_3P$, DMF, 120° C., 12 h;
D) 4N HCl, dioxane, rt, 1 hr; then acryloyl chloride, $Et_3N$, DCM, -10° C., 10 min.

Step-1

3

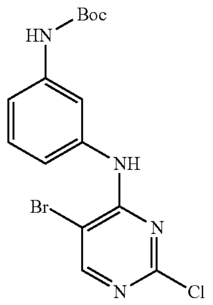

To a solution of 5-bromo-2,4-dichloropyrimidine (0.45 g, 2.0 mmol) and tert-butyl 3-aminophenylcarbamate (0.44 g, 2.1 mmol) in DMA (3 mL) was added $K_2CO_3$ (0.55 g, 4.0 mmol). The suspension was stirred for 10 hours. Water (10 mL) was added and the precipitate was collected by filtration. The solid was washed with ether and dried to yield 0.8 g of compound 3. MS: m/e=399.1, 401.2 (M+1).

Step-2

5

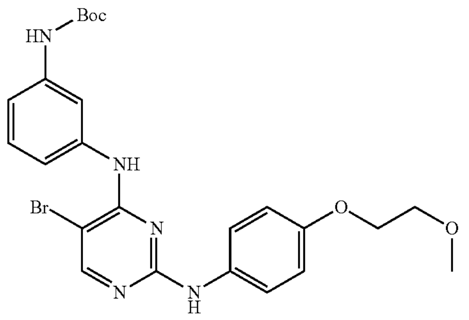

To a solution of compound 3 (400 mg, 1.0 mmol) and 4-(2-methoxyethoxy)aniline (0.2 g, 1.2 mmol) in 8 ml dioxane was added 4-methylbenzenesulfonic acid monohydrate (0.15 g, 0.8 mmol). The mixture was stirred at 100° C. for two hours. The solvent was evaporated. The residue was dissolved in 30 ml ethyl acetate and washed with $NaHCO_3$ aqueous solution, water and brine. The organic layer was separated and dried over $Na_2SO_4$. After removal of solvent, the crude product was subject to chromatography on silica gel (hexane:EtOAc=1:1). 0.40 g of the title compound 5 was obtained: MS m/z: 530.1, 532.1 (M+H$^+$).

Step-3

6

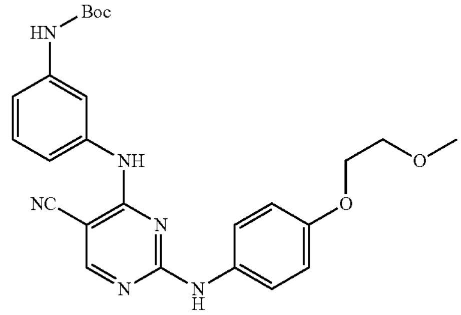

To a suspension of $Zn(CN)_2$ (0.24 g, 2.0 mmol), $Pd(PPh_3)_4$ (60 mg, 0.05 mmol) in 3 ml DMF was added to 5 (0.25 g, 0.5 mmol). The mixture was degassed and sealed under argon, and heated at 120° C. for 12 hours. Water (10 ml) was added and the precipitate was collected by filtration. The solid was washed with ether and dried to yield 0.2 g of compound 6. MS: m/e=477.1 (M+1).

Step-4

I-109

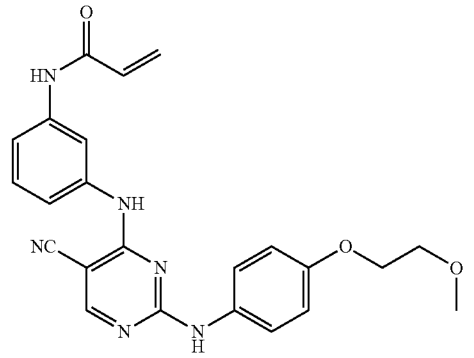

Compound 6 (0.10 g, 0.21 mmol) was dissolved in 4 N HCl (2 mL) in dioxane. The mixture was stirred at rt for 1 hour. After removal of solvents, a 5-mL portion of DCM was poured in followed by evaporation to dryness. This process of DCM addition followed by evaporation was repeated three times to give a residue solid which was used directly for the next step: MS m/z: 377.0 (M+H$^+$).

To a solution of the intermediate obtained above, triethylamine (0.1 ml, 0.8 mmol) in 2 ml dichloromethane was added acryloyl chloride (19 mg, 0.21 mmol) at −10° C. The reaction was stirred for 10 minutes at −10° C. and was quenched by $NaHCO_3$ aqueous solution. Ethyl acetate (10 mL) was added and washed with $NaHCO_3$ aqueous solution, water and brine. The organic layer was separated and dried over $Na_2SO_4$. After removal of solvent, the crude product was subject to chromatography on silica gel (hexane:EtOAc=1:2) to give 30 mg of the title compound. MS m/z: 431.1 (M+H$^+$).

Example 95

Preparation of N-(3-(5-cyano-2-(6-methoxypyridin-3-ylamino)pyrimidin-4-ylamino)phenyl)acrylamide I-173

I-173

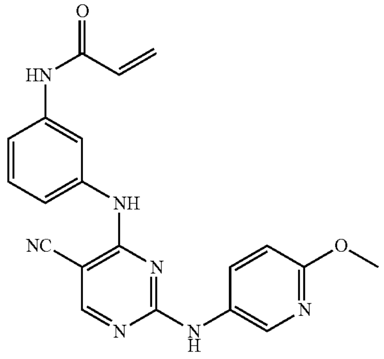

The title compound was prepared according to the schemes, steps and intermediates described in Example 94 by using 3-amino-6-methoxypyridine in place of 4 in Step-2. MS m/z: 388.2 (M+H+).

Example 96

Preparation of N-(3-(5-cyclopropyl-2-(4-(2-methoxyethoxy)phenylamino)pyrimidin-4-ylamino) phenyl)acrylamide I-139

I-139

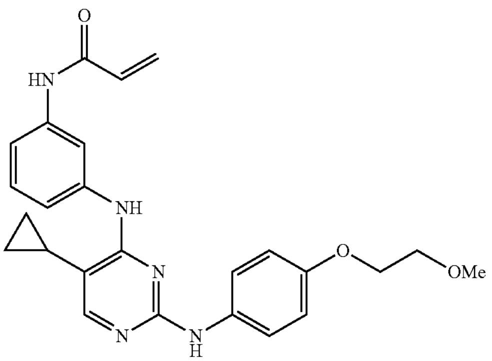

The title compound was prepared according to the steps and intermediates as described below.

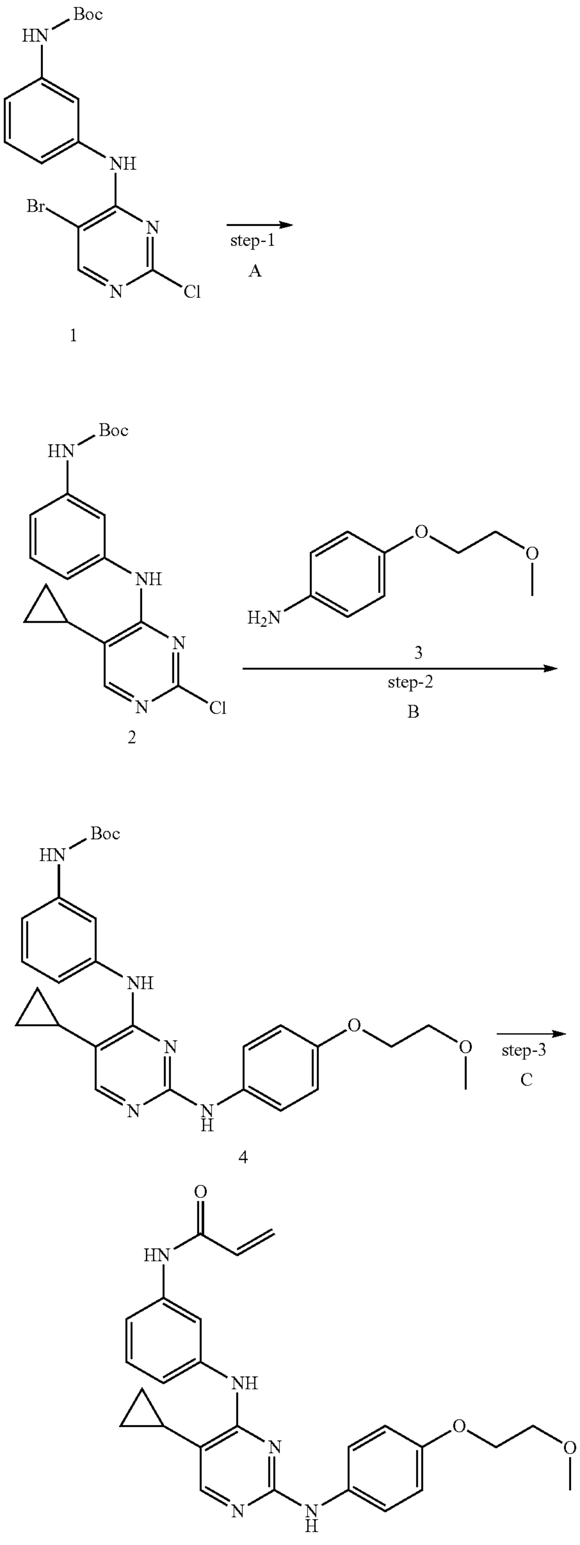

1

2

4

I-139

A) Potassium cyclopropyltrifluoroborate, $Pd(OAc)_2$, Xanphos, $Cs_2(CO_3)$, toluene, 100 C°., 12 h;
B) PTSA, dioxane, 100° C., 2 h;
C) $Zn(CN)_2$, $Ph_3P$, DMF, 120° C., 12 h;
D) 4N HCl, dioxane, rt, 1 hr; then acryloyl chloride, $Et_3N$, DCM, -10° C., 10 min.

Step-1

2

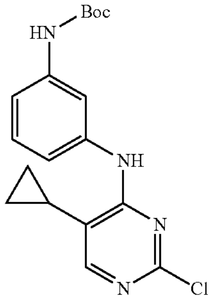

Potassium cyclopropyltrifluoroborate (0.4 g, 3.0 mmol), compound 1 (1.0 g, 2.5 mmol), palladium acetate (34 mg, 0.15 mmol), Xanphos (0.17 g, 0.3 mmol) and $Cs_2CO_3$ (2.4 g, 7.5 mmol) were suspended in 25 ml toluene and 5 ml water. The mixture was degassed, sealed under argon and heated at 100° C. for 12 hours. 50 ml ethyl acetate was added and washed with $NaHCO_3$ aqueous solution, water and brine. The organic layer was separated and dried over $Na_2SO_4$. After removal of solvent, the crude product was subject to chromatography on silica gel (hexane:EtOAc=3:2). 0.54 g of the title compound 2 was obtained: MS m/z: 361.2 ($M+H^+$).

Step-2

4

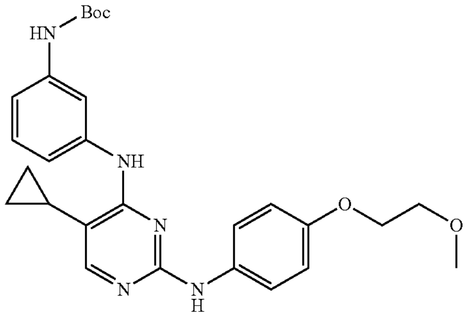

Compound 4 was prepared from compound 2 and 3 following the procedure described in Step-2 of Example 94. MS m/z: 492.2 ($M+H^+$).

Step-3

I-139

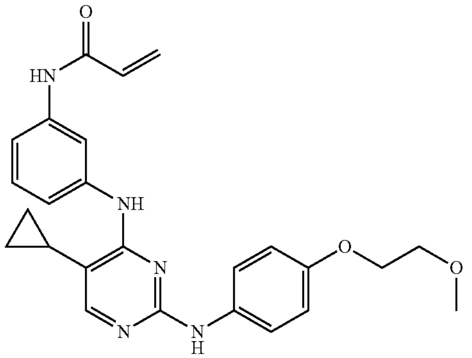

The title compound I-139 was prepared from compound 4 following the procedure described in Step-4 of Example 94. MS m/z: 446.1 ($M+H^+$).

Example 97

Preparation of N-(3-(5-cyclopropyl-2-(6-methoxy-pyridin-3-ylamino)pyrimidin-4-ylamino)phenyl) acrylamide I-167

I-167

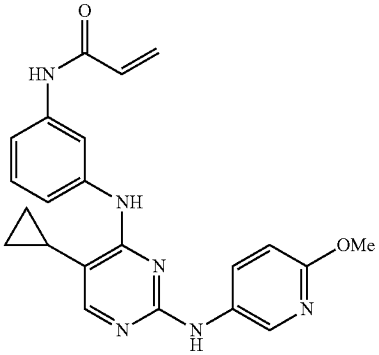

The title compound was prepared according to the schemes, steps and intermediates described in Example 96 by using 3-amino-6-methoxypyridine in place of 3 in Step-2. MS m/z: 403.2 ($M+H^+$).

Example 98

Preparation of N-(3-(5-fluoro-2-(3-(3-(2-oxopyrrolidin-1-yl)propoxy)phenylamino)pyrimidin-4-yloxy) phenyl)acrylamide I-162

I-162

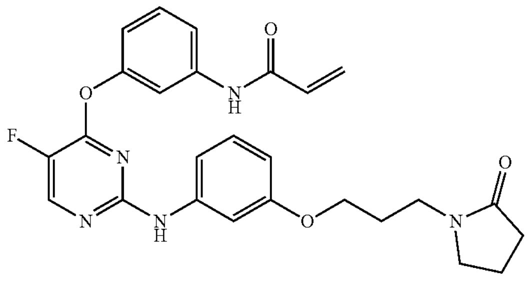

The title compound was prepared according to the schemes, steps and intermediates described below.

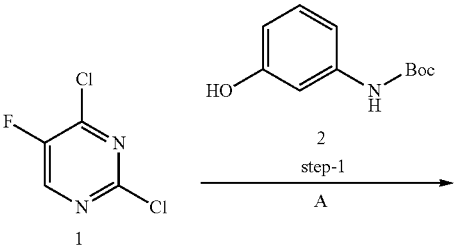

-continued

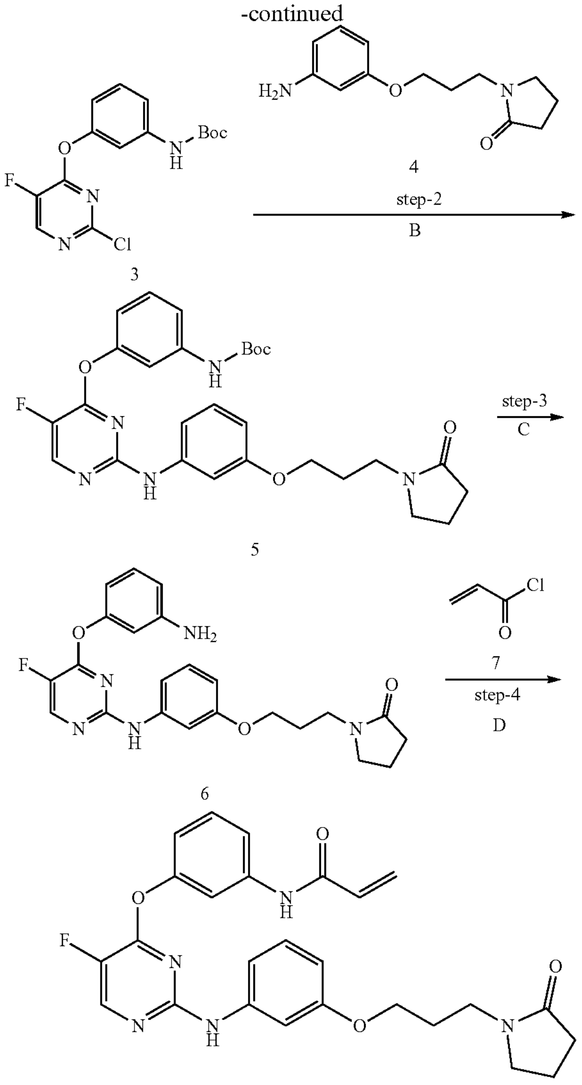

4

3

5

6

I-162

A) DIPEA, n-BuOH, 110° C., 16 h;
B) $Pd(OAc)_2$, BINAP, $Cs_2CO_3$, toluene, 100°C., 16 h;
C) TFA, $CH_2Cl_2$, rt. 2 h;
D) $K_2CO_3$, NMP, rt, 45 min.

Step-1

3

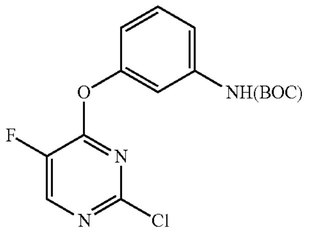

A pressure tube was charged with 2 (2.0 g, 9.61 mmol), 1 (3.21 g, 19.23 mmol), n-BuOH (30 mL) and DIPEA (1.86 g, 14.42 mmol) and the contents were stirred at 110° C. for 16 h. The reaction mixture was cooled, concentrated under reduced pressure, quenched with water (30 mL) and extracted with ethyl acetate (2×30 mL). The combined ethyl acetate extract was washed with water (20 mL), brine (20 mL), dried over $Na_2SO_4$ and concentrated under reduced pressure to get a residue. It was triturated with hexane to get 3 (2.5 g, 96%) as a yellow solid.

Step-2

5

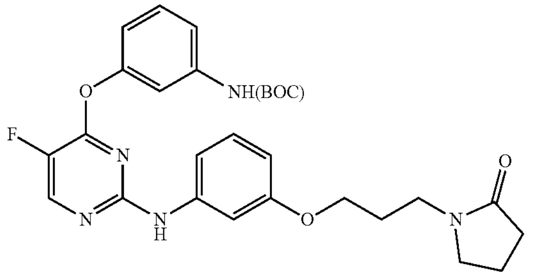

To a solution of 3 (0.36 g, 1.1 mmol) in toluene (15 mL) was added 3-(3-(2-oxopyrrolidin-1-yl)propoxyaniline 4 (0.25 g, 1.1 mmol) followed by BINAP (0.031 g, 0.05 mmol), palladium acetate (0.0022 g, 0.01 mmol), and $Cs_2CO_3$ (0.82 g, 2.5 mmol). The reaction mixture was stirred and $N_2$ was bubbled into it for 15 min. It was heated at 100° C. for 8 h under $N_2$ atmosphere. The reaction mixture was cooled to room temperature, diluted with ethyl acetate (30 mL), washed with water (15 mL), brine (15 mL), and dried over $Na_2SO_4$. Concentration under reduced pressure offered a residue which was purified by column chromatography ($SiO_2$, 60-120, product getting eluted in 3% methanol/chloroform: 3/97) to get 5 (0.3 g, 60%) as yellow solid.

Step-3

6

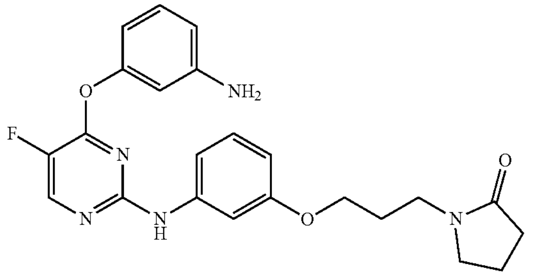

To a stirred solution of 5 (0.25 g, 0.46 mmol) in $CH_2Cl_2$ (10 mL) was added TFA (1.0 mL) at 0° C. under nitrogen atmosphere. The reaction mixture was allowed to come to rt and stirred at this temperature for 2 h. Crude reaction mixture was poured into ice cold water (10 mL), basified with sodium bicarbonate solution and extracted with ethyl acetate (3×15 mL). The combined ethyl acetate extract was washed with water (15 mL), brine (10 mL), dried over $Na_2SO_4$, and concentrated under reduced pressure to get 6 (0.130 g, 65%) as a yellow solid. It was used in the next step without further purifications Step-4

I-162

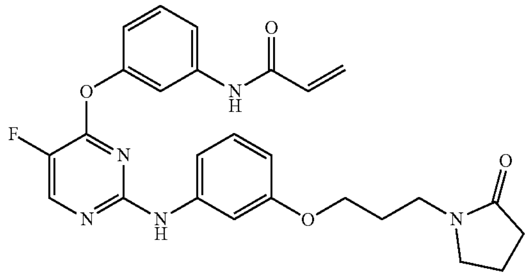

To a stirred solution of 6 (0.08 g, 0.18 mmol) and potassium carbonate (0.124 g, 0.9 mmol) in NMP (1.2 mL) at 0° C. was added acryloyl chloride (0.020 g, 0.22 mmol) and the reaction mixture was stirred at 0° C. for 45 min The reaction mixture was added drop wise to a cold, stirring solution of 10% $NaHCO_3$ and stirred at the same temperature (0° C.) for 30 min. A solid precipitated out which was isolated by filtration through a Buchner funnel. The solid was washed with cold water, hexane and dissolved in a mixture of methanol/dichloromethane (50:50, 5 mL) and concentrated under reduced pressure. The residue obtained was suspended in cold water (10 mL), $Et_3N$ was added to it and it was extracted with ethyl acetate (2×10 mL). The combined ethyl acetate extract was washed with water (5 mL), brine (5 mL), dried over $Na_2SO_4$ and concentrated under reduced pressure to get I-162 (0.050 mg, 56%). $^1H$ NMR (DMSO-$d_6$) δ ppm: 1.81-1.91 (m, 4H), 2.19 (t, J=7.84 Hz, 2H), 3.26-3.35 (m, 4H), 3.73 (t, J=6.04 Hz, 2H), 5.76 (dd, J=1.92 & 10.04 Hz, 1H), 6.25 (dd, J=1.88 & 16.9 Hz, 1H), 6.38-6.45 (m, 2H), 6.93 (t, J=8.12 Hz, 1H), 7.02-7.04 (m, 2H), 7.11 (s, 1H), 7.43 (t, J=8.16 Hz, 1H), 7.55 (d, J=8.24 Hz, 1H), 7.68 (d, J=1.8 Hz, 1H), 8.56 (d, J=2.88 Hz, 1H), 9.56 (s, 1H), 10.34 (s, 1H); LCMS: m/e 490.0 (M-2).

The intermediate 3-(3-(2-oxopyrrolidin-1-yl)propoxyaniline 4 was prepared according to the scheme shown below.

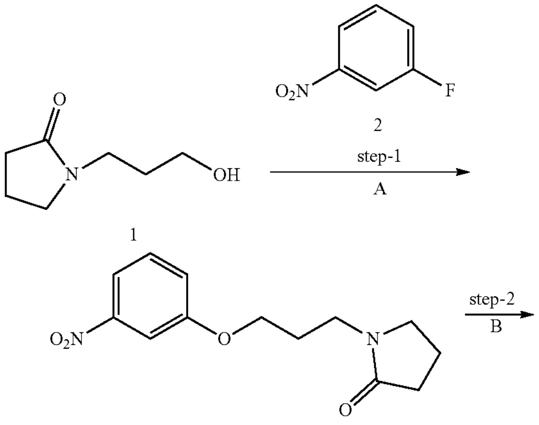

2

1

3

-continued

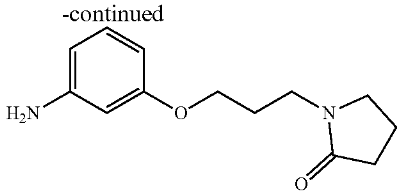

4

A) NaH, DMF, rt, 16 h;
B) $SnCl_2$, Conc. HCl, 50° C., 2 h.

Step-1

3

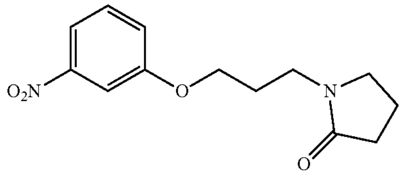

To a stirred solution of NaH (1.0 g, 20.94 mmol) in DMF (10 mL) was added 1 (2.0 g, 13.96 mmol) at 0° C. The reaction mixture was allowed to come to rt and stirred at it for 30 mins. To the reaction mixture was added 2 (1.96 g, 13.96 mmol), slowly and the reaction mixture was allowed to stir at rt for 16 h. The reaction mixture was concentrated under reduced pressure and the residue was diluted with ethyl acetate (20 mL). It was washed with water (2×5 mL), brine (5 mL) and dried over $Na_2SO_4$. Filtration followed by concentration under reduced pressure offered crude 3 (2 g, 55.5%) which was used in the next step without further purification.

Step-2

4

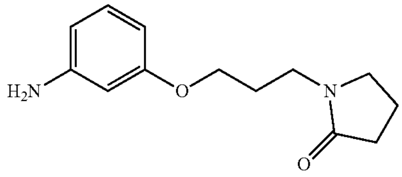

To a stirred solution of 3 (2 g, 7.57 mmol) in conc. HCl (20 mL) was added $SnCl_2$ (7.5 g, 34.06 mmol) in small portions. The reaction mixture was stirred at 50° C. for 2 h, cooled and basified with $NaHCO_3$. It was extracted with ethyl acetate (3×25 mL), washed with water (5 mL), brine solution (5 mL) and dried over anhydrous $Na_2SO_4$. Filtration followed by concentration under reduced pressure gave 4 (1.65 g, 93%) as dark brown solid which was used as such in the next step.

Example 99

Preparation of N-(4-(5-fluoro-2-(3-(2-(2-oxopyrrolidin-1-yl)ethoxy)phenylamino)pyrimidin-4-yloxy)benzyl)-N-methylacrylamide I-146

I-146

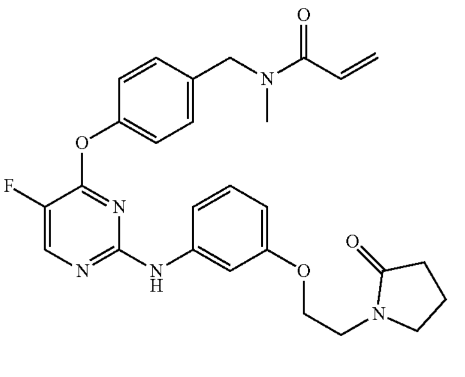

The title compound was prepared according to the schemes, steps and intermediates described in Example 98 by using (4-hydroxybenzyl)(methyl)carbamic acid tert-butyl ester in place of 2 in Step-1 and 3-(2-(2-oxopyrrolidin-1-yl)ethoxyaniline in place of 4 in Step-2. $^1H$ NMR ($CDCl_3$) δ ppm: 2.03 (quin, J=7.4 Hz, 2H), 2.39 (t, J=8 Hz, 2H), 3.07 & 3.06 (s, together 3H), 3.57 (t, J=6.96 Hz, 2H), 3.66 (t, J=5.08 Hz, 2H), 4.03-4.04 (bd, J=4.96 Hz, 2H), 4.67 & 4.72 (s, together 2H), 5.70-5.85 (m, 1H), 6.43 (d, J=16.72 Hz, 1H), 6.50 (d, J=5.72 Hz, 1H), 6.60-6.75 (m, 1H), 6.89-6.96 (m, 2H), 7.06-7.08 (m, 2H), 7.18-7.30 (m, 2H), 7.37 (d, J=8.44 Hz, 1H), 8.21 (d, J=2.36 Hz, 1H); LCMS: m/e 506.2 (M+1).

Example 100

Preparation of N-(4-(5-fluoro-2-(3-(3-(methylsulfonyl)propoxy)phenylamino)pyrimidin-4-yloxy)benzyl)-N-methylacrylamide I-136

I-136

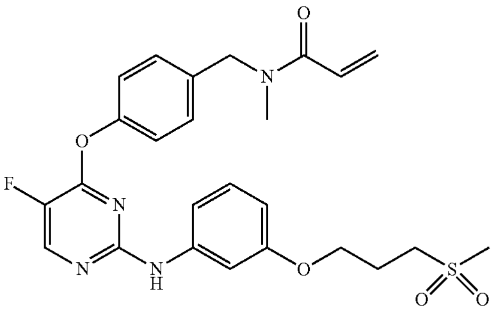

The title compound was prepared according to the schemes, steps and intermediates described in Example 98 by using (4-hydroxybenzyl)(methyl)carbamic acid tert-butyl ester in place of 2 in Step-1 and 3-(3-(3-methylsulfonyl)propoxyaniline in place of 4 in Step-2. $^1H$ NMR ($CDCl_3$) δ ppm: 2.25-2.40 (m, 2H), 2.97 (s, 3H), 3.07 (s, 3H), 3.20-3.30 (m, 2H), 3.98-4.05 (m, 2H), 4.67 (s, 1H), 4.72 (s, 1H), 5.7-5.82 (m, 1H), 6.43 (dd, J=1.96 & 16.96 Hz, 1H), 6.49-6.53 (m, 1H), 6.6-6.75 (m, 1H), 6.85-7.00 (m, 2H), 7.05-7.15 (m, 2H), 7.18-7.25 (m, 2H), 7.36 (d, J=8.36 Hz, 1H), 8.21 (bd, J=2.52 Hz, 1H); LCMS: m/e 515.0 (M+1).

Example 101

Preparation of N-(4-(5-fluoro-2-(6-methoxypyridin-3-ylamino)pyrimidin-4-yloxy)benzyl)-N-methylacrylamide I-117

I-117

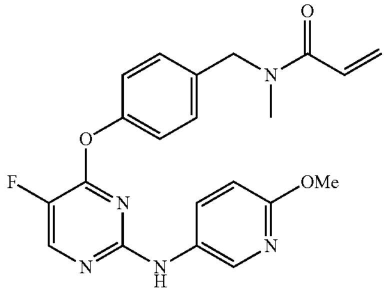

The title compound was prepared according to the schemes, steps and intermediates described in Example 98 by using (4-hydroxybenzyl)(methyl)carbamic acid tert-butyl ester in place of 2 in Step-1 and 6-methoxy-3-aminopyridine in place of 4 in Step-2. $^1H$ NMR (DMSO-$d_6$) δ ppm: 2.92 & 3.07 (s, together 3H), 3.76 (s, 3H), 4.62 & 4.74 (s, together 2H), 5.69 & 5.75 (dd, J=1.6 & 10.4 Hz, together 1H), 6.20 (dd, J=1.2 & 16.4 Hz, 1H), 6.56 (d, J=8.8 Hz, 1H), 6.82-6.90 (m, 1H), 7.28-7.35 (m, 4H), 7.71 (bd, J=7.6 Hz, 1H), 8.14 (s, 1H), 8.44 (bd, J=2.8 Hz, 1H), 9.48 (s, 1H); LCMS: m/e 410 (M+1).

Example 102

Preparation of N-(4-(5-fluoro-2-(3-(3-(2-oxopyrrolidin-1-yl)propoxy)phenylamino)pyrimidin-4-yloxy)benzyl)-N-methylacrylamide I-111

I-111

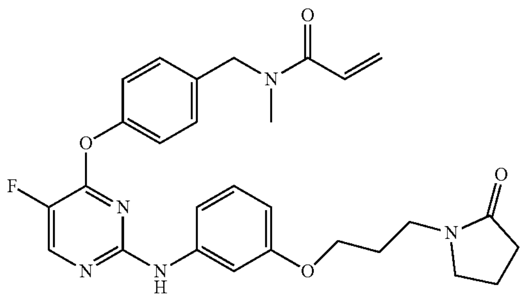

The title compound was prepared according to the schemes, steps and intermediates described in Example 98 by using (4-hydroxybenzyl)(methyl)carbamic acid tert-butyl ester in place of 2 in Step-1 and 3-(3-(2-oxopyrrolidin-1-yl)propoxy)aniline in place of 4 in Step-2. $^1H$ NMR (DMSO-$d_6$) δ ppm: 1.80-2.6 (m, 4H), 2.20 (t, J=7.6 Hz, 2H), 2.92 & 3.06 (s, together 3H), 3.20-3.40 (m, 4H), 3.75-3.90 (m, 2H), 4.62 & 4.73 (s, together 2H), 5.65-5.77 (m, 1H), 6.20 (dd, J=2.4 & 16.8 Hz, 1H), 6.24 (bd, J=8 Hz, 1H), 6.86 (dd, J=10.4 & 16.8 Hz, 1H), 6.93 (t, J=8 Hz, 1H), 7.08 (t, J=8 Hz, 2H), 7.28-7.36 (m, 4H), 8.48 (d, J=2.8 Hz, 1H), 9.51 (s, 1H); LCMS: m/e 520.2 (M+1).

Example 103

Preparation of N-(3-(5-fluoro-2-(3-(2-(2-oxopyrrolidin-1-yl)ethoxy)phenylamino)pyrimidin-4-yloxy)phenyl)acrylamide I-184

I-184

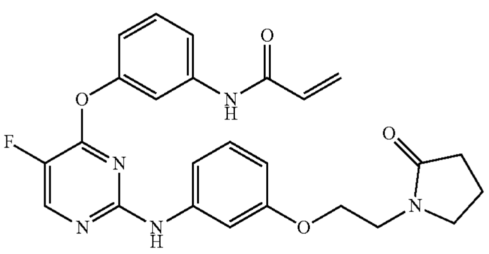

The title compound was prepared according to the schemes, steps and intermediates described below.

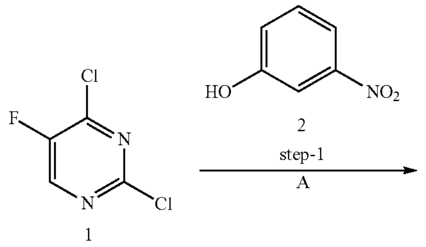

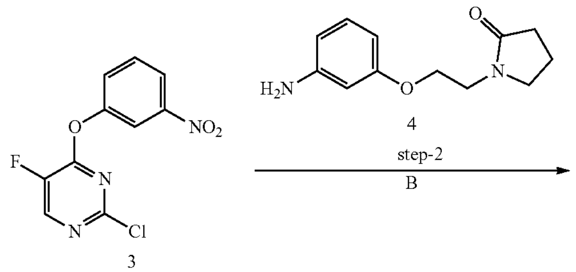

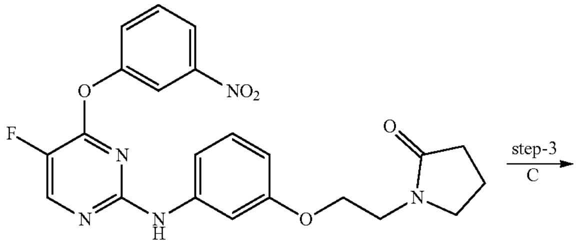

5

-continued

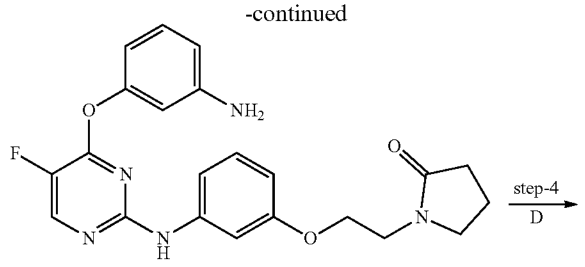

6

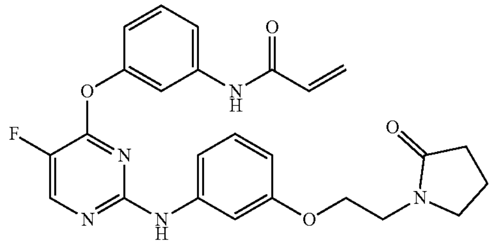

I-184

A) ) $K_2CO_3$, DMF, rt, 16 h;
B) $Pd(OAc)_2$, BINAP, $Cs_2CO_3$, toluene, 100° C., 8 h;
C) Pd-C, $H_2$, methanol, rt, 16 h;
D) ) acryloyl chloride, $K_2CO_3$, NMP, 0° C., 30 min.

Step-1

3

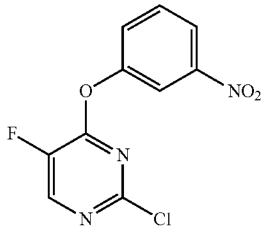

To a stirring solution of 1 (24 g, 143.7 mmol) and $K_2CO_3$ (20 g, 143.6 mmol) in dry DMF (300 mL) was added 2 (10 g, 71.8 mmol) and the reaction mixture was stirred at rt for 16 h under nitrogen atmosphere. It was cooled and quenched with water (600 mL). A white solid precipitated out which was isolated by filtration through Buchner funnel and vacuum dried to get 3 (13 g, 68%) as a white solid.

Step-2

5

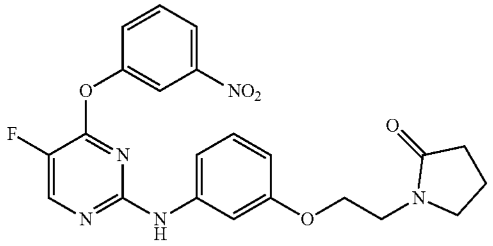

To a solution of 3 (0.9 g, 3.3 mmol) in toluene (30 mL) was added 4 (950 mg, 4.3 mmol) followed by BINAP (0.12 g, 0.19 mmol), palladium acetate (0.02 g, 0.09 mmol), and $Cs_2CO_3$ (2.7 g, 8.2 mmol). The reaction mixture was stirred and $N_2$ was bubbled into it for 15 min. It was then heated at 100° C. for 8 h under $N_2$ atmosphere. The reaction mixture was cooled to room temperature, diluted with ethyl acetate (60 mL), washed with water (35 mL), brine (35 mL), and dried over $Na_2SO_4$. Concentration under reduced pressure offered a residue which was purified by column chromatography ($SiO_2$, 60-120, product getting eluted in methanol/chloroform: 8/92) to get 5 (0.50 g, 33%) as a white solid.

Step-3

6

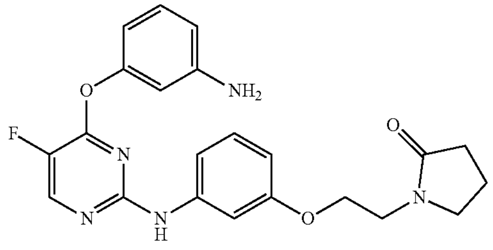

To a solution of 5 (0.5 g, 1.1 mmol) in methanol (50 mL)) was added 10% Pd/C (0.05 g, 10% w/w) and the reaction mixture was allowed to stir under $H_2$ atmosphere (1.5 Kg hydrogen pressure) at rt for 16 h. The reaction mixture was filtered through a pad of celite and concentrated under reduced pressure to get 6 (0.3 g, 65%) as a colorless viscous liquid.

Step-4

I-184

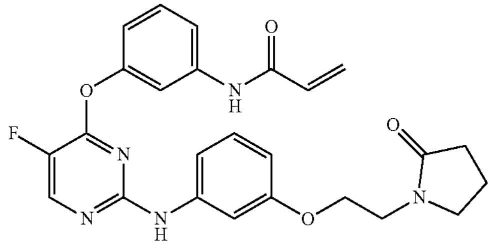

To a stirred solution of 6 (0.21 g, 0.5 mmol) and potassium carbonate (0.27 g, 2.0 mmol) in NMP (2.5 mL) at 0° C. was added acryloyl chloride (0.053 g, 0.6 mmol) and the reaction mixture was stirred at 0° C. for 30 min The reaction mixture was added drop wise to a cold, stirring solution of 10% $NaHCO_3$ and stirred at the same temperature (0° C.) for 30 min. A white solid precipitated out which was isolated by filtration through a Buchner funnel. The solid was washed with cold water and hexane and dissolved in mixture of methanol/dichloromethane (50:50, 10 mL) and concentrated under reduced pressure. The residue obtained was suspended in cold water (25 mL), $Et_3N$ was added to it and it was extracted with ethyl acetate (2×50 mL). The combined ethyl acetate extract was washed with water (50 mL), brine (50 mL), dried over $Na_2SO_4$ and concentrated under reduced pressure to get I-184 (0.150 g, 65%) as white solid. $^1H$ NMR (DMSO-$d_6$) δ ppm: 1.89 (quin, J=7.2 Hz, 2H), 2.21 (t, J=7.6 Hz, 2H), 3.39 (t, J=7.2 Hz, 2H), 3.49 (t, J=5.2 Hz, 2H), 3.87 (t, J=5.6 Hz, 2H), 5.77 (dd, J=1.6 & 10.4 Hz, 1H), 6.26 (dd, J=1.6 & 17.2 Hz, 1H), 6.39-6.46 (m, 2H), 6.95 (t, J=8.4 Hz, 1H), 7.03-7.12 (m, 3H), 7.44 (t, J=8.4 Hz, 1H), 7.56 (d, J=8.4 Hz, 1H), 7.70 (s, 1H), 8.51 (d, J=2.8 Hz, 1H), 9.56 (s, 1H), 10.35 (s, 1H); LCMS: m/e 478 (M+1).

The intermediate 3-(2-(2-oxopyrrolidin-1-yl)ethoxyaniline 4 was prepared according to the scheme shown below.

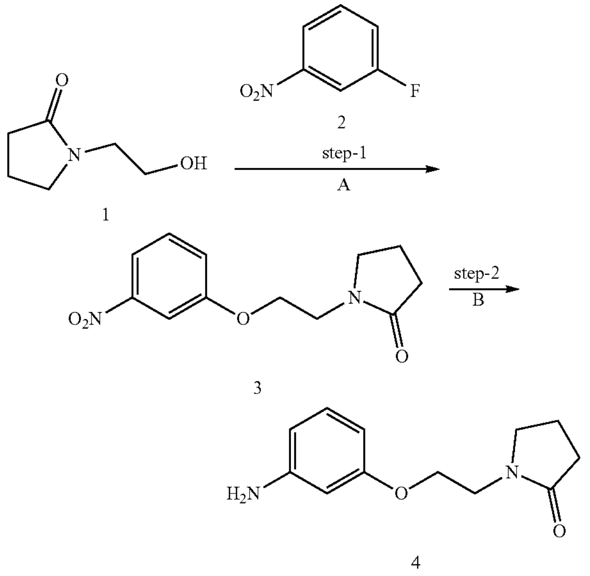

A) NaH, THF, rt, 16 h;
B) Pd-C, $H_2$, methanol, rt, 16 h.

Step-1

3

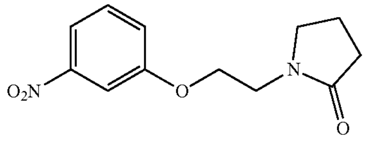

To a stirring solution of NaH (3.4 g, 141.6 mmol, 60% dispersion in paraffin oil) in dry THF (50 mL) was added 1 (6 g, 46.0 mmol) at 0° C. and the reaction mixture was stirred at rt for 15 min under nitrogen atmosphere. To it was added a solution of 2 (5.0 g, 35.4 mmol) in THF (10 mL) and the reaction mixture was stirred at rt for 16 h. It was quenched with cold water (40 mL), and extracted with ethyl acetate (35 mL). The ethyl acetate extract was washed with water (2×25 mL), brine (25 mL), dried over $Na_2SO_4$ and concentration under reduced pressure to get a residue which was purified by column chromatography ($SiO_2$, 60-120, product getting eluted in methanol/chloroform: 10/90) to get 3 (2.5 g, 30%) as a brownish liquid.

Step-2

4

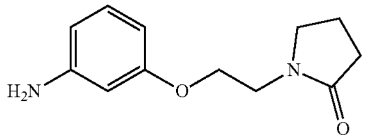

To a solution of 3 (2.2 g, 8.8 mmol) in methanol (50 mL)) was added 10% Pd/C (0.22 g, 10% w/w) and the reaction mixture was allowed to stir under $H_2$ atmosphere (1.5 Kg hydrogen pressure) at rt for 16 h. The reaction mixture was filtered through a pad of Celite® and concentrated under reduced pressure to get 4 (1.7 g, 89%) as a yellowish liquid. It was used in the next step without further purification.

Example 104

Preparation of N-(3-(2-(6-methoxypyridin-3-ylamino)-5-methylpyrimidin-4-yloxy)phenyl)acrylamide I-186

I-186

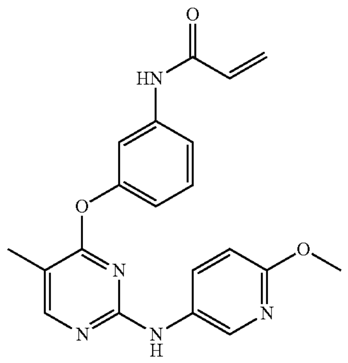

The title compound was prepared according to the schemes, steps and intermediates described in Example 103 by using 2,4-dichloro-5-methylpyrimidine in place of 1 in Step-1 and 6-methoxy-3-aminopyridine in place of 4 in Step-2. $^1$H NMR (DMSO-$d_6$) δ ppm: 2.16 (s, 3H), 3.73 (s, 3H), 5.76 (dd, J=1.92 & 10.04 Hz, 1H), 6.24 (dd, J=1.92 & 16.92 Hz, 1H), 6.39-6.49 (m, 2H), 6.92 (dd, J=1.48 & 8 Hz, 1H), 7.40 (t, J=8.08 Hz, 1H), 7.49 (d, J=8.16 Hz, 1H), 7.64 (d, J=1.84 Hz, 1H), 7.77-7.79 (m, 1H), 8.17 (bs, 1H), 8.20 (s, 1H), 9.27 (s, 1H), 10.29 (s, 1H); LCMS: m/e 378 (M+1).

Example 105

Preparation of N-(3-(5-methyl-2-(phenylamino)pyrimidin-4-yloxy)phenyl)acrylamide I-248

I-248

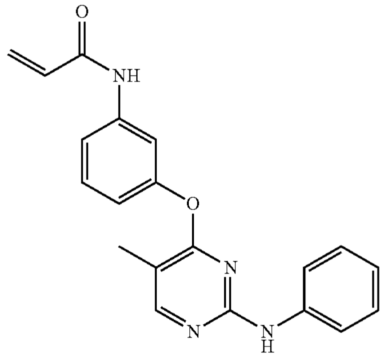

The title compound was prepared according to the schemes, steps and intermediates described below.

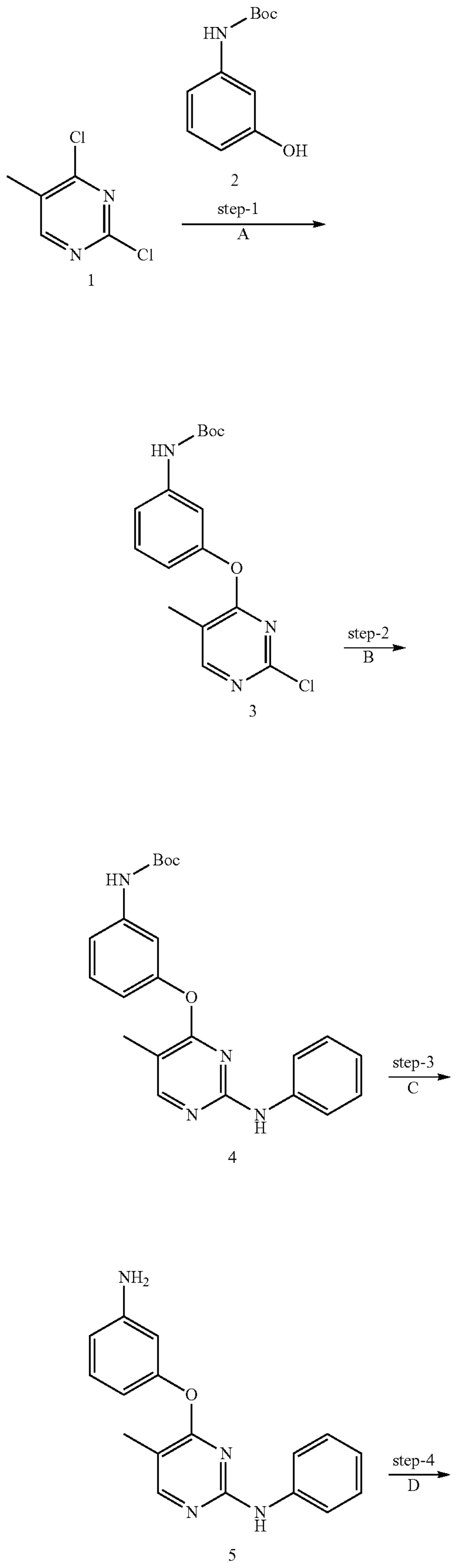

-continued

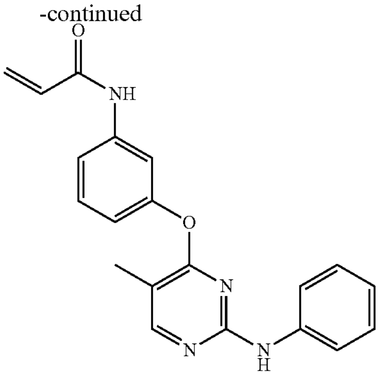

I-248

A) $K_2CO_3$, DMF, rt, 24 h;
A') $(Boc)_2O$, THF, 60° C., 2 h;
B) aniline, conc. HCl, EtOH, 80° C., 1 h;
C) TFA, $CH_2Cl_2$, 0° C. to rt, ½ h;
D) acryloyl chloride, NMP, 0° C., 10 min.

Step-1

3

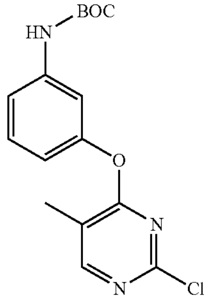

To a stirring solution of 2 (100 mg, 0.48 mmol) and $K_2CO_3$ (99.2 mg, 0.717 mmol) in dry DMF (5 mL) was added 1 (78 mg, 0.478 mmol) and the reaction was continued at rt for 24 h under nitrogen atmosphere. The reaction mixture was concentrated under reduced pressure and the residue was diluted with ethyl acetate (10 mL). It was washed with water (2×5 mL), brine (5 mL), dried over $Na_2SO_4$ and concentrated under reduced pressure to get 3 (120 mg, 75%) as a white solid. It was used for next step without further purification.

Step-2

4

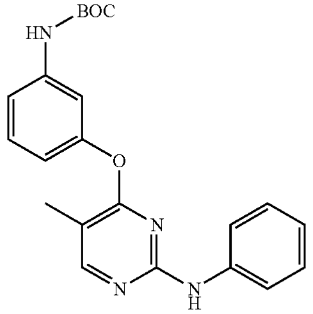

A pressure tube was charged with 3 (75 mg, 0.224 mmol), conc. HCl (40 mg, 0.4 mmol), aniline (83 mg, 0.89 mmol) and ethanol (2.0 mL). The tube was screw capped and the contents were stirred at 80° C. for 60 min. The reaction mixture was cooled, concentrated under reduced pressure and the residue was quenched with water (5.0 mL). It was basified with 10% $NaHCO_3$ soln. and extracted with Ethyl acetate (3×10 mL). The combined EtOAc layer was washed with water (2×5 mL), brine (5 mL), dried over $Na_2SO_4$ and concentrated under reduced pressure. The residue obtained was further purified by column chromatography ($SiO_2$, 60-120 mesh, EtoAc/Hexane: 50/50) to get 4 (0.04 g, 45.9%) as an off-white sold.

Step-3

5

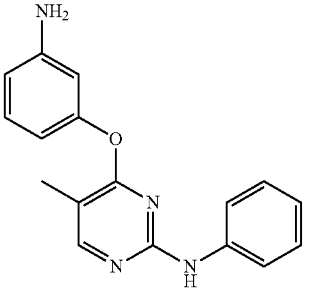

To a stirring solution of 4 (160 mg, 0.40 mmol) in dichloromethane (4.0 mL) was added at 0° C., trifluoroacetic acid (0.8 mL). Stirring was continued at the same temperature for 30 min after which the reaction mixture was concentrated under reduced pressure and the residue was dissolved in water (5.0 mL), basified with 10% $NaHCO_3$ solution and extracted with dichloromethane (2×5 mL). The dichloromethane extract was washed with water (5 mL), brine (5 mL), dried over $Na_2SO_4$ and concentrated under reduced pressure to get 5 (110 mg, 93.2%) as an off white solid. It was used for next step without further purification.

Step-4

I-248

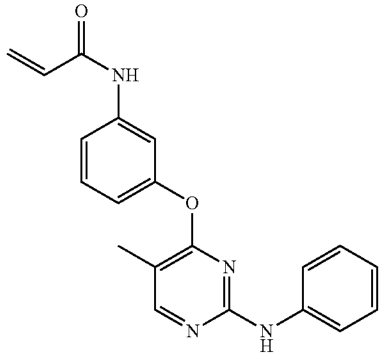

To a stirred solution of 5 (75 mg, 0.256 mmol) in NMP (0.8 mL) at 0° C. was added acryloyl chloride (34.8 mg, 0.38 mmol) and the reaction mixture was stirred at 0° C. for 10 min. The reaction mixture was quenched with water (4.0 mL), basified with 10% NaHCO3 soln. and extracted with dichloromethane (2×5 mL). The dichloromethane extract was washed with water (5 mL), brine (5 mL), dried over $Na_2SO_4$ and concentrated under reduced pressure. The residue obtained was further purified column chromatography ($SiO_2$, 60-120 mesh, $CHCl_3$/MeOH: 99/1) to get I-248

(0.035 g, 39.6%) as a white colored solid. $^1$H NMR (DMSO-$d_6$) δ ppm: 2.15 (s, 3H), 5.75 (dd, J=1.92 & 10.04 Hz, 1H), 6.24 (dd, J=1.96 & 16.96 Hz, 1H), 6.41 (dd, J=10.6 & 17 Hz, 1H), 6.78-6.8 (m, 1H), 6.94 (dd, J=1.44 & 8.04 Hz, 1H), 7.00 (t, J=7.52 Hz, 2H), 7.40-7.44 (m, 3H), 7.53 (d, J=8.24 Hz, 1H), 7.6 (t, J=2 Hz, 1H), 8.23 (d, J=1.04 Hz, 1H), 9.36 (s, 1H), 10.30 (s, 1H); LCMS: m/e 346.8 (M+1).

Example 106

Preparation of 1-(4-(5-fluoro-2-(phenylamino)pyrimidin-4-ylamino)piperidin-1-yl)prop-2-en-1-one I-229

I-229

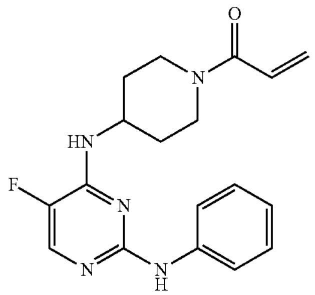

The title compound was prepared according to the schemes, steps and intermediates described in Example 20 by using 1-tert-butyloxycarbonyl-4-aminopiperidine in place of 2 in Step-1 and aniline in place of 4 in Step-2. $^1$H NMR (DMSO-$d_6$) δ ppm: 1.35-1.50 (m, 2H), 1.90-2.05 (m, 2H), 2.7-2.85 (m, 1H), 3.10-3.20 (m, 1H), 4.11-4.15 (m, 2H), 4.46 (bd, J=13.72 Hz, 1H), 5.67 (dd, J=2.44 & 10.4 Hz, 1H), 6.10 (dd, J=2.44 & 16.6 Hz, 1H), 6.82-6.88 (m, 2H), 7.22 (t, J=7.44 Hz, 2H), 7.35 (d, J=7.56 Hz, 1H), 7.70 (d, J=7.72 Hz, 2H), 7.87 (d, i=3.76 Hz, 1H), 9.07 (s, 1H); LCMS: m/e 341.383 (M+1).

Example 107

Preparation of 2-((3-(5-fluoro-2-(4-(2-methoxyethoxy)phenylamino)pyrimidin-4-ylamino)phenyl)(hydroxy)methyl)acrylonitrile I-71

I-71

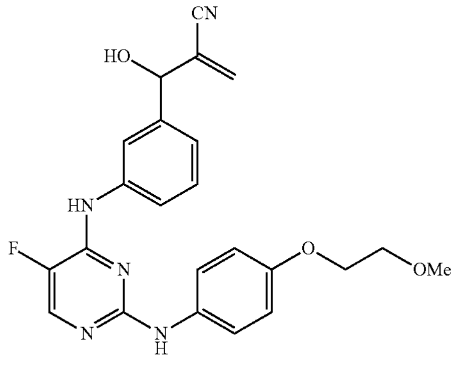

The title compound was prepared according to the schemes, steps and intermediates described below.

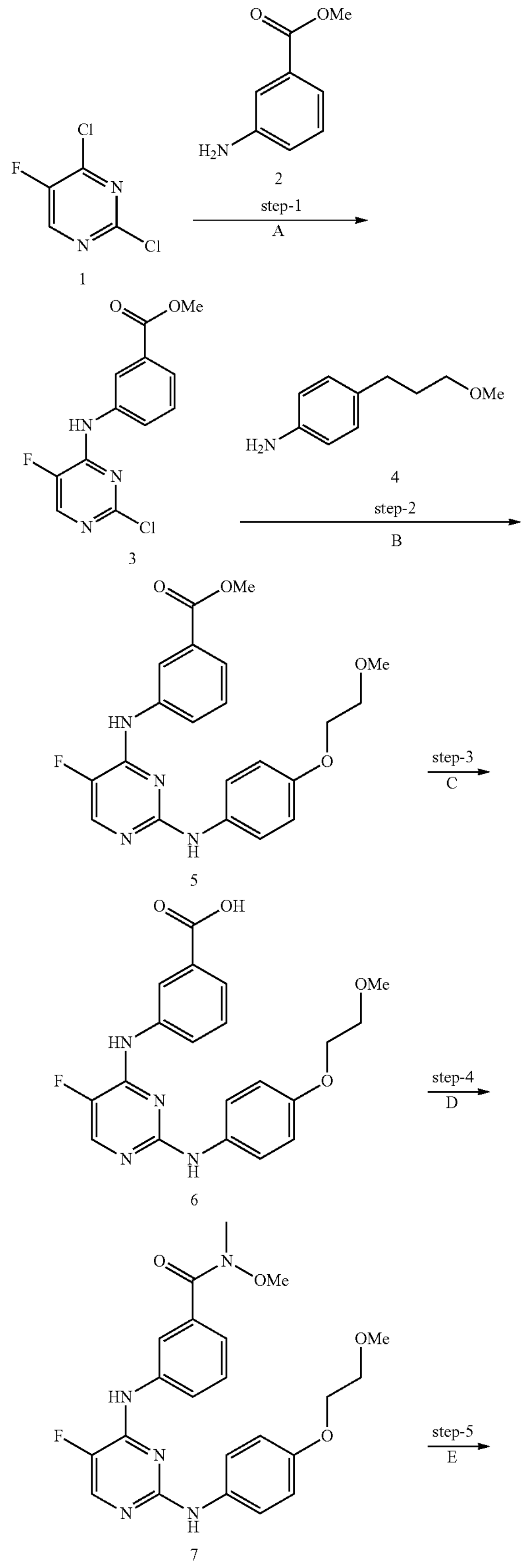

-continued

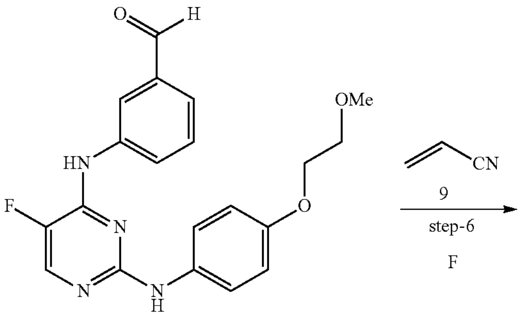

8

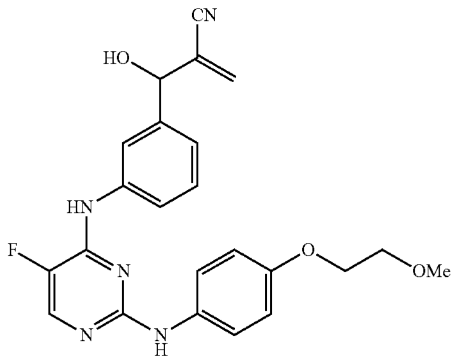

I-71

A) 2, DIPEA, n-BuOH, 120° C., 12 h;
B) conc. HCl, ethanol, 100° C., 5 h;
C) LiOH, MeOH/THF/H2O, rt, 6 h;
D) Me-NH-OMe•HCl, EDCI•HCl, HOBT, DIPEA, DMF, rt, 8 h;
E) LAH (1.0 M soln. in THF), -78° C., 30 min;
F) DABCO, 1,4-dioxan/water, rt, 48 h.

Step-1

3

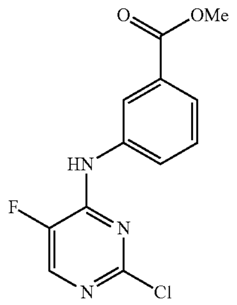

A solution of 1 (0.50 g, 2.99 mmol), 2 (0.45 g, 2.99 mmol) and DIPEA (0.57 g, 4.48 mmol) in n-butanol (5.0 mL) was heated in a pressure tube (120° C., 16 h). It was cooled, quenched with water (5 mL) and extracted with EtOAc (2×5 mL). The combined EtOAc extract was washed with water (2 mL), brine (2 mL), dried over $Na_2SO_4$ and concentrated under reduced pressure to afford 3 (0.70 g, 83.3%) as an off-white solid.

Step-2

5

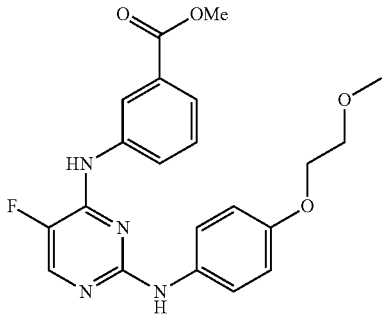

A solution of 3 (0.5 g, 1.77 mmol) and 4 (0.29 g, 1.77 mmol) in ethanol (2.5 mL) was taken in a pressure tube and acetic acid (0.1 mL) was added to it. The tube was tightly closed and the contents were stirred at 100° C. for 5 h. The reaction mixture was cooled, ethanol was removed under reduced pressure and the residue was taken in ethyl acetate (50 mL). It was washed with $NaHCO_3$ solution (5 mL), brine (5 mL), dried over $Na_2SO_4$ and concentrated under reduced pressure. The solid precipitated was isolated by filtration. It was dried under vacuum to get 5 (0.6 g, 80%).

Step-3

6

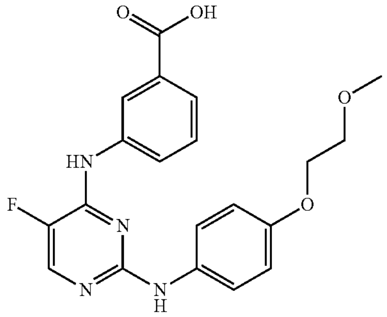

To a stirred solution of 5 (0.6 g, 1.4 mmol) in methanol/THF/water: δ 6 mL/6 mL/3 mL was added LiOH (0.298 g, 7 mmol) and the reaction mixture was stirred at rt for 2 h. It was concentrated under reduced pressure; residue was diluted with water (2 mL) and extracted with diethyl ether (5 mL). The aqueous layer was separated and acidified with 1.5 N HCl (pH~4-5), concentrated and dried under vacuum to get 6 (0.4 g, 70%) as a white solid which was taken for next step without further purification.

Step-4

7

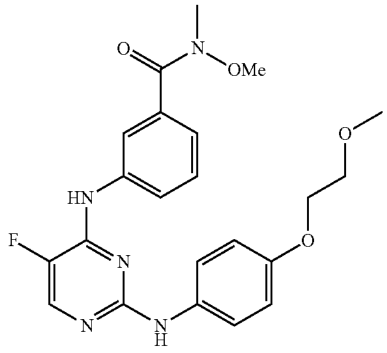

To a stirred solution of 6 (0.4 g, 1 mmol) in DMF (3 mL) were added MeNH-OMe.HCl (0.102 g, 0.1 mmol), EDCI.HCl (0.003 g, 1.5 mmol), HOBT (71 mg, 0.5 mmol) and DIPEA (0.204 g, 1.5 mmol). The reaction mixture was stirred at room temperature for 8 h and quenched with water and extracted with EtOAc (2×5 mL). The combined organic layer was washed with brine, dried over anhydrous $Na_2SO_4$, filtered and concentrated under reduced pressure to get 7 (0.4 g, 90.9%) as a white solid.

Step-5

8

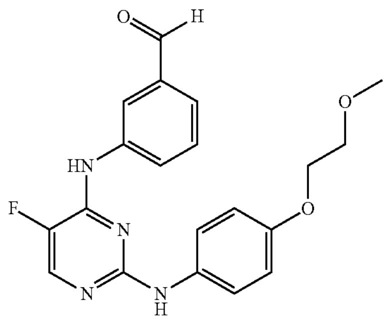

To a stirred solution of 7 (0.4 g, 0.9 mmol) in THF (10 mL) was added LAH (1.8 mL, 1.8 mmol) at −78° C. The reaction mixture was allowed to stir at the same temperature for 30 mins after which it was quenched with $Na_2SO_4$ solution (2 mL) and extracted with ethyl acetate (10 mL). The ethyl acetate layer was separated and washed with water (2 mL), brine solution (2 mL) and dried over anhydrous $Na_2SO_4$. Filtration followed by concentration under reduced pressure offered a residue which was purified by column chromatography ($SiO_2$, 60-120, pet ether/ethyl acetate 7/3) to get 8 (200 mg, 58%) as a yellow solid.

Step-6

I-71

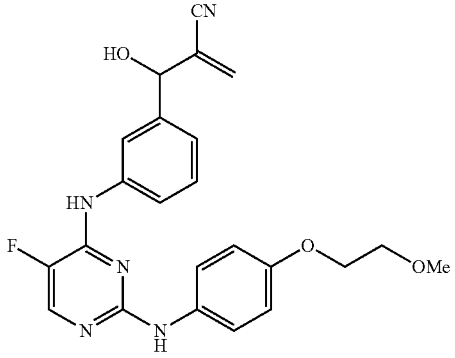

To a stirred solution of 8 (200 mg, 0.523 mmol) and 9 (69 mg, 1.3 mmol) in 1,4-dioxane/$H_2O$ (1.4 mL/0.6 mL) was added DABCO (50 mg, 0.2523 mmol) at rt. Stirring was continued at room temperature for 48 h after which the reaction mixture was concentrated under reduced pressure. The residue obtained was further purified by column chromatography ($SiO_2$, pet ether/ethyl acetate, 6/4) to get I-71 as greenish gummy material (0.05 g, 22.7%). $^1$H NMR (DMSO-$d_6$) δ ppm: 3.48 (s, 3H), 3.77 (t, J=4.4 Hz, 2H), 4.11-4.16 (m, 2H), 5.11 (s, 1H), 5.99 (s, 1H), 6.06 (s, 1H), 6.85 (s, 1H), 6.91 (d, J=8.84 Hz, 2H), 7.15 (d, J=7.44 Hz, 1H), 7.30-7.40 (m, LCMS: m/e (M+1).

Example 108

Preparation of 2-((4-(5-fluoro-2-(phenylamino)pyrimidin-4-ylamino)phenyl)(hydroxy)methyl)acrylonitrile I-161

I-161

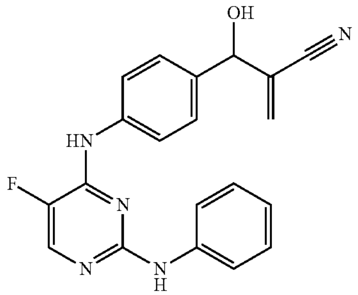

The title compound was prepared according to the schemes, steps and intermediates described in Example 107 by using aniline in place of 4 in Step-2. $^1$H NMR ($CDCl_3$) δ ppm: 5.32 (s, 1H), 6.07 (d, J=0.8 Hz, 1H), 6.15 (d, J=1.6 Hz, 1H), 6.84 (d, J=2.8 Hz, 1H), 7.03-7.06 (m, 2H), 7.29 (t, J=1.6 Hz, 2H), 7.38 (d, J=8.44 Hz, 2H), 7.52 (d, J=8.8 Hz, 2H), 7.67 (dd, J=1.6 & 6.4 Hz, 2H), 7.96 (d, J=3.2 Hz, 1H); LCMS: m/e 361.8 (M+1).

Example 109

Preparation of 2-((4-(5-fluoro-2-(3-trifluoromethoxyphenylamino)pyrimidin-4-ylamino)phenyl)(hydroxy)methyl)acrylonitrile I-163

I-163

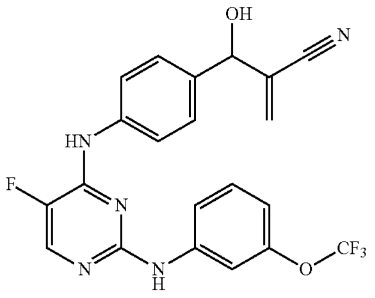

The title compound was prepared according to the schemes, steps and intermediates described in Example 107 by using 3-trifluoromethoxyaniline in place of 4 in Step-2. $^1$H NMR (DMSO-$d_6$) δ ppm: 5.29 (d, J=3.8 Hz, 1H), 6.13 (s, 1H), 6.19 (s, 1H), 6.31 (dd, J=3.8 Hz, 1H), 6.83 (d, J=7.76 Hz, 1H), 7.11 (d, J=7.8 Hz, 1H), 7.30-7.37 (m, 2H), 7.61-7.63 (m, 2H), 7.81 (s, 1H), 7.90 (d, J=7.4 Hz, 1H), 8.16 (dd, J=1.44 & 3.56 Hz, 1H), 9.45 (s, 1H), 9.53 (s, 1H); LCMS: m/e 446 (M+1).

Example 110

Preparation of N-(3-(5-fluoro-2-(3-(3-(methylsulfonyl)propoxy)phenylamino)pyrimidin-4-yloxy)phenyl)acrylamide I-116

I-116

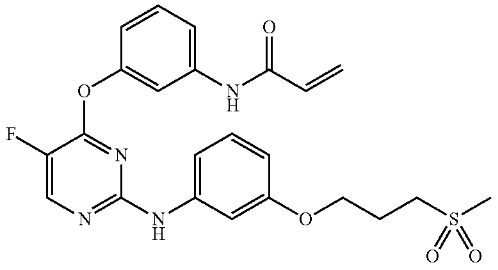

The title compound was prepared according to the schemes, steps and intermediates described in Example 98 by using 3-(3-methylsulfonyl)propoxyaniline in place of 4 in Step-2. $^1$H NMR (DMSO-$d_6$) δ ppm: 2.02-2.15 (m, 2H), 3.01 (s, 3H), 3.22 (t, J=7.56 Hz, 2H), 3.88 (t, J=6.12 Hz, 2H), 5.77 (dd, J=1.84 & 10.12 Hz, 1H), 6.25 (dd, J=1.72 & 16.88 Hz, 1H), 6.43 (d, J=9.96 & 16.76 Hz, 2H), 6.95 (t, J=8.12 Hz, 1H), 7.06 (t, J=7.48 Hz, 2H), 7.13 (s, 1H), 7.44 (t, J=8.12 Hz, 1H), 7.56 (d, J=8.44 Hz, 1H), 7.68 (s, 1H), 8.50 (d, J=2.84 Hz, 1H), 9.57 (s, 1H), 10.34 (s, 1H); LCMS: m/e 487.0 (M+2).

Example 111

Preparation of N-(3-(5-cyclopropyl-2-(4-(2-methoxyethoxy)phenylamino)pyrimidin-4-yloxy)phenyl)acrylamide I-131

I-131

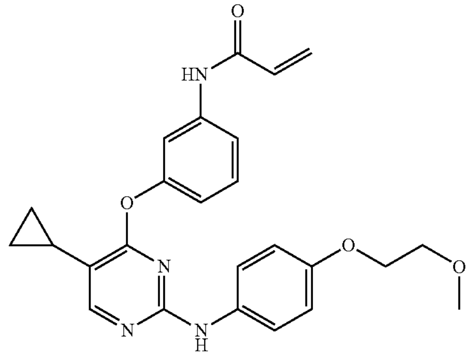

The title compound was prepared according to the steps and intermediates as described below.

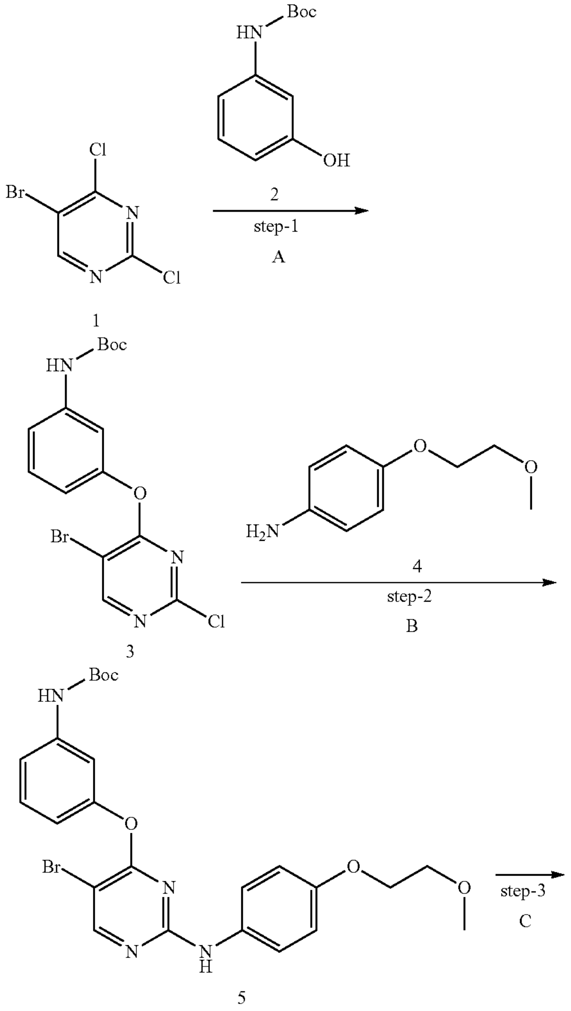

-continued

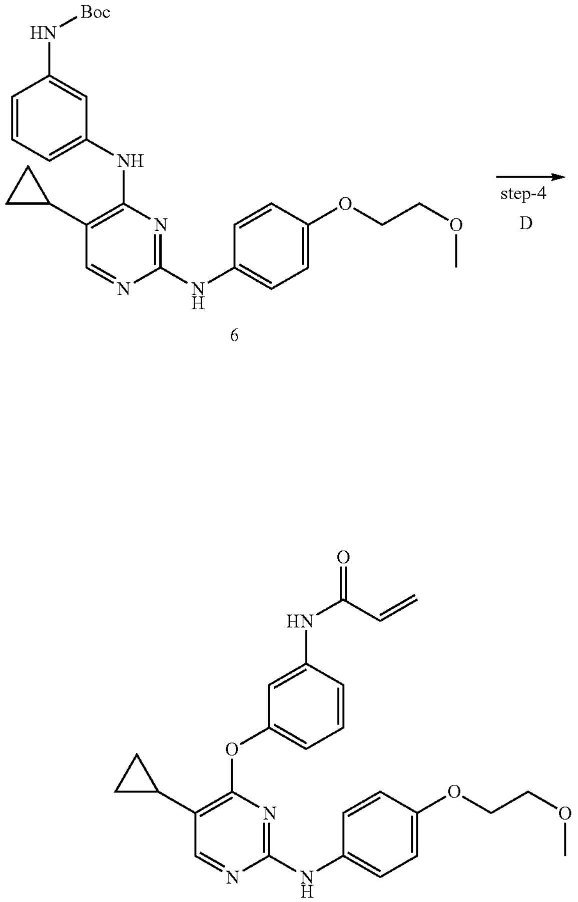

6

I-131

A) $K_2CO_3$, DMA, rt, 5 h;
B) PTSA, dioxane, 100° C., 2 h;
C) potassium cyclopropyltrifluoroborate, $Pd(OAc)_2$, Xanphos, $Cs_2CO_3$, toluene, 100° C., 12 h;
D) 4N HCL, dioxane, rt, 1 hr; then acryoyl chloride, $Et_3N$, DCM, -10° C., 10 min Step-1

3

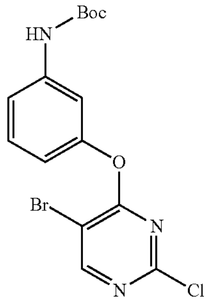

To a solution of 5-bromo-2,4-dichloropyrimidine (0.68 g, 3.0 mmol) and tert-butyl 3-hydroxyphenylcarbamate (0.65 g, 3.1 mmol) in DMA (4 mL) was added $K_2CO_3$ (0.83 g, 6.0 mmol). The suspension was stirred for 5 hours. Water (15 ml) was added and the precipitate was collected by filtration. The solid was washed with ether and dried to yield 1.2 g of compound 3. MS: m/e=400.2, 402.2 (M+1).

Step-2

5

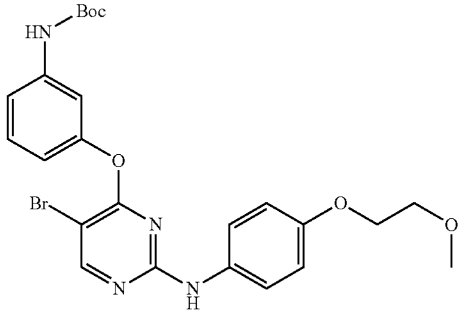

To a solution of compound 3 (200 mg, 0.5 mmol) and 4-(2-methoxyethoxy)aniline (0.1 g, 0.6 mmol) in 5 ml dioxane was added 4-methylbenzenesulfonic acid monohydrate (0.08 g, 0.4 mmol). The mixture was stirred at 100° C. for two hours. The solvent was evaporated. The residue was dissolved in 20 ml ethyl acetate and washed with $NaHCO_3$ aqueous solution, water and brine. The organic layer was separated and dried over $Na_2SO_4$. After removal of solvent, the crude product was subject to chromatography on silica gel (hexane:EtOAc=1:1). 0.10 g of compound 5 was obtained: MS m/z: 531.1, 531.0 ($M+H^+$).

Step-3

6

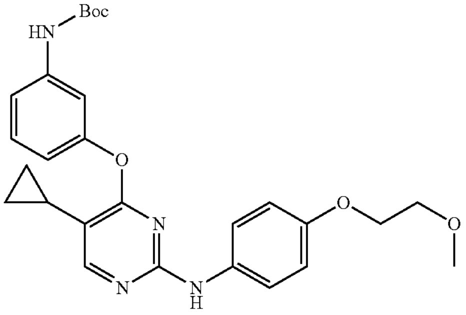

Potassium cyclopropyltrifluoroborate (36 mg, 0.25 mmol), compound 5 (0.10 g, 0.19 mmol), palladium acetate (3.4 mg, 0.015 mmol), Xantphos (17.5 mg, 0.03 mmol) and $Cs_2CO_3$ (186 mg, 0.57 mmol) were suspended in 5 mL toluene and 1 mL water. The mixture was degassed, sealed under argon and heated at 100° C. for 12 hours. 20 mL ethyl acetate was added and washed with $NaHCO_3$ aqueous solution, water and brine. The organic layer was separated and dried over $Na_2SO_4$. After removal of solvent, the crude product was subject to chromatography on silica gel (hexane:EtOAc=1:1). 50 mg of compound 6 was obtained: MS m/z: 493.2 ($M+H^+$).

Step-4
I-131
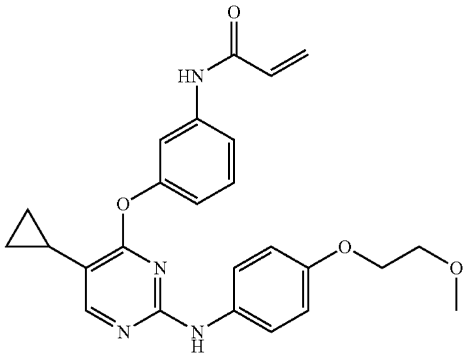
The title compound was prepared from compound 6 following the procedure described in Example 96. MS m/z: 447.1 (M+H$^+$).
Example 112
Preparation of 1-(4-(5-fluoro-2-(3-(2-dimethylaminoethoxy)phenylamino)pyrimidin-4-ylamino)phenyl)-2-methylprop-2-en-1-one I-207
I-207
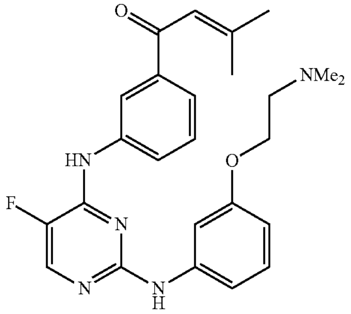
The title compound was prepared according to the schemes steps and intermediates described below.
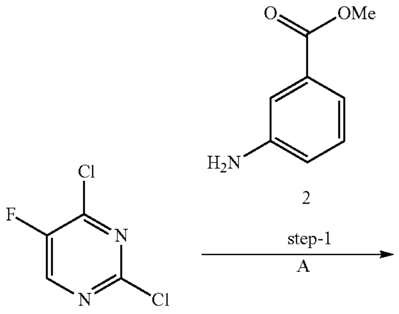
1
2
-continued
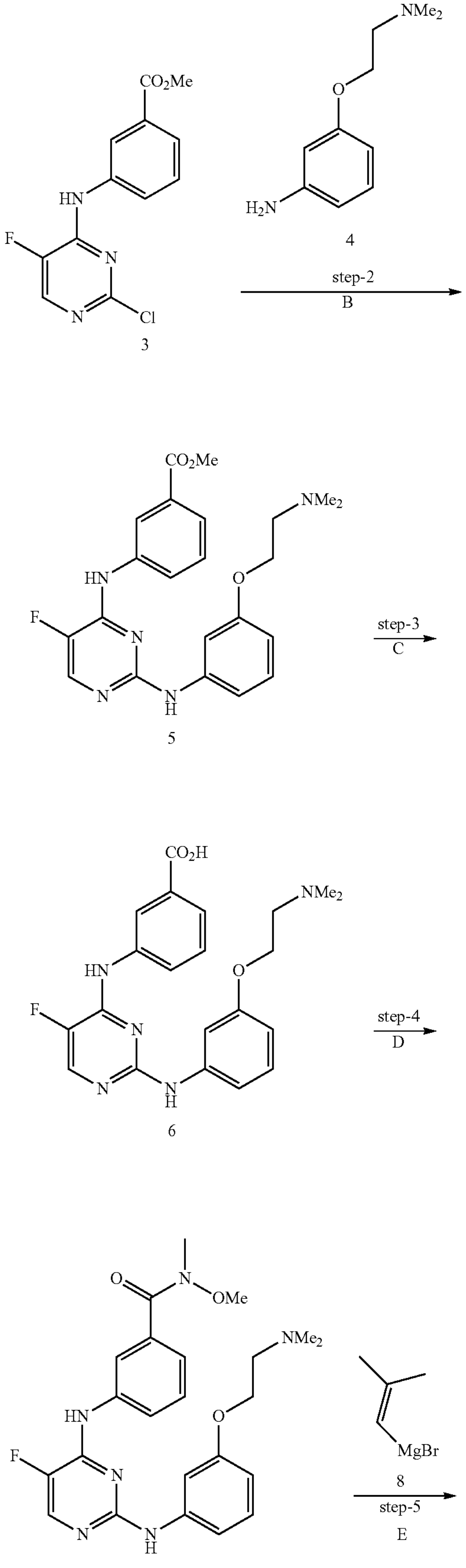
3
4
5
6
7
8

-continued

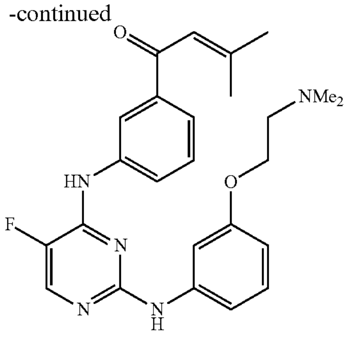

I-207

A) 2, DIPEA, n-BuOH, 90° C., 12 h;
B) 4, $Pd(OAc)_2$, BINAP, $Cs_2CO_3$, toluene, 110° C., 16 h;
C) LiOH, MeOH/THF/H2O, rt, 6 h;
D) MeNHOMe•HCl, EDCI•HCl, HOBT, DIPEA, DMF, rt, 3 h;
E) 8, THF, 0° C. to rt, 2 h Step-1

3

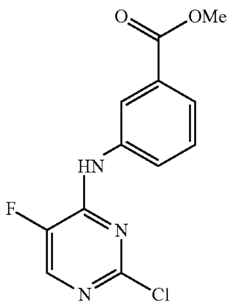

A solution of 1 (4 g, 23.9 mmol), 2 (3.6 g, 23.7 mmol) and DIPEA (4.6 g, 35.58 mmol) in n-butanol (40 mL) was heated in a pressure tube (90° C., 12 h). It was cooled, quenched with water (5 mL) and extracted with EtOAc (2×5 mL). The combined EtOAc extract was washed with water (60 mL), brine (40 mL), dried over $Na_2SO_4$ and concentrated under reduced pressure to afford 3 (5.5 g, 82%) as an off-white solid.

Step-2

5

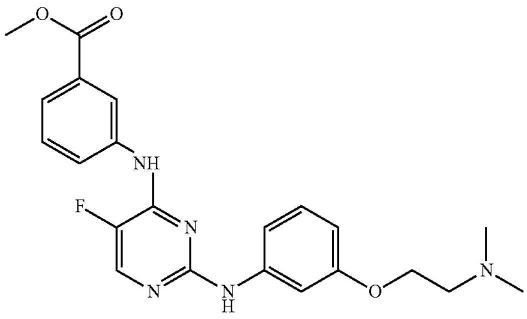

A solution of 4 (0.319 g, 1.76 mmol), 3 (0.5 g, 1.76 mmol), $Pd(OAc)_2$ (0.039 g, 0.17 mmol), BINAP (0.055 g, 0.08 mmol) and $Cs_2CO_3$ (1.44 g, 4.42 mmol) in degassed toluene (toluene was purged with $N_2$ for 30 min) was heated for 16 h at 110° C. under $N_2$ atmosphere. The reaction mixture was cooled, diluted with EtOAc (25 mL) and washed with water (5 mL), brine (2 mL) and dried over $Na_2SO_4$. Filtration followed by concentration under reduced pressure offered a residue which was further purified by column chromatography ($SiO_2$, 60-120, chloroform/methanol, 9/1) to get 4 (0.63 g, 84%) as yellow solid.

Step-3

6

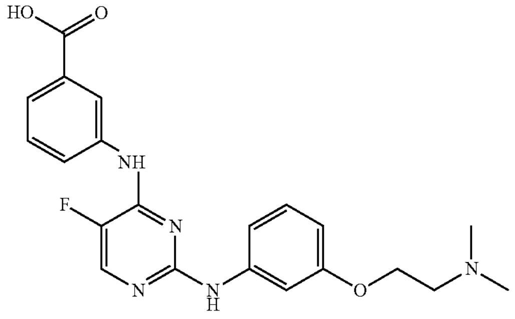

To a stirred solution of 5 (0.3 g, 0.70 mmol) in methanol/THF/water: 1 mL/1 mL/0.5 mL was added LiOH (0.147 g, 3.52 mmol) and the reaction mixture was stirred at rt for 6 h. It was concentrated under reduced pressure; residue was diluted with water (2 mL) and extracted with diethyl ether (5 mL). The aqueous layer was separated and acidified with 1.5 N HCl (pH~4-5) which was concentrated as such and dried under vacuum to get 6 (0.31 g, crude) as yellow gummy solid which was taken for next step without further purification.

Step-4

7

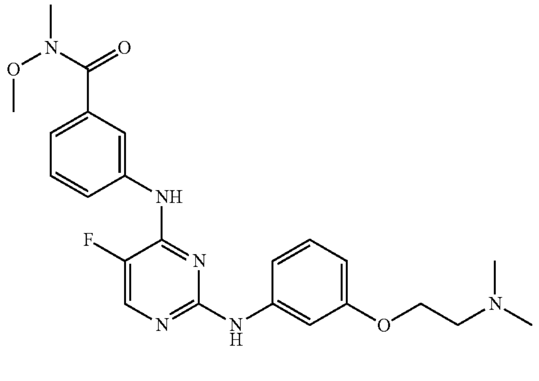

To a stirred solution of 6 (0.29 g, 0.70 mmol) in DMF (3 mL) were added MeNH-OMe.HCl (0.068 g, 0.70 mmol), EDCI.HCl (0.202 g, 1.05 mmol), HOBT (0.047 g, 0.35 mmol) and DIPEA (0.136 g, 1.05 mmol). The reaction mixture was stirred at room temperature for 3 h, quenched with water and extracted with EtOAc (2×5 mL). The combined organic layer was washed with brine, dried over anhydrous $Na_2SO_4$, filtered and concentrated under reduced pressure. The residue was further purified by column chromatography ($SiO_2$, 60-120, methanol/chloroform: 20/80) to get 7 (0.061 g, 19%) as gummy yellow solid.

Step-5

I-207

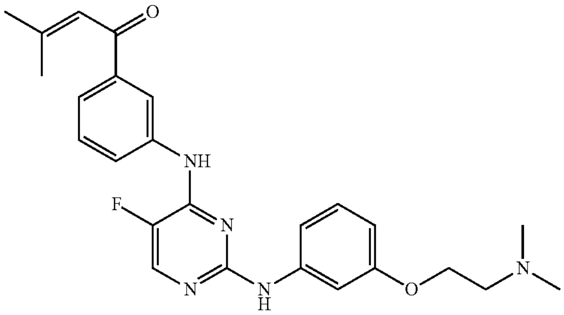

To a stirred solution of 7 (100 mg, 0.22 mmol) in THF (1 mL) at 0° C. was added 8 (17.6 mL, 8.80 mmol). The reaction mixture was allowed to stir at room temperature for 2 h. It was quenched with saturated $NH_4C1$ solution (0.5 mL) and extracted with EtOAc (2×3 mL). The combined organic layer was washed with brine, dried over anhydrous $Na_2SO_4$, filtered and concentrated under reduced pressure to get a white solid. It was further purified by column chromatography ($SiO_2$, 60-120, product getting eluted in 20% methanol/chloroform) to get I-207 (9 mg. 9%) as gummy yellow solid. $^1$H NMR (DMSO-$d_6$) δ ppm: 1.90 (s, 3H), 2.01 (s, 3H), 2.19 (s, 6H), 2.57 (t, J=5.64 Hz, 2H), 3.87 (t, J=5.84 Hz, 2H), 6.45 (dd, J=1.64 & 8.08 Hz, 1H), 6.82 (s, 1H), 7.04 (t, J=8.16 Hz, 1H), 7.18 (d, J=8.16 Hz, 1H), 7.33 (s, 1H), 7.47 (t, J=7.88 Hz, 1H), 7.62 (d, J=7.72 Hz, 1H), 8.13-8.16 (m, 3H), 9.24 (s, 1H), 9.56 (s, 1H); LCMS: m/e 450.1 (M+1).

Example 113

Preparation of 1-(4-(5-fluoro-2-(phenylamino)pyrimidin-4-ylamino)phenyl)-3-methylbut-2-en-1-one I-206

I-206

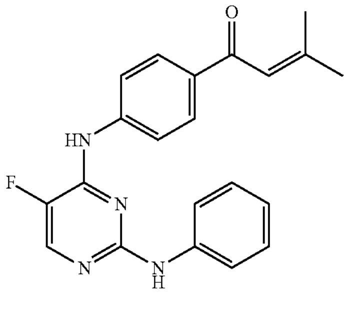

The title compound was prepared according to the schemes, steps and intermediates described in Example 112 by using methyl 4-aminobenzoate in place of 2 in step-1 and aniline in place of 4 in step-2. $^1$H NMR (DMSO-$d_6$) δ ppm: 1.98 (s, 3H), 2.12 (s, 3H), 6.90-7.00 (m, 2H), 7.20-7.30 (m, 2H), 7.65 (d, J=8.16 Hz, 2H), 7.90 (d, J=8.56 Hz, 2H), 7.98 (d, J=8.68 Hz, 2H), 8.18 (bs, 1H), 9.31 (s, 1H), 9.68 (s, 1H); LCMS: m/e 363.0 (M+1).

Example 114

Preparation of 1-(3-(5-fluoro-2-(3-(prop-2-ynyloxy)phenylamino)pyrimidin-4-ylamino)phenyl)-3-methylbut-2-en-1-one I-211

I-211

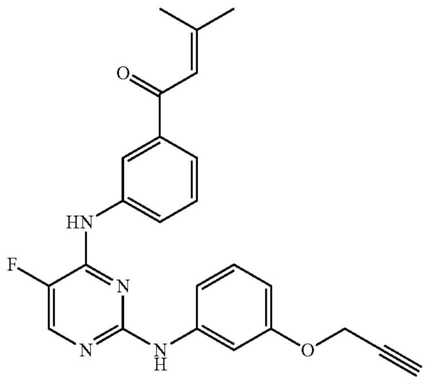

The title compound was prepared according to the schemes, steps and intermediates described in Example 112 by using 3-prop-2-ynyloxyaniline in place of 4 in step-2. $^1$H NMR ($CD_3OD$) δ ppm: 2.0 (d, J=1 Hz, 3H), 2.21 (d, J=1.04 Hz, 3H), 2.94-2.96 (d, J=2.44 Hz, 1H), 4.59 (d, J=2.36 Hz, 2H), 6.79-6.81 (m, 2H), 7.03 (dd, J=3.12 & 8.04 Hz, 1H), 7.14 (t, J=2.2 Hz, 1H), 7.23 (t, J=8.12 Hz, 1H), 7.54 (t, J=7.92 Hz, 1H), 7.83 (d, J=7.96 Hz, 1H), 7.86 (dd, J=2.08 & 8.08 Hz, 1H), 8.03 (d, J=4.96 Hz, 1H), 8.21 (t, J=1.88 Hz, 1H); LCMS: m/e 417.0 (M+1).

Example 115

Preparation of 1-(3-(5-fluoro-2-(3-(trifluoromethoxy)phenylamino)pyrimidin-4-ylamino)phenyl)-3-methylbut-2-en-1-one I-223

I-223

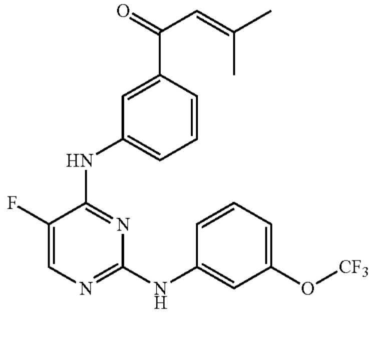

The title compound was prepared according to the schemes, steps and intermediates described in Example 112 by using 3-trifluoromethoxyaniline in place of 4 in step-2. $^1$H NMR ($CDCl_3$) δ ppm: 2.0 (d, J=1.08 Hz, 3H), 2.24 (d, J=1.04 Hz, 3H), 6.74 (t, J=1.24 Hz, 1H), 6.85 (dd, J=1.08 & 7.0 Hz, 1H), 6.90 (s, 1H), 7.08 (s, 1H), 7.24-7.28 (m, 1H), 7.35 (td, J=1.2 & 7.44 Hz, 1H), 7.49 (t, J=7.88 Hz, 1H), 7.63 (s, 1H), 7.72 (td, J=1.04 & 7.76 Hz, 1H), 7.90-7.92 (m, 1H), 8.00-8.05 (m, 2H); LCMS: m/e 447 (M+1).

Example 116

Preparation of 1-(3-(5-fluoro-2-(3-(trifluoromethoxy)phenylamino)pyrimidin-4-ylamino)phenyl)-2-methylprop-2-en-1-one I-199

I-199

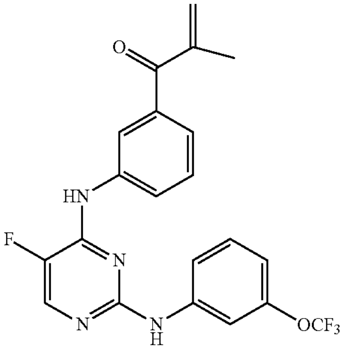

The title compound was prepared according to the schemes, steps and intermediates described in Example 112 by using 3-trifluoromethoxyaniline in place of 4 in step-2 and isopropenylmagnesium bromide in place of 8 in step-5. $^{1}$H NMR (DMSO-$d_6$) δ ppm: 1.97 (s, 3H), 5.6 (s, 1H), 6.0 (d, J=0.96 Hz, 1H), 6.82 (d, J=8.08 Hz, 1H), 7.27 (t, J=8.2 Hz, 1H), 7.41 (dd, J=1.12 & 7.56 Hz, 1H), 7.48 (t, J=7.76 Hz, 1H), 7.60 (dd, J=1.28 & 7.88 Hz, 1H), 7.78 (s, 1H), 7.90 (d, J=1.64 Hz, 1H), 8.15 (d, J=8 Hz, 1H), 8.19 (d, J=3.64 Hz, 1H), 9.55 (s, 1H), 9.65 (s, 1H); LCMS: m/e 433 (M+1).

Example 117

Preparation of 1-(4-(5-fluoro-2-(phenylamino)pyrimidin-4-ylamino)phenyl)-2-methylprop-2-en-1-one I-185

I-185

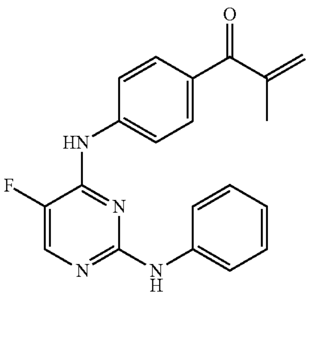

The title compound was prepared according to the schemes, steps and intermediates described in Example 112 by using methyl 4-aminobenzoate in place of 2 in step-1, aniline in place of 4 in step-2 and isopropenylmagnesium bromide in place of 8 in step-5. $^{1}$H NMR (DMSO-$d_6$) δ ppm: 1.99 (s, 3H), 5.54 (s, 1H), 1.01 (s, 1H), 6.93 (t, J=7.36 Hz, 1H), 7.24 (t, J=7.52 Hz, 2H), 7.66-7.72 (m, 4H), 8.01 (d, J=8.72 Hz, 2H), 8.19 (d, J=3.6 Hz, 1H), 9.32 (s, 1H), 9.72 (s, 1H); LCMS: m/e 348.8 (M+1).

Example 118

Preparation of N-(3-(2-(3-(2-(dimethylamino)ethoxy)phenylamino)-5-fluoropyrimidin-4-ylamino)phenyl)acrylamide I-233

I-233

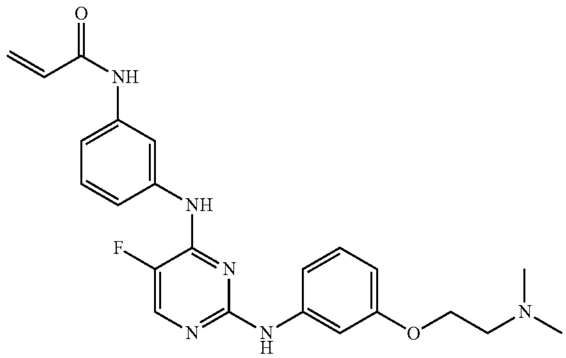

The title compound was prepared according to the steps, schemes and intermediates described in Example 20 by using 3-(2-dimethylaminoethoxy)aniline in place of 4 in step-2. $^{1}$H NMR ($CD_3OD$) δ ppm: 2.31 (s, 6H), 2.76 (t, J=5.6 Hz, 2H), 3.97 (t, J=5.2 Hz, 2H), 5.78 (dd, J=2 & 9.2 Hz, 1H), 6.38-6.42 (m, 2H), 6.52-6.55 (m, 1H), 7.1-7.11 (m 2H), 7.30 (t, J=8.0 Hz, 1H), 7.36 (s, 1H), 7.42-7.48 (m, 2H), 7.94 (d, J=3.6 Hz, 1H), 8.05 (s, 1H); LCMS: m/e 437 (M+1).

Example 119

Preparation of N-(3-(5-fluoro-4-(4-phenoxyphenoxy)pyrimidin-2-ylamino)phenyl)acrylamide I-130

I-130

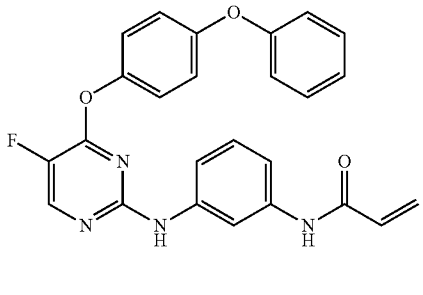

The title compound was prepared according to the steps, schemes and intermediates described in Example 11 by using 5-fluoro-2,4-dichloropyrimidine in place of 1 in step-1. $^{1}$H NMR (DMSO-$d_6$) δ ppm: 5.71 (dd, J=1.6 & 10 Hz, 1H), 6.22 (dd, J=1.6 & 16.8 Hz, 1H), 6.44 (dd, J=10.4 & 17.2 Hz, 1H), 6.98-7.05 (m, 3H), 7.1-7.12 (m, 2H), 7.17 (t, J=7.2 Hz, 1H), 7.24 (t, J=7.6 Hz, 2H), 7.35-7.37 (m, 2H), 7.42 (t, J=8.4 Hz, 2H), 7.71 (s, 1H), 8.5 (s, 1H), 9.6 (s, 1H), 10.05 (s, 1H); LCMS: m/e 443.0 (M+1).

Example 120

Preparation of (S)—N-(3-(5-fluoro-2-(4-(tetrahydrofuran-3-yloxy)phenylamino)pyrimidin-4-ylamino)phenyl)acrylamide I-43

I-43

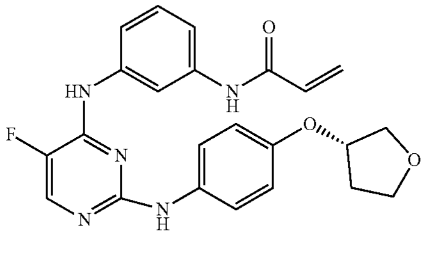

The title compound was prepared according to the steps, schemes and intermediates described in Example 20 by using (S)-4-(tetrahydrofuran-3-yloxyaniline in place of 4 in step-2. $^1$H NMR (DMSO-$d_6$, 500 MHz): δ 10.10 (s, 1H), 9.35 (s, 1H), 8.95 (s, 1H), 8.05 (d, J=4.0 Hz, 1H), 7.92 (s, 1H), 7.52 (d, J=9.0 Hz, 2H), 7.47 (d, J=7.5 Hz, 1H), 7.41 (d, J=8.5 Hz, 1H), 7.27 (t, J=8.0 Hz, 1H), 6.72 (d, J=9.0 Hz, 2H), 6.45 (dd, J=1.5, 17.0 Hz, 1H), 6.25 (dd, J=1.1, 16.5 Hz, 1H), 5.75 (dd, J=1.1, 10.0 Hz, 1H), 4.93-4.84 (m, 1H), 3.88-3.72 (m, 4H), 2.20-2.10 (m, 1H), 1.97-1.90 (m, 1H). MS m/e=436 [$M^+$+1]

Example 121

Preparation of (R)—N-(3-(5-fluoro-2-(4-(tetrahydrofuran-3-yloxy)phenylamino)pyrimidin-4-ylamino)phenyl)acrylamide I-46

I-46

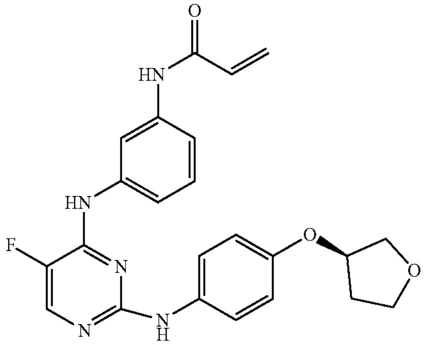

The title compound was prepared according to the steps, schemes and intermediates described in Example 20 by using (R)-4-(tetrahydrofuran-3-yloxyaniline in place of 4 in step-2. $^1$H NMR (DMSO-$d_6$, 500 MHz): δ 10.10 (s, 1H), 9.35 (s, 1H), 8.95 (s, 1H), 8.05 (d, J=4.0 Hz, 1H), 7.92 (s, 1H), 7.52 (d, J=9.0 Hz, 2H), 7.47 (d, J=7.5 Hz, 1H), 7.41 (d, J=8.5 Hz, 1H), 7.27 (t, J=8.0 Hz, 1H), 6.72 (d, J=9.0 Hz, 2H), 6.45 (dd, J=1.5, 17.0 Hz, 1H), 6.25 (dd, J=1.1, 16.5 Hz, 1H), 5.75 (dd, J=1.1, 10.0 Hz, 1H), 4.93-4.84 (m, 1H), 3.88-3.72 (m, 4H), 2.22-2.14 (m, 1H), 1.97-1.90 (m, 1H). MS: m/e=436 [$M^+$+1]

Example 122

Preparation of N-(3-(5-fluoro-2-(3-((1-methylpiperidin-3-yl)methoxy)phenylamino)pyrimidin-4-ylamino)phenyl)-acrylamide I-76)

I-76

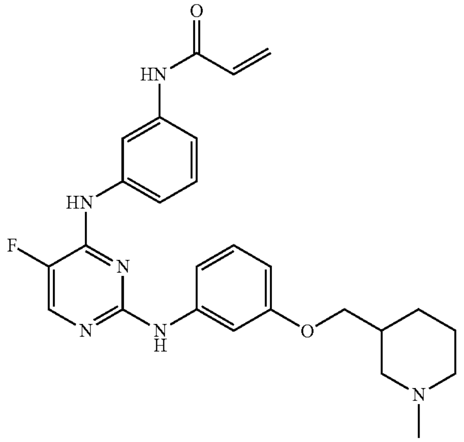

The title compound was prepared according to the steps, schemes and intermediates described in Example 20 by using 3-(1-methylpiperidin-3-yl)methoxyaniline in place of 4 in step-2. $^1$H NMR (DMSO-$d_6$, 500 MHz): δ 10.08 (s, 1H), 9.41 (s, 1H), 9.09 (s, 1H), 8.11 (d, J=3.5 Hz, 1H), 7.90 (s, 1H), 7.57 (d, J=8.0 Hz, 1H), 7.41 (d, J=8.0 Hz, 1H), 7.32 (s, 1H), 7.30-7.20 (m, 2H), 7.03 (t, J=8.0 Hz, 1H), 6.50-6.40 (m, 2H), 6.24 (dd, J=1.5, 17.0 Hz, 1H), 5.74 (dd, J=2.0, 10.5 Hz, 1H), 3.75-3.65 (m, 2H), 2.73 (d, J=10 Hz, 1H), 2.60 (d, J=10.5 Hz, 1H), 2.13 (s, 3H), 1.98-1.83 (m, 2H), 1.75-1.58 (m, 3H), 1.55-1.45 (m, 1H), 1.05-0.95 (m, 1H). MS: m/e=477 ($M^+$+1).

Example 123

Preparation of N-(3-(5-fluoro-2-(3-((1-methylpiperidin-4-yl)methoxy)phenylamino)pyrimidin-4-ylamino)phenyl)-acrylamide I-82

I-82

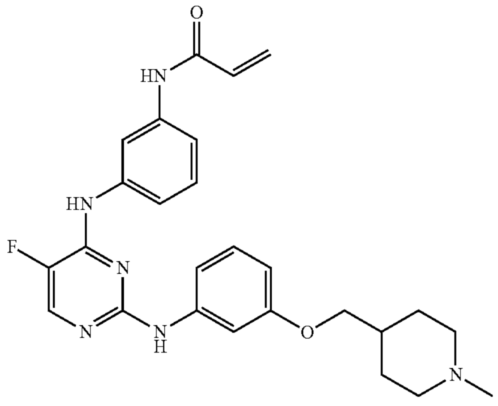

The title compound was prepared according to the steps, schemes and intermediates described in Example 20 by using 3-(1-methylpiperidin-4-yl)methoxyaniline in place of 4 in step-2. $^1$H-NMR ($CDCl_3$+DMSO-$D_6$, 500 MHz): δ 9.04 (bs, 1H), 8.30 (s, 1H), 7.96 (s, 1H), 7.75 (s, 1H), 7.63 (s, 1H), 7.59 (d, J=7.0 Hz, 1H), 7.38-7.33 (m, 2H), 7.27 (t, J=8.5 Hz, 1H), 7.16 (t, J=8 Hz, 1H), 7.09 (d, J=8.5 Hz, 1H), 6.52 (d, J=7.0 Hz, 1H), 6.51-6.38 (m, 2H), 5.73 (dd, J=2.0, 9.0 Hz, 1H), 3.77 (d, J=6.0 Hz, 2H), 2.90-2.84 (m, 2H), 2.28 (s, 3H), 1.95 (t, J=10.0 Hz, 1H), 1.85-1.74 (m, 2H), 1.45-1.32 (m, 2H), 1.28-1.25 (m, 2H). MS: m/e=477 ($M^+$+1).

Example 124

Preparation of N-(3-(2-(3-(4-(2-hydroxyethyl)piperazin-1-yl)phenylamino)-5-fluoropyrimidin-4-ylamino)phenyl)acrylamide I-83

I-83

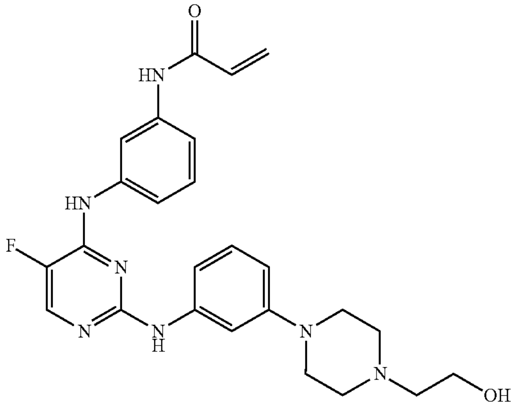

The title compound was prepared according to the steps, schemes and intermediates described in Example 20 by using 3-(4-(2-t-butyldimethylsilyloxyethyl)piperazin-1-ylaniline in place of 4 in step-2 and deprotecting the TBS ether with TFA in DCM as a step-5. $^1$H NMR (DMSO-$d_6$, 500 MHz): δ 8.99 (s, 1H), 8.85 (s, 1H), 8.04 (d, J=4.0 Hz, 1H), 7.28-7.19 (m, 2H), 7.08-7.00 (m, 2H), 6.94 (t, J=3.5 Hz, 2H), 6.48 (dd, J=2.0, 8.0 Hz, 1H), 6.35-6.31 (m, 1H), 4.94 (s, 2H), 3.71 (t, J=6.0 Hz, 2H), 3.02 (t, J=4.5 Hz, 4H), 2.57-2.50 (m, 4H), 2.46 (t, J=6.0 Hz, 2H), 0.87 (s, 9H), 0.05 (s, 6H). MS: m/e=538 ($M^+$+1).

Example 125

Preparation of N-(4-(5-fluoro-2-(3-methoxyphenylamino)pyrimidin-4-ylamino)benzyl)-N-methylacrylamide I-113

I-113

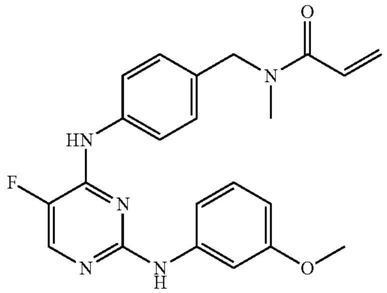

The title compound was prepared according to the steps, schemes and intermediates described in Example 20 by using 4-(N-methyl-N-tert-butyloxycarbonylamino)methylaniline in place of 2 in step-1 and 3-methoxyaniline in place of 4 in step-2. $^1$H-NMR (DMSO-$d_6$, 200 MHz): δ 9.36 (bs, 1H), 9.16 (bs, 1H), 8.10 (d, J=3.4 Hz, 1H), 7.83-7.70 (m, 2H), 7.34 (bs, 1H), 7.26-7.01 (m, 4H), 6.86-6.73 (m, 1H), 6.48 (d, J=8.0 Hz, 1H), 6.21 (dd, J=16.4, 2.2 Hz, 1H), 5.76-5.64 (m, 1H), 4.64-4.53 (two s, 2H), 3.65 (s, 3H), 3.00-2.88 (two s, 3H). MS: m/e=408.2 [$M^+$+1].

Example 126

Preparation of N-(4-(5-fluoro-2-(6-methoxypyridin-3-ylamino)pyrimidin-4-ylamino)benzyl)-N-methylacrylamide I-114

I-114

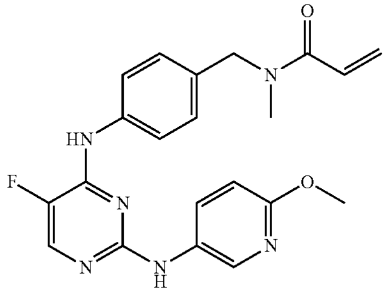

The title compound was prepared according to the steps, schemes and intermediates described in Example 20 by using 4-(N-methyl-N-tert-butyloxycarbonylamino)methylaniline in place of 2 in step-1 and 6-methoxy-3-aminopyridine in place of 4 in step-2. $^1$H-NMR (DMSO-$D_6$, 200 MHz): δ 9.36 (bs, 1H), 9.09 (bs, 1H), 8.32 (bs, 1H), 8.06 (dd, J=3.8 Hz, 1H), 7.97-7.92 (m, 1H), 7.76-7.68 (m, 2H), 7.20-7.08 (m, 2H), 6.87-6.75 (m, 1H), 6.72 (d, J=8.4 Hz, 1H), 6.22 (dd, J=19.4, 2.6 Hz, 1H), 5.74-5.65 (m, 1H), 4.64-4.53 (two s, 2H), 3.78 (s, 3H), 3.00-2.88 (two s, 3H). MS: m/e=409 ($M^+$+1).

Example 127

Preparation of N-(3-(5-fluoro-2-(3-methyoxyphenylamino)pyrimidin-4-ylamino)benzyl)-N-methylacrylamide I-115

I-115

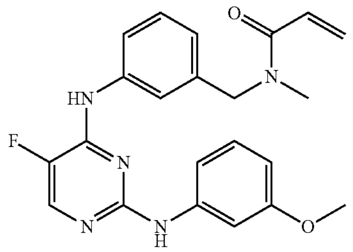

The title compound was prepared according to the steps, schemes and intermediates described in Example 20 by using 3-(N-methyl-N-tert-butyloxycarbonylamino)methylaniline in place of 2 in step-1 and 3-methoxyaniline in place of 4 in step-2. $^1$H-NMR (DMSO-d$_6$, 200 MHz): δ 9.50-9.30 (m, 1H), 9.15-8.96 (m, 1H), 8.15 (bs, 1H), 7.82-7.59 (m, 2H), 7.45-7.00 (m, 4H), 6.97-6.65 (m, 2H), 6.55-6.45 (m, 1H), 6.26-6.12 (m, 1H), 5.78-5.60 (m, 1H), 4.68 (s, 1H), 4.55 & 3.75 (two s, 3H), 2.90 & 3.00 (two s, 3H). MS: m/e=408.2 [M$^+$+1].

Example 128

Preparation of N-(3-(5-fluoro-2-(3-(4-(2-hydroxyethyl)piperazin-1-yl)phenylamino)pyrimidin-4-yloxy) phenyl)acrylamide I-84

I-84

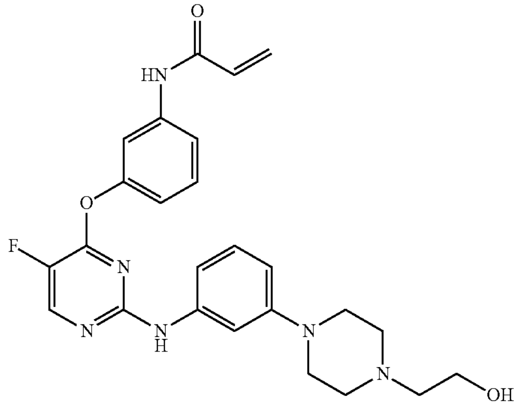

The title compound was prepared according to the steps, schemes and intermediates described in Example 98 by using 3-(4-(2-t-butyldimethylsilyloxyethyl)piperazin-1-ylaniline in place of 4 in step-2 and deprotecting the TBS ether with TFA in DCM as a step-5. $^1$H-NMR (DMSO-D$_6$, 500 MHz): δ 8.19 (s, 1H), 7.75-7.70 (m, 2H), 7.42-7.35 (m, 2H), 7.12-7.05 (m, 2H), 6.97 (dd, J=2.0, 10.5 Hz, 1H), 6.93 (s, 1H), 6.72 (d, J=6.5 Hz, 1H), 6.57-6.54 (m, 1H), 6.44 (d, J=17.0 Hz, 1H), 6.29-6.20 (m, 1H), 5.78 (d, J=10.0 Hz, 1H), 3.68 (t, J=5.5 Hz, 2H), 3.00-2.94 (m, 4H), 2.63-2.56 (m, 6H). MS: m/e=479 (M$^+$+1).

Example 129

Preparation of N-(3-(5-fluoro-2-(3-((1-methylpiperidin-3-yl)methoxy)phenylamino)pyrimidin-4-yloxy) phenyl)acrylamide I-81

I-81

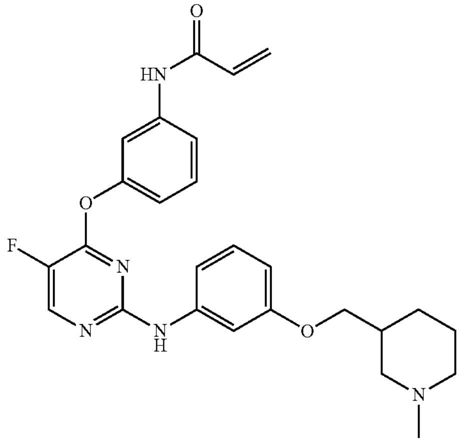

The title compound was prepared according to the steps, schemes and intermediates described in Example 98 by using 3-(1-methylpiperidin-3-yl)methoxyaniline in place of 4 in step-2. $^1$H-NMR (CDCl$_3$, 500 MHz): δ 8.19 (d, J=2.5 Hz, 1H), 7.82-7.75 (m, 2H), 7.42-7.36 (m, 2H), 7.08-7.02 (m, 3H), 6.99 (d, J=7.0 Hz, 1H), 6.91 (s, 1H), 6.79 (d, J=7.5 Hz, 1H), 6.48-6.44 (m, 1H), 6.42 (s, 1H), 6.29-6.23 (m, 1H), 5.77 (d, J=10 Hz, 1H), 3.67-3.62 (m, 2H), 2.95-2.91 (m, 1H), 2.82-2.76 (m, 1H), 2.28 (s, 3H), 2.11-2.05 (m, 1H), 1.98-1.92 (m, 1H), 1.79-1.70 (m, 3H), 1.11-1.04 (m, 1H). MS: m/e=478 (M$^+$+1).

Example 130

Preparation of N-(3-(5-fluoro-2-(3-((1-methylpiperidin-4-yl)methoxy)phenylamino)pyrimidin-4-yloxy) phenyl)-acrylamide I-75

I-75

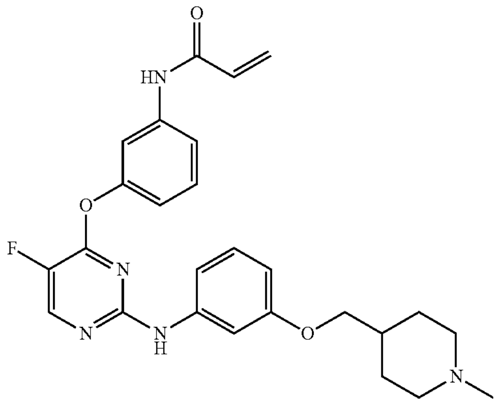

The title compound was prepared according to the steps, schemes and intermediates described in Example 98 by using 3-(1-methylpiperidin-4-yl)methoxyaniline in place of 4 in step-2. $^1$H-NMR (DMSO-$D_6$, 500 MHz): δ 10.31 (s, 1H), 9.50 (s, 1H), 8.50 (s, 1H), 7.67 (s, 1H), 7.55 (d, J=8.0 Hz, 1H), 7.42 (t, J=8.0 Hz, 1H), 7.10 (s, 1H), 7.04 (d, J=7.0 Hz, 2H), 6.94 (t, J=8.0 Hz, 1H), 6.45-6.39 (m, 2H), 6.27 (d, J=15.0 Hz, 1H), 5.78 (dd, J=2.0, 10.5 Hz, 1H), 3.64 (d, J=6.0 Hz, 2H), 2.75 (d, J=6.5 Hz, 2H), 2.14 (s, 3H), 1.83 (t, J=10.5 Hz, 2H), 1.66-1.64 (m, 3H), 1.25-1.23 (m, 2H). MS: m/e=478 ($M^+$+1).

Example 131

Preparation of N-(3-(5-cyano-2-(phenylamino)pyrimidin-4-ylamino)phenyl)acrylamide I-157

I-157

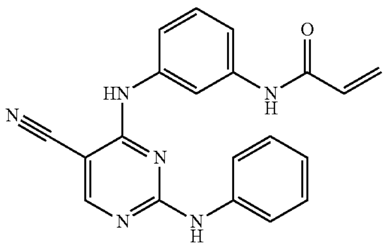

The title compound was prepared according to the schemes, steps and intermediates described in Example 94, by using 2,4-dichloro-5-cyanopyrimidine in the place of 4 in Step 2. MS 379.1 (M+Na).

Example 132

Preparation of N-(3-(5-fluoro-2-(3-(trifluoromethoxy)phenylamino)pyrimidin-4-ylamino)phenyl)acrylamide I-244

I-244

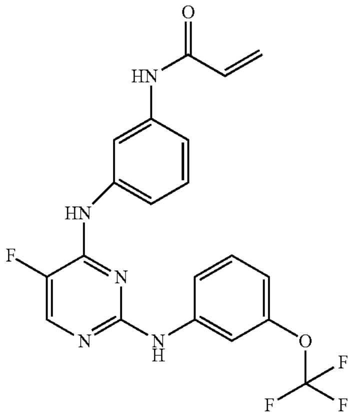

The title compound was prepared according to the schemes, steps and intermediates described in Example 20, by using 3-(trifluoromethoxy)aniline in the place of 4 in Step 2. MS 434.1 (M+1).

Example 133

Preparation of N-(3-(5-fluoro-2-(pyridin-3-ylamino)pyrimidin-4-ylamino)phenyl)acrylamide I-234

I-234

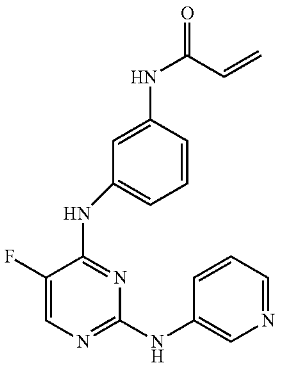

The title compound was prepared according to the schemes, steps and intermediates described in Example 20, by using 3-aminopyridine in the place of 4 in Step 2. MS 351.1 (M+1).

Example 134

Preparation of N-(3-(5-fluoro-2-(4-fluorophenylamino)pyrimidin-4-ylamino)phenyl)acrylamide I-247

I-247

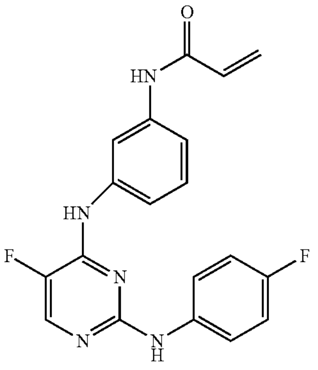

The title compound was prepared according to the schemes, steps and intermediates described in Example 20, by using 4-fluoroaniline in the place of 4 in Step 2. MS 368.1 (M+1)

Example 135

Preparation of N-(3-(5-fluoro-2-(3-(3-morpholinopropoxy)phenylamino)pyrimidin-4-ylamino)phenyl) acrylamide I-208

I-208

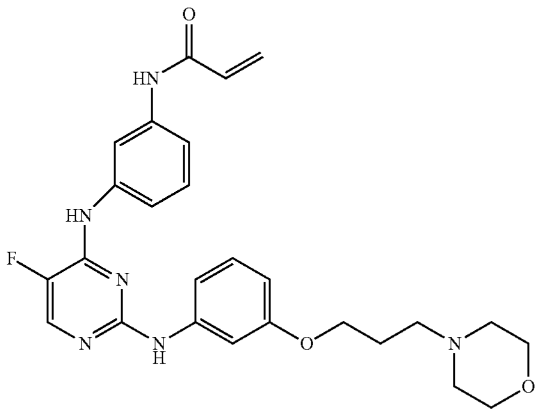

The title compound was prepared according to the schemes, steps and intermediates described in Example 20, by using 3-(3-morpholinopropoxy)aniline in the place of 4 in Step 2. MS 515.3 (M+Na).

Example 136

Preparation of N-(3-(2-(3-(3-(1H-imidazol-1-yl)propoxy)phenylamino)-5-fluoropyrimidin-4-ylamino)phenyl)acrylamide I-204

I-204

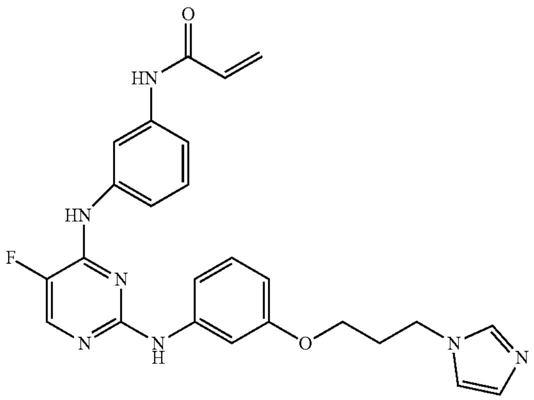

The title compound was prepared according to the schemes, steps and intermediates described in Example 20, by using 3-(3-(1H-imidazol-1-yl)propoxy)aniline in the place of 4 in Step 2. MS 474.3 (M+Na).

Example 137

Preparation of N-(3-(2-(1-acetylpiperidin-3-ylamino)-5-fluoropyrimidin-4-ylamino)phenyl)acrylamide I-238

I-238

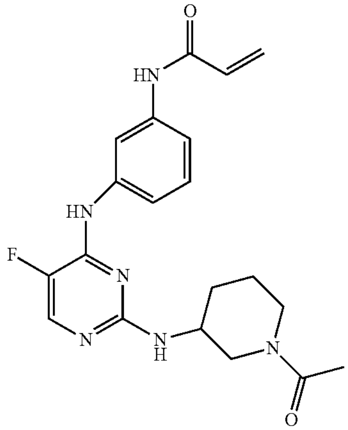

The title compound was prepared according to the schemes, steps and intermediates described in Example 20, by using 1-(3-aminopiperidin-1-yl)ethanone in the place of 4 in Step 2. MS 421.1 (M+Na).

Example 138

Preparation of N-(3-(5-fluoro-2-(phenylamino)pyrimidin-4-yloxy)phenyl)acrylamide I-228

I-228

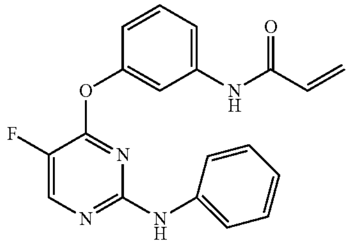

The title compound was prepared according to the schemes, steps and intermediates described in Example 98, by using aniline in the place of 4 in Step 2. MS 351.3 (M+1).

Example 139

Preparation of N-(3-(5-fluoro-2-(6-methoxypyridin-3-ylamino)pyrimidin-4-ylamino)phenyl)acrylamide I-243

I-243

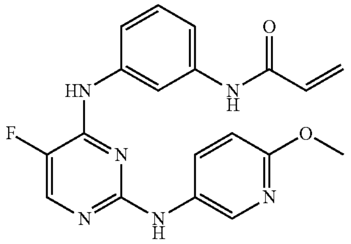

The title compound was prepared according to the schemes, steps and intermediates described in Example 20, by using 6-methoxypyridin-3-amine in the place of 4 in Step 2. MS 381.1 (M+1).

Example 140

Preparation of N-(3-(5-methoxy-2-(3-methoxyphenylamino)pyrimidin-4-ylamino)phenyl)acrylamide. I-158

I-158

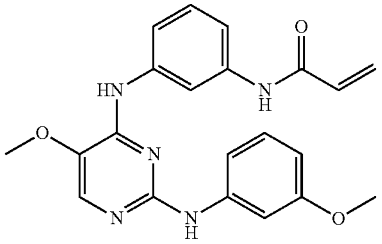

The title compound was prepared according to the schemes, steps and intermediates described in Example 1, by using 5-methoxy-2,4-dichloropyrimidine in the place of 1 in Step 1 and 3-methoxyaniline in place of 4 in step 2. MS 392.3 (M+1).

Example 141

Preparation of N-(3-(5-methoxy-2-(6-methoxypyridin-3-ylamino)pyrimidin-4-ylamino)phenyl)acrylamide I-192

I-192

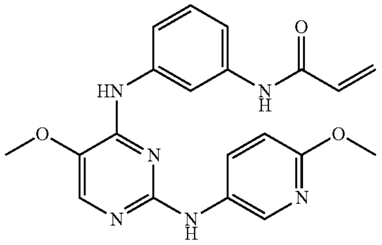

The title compound was prepared according to the schemes, steps and intermediates described in Example 1, by using 5-methoxy-2,4-dichloropyrimidine in the place of 1 in Step 1 and 5-amino-2-methoxypyridine in place of 4 in step 2. MS 393.3 (M+1).

Example 142

Preparation of N-(3-(5-fluoro-2-(6-methoxypyridin-3-ylamino)pyrimidin-4-yloxy)phenyl)acrylamide I-222

I-222

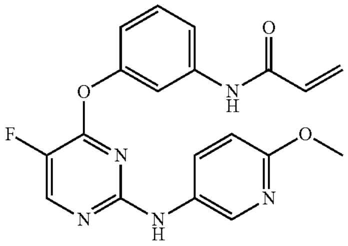

The title compound was prepared according to the schemes, steps and intermediates described in Example 98, by using 3-amino-6-methoxypyridine in the place of 4 in Step 2. MS 382.3 (M+1).

Example 143

Preparation of 4-(3-acrylamidophenylamino)-N-tert-butyl-2-(6-methoxypyridin-3-ylamino)pyrimidine-5-carboxamide I-216

I-216

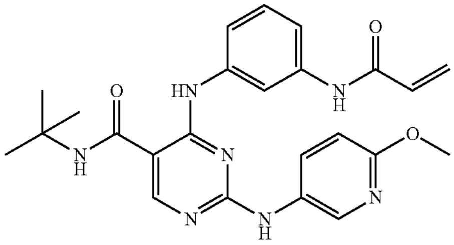

The title compound was prepared according to the schemes, steps and intermediates described in Example 37, by using tert-butylamine in the place of 2 in Step-1 and omitting Step-6. MS 484.3 (M+Na).

Example 144

Preparation of (R)-1-(3-(5-fluoro-2-(6-methoxypyridin-3-ylamino)pyrimidin-4-ylamino)piperidin-1-yl)prop-2-en-1-one I-202

I-202

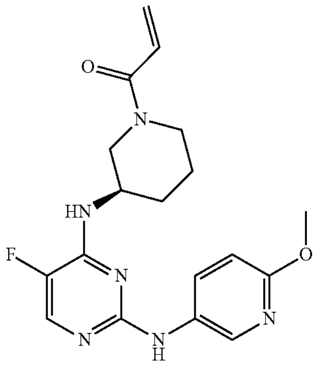

The title compound was prepared according to the schemes, steps and intermediates described in Example 20, by using (R)-tert-butyl 3-aminopiperidine-1-carboxylate in the place of 2 in Step 1 and 3-amino-6-methoxypyridine in place of 4 in step 2. MS 395.3 (M+Na).

Example 145

Preparation of (R)-1-(3-(5-fluoro-2-(3-methoxyphenylamino)pyrimidin-4-ylamino)piperidin-1-yl)prop-2-en-1-one I-195

I-195

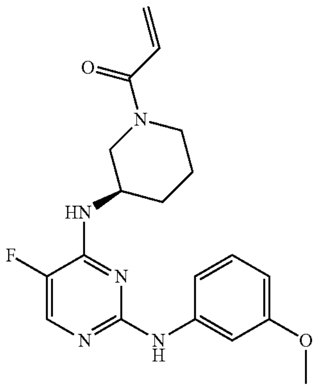

The title compound was prepared according to the schemes, steps and intermediates described in Example 20, by using (R)-tert-butyl 3-aminopiperidine-1-carboxylate in the place of 2 in Step 1 and 3-methoxyaniline in place of 4 in step 2. MS 394.3 (M+Na).

Example 146

Preparation of (S)-1-(3-(5-fluoro-2-(6-methoxypyridin-3-ylamino)pyrimidin-4-ylamino)piperidin-1-yl)prop-2-en-1-one I-197

I-197

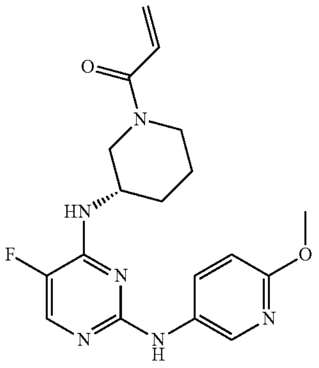

The title compound was prepared according to the schemes, steps and intermediates described in Example 20, by using (S)-tert-butyl 3-aminopiperidine-1-carboxylate in the place of 2 in Step 1 and 3-amino-6-methoxypyridine in place of 4 in step 2. MS 373.3 (M+1).

Example 147

Preparation of (S)-1-(3-(5-fluoro-2-(3-methoxyphenylamino)pyrimidin-4-ylamino)piperidin-1-yl)prop-2-en-1-one I-196

I-196

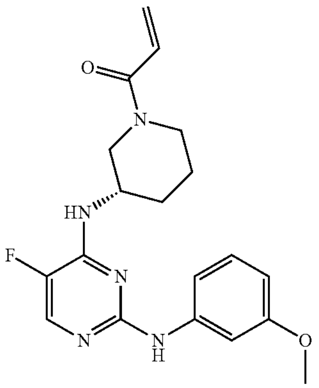

The title compound was prepared according to the schemes, steps and intermediates described in Example 20, by using (S)-tert-butyl 3-aminopiperidine-1-carboxylate in the place of 2 in Step 1 and 3-methoxyaniline in place of 4 in step 2. MS 372.3 (M+1).

Example 148

Preparation of (R)-1-(3-(5-fluoro-2-(6-methoxypyridin-3-ylamino)pyrimidin-4-yloxy)piperidin-1-yl)prop-2-en-1-one I-180

I-180

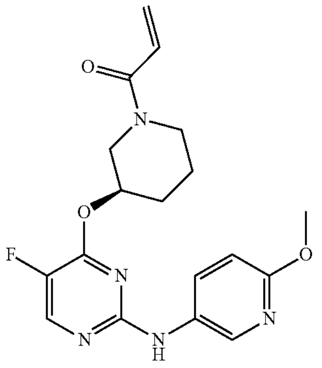

The title compound was prepared according to the schemes, steps and intermediates described in Example 98, by using (R)-tert-butyl 3-hydroxypiperidine-1-carboxylate in the place of 2 in Step 1 and 3-amino-6-methoxypyridine in place of 4 in step 2. MS 374.3 (M+1).

Example 149

Preparation of (R)-1-(3-(5-fluoro-2-(3-methoxyphenylamino)pyrimidin-4-yloxy)piperidin-1-yl)prop-2-en-1-one I-190

I-190

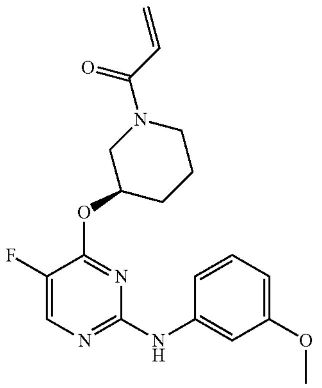

The title compound was prepared according to the schemes, steps and intermediates described in Example 98, by using (R)-tert-butyl 3-hydroxypiperidine-1-carboxylate in the place of 2 in Step 1 and 3-methoxyaniline in place of 4 in step 2. MS 395.3 (M+Na).

Example 150

Preparation of (S)-1-(3-(5-fluoro-2-(6-methoxypyridin-3-ylamino)pyrimidin-4-yloxy)piperidin-1-yl)prop-2-en-1-one I-193

I-193

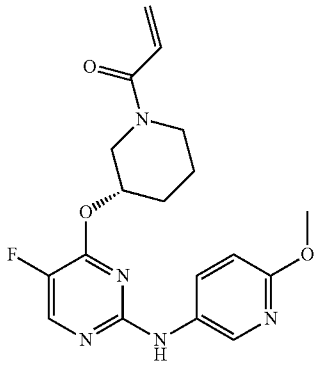

The title compound was prepared according to the schemes, steps and intermediates described in Example 98, by using (5)-tert-butyl 3-hydroxypiperidine-1-carboxylate in the place of 2 in Step 1 and 3-amino-6-methoxypyridine in place of 4 in step 2. MS 396.3 (M+Na).

Example 151

Preparation of (S)-1-(3-(5-fluoro-2-(3-methoxyphenylamino)pyrimidin-4-yloxy)piperidin-1-yl)prop-2-en-1-one I-179

I-179

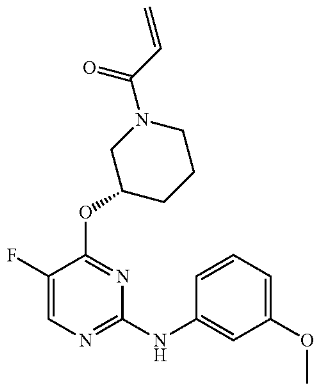

The title compound was prepared according to the schemes, steps and intermediates described in Example 98, by using (S)-tert-butyl 3-hydroxypiperidine-1-carboxylate in the place of 2 in Step 1 and 3-methoxyaniline in place of 4 in step 2. MS 395.3 (M+Na).

Example 152

Preparation of 1-(3-(5-fluoro-2-(6-methoxypyridin-3-ylamino)pyrimidin-4-ylamino)pyrrolidin-1-yl)prop-2-en-1-one I-203

I-203

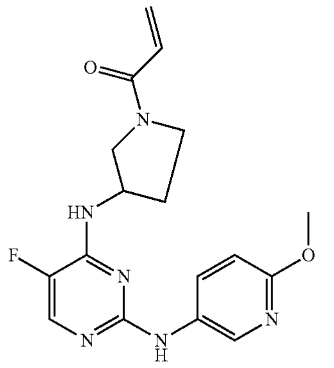

The title compound was prepared according to the schemes, steps and intermediates described in Example 20, by using tert-butyl 3-aminopyrrolidine-1-carboxylatein the place of 2 in Step 1 and 3-amino-6-methoxypyridine in place of 4 in step 2. MS 381.3 (M+Na).

Example 153

Preparation of 1-(3-(5-fluoro-2-(3-methoxyphenylamino)pyrimidin-4-ylamino)pyrrolidin-1-yl)prop-2-en-1-one I-201

I-201

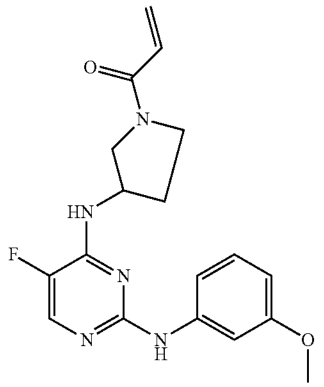

The title compound was prepared according to the schemes, steps and intermediates described in Example 20, by using tert-butyl 3-aminopyrrolidine-1-carboxylate in the place of 2 in Step 1 and 3-methoxyaniline in place of 4 in step 2. MS 358.3 (M+1).

Example 154

Preparation of (R)-1-(3-(5-fluoro-2-(3-methoxyphenylamino)pyrimidin-4-ylthio)piperidin-1-yl)prop-2-en-1-one I-137

I-137

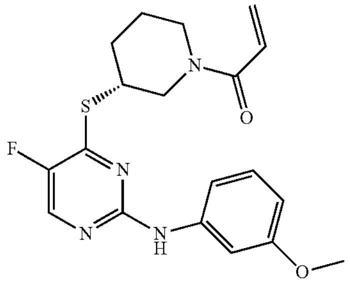

The title compound was prepared according to the schemes, steps and intermediates described in Example 20, by using (S)-tert-butyl 3-mercaptopiperidine-1-carboxylate in the place of 2 in Step 1 and 3-methoxyaniline in place of 4 in step 2. MS 411.1 (M+Na).

Example 155

Preparation of (R)-1-(3-(2-(3-chlorophenylamino)-5-fluoropyrimidin-4-ylamino)piperidin-1-yl)prop-2-en-1-one I-147

I-147

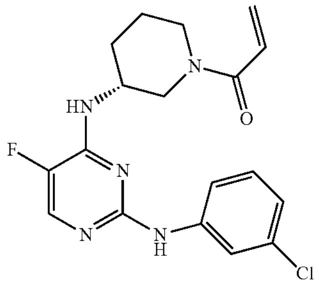

The title compound was prepared according to the schemes, steps and intermediates described in Example 20, by using (S)-tert-butyl 3-aminopiperidine-1-carboxylate in the place of 2 in Step 1 and 3-chloroaniline in place of 4 in step 2. MS 376.1 (M+1).

Example 156

Preparation of (R)-1-(3-(5-fluoro-2-(3-(2-morpholinoethoxy)phenylamino)pyrimidin-4-ylamino)piperidin-1-yl)prop-2-en-1-one I-135

I-135

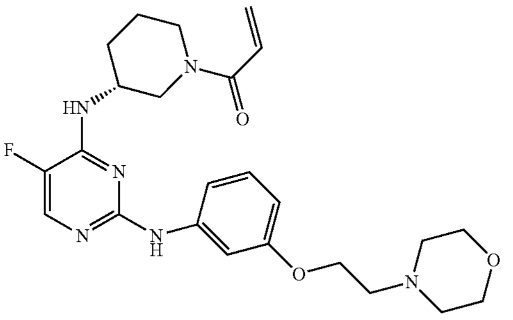

The title compound was prepared according to the schemes, steps and intermediates described in Example 20, by using (S)-tert-butyl 3-aminopiperidine-1-carboxylate in the place of 2 in Step 1 and 3-(2-morpholinoethoxy)aniline in place of 4 in step 2. MS 471.3 (M+1).

Example 157

Preparation of (E)-4-(dimethylamino)-N-(3-(5-fluoro-2-(6-methoxypyridin-3-ylamino)pyrimidin-4-ylamino)phenyl)but-2-enamide I-125

I-125

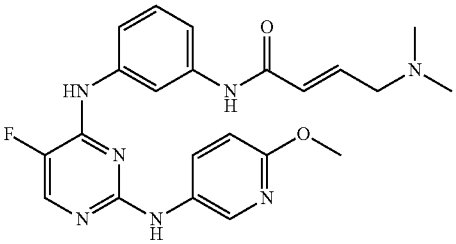

The title compound was prepared according to the schemes, steps and intermediates described in Example 139, by using (E)-4-(dimethylamino)but-2-enoyl chloride in the place of 7 in Step 4. MS 460.1 (M+Na).

Example 158

Preparation of 2-((1H-pyrazol-1-yl)methyl)-N-(3-(5-fluoro-4-(m-tolylamino)pyrimidin-2-ylamino)phenyl)acrylamide. I-98

I-98

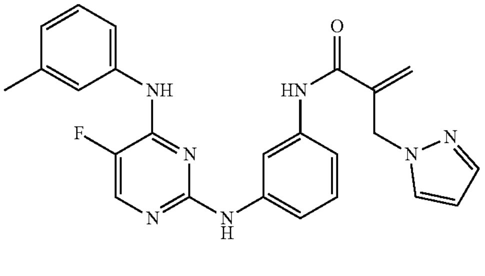

The title compound was prepared according to the schemes, steps and intermediates described in Example 4, by using 2-((1H-pyrazol-1-yl)methyl)acryloyl chloride in the place of 6 in Step 3. MS 466.1 (M+Na).

Example 159

Preparation of (E)-4-(azetidin-1-yl)-N-(3-(5-fluoro-4-(m-tolylamino)pyrimidin-2-ylamino)phenyl)but-2-enamide I-123

I-123

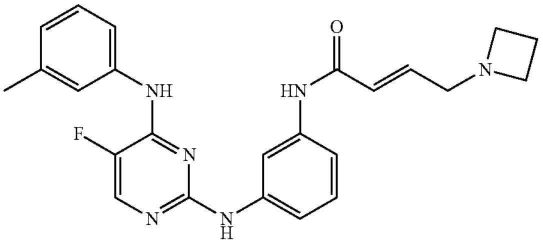

The title compound was prepared according to the schemes, steps and intermediates described in Example 4, by using (E)-4-(azetidin-1-yl)but-2-enoyl chloride in the place of 6 in Step 3. MS 455.1 (M+Na).

Example 160

Preparation of (E)-N-(3-(5-fluoro-4-(m-tolylamino)pyrimidin-2-ylamino)phenyl)-4-morpholinobut-2-enamide I-102

I-102

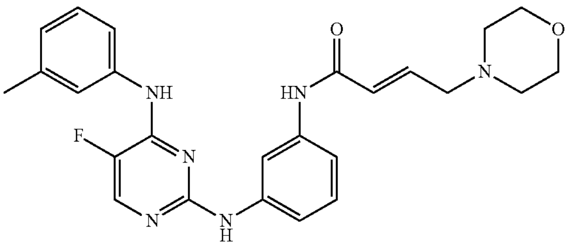

The title compound was prepared according to the schemes, steps and intermediates described in Example 4, by using (E)-4-(morpholin-4-yl)but-2-enoyl chloride in the place of 6 in Step 3. MS 485.3 (M+Na).

Example 161

Preparation of (E)-4-((1S,4S)-2,5-diazabicyclo[2.2.1]heptan-2-yl)-N-(3-(5-fluoro-4-(m-tolylamino)pyrimidin-2-ylamino)phenyl)but-2-enamide I-101

I-101

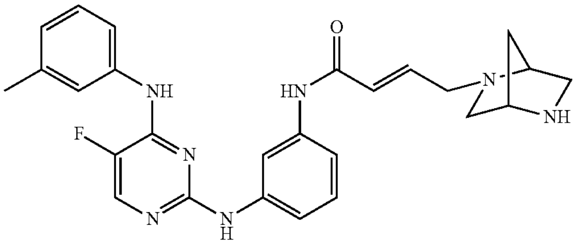

The title compound was prepared according to the schemes, steps and intermediates described in Example 4, by using (E)-4-((1S,4S)-2,5-diazabicyclo[2.2.1]heptan-2-yl)but-2-enoyl chloride in the place of 6 in Step 3. MS 496.1 (M+Na).

Example 162

Preparation of (E)-N-(3-(5-fluoro-4-(m-tolylamino)pyrimidin-2-ylamino)phenyl)-4-((2-methoxyethyl)(methyl)amino)but-2-enamide I-120

I-120

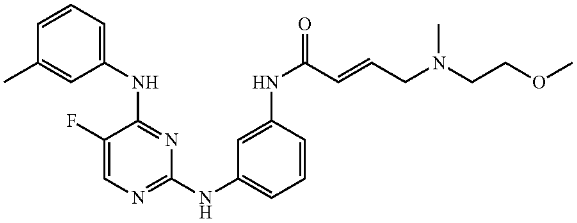

The title compound was prepared according to the schemes, steps and intermediates described in Example 4, by using (E)-4-((2-methoxyethyl)(methyl)amino)but-2-enoyl chloride in the place of 6 in Step 3. MS 487.3 (M+Na).

Example 163

Preparation of (S,E)-N-(3-(5-fluoro-4-(m-tolylamino)pyrimidin-2-ylamino)phenyl)-4-(3-hydroxypyrrolidin-1-yl)but-2-enamide I-99

I-99

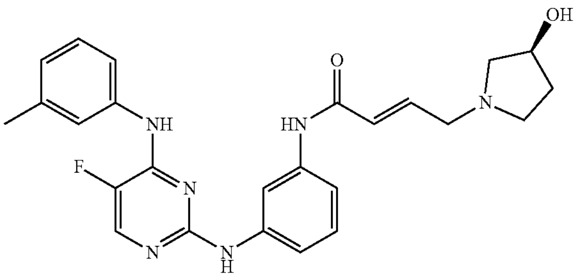

The title compound was prepared according to the schemes, steps and intermediates described in Example 4, by using (S,E)-4-(3-hydroxypyrrolidin-1-yl)but-2-enoyl chloride in the place of 6 in Step 3. MS 485.3 (M+Na)

Example 164

Preparation of (R,E)-N-(3-(5-fluoro-4-(m-tolylamino)pyrimidin-2-ylamino)phenyl)-4-(3-hydroxypyrrolidin-1-yl)but-2-enamide I-104

I-104

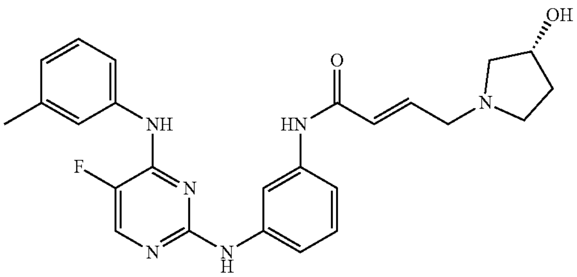

The title compound was prepared according to the schemes, steps and intermediates described in Example 4, by using (R,E)-4-(3-hydroxypyrrolidin-1-yl)but-2-enoyl in the place of 6 in Step 3. MS 485.3 (M+Na).

Example 165

Preparation of (E)-N-(3-(5-fluoro-4-(m-tolylamino)pyrimidin-2-ylamino)phenyl)-4-(1H-pyrazol-1-yl)but-2-enamide I-100

I-100

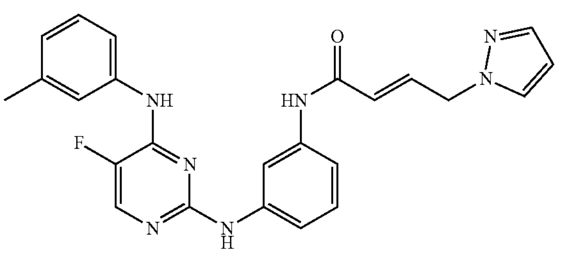

The title compound was prepared according to the schemes, steps and intermediates described in Example 4, by using (E)-4-(1H-imidazol-1-yl)but-2-enoyl chloride in the place of 6 in Step 3. MS 466.1 (M+Na).

Example 166

Preparation of (R,E)-N-(3-(5-fluoro-2-(4-(2-methoxyethoxy)phenylamino)pyrimidin-4-ylamino)phenyl)-4-(3-hydroxypyrrolidin-1-yl)but-2-enamide I-89

I-89

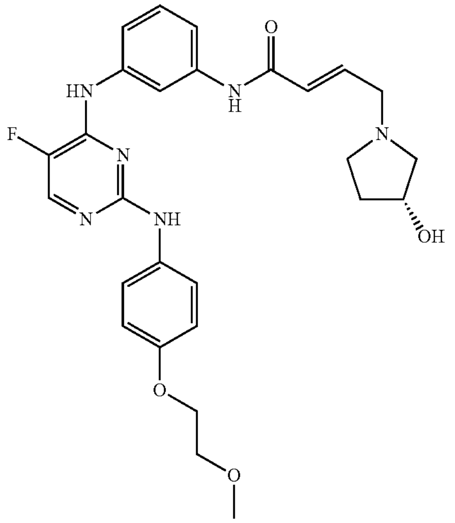

The title compound was prepared according to the schemes, steps and intermediates described in Example 20, by using (R,E)-4-(3-hydroxypyrrolidin-1-yl)but-2-enoyl chloride in the place of 7 in Step 4. MS 545.3 (M+Na).

Example 167

Preparation of (S,E)-N-(3-(5-fluoro-2-(4-(2-methoxyethoxy)phenylamino)pyrimidin-4-ylamino)phenyl)-4-(3-hydroxypyrrolidin-1-yl)but-2-enamide I-88

I-88

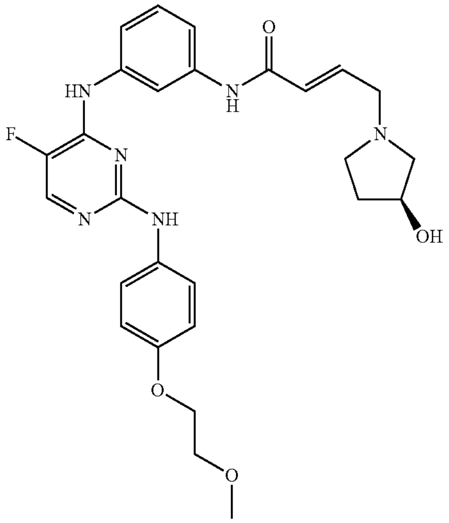

The title compound was prepared according to the schemes, steps and intermediates described in Example 20, by using (S,E)-4-(3-hydroxypyrrolidin-1-yl)but-2-enoyl chloride in the place of 7 in Step 4. MS 545.3 (M+Na).

Example 168

Preparation of 2-((1H-pyrazol-1-yl)methyl)-N-(3-(5-fluoro-2-(4-(2-methoxyethoxy)phenylamino)pyrimidin-4-ylamino))phenyl)acrylamide I-85

I-85

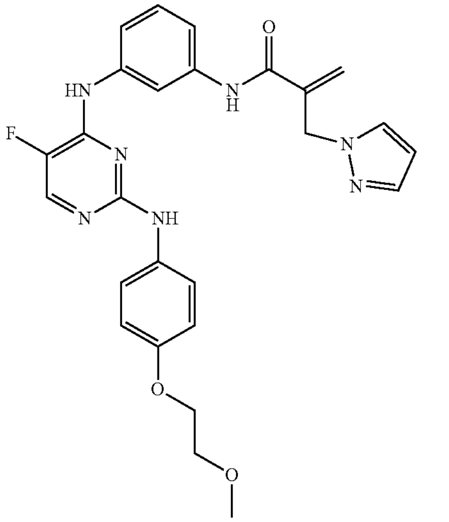

The title compound was prepared according to the schemes, steps and intermediates described in Example 20, by using 2-((1H-pyrazol-1-yl)methyl)acryloyl chloride in the place of 7 in Step 4. MS 526.1 (M+Na).

Example 169

Preparation of N-(3-(5-fluoro-2-(phenylamino)pyrimidin-4-ylamino)phenyl)acrylamide I-28

I-28

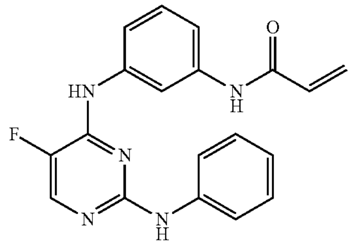

The title compound was prepared according to the schemes, steps and intermediates described in Example 20, by using aniline in the place of 4 in Step 2. MS 372.1 (M+Na).

Example 170

Preparation of (E)-4-((3R,5S)-3,5-dimethylpiperazin-1-yl)-N-(3-(5-fluoro-4-(m-tolylamino)pyrimidin-2-ylamino)phenyl)but-2-enamide I-119

I-119

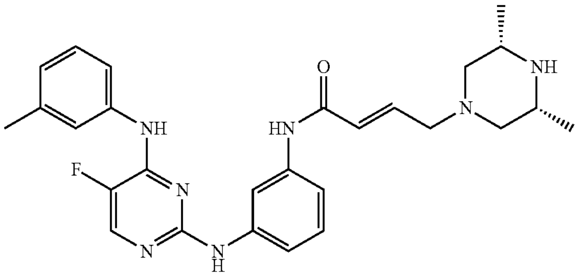

The title compound was prepared according to the schemes, steps and intermediates described in Example 4, by using (E)-4-((3R,5S)-3,5-dimethylpiperazin-1-yl)but-2-enoyl chloride in the place of 6 in Step 3. MS 512.3 (M+Na).

Example 171

Preparation of 1-(3-(5-methyl-2-(3-aminosulfonylphenylamino)pyrimidin-4-ylamino)phenyl)-3-methylbut-2-en-1-one I-224

I-224

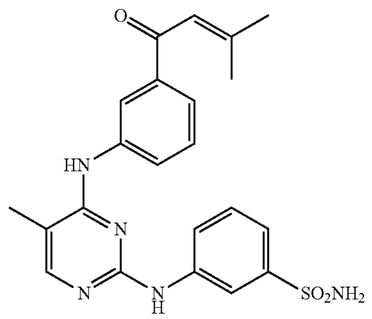

The title compound was prepared according to the schemes, steps and intermediates described in Example 112 using 2,4-dichloro-5-methylpyrimine in place of 1 in step-1 and 3-aminobenzenesulfonamide in place of 4 in step-2. $^1$H NMR (DMSO-$d_6$) δ ppm: 1.97 (s, 3H), 2.14 (s, 6H), 6.88 (s, 1H), 7.25-7.30 (m, 4H), 7.47 (t, J=7.92 Hz, 1H), 7.62 (d, J=7.72 Hz. 1H), 7.96 (s, 1H), 8.0-8.07 (m, 3H), 8.20 (t, J=7.36 Hz, 1H), 8.55 (s, 1H), 9.37 (s, 1H); LCMS: m/e 438 (M+1).

Example 172

Preparation of N-(3-acrylamidophenyl)-N-(5-cyano-2-(6-methoxypyridin-3-ylamino)pyrimidin-4-yl) acrylamide I-171

I-171

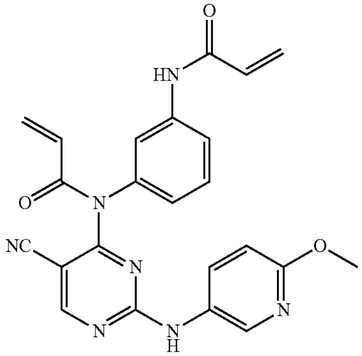

The title compound was prepared according to the schemes, steps and intermediates described in Example 95 using excess acroyl chloride in step-4. MS m/z: 442.1 (M+H$^+$).

Example 173

Preparation of N-3-(N-methyl-N-(5-fluoro-2-(4-methyl-3,4-dihydro-2H-benzo[b][1,4]oxazin-6-ylamino)pyrimidin-4-yl)aminophenylacrylamide I-127

I-127

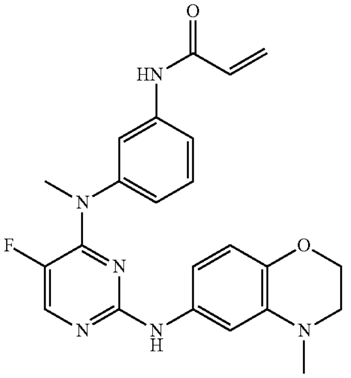

The title compound was prepared by treating the product of Example 88 with excess formaldehyde and $NaBH_3CN$ (2 equiv.) in acetonitrile and acetic acid (4:1). MS m/z: 435.1 (M+H$^+$).

Example 174

Preparation of N-(3-(5-methyl-2-(phenylamino)pyrimidin-4-ylamino)benzyl)acrylamide I-205

I-205

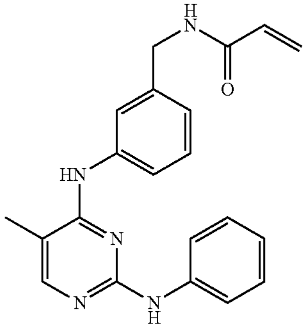

The title compound was prepared according to the schemes, steps and intermediates described in Example 20 using 2,4-dichloro-5-methylpyrimidine in place of 1 and 3-(tert-butoxycarbonylamino)methylaniline in place of 2 in step-1, and aniline in place of 4 on step-2. $^1$H-NMR ($CDCl_3$, 500 MHz): δ 7.91 (s, 1H), 7.77 (s, 1H), 7.57 (d, J=9.0 Hz, 2H), 7.41 (d, J=8.0 Hz, 1H), 7.36-7.26 (m, 2H), 7.13-6.96 (m, 4H), 6.36-6.25 (m, 2H), 5.97 (dd, J=10.5, 17.0 Hz, 1H), 5.78 (bs, 1H), 5.63 (d, J=10.5 Hz, 1H), 4.51 (d, J=6.0 Hz, 2H), 2.12 (s, 3H). MS: m/e=360 (M$^+$+1).

Example 175

Preparation of (E)-3-(5-methyl-2-(phenylamino) pyrimidin-4-ylamino)benzyl but-2-enoate I-246

I-246

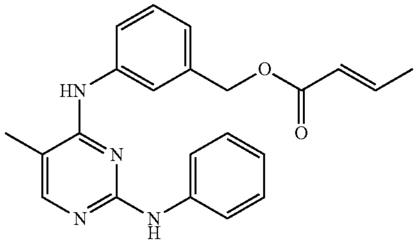

The title compound was prepared according to the schemes, steps, and intermediates described below.

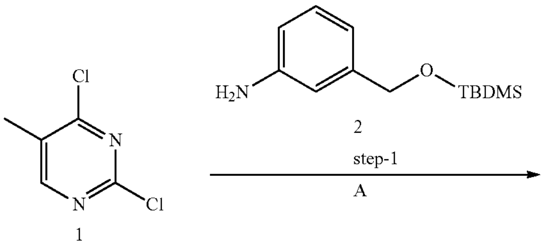

-continued

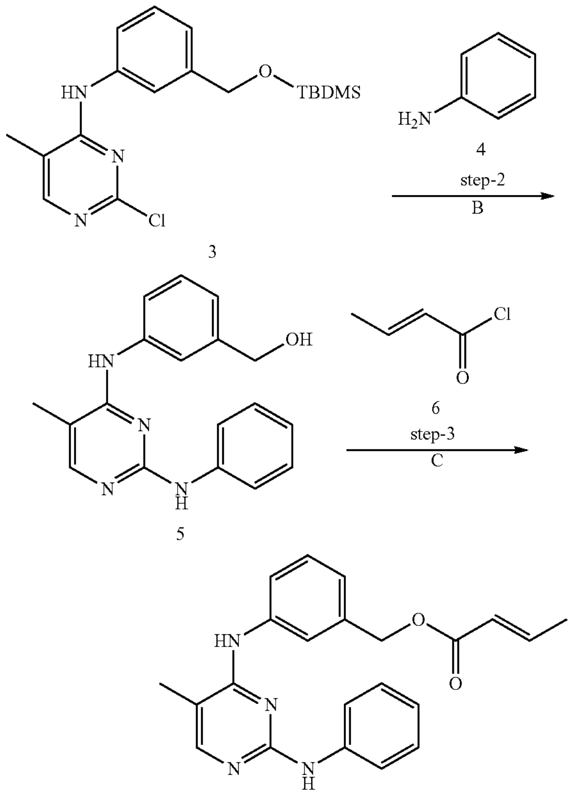

I-246

A) 2, Xanthophos, $Pd_2(dba)_3$, $Cs_2CO_3$, $CH_3CN$, 90° C., 12 hr;
B) 4, t-BuOH, 90° C., 4 hr;
C) 6, TEA, DCM, -30° C., 5 min Step-1

3

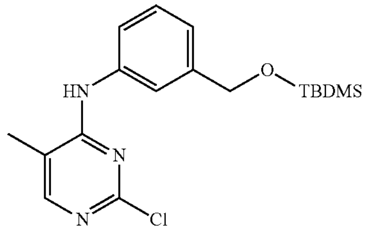

To a stirred solution of 1 (0.34 g, 2.08 mmol) in acetonitrile (5 mL) were added $Cs_2CO_3$ (1.09 g, 3.35 mmol), Xanthophos (0.024 g, 0.041 mmol), $Pd_2(dba)_3$ (38 mg, 0.04 mmol) and 2 (0.5 g, 2.1 mmol) at RT under $N_2$ atmosphere. Argon gas was purged in to the reaction mixture for 1 h and stirred at 90° C. for 12 h. The progress of the reaction was monitored by TLC. The reaction mixture was filtered through a pad of celite, and the filtrate was concentrated under reduced pressure. The crude compound was purified by silica gel column chromatography to afford 3 (0.56 g, 29.16%) as light yellow liquid. $^1$H-NMR ($CDCl_3$, 500 MHz): δ 8.0 (s, 1H), 7.55 (s, 1H), 7.51 (d, J=8.0 Hz, 1H), (t, J=7.5 Hz, 1H), (d, J=7.5 Hz, 1H), 6.48 (s, 1H), 4.76 (s, 2H), 2.18 (s, 3H), 0.95 (s, 9H), 0.10 (s, 6H). MS: m/e=364 [$M^+$+1].

Step-2

5

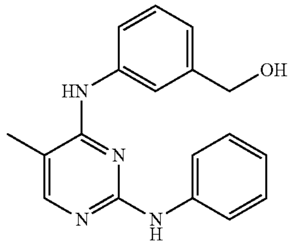

To a stirred solution of 3 (0.07 g, 0.19 mmol) in t-BuOH (1.5 mL) was added aniline (4) (0.018 g, 0.19 mmol) at room temperature. The reaction mixture was heated up to 90° C. and stirred for 4 h at the same temperature. The progress of the reaction was monitored by TLC. After the completion of starting materials, the volatiles were removed under reduced pressure to give 5 (0.033 g, 55.9%) as light yellow solid. $^1$H-NMR (DMSO-$d_6$, 500 MHz): δ 10.45 (s, 1H), 9.82 (s, 1H), 7.91 (s, 1H), 7.58-7.01 (m, 9H), 4.50 (s, 2H), 2.16 (s, 3H). MS: m/e=307 [$M^+$+1].

Step-3

I-246

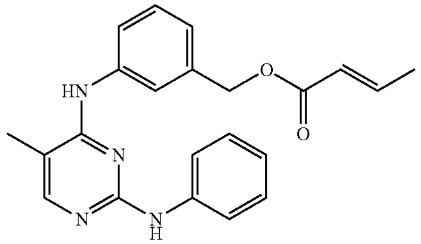

To a stirred solution of 5 (0.5 g, 1.63 mmol) in DCM (5 mL) was added 6 (0.18 g, 1.72 mmol) followed by TEA (0.66 mL, 4.78 mmol) at −30° C. under $N_2$ atmosphere. The reaction mixture was stirred for 5 minutes at −30° C. and the progress of the reaction was monitored by TLC. After the completion of reaction, quenched with water and extracted with DCM (2×50 mL). The organic layer was separated, dried over anhydrous $Na_2SO_4$ and concentrated under reduced pressure. The crude material was purified by silica gel column chromatography to give 50 mg of an isomeric mixture of the title compound. This mixture in DCM (2 mL) was treated with DBU (0.02 g, 0.127 mmol) at room temperature. The reaction mixture was stirred for 2 h at room temperature, quenched with water and extracted with DCM (2×10 mL). The organic layer was separated, dried over anhydrous $Na_2SO_4$ and concentrated under reduced pressure to afford I-246 (0.05 g, 10%) as light yellow solid. $^1$H-NMR ($CDCl_3$, 500 MHz): δ 7.87 (s, 1H), 7.65 (s, 1H), 7.58-7.51 (m, 3H), 7.34 (t, J=7.5 Hz, 1H), 7.30-7.23 (m, 3H), 7.13 (d, J=7.5 Hz, 1H), 7.08-6.96 (m, 2H), 6.40 (s, 1H), 5.87 (dd, J=1.5, 15.5 Hz, 1H), 5.16 (s, 2H), 2.13 (s, 3H), 1.87 (dd, J=2.0, 7.0 Hz, 3H). $^{13}$C-NMR ($CDCl_3$, 125 MHz): δ 166.3, 159.1, 158.4, 155.4, 145.3, 139.9, 138.9, 137.0, 128.9, 128.7, 123.2, 122.4, 121.9, 121.2, 121.0, 119.3, 105.2, 65.7, 17.9, 13.2. MS: m/e=375 [$M^+$+1].

Example 176

Preparation of (E)-4-(5-methyl-2-(phenylamino)pyrimidin-4-ylamino)benzyl but-2-enoate I-60

I-60

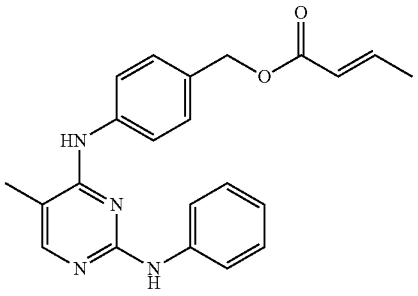

The title compound was prepared according to the schemes, steps and intermediates described in Example 175 using 4-((tert-butyldimethylsilyloxy) methyl) aniline in place of 2 in step-1. $^1$H-NMR ($CDCl_3$, 500 MHz): δ 8.19 (bs, 1H), 7.81 (s, 1H), 7.56 (d, J=8.5 Hz, 2H), 7.53 (d, J=7.5 Hz, 2H), 7.42-7.36 (m, 3H), 7.28-7.22 (m, 1H), 7.08-6.98 (m, 2H), 6.54 (s, 1H), 5.89 (dd, J=12.5, 14.0 Hz, 1H), 5.17 (s, 2H), 2.15 (s, 3H), 1.89 (dd, J=1.5, 7.0 Hz, 3H). MS: m/e=375 [$M^+$+1].

Example 177

Preparation of N-methyl-N-(3-(5-methyl-2-(phenylamino)pyrimidin-4-ylamino)benzyl)acrylamide I-220

I-220

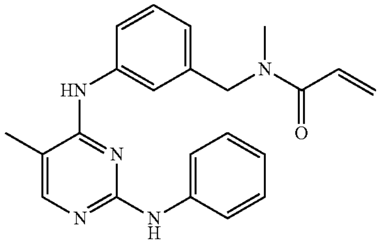

The title compound was prepared according to the schemes, steps, and intermediates described below.

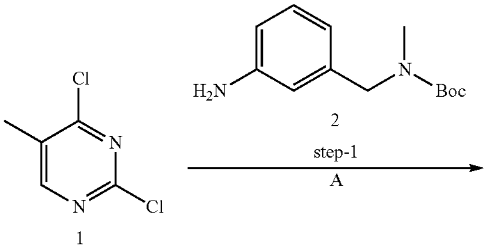

-continued

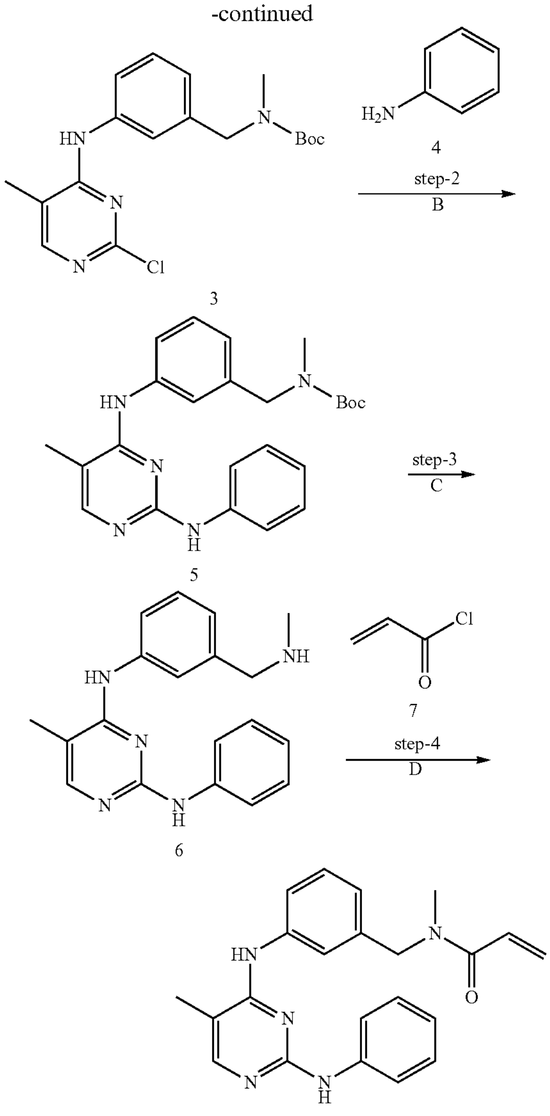

I-220

A) 2, Xanthophos, $Pd_2(dba)_3$, $Cs_2CO_3$, $CH_3CN$, 100° C., 12 hr;
B) 4, t-BuOH, 90° C., 4 hr;
C) 10 N HCl, DCM, rt, 30 min:
D) 7, TEA, DCM, -10° C., 10 min.

Step-1

3

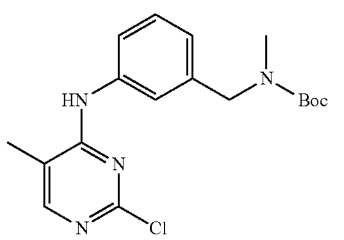

To a stirred solution of 1 (2.6 g, 15.7 mmol) in acetonitrile (26.7 mL) was added 2 (2.67 g, 11.3 mmol), $Pd_2$ $(dba)_3$ (0.31 g, 0.33 mmol), Xanthophos (0.52 g, 0.89 mmol) and $Cs_2CO_3$ (6.6 g, 20.0 mmol). The reaction mixture was then degassed by purging argon for 1 h and further heated to 100° C. for 12 h. After the completion of the reaction (monitored by TLC), the reaction mixture was filtered through celite bed and the filtrate was concentrated under reduced pressure. The resulting crude material was purified by column chromatography (60-120 mesh silica gel; 20% ethyl acetate/Hexane) to afford 3 (2.32 g, 56.71%) as light brown solid. $^1$H-NMR ($CDCl_3$, 500 MHz): □ 8.01 (s, 1H), 7.56 (d, J=7.5 Hz, 1H), 7.43 (s, 1H), 7.35 (t, J=7.0 Hz, 1H), 7.05 (s, 1H), 6.80 (bs, 1H), 4.45 (s, 2H), 2.87 (s, 3H), 2.30 (s, 3H), 1.48 (s, 9H).

Step-2

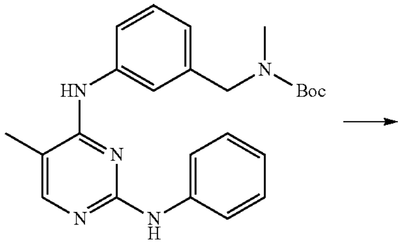

5

To a stirred solution of 3 (2.32 g, 6.0 mmol) in t-BuOH (11.6 mL) was added 4 (0.65 g, 6.9 mmol) at RT and the reaction mixture was further heated at reflux for 48 h. The progress of the reaction was monitored by TLC. After the completion of the reaction, t-BuOH was concentrated under reduced pressure to dryness to give 5 (2.3 g, 85.82%) as light yellow solid. $^1$H-NMR (DMSO-$d_6$, 500 MHz): δ 10.32 (s, 1H), 9.78 (s, 1H), 7.91 (s, 1H), 7.50 (d, J=8.0 Hz, 1H), 7.45-7.30 (m, 4H), 7.24 (t, J=7.0 Hz, 2H), 7.15-7.06 (m, 2H), 4.36 (s, 2H), 2.72 (s, 3H), 2.17 (s, 3H), 1.41, 1.34 (two s, 9H). MS: m/e=420 ($M^+$+1).

Step-3

6

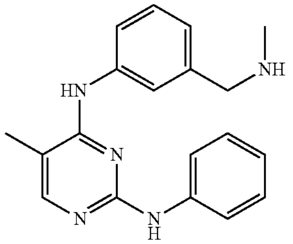

To a stirred solution of 5 (0.05 mg, 0.11 mmol) in DCM (5 mL) was added 37% HCl (1.0 mL) and stirred at RT for 30 min. After the completion of the reaction (monitored by TLC), volatiles were removed under reduced pressure. The aqueous layer was cooled to 0° C., basified up to pH~8-9 with 10% NaOH solution and extracted with DCM (50 mL). The organic portion was separated, washed with water, brine, dried over anhydrous $Na_2SO_4$ and evaporated under reduced pressure to afford 6 (0.015 g, 48.36%) as light yellow solid. $^1$H-NMR ($CDCl_3$, 500 MHz): δ 7.95-7.85 (m, 2H), 7.68-7.60 (m, 3H), 7.42 (d, J=8.0 Hz, 1H), 7.32-7.20 (m, 4H), 7.05 (d, J=7.5 Hz, 1H), 7.00-6.95 (m, 1H), 6.40 (s, 1H), 3.84 (s, 2H), 2.48 (s, 3H), 2.06 (s, 3H). MS: m/e=320 ($M^+$+1).

Step-4

I-220

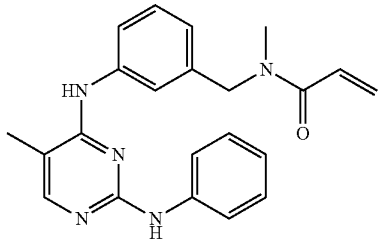

To a stirred solution of 6 (0.3 g, 0.94 mmol) in DCM (12 mL) was added TEA (0.10 g, 0.99 mmol) and 7 (0.08 g, 0.88 mmol) dropwise over a period of 5 min at −10° C. under inert atmosphere. The reaction mixture was then stirred at −10° C. for 5-10 min. After the completion of the reaction (monitored by TLC), the reaction mixture was quenched with cold water (5 mL) and extracted with DCM (2×50 mL). The DCM layer was washed with water, brine, dried over anhydrous $Na_2SO_4$ and concentrated under reduced pressure. The crude material was purified by column chromatography (60-120 mesh silica gel; 30% Ethyl acetate/Hexane) to afford I-220 (0.15 g, 42.85%) as off white solid. $^1$H-NMR (DMSO-$d_6$, 500 MHz, at 80° C.): δ 8.48 (bs, 1H), 8.07 (s, 1H), 7.88 (s, 1H), 7.69-7.58 (m, 4H), 7.28 (t, J=8.0 Hz, 1H), 7.16 (t, J=8.0 Hz, 2H), 6.91-6.85 (m, 2H), 6.75 (dd, J=2.5, 15.3 Hz, 1H), 6.13 (d, J=15.0 Hz, 1H), 5.66 (d, J=7.5 Hz, 1H), 4.60 (s, 2H), 2.95 (s, 3H), 2.12 (s, 3H). MS: m/e=374 ($M^+$+1).

Example 178

Preparation of N-methyl-N-(4-(5-methyl-2-(phenylamino)pyrimidin-4-ylamino)benzyl)acrylamide I-219

I-219

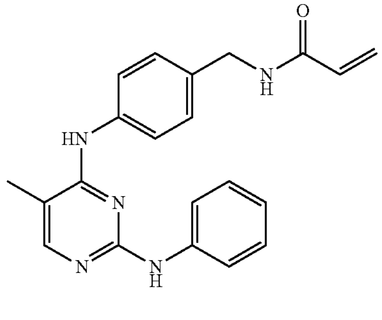

The title compound was prepared according to the schemes, steps and intermediates described in Example 177 using tert-butyl-4-aminobenzyl(methyl)-carbamate in place of 2 in step-1. $^1$H NMR (DMSO-$d_6$, 500 MHz at 80° C.): δ 8.55 (s, 1H), 8.03 (s, 1H), 7.86 (s, 1H), 7.65 (d, J=8.0 Hz, 2H), 7.62 (d, J=8.0 Hz, 2H), 7.20-7.13 (m, 4H), 6.86-6.75 (m, 2H), 6.14 (dd, J=2.5, 17.0 Hz, 1H), 5.67 (d, J=15.0 Hz, 1H), 4.58 (s, 2H), 2.96 (s, 3H), 2.10 (s, 3H). MS: m/e=374 ($M^+$+1).

Example 179

Preparation of N-(5-(5-acetyl-4-(4-acryloyl-3,4-dihydro-2H-benzo[b][1,4]oxazin-6-ylamino)pyrimidin-2-ylamino)pyridin-2-yl)-2,2,2-trifluoro-N-methylacetamide I-142

I-142

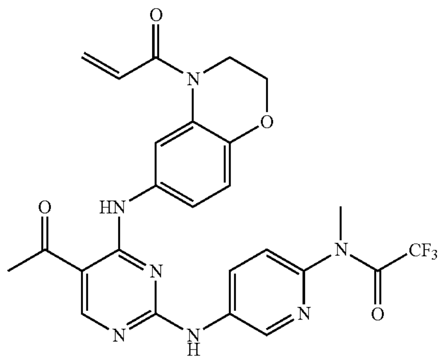

The title compound was prepared according to the schemes, steps and intermediates described in Example 42 using 5-amino-2(2,2,2-trifluoroacetamido)pyridine in place of 9 in step-5. LC-MS: m/z 542.2 (ES+), 540.2.2 (ES−).

Example 180

Preparation of 1-(6-(5-fluoro-2-(4-(2-methoxyethoxy)phenylamino)pyrimidin-4-ylamino)indolin-1-yl)prop-2-en-1-one I-94

I-94

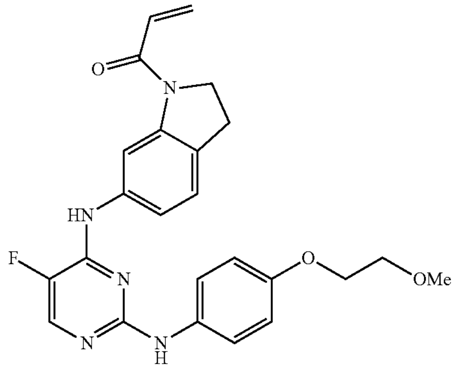

The title compound was prepared according to the schemes, steps and intermediates described in Example 20 using N-Boc-6-aminoindoline in place of 2 in step-1. LC-MS: m/z 450.1 (ES+), 448.1 (ES−).

Example 181

Preparation of N-(3-(5-fluoro-2-(6-(2-methoxyethoxy)pyridine-3-ylamino)pyrimidin-4-ylamino)phenyl)acrylamide I-103

I-103

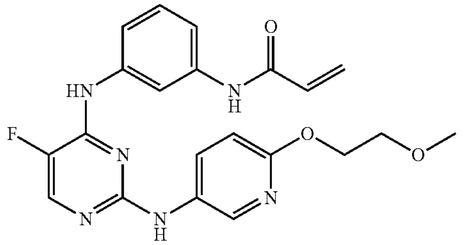

The title compound was prepared according to the schemes, steps and intermediates described in Example 20 by using 3-amino-6-(2-methoxyethoxy)pyridine in place of 4 in Step-2. $^1$H NMR ($CDCl_3$+trace of DMSO-$d_6$) δ ppm: 3.44 (s, 3H), 3.75 (t, J=4.4 Hz, 2H), 4.43 (t, J=4.4 Hz, 2H), 5.81 (dd, J=1.8 & 9.6 Hz, 1H), 6.45 (m, 1H), 6.80 (m, 3H), 7.17 (m, 1H), 7.29 (m, 1H), 7.43 (m, 1H), 7.49 (m, 1H), 7.60 (m, 1H), 7.80 (dd, J=2.8 & 9.2 Hz, 1H), 7.94 (d, J=3.1 Hz, 1H), 8.14 (s, 1H), 8.32 (d, J=2.9 Hz, 1H); LCMS: m/e 425.1 (M+1).

Example 182

Preparation of N-(3-(5-fluoro-2-(4-(3-methylsulfonylpropoxy)phenyl)aminopyrimidin-4-ylamino)phenyl)acrylamide I-97

I-97

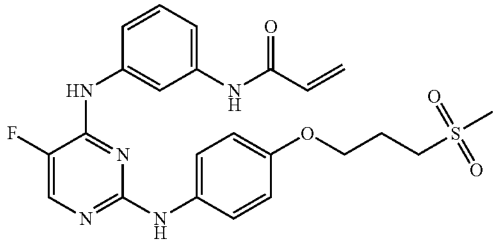

The title compound was prepared as a TFA salt according to the schemes, steps and intermediates described in Example 20 by using 4-(3-methylsulfonylpropoxy)aniline in place of 4 in Step-2. $^1$H NMR ($CDCl_3$+trace of DMSO-$d_6$) δ ppm: 1.95 (m, 2H), 2.67 (s, 3H), 2.98 (m, 5H), 3.74 (t, J=6.0 Hz, 2H), 5.45 (dd, J=4.1 & 7.3 Hz, 1H), 6.07 (m, 2H), 6.48 (d, J=8.2 Hz, 1H), 6.77 (m, 4H), 7.09 (d, J=7.4 Hz, 1H), 7.51 (d, J=4.1 Hz, 1H), 7.70 (br, 1H); LCMS: m/e 486.1 (M+1).

Example 183

Preparation of N-(3-(5-fluoro-2-(6-(trideuteromethoxy)pyridine-3-ylamino)pyrimidin-4-ylamino)phenyl)acrylamide I-95

I-95

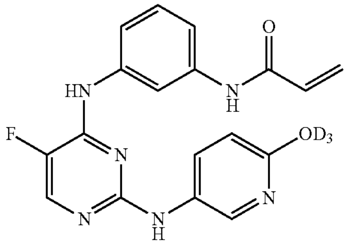

The title compound was prepared as a TFA salt according to the schemes, steps and intermediates described in Example 20 by using 6-(trideuteriomethoxy)pyridin-3-amine in place of 4 in Step-2. $^1$H NMR ($CDCl_3$+trace of DMSO-$d_6$) δ ppm: 5.78 (dd, J=3.7 & 7.8 Hz, 1H), 6.40 (m, 2H), 6.71 (d, J=8.7 Hz, 1H), 7.3 (m, 3H), 7.75 (dd, J=2.7 & 8.7 Hz, 1H), 7.82 (d, J=4.6 Hz, 1H), 7.95 (s, 1H), 8.33 (d, J=2.3 Hz, 1H); LCMS: m/e 384.1 (M+1).

The intermediate 6-(trideutratedmethoxy)pyridin-3-amine was prepared by the scheme shown below.

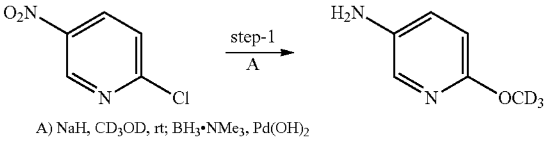

Step 1

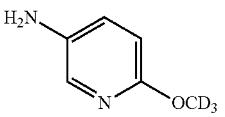

To NaH (60%, 0.30 g) in 5 mL of $CD_3OD$ at 0° C. was added 2-chloro-5-nitropyridine (1.0 g). The mixture was stirred at rt overnight. To this mixture were added $BH_3$.$NMe_3$ (550 mg) and $Pd(OH)_2$ (100 mg). The resulting mixture was refluxed for 2 h. After cooling down, the mixture was concentrated and purified using silica gel chromatography to give the desired 6-(trideuterated-methoxy)pyridin-3-amine (130 mg). $^1$H NMR ($CDCl_3$) δ ppm: 3.30 (br, 2H), 6.60 (d, J=8.7 Hz, 1H), 7.03 (dd, J=3.2 & 8.7 Hz, 1H), 7.66 (d, J=3.2 Hz, 1H).

Example 184

Preparation of N-(3-(5-fluoro-2(3,4,5-trimethoxyphenylamino)pyrimidin-4-yloxy)phenyl)acrylamide I-148

I-148

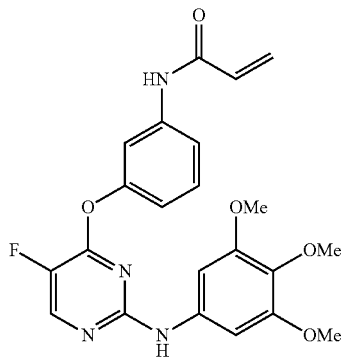

The title compound was prepared according to the schemes, steps and intermediates described in Example 98 by using 3,4,5-trimethoxyaniline in place of 4 in Step-2. MS: m/e 441 [M+1].

Example 185

Preparation of 3-methyl-1-(3-(5-methyl-2-(phenylamino)pyrimidin-4-ylamino)phenyl)but-2-en-1-one I-232

I-232

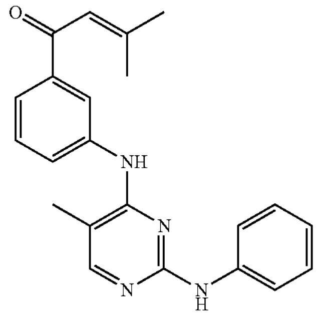

The title compound was prepared according to the schemes, steps and intermediates described in Example 112 using 2,4-dichloro-5-methylpyrimidine in place of 1 in step-1 and aniline in place of 4 in step-2. $^1$H NMR ($CDCl_3$) δ ppm: 1.97 (s, 3H), 2.15 (s, 3H), 2.22 (s, 3H), 6.47 (s, 1H), 6.71 (s, 1H), 6.97 (t, J=9.8 Hz, 1H), 7.17 (s, 1H), 7.24 (t, J=10.36 Hz, 1H), 7.27 (s, 1H), 7.44 (t, J=10.64 Hz, 1H), 7.53 (d, J=10.48 Hz, 2H), 7.68 (d, J=10.28 Hz, 1H), 7.94 (d, J=10 Hz, 1H), 7.98 (s, 1H); LCMS: m/e 359 (M+1).

Example 186

Preparation of 1-(3-(5-methyl-2-phenylamino)pyrimidin-4-ylamino(piperidin-1-yl)prop-2-en-one I-27

I-27

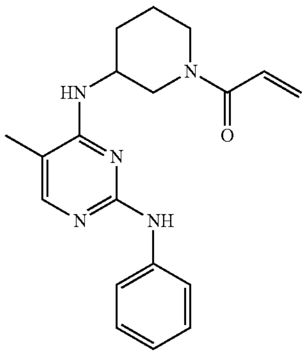

The title compound was prepared according to the schemes, steps and intermediates described in Example 1 using 1-tert-butoxycarbonyl-3-aminopiperidine in place of 1 in step-1. $^1$H NMR (DMSO-$d_6$) δ ppm: 1.30-1.50 (m, 1H), 1.55-1.75 (m, 1H), 1.75-1.90 (m, 1H), 1.92 (s, 3H), 1.95-2.05 (m, 1H), 2.75-3.31 (m, 2H), 3.99-4.09 (m, 2H), 4.10-4.15 & 4.40-4.47 (m, 1H), 5.49 & 5.70 (d, J=10.8 Hz & d, J=9.2 Hz respectively, together 1H), 6.02 & 6.13 (d, J=17.6 Hz & d, J=16.8 Hz respectively, together 1H), 6.25-6.40 (m, 1H), 6.63 & 6.80-6.90 (dd, J=10.8, 16.8 Hz & m respectively, together 1H), 6.75-6.85 (m, 1H), 7.15 (t, J=8 Hz, 2H), 7.69 (bs, 3H), 8.81 (s, 1H); LCMS: m/e 337.8 (M+1).

Example 187

Preparation of 3-(4-(2-acryloyl-1,2,3,4-tetrahydroisoquinolin-6-ylamino)-5-methylpyrimidin-2-ylamino)benzenesulfonamide I-40

I-40

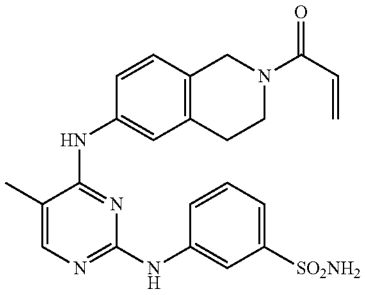

The title compound was prepared according to the schemes, steps and intermediates described in Example 1 using 6-amino-2-tert-butoxycarbonyl-1,2,3,4-tetrahydroisoquinoline in place of 1 in step-1. $^1$H NMR (DMSO-$d_6$) δ ppm: 2.10 (s, 3H), 2.80-2.83 (m, 2H), 3.75-3.90 (m, 2H), 4.66 (s, 1H), 4.76 (s, 1H), 5.71-5.74 (m, 1H), 6.16 (dd, J=2.32 & 16.76 Hz, 1H), 6.87-6.91 (m, 1H), 7.13-7.18 (m, 1H), 7.25-7.31 (m, 4H), 7.53-7.57 (m, 2H), 7.90 (s, 1H), 8.05 (s, 2H), 8.28 (s, 1H), 9.31 (s, 1H); LCMS: m/e 464.8 (M+1).

Example 188

Preparation of (S)—N-(3-(5-fluoro-2-(tetrahydrofuran-3-yloxy)pyridine-3-ylamino)pyrimidin-4-ylamino)phenyl)acrylamide I-54

I-54

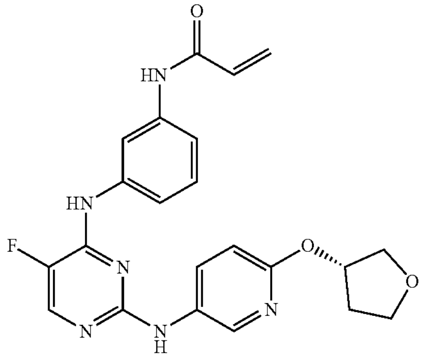

The title compound was prepared according to the schemes, steps and intermediates described in Example 20 using (S)-3-amino-6-(tetrahydrofuran-3-yloxy)pyridine in place of 4 in step-2. MS: m/e=437 [M+1].

Example 189

Preparation of N-(3-(5-trifluoromethyl-2-(phenylamino)pyrimidin-4-ylamino)phenyl)acrylamide I-245

I-245

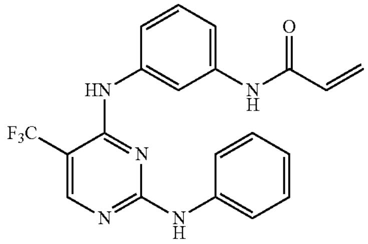

The title compound was prepared according to the schemes, steps, and intermediates described below.

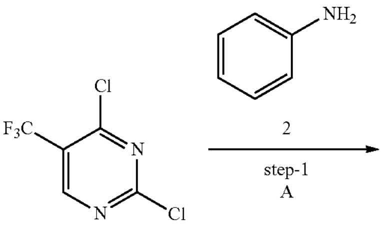

-continued

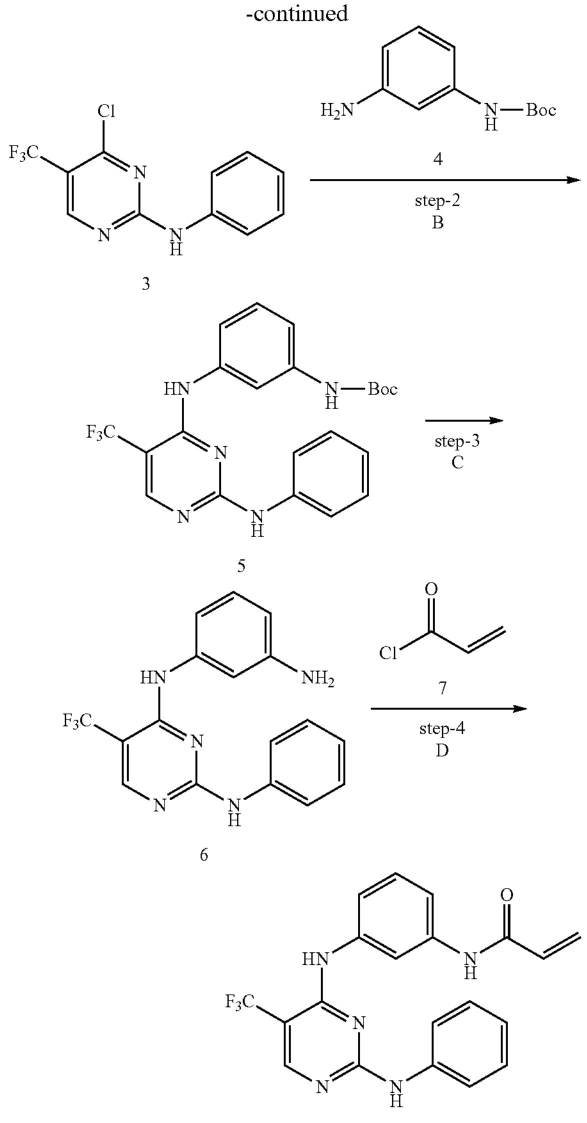

A) 2, $ZnCl_2$, DCE, t-BuOH (1:1), 0° C., 30 min; B) 4, DMF, DIEPA, 70° C., 16 hr; C) TFA, DCM, rt, 1 hr; D) 7, TEA, DCM.

Step-1

3

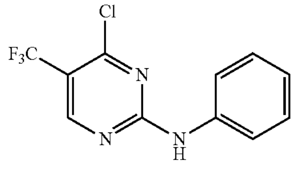

To a cold (0° C.) solution of 1 (2 g, 9.2 mmol) in 80 mL of a 1:1 mixture of tBuOH/DCE was added zinc chloride (11 mL of a 1 M solution in ether, 1.2 eq). After one hour, 2 (0.858 g, 9.2 mmol) was added followed by dropwise addition of triethylamine (1.03 g; 1.1 eq) in 10 mL of DCE/t-BuOH. After stirring for 30 minutes, the solvents were removed under reduced pressure and the residue was dissolved in ethyl acetate (50 mL) and washed with brine (10 mL). The organic layer was dried over sodium sulphate, filtered and concentrated in vacuo. The desired product 3 was obtained as a white solid following recrystallization from EtOAc/Hexane (1:9), (2 g, 80%).

Step-2

5

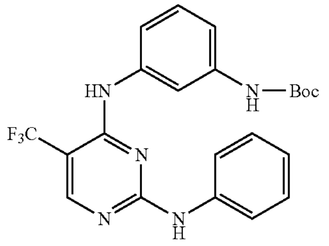

To a solution of 3 (0.5 g, 1.82 mmol) and 4 (0.38 g, 1.83 mmol) in DMF (10 mL) was added DIPEA (0.283 g, 2.192 mmol) and the mixture was heated to 60° C. under an argon atmosphere for 16 h. The solvent was distilled off and the residue was dissolved in ethyl acetate (50 mL) and washed with brine (10 mL). The organic layer was dried over sodium sulphate, filtered and concentrated in vacuo. The crude mixture was purified by flash column chromatography (eluent: EtOAc/hexane 1:1) to afford 5 as a white solid (0.48 g, 60%).

Step-3

6

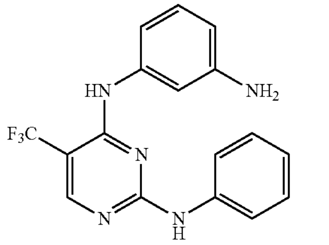

To a solution of 6 (0.25 g, 0.63 mmol) in $CH_2Cl_2$ (10 mL) was added trifluoroacetic acid (2 mL) and the mixture was stirred at room temperature for 1 hour. Solvents were removed under reduced pressure and the residue was dissolved in $CH_2Cl_2$, washed with 10% aqueous $NaHCO_3$ solution, dried ($Na_2SO_4$), filtered, and evaporated under reduced pressure to provide the free amine as white solid.

Step-4

I-245

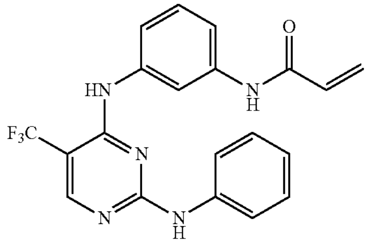

To a stirred solution of 6 (0.2 g) in DCM (20 mL) under argon atmosphere cooled to −40° C. was added triethylamine followed by dropwise addition of 7 (0.069 g, 0.686 mmol). The resulting mixture was stirred at −40° C. for 10 min. The reaction mixture was diluted with DCM (50 mL) and washed with brine (10 mL). The organic layer was dried over sodium sulfate, filtered, and evaporated under reduced pressure. The residue was purified by flash chromatography on silica gel using (MeOH-EtOAc 5:95) as eluent to provide the target compound I-245. $^1$H NMR (200 MHz, $CD_3OD$) δ 8.25 (s, 1H), 7.80 (s, 1H), 7.60-7.05 (m, 7H), 6.90 (m, 1H), 6.35 (m, 2H), 5.75 (dd, J=8.0, 2.0 Hz, 1H).

Example 190

Preparation of N-(3-(5-trifluoromethyl-2-(3-methoxyphenylamino)pyrimidin-4-ylamino)phenyl) acrylamide I-242

I-242

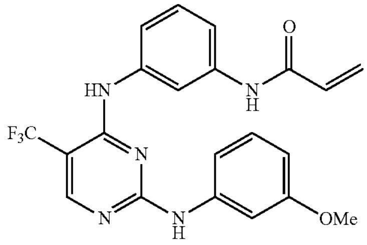

The title compound was prepared according to the schemes, steps and intermediates described in Example 189 using 3-methoxyaniline in place of 2 in step-1. $^1$H NMR (200 MHz, $CD_3OD$) δ 8.31 (s, 1H), 7.84 (s, 1H), 7.59 (m, 1H), 7.37-7.09 (m, 5H) 6.53 (m, 1H), 6.41 (m, 2H), 5.79 (dd, J=8.0, 2.0, Hz, 1H), 3.66 (s, 3H).

Example 191

Preparation of N-(4-(5-trifluoromethyl-2-(3-methoxyphenylamino)pyrimidin-4-ylamino)phenyl) acrylamide I-236

I-236

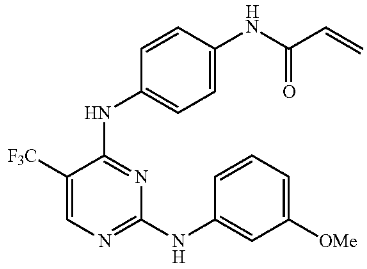

The title compound was prepared according to the schemes, steps and intermediates described in Example 189 using 3-methoxyaniline in place of 2 in step-1 and 4-amino-N-tert-butoxycarbonylaniline in place of 4 in step-2. $^1$H NMR (200 MHz, $CD_3OD$) δ 8.27 (s, 1H), 7.70 (d, J=6.0 Hz) 1H), 7.46 (d, J=6.0 Hz, 1H), 7.09 (brs, 1H), 7.07 (m, 2H) 6.51 (m, 1H), 6.44 (m, 2H), 5.80 (dd, J=8.0, 2.0 Hz, 1H), 3.56 (s, 3H).

Example 192

Preparation of N-(4-(5-trifluoromethyl-2-(3-methoxyphenylamino)pyrimidin-4-ylamino)phenyl) methylacrylamide I-235

I-235

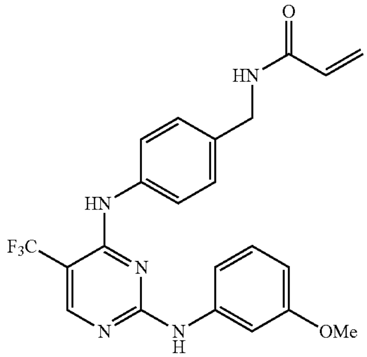

The title compound was prepared according to the schemes, steps and intermediates described in Example 189 using 3-methoxyaniline in place of 2 in step-1 and 4-aminophenylmethyl-N-tert-butoxycarbonylamine in place of 4 in step-2. $^1$H NMR (200 MHz, $CD_3OD$) δ 8.30 (s, 1H), 7.49 (d, J=8.0 Hz, 1H), 7.37 (d, J=8.0 Hz, 1H), 7.10 (m, 3H), 6.60 (m, 1H) 6.34 (m, 2H), 5.75 (dd, J=8.0, 2.0 Hz, 1H), 4.51 (s, 2H), 3.68 (s, 3H).

Example 193

Preparation of N-(4-chloro-3-(5-trifluoromethyl-2-(3-methoxyphenylamino)pyrimidin-4-ylamino)phenyl)acrylamide I-227

I-227

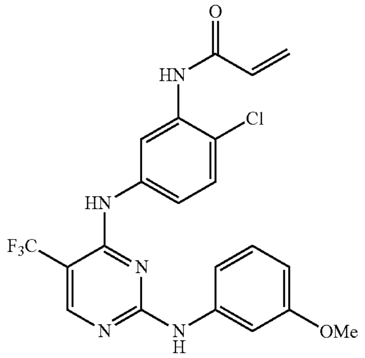

The title compound was prepared according to the schemes, steps and intermediates described in Example 189 using 3-methoxyaniline in place of 2 in step-1 and N-tert-butoxycarbony-3-amino-6-chloroaniline in place of 4 in step-2. $^1$H NMR (200 MHz, $CD_3OD$) δ 8.33 (s, 1H), δ 8.08 (s, 1H), 7.45 (m, 2H), 7.21-7.07 (m, 3H), 6.60-6.36 (m, 3H), 5.84 (dd, J=8.0, 2.0 Hz, 1H), 3.71 (s, 3H).

Example 194

Preparation of N-(3-(5-trifluoromethyl-2-(3-methoxyphenylamino)pyrimidin-4-ylamino)phenyl)methylacrylamide I-226

I-226

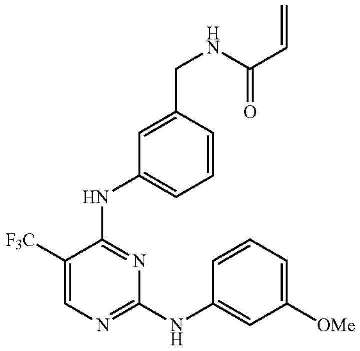

The title compound was prepared according to the schemes, steps and intermediates described in Example 189 using 3-methoxyaniline in place of 2 in step-1 and 3-aminophenylmethyl-N-tert-butoxycarbonylamine in place of 4 in step-2. $^1$H NMR (200 MHz, $CD_3OD$) δ 8.31 (s, 1H), 7.71-7.33 (m, 3H), 7.21-7.08 (m, 4H), 6.57 (m, 1H), 6.26 (d, J=4 Hz, 2H), 5.69 (dd, J=8.0, 2.0 Hz, 1H), 4.47 (s, 2H), 3.67 (s, 3H).

Example 195

Preparation of N-(4-(5-trifluoromethyl-2-(6-methoxypyridin-3-ylamino)pyrimidin-4-ylamino)phenyl)acrylamide I-218

I-218

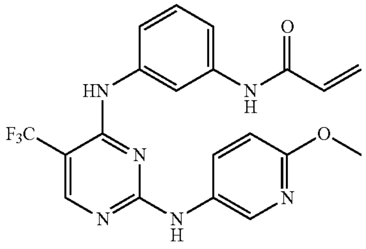

The title compound was prepared according to the schemes, steps and intermediates described in Example 189 using 3-amino-6-methoxypyridine in place of 2 in step-1. $^1$H NMR (200 MHz, $CD_3OD$) δ 8.21 (s, 1H), 7.90-7.78 (m, 3H), 7.48 (m, 2H), 7.30 (m, 2H), 6.40 (m, 2H), 5.75 (dd, J=8.0, 2.0 Hz, 1H), 3.81 (s, 3H).

Example 196

Preparation of N-(4-(5-trifluoromethyl-2-(5-methoxypyridin-3-ylamino)pyrimidin-4-ylamino)phenyl)acrylamide I-214

I-214

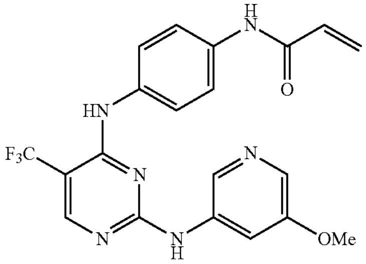

The title compound was prepared according to the schemes, steps and intermediates described in Example 189 using 3-amino-5-methoxypyridine in place of 2 in step-1 and 4-amino-N-tert-butoxycarbonylaniline in place of 4 in step-2. MS: m/e=431 [M+1].

Example 197

Preparation of 1-(3-(5-trifluoromethyl-2-(3-methoxyphenylamino)pyrimidin-4-ylamino)phenyl)-3-methyl-but-2-en-1-one I-225

I-225

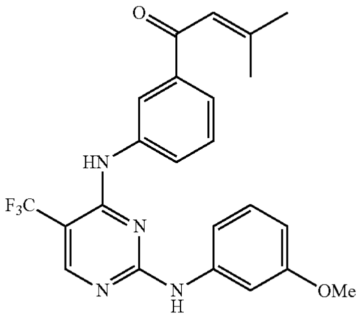

The title compound was prepared according to the schemes, steps and intermediates described in Example 189 using 3-methoxyaniline in place of 2 in step-1 and 1-(3-aminophenyl)-3-methylbut-2-en-1-one in place of 4 in step-2. $^1$H NMR (200 MHz, $CDCl_3$) δ 8.33 (s, 1H), δ 8.38 (s, 1H), 7.99-7.77 (m, 4H), 7.50 (m, 2H), 7.20-7.01 (m, 4H), 6.68-6.60 (m, 2H), 3.68 (s, 3H), 2.25 (s, 3H), 1.99 (s, 3H).

1-(3-Aminophenyl)-3-methylbut-2-en-1-one was prepared according to the scheme, steps, and intermediates described below.

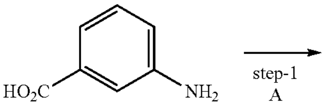

1

-continued

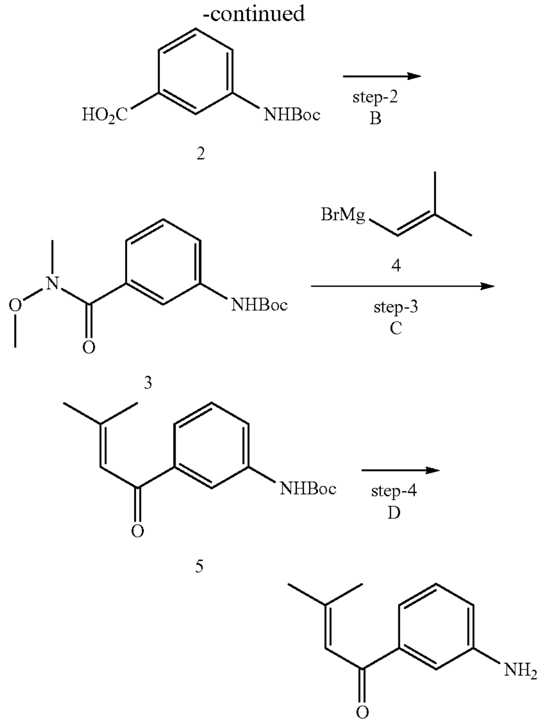

2

4

3

5

6

A) $Boc_2O$, $NEt_3$, DMAP, DCM; B) NHMe(OMe)—HCl, TBTU, DCM, 0° C. to rt; C) 4, THF, 0° C. to rt; D) TFA, DCM.

Step-1

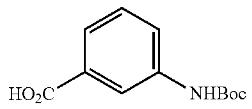

2

Di-tert-butyldicarbonate (6.54 g, 30 mmol, 1.5 eq.) was added to a solution of 1 (2.70 g, 20 mmol) in $CH_2Cl_2$ (100 mL) containing $Et_3N$ (3.4 mL, 24 mmol, 1.2 eq.) and DMAP (122 mg, 1.0 mmol, 5 mol %). The mixture was stirred overnight under a $CaCl_2$ drying tube. The solvents were evaporated and the residue was partitioned between ether (50 mL) and water (50 mL). The aqueous phase was extracted with ether then acidified to pH 3 with 1N HCl and extracted with EtOAc (2×50 mL). The combined organic layers were washed with water and brine and dried over $NaSO_4$. Concentration afforded the crude product which was recrystallized from EtOAc/hexanes to give 2 (2.92 g, 62%).

Step-2

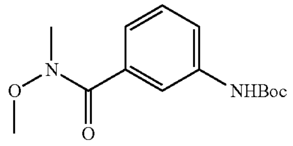

3

To a mixture of 2 (1.5 g, 6.33 mmol), N-methoxy-N-methylamine hydrochloride (614 mg, 6.33 mmol), and TBTU (2.05 g, 6.33 mmol) in DCM (30 mL) at 0° C. was added NEt3 (2.7 mL, 19 mmol, 3 eq.). The mixture was stirred for 30 min at 0° C. then at room temperature for 2 h whereupon HPLC analysis indicated the reaction to be complete. The reaction mixture was poured into 150 mL of cold water and the product precipitated as a white solid which was collected and washed with cold water. The product was dried in a vacuum oven overnight to give 3 (1.34 g, 75%) as a white solid.

Step-3

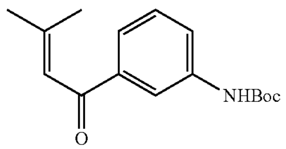

5

To a solution of 3 (546 mg, 1.95 mmol) in THF (3 mL) at 0° C. under Ar was added dropwise 4 (0.5 M in THF, 9.75 mL, 4.9 mmol, 2.5 eq.). The reaction mixture was stirred at 0° C. for 30 min then the cooling bath was removed and the reaction was stirred at rt for 2 h. The reaction mixture was cooled to 0° C. and quenched with 5% citric acid solution. After dilution with water (10 mL) the aqueous phase was extracted with ether (2×15 mL) and the combined organic layers were washed with water and brine and dried over $NaSO_4$. Concentration afforded 5 (82%) as a yellow solid which was sufficiently pure to be used directly in the next step.

Step-4

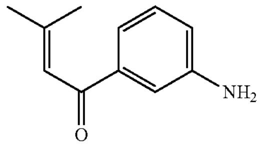

6

A sample of 400 mg of 5 was treated with 5 mL 1:3 $CH_2Cl_2$:trifluoroacetic acid and the resulting solution stirred at room temperature for 15 minutes. The solvents were removed in vacuo and the residue redissolved in $CH_2Cl_2$ and re-evaporated three times. The residue was again taken up in $CH_2Cl_2$ and the solution washed with saturated sodium bicarbonate solution. The $CH_2Cl_2$ layer was dried over sodium sulphate, filtered and evaporated to afford 6 as a white solid that was used directly in the next reaction.

Example 198

Preparation of 1-(3-(2-(3-Methoxy-phenylamino)-5-trifluoromethyl-pyrimidin-4-ylamino)-cyclohexyl)-3-methyl-but-2-en-1-one I-213

I-213

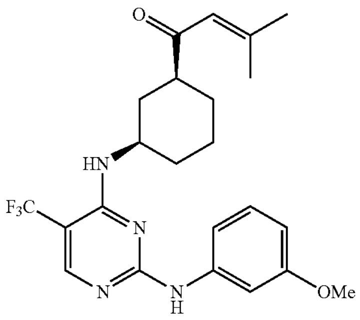

The title compound was prepared according to the schemes, steps and intermediates described in Example 189 using 3-methoxyaniline in place of 2 in step-1 and (d,l)-cis-1-(3-Amino-cyclohexyl)-3-methyl-but-2-en-1-one in place of 4 in step-2. $^1$H NMR (200 MHz, $CDCl_3$) δ 8.07 (s, 1H), 7.33 (s, 1H), 7.19-7.0 (m, 3H), 6.54 (d, J=2.7 Hz, 1H), 6.02 (s, 1H), 4.04 (m, 1H), 3.75 (s, 3H), 2.50 (m, 1H), 2.10 (m, 1H), 1.89-1.15 (m, 14H).

(D,L)-cis-1-(3-Amino-cyclohexyl)-3-methyl-but-2-en-1-one was prepared according to the scheme, steps, and intermediates described below.

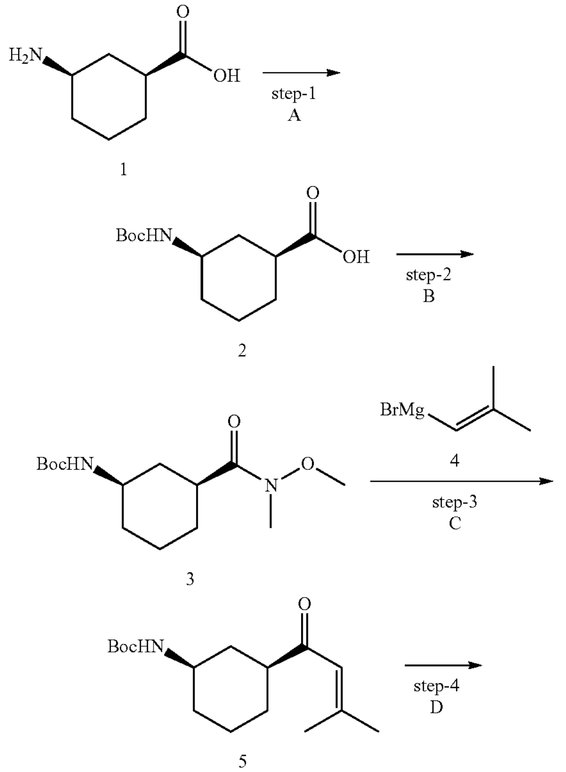

-continued

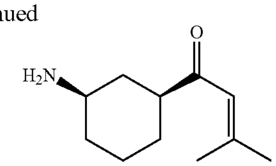

6

A) $Boc_2O$, $Na_2CO_3$, acetone, $H_2O$; B) NHMe(OMe)—HCl, TBTU, DCM, 0° C. to rt; C) 4, THF, 0° C. to rt; D) TFA, DCM.

Step-1

2

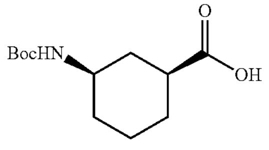

To a stirred solution of (+)-1 (4.05 g, 28.2 mmol) in water (150 mL) containing $Na_2CO_3$ (3.0 g, 28.2 mmol) and acetone (100 mL) was added $BOC_2O$ (7.4 g, 33.8 mmol, 1.2 eq) and the mixture was stirred at 25° C. overnight. The acetone was stripped and the aqueous layer was extracted with ether (2×). The aqueous layer was acidified to pH 3 and the precipitated product was collected and washed with water. The product was dried in a vacuum oven overnight to give 2 (5.90 g, 85%) as a white solid.

Step-2

3

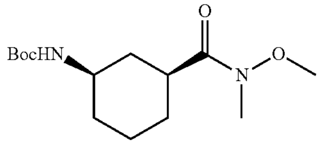

To a stirred solution of 2 (2.45 g, 10.1 mmol), TBTU (3.44 g, 10.6 mmol, 1.05 eq) and N-methyl-N-methoxyamine hydrochloride (1.03 g, 10.6 mmol, 1.05 eq) in $CH_2Cl_2$ (40 mL) at 0° C. was added triethylamine (4.25 mL, 30.3 mmol, 3 eq). The mixture was stirred at 0° C. for 20 min and the bath was removed and stirring was continued for 3 h at 25° C. After quenching with water, the $CH_2Cl_2$ was stripped and the residue was partitioned between ether and water. The aqueous phase was extracted with ether and the combined organic layers were washed with water and brine and dried over $MgSO_4$. Evaporation of the solvents gave 3 (2.37 g, 82%) as a white solid.

Step-3

5

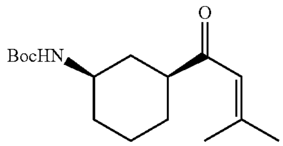

To a solution of 3 (1.23 g, 4.32 mmol) in THF (20 mL) at 0° C. under argon was added dropwise 4 (27 mL, 0.5 M in THF, 10.8 mmol, 2.5 eq). After the addition was complete the mixture was stirred at 0° C. for 30 min, then at rt for 1 h. The reaction mixture was cooled to 0° C. then quenched with 5% citric acid solution (5 mL). After dilution with water the mixture was extracted with ether (2×) and the combined organic layers were washed with water and brine and dried over $NaSO_4$. Evaporation left an orange residue which was chromatographed on silica gel eluting with 20% EtOAc in hexanes to give 5 (600 mg, 56%) as a light yellow solid.

Step-4

6

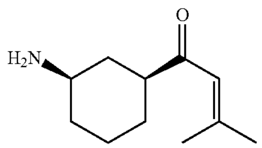

A sample of 500 mg of 5 was treated with 6 mL 1:3 $CH_2Cl_2$:trifluoroacetic acid and the resulting solution stirred at room temperature for 15 minutes. The solvents were removed in vacuo and the residue redissolved in $CH_2Cl_2$ and re-evaporated three times. The residue was again taken up in $CH_2Cl_2$ and the solution washed with saturated sodium bicarbonate solution. The $CH_2Cl_2$ layer was dried over sodium sulphate, filtered and evaporated to afford 6 as a white solid that was used directly without purification.

Example 199

Preparation of 1-(5-(5-trifluoromethyl-2-(3-methoxyphenylamino)pyrimidin-4-yl)amino-1,3-dihydroisoindol-2-yl)2-propen-1-one I-132

I-132

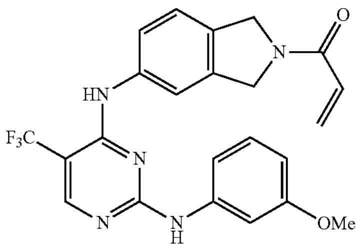

The title compound was prepared according to the schemes, steps and intermediates described in Example 189 using 3-methoxyaniline in place of 2 in step-1 and 2-(N-tert-butoxycarbonyl)-5-aminoisoindoline in place of 4 in step-2. MS m/e=456 [M+1].

Example 200

Preparation of 3-(2-(2-acryloylisoindolin-5-ylamino)-5-fluoropyrimidin-4-ylamino)benzonitrile I-106

I-106

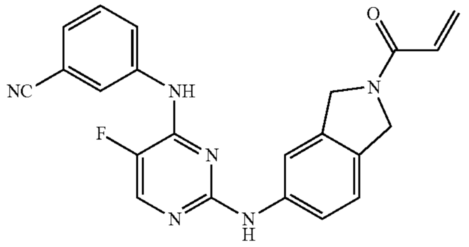

The title compound was prepared according to the schemes, steps and intermediates described in Example 2 using 5-fluoro-2,4-dichloropyrimidine in place of 1 and 3-aminobenzonitrile in place of 2 in step-1 and 2-(tert-butoxycarbonyl-5-aminoisoindoline in place of 4 in step-2. LC/MS (RT=2.82/(M+H)) 401.1

Example 201

Preparation of N-(3-(5-fluoro-4-((6-(trifluoromethyl)pyridin-3-yl)methylamino)pyrimidin-2-ylamino)phenyl)acrylamide I-53

I-53

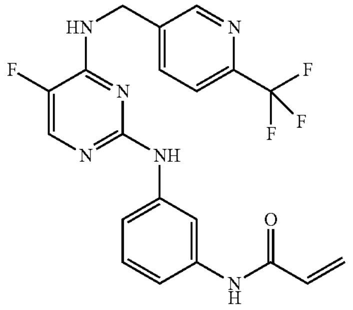

The title compound was prepared according to the schemes, steps and intermediates described in Example 2 using 5-fluoro-2,4-dichloropyrimidine in place of 1 and 3-aminomethyl-6-trifluoromethylpyridine in place of 2 in step-1. LC/MS (RT=2.805/(M+H)) 433.0

Example 202

Preparation of N-(3-(4-((2,3-dihydrobenzofuran-5-yl)methylamino)-5-fluoropyrimidin-2-ylamino)phenyl)acrylamide I-6

I-6

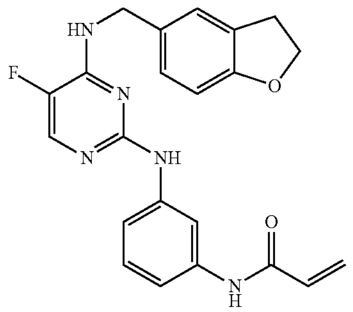

The title compound was prepared according to the schemes, steps and intermediates described in Example 2 using 5-fluoro-2,4-dichloropyrimidine in place of 1 and 3-aminomethyl-2,3-dihydrobenzofuran in place of 2 in step-1. LC/MS (RT=2.815/(M+H)) 406.2

Example 203

Preparation of N-(3-(5-fluoro-2-(4-methoxybenzylamino)pyrimidin-4-ylamino)phenyl)acrylamide I-241

I-241

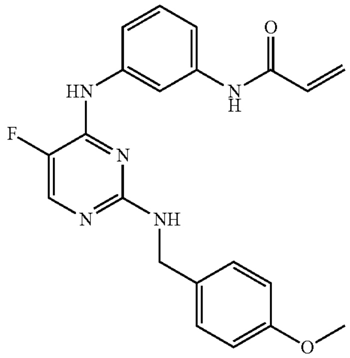

The title compound was prepared according to the schemes, steps and intermediates described in Example 20 using 4-methoxybenzylamine in place of 4 in step-2. LC/MS (RT=2.801/(M+H)) 394.2

Example 204

Preparation of $N^1$-(3-(3-(4-(3-acrylamidophenylamino)-5-methylpyrimidin-2-ylamino)phenoxy)propyl)-$N^5$-(15-oxo-19-((3aR,4R,6aS)-2-oxohexahydro-1H-thieno[3,4-d]imidazol-4-yl)-4,7,10-trioxa-14-azanonadecyl)glutaramide I-215

I-215

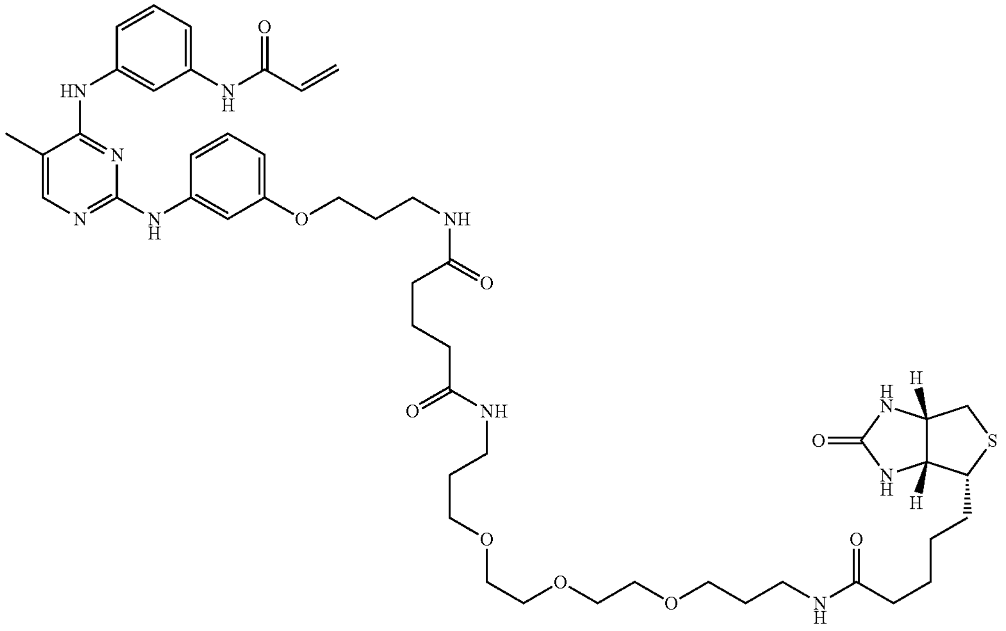

The title compound was prepared according to the schemes steps and intermediates described below.
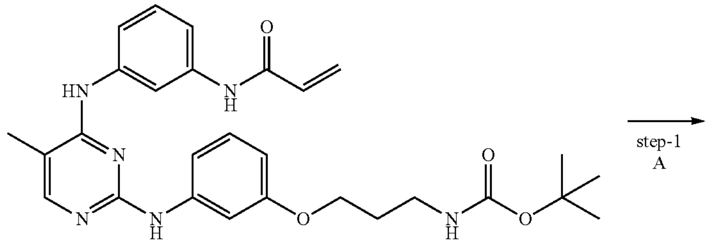
I-45
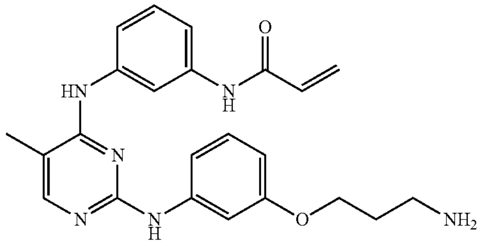
1
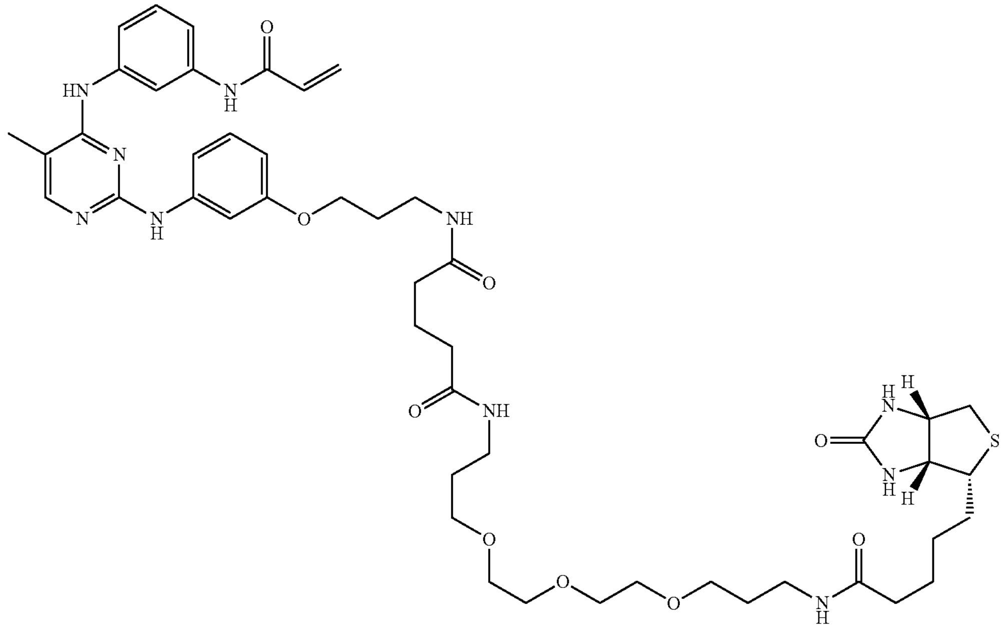
I-215
A) TFA, DCM; B) N-Biotinyl-NH—(PEG)$_2$—COOH—DIPEA, HOBt, EDC, NMM, DMF.

Step-1

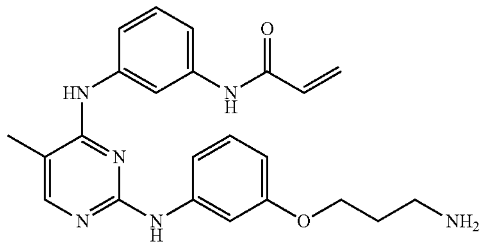

I-45 (97 mg, 0.19 mmol; synthesis of I-45 provided in Example 62) was dissolved in DCM (10 mL). Trifluoroacetic acid (200 μL) was added and allow to stir at rt for 24 hr. The solvent was removed via rotary evaporation to give a tan-brown foam (130 mg) which was used without purification in the next reaction. LC/MS (RT=2.63/(MH+) 419.2)

Step-2

I-215

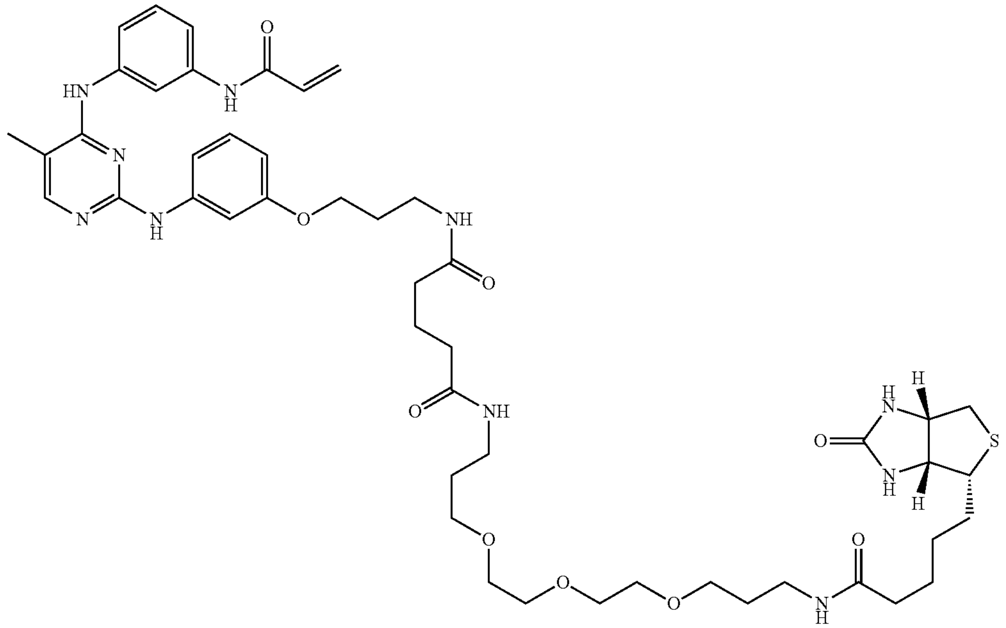

1 (80 mg, 0.15 mmoL) was dissolved in DMF (2 mL). To the mixture was added N-Biotinyl-NH-$(PEG)_2$-COOH-DIPEA (114 mg, 0.16 mmol) and HOBt (25 mg, 0.16 mmoL (89%)), and the mixture was cooled in an ice-water bath. EDC (32 mg, 0.16 mmoL) was added, followed by N-methylmorpholine (50 μL, 0.45 mmoL). The mixture was allowed to warm to room temperature and continue to stir for 30 min. Direct purification by flash chromatography using 10% gradient of MeOH in DCM gave 40 mg of I-215 as a yellow film. LC/MS (RT=2.654/(MH+) 961.3).

Example 205

Preparation of N-(3-(3-(4-(3-acrylamidophenylamino)-5-methylpyrimidin-2-ylamino)phenoxy)propyl)-5-((3aS,4S,6aR)-2-oxohexahydro-1H-thieno[3,4-d]imidazol-4-yl)pentanamide I-237

I-237

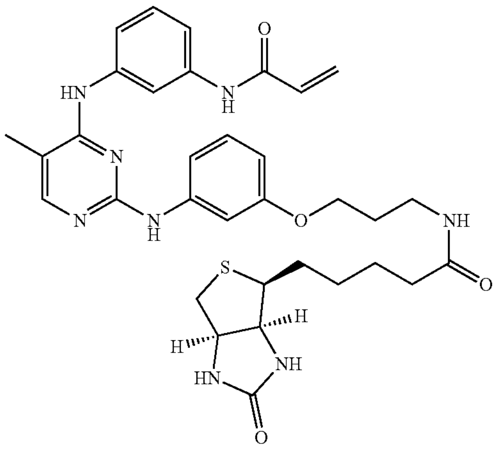

The title compound was prepared according to the schemes, steps and intermediates described in Example 204 using D-(+)-biotin in place of N-Biotinyl-NH-(PEG)$_2$-COOH-DIPEA in step-2. LC/MS (RT=2.686/(M+H)) 645.2

Example 206

Preparation of (R)—N-(3-(5-fluoro-2-(3-fluoro-4-(tetrahydrofuran-3-yloxy)phenylamino)pyrimidin-4-ylamino)phenyl)acrylamide I-316

I-316

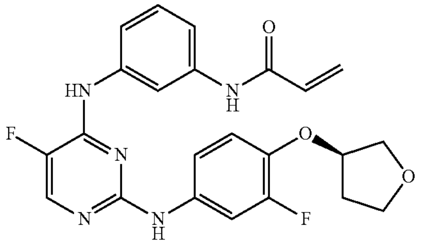

The title compound was prepared according to the schemes, steps and intermediates described in Example 20, by using (R)-3-fluoro-4-(tetrahydrofuran-3-yloxyaniline in place of 4 in step 2. $^1$H NMR (DMSO-d$_6$) δ ppm: 1.85-2.00 (m, 1H), 2.20 (m, 1H), 3.70-3.90 (m, 4H), 4.90 (s, 1H), 5.73 (dd, J=1.56 & 10.04 Hz, 1H), 6.23 (dd, J=1.76 & 17.00 Hz, 1H), 6.44 (dd, J=10.08 & 16.88 Hz, 1H), 7.28 (t, J=8.04 Hz, 1H), 7.40-7.47 (m, 2H), 7.67-7.71 (m, 2H), 7.68 (dd, J=1.96 & 14.08 Hz, 1H), 7.92 (s, 1H), 8.1 (d, J=3.64 Hz, 1H), 9.21 (s, 1H), 9.44 (s, 1H), 10.12 (s, 1H); LCMS: m/e 452.0 (M−1).

Example 207

Preparation of 1-(4-(5-fluoro-2-(3-fluoro-4-(2-methoxyethoxy)phenylamino)pyrimidin-4-ylamino)phenyl)-3-methylbut-2-en-1-one I-325

I-325

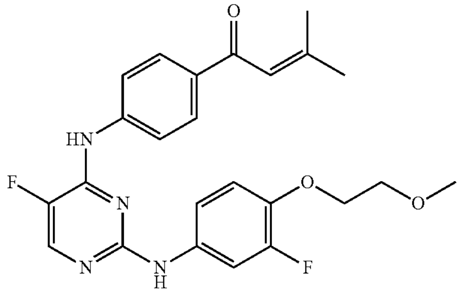

The title compound was prepared according to the schemes, steps and intermediates described in Example 112, by using methyl 4-aminobenzoate in place of 2 in step 1 and 3-fluoro-4-(2-methoxyethoxy)aniline in place of 4 in step 2. $^1$H NMR (DMSO-d$_6$) δ ppm: 2.01 (s, 3H), 2.15 (d, J=0.72 Hz, 3H), 3.31 (s, 3H), 3.66 (dd, J=3.64 & 4.56 Hz, 2H), 4.11 (dd, J=4.44 & 6.12 Hz, 2H), 6.93 (s, 1H), 7.08 (t, J=9.44 Hz, 1H), 7.27 (d, J=8.88 Hz, 1H), 7.74 (dd, J=2.44 & 14.24 Hz, 1H), 7.93 (d, J=8.96 Hz, 2H), 7.98 (d, J=8.92 Hz, 2H), 8.20 (d, J=3.64 Hz, 1H), 9.35 (s, 1H), 9.73 (s, 1H); LCMS: m/e 455 (M+1).

Example 208

Preparation of 1-(3-(5-fluoro-2-(3-fluoro-4-(2-methoxyethoxy)phenylamino)pyrimidin-4-ylamino)phenyl)-3-methylbut-2-en-1-one I-323

I-325

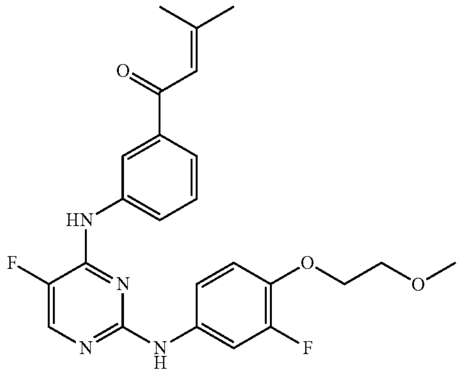

The title compound was prepared according to the schemes, steps and intermediates described in Example 112, by using 2-(3-fluoro-4-(2-methoxyethoxy)aniline in place of 4 in step 2. $^1$H NMR (DMSO-d$_6$) δ ppm: 1.95 (s, 3H), 2.14 (s, 3H), 3.31 (s, 3H), 3.63 (t, J=4.64 Hz, 2H), 4.06 (t, J=4.36 Hz, 2H), 6.85 (bs, 1H), 6.97 (t, J=9.52 Hz, 1H), 7.26 (bd, J=8.32 Hz, 1H), 7.48 (t, J=7.92 Hz, 1H), 7.62-7.67 (m, 2H), 8.08 (bd, J=7.04 Hz, 1H), 8.15-8.16 (m, 2H), 9.29 (s, 1H), 9.58 (s, 1H); LCMS: m/e 455 (M+1).

Example 209

Preparation of 1-(4-(5-fluoro-2-(3-fluoro-4-(2-methoxyethoxy)phenylamino)pyrimidin-4-ylamino)phenyl)-2-methylprop-2-en-1-one I-324

I-324

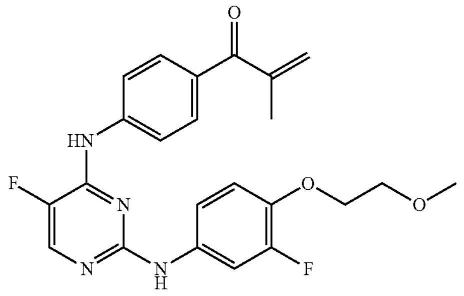

The title compound was prepared according to the schemes, steps and intermediates described in Example 112, by using methyl 4-aminobenzoate in place of 2 in step 1,3-fluoro-4-(2-methoxyethoxy)aniline in place of 4 in step 2 and isopropenylmagnesium bromide in place of 8 in step 5. $^1$H NMR (DMSO-$d_6$) δ ppm: 2.0 (s, 3H), 3.32 (s, 3H), 3.66 (t, J=4.36 Hz, 2H), 4.11 (t, J=4.44 Hz, 2H), 5.55 (s, 1H), 5.94 (s, 1H), 7.07 (t, J=9.32 Hz, 1H), 7.26 (t, J=9.4 Hz, 1H), 7.72-7.76 (m, 3H), 7.99 (d, J=8.44 Hz, 2H), 8.21 (d, J=3.56 Hz, 1H), 9.38 (s, 1H), 9.75 (s, 1H); LCMS: m/e 441.2 (M+1).

Example 210

Preparation of 1-(4-(5-fluoro-2-(3-fluoro-4-(2-methoxyethoxy)phenylamino)pyrimidin-4-ylamino)phenyl)-3-methylbut-3-en-2-one I-329

I-329

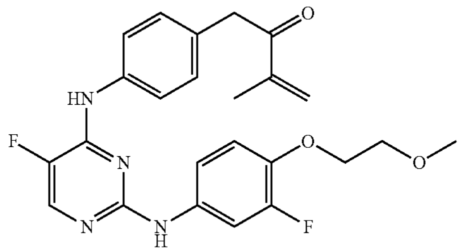

The title compound was prepared according to the schemes, steps and intermediates described in Example 112, by using ethyl 4-aminophenylacetate in place of 2 in step 1, 3-fluoro-4-(2-methoxyethoxy)aniline in place of 4 in step 2 and isopropenylmagnesium bromide in place of 8 in step 5. $^1$H NMR (DMSO-$d_6$) δ ppm: 1.79 (s, 3H), 3.30 (s, 3H), 3.62-3.65 (m, 2H), 4.06 (s, 2H), 4.08-4.10 (m, 2H), 5.95 (d, J=1 Hz, 1H), 6.27 (s, 1H), 7.01 (t, J=9.44 Hz, 1H), 7.15 (d, J=8.52 Hz, 2H), 7.28 (d, J=8.88 Hz, 1H), 7.64-7.70 (m, 3H), 8.08 (d, J=3.72 Hz, 1H), 9.19 (s, 1H), 9.33 (s, 1H); LCMS: m/e 455.3 (M+1).

Example 211

Preparation of 1-(4-(5-fluoro-2-(3-fluoro-4-(2-methoxyethoxy)phenylamino)pyrimidin-4-ylamino)phenyl)-4-methylpent-3-en-2-one I-331

I-331

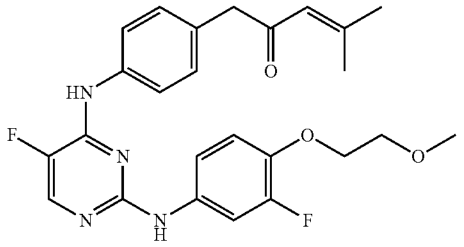

The title compound was prepared according to the schemes, steps and intermediates described in Example 112, by using ethyl 4-aminophenylacetate in place of 2 in step 1, 3-fluoro-4-(2-methoxyethoxy)aniline in place of 4 in step 2. $^1$H NMR (DMSO-$d_6$) δ ppm: 1.84 (d, J=1 Hz, 3H), 2.05 (d, J=0.92 Hz, 3H), 3.30 (s, 3H), 3.62-3.64 (m, 2H), 3.68 (s, 2H), 4.07-4.09 (m, 2H), 6.21 (t, J=1.2 Hz, 1H), 7.01 (t, J=8.68 Hz, 1H), 7.16 (d, J=8.48 Hz, 2H), 7.26 (d, J=8.96 Hz, 1H), 7.65-7.72 (m, 3H), 8.08 (d, J=3.72 Hz, 1H), 9.20 (s, 1H), 9.34 (s, 1H); LCMS: m/e 469.3 (M+1).

Example 212

Preparation of 1-(3-(5-fluoro-2-(3-fluoro-4-(2-methoxyethoxy)phenylamino)pyrimidin-4-ylamino)phenyl)-2-methylprop-2-en-1-one I-322

I-322

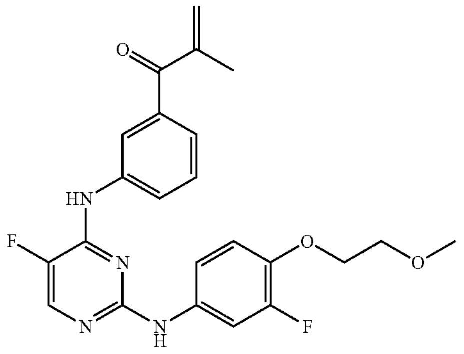

The title compound was prepared according to the schemes, steps and intermediates described in Example 112, by using 1,3-fluoro-4-(2-methoxyethoxy)aniline in place of 4 in step 2 and isopropenylmagnesium bromide in place of 8 in step 5. $^1$H NMR (DMSO-$d_6$) δ ppm: 1.96 (s, 3H), 3.30 (s, 3H), 3.63 (t, J=4.6 Hz, 2H), 4.07 (t, J=4.36 Hz, 2H), 5.62 (s, 1H), 6.00 (s, 1H), 6.99 (t, J=9.24 Hz, 1H), 7.26 (d, J=8.92 Hz, 1H), 7.39 (d, J=7.56 Hz, 1H), 7.46 (t, J=7.72 Hz, 1H), 7.62 (bd, J=14.4 Hz, 1H), 7.93 (s, 1H), 8.12-8.14 (m, 2H), 9.25 (s, 1H), 9.58 (s, 1H); LCMS: m/e 441.2 (M+1).

Example 213

Preparation of 1-(3-(5-fluoro-2-(3-fluoro-4-(2-methoxyethoxy)phenylamino)pyrimidin-4-ylamino)phenyl)-3-methylbut-3-en-2-one I-328

I-328

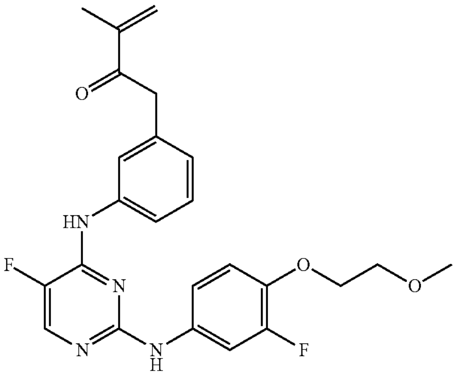

The title compound was prepared according to the schemes, steps and intermediates described in Example 112, by using ethyl 3-aminophenylacetate in place of 2 in step 1, 3-fluoro-4-(2-methoxyethoxy)aniline in place of 4 in step 2 and isopropenylmagnesium bromide in place of 8 in step 5. $^{1}$H NMR (DMSO-$d_6$) δ ppm: 1.8 (s, 3H), 3.31 (s, 3H), 3.64 (t, J=4.56 Hz, 2H), 4.06 (s, 2H), 4.09 (t, J=4.37 Hz, 2H), 5.95 (s, 1H), 6.23 (s, 1H), 6.92 (d, J=7.52 Hz, 1H), 7.02 (t, J=9.4 Hz, 1H), 7.27 (t, J=7.8 Hz, 2H), 7.50 (s, 1H), 7.66-7.72 (m, 2H), 8.10 (d, J=3.56 Hz, 1H), 9.21 (s, 1H), 9.36 (s, 1H); LCMS: m/e 455.1 (M+1).

Example 214

Preparation of 2-((3-(5-fluoro-2-(3-fluoro-4-(2-methoxyethoxy)phenylamino)pyrimidin-4-ylamino)phenyl)(hydroxy)methyl)acrylonitrile I-326

I-326

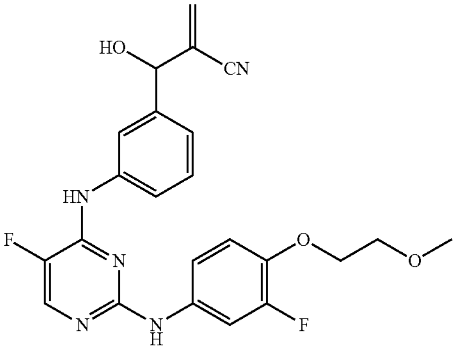

The title compound was prepared according to the schemes, steps and intermediates described in Example 107, by using 3-fluoro-4-(2-methoxyethoxy)aniline in place of 4 in step 2. $^{1}$H NMR (DMSO-$d_6$) δ ppm: 3.30 (s, 3H), 3.62-3.65 (m, 2H), 4.09 (t, J=4.6 Hz, 2H), 5.29 (d, J=3.84 Hz, 1H), 6.13 (s, 1H), 6.19 (s, 1H), 6.31 (d, J=4.04 Hz, 1H), 7.03 (t, J=9.24 Hz, 1H), 7.10 (d, J=7.44 Hz, 1H), 7.28 (d, J=8.72 Hz, 1H), 7.36 (t, J=7.8 Hz, 1H), 7.62 (s, 1H), 7.66 (dd, J=2.32 & 14.44 Hz, 1H), 7.89 (d, J=8.2 Hz, 1H), 8.10 (d, J=3.68 Hz, 1H), 9.14 (s, 1H), 9.45 (s, 1H); LCMS: m/e 454 (M+1).

Example 215

Preparation of 2-((4-(5-fluoro-2-(3-fluoro-4-(2-methoxyethoxy)phenylamino)pyrimidin-4-ylamino)phenyl)(hydroxy)methyl)acrylonitrile I-327

I-327

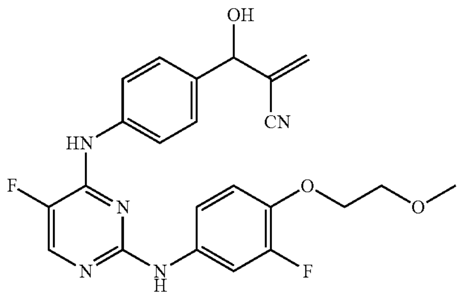

The title compound was prepared according to the schemes, steps and intermediates described in Example 107, by using methyl 4-aminobenzoate in place of 2 in step 1 and 3-fluoro-4-(2-methoxyethoxy)aniline in place of 4 in step 2. $^{1}$H NMR (DMSO-$d_6$) δ ppm: 3.30 (s, 3H), 3.64 (dd, J=2.96 & 4.56 Hz, 2H), 4.08 (t, J=4.48 Hz, 2H), 5.29 (d, J=3.8 Hz, 1H), 6.11 (s, 1H), 6.21 (s, 1H), 6.24 (d, J=4.12 Hz, 1H), 7.01 (t, J=9.4 Hz, 1H), 7.29-7.34 (m, 3H), 7.68 (dd, J=2.2 & 14.16 Hz, 1H), 7.77 (d, J=8.52 Hz, 2H), 8.11 (d, J=3.68 Hz, 1H), 9.23 (s, 1H), 9.42 (s, 1H); LCMS: m/e 454.0 (M+1).

Example 216

Preparation of N-(3-(2-(4-chloro-3-(2-hydroxy-2-methylpropoxy)phenylamino)-5-fluoropyrimidin-4-ylamino)phenyl)acrylamide I-249

I-249

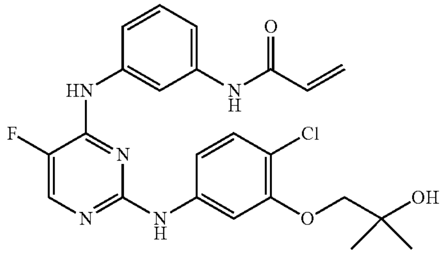

The title compound was prepared according to the schemes, steps and intermediates described in Example 20, by using 4-chloro-3-(2-hydroxy-2-methylpropoxy)aniline in place of 4 in step 2. $^{1}$H NMR (DMSO-$d_6$) δ ppm: 1.20 (s, 6H), 3.61 (s, 2H), 4.61 (s, 1H), 5.75 (d, J=11.4 Hz, 1H), 6.24 (d, J=18.36 Hz, 1H), 6.44 (dd, J=10.32 & 17.08 Hz, 1H), 7.13 (d, J=8.64 Hz, 1H), 7.28 (t, J=8 Hz, 1H), 7.37-7.44 (m, 3H), 7.55 (d, J=7.08 Hz, 1H), 7.93 (s, 1H), 8.12 (d, J=3.44 Hz, 1H), 9.23 (s, 1H), 9.47 (s, 1H), 10.11 (s, 1H); LCMS: m/e 472.0 (M+1).

Example 217

Preparation of N-(3-(5-fluoro-2-(3-fluoro-4-(2-hydroxy-2-methylpropoxy)phenylamino)pyrimidin-4-ylamino)phenyl)acrylamide I-315

I-315

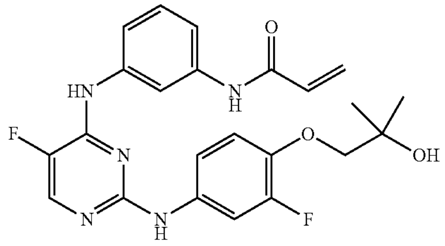

The title compound was prepared according to the schemes, steps and intermediates described in Example 20, by using 3-fluoro-4-(2-hydroxy-2-methylpropoxy)aniline in place of 4 in step 2. $^1$H NMR (DMSO-$d_6$) δ ppm: 1.19 (s, 6H), 3.67 (s, 2H), 4.62 (s, 1H), 5.75 (d, J=10.4 Hz, 1H), 6.25 (d, J=17.2 Hz, 1H), 6.45 (dd, J=10 & 16.8 Hz, 1H), 6.94 (t, J=9.2 Hz, 1H), 7.29 (t, J=8 Hz, 2H), 7.43 (d, J=8.4 Hz, 1H), 7.49 (d, J=7.6 Hz, 1H), 7.67 (d, J=13.6 Hz, 1H), 7.94 (s, 1H), 8.11 (d, J=3.6 Hz, 1H), 9.19 (s, 1H), 9.45 (s, 1H), 10.14 (s, 1H); LCMS: m/e 456 (M−1).

Example 218

Preparation of N-(3-(5-fluoro-2-(3-fluoro-4-(1-hydroxypropan-2-yloxy)phenylamino)pyrimidin-4-ylamino)phenyl)acrylamide I-333

I-333

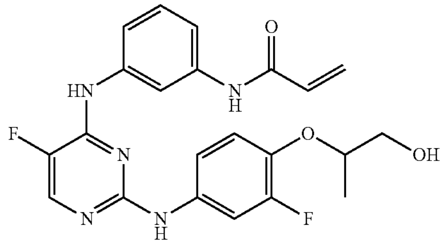

The title compound was prepared according to the schemes, steps and intermediates described in Example 20, by using 3-fluoro-4-(2-hydroxy-1-methylethoxy)aniline in place of 4 in step 2. $^1$H NMR (DMSO-$d_6$) δ ppm: 1.16 (d, J=6.12 Hz, 3H), 3.40-3.46 (m, 1H), 3.50-3.56 (m, 1H), 4.22 (sextet, J=5.6 Hz, 1H), 4.84 (t, J=5.68 Hz, 1H), 5.75 (dd, J=1.96 & 10.08 Hz, 1H), 6.25 (dd, J=1.92 & 16.92 Hz, 1H), 6.46 (dd, J=10.08 & 16.92 Hz, 1H), 6.98 (t, J=9.32 Hz, 1H), 7.26-7.31 (m, 2H), 7.43 (d, J=8.76 Hz, 1H), 7.49 (d, J=8 Hz, 1H), 7.68 (dd, J=2.44 & 14.28 Hz, 1H), 7.95 (s, 1H), 8.11 (d, J=3.68 Hz, 1H), 9.23 (s, 1H), 9.46 (s, 1H), 10.17 (s, 1H); LCMS: m/e 442.2 (M+1).

Example 219

Preparation of N-(3-(2-(4-(2,3-dihydroxypropoxy)-3-fluorophenylamino)-5-fluoropyrimidin-4-ylamino)phenyl)acrylamide I-334

I-334

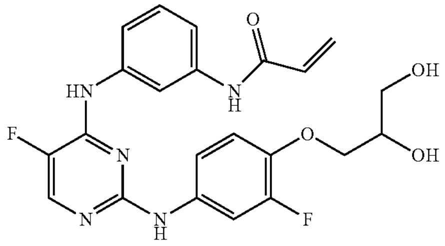

The title compound was prepared according to the schemes, steps and intermediates described in Example 20, by using 4-(2,3-dihydroxypropoxy)-3-fluoroaniline in place of 4 in step 2. $^1$H NMR (DMSO-$d_6$) δ ppm: 3.42 (t, J=5.6 Hz, 2H), 3.7-3.8 (m, 1H), 3.8-3.9 (m, 1H), 3.94 (dd, J=4.36 & 9.92 Hz, 1H), 4.65 (t, J=5.64 Hz, 1H), 4.93 (d, J=5.08 Hz, 1H), 5.7-5.8 (m, 1H), 6.24 (dd, J=1.64 & 16.84 Hz, 1H), 6.44 (dd, J=10 & 16.96 Hz, 1H), 6.94 (t, J=9.32 Hz, 1H), 7.28 (t, J=7.96 Hz, 2H), 7.40 (d, J=8.28 Hz, 1H), 7.49 (d, J=7.44 Hz, 1H), 7.66 (d, J=14.24 Hz, 1H), 7.92 (s, 1H), 8.09 (d, J=3.6 Hz, 1H), 9.17 (s, 1H), 9.45 (s, 1H), 10.15 (s, 1H); LCMS: m/e 456 (M−1).

Example 220

Preparation of N-(3-(2-(4-chloro-3-(1-hydroxy-2-methylpropan-2-yloxy)phenylamino)-5-fluoropyrimidin-4-ylamino)phenyl)acrylamide I-336

I-336

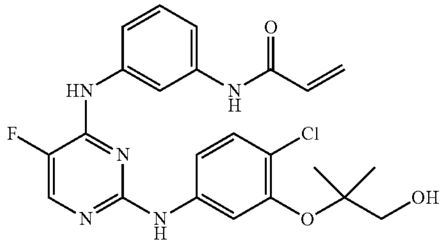

The title compound was prepared according to the schemes, steps and intermediates described in Example 20, by using 4-chloro-3-(1-hydroxy-2-methylpropan-2-yloxy)aniline in place of 4 in step 2. $^1$H NMR (DMSO-$d_6$) δ ppm: 1.22 (s, 6H), 3.47 (d, J=5.88 Hz, 2H), 4.88 (t, J=5.84 Hz, 1H), 5.75 (dd, J=3.24 & 10 Hz, 1H), 6.25 (dd, J=2 & 16.92 Hz, 1H), 6.46 (dd, J=10.12 & 17.08 Hz, 1H), 7.15 (d, J=8.8 Hz, 1H), 7.31 (t, J=8.2 Hz, 1H), 7.40-7.45 (m, 1H), 7.51-7.60 (m, 3H), 7.93 (s, 1H), 8.13 (d, J=3.56 Hz, 1H), 9.24 (s, 1H), 9.47 (s, 1H), 10.12 (s, 1H); LCMS: m/e 472.2 (M+1).

Example 221

Preparation of N-(3-(2-(4-chloro-3-(1-hydroxypropan-2-yloxy)phenylamino)-5-fluoropyrimidin-4-ylamino)phenyl)acrylamide I-337

I-337

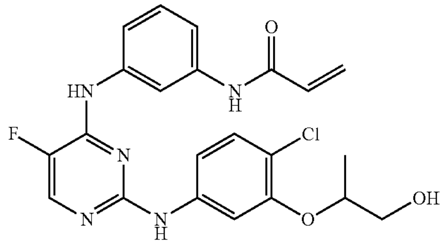

The title compound was prepared according to the schemes, steps and intermediates described in Example 20, by using 4-chloro-3-(1-hydroxypropan-2-yloxy)aniline in place of 4 in step 2. $^1$H NMR (DMSO-$d_6$) δ ppm: 1.18 (d, J=6.12 Hz, 3H), 3.40-3.47 (m, 1H), 3.50-3.56 (m, 1H), 4.20-4.30 (m, 1H), 4.82 (t, J=5.6 Hz, 1H), 5.75 (dd, J=1.88 & 10.08 Hz, 1H), 6.25 (dd, J=1.92 & 16.92 Hz, 1H), 6.45 (dd, J=10.08 & 16.92 Hz, 1H), 7.12 (d, J=8.76 Hz, 1H), 7.29 (t, J=8.08 Hz, 1H), 7.40-7.44 (m, 3H), 7.52 (d, J=8.44 Hz, 1H), 7.91 (s, 1H), 8.12 (d, J=3.64 Hz, 1H), 9.21 (s, 1H), 9.45 (s, 1H), 10.12 (s, 1H); LCMS: m/e 458.0 (M+1).

Example 222

Preparation of N-(3-(2-(4-(2,3-dihydroxypropoxy)phenylamino)-5-fluoropyrimidin-4-ylamino)phenyl)acrylamide I-335

I-335

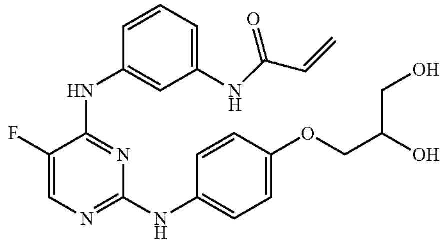

The title compound was prepared according to the schemes, steps and intermediates described in Example 20, by using 4-(1-hydroxypropan-2-yloxy)aniline in place of 4 in step 2. $^1$H NMR (DMSO-$d_6$) δ ppm: 3.43 (dd, J=0.64 & 6.84 Hz, 2H), 3.70-3.80 (m, 2H), 3.85-3.95 (m, 1H), 4.62 (t, J=5.6 Hz, 1H), 4.88 (d, J=4.76 Hz, 1H), 5.75 (dd, J=1.76 & 10.08 Hz, 1H), 6.25 (dd, J=1.72 & 16.92 Hz, 1H), 6.45 (dd, J=10.08 & 16.88 Hz, 1H), 6.74 (d, J=9 Hz, 2H), 7.27 (t, J=8.08 Hz, 1H), 7.39 (d, J=8.04 Hz, 1H), 7.38-7.53 (m, 3H), 7.93 (s, 1H), 8.05 (d, J=3.68 Hz, 1H), 8.93 (s, 1H), 9.35 (s, 1H), 10.11 (s, 1H); LCMS: m/e 440.3 (M+1).

Example 223

Preparation of (R)—N-(3-(2-(4-chloro-3-(tetrahydrofuran-3-yloxy)phenylamino)-5-fluoropyrimidin-4-ylamino)phenyl)acrylamide I-341

I-341

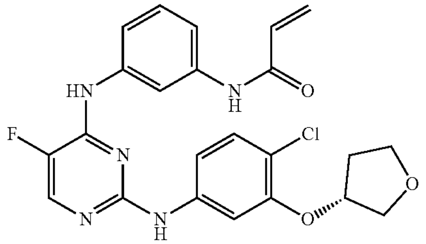

The title compound was prepared according to the schemes, steps and intermediates described in Example 20, by using (R)-4-chloro-3-(tetrahydrofuran-3-yloxy)aniline in place of 4 in step 2. $^1$H NMR (DMSO-$d_6$) δ ppm: 1.85-1.95 (m, 1H), 2.0-2.15 (m, 1H), 3.60-3.70 (m, 1H), 3.73-3.83 (m, 3H), 4.68 (s, 1H), 5.74 (dt, J=1.92 & 10.0 Hz, 1H), 6.23 (dd, J=1.88 & 16.92 Hz, 1H), 6.43 (dd, J=10.12 & 16.96 Hz, 1H), 7.14 (d, J=8.72 Hz, 1H), 7.29 (t, J=8.08 Hz, 1H), 7.33 (dd, J=4.16 & 8.76 Hz, 1H), 7.41-7.47 (m, 3H), 7.90 (s, 1H), 8.13 (d, J=3.56 Hz, 1H), 9.28 (s, 1H), 9.47 (s, 1H), 10.13 (s, 1H); LCMS: m/e 469.8 (M+1).

Example 224

Preparation of N-(3-(5-fluoro-2-(3-fluoro-4-(1-hydroxy-2-methylpropan-2-yloxy)phenylamino)pyrimidin-4-ylamino)phenyl)acrylamide I-332

I-332

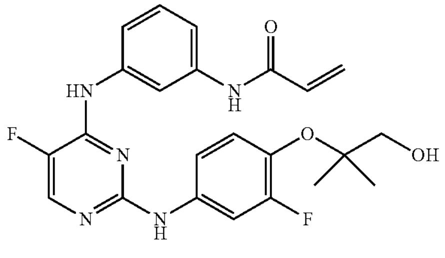

The title compound was prepared according to the schemes, steps and intermediates described in Example 20, by using 3-fluoro-4-(1-hydroxy-2-methylpropan-2-yloxy)aniline in place of 4 in step 2. $^1$H NMR (DMSO-$d_6$) δ ppm: 1.13 (s, 6H), 3.36 (d, J=5.84 Hz, 2H), 4.86 (t, J=5.84 Hz, 1H), 5.73 (dd, J=1.96 & 10.04 Hz, 1H), 6.24 (dd, J=1.96 & 16.96 Hz, 1H), 6.44 (dd, J=10.08 & 16.92 Hz, 1H), 6.95 (t, J=9.16 Hz, 1H), 7.23 (dd, J=1.64 & 8.96 Hz, 1H), 7.28 (t, J=8.12 Hz, 1H), 7.43 (d, J=8.8 Hz, 1H), 7.48 (d, J=7.92 Hz, 1H), 7.70 (dd, J=2.48 & 13.84 Hz, 1H), 7.92 (s, 1H), 8.11 (d, J=3.68 Hz, 1H), 9.25 (s, 1H), 9.45 (s, 1H), 10.10 (s, 1H); LCMS: m/e 456.2 (M+1).

Example 225

Preparation of N-(3-(2-(3-(2,3-dihydroxypropoxy)phenylamino)-5-fluoropyrimidin-4-ylamino)phenyl)acrylamide I-339

I-339

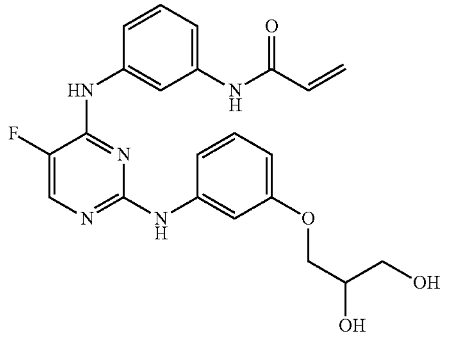

The title compound was prepared according to the schemes, steps and intermediates described in Example 20, by using 3-(2,3-dihydroxypropoxy)aniline in place of 4 in step 2. $^1H$ NMR (MeOD) δ ppm: 3.59-3.69 (m, 2H), 3.88-3.98 (m, 3H), 5.78 (dd, J=2.16 & 9.6 Hz, 1H), 6.36 (dd, J=2.24 & 17.04 Hz, 1H), 6.44 (dd, J=9.56 & 16.96 Hz, 1H), 6.54-6.57 (m, 1H), 7.08-7.12 (m, 2H), 7.32 (t, J=7.92 Hz, 2H), 7.44 (dd, J=7.88 & 13.4 Hz, 2H), 7.94 (d, J=3.8 Hz, 1H), 8.09 (s, 1H); LCMS: m/e 440.1 (M+1).

Example 226

Preparation of N-(4-(5-fluoro-2-(3-fluoro-4-(2-methoxyethoxy)phenylamino)pyrimidin-4-ylamino)phenyl)acrylamide I-351

I-351

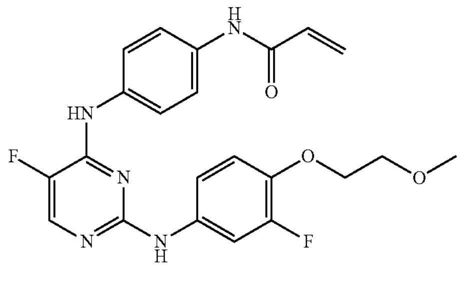

The title compound was prepared according to the schemes, steps and intermediates described in Example 20, by using tert-butoxycarbonylamino-4-aminoaniline in place of 2 in step 1 and 3-fluoro-4-(2-methoxyethoxy)aniline in place of 4 in step 2. $^1H$ NMR (DMSO-$d_6$) δ ppm: 3.30 (s, 3H), 3.63 (t, J=4.6 Hz, 2H), 4.08 (t, J=4.48 Hz, 2H), 5.74 (dd, J=2 & 10.08 Hz, 1H), 6.25 (dd, J=1.96 & 16.92 Hz, 1H), 6.44 (dd, J=10.04 & 16.96 Hz, 1H), 7.02 (t, J=9.48 Hz, 1H), 7.23 (bd, J=7.44 Hz, 1H), 7.64 (d, J=9 Hz, 2H), 7.70-7.74 (m, 3H), 8.07 (d, J=3.72 Hz, 1H), 9.19 (s, 1H), 9.34 (s, 1H), 10.13 (s, 1H); LCMS: m/e 442.0 (M+1).

Example 227

Preparation of 2-((3-(5-fluoro-2-(6-(2-hydroxy-2-methylpropoxy)pyridin-3-ylamino)pyrimidin-4-ylamino)phenyl)(hydroxy)methyl)acrylonitrile I-312

I-312

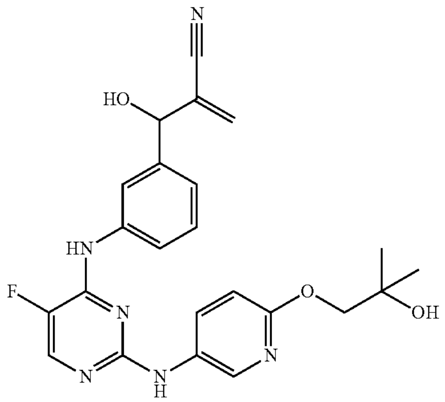

The title compound was prepared according to the schemes, steps and intermediates described in Example 107, by using 3-amino-6-(2-hydroxy-2-methylpropoxy)pyridine in place of 4 in step 2. $^1H$ NMR (DMSO-$d_6$) δ ppm: 1.18 (s, 6H), 3.98 (s, 2H), 4.61 (s, 1H), 5.31 (d, J=3.88 Hz, 1H), 6.13 (s, 1H), 6.19 (s, 1H), 6.32 (d, J=4 Hz, 1H), 6.75 (d, J=8.88 Hz, 1H), 7.10 (d, J=7.72 Hz, 1H), 7.33 (t, J=7.84 Hz, 1H), 7.68 (s, 1H), 7.84 (d, J=7.52 Hz, 1H), 7.96 (dd, J=2.72 & 8.88 Hz, 1H), 8.08 (d, J=3.64 Hz, 1H), 8.33 (d, J=1.76 Hz, 1H), 9.06 (s, 1H), 9.44 (s, 1H); LCMS: m/e 451 (M+1).

Example 228

Preparation of 4-(4-(4-(3-acrylamidophenylamino)-5-fluoropyrimidin-2-ylamino)phenoxy)-N-methylpicolinamide I-342

I-342

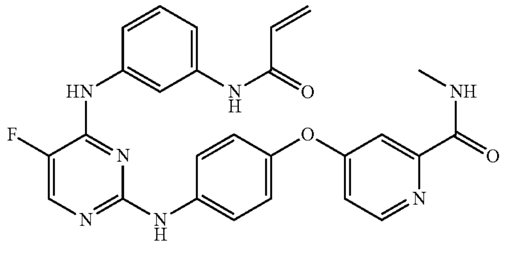

The title compound was prepared according to the schemes, steps and intermediates described in Example 20, by using 4-(4-aminophenoxy)-N-methylpicolinamide in place of 4 in step 2. LC/MS (M+H) 500.2

Example 229

Preparation of (R)-1-(3-(3-fluoro-4-(2-methoxyethoxy)phenylamino)pyrimidin-4-ylamino)piperidin-1-yl)prop-2-en-1-one I-344

I-344

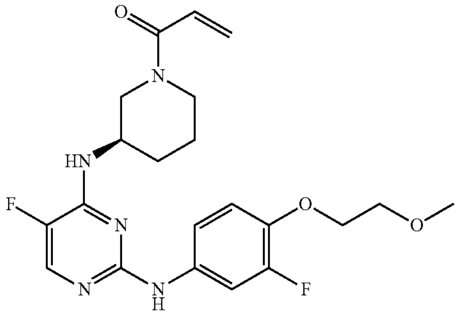

The title compound was prepared according to the schemes, steps and intermediates described in Example 20, by using (R)-1-tert-butoxycarbonyl-3-aminopiperidine in place of 2 in step 1 and 3-fluoro-4-(2-methoxyethoxy)aniline in place of 4 in step 2. LC/MS (M+H) 434.1.

Example 230

Preparation of (R)-1-(3-(4-(2-methoxyethoxy)phenylamino)pyrimidin-4-ylamino)piperidin-1-yl)prop-2-en-1-one I-345

I-345

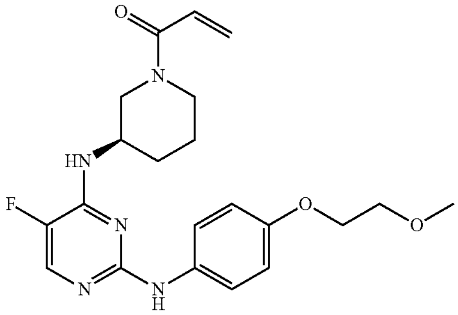

The title compound was prepared according to the schemes, steps and intermediates described in Example 20, by using (R)-1-tert-butoxycarbonyl-3-aminopiperidine in place of 2 in step 1 and 4-(2-methoxyethoxy)aniline in place of 4 in step 2. LC/MS (M+H) 416.2

Example 231

Preparation of 4-(4-(4-(3-acrylamidophenylamino)-5-fluoropyrimidin-2-ylamino)phenoxy)pyridine I-346

I-346

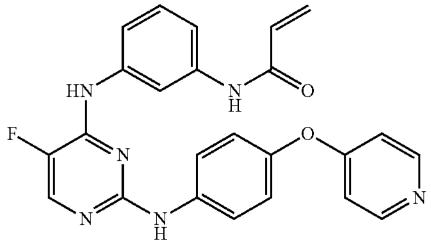

The title compound was prepared according to the schemes, steps and intermediates described in Example 20, by using 4-(4-aminophenoxy)pyridine in place of 4 in step 2. LC/MS (RT=2.802/(M+H)) 500.2

Example 232

Preparation of 1-((R)-3-(5-fluoro-2-(4-((S)-tetrahydrofuran-3-yloxy)phenylamino)pyrimidin-4-ylamino)piperidin-1-yl)prop-2-en-1-one I-347

I-347

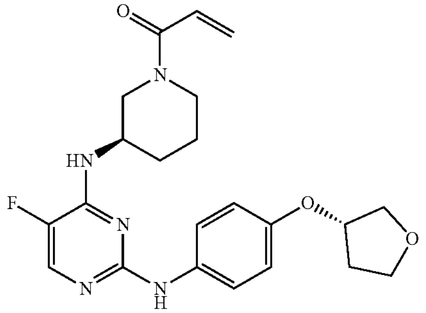

The title compound was prepared according to the schemes, steps and intermediates described in Example 20, by using (R)-1-tert-butoxycarbonyl-3-aminopiperidine in place of 2 in step 1 and 4-(S)-(tetrahydrofuran-3-yloxy) aniline in place of 4 in step 2. LC/MS (M+H) 428.3.

Example 233

Preparation of 1-((R)-3-(5-fluoro-2-(4-((R)-tetrahydrofuran-3-yloxy)phenylamino)pyrimidin-4-ylamino)piperidin-1-yl)prop-2-en-1-one I-348

I-348

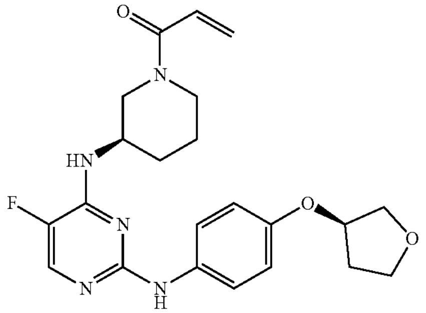

The title compound was prepared according to the schemes, steps and intermediates described in Example 20, by using (R)-1-tert-butoxycarbonyl-3-aminopiperidine in place of 2 in step 1 and 4-(R)-(tetrahydrofuran-3-yloxy) aniline in place of 4 in step 2. LC/MS (M+H) 428.3.

Example 234

Preparation of N-(3-(2-(2,3-dihydrobenzo[b]1,4] dioxin-6-ylamino)-5-fluoropyrimidin-4-ylamino) phenyl)acrylamide I-349

I-349

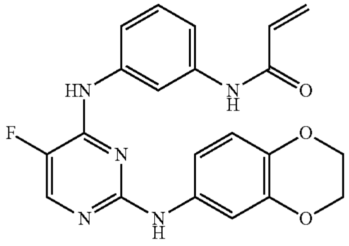

The title compound was prepared according to the schemes, steps and intermediates described in Example 20, by using 6-amino-2,3-dihydrobenzo[b]1,4]dioxane in place of 4 in step 2. LC/MS (M+H) 408.

Example 235

Preparation of 1-(6-(4-(3-chloro-4-(pyridine-2-yl-methoxy)phenylamino)-5-fluoropyrimidin-2-ylamino)-2H-benzo[b][1,4]oxazin-4(3H)-yl)prop-2-en-1-one I-343

I-343

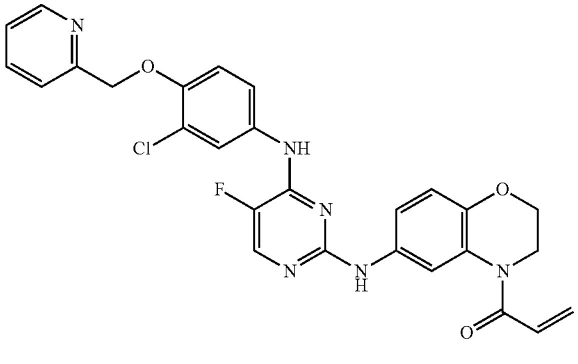

The title compound was prepared according to the schemes, steps and intermediates described in Example 35, using 3-chloro-4-(pyridine-2-ylmethoxy)aniline in place of 2 in step 1. LC/MS (M+H) 533.1.

Example 236

Preparation of N-(3-(5-cyano-2-(3-fluoro-4-(2-methoxyethoxy)phenylamino)pyrimidin-4-ylamino) phenyl)acrylamide I-350

I-350

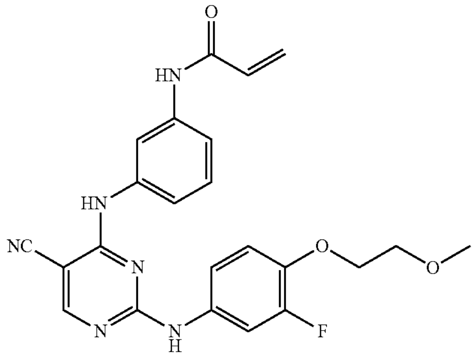

The title compound was prepared according to the schemes, steps and intermediates described in Example 94, by using 3-fluoro-4-(2-methoxyethoxy)aniline for 4 in step 2. LC/MS (M+H) 449.1

Example 237

Preparation of N-(3-(5-trifluoromethyl-2-(3-fluoro-4-(2-methoxyethoxy)phenylamino)pyrimidin-4-ylamino)phenyl)acrylamide I-352

I-352

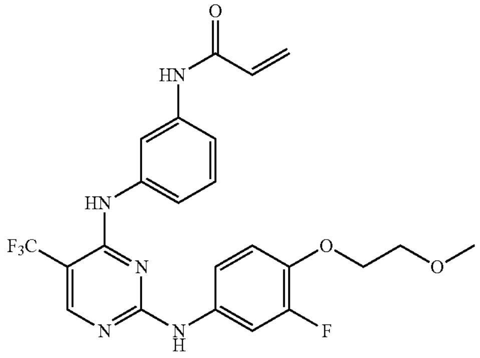

The title compound was prepared according to the schemes, steps and intermediates described in Example 189 using 3-fluoro-4-(2-methoxyethoxy)aniline for 2 in step 1. LC/MS (M+H) 492.1

Example 238

Preparation of N-(3-(2-(4-chloro-3-(2-methoxy-ethoxy)phenylamino)-5-fluoropyrimidin-4-ylamino) phenyl)acrylamide I-321

I-321

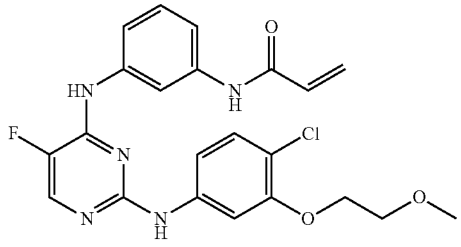

The title compound was prepared according to the schemes, steps and intermediates described in Example 20, by using 4-chloro-3-(2-methoxyethoxy)aniline in place of 4 in step 2. $^1$H NMR (DMSO-$d_6$) δ ppm: 3.30 (s, 3H), 3.60 (t, J=4.56 Hz, 2H), 3.88 (t, J=3.48 Hz, 2H), 5.74 (dd, J=4.36 & 10.0 Hz, 1H), 6.24 (dd, J=1.8 & 16.88 Hz, 1H), 6.44 (dd, J=4.36 & 10.0 Hz, 1H), 7.13 (d, J=8.72 Hz, 1H), 7.28 (t, J=8.04 Hz, 1H), 7.33 (dd, J=2.16 & 8.8 Hz, 1H), 7.41 (d, J=7.96 Hz, 1H), 7.47-7.49 (m, 2H), 7.84 (s, 1H), 8.13 (d, J=3.6 Hz, 1H), 9.27 (s, 1H), 9.47 (s, 1H), 10.12 (s, 1H); LCMS: m/e 458.0 (M+1).

Example 239

Preparation of N-(3-(5-fluoro-2-(6-(2-hydroxy-2-methylpropoxy)pyridin-3-ylamino)pyrimidin-4-ylamino)phenyl)acrylamide I-313

I-313

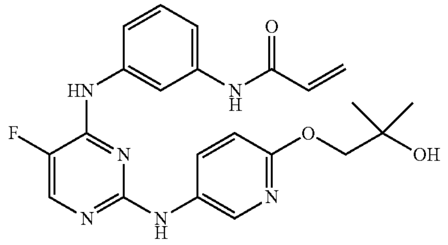

The title compound was prepared according to the schemes, steps and intermediates described in Example 20, by using 3-amino-6-(2-hydroxy-2-methylpropoxy)pyridine in place of 4 in step 2. $^1$H NMR (DMSO-$d_6$) δ ppm: 1.16 (s, 6H), 3.93 (s, 2H), 4.57 (s, 1H), 5.74 (dd, J=1.68 & 10.04 Hz, 1H), 6.24 (dd, J=1.84 & 16.92 Hz, 1H), 6.45 (dd, J=10.04 & 16.88 Hz, 1H), 6.65 (d, J=8.88 Hz, 1H), 7.26 (t, J=8.04 Hz, 1H), 7.39 (d, J=8 Hz, 1H), 7.48 (d, J=7.8 Hz, 1H), 7.91 (s, 1H), 7.99 (dd, J=2.72 & 8.92 Hz, 1H), 8.07 (d, J=3.68 Hz, 1H), 8.27 (d, J=2.52 Hz, 1H), 9.06 (s, 1H), 9.41 (s, 1H), 10.1 (s, 1H); LCMS: m/e 439.0 (M+1).

Example 240

Preparation of N-(3-(5-fluoro-2-(3-fluoro-4-(3-(methylsulfonyl)propoxy)phenylamino)pyrimidin-4-ylamino)phenyl)acrylamide I-318

I-318

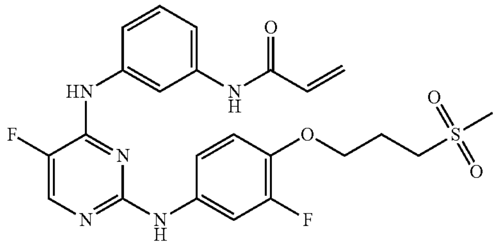

The title compound was prepared according to the schemes, steps and intermediates described in Example 20, by using 3-fluoro-4-(3-(methylsulfonyl)propoxy)aniline in place of 4 in step 2. $^1$H NMR (DMSO-$d_6$) δ ppm: 2.05-2.15 (m, 2H), 3.01 (s, 3H), 3.24 (t, J=7.56 Hz, 2H), 4.05 (t, J=6.12 Hz, 2H), 5.74 (dd, J=1.84 & 9.72 Hz, 1H), 6.24 (dd, J=1.72 & 16.96 Hz, 1H), 6.44 (dd, J=10 & 16.84 Hz, 1H), 6.96 (t, J=9.36 Hz, 1H), 7.28 (t, J=8.04 Hz, 2H), 7.40 (d, J=7.8 Hz, 1H), 7.48 (d, J=8.32 Hz, 1H), 7.69 (dd, J=2.2 & 14.4 Hz, 1H), 7.91 (s, 1H), 8.10 (d, J=3.64 Hz, 1H), 9.20 (s, 1H), 9.44 (s, 1H), 10.12 (s, 1H); LCMS: m/e 504.2 (M+1).

Example 241

Preparation of 1-(3-(5-fluoro-2-(3-fluoro-4-(2-methoxyethoxy)phenylamino)pyrimidin-4-ylamino) phenyl)-4-methylpent-3-en-2-one I-330

I-330

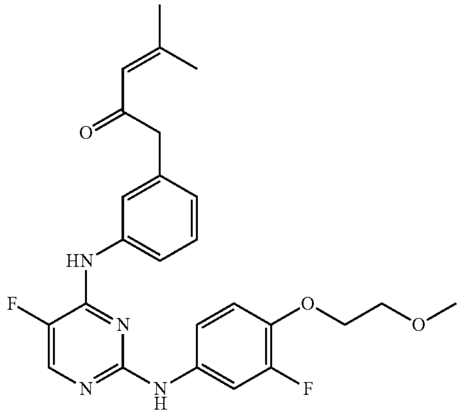

The title compound was prepared according to the schemes, steps and intermediates described in Example 112, by using ethyl 4-aminomethylbenzoate in place of 2 in step 1 and 3-fluoro-4-(2-methoxyethoxy)aniline in place of 4 in step 2. $^1$H NMR (DMSO-$d_6$) δ ppm: 1.83 (s, 3H), 2.05 (s, 3H), 3.31 (s, 3H), 3.64 (t, J=4.56 Hz, 2H), 3.69 (s, 2H), 4.08 (t, J=4.4 Hz, 2H), 6.18 (s, 1H), 6.92 (d, J=7.44 Hz, 1H), 7.01 (t, J=9.36 Hz, 1H), 7.27 (t, J=7.84 Hz, 2H), 7.51 (s, 1H), 7.64-7.71 (m, 2H), 8.09 (d, J=3.64 Hz, 1H), 9.19 (s, 1H), 9.34 (s, 1H); LCMS: m/e 469.1 (M+1).

Example 242

Preparation of N-(3-(2-(4-chloro-3-(2,3-dihydroxy-propoxy)phenylamino)-5-fluoropyrimidin-4-ylamino)phenyl)acrylamide I-353

I-353

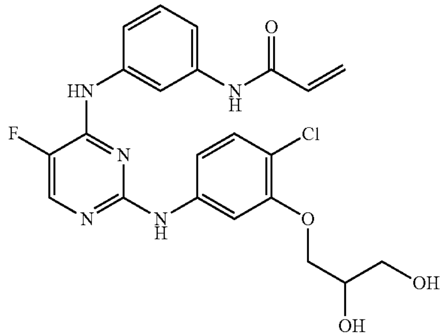

The title compound was prepared according to the schemes, steps and intermediates described below.

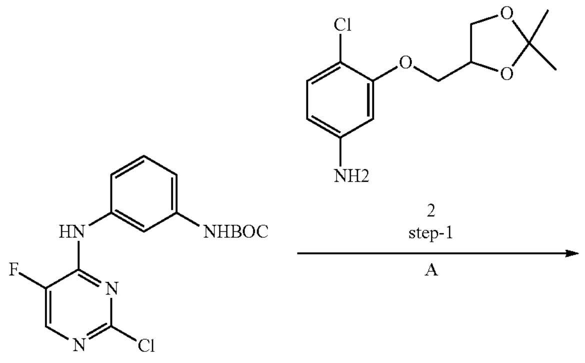

2

1

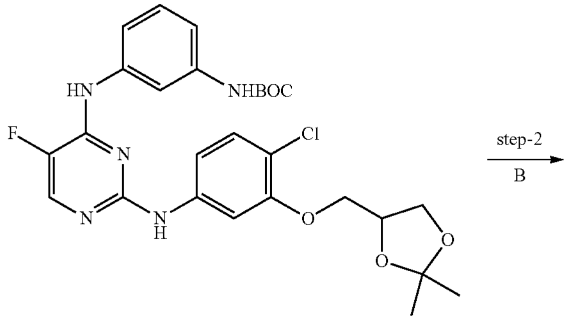

3

-continued

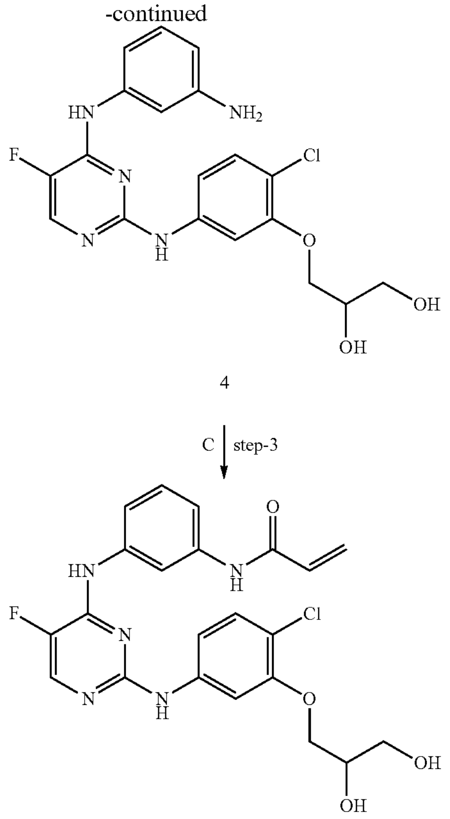

4

I-353

1) $Pd(OAc)_2$, BINAP, $Cs_2CO_3$, toluene, 110° C. 16 h; B) TFA, $CH_2Cl_2$, rt, 2 h; C) acryloyl chloride, $K_2CO_3$, NMP, rt, 45 min.

Step-1

3

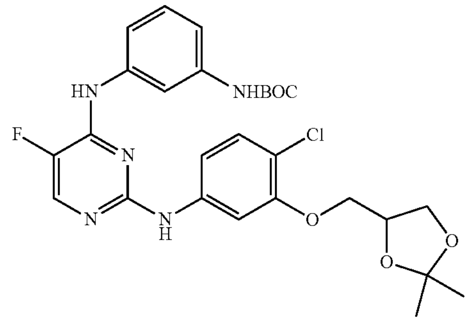

A solution of 2 (200 mg, 0.77 mmol), 1 (262 mg, 0.77 mmol), $Pd(OAc)_2$ (17.3 mg, 0.07 mmol), BINAP (24 mg, 0.038 mmol) and $Cs_2CO_3$ (630 mg, 1.9 mmol) in degassed toluene (toluene was purged with $N_2$ for 30 min) was heated for 16 h at 100° C. under $N_2$ atmosphere. The reaction mixture was cooled, diluted with EtOAc (15 mL) and filtered through Celite®. The filtrate was washed with water (5 mL) and brine (3 mL), dried over $Na_2SO_4$, filtered, and concentrated under reduced pressure to give 3 (0.3 g, 69%) as a yellow solid.

Step-2

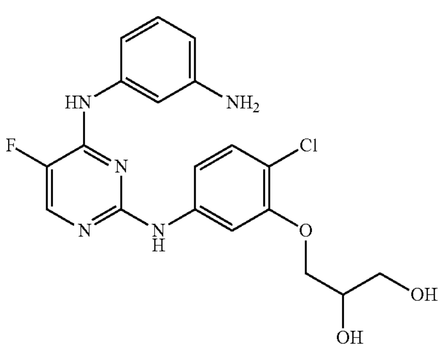

To a stirred solution of 3 (300 mg, 0.5 mmol) in dry $CH_2Cl_2$ (6 mL) at 0° C. was added $CF_3COOH$ (3 mL), and the reaction mixture was kept at this temperature for 30 min. The reaction was allowed to come to rt and stirred at this temperature for 3 h. The reaction mixture was concentrated under reduced pressure, and the residue was quenched with water (5 mL), basified with $NaCO_3$ solution, and extracted with ethyl acetate (2×10 mL). The combined extracts were washed with water (5 mL) and brine (5 mL), dried over $Na_2SO_4$, and concentrated under reduced pressure to get 4 (200 mg, 88%) as a yellow solid.

Step-3

I-353

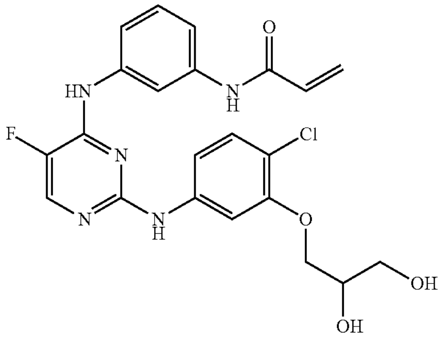

To a stirred solution of 4 (240 mg, 0.5 mmol), in NMP (1.5 mL) at 0° C. was added potassium carbonate (780 mg, 5.7 mmol) and acryloyl chloride (57 mg, 0.5 mmol), and the reaction mixture was stirred at 0° C. for 3 h. The reaction mixture was further stirred at rt for 30 min and quenched by dropwise addition to a cold, stirring solution of 10% $NaHCO_3$ and stirred at 0° C. for 30 min. A solid precipitated out and was isolated by filtration through a Buchner funnel. The solid was washed with cold water, dissolved in EtOAc (20 mL) and was basified by using triethylamine and washed with water (2 mL), brine (1 mL), dried over $Na_2SO_4$ and concentrated under reduced pressure. The residue was purified by preparative HPLC to give the title compound (45 mg, 15.5%) as a white solid. $^1$H NMR (DMSO-d6) δ ppm: 3.43-3.50 (m, 2H), 3.78-3.85 (m, 2H), 3.89-3.92 (m, 1H), 4.65 (t, J=5.6 Hz, 1H), 4.93 (d, J=4.8 Hz, 1H), 5.76 (dd, J=1.92 & 10.04 Hz, 1H), 6.26 (dd, J=1.92 & 16.92 Hz, 1H), 6.46 (dd, J=10.08 & 16.92 Hz, 1H), 7.14 (d, J=8.72 Hz, 1H), 7.30 (t, J=8.08 Hz, 1H), 7.39-7.43 (m, 2H), 7.46 (dd, J=2.2 & 8.72 Hz, 1H), 7.56 (d, J=8.04 Hz, 1H), 7.94 (s, 1H), 8.14 (d, J=3.6 Hz, 1H), 9.24 (s, 1H), 9.48 (s, 1H), 10.13 (s, 1H); LCMS: m/e 473.8 (M+).

Synthesis of Intermediate 2

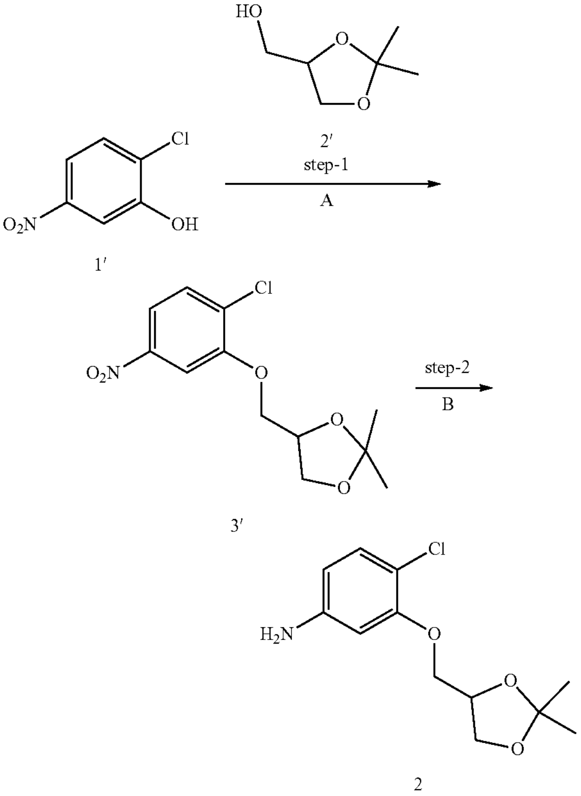

A) DIAD, $PPh_3$, $Et_3N$, dry THF, rt, 1 h; B) $H_2$, Ra Ni, methanol, 2 h.

Step-1

3'

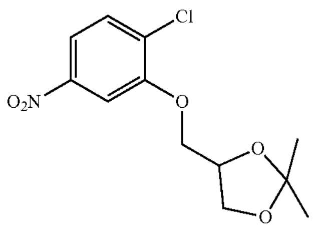

To a stirred solution of 2' (0.640 g, 3.7 mmol) in THF (20 mL) were added 1' (0.5 g, 3.7 mmol), $PPh_3$ (1.09 g, 4.1 mmol) and $Et_3N$ (0.73 g, 5.6 mmol) under $N_2$ atmosphere. The reaction mixture was cooled to 0° C. and DIAD (0.84 g, 4.1 mmol) was added. The reaction mixture was allowed to come to rt and stir for 1 h. The reaction was quenched with water, extracted with ethyl acetate (3×10 mL), and the combined extracts were washed with water and brine solution (5 mL each). The residue obtained after concentration under reduced pressure was purified by column chromatography ($SiO_2$, 60-120, pet ether/ethyl acetate, 9/1) to give 3' (0.6 g, 60%) as a white solid.

Step-2

2

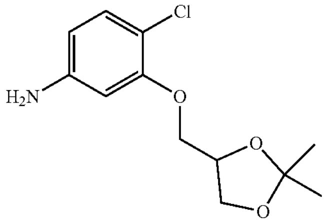

To a solution of 3' (0.3 g, 1.04 mmol) in methanol was added Raney Ni (60 mg, 20% w/w) under $N_2$, and the reaction mixture was kept under $H_2$ atmosphere (bladder pressure) for 16 h. The reaction mixture was filtered through a bed of Celite®, and the filtrate was concentrated under reduced pressure. The residue was diluted with 1.5 N HCl (2 mL) and washed with ethyl acetate (5 mL) to remove organic impurities. The aqueous layer was basified with $NaHCO_3$ solution (5 mL), extracted with ethyl acetate, washed with water (2 mL) and brine (2 mL), and dried over anhydrous $Na_2SO_4$. Filtration followed by concentration under reduced pressure gave 2 (0.2 g, 76.9%) as a brown liquid.

Example 243

Preparation of (S)—N-(3-(2-(4-chloro-3-(tetrahydrofuran-3-yloxy)phenylamino)-5-fluoropyrimidin-4-ylamino)phenyl)acrylamide I-354

I-354

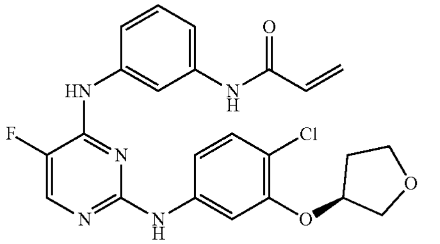

The title compound was prepared according to the schemes, steps and intermediates described in Example 20, by using (S)-4-chloro-3-(tetrahydrofuran-3-yloxy)aniline in place of 4 in step 2. LCMS: m/e 469.8 (M+1).

Example 244

Preparation of (N-(3-(5-fluoro-2-(3-fluoro-4-(((2S, 4R)-4-hydroxypyrrolidin-2-yl)methoxy)phenylamino)pyrimidin-4-ylamino)phenyl)acrylamide I-355

I-355

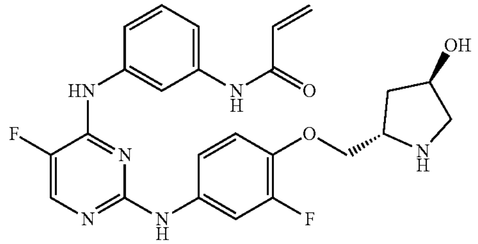

The title compound was prepared according to the schemes, steps and intermediates described below.

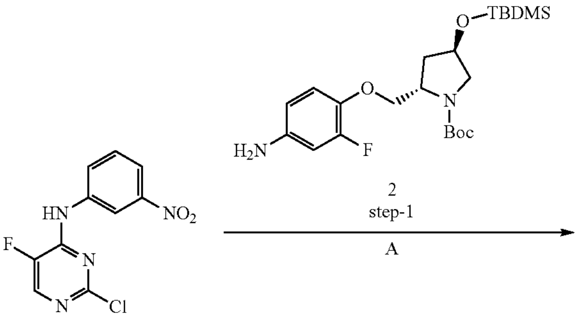

2

1

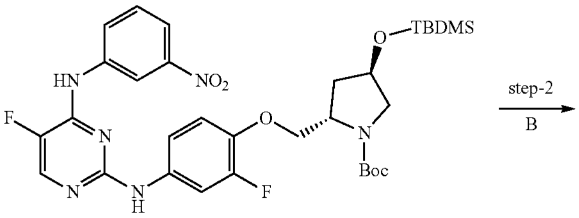

3

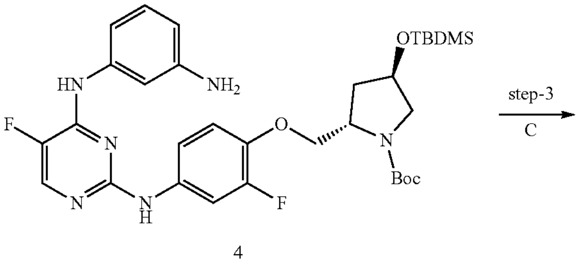

4

-continued

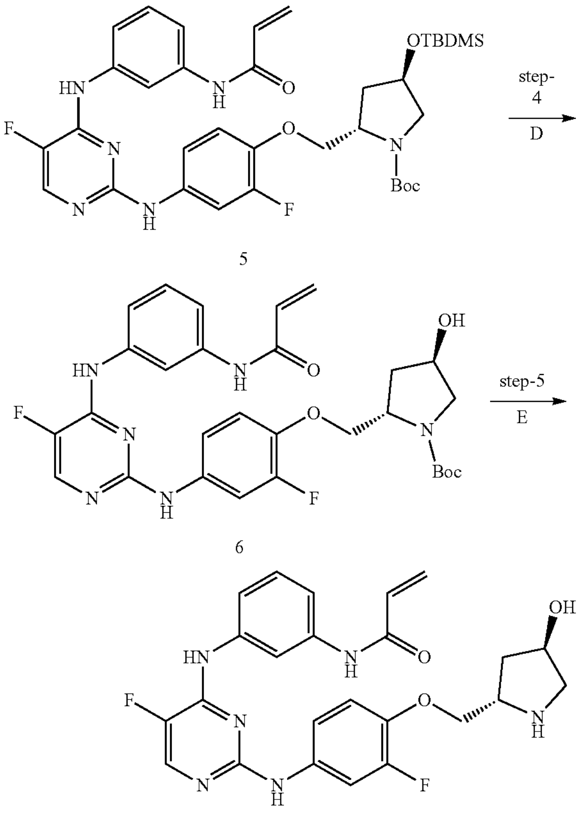

5

6

I-355

1) $Pd(OAc)_2$, BINAP, $Cs_2CO_3$, toluene, 110° C., 6 h; B) TFA, $CH_2Cl_2$, rt, 1 h; C) $(Boc)_2O$, 30 min then acryloyl chloride, $K_2CO_3$, NMP, 0° C., 90 min; D) HF (49% aq. Solution), $CH_3CN$, rt 2 h; E) TFA, DCM, rt, 2 h.

Step-1

3

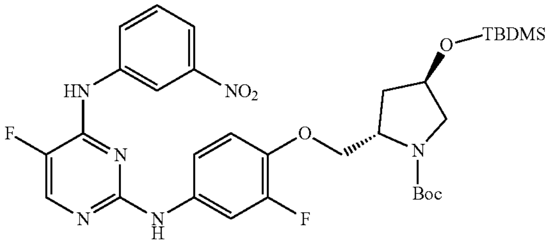

A solution of 2 (0.50 g, 1.13 mmol), 1 (0.30 g, 1.13 mmol), $Pd(OAc)_2$ (0.0025 g, 0.1 mmol), BINAP (0.0035 g, 0.05 mmol) and $Cs_2CO_3$ (0.92 g, 2.8 mmol) in degassed toluene (toluene was purged with $N_2$ for 30 min) was heated at 110° C. for 16 h under $N_2$ atmosphere. The reaction mixture was cooled, diluted with EtOAc (20 mL), washed with water (10 mL), brine (10 mL) and dried over $Na_2SO_4$. Filtration followed by concentration under reduced pressure offered a residue which was further washed with hexane to give 3 (0.3 g, 42.8%) as a yellow solid.

Step-2

4

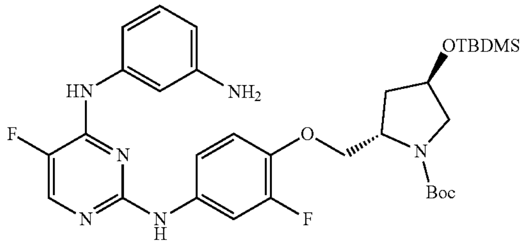

To solution of 3 (0.3 g, 0.44 mmol) in methanol (5 mL)) was added Pd/C (0.030 g, 10% w/w) and the reaction mixture was allowed to stir under $H_2$ atmosphere (balloon) at rt for 16 h. The reaction mixture was filtered through a pad of Celite® and was concentrated under reduced pressure to give 4 (0.19 g, 67.6%) as a yellow solid.

Step-3

5

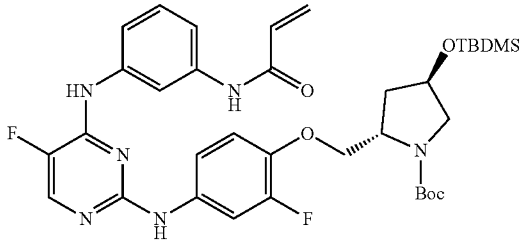

To a stirred solution of 4 (0.1 g, 0.15 mmol) in NMP (1.0 mL) at rt was added Boc anhydride (0.046 g, 0.212 mmol) and the reaction mixture was stirred at rt for 60 min. It was then cooled to 0° C. and to it was added $K_2CO_3$ (0.107 g, 0.77 mmol), acryloyl chloride (0.016 g, 0.18 mmol) and the reaction mixture was stirred at 0° C. for 90 min. The reaction mixture was added drop wise, to a cold, stirring solution of 10% $NaHCO_3$. After the addition was over, the solution was stirred for another 30 min at 0° C., and the solid was isolated by filtration through a Buchner funnel. The solid was washed with cold water, hexane and was dissolved in methanol:dichloromethane (50:50, 10 mL) and concentrated under reduced pressure. The residue obtained was suspended in cold water (5 mL), $Et_3N$ was added to it and it was extracted with ethyl acetate (2×10 mL). The combined ethyl acetate extract was washed with water (5 mL), brine (5 mL), dried over $Na_2SO_4$ and concentrated under reduced pressure. The residue was further purified by column chromatography ($SiO_2$, methanol/chloroform: 4/96) to give 5 (0.075 g, 71.4%) as yellow solid.

Step-4

6

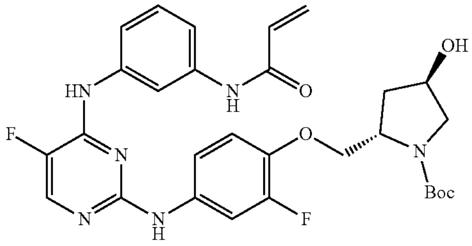

To a solution of 5 (15 mg, 0.02 mmol) in acetonitrile was added HF (49% aq. Solution, 0.0048 mL, 0.024 mmol) at 0° C. The reaction mixture stirred at rt for 2 h, was extracted with ethyl acetate (2 mL), was washed with water (1 mL), and was dried over $Na_2SO_4$ and filtered. The filtrate was concentrated under reduced pressure. The residue showed 60% purity by LCMS and was used in the next step without further purification.

Step-5

I-355

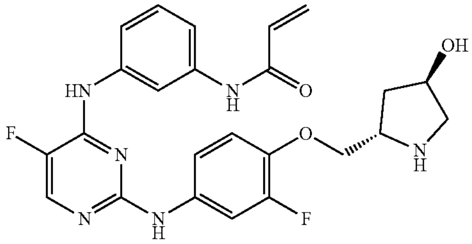

To a stirred solution of 6 (0.008 g, 0.013 mmol) in $CH_2Cl_2$ (0.024 mL) was added TFA (0.016 mL) at 0° C. The reaction mixture was allowed to come to rt and was stirred for additional 2 h. It was then concentrated and was stirred with cold 10% $NaHCO_3$ (1.0 mL). It was extracted with EtOAc (2×2 mL) and the combined EtOAc extract was washed with brine (1 mL), was dried over $Na_2SO_4$ and was concentrated under reduced pressure. The crude residue was further purified by column chromatography ($SiO_2$, methanol/chloroform: 2/98) and was then purified by preparative TLC to give the title compound (2 mg, 81% purity by HPLC, and 79% purity by LCMS) as a white solid. LCMS: m/e 483 (M+).

Compound 2 was prepared according to the schemes, steps and intermediates described below.

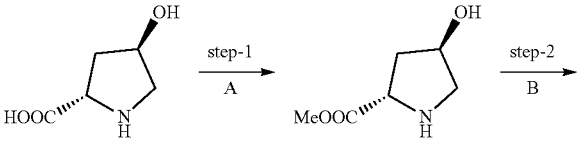

1′ 2′

-continued

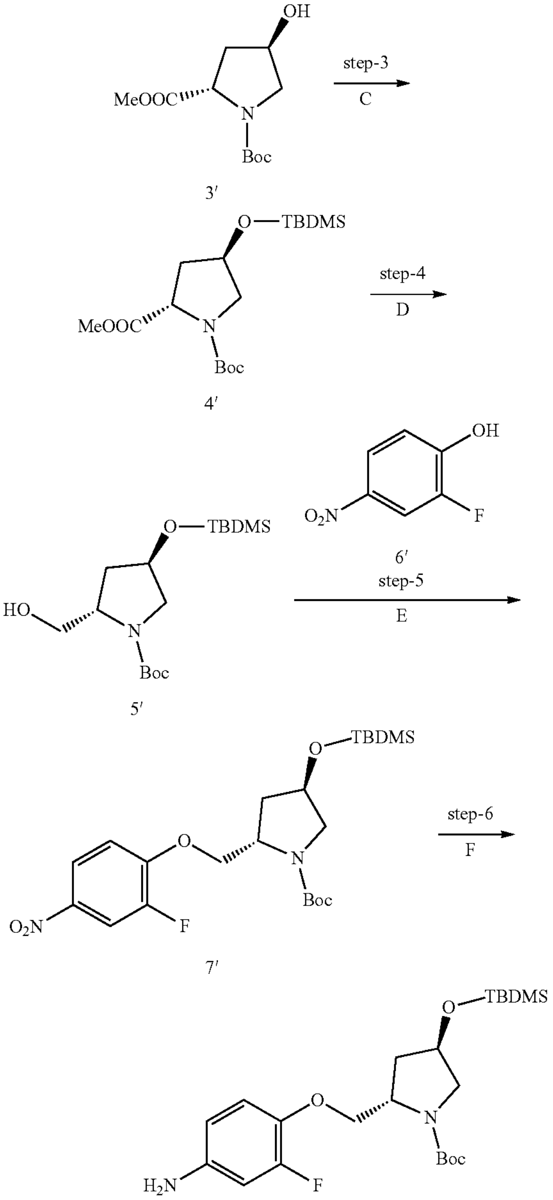

3′ 4′ 6′ 5′ 7′ 2

A) MeOH, $SOCl_2$, reflux, 5 h; B) $(Boc)_2O$, $Et_3N$, $CH_2Cl_2$, rt, 5 h; C) TBDMS—Cl, imidazole, DMF, rt, 16 h; D) LAH solution (1M in THF), -20° C., 20 min; E) DIAD, $PPh_3$, $Et_3N$, THF, 16 h; F) $H_2$, Pd/C, methanol, rt, 16 h.

Step-1

2′

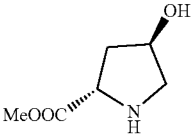

To a stirred solution of 1' (2 g, 15.26 mmol) was added a solution prepared by adding thionyl chloride (2 mL) to methanol (20 mL). The reaction mixture was heated at reflux for 5 h. After completion of the reaction, methanol was removed under reduced pressure to give 2' as colorless salt (3.0 g) it was used as such in the next reaction.

Step-2

3'

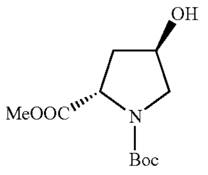

To a stirred solution of 2' (3.0 g, 12.24 mmol) in DCM (30 mL) was added $Et_3N$ (1.85 g, 18.31 mmol) and Boc anhydride (2.92 g, 13.46 mmol). Stirring was continued at rt for 5 h after which the reaction was quenched with water. The organic layer was separated, dried and concentrated under reduced pressure. The residue was purified by column chromatography ($SiO_2$, 60-120, 100% ethyl acetate) to give 3' (3.2 g, 64%) as a white solid.

Step-3

4'

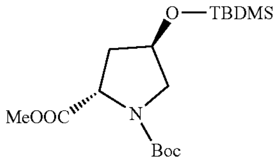

To a stirred solution of 3' (3 g, 12.24 mmol) in DMF (30 mL) was added imidazole (1.2 g, 18.36 mmol) followed by TBDMS chloride (1.84 g, 12.24 g). Stirring was continued for 16 h. The reaction mixture was diluted with ethyl acetate (50 mL) and the ethyl acetate layer was separated. It was washed with water (5 mL), brine solution (5 mL) and dried over $Na_2SO_4$. Filtration followed by concentration under reduced pressure offered a residue which was purified by column chromatography ($SiO_2$, 60-120, petroleum ether/ethyl acetate:6/4) to give 4' (3.2 g, 80%) as a colorless liquid.

Step-4

5'

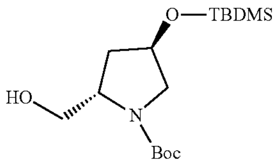

To a stirred solution of 4' (0.5 g, 1.39 mmol) in THF (5 mL) was added LAH (1.39 mL, 1M solution, 1.39 mmol) at −20° C. The reaction was continued at the same temperature for 15 min after which it was quenched with $Na_2SO_4$ solution. The reaction mass was filtered through Celite® and filtrate was concentrated under reduced pressure. The residue was diluted with ethyl acetate (10 mL), dried over anhydrous $Na_2SO_4$, filtered and concentrated under reduced under reduced pressure to give 5' (0.3 g, 65%) as a colorless liquid.

Step-5

7'

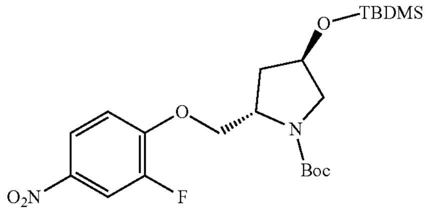

To a stirred solution of 5' (0.1 g, 0.3 mmol) in THF (6 mL) were added 6' (0.047 g, 0.3 mmol), $PPh_3$ (0.16 g, 0.64 mmol) and $Et_3N$ (0.048 g, 0.48 mmol) under $N_2$ atmosphere. The reaction mixture was cooled to 0° C. and to it was added DIAD (0.094 g, 0.48 mmol). The reaction mixture was allowed to come to rt and stirred at it for 1 h. It was quenched with water, was extracted with ethyl acetate (2×5 mL) and the combined ethyl acetate extract was washed with water and brine solution (5 mL each). The residue obtained after concentration under reduced pressure was purified by column chromatography ($SiO_2$, 60-120, pet ether/ethyl acetate, 9/1) to give 7' (0.120 g, 85%) as a yellow solid Step-6

2

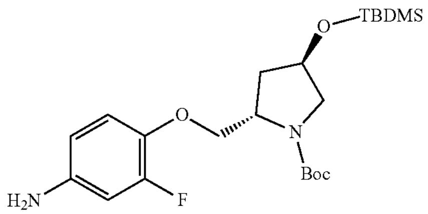

To a solution of 7' (0.1 g, 0.21 mmol) in methanol (5 mL)) was added Pd/C (0.010 g, 10% w/w) and the reaction mixture was allowed to stir under $H_2$ atmosphere (bladder) at rt for 16 h. The reaction mixture was filtered through a pad of Celite® and concentrated under reduced pressure to give 2 (0.085 g, 91%) as a brownish viscous oil. It was used in the next step without further purification.

Example 245

Preparation of tert-butyl 2-(2-(4-(4-(3-acrylamidophenylamino)-5-fluoropyrimidin-2-ylamino)-2-fluorophenoxy)ethoxy)ethylcarbamate I-356

I-356

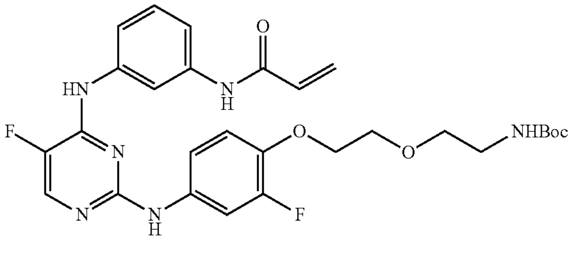

The title compound was prepared according to the schemes, steps and intermediates described below.

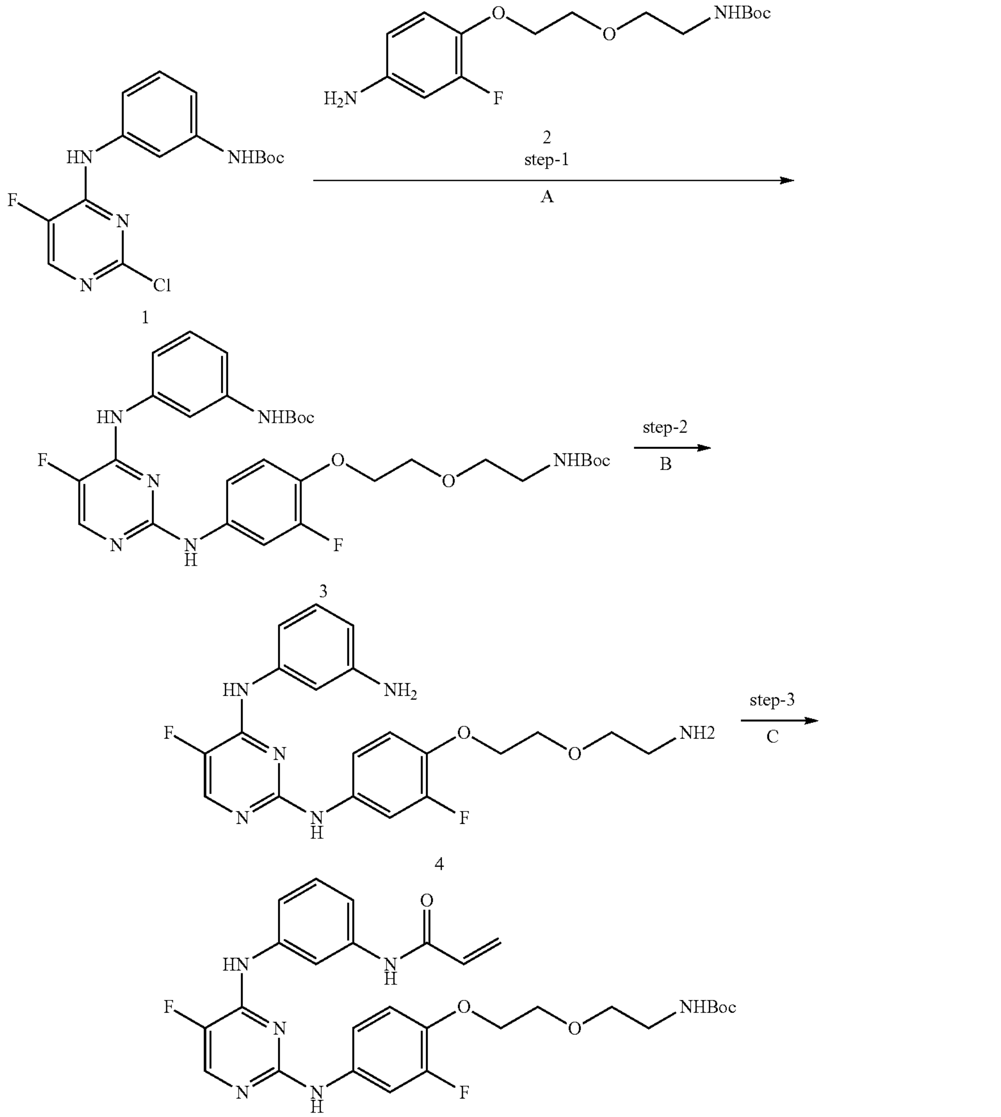

A) $Pd(OAc)_2$, BINAP, $Cs_2CO_3$, toluene, 110° C., 6 h; B) TFA, $CH_2Cl_2$, RT 1 h; C) $(Boc)_2O$, 30 min then acryloyl chloride, $K_2CO_3$, NMP, 0° C., 90 min.

Step-1

3

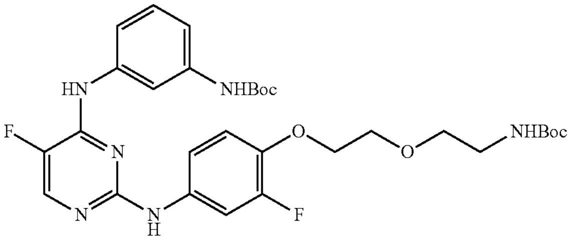

A solution of 2 (0.050 g, 0.159 mmol), 1 (0.053 g, 0.159 mmol), $Pd(OAc)_2$ (0.0035 g, 0.01590 mmol), BINAP (0.0049 g, 0.0079 mmol) and $Cs_2CO_3$ (0.129 g, 0.3975 mmol) in degassed toluene (toluene was purged with $N_2$ for 30 min) was heated at 110° C. for 16 h under $N_2$ atmosphere. The reaction mixture was cooled, diluted with EtOAc (20 mL), washed with water (10 mL), brine (10 mL) and dried over $Na_2SO_4$. Filtration followed by concentration under reduced pressure offered a residue which was further washed with hexane to give 3 (0.049 g, 50%) as a brown solid.

Step-2

4

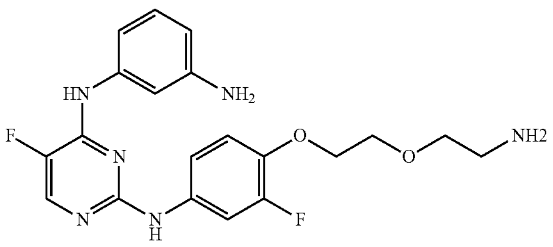

To a stirred solution of 3 (0.047 g, 0.0762 mmol) in dry $CH_2Cl_2$ (3 mL) at 0° C. was added $CF_3COOH$ (1.0 mL) and the reaction mixture was stirred at 0° C. for 30 min. The reaction was allowed to come to rt and stirred at it for 1 h. It was concentrated under reduced pressure and the residue was quenched with $NaHCO_3$ solution (3 mL). The contents were extracted with ethyl acetate (3×10 mL) and the combined EtOAc extract was washed with water (10 mL) followed by 10% citric acid solution (3×10 mL). The combined citric acid extract was basified with 10% NaOH solution and extracted with EtOAc (3×25 mL). The EtOAc extract was washed with water (20 mL), brine (10 mL) and dried over $Na_2SO_4$. to get 4 (0.028 g, 88%) as a light yellow solid.

Step-3

I-356

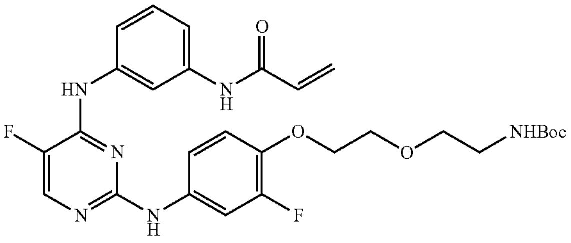

To a stirred solution of 4 (0.028 g, 0.06731 mmol) in NMP (1.0 mL) at rt was added $(Boc)_2O$ (0.016 g, 0.07404 mmol) and the reaction mixture was stirred at rt for 30 min. It was cooled to 0° C. and to it was added $K_2CO_3$ (0.051 g, 0.372 mmol) and acryloyl chloride (0.0067 g, 0.07404 mmol) and the reaction mixture was stirred at 0° C. for 30 min. The reaction mixture was added dropwise, to a cold, stirring solution of 10% $NaHCO_3$. After the addition was over, the solution was stirred for another 30 min at 0° C., and the solid was isolated by filtration through a Buchner funnel. The solid was washed with cold water, hexane and was dissolved in methanol:dichloromethane (50:50, 5 mL) and concentrated under reduced pressure. The residue obtained was suspended in cold water (3 mL), $Et_3N$ was added to it and it was extracted with ethyl acetate (2x5 mL). The combined ethyl acetate extract was washed with water (5 mL), brine (5 mL), dried over $Na_2SO_4$ and concentrated under reduced pressure to give the title compound (0.016 g, 42%) as a grey solid. $^1H$ NMR (DMSO-d6) δ ppm: 1.37 (s, 9H), 3.09 (d, J=5.5 Hz, 2H), 3.43 (d, J=5.84 Hz, 2H), 3.69 (s, 2H), 4.05 (s, 2H), 5.75 (d, J=11.12 Hz, 1H), 6.25 (d, J=16.76 Hz, 1H), 6.46 (dd, J=10.12 & 16.84 Hz, 1H), 6.81 (s, 1H), 6.96 (t, J=9.12 Hz, 1H), 7.24-7.31 (m, 2H), 7.43 (d, J=7.96 Hz, 1H), 7.49 (d, J=7.56 Hz, 1H), 7.68 (d, J=14 Hz, 1H), 7.94 (s, 1H), 8.11 (d, J=3.24 Hz, 1H), 9.21 (s, 1H), 9.46 (s, 1H), 10.15 (s, 1H); LCMS: m/e 571.1 (M+1).

The intermediate 2 was prepared according to the schemes, steps and intermediates described below.

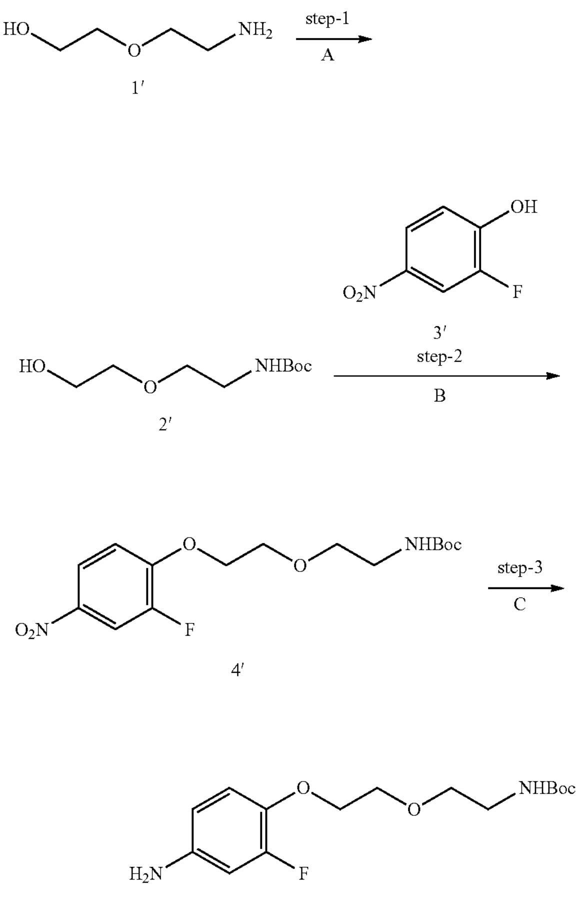

1'

3'

2'

4'

2

A) $(Boc)_2O$, aq. NaOH, rt, 16 h; B) DIAD, $PPh_3$, $Et_3N$, dry THF, rt, 1 h; C) $H_2$, Pd/C, ethanol, rt, 16 h.

Step-1

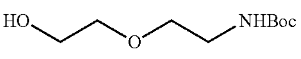

2'

To a solution of NaOH (0.76 g, 0.019 mmol) in water (9.6 mL) at rt was added 1' (2.0 g, 19.022 mmol) and the reaction was stirred for 30 min. A solution of Boc-anhydride (4.561 g, 20.92 mmol) in THF (12.0 mL) was added dropwise over 5 min to it. The reaction mixture was stirred at rt for 16 h. It was concentrated under reduced pressure, diluted with water (20 mL) and extracted with EtOAc (4×50 mL). The combined EtOAc extract was washed with water (50 mL), brine (50 mL), dried over $Na_2SO_4$ to give 2' (3.2 g, 82%) as a viscous oil.

Step-2

4'

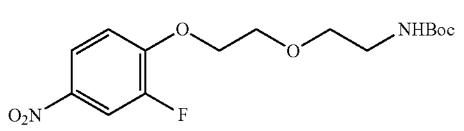

To a stirred solution of 2' (0.38 g, 1.851 mmol) in THF (6 mL) were added 3' (0.29 g, 1.851 mmol), $PPh_3$ (0.534 g, 2.0361 mmol) and $Et_3N$ (0.280 g, 2.776 mmol) under $N_2$ atmosphere. The reaction mixture was cooled to 0° C. and to it was added DIAD (0.411 g, 2.0361 mmol). The reaction mixture was allowed to come to rt and stirred at it for 1 h. It was quenched with water, extracted with ethyl acetate (3×5 mL) and the combined ethyl acetate extract was washed with water and brine solution (5 mL each). The residue obtained after concentration under reduced pressure was purified by column chromatography ($SiO_2$, 60-120, pet ether/ethyl acetate, 9/1) to give 4' (0.360 g, crude) as a yellow solid Step-3

2

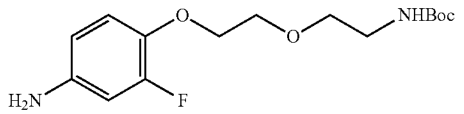

To a solution of 4' (0.360 g, 1.0456 mmol) in ethanol (10 mL)) was added Pd/C (0.072 g, 20% w/w) and the reaction mixture was allowed to stir under $H_2$ atmosphere (1.5 Kg hydrogen pressure) at rt for 16 h. The reaction mixture was filtered through a pad of Celite® and concentrated under reduced pressure to give 2 (0.28 g, 85%) as a brownish viscous oil. It was used in the next step without further purification.

Example 246

Preparation of N[1]-(2-(2-(4-(4-(3-acrylamidophenylamino)-5-fluoropyrimidin-2-ylamino)-2-fluorophenoxy)ethoxy)ethyl)-N[5]-(15-oxo-18-((3aR,4R,6aS)-2-oxohexahydro-1H-thieno[3,4-d]imidazol-4-yl)-4,7,10-trioxa-14-azaoctadecyl)glutaramide I-362

The title compound was prepared according to the schemes, steps and intermediates described in Example 204, by using tert-butyl 2-(2-(4-(4-(3-acrylamidophenylamino)-5-fluoropyrimidin-2-ylamino)-2-fluorophenoxy)ethoxy)ethylcarbamate (I-356, described in Example 245) in place of I-45 in step 1. $^1H$ NMR (DMSO-$d_6$) δ ppm: 10.1 (s, 1H), 9.87 (s, 1H), 9.52 (s, 1H), 8.09 (d, J=4.1 Hz, 1H), 7.86 (s, 1H), 7.78 (t, J=5.5 Hz, 1H), 7.66 (m, 3H), 7.48 (dd, J=2.3 & 13.8 Hz, 1H), 7.33 (m, 2H), 7.21 (t, J=7.8 Hz, 1H), 7.11 (d, J=9.2 Hz, 1H), 6.90 (t, J=9.2 Hz, 1H), 6.34 (m, 2H), 6.14 (dd, J=2.3 & 17.0 Hz, 1H), 5.66 (dd, J=2.3 & 17.0 Hz, 1H), 4.20 (dd, J=5.0 & 7.3 Hz, 1H), 3.99 (m, 3H), 3.61 (m, 2H), 3.12 (q, J=6.0 Hz, 2H), 2.97 (m, 9H), 2.72 (m, 2H), 2.46 (m, 2H), 1.95 (m, 9H), 1.1-1.6 (m, 18H); LCMS: m/e 1013. (M+1).

Example 247

Preparation of N-(3-(5-fluoro-2-(3-fluoro-4-(2-(2-methoxyethoxy)ethoxy)-phenylamino)pyrimidin-4-ylamino)phenyl)acrylamide I-359

I-359

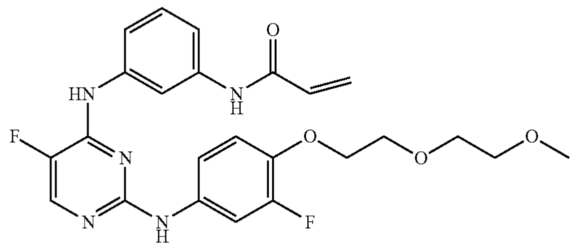

The title compound was prepared according to the schemes, steps and intermediates described below.

I-362

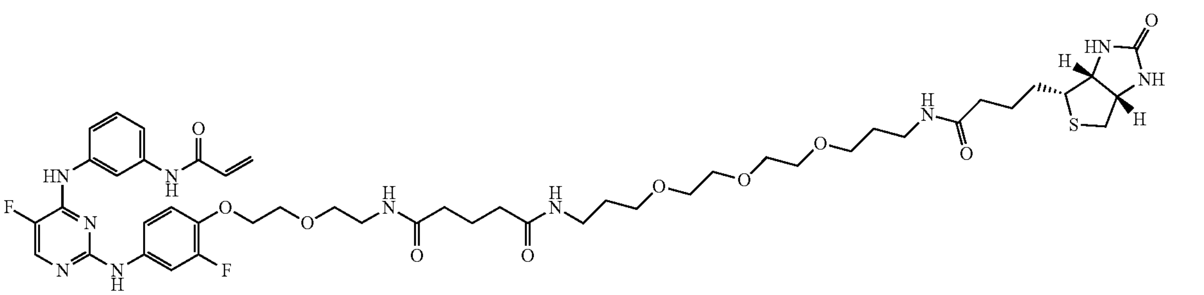

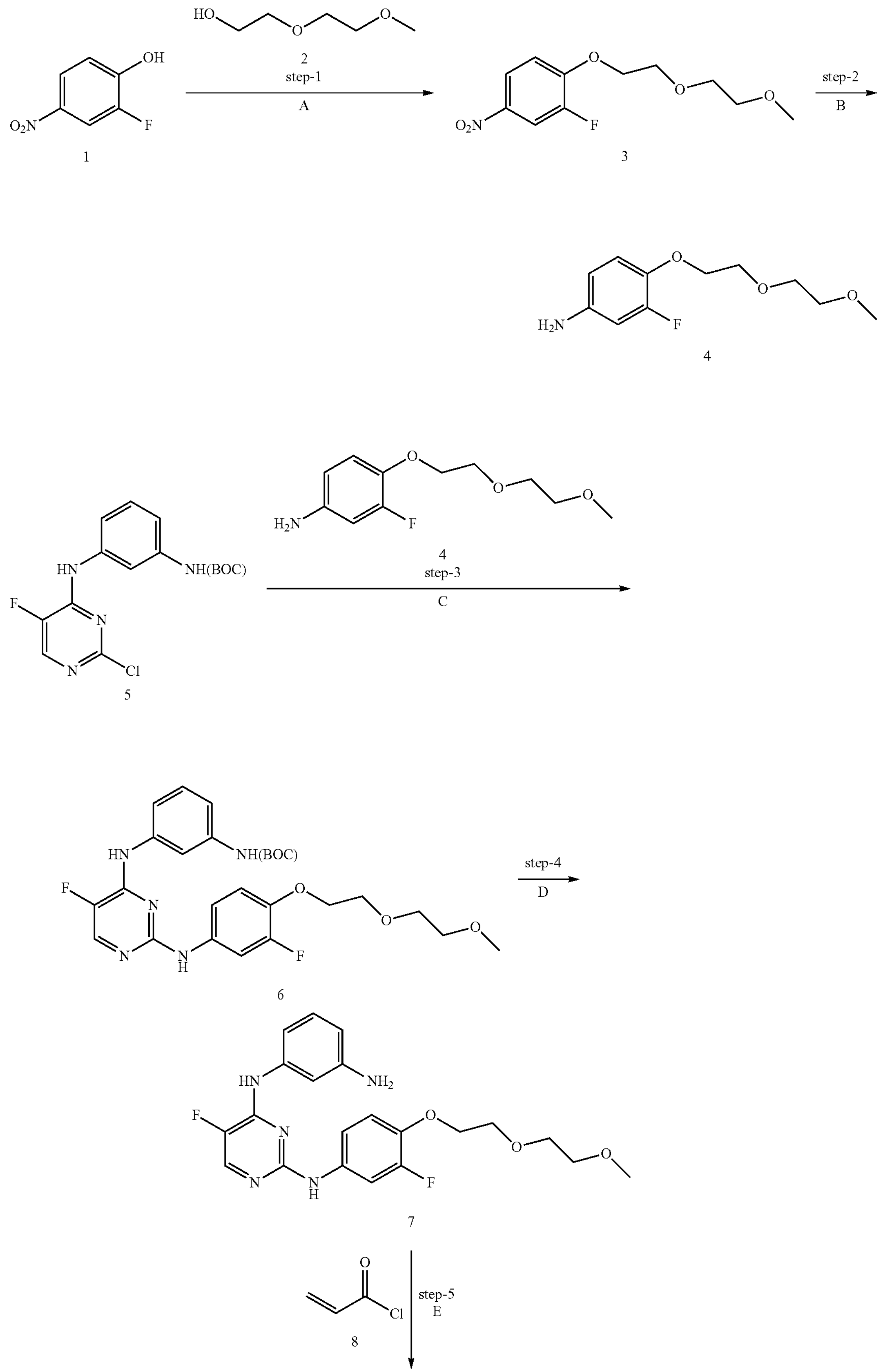
1 2 3 4 5 4 6 7 8

-continued

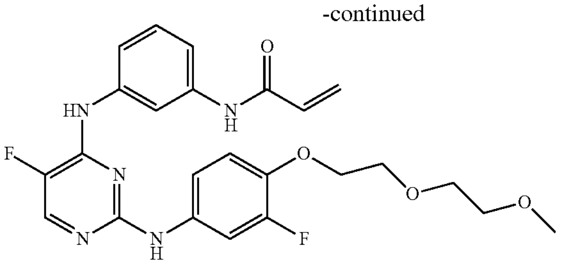

I-359

A) DIAD, $PPh_3$, $Et_3N$, dry THF, rt, 1 h; B) $H_2$, Pd/C, methanol, rt, 16 h; C) $Pd(OAc)_2$, BINAP, $Cs_2CO_3$, toluene, 110° C., 6 h; D) TFA, $CH_2Cl_2$, rt, 1 h; E) $(BOC)_2O$, 30 min, then $K_2CO_3$ NMP, 0° C., 15 min.

Step-1

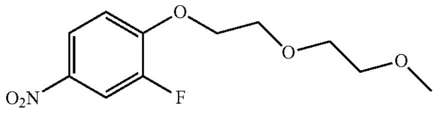

3

To a stirred solution of 1 (0.5 g, 3.18 mmol) in THF (10 mL) were added 2 (0.38 g, 3.18 mmol), $PPh_3$ (0.91 g, 3.498 mmol) and $Et_3N$ (0.48 g, 4.776 mmol) under $N_2$ atmosphere. The reaction mixture was cooled to 0° C. and to it was added DIAD (0.707 g, 3.5 mmol). The reaction mixture was allowed to come to rt and stirred at it for 1 h. It was quenched with water, extracted with ethyl acetate (3×5 mL) and the combined EtOAc extract was washed with water and brine solution (5 mL each). The residue obtained after concentration under reduced pressure was purified by column chromatography ($SiO_2$, 60-120, pet ether/ethyl acetate, 7/3) to give 3 (0.61 g, 65%) as a white solid.

Step-2

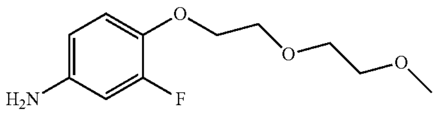

4

To a solution of 3 (0.6 g, 2.31 mmol) in ethanol (20 mL)) was added Pd/C (0.060 g, 10% w/w) and the reaction mixture was allowed to stir under $H_2$ atmosphere (bladder pressure) at rt for 16 h. The reaction mixture was filtered through a pad of Celite® and concentrated under reduced pressure to give 4 (0.375 g, 70.7%) as a brownish viscous oil.

Step-3

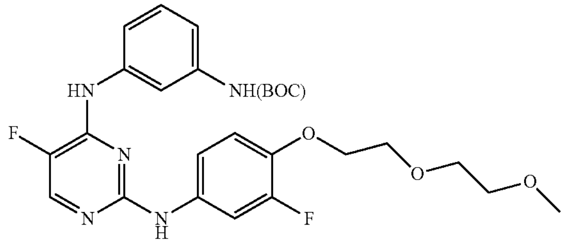

6

A solution of 4 (0.275 g, 1.19 mmol), 5 (0.403 g, 1.19 mmol), prepared according to Step-1 of Example 20, $Pd(OAc)_2$ (0.0026 g, 0.11 mmol), BINAP (0.0037 g, 0.059 mmol) and $Cs_2CO_3$ (0.969 g, 2.95 mmol) in degassed toluene (toluene was purged with $N_2$ for 30 min) was heated at 110° C. for 16 h under $N_2$ atmosphere. The reaction mixture was cooled, diluted with EtOAc (20 mL), washed with water (10 mL), brine (10 mL) and dried over $Na_2SO_4$. Filtration followed by concentration under reduced pressure offered a residue which was further purified by column chromatography ($SiO_2$, 60-120, pet ether/ethyl acetate 5/5) to give 6 (0.350 g, 55%) as a yellow solid.

Step-4

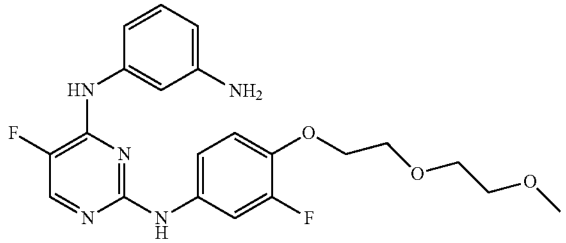

7

To a stirred solution of 6 (0.3 g, 0.56 mmol) in dry $CH_2Cl_2$ (3 mL) at 0° C. was added $CF_3COOH$ (1.0 mL) and the reaction mixture was stirred at 0° C. for 30 min. The reaction was allowed to come to rt and stirred at it for 1 h. It was concentrated under reduced pressure and the residue was quenched with $NaHCO_3$ solution (3 mL) and extracted with EtOAc (3×25 mL). The combined EtOAc extract was washed with water (20 mL), brine (10 mL) and dried over $Na_2SO_4$ to give 7 (0.15 g, 62.5%) as a light brown viscous liquid.

Step-5

I-359

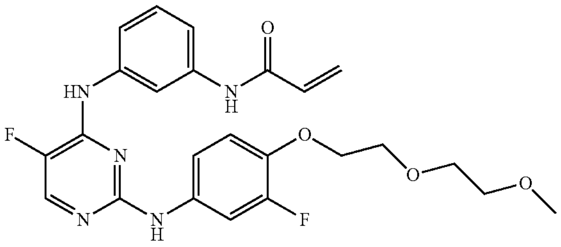

To a cooled solution of 7 (0.1 g, 0.23 mmol) in NMP (1.0 mL) at about 0° C. was added $K_2CO_3$ (0.15 g, 1.1 mmol), acryloyl chloride (0.0022 g, 0.25 mmol) and the reaction mixture was stirred at 0° C. for 30 min. The reaction mixture was added dropwise to a cold, stirring solution of 10% $NaHCO_3$. After the addition was over, the solution was stirred for another 30 min at 0° C., and the solid was isolated by filtration through a Buchner funnel. The solid was washed with cold water, hexane and was dissolved in methanol:dichloromethane (50:50, 25 mL) and concentrated under reduced pressure. The residue obtained was suspended in cold water (3 mL), $Et_3N$ was added to it and it was extracted with ethyl acetate (2×5 mL). The combined ethyl acetate extract was washed with water (5 mL), brine (5 mL), dried over $Na_2SO_4$ and concentrated under reduced pressure to give the title compound (0.055 g, 50%) as yellow solid. $^1H$ NMR (DMSO-d6) δ ppm: 3.24 (s, 3H), 3.44 (t, J=4.88 Hz, 2H), 3.57 (t, J=4.04 Hz, 2H), 3.69 (t, J=4.24 Hz, 2H), 4.04 (t, J=4.04 Hz, 2H), 5.73 (d, J=10.12 Hz, 1H), 6.23 (d, J=16.8 Hz, 1H), 6.45 (dd, J=10.12 & 16.92 Hz, 1H), 6.95 (t, J=9.4 Hz, 1H), 7.28-7.30 (m, 2H), 7.42 (d, J=8.04 Hz, 1H), 7.48 (d, J=7.48 Hz, 1H), 7.67 (d, J=14.36 Hz, 1H), 7.93 (s, 1H), 8.10 (d, J=3.44 Hz, 1H), 9.20 (s, 1H), 9.44 (s, 1H), 10.14 (s, 1H); LCMS: m/e 486.1 (M+1).

Example 248

Preparation of (S)—N-(3-(2-(4-chloro-3-(1-hydroxypropan-2-yloxy)phenylamino)-5-fluoropyrimidin-4-ylamino)phenyl)acrylamide I-357

I-357

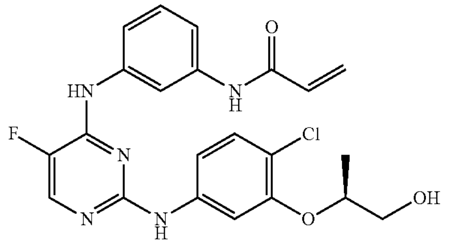

The title compound was prepared according to the schemes, steps and intermediates described below.

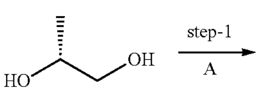

1

-continued

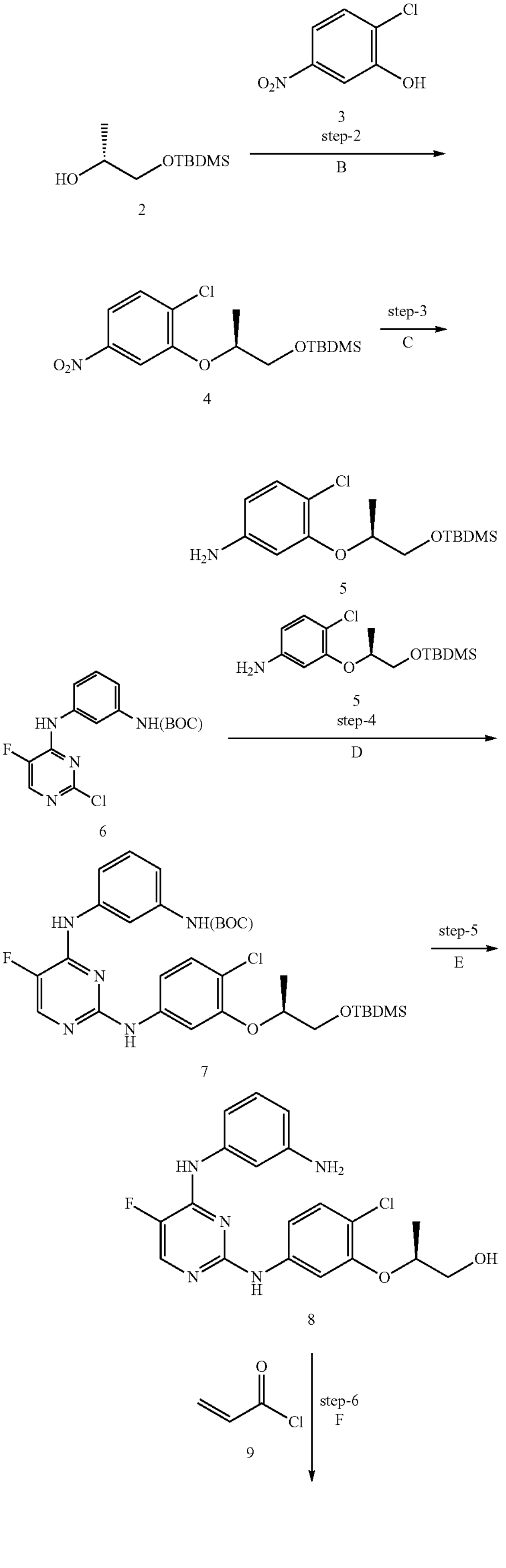

-continued

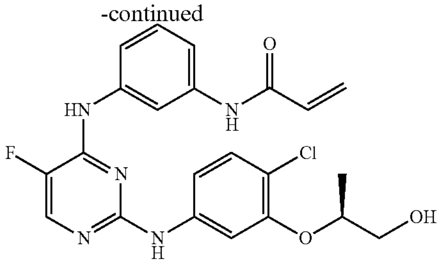

I-357

A) TBDMSCl, imidazole, $CH_2Cl_2$, 0° C., 2 h; B) DIAD, $PPh_3$, $Et_3N$, dry THF, rt, 1 h; C) $H_2$, Raney Ni, MeOH, 2 h; D) $Pd(OAc)_2$, BINAP, $Cs_2CO_3$, toluene, 110° C., 6 h; E) TFA, $CH_2Cl_2$, rt, 1 h; F) $(BOC)_2O$, 30 min, then $K_2CO_3$, NMP, 0° C., 15 min.

Step-1

2

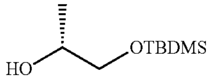

To stirred solution of 1 (1 g, 13.1 mmol) in DCM was added at 0° C., imidazole (0.875 g, 13.1 mmol) and tert-butyldimethylsilyl chloride (1.98 g, 13.1 mmol). The same temperature was maintained for 2 h, and then the reaction mixture was filtered and concentrated. The residue was purified by column chromatography (neutral alumina, pet ether/ethyl acetate 7/3) to give 2 (1.4 g, 56%) as a colorless liquid.

Step-2

4

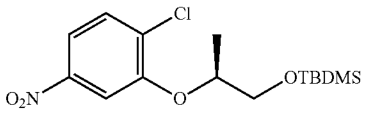

To a stirred solution of 2 (1.5 g, 7.89 mmol) in THF (15 mL) were added 3 (1.36 g, 7.89 mmol), $PPh_3$ (2.27 g, 8.6 mmol) and $Et_3N$ (1.19 g, 11.1 mmol) under $N_2$ atmosphere. The reaction mixture was cooled to 0° C. and to it was added DIAD (1.75 g, 8.6 mmol). The reaction mixture was allowed to come to rt and stirred at it for 1 h. It was quenched with water, extracted with ethyl acetate (3×5 mL) and the combined EtOAc extract was washed with water and brine solution (5 mL each). The residue obtained after concentration under reduced pressure was purified by column chromatography ($SiO_2$, 60-120, pet ether/ethyl acetate, 7/3) to give 4 (2.1 g, 76.9%) as a yellow oil.

Step-3

5

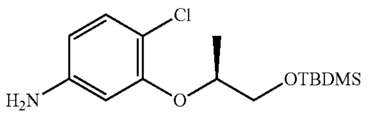

To a solution of 4 (2 g, 5.7 mmol) in methanol (20 mL)) was added Raney Ni (3 g). The reaction mixture was allowed to stir under $H_2$ atmosphere (bladder pressure) at room temperature for 2 h. The reaction mixture was filtered through a pad of Celite® and concentrated under reduced pressure and the residue was purified by column chromatography (neutral alumina, pet ether/ethyl acetate, 8/2) to give 5 (1.4 g, 77%) as a brownish viscous oil.

Step-4

7

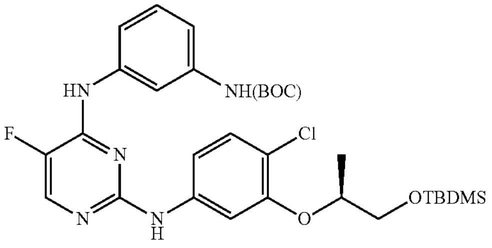

A solution of 6 (0.2 g, 0.63 mmol), prepared according to Step-1 of Example 20, 1 (0.213. g, 0.63 mmol), $Pd(OAc)_2$ (0.014 g, 0.063 mmol), BINAP (0.0019 g, 0.031 mmol) and $Cs_2CO_3$ (0.511 g, 1.5 mmol) in degassed toluene (toluene was purged with $N_2$ for 30 min) was heated at 110° C. for 16 h under $N_2$ atmosphere. The reaction mixture was cooled, diluted with EtOAc (20 mL), washed with water (10 mL), brine (10 mL) and dried over $Na_2SO_4$. Filtration followed by concentration under reduced pressure offered a residue which was further purified using column chromatography ($SiO_2$, 60-120, pet ether/ethyl acetate 7/3) to give 7 (0.15 g, 38.4%) as a yellow solid.

Step-5

8

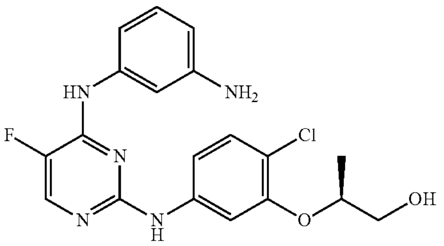

To a stirred solution of 7 (0.15 g, 0.24 mmol) in dry $CH_2Cl_2$ (5 mL) at 0° C. was added $CF_3COOH$ (1.5 mL) and the reaction mixture was stirred at 0° C. for 30 min. The reaction was allowed to come to rt and stirred at it for 1 h. It was concentrated under reduced pressure and the residue was quenched with $NaHCO_3$ solution (3 mL) and extracted with EtOAc (3×25 mL). The combined EtOAc extract was washed with water (20 mL), brine (10 mL) and dried over $Na_2SO_4$ and concentrated under reduced pressure to give 8 (0.085 g, 86.7%) as a white solid.

Step-6

I-357

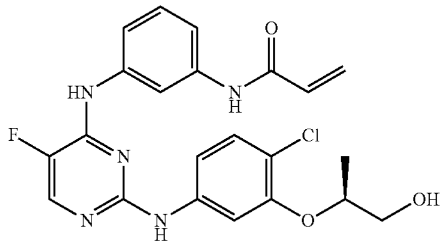

A stirred solution of 8 (0.085 g, 0.21 mmol) in NMP (2.0 mL) was cooled to 0° C. and to it was added $K_2CO_3$ (0.29 g, 2.1 mmol) and acryloyl chloride (1 M solution in THF, 0.21 mL, 0.21 mmol) and the reaction mixture was stirred at 0° C. for 30 min. The reaction mixture was added dropwise to a cold, stirring solution of 10% $NaHCO_3$. After the addition was over, the solution was stirred for another 30 min at 0° C., and the solid was isolated by filtration through a Buchner funnel. The solid was washed with cold water, hexane and was dissolved in methanol:dichloromethane (50:50, 25 mL) and concentrated under reduced pressure. The residue obtained was suspended in cold water (3 mL), $Et_3N$ was added to it and it was extracted with ethyl acetate (2×5 mL). The combined ethyl acetate extract was washed with water (5 mL), brine (5 mL), dried over $Na_2SO_4$ and concentrated under reduced pressure to give the title compound (65 mg, 67%) as yellow solid. $^1H$ NMR (DMSO-d6) δ ppm: 1.18 (d, J=6.12 Hz, 3H), 3.40-3.47 (m, 1H), 3.50-3.56 (m, 1H), 4.20-4.30 (m, 1H), 4.82 (t, J=5.6 Hz, 1H), 5.75 (dd, J=1.88 & 10.08 Hz, 1H), 6.25 (dd, J=1.92 & 16.92 Hz, 1H), 6.45 (dd, J=10.08 & 16.92 Hz, 1H), 7.12 (d, J=8.76 Hz, 1H), 7.29 (t, J=8.08 Hz, 1H), 7.40-7.44 (m, 3H), 7.52 (d, J=8.44 Hz, 1H), 7.91 (s, 1H), 8.12 (d, J=3.64 Hz, 1H), 9.21 (s, 1H), 9.45 (s, 1H), 10.12 (s, 1H); LCMS: m/e 458.0 (M+1).

Example 249

Preparation of (R)—N-(3-(2-(4-chloro-3-(1-hydroxypropan-2-yloxy)phenylamino)-5-fluoropyrimidin-4-ylamino)phenyl)acrylamide I-358

I-358

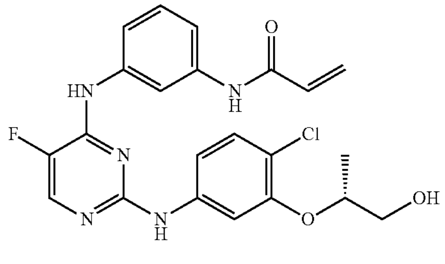

The title compound was prepared according to the schemes, steps and intermediates described in Example 248 by using (R)-propane-1,2-diol in place of 1 in Step-1. $^1H$ NMR (DMSO-d6) δ ppm: 1.18 (d, J=6.12 Hz, 3H), 3.40-3.47 (m, 1H), 3.50-3.56 (m, 1H), 4.20-4.30 (m, 1H), 4.82 (t, J=5.6 Hz, 1H), 5.75 (dd, J=1.88 & 10.08 Hz, 1H), 6.25 (dd, J=1.92 & 16.92 Hz, 1H), 6.45 (dd, J=10.08 & 16.92 Hz, 1H), 7.12 (d, J=8.76 Hz, 1H), 7.29 (t, J=8.08 Hz, 1H), 7.40-7.44 (m, 3H), 7.52 (d, J=8.44 Hz, 1H), 7.91 (s, 1H), 8.12 (d, J=3.64 Hz, 1H), 9.21 (s, 1H), 9.45 (s, 1H), 10.12 (s, 1H); LCMS: m/e 458.0 (M+1).

Example 250

Preparation of (E)-4-(dimethylamino)-N-(3-(5-methyl-4-(m-tolylamino)pyrimidin-2-ylamino)phenyl)but-2-enamide I-360

I-360

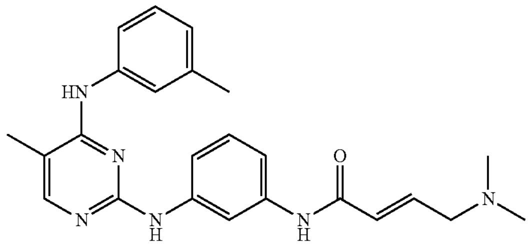

The title compound was prepared according to the schemes, steps and intermediates described in Example 3 by using (E)-4-(dimethylamino)but-2-enoyl chloride place of acryloyl chloride in Step-3. $^1H$ NMR (DMSO-d6) δ ppm: 7.91 (s, 1H), 7.85 (s, 1H), 7.52 (d, J=6.4 Hz, 1H), 7.45 (d, J=7.8 Hz, 1H), 7.34 (s, 1H), 7.31-7.26 (m, 1H), 7.21 (dd, J=8.2, 8.0 Hz, 1H), 7.01-6.92 (m, 4H); 6.27 (s, 1H), 6.06 (d, J=15.1 Hz, 1H), 3.14 (d, J=5.5 Hz, 2H), 2.37 (s, 3H), 2.31 (s, 6H), 2.13 (s, 3H); LCMS m/z 417 (M+1).

Example 251

Preparation of N-(3-(2-(3,4-bis(2-methoxyethoxy)phenylamino)-5-fluoropyrimidin-4-ylamino)phenyl)acrylamide I-277

I-277

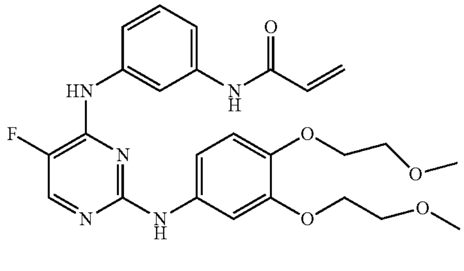

The title compound was prepared according to the schemes, steps and intermediates described below.

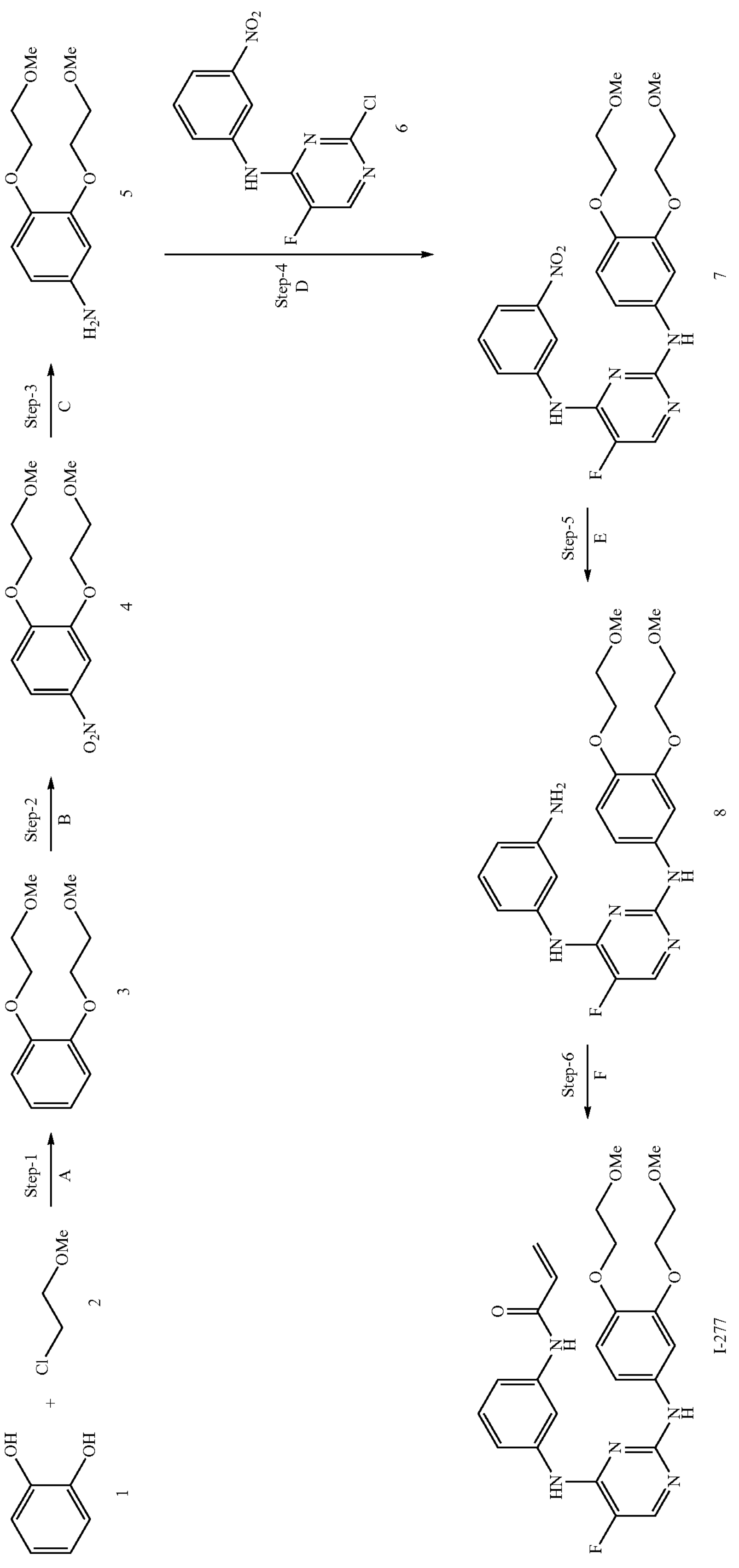
1 2 3 4 5 6 7 8 I-277
A) $K_2CO_3$, $Cs_2CO_3$, DMF, 90° C., 16 h; B) $HNO_3$, Acetic acid, r.t., 1 h; C) Pd/C, methanol, r.t., 3 h; D) Acetic acid, ethanol, 80° C., 16 h; E) Pd/C, methanol, r.t., 16 h; F) Acryloyl chloride, $K_2CO_3$, NMP, r.t., 30 min.

Step-1

3

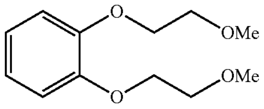

To a stirred solution of 1 (5 g, 45.4 mmol) in DMF (100 mL) were added $K_2CO_3$ (15.6 g, 112.9 mmol), $Cs_2CO_3$ (36.6 g, 112.3 mmol) followed by 2 (12.4 mL, 135.8 mmol) and the reaction mixture was heated to 90° C. for 16 h. Then the reaction mixture was cooled, filtered and the filtrate was concentrated under reduced pressure. The residue was diluted with ethyl acetate, washed with water and brine, dried over anhydrous $Na_2SO_4$, filtered and concentrated to give 3 (9.9 g, 96%) as brown liquid.

Step-2

4

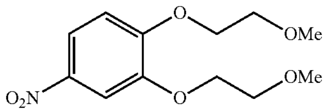

To a stirred solution of 3 (2.5 g, 11 mmol) in acetic acid (50 mL) was added fuming nitric acid (0.83 g, 13.2 mmol) at 0° C. drop wise and stirred at room temperature for 1 h. The reaction mixture was poured onto crushed ice and the solid obtained was collected by filtration and dried under vacuum to give 4 (2.23 g, 74%) as yellow solid.

Step-3

5

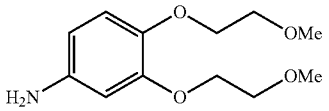

To a solution of 4 (1 g, 3.68 mmol) in methanol (20 mL) was added Pd/C (0.2 g, 20% w/w) under $N_2$ atmosphere. Then the reaction mixture was stirred under $H_2$ pressure (bladder) for 3 h. It was filtered through celite bed and the filtrate was concentrated to give 5 (0.87 g, 98%) as brown oil.

Step-4

7

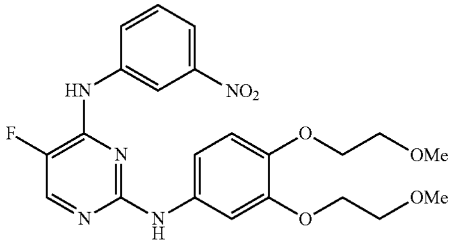

To a solution of 6 (0.45 g, 1.675 mmol) in ethanol (4 mL) were added 5 (0.4 g, 1.658 mmol) and acetic acid (0.2 ml) and the reaction mixture was heated to 80° C. for 16 h. Then it was concentrated under vacuum and the residue was purified by column chromatography ($SiO_2$, petroleum ether: ethyl acetate, 6:4) to get 7 (0.13 g, 17%) as yellow solid.

8

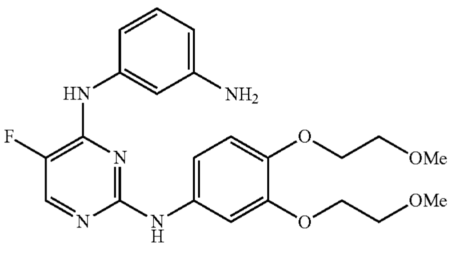

Step-5

To a solution of 7 (0.13 g, 0.275 mmol) in methanol (3 mL) was added Pd/C (26 mg, 20% w/w) under $N_2$ atmosphere. Then the reaction mixture was stirred at room temperature under $H_2$ pressure (bladder) for 16 h. It was filtered through celite bed and the filtrate was concentrated to give 8 (0.10 g, 82%) as green solid.

Step-6

I-277

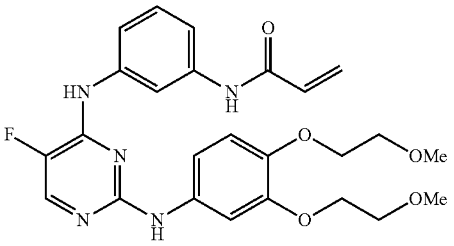

To a cooled solution of 8 (0.1 g, 0.225 mmol) in NMP (1.0 mL) was added $K_2CO_3$ (0.15 g, 1.1 mmol), acryloyl chloride (0.002 g, 0.25 mmol) and the reaction mixture was stirred at 0° C. for 30 min. Then the reaction mixture added drop-wise to a cold, stirring solution of 10% $NaHCO_3$ (~5 ml) and stirred at 0° C. for 30 min. A solid precipitated out was isolated by filtration through a Buchner funnel. The solid was dissolved in methanol:dichloromethane (1:1, 25 mL) and concentrated under reduced pressure. The residue obtained was suspended in cold water (3 mL), $Et_3N$ was added to it and it was extracted with ethyl acetate. The combined ethyl acetate extract was washed with water and brine, dried over $Na_2SO_4$ and concentrated under reduced pressure to get I-277 (0.049 g, 44%) as yellow solid.

$^1H$ NMR (DMSO-$d_6$): δ=3.28 (s, 3H), 3.29 (s, 3H), 3.56-3.60 (m, 4H), 3.88 (t, J=4.8 Hz, 2H), 3.98 (t, J=4.9 Hz, 2H), 5.74 (d, J=12.1 Hz, 1H), 6.24 (d, J=14 Hz, 1H), 6.45 (dd, J=16, 10 Hz, 1H), 6.75 (d, J=8.7 Hz, 1H), 7.21-727 (m, 3H), 7.41 (d, J=8 Hz, 1H), 7.52 (d, J=8 Hz, 1H), 7.89 (s, 1H), 8.07 (d, J=3.7 Hz, 1H), 8.95 (s, 1H), 9.38 (s, 1H), 10.12 (s, 1H); LCMS: m/e: 498.2 (M+1).

Example 252

Preparation of tert-butyl 2-(2-(4-(4-(3-acrylamidophenylamino)-5-fluoropyrimidin-2-ylamino)phenoxy)ethoxy)ethylcarbamate I-370

I-370

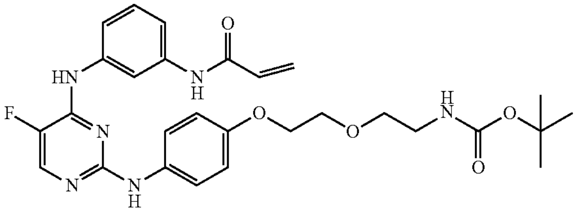

The title compound was prepared according to the schemes, steps and intermediates described in Example 245, by using tert-butyl 2-(2-(4-aminophenoxy)ethoxy)ethylcarbamate in the place of 2 in Step 1. $^{1}$H NMR (DMSO-$d_6$): δ=1.37 (s, 9H), 3.09 (m, 2H), 3.43 (t, J=6.0 Hz, 2H), 3.68 (d, J=4.3 Hz, 2H), 3.98 (t, J=4.3 Hz, 2H), 5.75 (d, J=11.4 Hz, 1H), 6.25 (d, J=15.6 Hz, 1H), 6.45 (dd, J=16.9, 10 Hz, 1H), 6.73-6.81 (m, 3H), 7.27 (t, J=8.1 Hz, 1H), 7.40 (d, J=7.9 Hz, 1H), 7.47-7.53 (m, 3H), 7.92 (s, 1H), 8.06 (d, J=3.6 Hz, 1H), 8.96 (s, 1H), 9.36 (s, 1H), 10.12 (s, 1H); LCMS: m/e: 553.2 (M+1).

Example 253

Preparation of N1-(2-(2-(4-(4-(3-acrylamidophenylamino)-5-fluoropyrimidin-2-ylamino)phenoxy)ethoxy)ethyl)-N5-(15-oxo-19-((3aS,4S,6aR)-2-oxohexahydro-1H-thieno[3,4-d]imidazol-4-yl)-4,7,10-trioxa-14-azanonadecyl)glutaramide I-363

The title compound was prepared according to the schemes, steps and intermediates described in Example 204, by using tert-butyl 2-(2-(4-(4-(3-acrylamidophenylamino)-5-fluoropyrimidin-2-ylamino)phenoxy)ethoxy)ethylcarbamate (I-370, described in Example 252) in the place of I-45 in Step 1. LC/MS (RT=2.045/(M+H)) 995.4.

Example 254

Preparation of (R)—N-(3-(5-fluoro-2-(3-fluoro-4-(1-hydroxypropan-2-yloxy)phenylamino)pyrimidin-4-ylamino)phenyl)acrylamide I-372

I-372

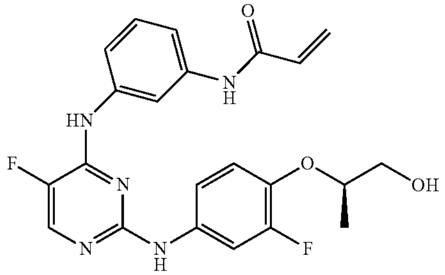

The title compound was prepared according to the schemes, steps and intermediates described in Example 20, by using (R)-2-(4-amino-2-fluorophenoxy)propan-1-ol in the place of 4 in Step 2. $^{1}$H NMR (DMSO-$d_6$): δ=1.17 (d, J=6.2 Hz, 3H), 3.40-3.46 (m, 1H), 3.50-3.56 (m, 1H), 4.22 (q, J=5.9 Hz, 1H), 4.83 (t, J=5.8 Hz, 1H), 5.75 (dd, J=10.1, 1.9 Hz, 1H), 6.25 (dd, J=16.9, 1.9 Hz, 1H), 6.46 (dd, J=16.9, 10.1 Hz, 1H), 6.98 (t, J=9.4 Hz, 1H), 7.24-7.31 (m, 2H), 7.42 (d, J=8.2 Hz, 1H), 7.49 (d, J=7.9 Hz, 1H), 7.68 (dd, J=14.3, 2.4 Hz, 1H), 7.93 (s, 1H), 8.11 (d, J=3.7 Hz, 1H), 9.20 (s, 1H), 9.45 (s, 1H), 10.14 (s, 1H); LCMS: m/e 442.2 (M+1).

I-363

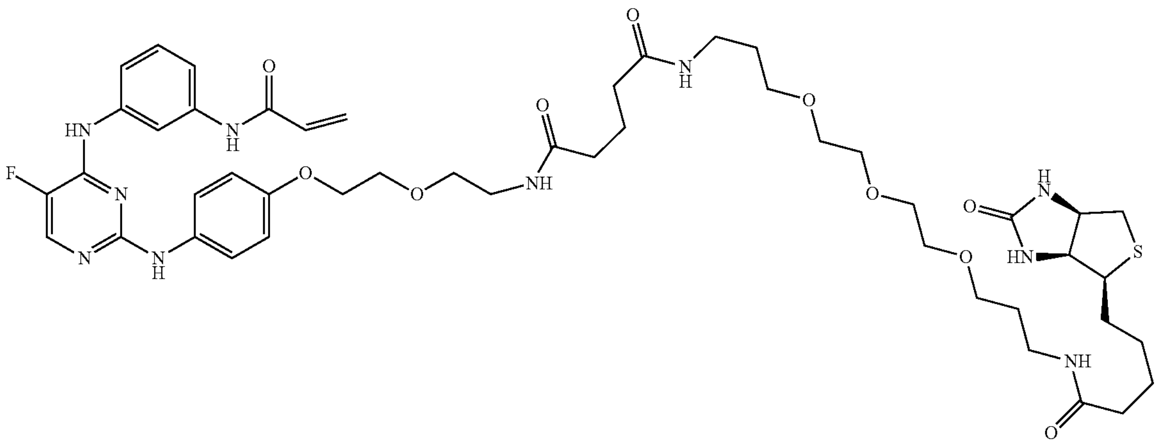

Example 255

Preparation of (S)—N-(3-(5-fluoro-2-(3-fluoro-4-(1-hydroxypropan-2-yloxy)phenylamino)pyrimidin-4-ylamino)phenyl)acrylamide I-373

I-373

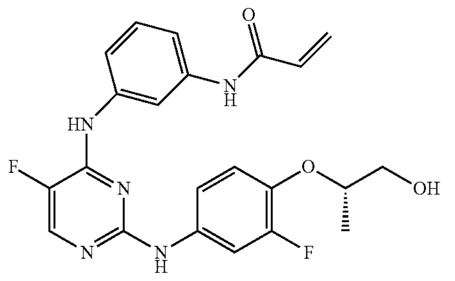

The title compound was prepared according to the schemes, steps and intermediates described in Example 20, by using (S)-2-(4-amino-2-fluorophenoxy)propan-1-ol in the place of 4 in Step 2. LC/MS (RT=3.316/(M+H)) 442.0.

Example 256

Preparation of (S)-((R)-2-(4-(4-(3-acrylamidophenylamino)-5-fluoropyrimidin-2-ylamino)-2-fluorophenoxy)propyl) 2-amino-3-methylbutanoate I-374

I-374

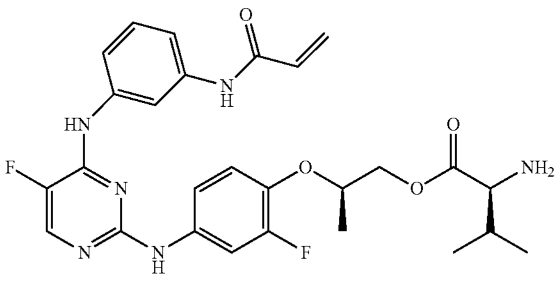

The title compound was prepared according to the schemes, steps and intermediates described below.

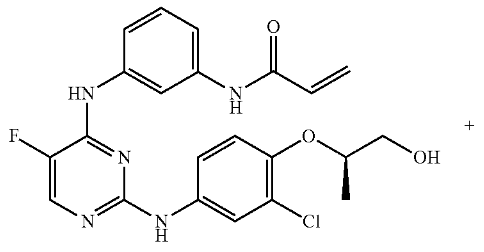

I-372

-continued

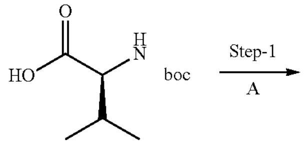

2

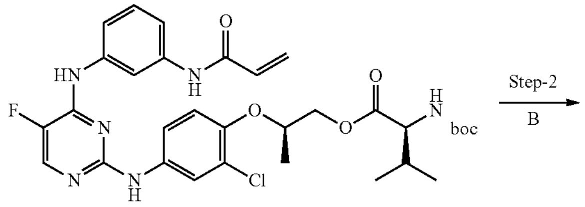

3

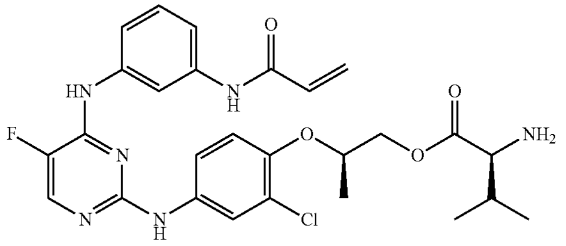

I-374

A) EDC•HCl, HOBT, DMAP, NMM, DMF, r.t., 16 h; B) HCl (1M in Diethylether), 0° C., 1 h.

3

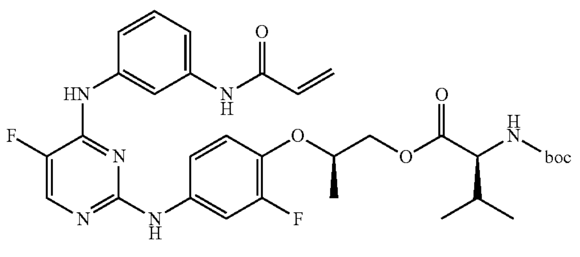

To a stirred solution of I-372 (0.08 g, 0.18 mmol) in DMF (0.8 mL) were added 2 (0.057 g, 0.26 mmol), EDC.HCl (0.086 g, 0.45 mmol), HOBT (0.06 g, 0.44 mmol), 4-DMAP (0.008) and NMM (0.036 g, 0.36 mmol). And the reaction mixture was stirred at room temperature for 16 h. Then it was quenched with water and extracted with ethyl acetate. The ethyl acetate layer was washed with water and brine, dried over anhydrous $Na_2SO_4$, filtered and concentrated. The residue was purified by column chromatography ($SiO_2$, chloroform:methanol, 9:1) to obtain 3 (0.06 g, 51.7%) as off white solid.

Step-2

I-374

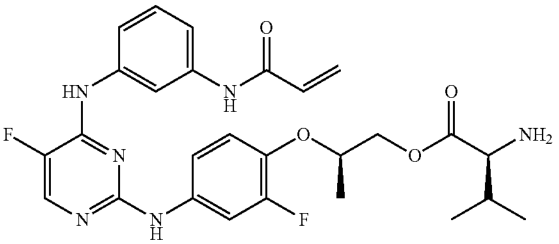

A cold solution of HCl in diethyl ether (1M, 6 ml) was added to 3 (60 mg, 0.09 mmol) and the reaction mixture was stirred at 0° C. for 45 min. Then the reaction mixture was concentrated and the solid obtained was washed with diethyl ether and dried to yield I-374 (as its HCl salt) as yellow solid (20 mg). 1H NMR (DMSO-$d_6$) δ=0.77 (d, J=6.8 Hz, 3H), 0.83 (d, J=6.8 Hz, 3H), 1.23 (d, J=6.3 Hz, 3H), 1.75-1.83 (m, 1H), 3.10 (d, J=5.2 Hz, 1H), 4.05-4.11 (m, 1H), 4.22 (dd, J=11.7, 3.3 Hz, 1H), 4.40-4.50 (m, 1H), 5.73 (d, J=10.2 Hz, 1H), 6.23 (d, J=17.1 Hz, 1H), 6.44 (dd, J=17, 10.2 Hz, 1H), 6.98 (t, J=9.2 Hz, 1H), 7.24-7.29 (m, 2H), 7.41 (d, J=7.8 Hz, 1H), 7.48 (d, J=7.8 Hz, 1H), 7.68 (d, J=14.3 Hz, 1H), 7.91 (s, 1H), 8.10 (d, J=3.5 Hz, 1H), 9.23 (s, 1H), 9.44 (s, 1H), 10.13 (s, 1H). LCMS: m/e 541.2 (M+1).

Example 257

Preparation of (S)-((S)-2-(4-(4-(3-acrylamidophenylamino)-5-fluoropyrimidin-2-ylamino)-2-fluorophenoxy)propyl) 2-amino-3-methylbutanoate I-377

I-377

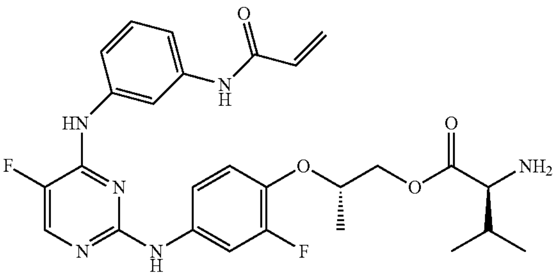

The title compound was prepared according to the schemes, steps and intermediates described in Example 256, by using (S)—N-(3-(5-fluoro-2-(3-fluoro-4-(1-hydroxypropan-2-yloxy)phenylamino)pyrimidin-4-ylamino)phenyl) acrylamide (I-373 described in example 255) in the place of I-372 in Step 1. LC/MS (RT=3.227/(M+H)) 542.2.

Example 258

Preparation of (S)-((S)-2-(5-(4-(3-acrylamidophenylamino)-5-fluoropyrimidin-2-ylamino)-2-chlorophenoxy)propyl)-2-amino-3-methylbutanoate I-369

I-369

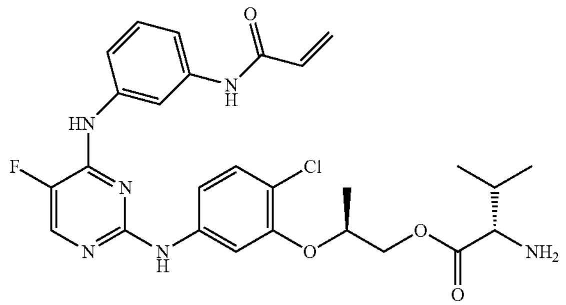

The title compound was prepared according to the schemes, steps and intermediates described in Example 256, by using (S)—N-(3-(2-(4-chloro-3-(1-hydroxypropan-2-yloxy)phenylamino)-5-fluoropyrimidin-4-ylamino)phenyl) acrylamide (I-357 described in example 248) in the place of I-372 in Step 1. LC/MS (RT=3.54/(M+H)) 557.2.

Example 259

Preparation of N-(3-(2-(4-(2-(2-azidoethoxy)ethoxy) phenylamino)-5-fluoropyrimidin-4-ylamino)phenyl) acrylamide I-371

I-371

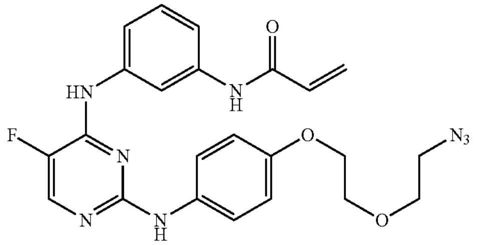

The title compound was prepared according to the schemes, steps and intermediates described below.

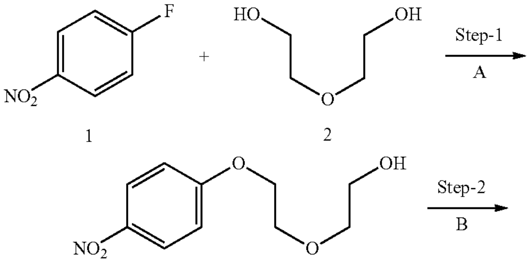

1
2
3

-continued

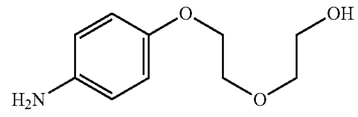

4

4 +

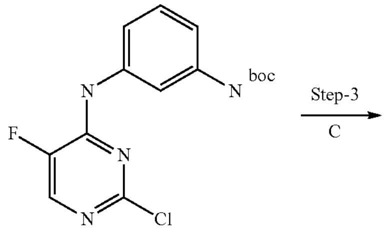

5

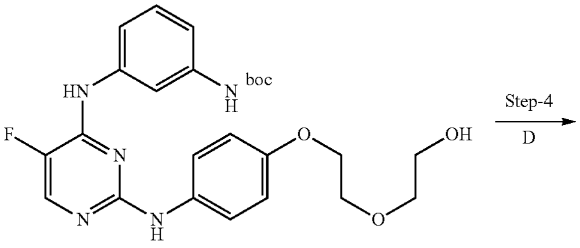

6

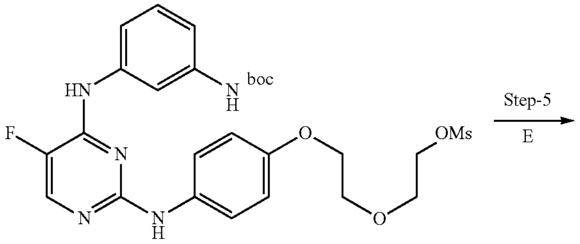

7

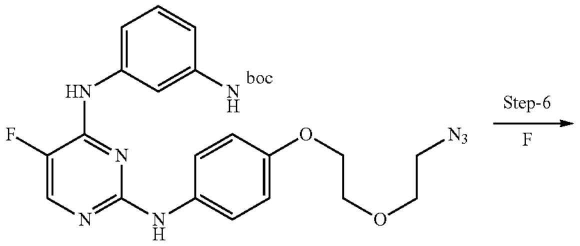

8

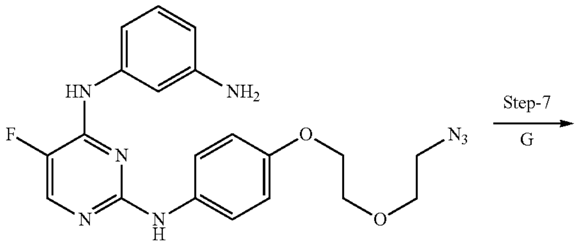

9

-continued

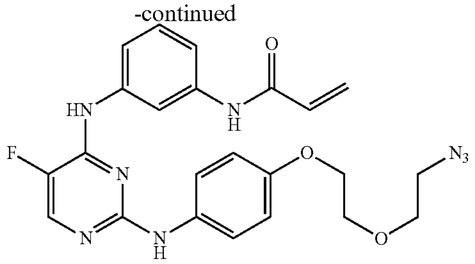

I-371

A) $K_2CO_3$, DMSO, r.t., 16 h; B) Pd/C, Ethanol, 16 h; C) $Pd(OAc)_2$, BINAP, $Cs_2CO_3$, Toluene, 110° C., 16 h; D) Mesyl chloride, $Et_3N$, $CH_2Cl_2$, r.t., 1 h; E) Sodium azide, DMF, 70° C., 4 h; F) TFA, $CH_2Cl_2$, 0° C.-r.t., 1.5 h; G) Acryloyl chloride, NMP, $K_2CO_3$, 30 min.

Step-1

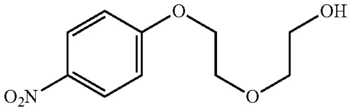

3

To a stirred solution of 1 (1 g, 7.09 mmol) in DMSO (20 mL) was added $K_2CO_3$ (0.96 g, 6.95 mmol) and stirred at room temperature for 15 min. Then 2 (3.7 g, 34.86 mmol) was added and stirring continued at room temperature for 16 h. The reaction mixture was poured into ice water and extracted with ethyl acetate. The organic layer was washed with water and brine, dried over anhydrous $Na_2SO_4$, filtered and concentrated to obtain 3 as yellow solid (1.0 g, 62%).

Step-2

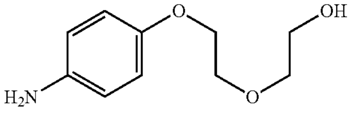

4

To a solution of 3 (1.0 g, 4.4 mmol) in ethanol was added Pd/C (0.1 g, 10% w/w) under $N_2$ and then the reaction mixture was stirred under $H_2$ pressure (bladder) for 16 h. Then the reaction mixture was filtered and the filtrate was concentrated to obtain 4 as brown viscous liquid (0.8 g, 92.2%).

Step-3

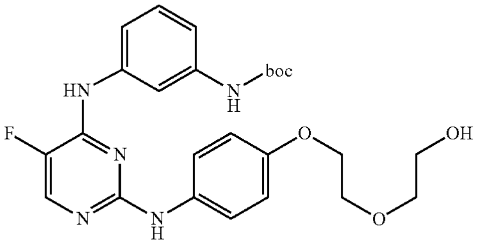

6

A mixture of 4 (0.3 g, 1.52 mmol), 5 (0.61 g, 1.8 mmol), $Pd(OAc)_2$ (0.017 g, 0.076 mmol), BINAP (0.066 g, 0.106 mmol) and $Cs_2CO_3$ (1.23 g, 3.78 mmol) in degassed toluene (20 mL) (toluene was purged with $N_2$ for 30 min) was heated at 110° C. for 16 h under $N_2$ atmosphere. The reaction mixture was cooled, diluted with EtOAc, washed with water and brine and dried over $Na_2SO_4$. Filtration followed by concentration under reduced pressure offered a residue which was further purified by column chromatography ($SiO_2$, petroleum ether:ethyl acetate; 6:4) to obtain 6 (0.3 g, 39.5%) as a brown solid.

Step-4

7

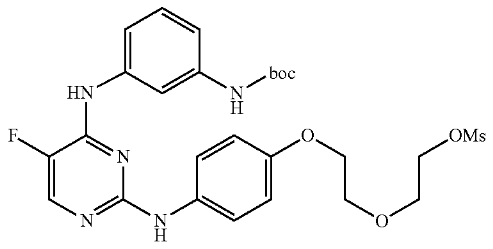

To a stirred solution of 6 (0.35 g, 0.7 mmol) and triethylamine (0.2 mL, 1.4 mmol) in dichloromethane (10 mL) at 0° C. was added mesyl chloride (0.12 g, 1.05 mmol) and then the reaction mixture stirred at room temperature for 1 h. It was quenched with water; the organic layer was separated, dried over anhydrous $Na_2SO_4$ and concentrated to obtain 7 as colorless oil (0.4 g, crude).

Step-5

8

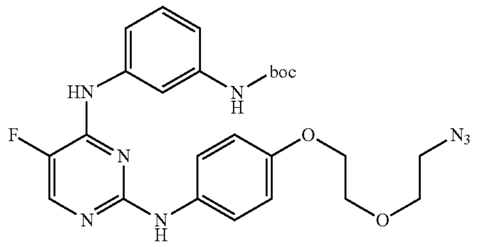

To a stirred solution of 7 (0.4 g, 0.69 mmol) in DMF (5 mL) was added sodium azide (0.054 g, 0.83 mmol) and the reaction mixture was heated to 70° C. for 4 h. Then it was treated with ice water and extracted with ethyl acetate. The ethyl acetate layer was washed with water and with brine, dried over anhydrous $Na_2SO_4$, filtered and concentrated to obtain 8 as viscous oil 8 (0.3 g, 82.6%).

Step-6

9

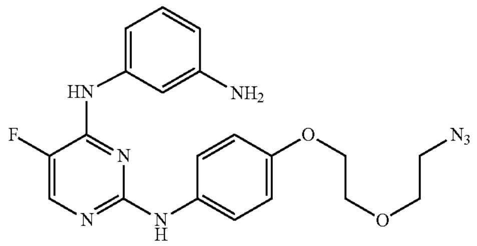

To a stirred solution of 3 (0.3 g, 0.57 mmol) in dry $CH_2Cl_2$ (10 mL) at 0° C. was added $CF_3COOH$ (1.0 mL) and the reaction mixture was stirred at 0° C. for 30 min and then at r.t. for 1 h. It was concentrated under reduced pressure and the residue was treated with $NaHCO_3$ solution and extracted with ethyl acetate. The combined EtOAc extract was washed with water. Then it was extracted with 10% citric acid solution. The combined citric acid extract was basified with 10% NaOH solution and then extracted with EtOAc. The EtOAc extract was washed with water and brine, dried over $Na_2SO_4$ and concentrated to get 9 (0.17 g, 70%) as brown solid.

Step-7

I-371

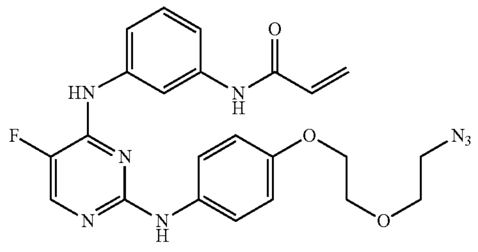

To a stirred solution of 9 (0.075 g, 0.177 mmol) in NMP (1.5 mL) at 0° C. was added $K_2CO_3$ (0.05 g, 0.36 mmol) followed by acryloyl chloride (0.017 g, 0.188 mmol) and the reaction mixture was stirred at 0° C. for 30 min. Then the reaction mixture was added drop wise to a cold stirring solution of 10% $NaHCO_3$. After the addition was over, the solution was stirred for another 30 min at 0° C. and the solid separated was isolated by filtration through a Buchner funnel. The solid was washed with cold water, hexane and was dissolved in methanol:dichloromethane (1:1, 5 mL) and then concentrated under reduced pressure. The residue obtained was suspended in cold water (3 mL) and $Et_3N$ (~1 ml), stirred for a while and extracted with ethyl acetate. The combined ethyl acetate extract was washed with water and brine, dried over $Na_2SO_4$ and concentrated under reduced pressure. The residue obtained was purified by column chromatography twice ($SiO_2$, petroleum ether:ethyl acetate, 1:1) to get I-371 (0.04 g, 47.3%) as white solid. $^1H$ NMR (DMSO-$d_6$): δ=3.42 (t, J=4.9 Hz, 1H), 3.66 (t, J=4.9 Hz, 1H), 3.72-3.77 (m, 4H), 4.00 (t, J=4.6 Hz, 2H), 5.75 (dd, J=10.1, 1.8 Hz, 1H), 6.25 (dd, J=17, 1.9 Hz, 1H), 6.45 (dd, J=16.9, 10.1 Hz, 1H), 6.75 (d, J=9 Hz, 2H), 7.27 (t, J=8.1 Hz, 1H), 7.40 (d, J=8 Hz, 1H), 7.47-7.53 (m, 3H), 7.92 (s, 1H), 8.06 (d, J=3.7 Hz, 1H), 8.97 (s, 1H), 9.37 (s, 1H), 10.12 (s, 1H); LCMS: m/e 479.2 (M+1).

Example 260

Preparation of N-(3-(2-(4-(2-azidoethoxy)phenylamino)-5-fluoropyrimidin-4-ylamino)phenyl) acrylamide I-376

I-376

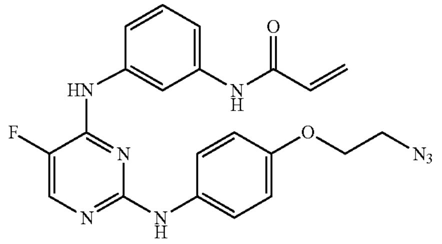

The title compound was prepared according to the schemes, steps and intermediates described in Example 259, by using 2-(4-aminophenoxy)ethanol in the place of 4 in Step 3. LC/MS (RT=3.447/(M+H)) 435.2.

Example 261

Preparation of N-(3-(2-(4-(2-(2-(2-azidoethoxy) ethoxy)ethoxy)phenylamino)-5-fluoropyrimidin-4-ylamino)phenyl)acrylamide I-379

I-379

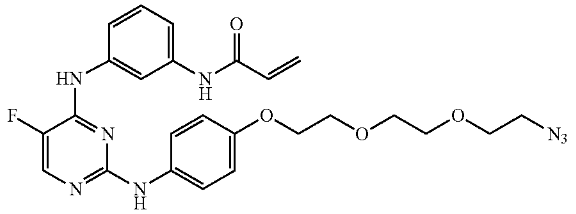

The title compound was prepared according to the schemes, steps and intermediates described in Example 259, by using 2,2'-(ethane-1,2-diylbis(oxy))diethanol in the place of 2 in Step 1. LC/MS (RT=4.454/(M+H)) 475.6.

Example 262

Preparation of (E)-N-(3-(2-(4-chloro-3-(2-methoxyethoxy)phenylamino)-5-fluoropyrimidin-4-ylamino) phenyl)but-2-enamide I-375

I-375

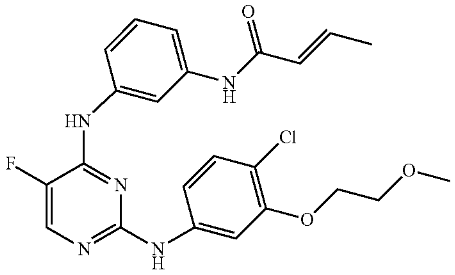

The title compound was prepared according to the schemes, steps and intermediates described in Example 238, by using (E)-but-2-enoyl chloride in the place of 7 in Step 4. LC/MS (RT=4.026/(M+H)) 473.2.

Example 263

Preparation of N-(3-(5-fluoro-4-(4-(2-methoxyethoxy)phenylamino)pyrimidin-2-ylamino)phenyl) acrylamide I-381

I-381

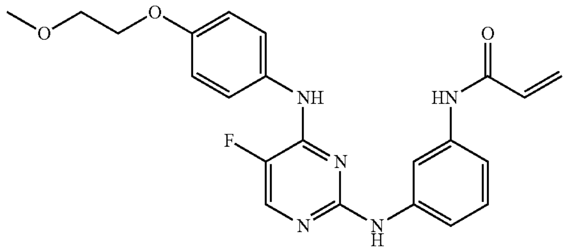

The title compound was prepared according to the schemes, steps and intermediates described in Example 4, by using 4-(2-methoxyethoxy)aniline in the place of 2 in Step 1. LC/MS (RT=2.275/(M+H)) 424.1.

Example 264

Preparation of N-(3-(5-fluoro-4-(3-(2-morpholinoethoxy)phenylamino)pyrimidin-2-ylamino)phenyl)acrylamide I-382

I-382

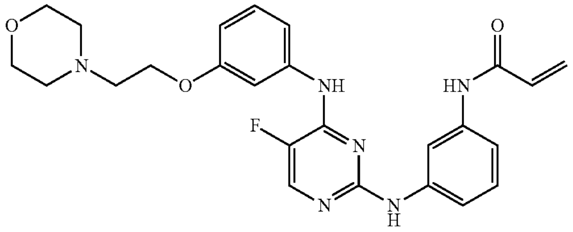

The title compound was prepared according to the schemes, steps and intermediates described in Example 4, by using 3-(2-morpholinoethoxy)aniline in the place of 2 in Step 1. LC/MS (RT=2.108/(M+H)) 479.2.

Example 265

Preparation of (S)—N-(3-(5-fluoro-4-(4-(tetrahydrofuran-3-yloxy)phenylamino)pyrimidin-2-ylamino)phenyl)acrylamide I-338

I-338

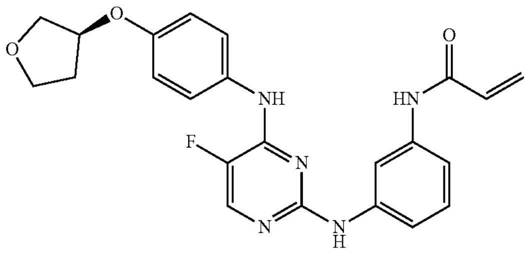

The title compound was prepared according to the schemes, steps and intermediates described in Example 4, by using (S)-4-(tetrahydrofuran-3-yloxy)aniline in the place of 2 in Step 1. LC/MS (RT=1.71/(M+H)) 458.1.

Biological Examples

Described below are assays used to measure the biological activity of provided compounds as inhibitors of BTK, TEC, ITK, BMX, ErbB1 (EGFR), ErbB2, ErbB4, and JAK3.

Example 266

Omnia Assay Protocol for Potency Assessment Against BTK

Below describes the protocol using EGFR-WT and EGFR-T790M/L858R and the protocol BTK-optimized reagent conditions then follow.

The mechanics of the assay platform are best described by the vendor (Invitrogen, Carlsbad, Calif.) on their website at the following URL: www.invitrogen.com/content.cfm?pageid=11338 or www.invitrogen.com/site/us/en/home/Products-and-Services/Applications/Drug-Discovery/Target-and-Lead-Identification-and-Validation/KinaseBiology/KB-Misc/Biochemical-Assays/Omnia-Kinase-Assays.html.

Briefly, 10× stocks of EGFR-WT (PV3872) from Invitrogen and EGFR-T790M/L858R (40350) from BPS Bioscience, San Diego, Calif., 1.13×ATP (AS001A) and appropriate Tyr-Sox conjugated peptide substrates (KCZ1001) were prepared in 1× kinase reaction buffer consisting of 20 mM Tris, pH 7.5, 5 mM $MgCl_2$, 1 mM EGTA, 5 mM β-glycerophosphate, 5% glycerol (10× stock, KB002A) and 0.2 mM DTT (DS001A). 5 μL of each enzyme were pre-incubated in a Corning (#3574) 384-well, white, non-binding surface microtiter plate (Corning, N.Y.) for 30 min. at 27° C. with a 0.5 μL volume of 50% DMSO and serially diluted compounds prepared in 50% DMSO. Kinase reactions were started with the addition of 45 μL of the ATP/Tyr-Sox peptide substrate mix and monitored every 30-90 seconds for 60 minutes at $\lambda_{ex}360/\lambda_{em}485$ in a Synergy[4] plate reader from BioTek (Winooski, Vt.). At the conclusion of each assay, progress curves from each well were examined for linear reaction kinetics and fit statistics ($R^2$, 95% confidence interval, absolute sum of squares). Initial velocity (0 minutes to ~30 minutes) from each reaction was determined from the slope of a plot of relative fluorescence units vs time (minutes) and then plotted against inhibitor concentration to estimate $IC_{50}$ from log[Inhibitor] vs Response, Variable Slope model in GraphPad Prism from GraphPad Software (San Diego, Calif.).

The modified BTK-optimized reagent conditions for the above protocol are:

[BTK]=5 nm, [ATP]=40 mM, [Y5-Sox]=10 mM (ATP KMapp~36 mM).

Example 267

Table 6 shows the activity of selected compounds of this invention in the BTK inhibition assay. The compound numbers correspond to the compound numbers in Table 5. Compounds having an activity designated as "A" provided an $IC_{50}\leq 10$ nM; compounds having an activity designated as "B" provided an $IC_{50}$ 10-100 nM; compounds having an activity designated as "C" provided an $IC_{50}$ of 100-1000 nM; compounds having an activity designated as "D" provided an $IC_{50}$ of 1000-10,000 nM; and compounds having an activity designated as "E" provided an $IC_{50}\geq 10{,}000$ nM.

TABLE 6

BTK Inhibition Data

| Compound # | BTK Inhibition |
|---|---|
| I-1 | A |
| I-2 | A |
| I-3 | A |
| I-4 | A |
| I-5 | A |
| I-7 | A |
| $I^R$-7 | C |
| I-8 | A |
| I-9 | A |
| I-10 | C |
| I-11 | A |
| I-23 | B |
| I-27 | A |
| I-28 | A |
| I-33 | A |
| I-34 | B |
| I-35 | A |
| I-38 | A |
| I-39 | A |
| I-40 | A |
| I-45 | A |
| I-54 | A |
| I-55 | A |
| I-56 | C |
| I-60 | C |
| I-69 | A |
| I-70 | A |
| I-71 | A |
| I-72 | A |
| I-73 | A |
| I-74 | A |
| I-75 | A |
| I-76 | A |
| I-77 | A |
| I-78 | A |
| I-79 | A |
| I-80 | A |
| I-81 | A |
| I-82 | A |
| I-83 | A |
| I-84 | A |
| I-85 | B |
| I-86 | A |
| I-87 | A |
| I-88 | A |
| I-89 | A |
| I-90 | A |

TABLE 6-continued

BTK Inhibition Data

| Compound # | BTK Inhibition |
|---|---|
| I-91 | A |
| I-92 | A |
| I-93 | A |
| I-94 | A |
| I-95 | A |
| I-96 | A |
| I-97 | A |
| I-98 | C |
| I-99 | A |
| I-100 | C |
| I-101 | B |
| I-102 | B |
| I-103 | A |
| I-104 | A |
| I-105 | A |
| I-106 | B |
| I-107 | A |
| I-108 | A |
| I-109 | A |
| I-110 | A |
| I-111 | A |
| I-112 | A |
| I-113 | A |
| I-114 | A |
| I-115 | B |
| I-116 | A |
| I-117 | A |
| I-118 | A |
| I-119 | B |
| I-120 | A |
| I-121 | A |
| I-122 | A |
| I-123 | B |
| I-124 | A |
| I-125 | A |
| I-126 | A |
| I-127 | B |
| I-128 | A |
| I-129 | A |
| I-130 | A |
| I-131 | A |
| I-132 | A |
| I-133 | A |
| I-134 | A |
| I-135 | A |
| I-136 | A |
| I-137 | C |
| I-138 | A |
| I-139 | A |
| I-140 | A |
| I-141 | A |
| I-142 | A |
| I-143 | A |
| I-144 | A |
| I-145 | A |
| I-146 | A |
| I-147 | A |
| I-148 | D |
| I-149 | A |
| I-150 | A |
| I-151 | A |
| I-152 | A |
| I-153 | A |
| I-154 | A |
| I-155 | A |
| I-156 | A |
| I-157 | A |
| I-158 | A |
| I-159 | A |
| I-160 | A |
| I-161 | A |
| I-162 | A |
| I-163 | B |
| I-164 | A |
| I-165 | A |
| I-166 | A |

TABLE 6-continued

BTK Inhibition Data

| Compound # | BTK Inhibition |
|---|---|
| I-167 | A |
| I-168 | A |
| I-169 | A |
| I-170 | A |
| I-171 | A |
| I-172 | A |
| I-173 | A |
| I-174 | A |
| I-175 | C |
| I-176 | A |
| I-177 | A |
| I-178 | A |
| I-179 | C |
| I-180 | A |
| I-181 | A |
| I-182 | A |
| I-183 | A |
| I-184 | A |
| I-185 | A |
| I-186 | A |
| I-187 | B |
| I-188 | A |
| I-189 | A |
| I-190 | A |
| I-191 | A |
| I-192 | A |
| I-193 | C |
| I-194 | A |
| I-195 | A |
| I-196 | B |
| I-197 | C |
| I-198 | A |
| I-199 | A |
| I-200 | A |
| I-201 | A |
| I-202 | A |
| I-203 | B |
| I-204 | A |
| I-205 | B |
| I-206 | E |
| I-207 | A |
| I-208 | A |
| I-209 | A |
| I-210 | A |
| I-211 | D |
| I-212 | D |
| I-213 | E |
| I-214 | B |
| I-215 | A |
| I-216 | C |
| I-217 | A |
| I-218 | A |
| I-219 | A |
| I-220 | A |
| I-221 | B |
| I-222 | B |
| I-223 | E |
| I-224 | B |
| I-225 | C |
| I-226 | B |
| I-227 | A |
| I-228 | A |
| I-229 | B |
| I-230 | A |
| I-231 | C |
| I-232 | B |
| I-233 | A |
| I-234 | D |
| I-235 | B |
| I-236 | B |
| I-237 | A |
| I-238 | D |
| I-241 | D |
| I-242 | A |
| I-243 | A |
| I-244 | A |

TABLE 6-continued

| BTK Inhibition Data | |
|---|---|
| Compound # | BTK Inhibition |
| I-245 | A |
| I-246 | B |
| I-247 | A |
| I-248 | A |
| I-249 | A |
| I-277 | A |
| I-312 | A |
| I-313 | A |
| I-315 | A |
| I-316 | A |
| I-318 | A |
| I-321 | A |
| I-322 | A |
| I-323 | C |
| I-324 | A |
| I-325 | C |
| I-326 | A |
| I-327 | A |
| I-328 | A |
| I-329 | A |
| I-330 | B |
| I-331 | B |
| I-332 | A |
| I-333 | A |
| I-334 | A |
| I-335 | A |
| I-336 | A |
| I-337 | A |
| I-338 | A |
| I-339 | A |
| I-341 | A |
| I-342 | A |
| I-343 | B |
| I-344 | A |
| I-345 | A |
| I-346 | A |
| I-347 | A |
| I-348 | A |
| I-349 | A |
| I-350 | A |
| I-351 | A |
| I-352 | A |
| I-353 | A |
| I-354 | A |
| I-355 | A |
| I-356 | A |
| I-357 | A |
| I-358 | A |
| I-359 | A |
| I-360 | A |
| I-362 | A |
| I-363 | A |
| I-369 | A |
| I-370 | A |
| I-371 | A |
| I-372 | A |
| I-373 | A |
| I-374 | A |
| I-375 | D |
| I-376 | A |
| I-377 | A |
| I-378 | A |
| I-379 | A |
| I-381 | A |
| I-382 | B |

Example 268

BTK Ramos Cellular Assay

Compounds I-2, I-4, and I-7 were assayed in Ramos human Burkitt lymphoma cells. Ramos cells were grown in suspension in T225 flasks, spun down, resuspended in 50 ml serum-free media and incubated for 1 hour. Compound was added to Ramos cells in serum free media to a final concentration of 1, 0.1, 0.01, or 0.001 μM. Ramos cells were incubated with compound for 1 hour, washed again and resuspended in 100 ul serum-free media. Cells were then stimulated with 1 μg of goat F(ab')2 Anti-Human IgM and incubated on ice for 10 minutes to activate B cell receptor signaling pathways. After 10 minutes, the cells were washed once with PBS and then lysed on ice with Invitrogen Cell Extraction buffer. 16 μg total protein from lysates were loaded on gel and blots were probed for phosphorylation of the BTK substrate PLCγ2. Dose response inhibition of BTK signaling in Ramos cells is depicted in FIGS. 1, 2, 3, 4 and 5.

Table 7 shows the activity of selected compounds of this invention in the BTK Ramos cellular inhibition assay. The compound numbers correspond to the compound numbers in Table 5. Compounds having an activity designated as “A” provided an $IC_{50} \leq 10$ nM; compounds having an activity designated as “B” provided an $IC_{50}$ 10-100 nM; compounds having an activity designated as “C” provided an $IC_{50}$ of 100-1000 nM; compounds having an activity designated as “D” provided an $IC_{50}$ of 1000-10,000 nM; and compounds having an activity designated as “E” provided an $IC_{50} \geq 10$,000 nM.

TABLE 7

| BTK Ramos Cellular Inhibition Data | |
|---|---|
| Compound # | BTK Inhibition |
| I-3 | B |
| I-4 | B |
| I-7 | A |
| I-8 | C |
| I-27 | B |
| I-33 | A |
| I-35 | A |
| I-38 | B |
| I-39 | B |
| I-40 | B |
| I-45 | A |
| I-77 | A |
| I-78 | A |
| I-79 | A |
| I-80 | A |
| I-86 | A |
| I-87 | A |
| I-95 | A |
| I-96 | A |
| I-97 | A |
| I-103 | A |
| I-105 | A |
| I-107 | B |
| I-108 | B |
| I-110 | B |
| I-114 | B |
| I-116 | A |
| I-118 | A |
| I-121 | B |
| I-122 | A |
| I-124 | A |
| I-125 | B |
| I-126 | B |
| I-128 | B |
| I-129 | A |
| I-131 | A |
| I-133 | B |
| I-134 | B |
| I-135 | B |
| I-138 | A |
| I-139 | B |
| I-140 | B |
| I-142 | B |
| I-143 | A |
| I-147 | B |
| I-149 | B |

TABLE 7-continued

| BTK Ramos Cellular Inhibition Data | |
|---|---|
| Compound # | BTK Inhibition |
| I-150 | B |
| I-151 | A |
| I-152 | B |
| I-153 | A |
| I-154 | A |
| I-156 | A |
| I-157 | A |
| I-158 | B |
| I-159 | C |
| I-160 | B |
| I-162 | A |
| I-163 | B |
| I-164 | A |
| I-165 | B |
| I-166 | B |
| I-167 | B |
| I-168 | B |
| I-169 | A |
| I-170 | B |
| I-172 | A |
| I-173 | A |
| I-174 | A |
| I-176 | C |
| I-177 | C |
| I-178 | B |
| I-180 | C |
| I-182 | A |
| I-185 | C |
| I-186 | A |
| I-188 | A |
| I-189 | B |
| I-190 | B |
| I-192 | B |
| I-194 | A |
| I-195 | B |
| I-198 | A |
| I-201 | C |
| I-202 | C |
| I-204 | A |
| I-207 | C |
| I-208 | B |
| I-209 | B |
| I-210 | A |
| I-217 | A |
| I-219 | B |
| I-220 | B |
| I-227 | A |
| I-228 | A |
| I-230 | A |
| I-233 | A |
| I-242 | A |
| I-243 | A |
| I-244 | B |
| I-245 | A |
| I-247 | A |
| I-248 | A |
| I-249 | A |
| I-313 | A |
| I-315 | A |
| I-316 | A |
| I-318 | A |
| I-321 | A |

Example 269

Washout Experiment with Ramos Cells

Figure 2:
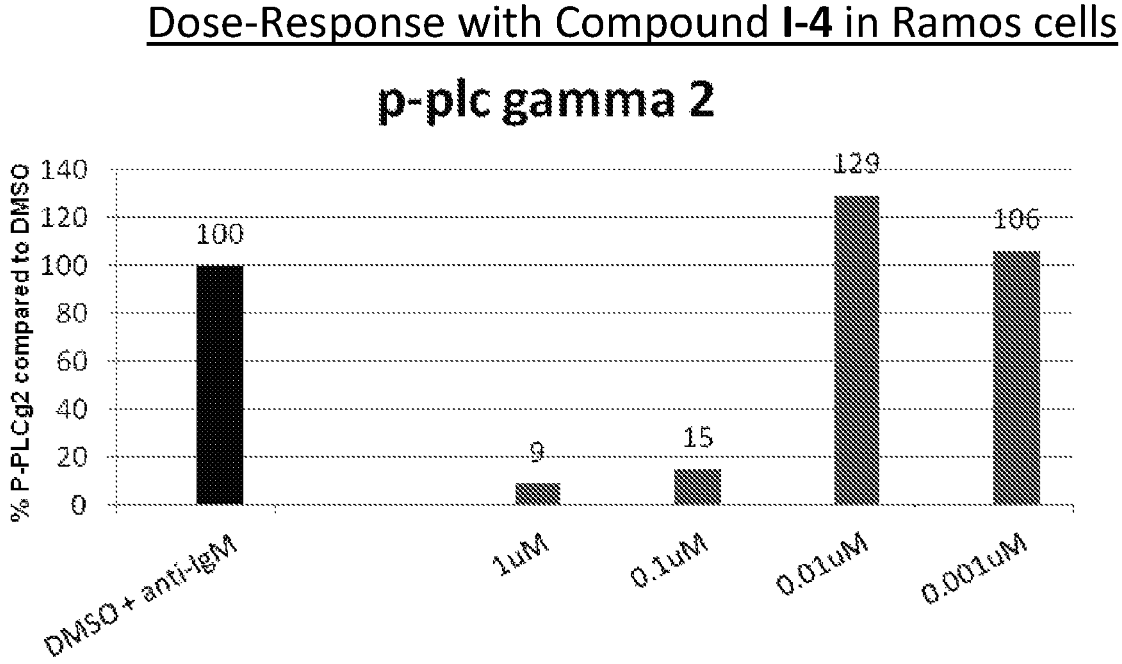
FIG. 2 depicts dose-response inhibition of p-plc gamma2 with compound I-4 in Ramos Cells; and the results of compound I-4 in a "washout" experiment.
Figure 2:
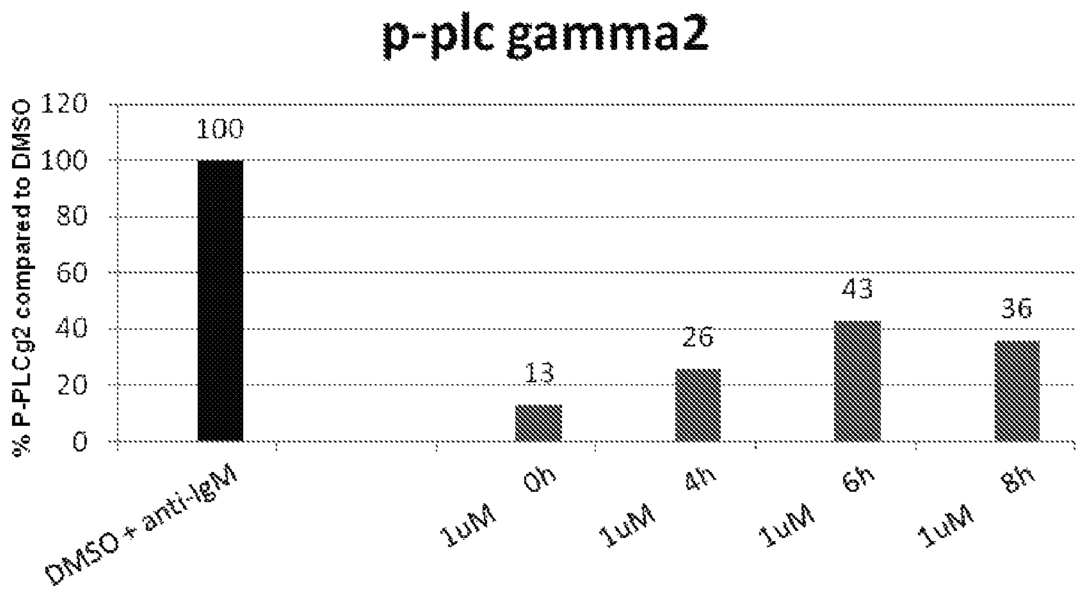
Figure 3:
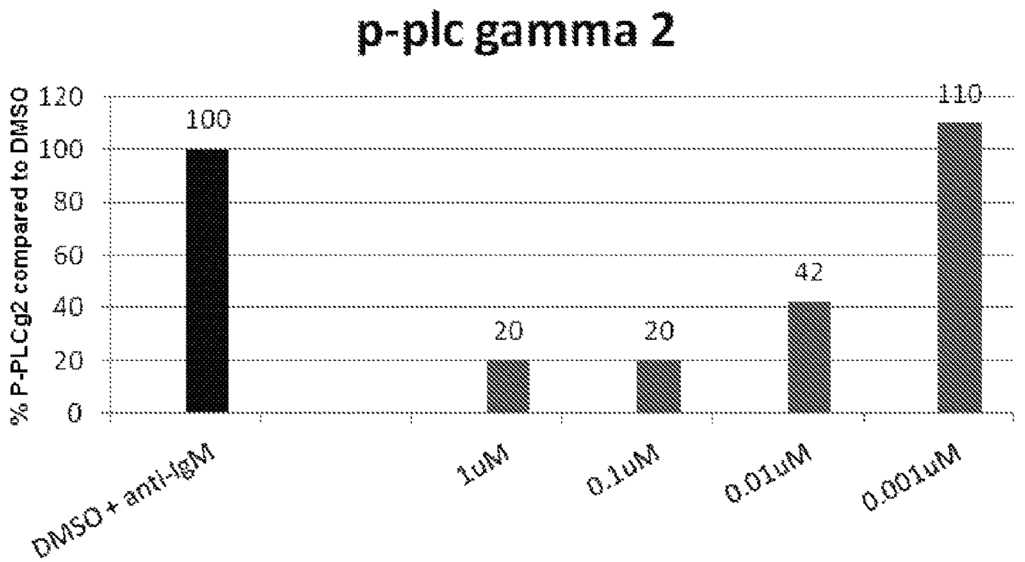
FIG. 3 depicts dose response inhibition of p-plc gamma2 with compound I-7 in Ramos cells; and the results of compound I-7 in a "washout" experiment.
Figure 3:
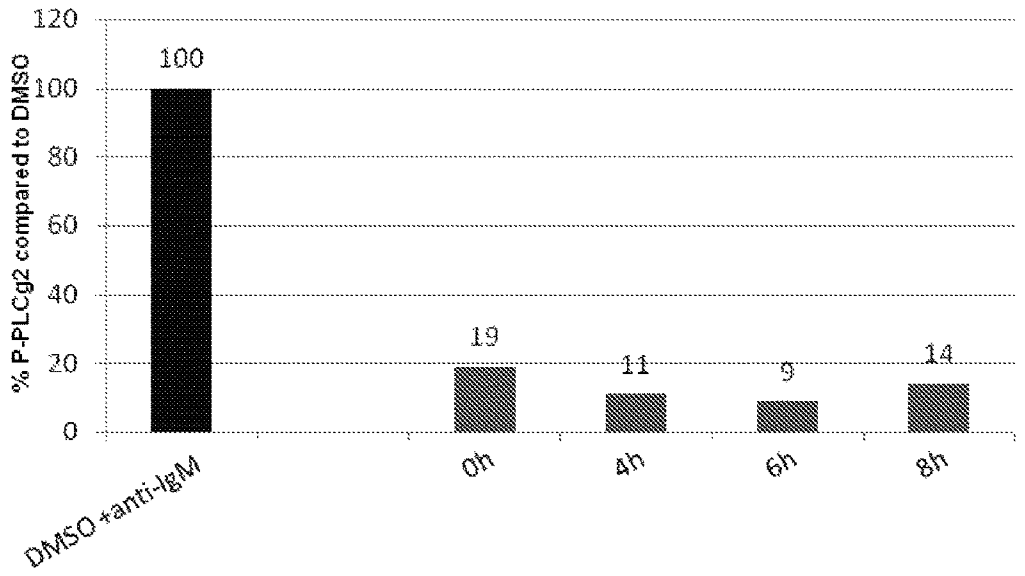
Figure 4:
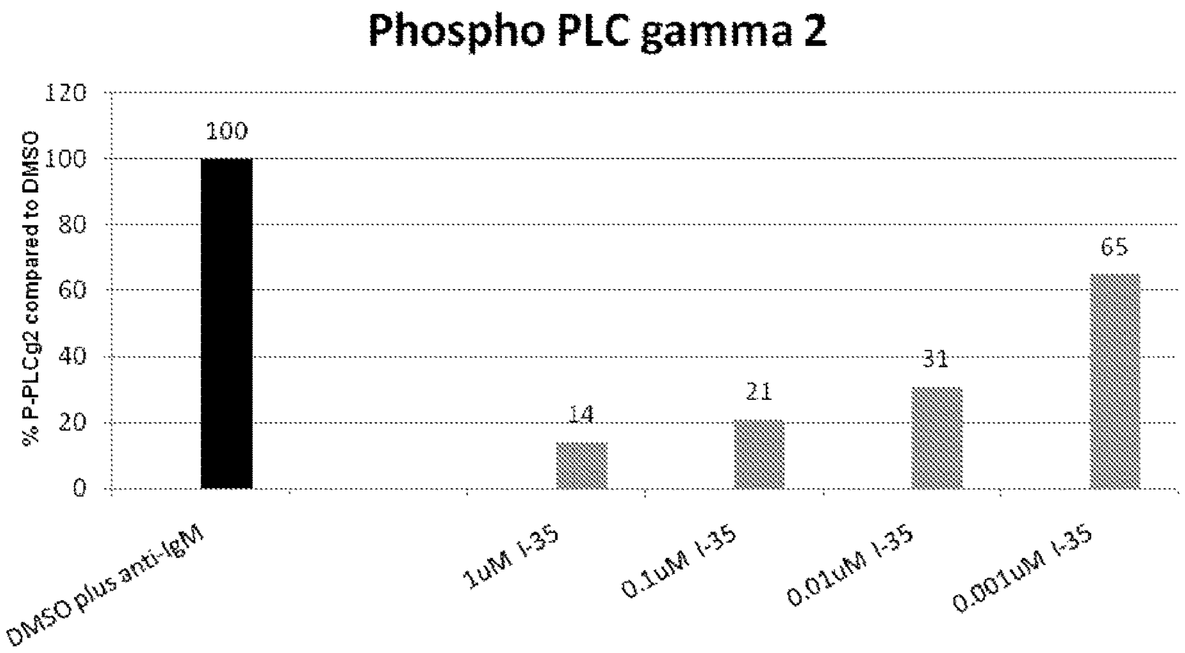
FIG. 4 depicts dose response inhibition of p-plc gamma2 with compound I-35 in Ramos cells.
Figure 5:
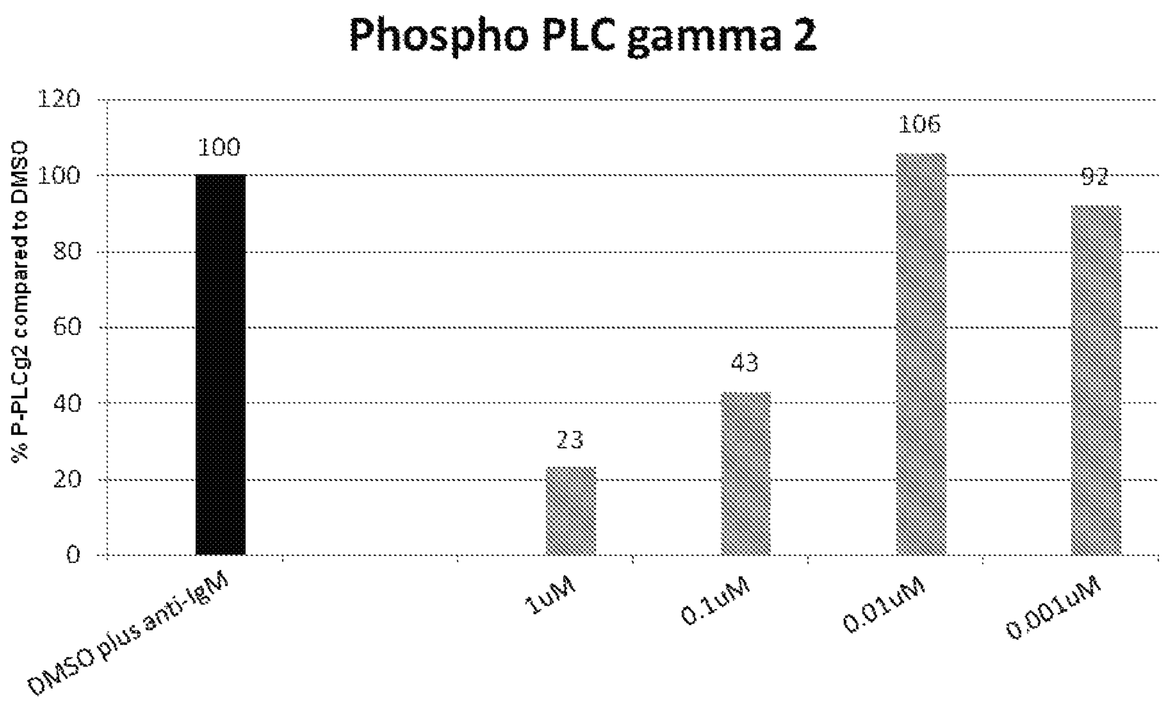
FIG. 5 depicts dose response inhibition of p-plc gamma2 with compound I-38 in Ramos cells.

Ramos cells were serum starved for one hour in RPMI media +1% glutamine at 37° C. After starvation, Ramos cells were treated with 100 nM compound diluted in serum free RPMI media for 1 hour. After compound treatment, the media was removed and cells were washed with compound-free media. Subsequently, Ramos cells were washed every 2 hours and resuspended in fresh compound-free media. Cells were collected at specified timepoints, treated with 1 ug anti-human IgM (Southern Biotech cat #2022-01) for 10 minutes on ice to induce BCR signaling and then washed in PBS. Ramos cells were then lysed in Cell Extraction Buffer (Invitrogen FNN0011) supplemented with Roche complete protease inhibitor tablets (Roche 11697498001) and phosphatase inhibitors (Roche 04 906 837 001) and 18 ug total protein lysate was loaded in each lane. Inhibition of BTK kinase activity was assayed by measuring its substrate (PLCγ2) phosphorylation by western blot with phospho-specific antibodies from Cell Signaling Technologies cat #3871. The results of this experiment with compounds I-2, I-4 and I-7 are depicted in FIGS. 1, 2 and 3.

Table 8 provides data for selected compounds in the Ramos washout assay.

TABLE 8

| BTK Washout Data | |
|---|---|
| Compound # | BTK Inhibition Type |
| I-2 | irreversible |
| I-4 | irreversible |
| I-7 | irreversible |
| I-28 | irreversible |
| I-35 | irreversible |
| I-38 | reversible |
| I-228 | irreversible |
| I-230 | irreversible |
| I-242 | irreversible |
| I-243 | irreversible |
| I-247 | irreversible |
| I-248 | irreversible |

Example 270

Mass Spectrometry for BTK

Figure 15:
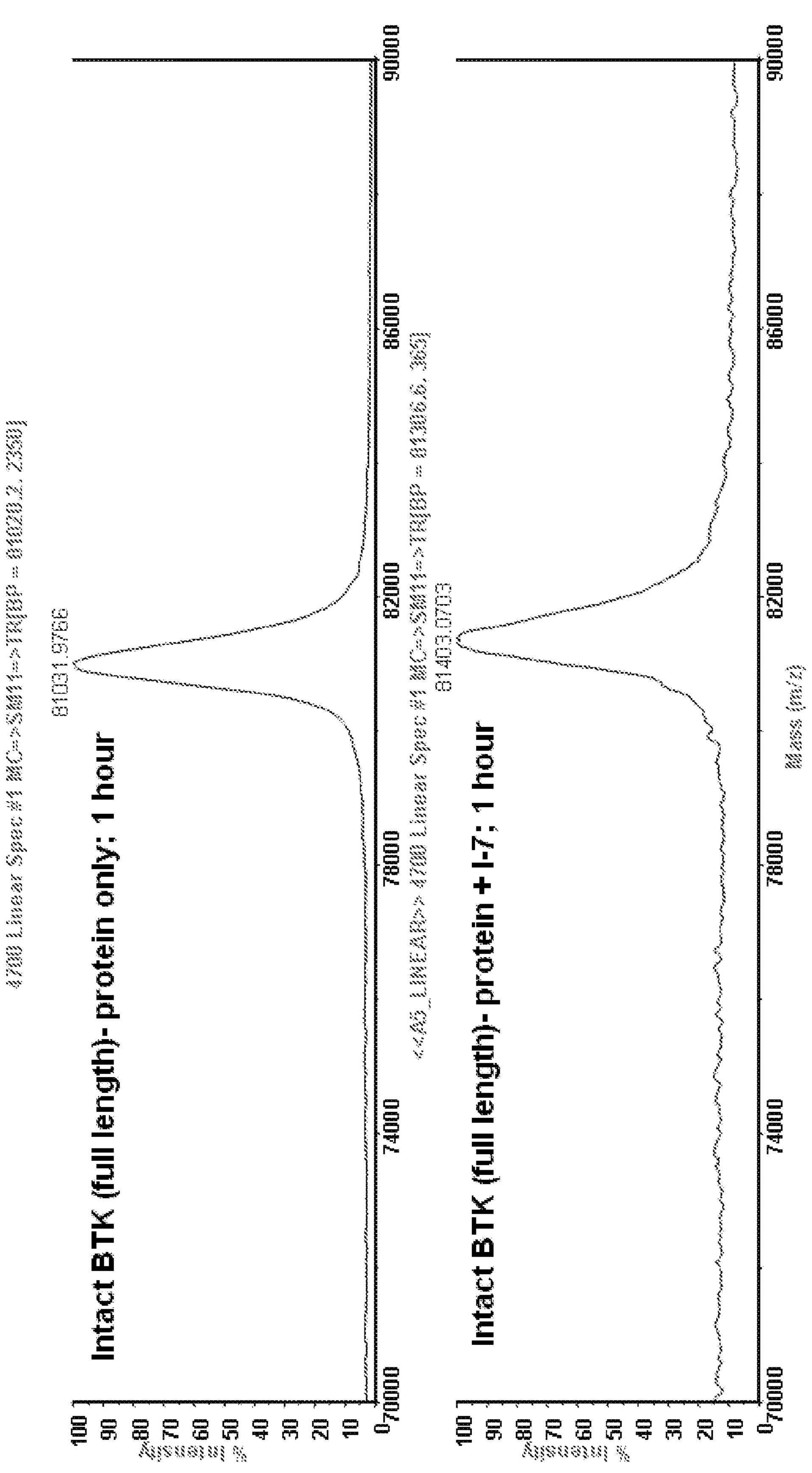
FIG. 15 depicts MS analysis confirming covalent modification of BTK by compound I-7.

Intact BTK was incubated for 1 hr at a 10× fold excess of I-7 to protein. Aliquots (2 μl) of the samples were diluted with 10 μl of 0.1% TFA prior to micro C4 ZipTipping directly onto the MALDI target using Sinapinic acid as the desorption matrix (10 mg/ml in 0.1% TFA:Acetonitrile 20:80). See FIG. 15. Top panel shows the mass spec trace of the intact BTK protein (m/z 81,032 Da). The bottom panel shows mass spec trace when BTK was incubated with I-7 (mw=345.4). The centroid mass (m/z=81,403 Da) shows a positive shift of about 371.1 Da indicating complete modification of BTK by I-7. Other compounds that completely modify BTK include I-96, I-71, I-149, I-161, I-163, I-182, I-195, I-207, I-219, and I-244.

Example 271

Human Primary B Cell Proliferation Assay

Human naïve B cells were purified from 100 mL whole blood using a MACS purification kit designed to isolate CD19+, IgD+ cells by negative selection. Purified naïve B cells were resuspended in RPMI complete and stimulated with 5 μg/ml α-IgM for 72 hours. $^{3}$H-Thymidine was included in the culture media for the final 16 h, cells were harvested and $^{3}$H incorporation measured. Inhibition of B cell proliferation correlates with inhibition of BTK substrate phosphorylation after α-IgM stimulation. Importantly, a molecule with the same scaffold as I-7 but biochemically inactive against BTK, $I^{R}$-7, is not active in the naïve B cell proliferation assay.

TABLE 9

| Compound # | $EC_{50}$ (nM) |
|---|---|
| I-7 | 1-10 |
| $I^R$-7 | >1000 |
| I-190 | 10-100 |
| I-182 | 1-10 |
| I-96 | 1-10 |

Example 272

B Cell Lymphoma Proliferation Assay

Provided compounds inhibit proliferation of various B cell lymphoma cell lines, as shown in Table 10. The compound numbers correspond to the compound numbers in Table 5. Compounds having an activity designated as "A" provided an $EC_{50}$<0.1 μM; compounds having an activity designated as "B" provided an $EC_{50}$ 0.1-1 μM; compounds having an activity designated as "C" provided an $EC_{50}$ of 1-10 μM; and compounds having an activity designated as "D" provided an $EC_{50}$ of >10 μM.

TABLE 10

| | EC50 (μM) | | |
|---|---|---|---|
| Compound # | DOHH2 | WSU-DLCL2 | DHL4 |
| I-2 | B | — | — |
| I-3 | B | — | — |
| I-4 | B | B | B |
| I-7 | C | C | C |
| I-27 | C | D | — |
| I-28 | C | C | — |
| I-35 | C | C | — |
| I-38 | C | C | — |
| I-39 | C | C | — |
| I-40 | B | C | — |
| I-77 | B | — | — |
| I-78 | B | — | — |
| I-79 | C | — | — |
| I-80 | B | — | — |
| I-81 | B | — | — |
| I-86 | D | — | — |
| I-87 | C | — | — |
| I-88 | C | — | — |
| I-89 | C | — | — |
| I-90 | B | — | — |
| I-91 | C | C | — |
| I-96 | B | C | |
| I-103 | — | C | — |
| I-105 | B | C | — |
| I-116 | D | D | — |
| I-121 | C | — | — |
| I-122 | C | — | — |
| I-124 | C | — | — |
| I-126 | A | — | — |
| I-128 | C | — | — |
| I-129 | C | — | — |
| I-132 | C | — | C |
| I-133 | B | — | A |
| I-134 | B | — | A |
| I-135 | D | — | D |
| I-138 | C | — | C |
| I-141 | C | — | — |
| I-142 | C | — | — |
| I-143 | C | C | C |
| I-147 | C | — | — |
| I-149 | C | — | — |
| I-150 | C | C | C |
| I-151 | C | — | C |
| I-152 | C | — | — |
| I-153 | C | C | C |
| I-154 | C | C | C |
| I-155 | C | C | C |

TABLE 10-continued

| | EC50 (μM) | | |
|---|---|---|---|
| Compound # | DOHH2 | WSU-DLCL2 | DHL4 |
| I-156 | B | C | C |
| I-157 | C | C | C |
| I-158 | C | C | C |
| I-159 | C | — | — |
| I-160 | C | C | C |
| I-161 | C | — | C |
| I-162 | C | C | C |
| I-163 | C | C | C |
| I-164 | C | C | C |
| I-165 | C | C | C |
| I-166 | C | C | C |
| I-167 | C | — | — |
| I-168 | C | — | — |
| I-169 | C | — | — |
| I-170 | C | — | — |
| I-171 | C | — | — |
| I-172 | C | — | — |
| I-173 | C | — | — |
| I-174 | C | — | — |
| I-178 | C | D | D |
| I-182 | C | C | C |
| I-184 | C | — | — |
| I-186 | C | — | C |
| I-188 | C | — | — |
| I-189 | D | D | C |
| I-190 | D | — | — |
| I-192 | C | D | — |
| I-194 | C | C | C |
| I-195 | C | D | D |
| I-204 | C | C | — |
| I-207 | B | C | — |
| I-208 | C | C | — |
| I-209 | D | C | — |
| I-210 | C | C | — |
| I-217 | D | D | — |
| I-227 | C | C | — |
| I-228 | D | D | — |
| I-230 | C | C | — |
| I-242 | C | C | — |
| I-243 | C | C | — |
| I-244 | B | C | C |
| I-245 | C | D | — |
| I-247 | B | C | — |
| I-248 | C | C | — |
| I-298 | — | C | — |

Example 273

In Vivo Thymus-Independent (TI-2) B Cell Activation

C57/B6 mice were dosed daily with 100 mg/kg of the appropriate compound on day 0 through 5. Mice were immunized once with 25 μg TNP-Ficoll on day 1, serum was collected on day 6 and analyzed for circulating α-TNP IgM (1:1600 serum dilution) and IgG3 (1:200 serum dilution) antibody production by ELISA. Results represent the average of 10 mice per treatment group and are given in Table 11 as % inhibition of TI-2 independent B cell activation.

TABLE 11

| | % Inhibition | |
|---|---|---|
| Compound # | IgM (1:1600) | IgG3 (1:100) |
| I-7 | 48 | 57 |
| I-182 | 25 | 40 |
| I-96 | 43 | 37.2 |

Example 274

Collagen Antibody Induced Arthritis Model

On day 0 baseline footpad measurements were made and animals were distributed to the experimental groups in such a way as to generate groups with no significant differences between the groups. Each animal was then inoculated intravenously with 2 mg Arthritomab monoclonal antibody cocktail. Treatment with test agents began at this time. On day 6, each animal was injected intraperitoneally with 50 μg LPS in 200 μl of sterile PBS. Footpad measurements and clinical scoring were conducted on days 6, 7, 8, 9, 10, 11, 12, 14, 18, and 21. Table 12 shows the results.

TABLE 12

| Compound # | Dose | % inhibition foot pad swelling |
| --- | --- | --- |
| I-7 | 30 mg/kg | 83 |

Example 275

PG-PS Arthritis Model

On day 0, female Lewis rats received an intraperitoneal (IP) bolus of peptidoglycan-polysaccharide (PG-PS) in an amount of 15 μg/g rat body weight. Baseline control rats received an IP bolus of PBS. The vehicle and treatment groups were dosed via oral gavage just prior to PG-PS administration. Treatment with vehicle and compound continued each day through day 22. Maximal lateral ankle width measurements of both rear limbs were collected with a caliper throughout the study. On day 23, study was terminated and the final change in ankle swelling was calculated and compared to vehicle controls. Table 13 shows the results for two compounds (n=number of experiments).

TABLE 13

| Compound # | n | % inhibition ankle swelling |
| --- | --- | --- |
| I-7 | 1 | 77.5 |
| I-96 | 2 | 82.8 |

Example 276

Mass Spectrometry for TEC Kinase (Compound I-2)

TEC kinase (45 pmols; Invitrogen) was incubated with (I-2) (450 pmols) for 3 hrs at 10× excess prior to tryptic digestion. Iodoacetamide was used as the alkylating agent after compound incubation. A control sample (45 pmols) was also prepared which did not have the addition of (I-2). For tryptic digests a 5 ul aliquot (7.5 pmols) was diluted with 15 ul of 0.1% TFA prior to micro C18 Zip Tipping directly onto the MALDI target using alpha cyano-4-hydroxy cinnamic acid as the matrix (5 mg/ml in 0.1% TFA:Acetonitrile 50:50).

Figure 6:
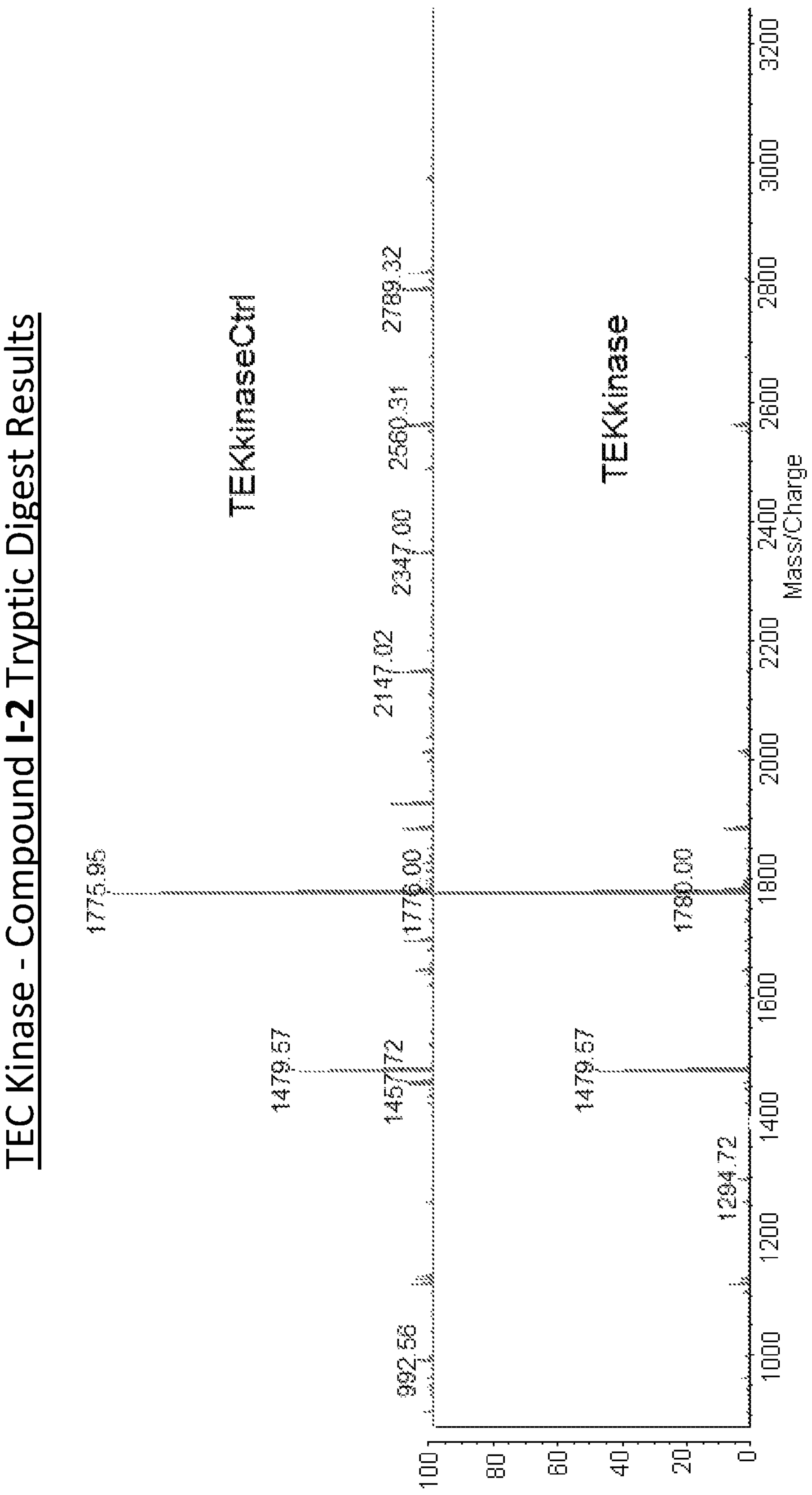
FIG. 6 depicts MS analysis confirming covalent modification of TEC kinase at Cys449 by compound I-2.
Figure 6:
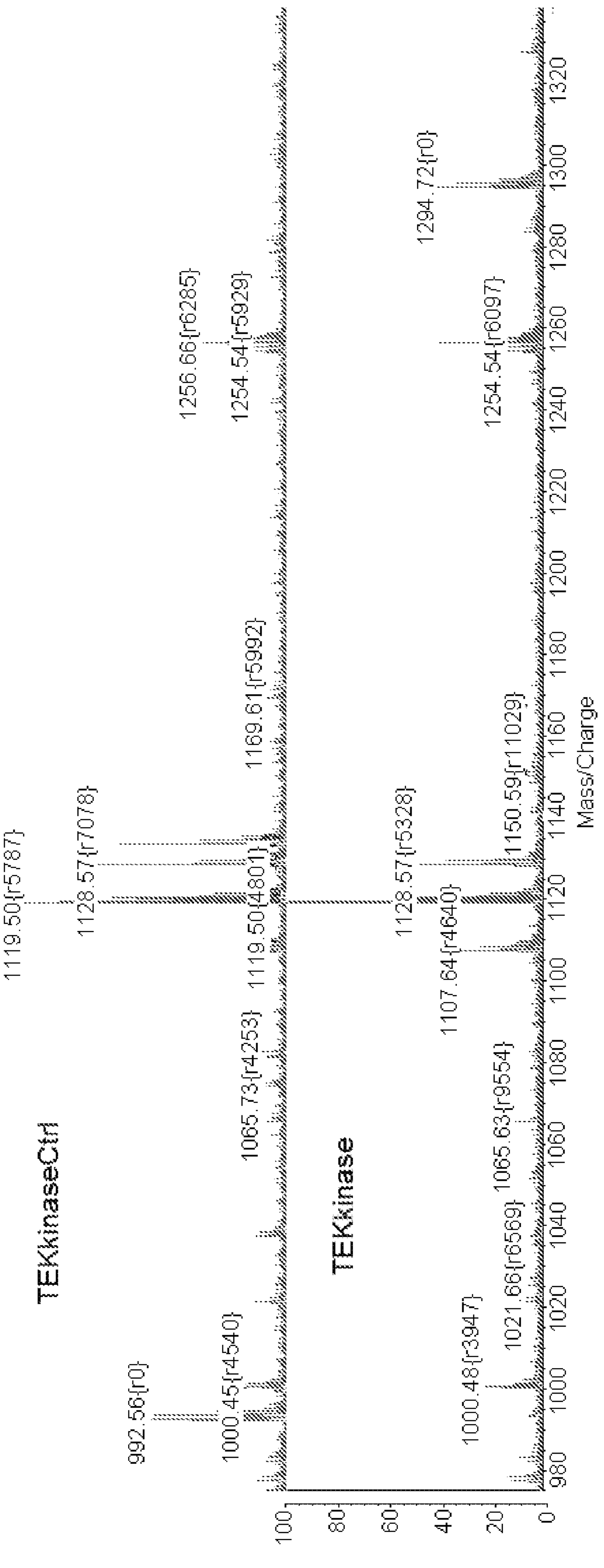

As depicted in FIG. 6, the expected peptide (G CLLNFLR) to be modified was immediately evident after reaction with I-2 (MI mass of 359.17 Da) at MH+ of 1294.72. The peptide was also quite evident in the control sample as modified by Iodacetamide at MH+ of 992.56. Interestingly the iodoacetamide modified peptide was not evident in the digest reacted with compound I-2 indicating that the reaction was complete. There was no evidence of other modified peptides.

Evidence of compound I-2 was observed at MH+ of 360.17 in the low mass range of the spectra. The fragmentation spectra of the 360.17 peak did show diagnostic fragments that were apparent in the PSD spectra of the modified peptide at 1294.72 (See FIG. 6).

To further verify the presence of the modified peptides, both the iodoacetamide labeled (992.56) and I-2 labeled (1294.72) were subjected to PSD (MS/MS) analysis. After a database search of the NCBI nr Homo sapien database using Mascot MS/MS Ion Search program the top match was the expected peptide in both cases.

Instrumental:

For tryptic digests the instrument was set in Reflectron mode with a pulsed extraction setting of 2200. Calibration was done using the Laser Biolabs Pep Mix standard (1046.54, 1296.69, 1672.92, 2093.09, 2465.20). For CID/PSD analysis the peptide was selected using cursors to set ion gate timing and fragmentation occurred at a laser power about 20% higher and He was used as the collision gas for CID. Calibration for fragments was done using the P14R fragmentation calibration for the Curved field Reflectron.

Example 277

Mass Spectrometry for TEC Kinase (Compound I-4)

TEC kinase (45 pmols; Invitrogen) was incubated with (I-4) (450 pmols) for 3 hrs at 10× excess prior to tryptic digestion. Iodoacetamide was used as the alkylating agent after compound incubation. A control sample (45 pmols) was also prepared which did not have the addition of (I-4). For tryptic digests a 5 ul aliquot (7.5 pmols) was diluted with 15 ul of 0.1% TFA prior to micro C18 Zip Tipping directly onto the MALDI target using alpha cyano-4-hydroxy cinnamic acid as the matrix (5 mg/ml in 0.1% TFA:Acetonitrile 50:50).

Figure 7:
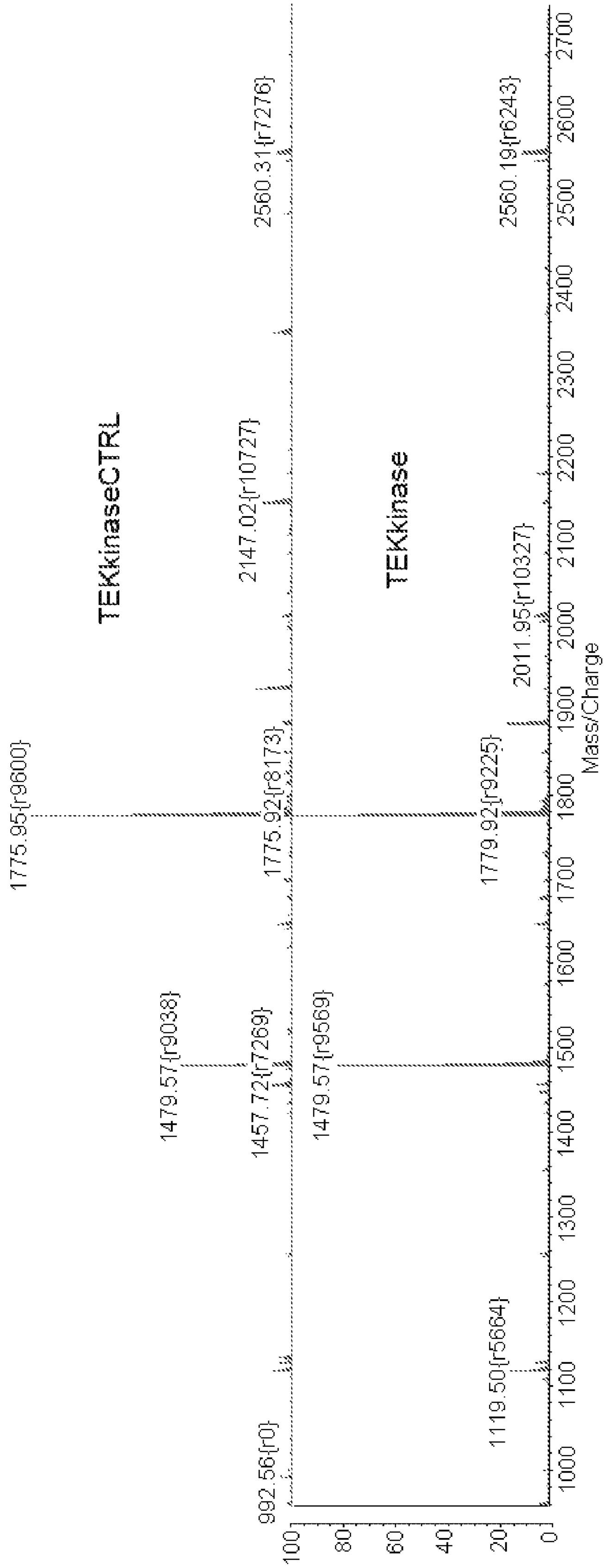
FIG. 7 depicts MS analysis confirming covalent modification of TEC kinase at Cys449 by compound I-4.
Figure 7:
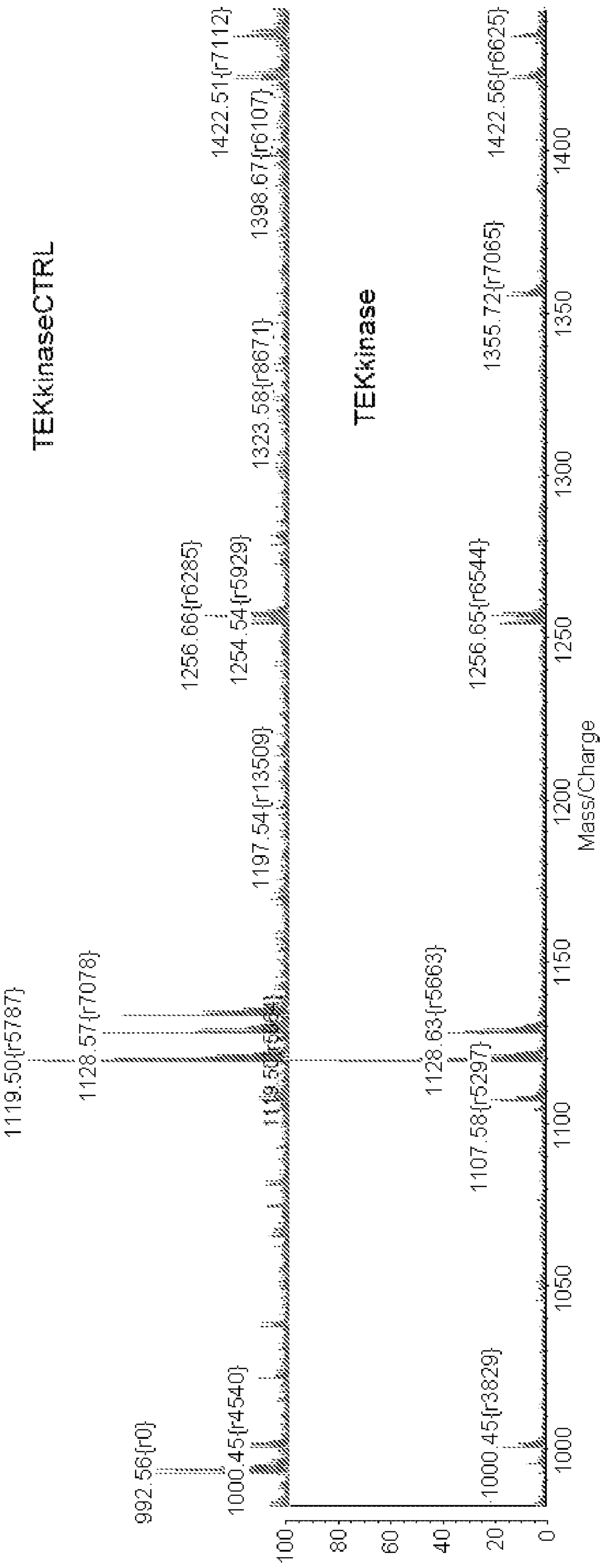

As depicted in FIG. 7, the expected peptide (G CLLNFLR) to be modified was immediately evident at MH+ of 1355.72. This is the mass to be expected when compound I-4, with an adduct mass of 420.21, is added to the peptide mass of 935.51. The peptide was also quite evident in the control sample as modified by Iodacetamide at $MH^+$ of 992.56. Interestingly the iodoacetamide modified peptide was not evident in the digest reacted with compound I-4 indicating that the reaction was complete. There was no evidence of other modified peptides.

Evidence of compound I-4 was observed at MH+ of 421.35 in the low mass range of the spectra. The fragmentation spectra of the 421.35 peak did reveal two prominent peaks that were apparent in the PSD spectra of the modified peptide at 1355.72 (See FIG. 7).

To further verify the presence of the modified peptide with compound I-4, the peptide at MH+ of 1355.72 was subjected to PSD (MS/MS) analysis. Because of the low intensity of fragments, a database correlation was not possible. However, diagnostic fragments from the I-4 molecule itself provided confidence in the identification. Diagnostic fragments at MH+ of 376.38 and 421.83 are from I-4.

Instrumental:

For tryptic digests the instrument was set in Reflectron mode with a pulsed extraction setting of 1800. Calibration was done using the Laser Biolabs Pep Mix standard (1046.54, 1296.69, 1672.92, 2093.09, 2465.20). For CID/PSD analysis the peptide was selected using cursors to set ion gate timing and fragmentation occurred at a laser power about 20% higher and He was used as the collision gas for CID. Calibration for fragments was done using the P14R fragmentation calibration for the Curved field Reflectron.

Example 278

Mass Spectrometry for TEC Kinase (Compound I-7)

TEC kinase (45 pmols; Invitrogen) was incubated with (I-7) (450 pmols) for 3 hrs at 10× excess prior to tryptic digestion. Iodoacetamide was used as the alkylating agent after compound incubation. A control sample (45 pmols) was also prepared which did not have the addition of (I-7). For tryptic digests a 5 ul aliquot (7.5 pmols) was diluted with 15 ul of 0.1% TFA prior to micro C18 Zip Tipping directly onto the MALDI target using alpha cyano-4-hydroxy cinnamic acid as the matrix (5 mg/ml in 0.1% TFA:Acetonitrile 50:50).

Figure 8:
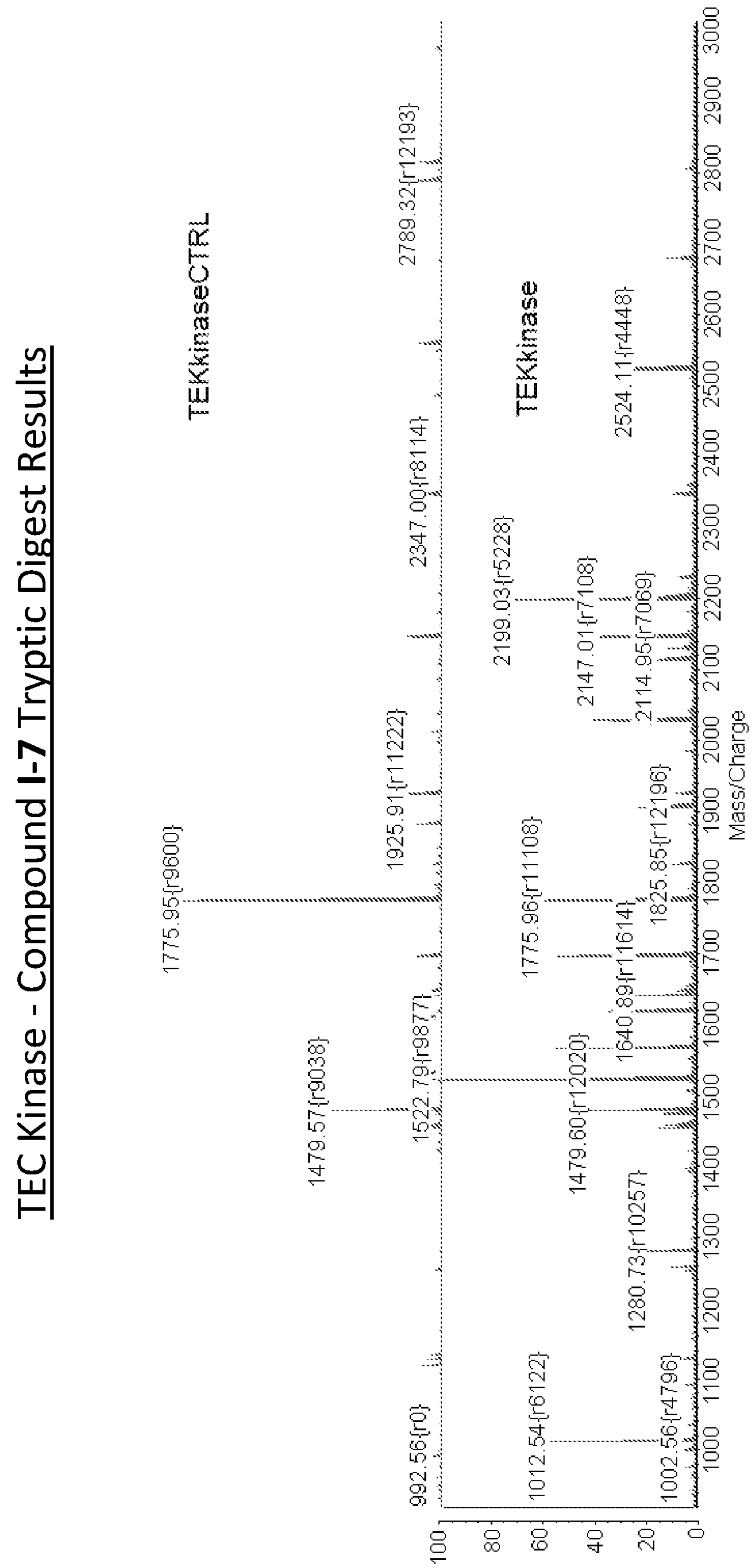
FIG. 8 depicts MS analysis confirming covalent modification of TEC kinase at Cys449 by compound I-7.
Figure 8:
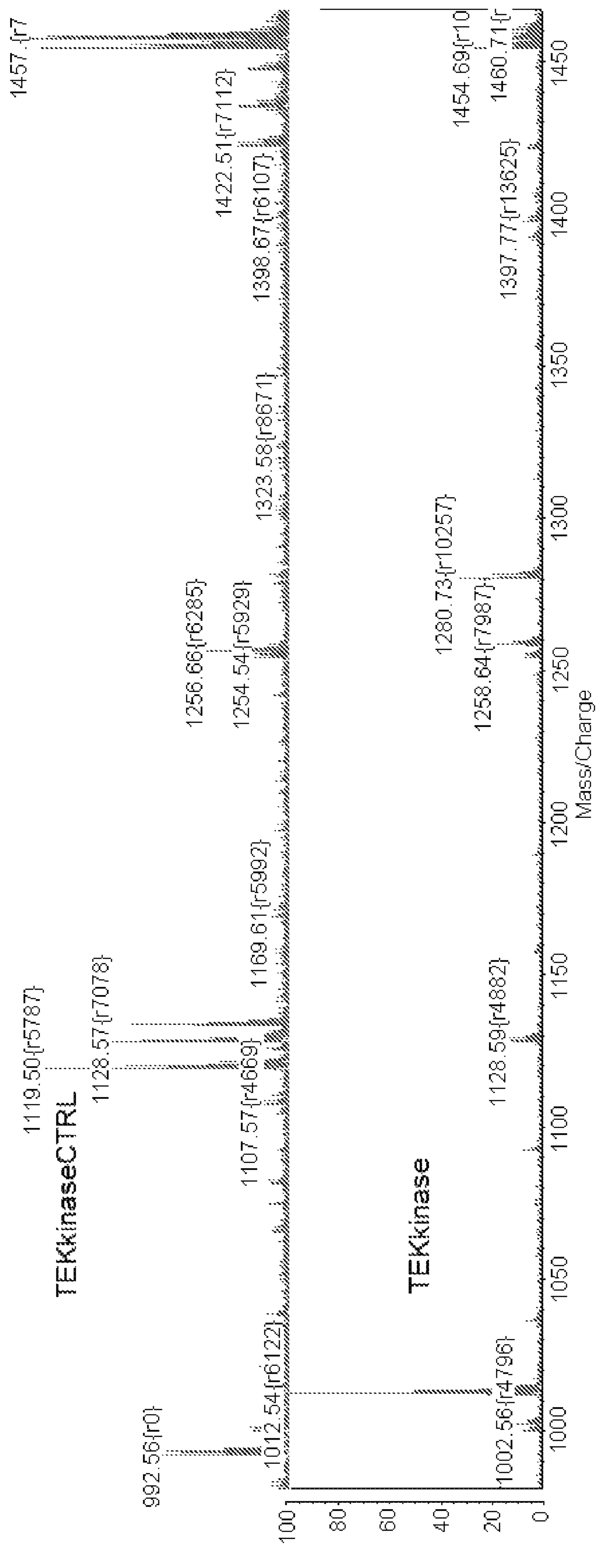
Figure 8:
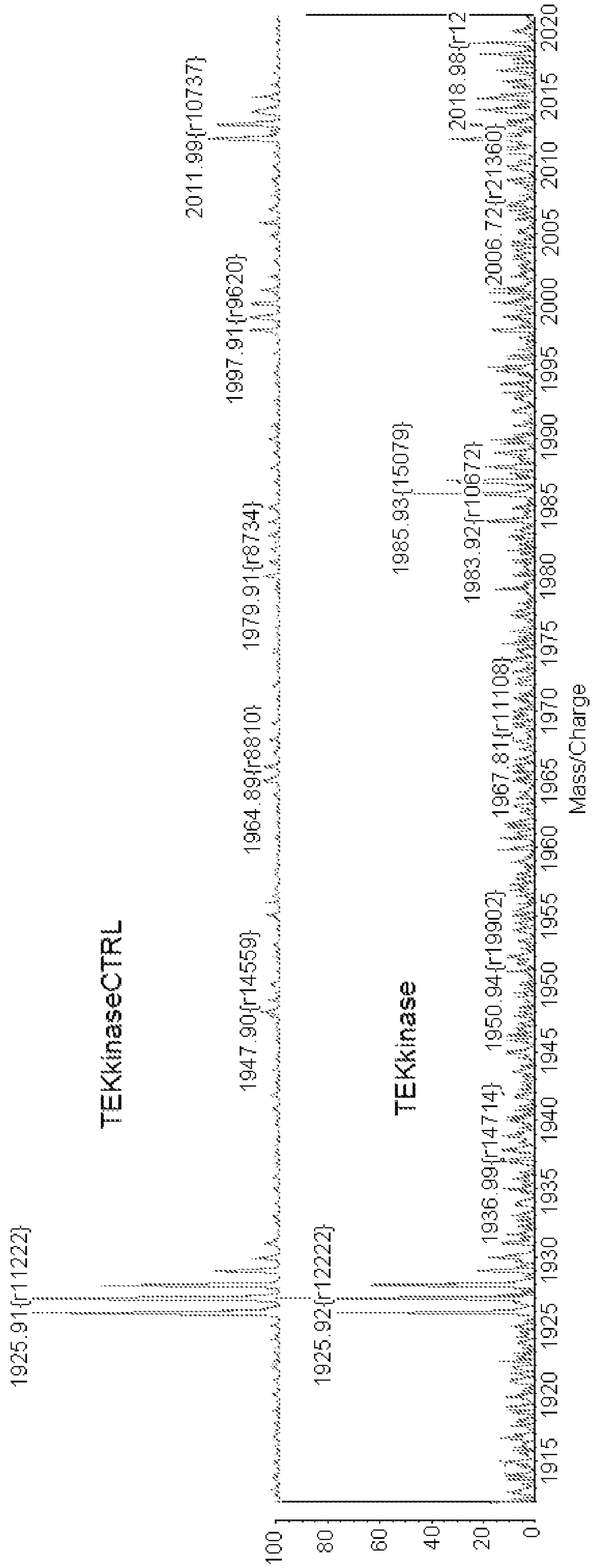

As depicted in FIG. 8, the expected peptide (GCLLNFLR) to be modified was immediately evident at MH+ of 1280.73. This is the mass to be expected when compound I-7, with an adduct mass of 345.16, is added to the peptide mass of 935.51. The peptide was also quite evident in the control sample as modified by Iodacetamide at MH+ of 992.56. Interestingly the iodoacetamide modified peptide was not evident in the digest reacted with compound I-7 indicating that the reaction was complete. There was no evidence of any other modified peptide at MH+ of 1985.93 (TIDELVECEETFGR).

Evidence of compound I-7 was observed at MH+ of 346.32 in the low mass range of the spectra. The fragmentation spectra of the 346.32 peak did show many diagnostic fragments that were apparent in the PSD spectra of the two modified peptides (See FIG. 8).

To further verify the presence of the modified peptides with compound I-7, the peptides at MH+ of 1280.73 and 1985.93 were subjected to PSD (MS/MS) analysis. A correlational analysis with the homo sapien database identified the correct peptide modified by I-7.

Instrumental:

For tryptic digests the instrument was set in Reflectron mode with a pulsed extraction setting of 2200. Calibration was done using the Laser Biolabs Pep Mix standard (1046.54, 1296.69, 1672.92, 2093.09, 2465.20). For CID/PSD analysis the peptide was selected using cursors to set ion gate timing and fragmentation occurred at a laser power about 20% higher and He was used as the collision gas for CID. Calibration for fragments was done using the P14R fragmentation calibration for the Curved field Reflectron.

Example 279

Omnia Assay Protocol for Potency Assessment Against Active Forms of ITK Kinase

This example describes continuous-read kinase assays to measure inherent potency of compound against active forms of ITK enzymes as described in Example 251 above except that the modified ITK-optimized reagent conditions are:

[ITK]=10 nM, [ATP]=25 μM, [Y6-Sox]=10 μM (ATP $K_{Mapp}$=33 μM).

Example 280

Table 14 shows the activity of selected compounds of this invention in the ITK inhibition assay. The compound numbers correspond to the compound numbers in Table 5. Compounds having an activity designated as “A” provided an $IC_{50}$≤10 nM; compounds having an activity designated as “B” provided an $IC_{50}$ 10-100 nM; compounds having an activity designated as “C” provided an $IC_{50}$ of 100-1000 nM; compounds having an activity designated as “D” provided an $IC_{50}$ of 1000-10,000 nM; and compounds having an activity designated as “E” provided an $IC_{50}$≥10,000 nM.

TABLE 14

ITK Inhibition Data

| Compound # | ITK Inhibition |
|---|---|
| I-1 | C |
| I-2 | B |
| I-4 | B |
| I-7 | A |
| I-27 | B |
| I-28 | B |
| I-33 | A |
| I-35 | B |
| I-38 | B |
| I-39 | C |
| I-40 | A |
| I-45 | B |
| I-54 | B |
| I-55 | B |
| I-56 | C |
| I-69 | B |
| I-70 | A |
| I-72 | A |
| I-73 | A |
| I-75 | A |
| I-76 | A |
| I-77 | B |
| I-78 | A |
| I-79 | B |
| I-80 | A |
| I-88 | B |
| I-89 | B |
| I-90 | A |
| I-91 | B |
| I-94 | B |
| I-95 | B |
| I-96 | B |
| I-97 | B |
| I-103 | B |
| I-105 | B |
| I-107 | C |
| I-108 | B |
| I-110 | B |
| I-114 | D |
| I-116 | A |
| I-118 | B |
| I-121 | A |
| I-122 | A |
| I-124 | A |
| I-125 | B |
| I-126 | B |
| I-128 | A |
| I-129 | A |
| I-131 | A |
| I-133 | C |
| I-134 | B |
| I-135 | B |
| I-138 | B |
| I-139 | A |
| I-140 | B |
| I-142 | A |
| I-143 | B |
| I-146 | B |
| I-147 | A |
| I-149 | D |
| I-150 | A |
| I-151 | B |
| I-152 | A |
| I-153 | A |
| I-154 | A |
| I-155 | A |
| I-156 | A |
| I-157 | A |
| I-158 | B |
| I-159 | C |

TABLE 14-continued

ITK Inhibition Data

| Compound # | ITK Inhibition |
|---|---|
| I-160 | A |
| I-162 | A |
| I-163 | D |
| I-164 | B |
| I-165 | A |
| I-166 | A |
| I-167 | A |
| I-168 | A |
| I-169 | A |
| I-170 | A |
| I-172 | B |
| I-173 | A |
| I-174 | A |
| I-176 | B |
| I-177 | B |
| I-178 | B |
| I-180 | C |
| I-182 | B |
| I-183 | C |
| I-185 | A |
| I-186 | A |
| I-188 | A |
| I-189 | A |
| I-190 | B |
| I-192 | A |
| I-194 | A |
| I-195 | B |
| I-198 | C |
| I-199 | B |
| I-200 | E |
| I-201 | C |
| I-202 | C |
| I-204 | B |
| I-207 | A |
| I-208 | B |
| I-209 | A |
| I-210 | B |
| I-215 | B |
| I-217 | B |
| I-218 | A |
| I-219 | B |
| I-220 | C |
| I-227 | A |
| I-228 | B |
| I-230 | A |
| I-233 | A |
| I-237 | A |
| I-242 | A |
| I-243 | B |
| I-244 | C |
| I-245 | A |
| I-247 | B |
| I-248 | A |
| I-249 | C |
| I-313 | B |
| I-315 | B |
| I-316 | B |
| I-318 | B |
| I-321 | C |
| I-322 | A |
| I-324 | A |
| I-329 | A |
| I-333 | B |
| I-336 | C |
| I-337 | B |
| I-342 | B |
| I-353 | B |
| I-354 | C |
| I-355 | B |
| I-356 | B |
| I-357 | B |
| I-359 | A |
| I-362 | B |

Example 281

Omnia Assay Protocol for Potency Assessment Against Active Forms of BMX Kinase

This example describes continuous-read kinase assays to measure inherent potency of compound against active forms of BMX enzymes as described in Example 251 above except that the modified BMX-optimized reagent conditions are:

[BMX]=2.5 nM, [ATP]=100 μM, [Y5-Sox]=7.5 μM (ATP $K_{Mapp}$=107 μM).

Example 282

Table 15 shows the activity of selected compounds of this invention in the BMX inhibition assay. The compound numbers correspond to the compound numbers in Table 5. Compounds having an activity designated as "A" provided an $IC_{50}$≤10 nM; compounds having an activity designated as "B" provided an $IC_{50}$ 10-100 nM; compounds having an activity designated as "C" provided an $IC_{50}$ of 100-1000 nM; compounds having an activity designated as "D" provided an $IC_{50}$ of 1000-10,000 nM; and compounds having an activity designated as "E" provided an $IC_{50}$≥10,000 nM.

TABLE 15

BMX Inhibition Data

| Compound # | BMX Inhibition |
|---|---|
| I-4 | A |
| I-7 | A |
| I-27 | A |
| I-28 | A |
| I-33 | A |
| I-35 | A |
| I-38 | A |
| I-39 | A |
| I-40 | A |
| I-45 | A |
| I-126 | A |
| I-128 | A |
| I-129 | A |
| I-131 | A |
| I-133 | A |
| I-134 | A |
| I-135 | A |
| I-244 | A |
| I-245 | A |
| I-247 | A |
| I-248 | A |

Example 283

Cloning, Expression and Purification of EGFR-WT and EGFR C797S Mutant Using Baculovirus and Insect Cells (i) Subcloning of EGFR-WT and Mutant Kinase Domains Amino acids 696 to 1022 of the EGFR-WT kinase domain (NM_005228, NP_005219.2) was subcloned into the NcoI and HindIII sites of the pFastHTa vector (Invitrogen, Carlsbad, Calif.). To make the EGFR-mutant protein, the cysteine at position 797 was changed to a serine using the Stratagene QuikChange kit (Stratagene, Cedar Creek, Tex.), according to manufacturer's instructions.

(ii) Expression

P1 baculovirus stocks were generated in SF9 cells via Blue Sky Biotech's suspension transfection protocol (Worcester, Mass.). Expression analysis was conducted in 125 ml culture of SF21 insect cells ((grown in SF900I SFM (Invitrogen cat #10902-088), supplemented with 10 mg/L gentamicin (Invitrogen, Carlsbad, Calif., cat #15710-064))

using a viral load of 0.1 ml of virus per 100 ml of cell suspension. Expression was optimized using Blue Sky Biotech's Infection Kinetics Monitoring system (Worcester, Mass.).

(iii) Purification

Infected insect cells were pelleted. Cell pellets were resuspended in Blue Sky Biotech's lysis buffer (Worcester, Mass., 1× WX; solubilization buffer, containing a protease inhibitor cocktail of leupeptin, pepstatin, PMSF, aprotinin and EDTA) at a ratio of 10 ml per gram of wet cell paste. Cells were lysed by sonication and the lysate was clarified by centrifugation at 9,000 RPM for 30 minutes in a GSA rotor. 500 μl bed volume of NiNTA resin (Qiagen, Valencia, Calif.) was added to the supernatants and batch bound for two hours with constant agitation. The material was transferred by gravity into an empty 2 ml column. The column was washed with 2 ml of wash buffer (Blue Sky Biotech, Worcester, Mass., 1× WX, 25 mM imidazole). The protein was eluted with 1× WX+imidazole at varying concentrations: Elution 1: 75 mM imidazole (2 fractions, 1 column volume); Elution 2: 150 mM imidazole (2 fractions, 1 column volume); Elution 3: 300 mM imidazole (2 fractions, 1 column volume). All the elution fractions were analyzed by SDS page followed by Coomassie staining and Western Blotting using anti-penta-his antibody (Qiagen, Valencia, Calif.). The carboxy-terminal six-histidine "tag" was removed from some of the purified protein using AcTEV Protease kit (Invitrogen, Carlsbad, Calif., Cat #12575-015), following manufacturer's instructions. All the samples (pre- and post-Tev cut) were analyzed by SDS page followed by Coomassie staining and Western Blotting, as described above.

Example 284

Mass Spectrometry for EGFR

EGFR wild type and EGFR (mutant C797S) is incubated with 10-fold excess of test compound for 1 hr and 3 hrs. 1 μl aliquots of the samples (total volume 5-8 ul) are diluted with 10 ul of 0.1% TFA prior to micro C4 ZipTipping directly onto the MALDI target using Sinapinic acid as the desorption matrix (10 mg/ml in 0.1% TFA:Acetonitrile 50:50). Intact mass measurement reveals that the wild type has a nominal mass of about 37557 and the mutant slightly lower at 37500. Reactivity is only observed for the wild type EGFR with a new peak appearing at a mass consistent with a single site covalent modification with test compound which has a mass of 410 Da.

Example 285

Omnia Assay Protocol for Potency Assessment Against EGFR (WT) and EGFR (T790M/L858R) Active Enzymes The Omnia Assay Protocol for potency assessment against EGFR is performed as described in Example 251 above except that the EGFR-WT- and EGFR T790M/L858R-modified optimized reagent conditions are:

[EGFR-WT]=5 nM, [ATP]=15 mM, [Y12-Sox]=5 mM (ATP KMapp~12 mM); and [EGFR-T790M/L858R]=3 nM, [ATP]=50 mM, [Y12-Sox]=5 mM (ATP KMapp~45 mM).

Example 286

Tables 16 and 17 show the activity of selected compounds of this invention in the EGFR inhibition assay. Table 16 shows wild-type EGFR data; Table 17 shows data for two EGFR mutants. The compound numbers correspond to the compound numbers in Table 5. Compounds having an activity designated as "A" provided an $IC_{50}$≤10 nM; compounds having an activity designated as "B" provided an $IC_{50}$ 10-100 nM; compounds having an activity designated as "C" provided an $IC_{50}$ of 100-1000 nM; compounds having an activity designated as "D" provided an $IC_{50}$ of 1000-10,000 nM; and compounds having an activity designated as "E" provided an $IC_{50}$≥10,000 nM.

TABLE 16

EGFR Wild Type Inhibition Data

| Compound # | EGFR |
|---|---|
| I-1 | A |
| I-2 | B |
| I-3 | A |
| I-4 | A |
| I-5 | A |
| I-7 | A |
| I-8 | A |
| I-9 | B |
| I-10 | B |
| I-11 | A |
| I-23 | C |
| I-27 | B |
| I-28 | B |
| I-33 | A |
| I-34 | C |
| I-35 | B |
| I-38 | B |
| I-39 | D |
| I-45 | C |
| I-56 | B |
| $I^R$-7 | D |
| I-54 | B |
| I-55 | C |
| I-60 | D |
| I-69 | B |
| I-70 | B |
| I-71 | B |
| I-72 | A |
| I-74 | C |
| I-75 | A |
| I-76 | A |
| I-77 | B |
| I-78 | A |
| I-79 | C |
| I-80 | B |
| I-81 | A |
| I-82 | A |
| I-83 | B |
| I-84 | A |
| I-85 | D |
| I-86 | D |
| I-87 | B |
| I-88 | B |
| I-89 | B |
| I-90 | A |
| I-91 | B |
| I-92 | B |
| I-93 | B |
| I-94 | C |
| I-95 | C |
| I-96 | B |
| I-97 | B |
| I-98 | C |
| I-99 | A |
| I-100 | D |
| I-101 | B |
| I-102 | C |
| I-103 | B |
| I-104 | A |
| I-105 | B |
| I-106 | D |
| I-107 | C |
| I-108 | C |
| I-109 | A |
| I-110 | B |

TABLE 16-continued

EGFR Wild Type Inhibition Data

| Compound # | EGFR |
|---|---|
| I-111 | C |
| I-112 | B |
| I-113 | C |
| I-114 | D |
| I-115 | D |
| I-116 | A |
| I-117 | D |
| I-118 | B |
| I-119 | C |
| I-120 | A |
| I-121 | B |
| I-122 | B |
| I-123 | B |
| I-124 | B |
| I-125 | C |
| I-126 | B |
| I-127 | C |
| I-128 | B |
| I-129 | B |
| I-130 | B |
| I-131 | A |
| I-132 | B |
| I-133 | C |
| I-134 | B |
| I-135 | B |
| I-136 | C |
| I-137 | E |
| I-138 | B |
| I-139 | B |
| I-140 | B |
| I-141 | B |
| I-142 | B |
| I-143 | B |
| I-144 | A |
| I-145 | A |
| I-146 | D |
| I-147 | A |
| I-148 | D |
| I-149 | D |
| I-150 | A |
| I-151 | B |
| I-152 | B |
| I-153 | B |
| I-154 | B |
| I-155 | A |
| I-156 | A |
| I-157 | A |
| I-158 | B |
| I-159 | A |
| I-160 | A |
| I-161 | B |
| I-162 | A |
| I-163 | D |
| I-164 | B |
| I-165 | C |
| I-166 | C |
| I-167 | A |
| I-168 | B |
| I-169 | A |
| I-170 | B |
| I-171 | B |
| I-172 | C |
| I-173 | A |
| I-174 | A |
| I-175 | D |
| I-176 | A |
| I-177 | A |
| I-178 | A |
| I-179 | E |
| I-180 | C |
| I-181 | A |
| I-182 | A |
| I-183 | D |
| I-184 | A |
| I-185 | B |
| I-186 | A |

TABLE 16-continued

EGFR Wild Type Inhibition Data

| Compound # | EGFR |
|---|---|
| I-187 | C |
| I-188 | A |
| I-189 | B |
| I-190 | C |
| I-191 | D |
| I-192 | B |
| I-193 | D |
| I-194 | B |
| I-195 | B |
| I-196 | D |
| I-197 | C |
| I-198 | A |
| I-199 | B |
| I-200 | A |
| I-201 | B |
| I-202 | C |
| I-203 | C |
| I-204 | B |
| I-205 | B |
| I-206 | D |
| I-207 | C |
| I-208 | B |
| I-209 | B |
| I-210 | B |
| I-211 | D |
| I-212 | D |
| I-213 | C |
| I-214 | C |
| I-215 | B |
| I-216 | D |
| I-217 | B |
| I-218 | A |
| I-219 | B |
| I-220 | C |
| I-221 | B |
| I-222 | C |
| I-223 | D |
| I-224 | C |
| I-225 | D |
| I-226 | D |
| I-227 | C |
| I-228 | B |
| I-229 | D |
| I-230 | B |
| I-231 | E |
| I-232 | D |
| I-233 | A |
| I-234 | E |
| I-235 | E |
| I-236 | D |
| I-237 | B |
| I-238 | E |
| I-241 | D |
| I-242 | B |
| I-243 | B |
| I-244 | C |
| I-245 | A |
| I-246 | D |
| I-247 | B |
| I-248 | A |
| I-249 | C |
| I-277 | B |
| I-312 | B |
| I-313 | B |
| I-315 | B |
| I-316 | B |
| I-318 | B |
| I-321 | C |
| I-322 | B |
| I-323 | E |
| I-324 | B |
| I-325 | D |
| I-326 | C |
| I-327 | B |
| I-328 | A |
| I-329 | B |

TABLE 16-continued

| EGFR Wild Type Inhibition Data | |
|---|---|
| Compound # | EGFR |
| I-330 | E |
| I-331 | D |
| I-332 | B |
| I-333 | B |
| I-334 | A |
| I-335 | A |
| I-336 | C |
| I-337 | B |
| I-338 | B |
| I-339 | A |
| I-341 | C |
| I-342 | C |
| I-343 | C |
| I-344 | C |
| I-345 | C |
| I-346 | C |
| I-347 | B |
| I-348 | B |
| I-349 | B |
| I-350 | A |
| I-351 | C |
| I-352 | A |
| I-353 | B |
| I-354 | C |
| I-355 | B |
| I-356 | C |
| I-357 | C |
| I-358 | C |
| I-359 | B |
| I-360 | A |
| I-362 | B |
| I-363 | A |
| I-369 | C |
| I-370 | A |
| I-371 | B |
| I-372 | B |
| I-373 | B |
| I-374 | A |
| I-375 | D |
| I-376 | B |
| I-377 | B |
| I-378 | B |
| I-379 | C |
| I-381 | A |
| I-382 | C |

TABLE 17

| EGFR mutant (T790M/L858R and T790M) Inhibition Data | | |
|---|---|---|
| Compound # | EGFR (T790M/L858R) | EGFR (T790M) |
| I-1 | A | — |
| I-2 | A | A |
| I-3 | A | A |
| I-4 | A | A |
| I-5 | A | — |
| I-7 | A | — |
| I-8 | A | — |
| I-9 | B | — |
| I-10 | B | — |
| I-11 | A | — |
| I-23 | B | — |
| I-35 | A | — |
| I-38 | A | — |
| I-39 | C | — |
| I-56 | A | B |
| $I^R$-7 | D | — |
| I-96 | A | A |

Example 287

Cellular Assays for EGFR Activity

Compounds were assayed in A431 human epidermoid carcinoma cells using a method substantially similar to that described in Fry, et al., *Proc. Natl. Acad. Sci. USA* Vol 95, pp 12022-12027, 1998. Specifically, A431 human epidermoid carcinoma cells were grown in 6-well plates to 90% confluence and then incubated in serum-free media for 18 hr. Duplicate sets of cells were treated with 1 μM designated compound for 2, 5, 10, 30, or 60 min. Cells were washed free of the compound with warmed serum-free medium, incubated for 2 hr, washed again, incubated another 2 hr, washed again, and then incubated another 2 hr washed again and incubated for additional 2 hr and then stimulated with 100 ng/ml EGF for 5 min. Extracts were made as described Fry, et al.

Compounds were assayed in A431 human epidermoid carcinoma cells using a method substantially similar to that described in Fry, et al. Specifically, A431 human epidermoid carcinoma cells were grown in 6-well plates to 90% confluence and then incubated in serum-free media for 18 hr. Cells were then treated with 10, 1, 0.1, 0.01, or 0.001 μM test compound for 1 hr. Cells were then stimulated with 100 ng/ml EGF for 5 min, and extracts were made as described in Fry, et al. 20 ug total protein from lysates were loaded on gel and blots were probed for either EGFR phosphorylation or p42/p44 Erk phosphorylation.

Example 288

Washout Experiment for EGFR Activity

Figure 10:
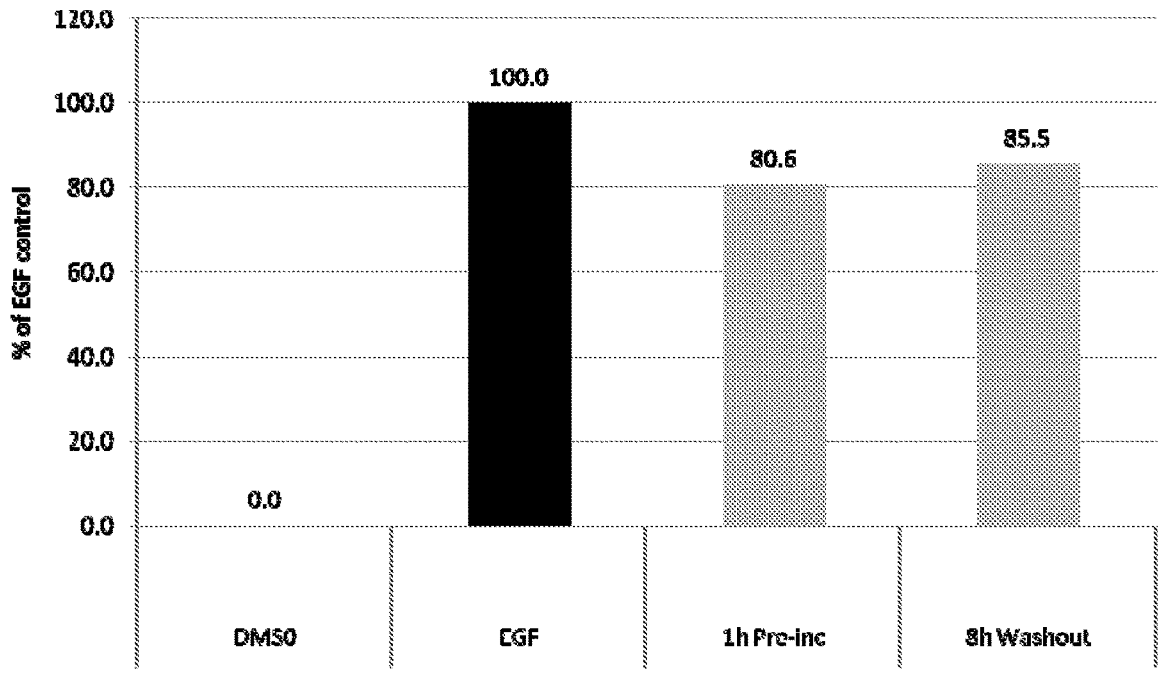
FIG. 10 depicts the results of compound I-7 in a "washout" experiment as compared to results of an EGF control in A431 cells containing EGFR wild type.

A431 human epidermoid carcinoma cells were grown in 6-well plates to ’90% confluence and then incubated in serum-free media for 18 hr. Duplicate sets of cells were treated with 1 μM designated compound for 1 hr. One set of cells was then stimulated with 100 ng/ml EGF for 5 min, and extracts were made as described. The other set of cells was washed free of compound I-7 with warmed compound-free medium, incubated for 2 hr, washed again, incubated another 2 hr, washed again, and then incubated another 2 hr washed again and incubated for additional 2 hr and then stimulated with EGF. The results of this experiment with compound I-7 are depicted in FIG. 10.

Example 289

Washout Experiment in HCC827 Cells Containing EGFR Deletion Mutant HCC827

Cells (ATCC, Manassas, Va.) were plated in Growth Media (RPMI 1640) supplemented with 10% FBS, 10 uM HEPES, 2 mM 1-glutamine, 1 mM Na Pyruvate and pen/strep (Invitrogen, Carlsbad, Calif.) at a density of $2.5\times10^5$ cells per well in 6 well tissue culture plates. Twenty four hours later the cells were washed 2× with PBS then serum starved overnight in Basal Media (Growth Media without FBS).

The following morning the media was removed and 2 ml fresh Basal Media containing 1 uM compound in 0.1% DMSO was added to duplicate wells. At 1 hour, one well of cells was treated with 100 ng/ml of EGF for 5 minutes, rinsed with PBS, then lysed by scraping into 75 ul of Cell Extraction Buffer (Invitrogen, Carlsbad, Calif.) plus PhosS-TOP Phosphatase Inhibitor and Complete Protease Inhibitor (Roche, Indianapolis, Ind.) for the 0 h time point. The compound was removed from the second set of wells and they were washed 2× with Basal Media. The cells were washed with Basal Media every 2 hours until 8 hours when they were treated with EGF and lysed as at the 0 h time point.

Figure 9:
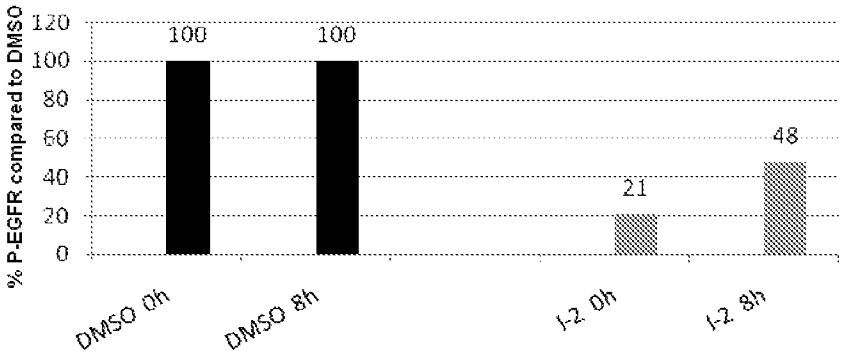
FIG. 9 depicts the results of compound I-2 in a "washout" experiment as compared to results of compound I-4 and compound I-7 in the same "washout" experiment in HCC827 cells containing EGFR deletion mutant.
Figure 9:
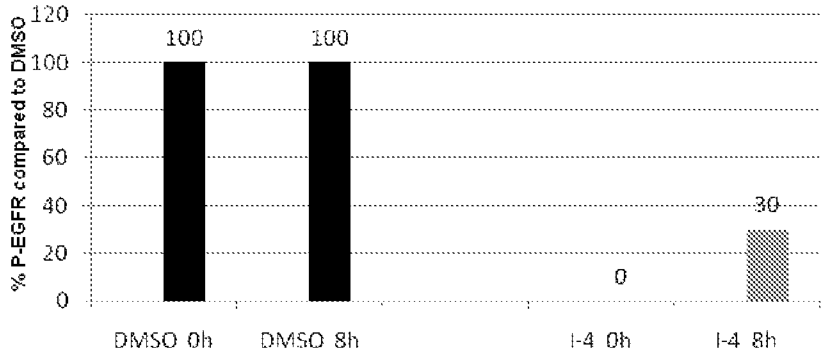
Figure 9:
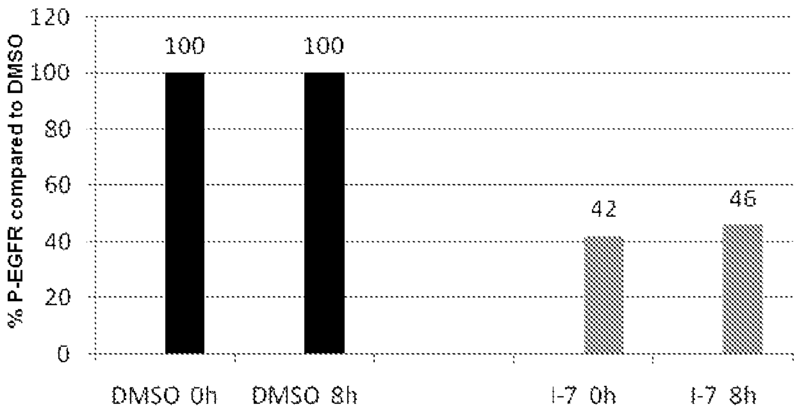

Lysate protein concentrations were determined by BCA Assay (Pierce, Rockford, Ill.) and 10 ug of each lysate was separated by 4-12% gradient SDS-PAGE (Invitrogen), transferred to Immobilon-FL membrane (Millipore) and probed with rabbit anti-Phospho-EGFR (Tyr1068) (Zymed-now Invitrogen) and mouse anti-EGFR (Cell Signaling Technologies, Danvers, Mass.) antibodies. Phospho-protein signals were quantitated using Odyssey Infrared Imaging (Li-Cor Biosciences, Lincoln, Nebr.). The results of this experiment are depicted in FIG. 9 where it shows compound I-2 compared to results of compound I-4 and compound I-7 in the same "washout" experiment.

Example 290

Mass Spectrometry for ERBB4

Erbb4 kinase domain (Upstate) was incubated with compound for 60 minutes at 10-fold excess of compound I-4 and I-11 to protein. 1 μl aliquots of the samples (total volume of 4.24 ul) were diluted with 10 μl of 0.1% TFA prior to micro C4 ZipTipping directly onto the MALDI target using Sinapinic acid as the desorption matrix (10 mg/ml in 0.1% TFA:Acetonitrile 50:50). For intact protein mass measurement the instrument was set in Linear mode using a pulsed extraction setting of 16,952 for the myoglobin standard used to calibrate the instrument (Shimadzu Axima $TOF^2$).

Intact ErbB4 protein occurs at MH+ of 35850 with corresponding sinapinic (matrix) adducts occurring about 200 Da higher. A stoichiometric incorporation of the test compound (I-4 and I-11) (Mw of 410 Da) produced a new mass peak which is approximately 410 Da higher (MH+ of 36260). This is consistent with covalent modification of ErbB4 with compounds I-4 and I-11.

Example 291

ErbB1, ErbB2 and/or ErbB4 Kinase Inhibition

Compounds of the present invention were assayed as inhibitors of one or more of ErbB1, ErbB2, and/or ErbB4 in a manner substantially similar to the method described by Invitrogen Corp (Invitrogen Corporation, 1600 Faraday Avenue, Carlsbad, California, Calif.; http://www.invitrogen.com/downloads/Z-LYTE_Brochure_1205.pdf) using the Z'-LYTE™ biochemical assay procedure or similar biochemical assay. The T-LYTE™ biochemical assay employs a fluorescence-based, coupled-enzyme format and is based on the differential sensitivity of phosphorylated and non-phosphorylated peptides to proteolytic cleavage. Using this assay, Compound I-56 was found to inhibit ERBB1 with an $IC_{50}$ of 2,233 nM. Using this assay, Compound I-56 was found to inhibit ERBB4 (HER4) with an $IC_{50}$ of 2,165 nM.

Example 292

Mass Spectrometry for Janus-3 Kinase (JAK3)

JAK3 kinase (33 pmols; Invitrogen) was incubated with (I-7) (327 pmols) for 3 hrs at 10× excess prior to tryptic digestion. Iodoacetamide was used as the alkylating agent after compound incubation. For tryptic digests a 5 ul aliquot (5.5 pmols) was diluted with 15 ul of 0.1% TFA prior to micro C18 Zip Tipping directly onto the MALDI target using alpha cyano-4-hydroxy cinnamic acid as the matrix (5 mg/ml in 0.1% TFA:Acetonitrile 50:50).

Figure 11:
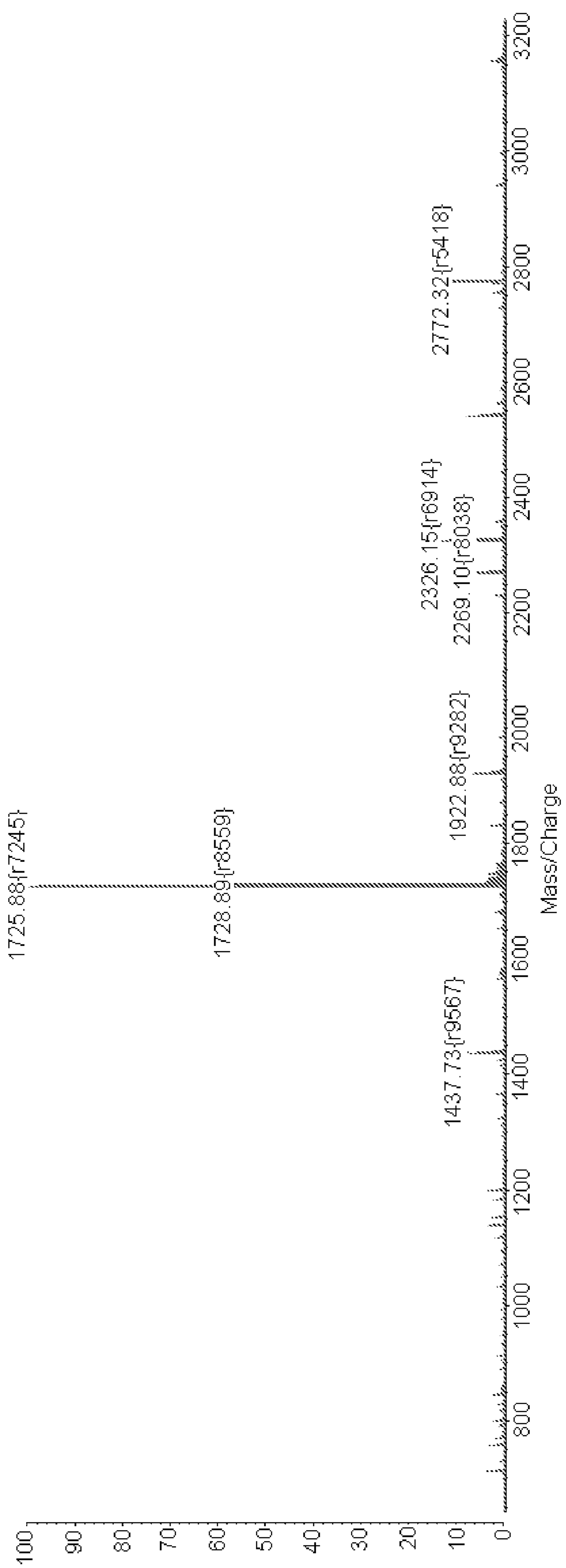
FIG. 11 depicts MS analysis confirming covalent modification of JAK-3 kinase at Cys909 by compound I-7.

As depicted in FIG. 11, the expected peptide (LVMEYLPSGCLR) to be modified was immediately evident as the largest peak at MH+ of 1725.88. This is the mass to be expected when compound I-7, with an adduct mass of 345.16, is added to the peptide mass of 1380.70. Interestingly the iodoacetamide modified peptide was not evident at MH+ of 1437.73 in the digest reacted with compound I-7 indicating that the reaction was not entirely complete. There was also evidence for a number of other modified peptides, however, their signals were low.

Evidence of compound I-7 was observed at MH+ of 346.12 in the low mass range of the spectra. The fragmentation spectra of the 346.12 peak did not show diagnostic fragments that were apparent in the PSD spectra of the modified peptides (See FIG. 11).

To further verify the presence of the modified peptides with compound I-7, the peptides at MH+ of 1725.88 and 1118.55 were subjected to PSD (MS/MS) analysis. A correlational analysis with the homo sapien database identified the correct peptides as being modified by I-7. Compound I-11 was also tested using the same procedure and showed measurable modification.

Instrumental:

For tryptic digests the instrument was set in Reflectron mode with a pulsed extraction setting of 2200. Calibration was done using the Laser Biolabs Pep Mix standard (1046.54, 1296.69, 1672.92, 2093.09, 2465.20). For CID/PSD analysis the peptide was selected using cursors to set ion gate timing and fragmentation occurred at a laser power about 20% higher and He was used as the collision gas for CID. Calibration for fragments was done using the P14R fragmentation calibration for the Curved field Reflectron.

Example 293

Omnia Assay Protocol for Potency Assessment Against the Active Form of JAK3:

The Omnia Assay Protocol for potency assessment against JAK3 was performed in a substantially similar manner as that described in Example 251 above except that the modified JAK3-optimized reagent conditions were:

[JAK3]=5 nM, [ATP]=5 μM, [Y12-Sox]=5 μM (ATP KMapp~5 μM).

Example 294

Table 18 shows the activity of selected compounds of this invention in the JAK3 inhibition assay. The compound numbers correspond to the compound numbers in Table 5. Compounds having an activity designated as "A" provided an $IC_{50} \leq 10$ nM; compounds having an activity designated as "B" provided an $IC_{50}$ 10-100 nM; compounds having an activity designated as "C" provided an $IC_{50}$ of 100-1000 nM; compounds having an activity designated as "D" provided an $IC_{50}$ of 1000-10,000 nM; and compounds having an activity designated as "E" provided an $IC_{50} \geq 10{,}000$ nM.

TABLE 18

JAK3 Inhibition Data

| Compound # | JAK3 Inhibition |
|---|---|
| I-1 | A |
| I-2 | A |
| I-3 | A |
| I-4 | A |
| I-5 | A |
| I-7 | A |
| I-8 | A |
| I-9 | A |
| I-10 | B |
| I-11 | A |

TABLE 18-continued

| JAK3 Inhibition Data | |
|---|---|
| Compound # | JAK3 Inhibition |
| I-23 | A |
| I-27 | B |
| I-28 | A |
| I-33 | A |
| I-34 | B |
| I-35 | A |
| I-38 | B |
| I-39 | A |
| I-40 | A |
| I-45 | A |
| I-56 | B |
| $I^R$-7 | D |
| I-96 | A |
| I-182 | A |
| I-238 | D |
| I-241 | C |
| I-242 | A |
| I-243 | A |
| I-244 | A |
| I-245 | A |
| I-246 | C |
| I-247 | A |
| I-248 | A |
| I-323 | E |
| I-360 | A |

Example 295

JAK3 Cellular Assay Protocol in CTLL2 Cells

Figure 12:
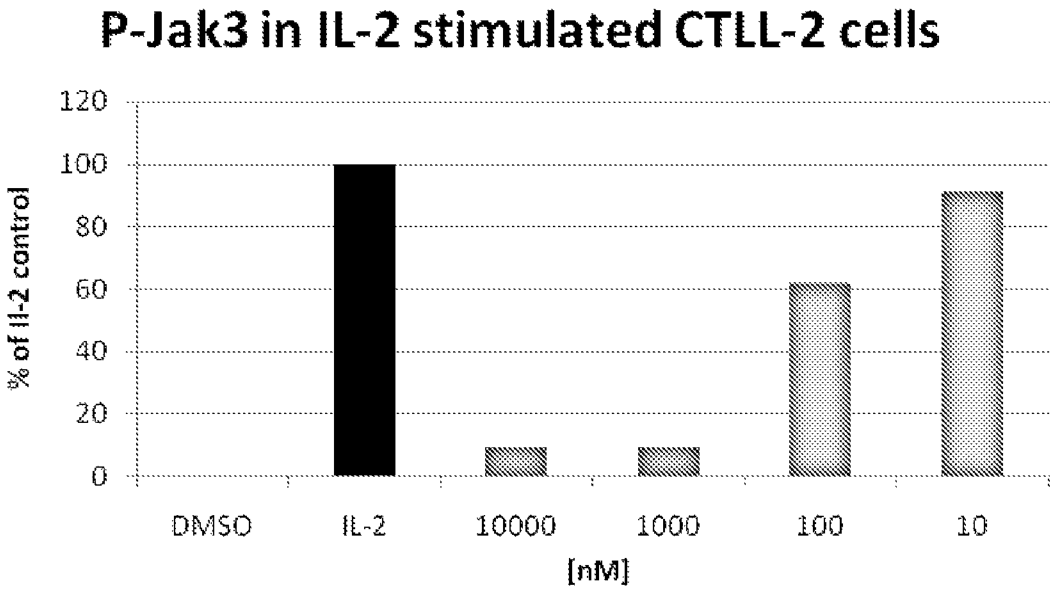
FIG. 12 depicts dose-response inhibition of P-Stat5 with compound I-2 in IL-2 stimulated CTLL-2 cells; and dose-response inhibition of P-JAK-3 with compound I-2 in IL-2 stimulated CTLL-2 cells.
Figure 12:
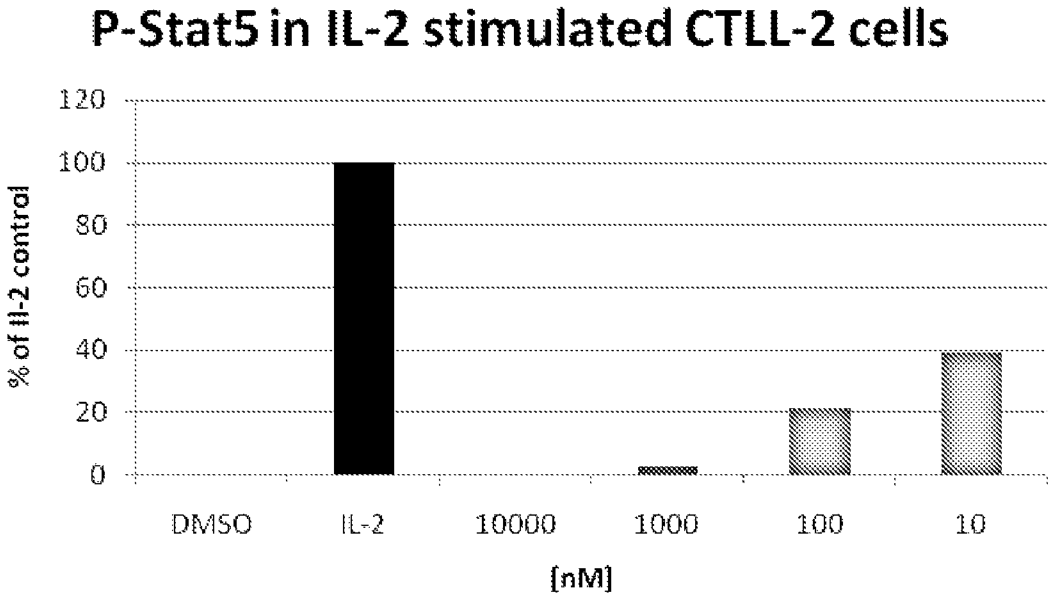
Figure 13:
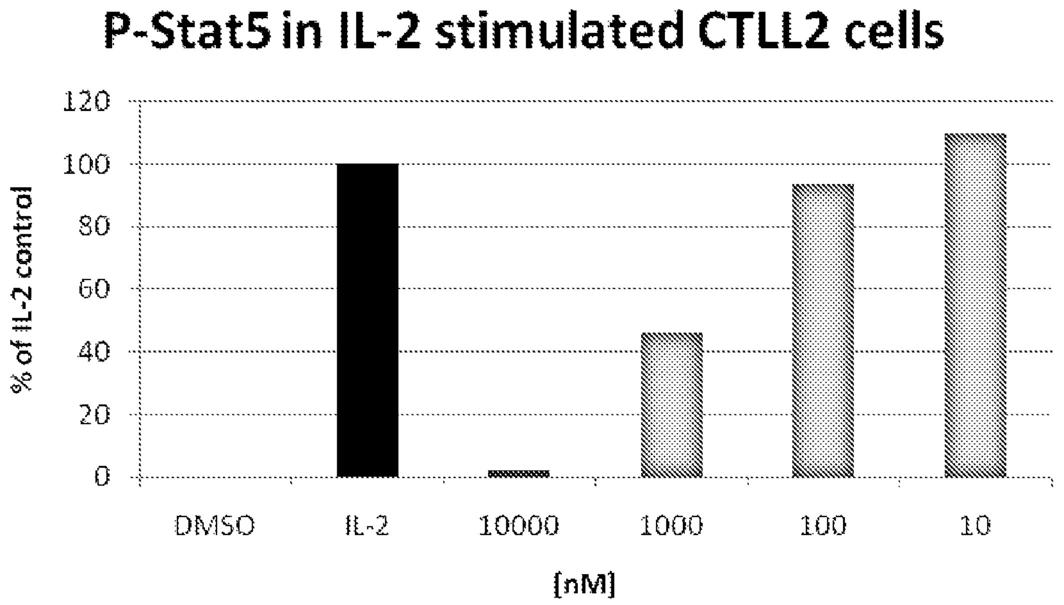
FIG. 13 depicts dose-response inhibition of P-Stat5 with compound I-4 in IL-2 stimulated CTLL-2 cells; and dose-response inhibition of P-JAK-3 with compound I-4 in IL-2 stimulated CTLL-2 cells.
Figure 13:
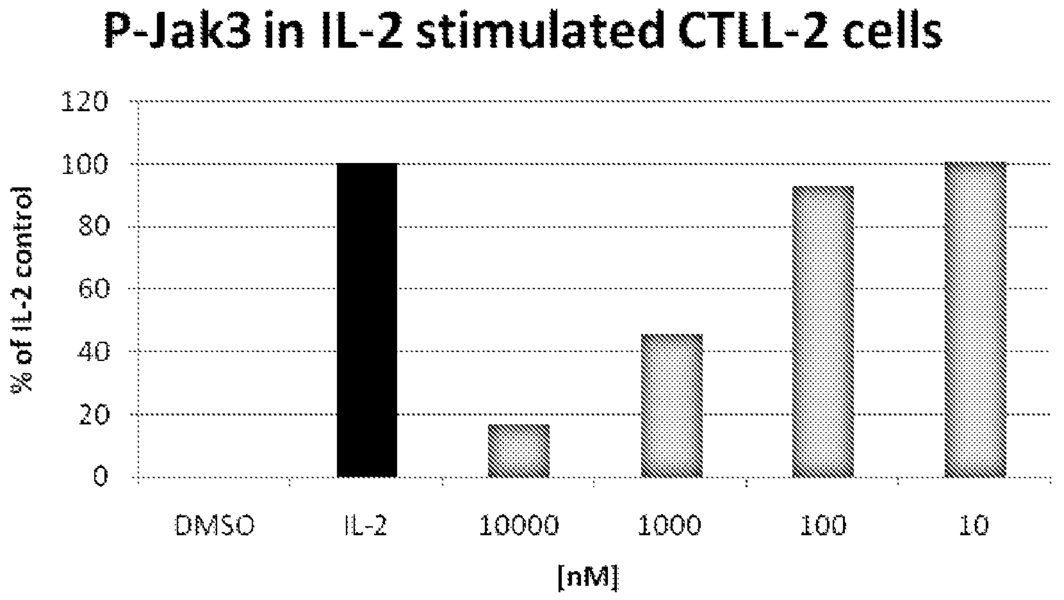
Figure 14:
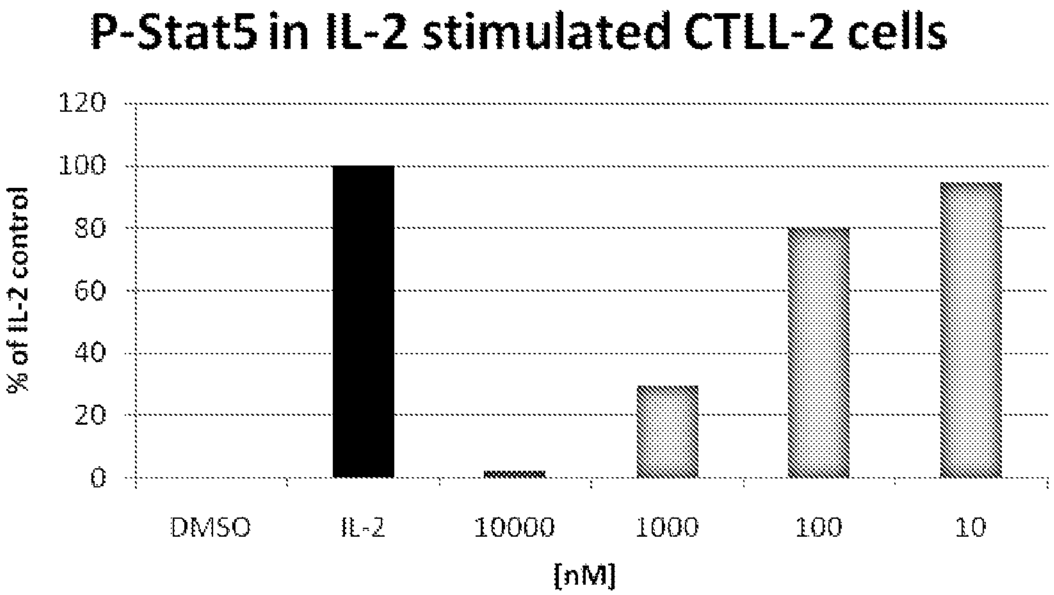
FIG. 14 depicts dose-response inhibition of P-Stat5 with compound I-7 in IL-2 stimulated CTLL-2 cells.

Compounds I-2, I-4 and I-7 were tested in the following protocol. CTLL2: murine lymphoma cell line ATCC: TIB-214. $5\times10^6$ cells/sample were IL-2 starved in RPMI-1640 media for 2 hours. Designated samples were then treated with compound for 90 minutes. Samples, except DMSO control were then stimulated with 100 nM IL-2 for 10 minutes. Samples were lysed and subjected to Western Analysis. The results are displayed in FIG. 12, FIG. 13 and FIG. 14.

Example 296

BTK Occupancy in Ramos Cells With I-7 and I-215 Using Streptavidin Beads

Figure 16:
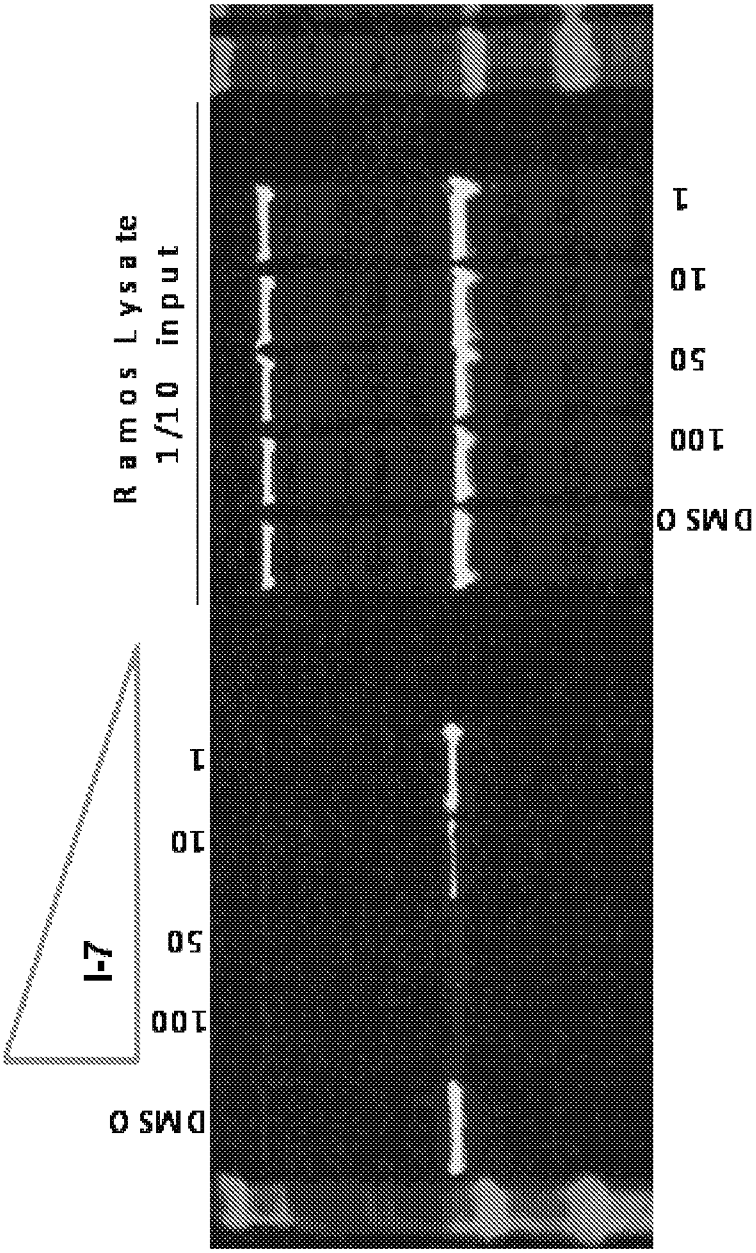
FIG. 16 depicts a Western blot showing BTK protein available to the probe compound I-215 after treating with varying amounts of I-7.
Figure 17:
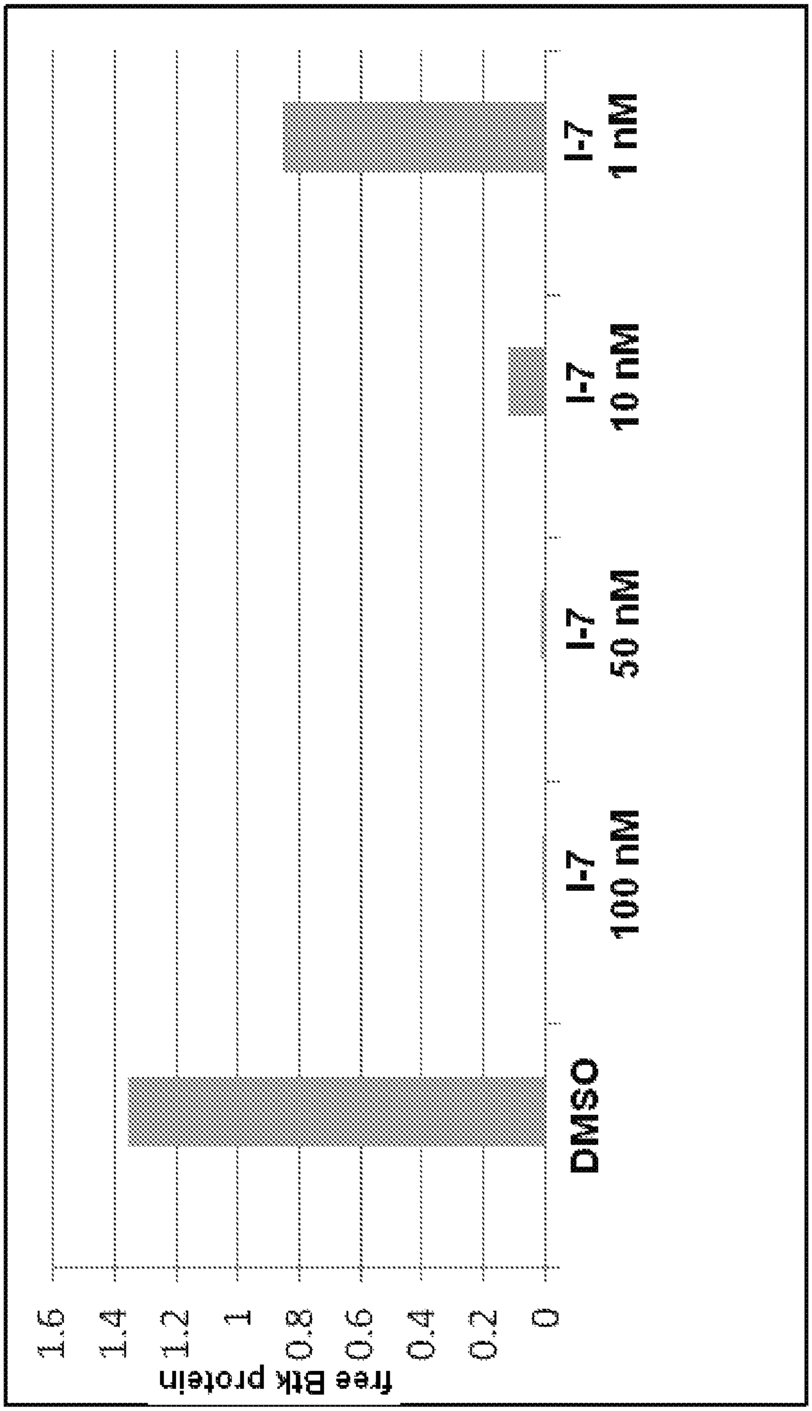
FIG. 17 depicts quantitation of the Western blot results in FIG. 16.

Ramos cells were incubated with 0.1, 0.05, 0.01, or 0.001 μM I-7 in serum free media for 1 hour at 37° C. The cells were pelleted by centrifugation and lysed in Cell Extraction buffer (Invitrogen) for 10 minutes on ice, centrifuged (10 minutes at 14,000 rpm) and the supernatant was collected. Cell lysates were incubated with 1 μM I-215 for 1 hour at room temperature, then incubated with streptavidin-coupled agarose beads (ThermoFisher) overnight at 4° C. The beads were washed three times with lysis buffer and the bound proteins were boiled off the beads at 95° C. for 5 minutes in 4×LDS Sample Buffer. The amount of BTK associated with the probe I-215 was assessed by BTK western blot. All values were normalized to the DMSO-treated sample which is set to 100%. FIG. 16 shows the western blot; FIG. 17 shows quantitation of FIG. 16 demonstrating unoccupied BTK protein is available to the probe I-215 when the cells have been exposed to low concentrations (10 nM, 1 nM) of I-7 but at higher concentrations of I-7 the BTK protein is fully occupied and cannot interact with I-215.

Example 297

Washout Experiment with I-7 and Probe Compound I-215

Figure 18:
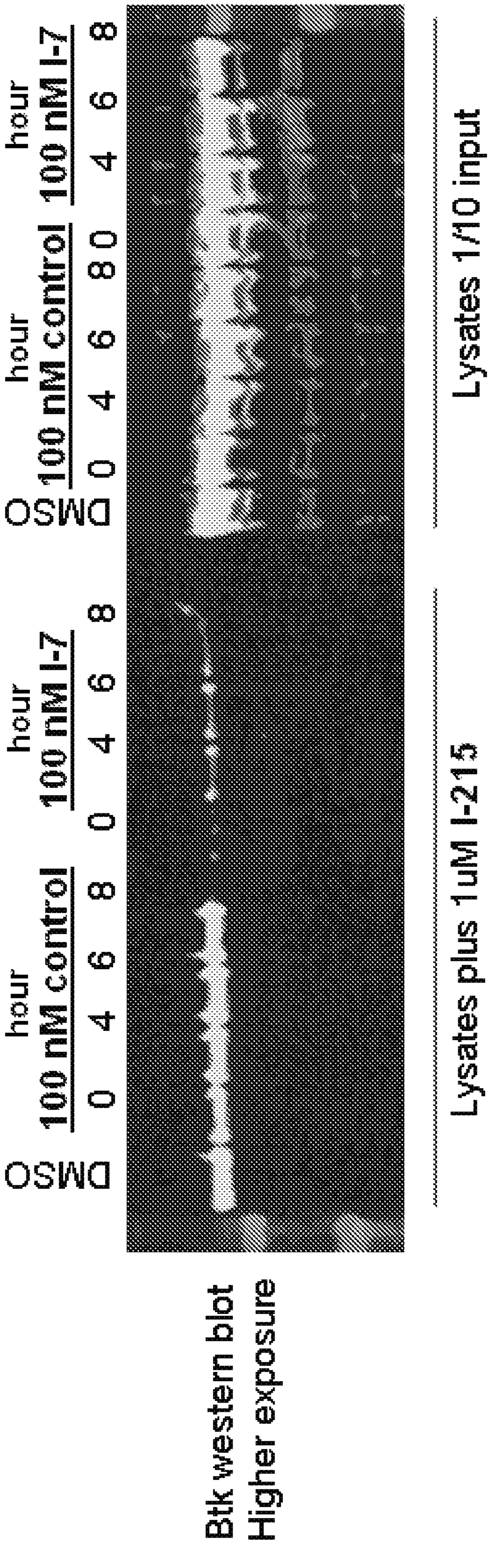
FIG. 18 depicts a Western blot for a washout experiment with compound I-7 and probe compound I-215.
Figure 19:
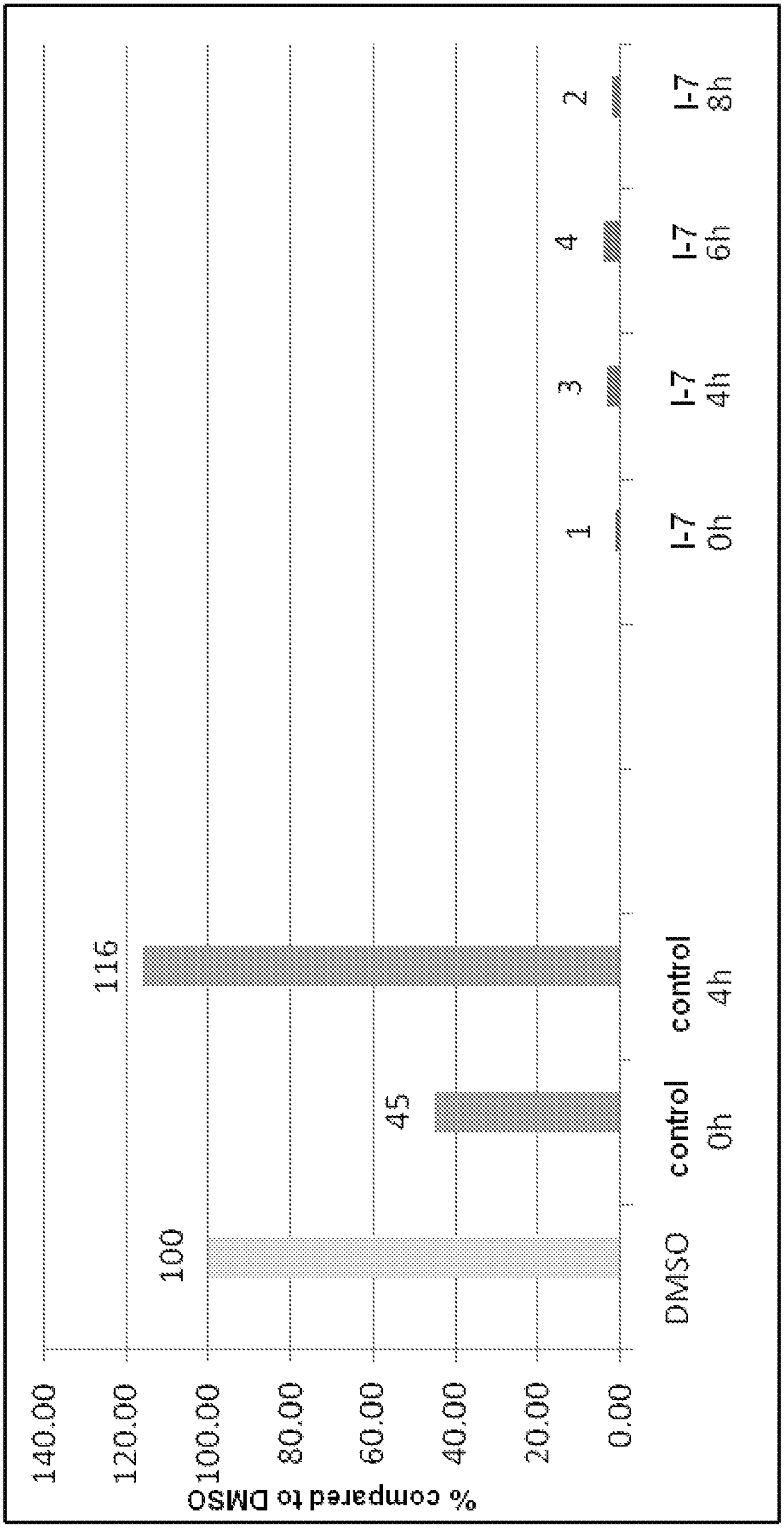
FIG. 19 depicts quantitation of the Western blot results in FIG. 18.

Ramos cells were incubated with 0.1 μM I-7 or a reversible BTK inhibitor control compound in serum free media for 1 hour at 37° C. The cells were then washed in compound-free media and lysed 0, 4, 6, or 8 hours after compound removal. Cell lysates were incubated with 1 μM I-215 for 1 hour at room temperature, then overnight at 4° C. with streptavidin-coupled agarose beads. Protein was boiled off the beads and BTK association was assessed by western blot. FIG. 18 shows the Western blot; FIG. 19 shows the quantitation of FIG. 18 and demonstrates all the BTK protein remains occupied by I-7 for over 8 hours. This suggests that the timeframe for re-synthesis of detectable BTK protein in Ramos cells is greater than 8 hours. In contrast, with the reversible inhibitor control, 45% of BTK protein is unbound and available to the probe at 0 hours and by 4 hours 100% of BTK protein is unbound and available to bind the probe. All samples were normalized to the DMSO-treated cells harvested at 0 hours.

Example 298

Measuring BTK Occupancy from In Vitro Samples by ELISA

In order to determine the amount of free BTK in cell or tissue lysates, an ELISA protocol was employed that utilizes a biotinylated probe compound that binds only to free, unoccupied BTK. The conjugated biotin is captured on a streptavidin-coated ELISA plate and detected with a mouse anti-BTK antibody (Becton Dickinson, Franklin Lakes, N.J., USA) and a secondary goat anti-mouse HRP antibody (Zymed, South San Francisco, Calif., USA).

All samples were prepared with equal concentrations of Biorad lysis buffer (Hercules, Calif., USA), 0.5% bovine serum albumin in PBS with 0.05% Tween-20 to give a final concentration of 1 μM I-215. Samples were incubated in a mixing plate for 1 hr at room temperature while shaking to allow probe compound I-215 to bind to free BTK. After incubation with I-215, samples were added to a washed, streptavidin-coated ELISA plate (Pierce, Rockford, Ill., USA) and incubated for 1 hr at room temperature while shaking. The plate was then washed with PBS containing 0.05% Tween-20 using an automatic plate washer. Anti-BTK antibody was prepared at 1:1000 dilution in 0.5% BSA in PBS (0.05% Tween-20) and added to the ELISA plate. The plate was incubated for 1 hr at room temperature while shaking. The plate was washed as described above and the secondary HRP antibody was prepared at 1:5000 dilution in 0.5% BSA in PBS (0.05% Tween-20). The plate was incubated and washed as described above. TMB was added to the plate, and $OD_{650}$ was monitored until reaching 1 OD unit. The reaction was then stopped with addition of $H_2SO_4$. The plate was analyzed using Gen 5 software, and a 4 Parameter Logistic curve was employed to quantitate samples. Recombinant BTK (Invitrogen, Carlsbad, Calif., USA) was used for the standard curve.

Table 19 shows results with Ramos cells reported as concentration at which >50% or >90% of BTK is occupied. A concentration designated as “A” is greater than 1 nM; a concentration designated as “B” is greater than 10 nM; and a concentration designated as “C” is greater than 50 nM.

TABLE 19

| Compound # | >50% occupancy | >90% occupancy |
|---|---|---|
| I-7 | A | B |
| I-182 | A | C |
| I-96 | A | B |

Example 299

Human Primary B Cell Covalent Probe Occupancy In Vitro

Human primary B cells were isolated as described in Example 256, then resuspended in RPMI media (10% serum). The compound to be analyzed was added at a 1:1000 dilution to media. Cells were incubated with compound in a tissue culture incubator for 1 h at 37° C. After incubation, the cells were pelleted, washed with 1×PBS, and lysed on ice for 45 min with occasional agitation. Samples were spun in a chilled microcentrifuge for 30 min at 14,000 rpm and the supernatant was isolated. The supernatant was analyzed as described in Example 283 using I-215. I-96 and I-182 occupied at least 50% of BTK at concentrations greater than 10 nM.

Example 300

Dog Primary B Cell Covalent Probe Occupancy In Vitro

Canine whole blood (30 mL) was diluted to 50 mL total with 1×PBS and layered on top of Histopaque-1077 (Sigma Aldrich). The whole blood-Histopaque was spun at 400×g for 30 min in a Beckman centrifuge with no brake. Peripheral blood mononuclear cells (PBMCs) were collected and pelleted at 400×g for 15 min. Red blood cells (RBCs) were lysed with 2.5 mL RBC lysis buffer (Boston Bioproducts) and the remaining PBMCs were washed 3 times in 1×PBS at 250×g. PBMCs were treated with compound at a 1:1000 dilution for one hour at 37° C., washed with PBS and lysed on ice for 45 minutes. The lysate was centrifuged for 30 minutes at 14,000×g and the supernatant collected. The supernatant was analyzed as described in Example 283 using I-215. I-96 occupied at least 50% of BTK at concentrations greater than 10 nM.

Example 301

Measuring BTK Occupancy from In Vivo Samples by ELISA

Rats were dosed orally with 30 mg/kg of compound and spleens were harvested either 2 or 24 hours after compound treatment. Rat spleens were disrupted between two microscope slides coated with frosted glass to recover single cell suspensions. Red blood cells were lysed by incubating with RBC lysis buffer (Boston BioProducts) for 2 minutes at room temperature, the cells were then resuspended in RPMI complete media and pelleted by centrifugation. Rat B cells were isolated by positive selection with B220+ antibody-magnetic bead conjugates, purified by MACS column and lysed in Bio-Rad lysis buffer at a concentration of 10 million cells/100 µl. Lysates were analyzed employing the biotinylated probe compound I-215 in an ELISA protocol as described in detail in Example 278. Table 20 shows the results.

TABLE 20

| Treatment | % BTK Occupancy 2 h | % BTK Occupancy 24 h |
|---|---|---|
| Vehicle | 0 | 0 |
| I-96 | 87 | 60 |
| I-4 | 87 | 68 |
| I-7 | 98 | 78 |
| I-190 | 18 | 13 |
| I-182 | 99 | 79 |

Example 302

Proteomics Analysis

Proteins that are covalently bound to I-215 in a cell lysate are identified using mass spectrometry. Cell lysate is incubated with 1 µM I-215 for 1 hour at room temperature, followed by the addition of streptavidin-coupled agarose beads. Mass spectrometry is used to identify proteins other than BTK. These are potential "off-target" interactions.

While a number of embodiments of this invention are described herein, it is apparent that the basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A method for inhibiting the activity of one or more of ErbB1, ErbB2, ErbB3, or ErbB4, or a mutant thereof, in a patient or in a biological sample comprising the step of administering to said patient or contacting said biological sample with a compound selected from the group consisting of:

I-338

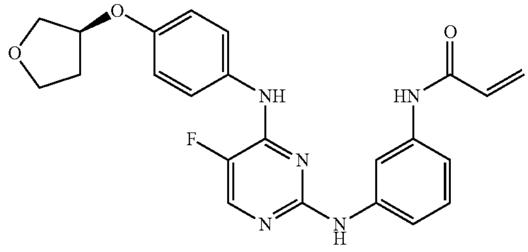

I-369

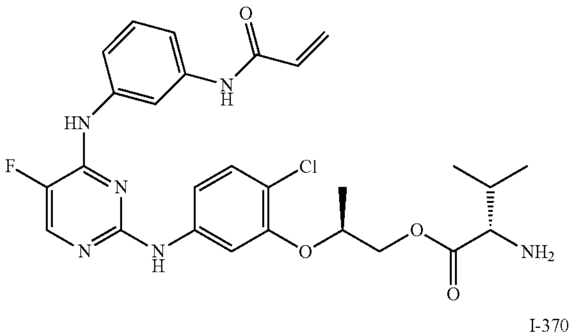

I-370

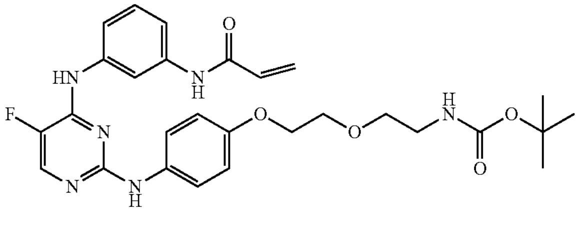

-continued

I-371

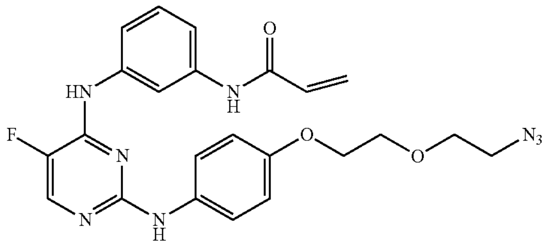

I-372

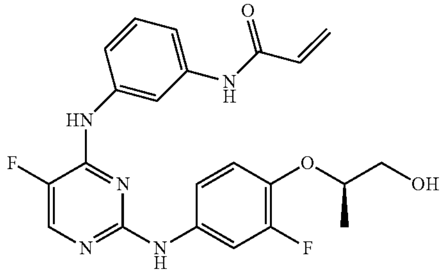

I-373

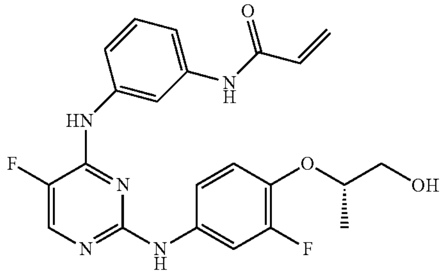

I-374

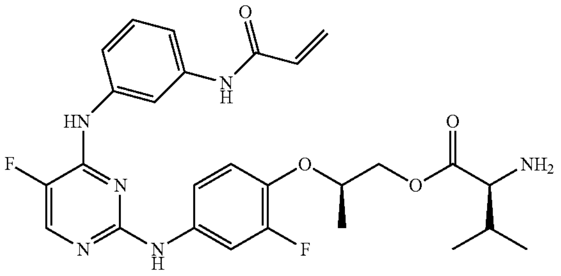

-continued
I-375
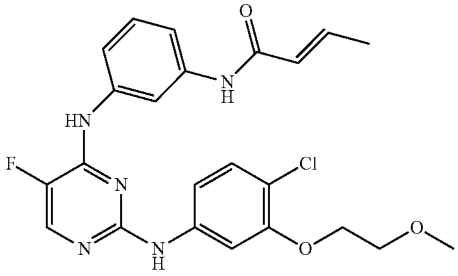
I-376
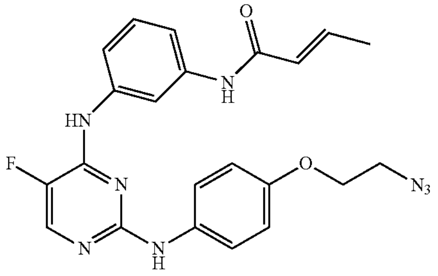
I-377
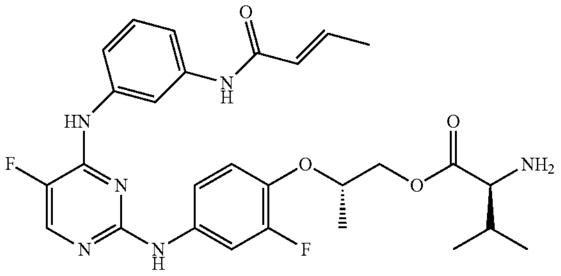
I-378
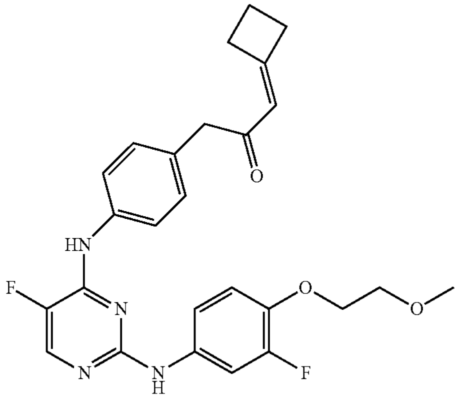
-continued
I-379
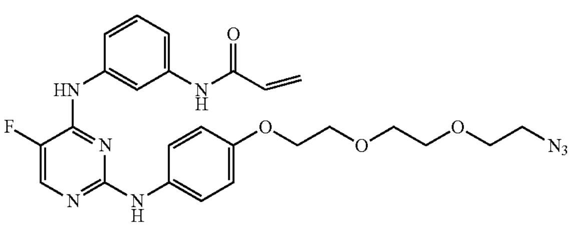
I-380
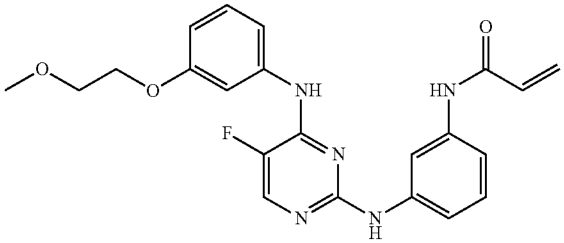
I-381
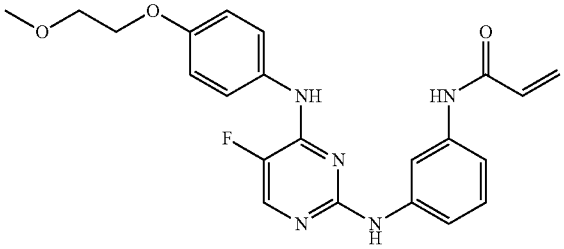
I-382
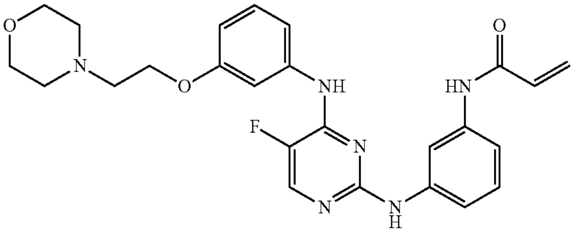
I-383
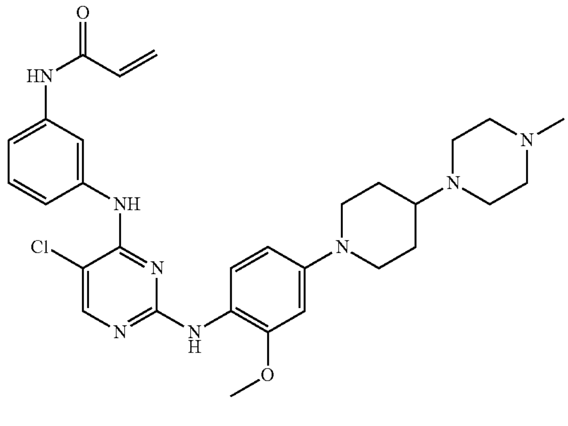

-continued
I-384
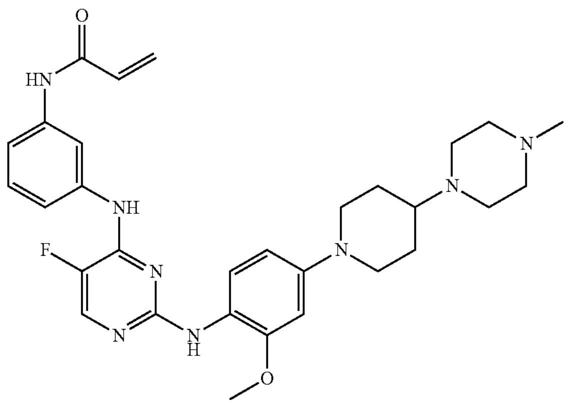
I-385
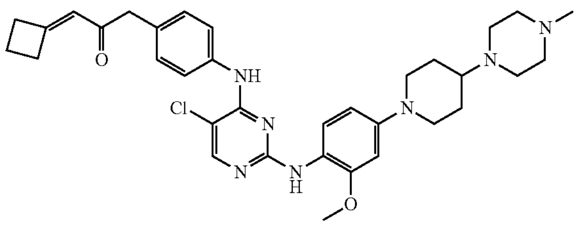
I-386
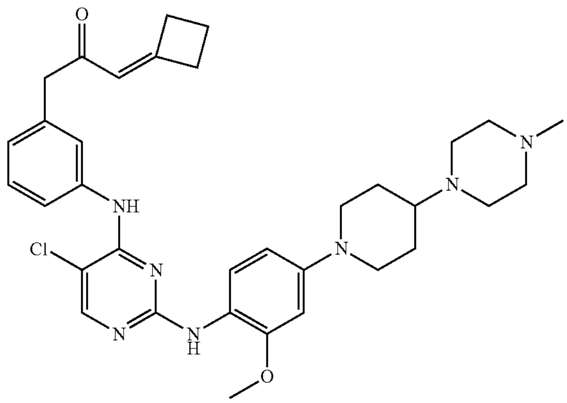
I-387
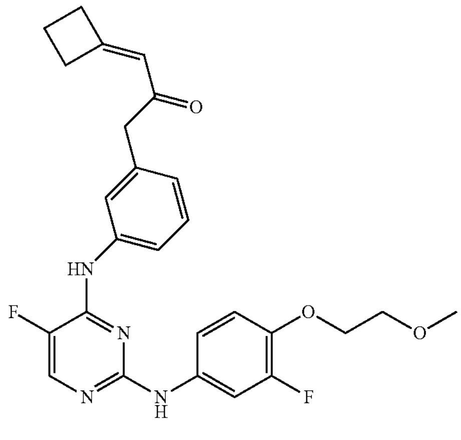
-continued
I-388
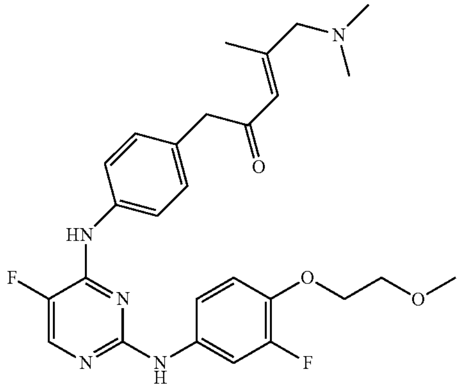
I-389
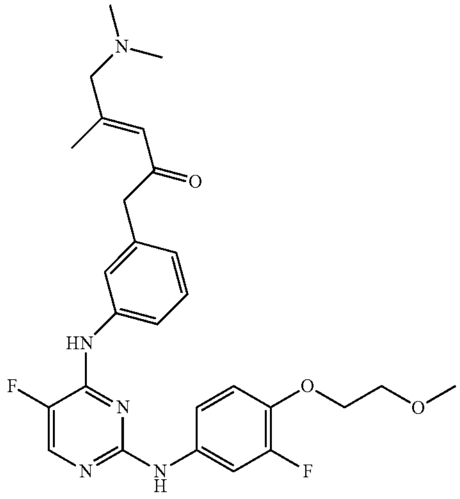
I-390
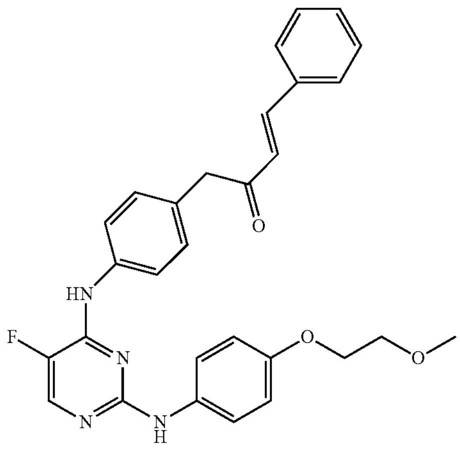

-continued

I-391

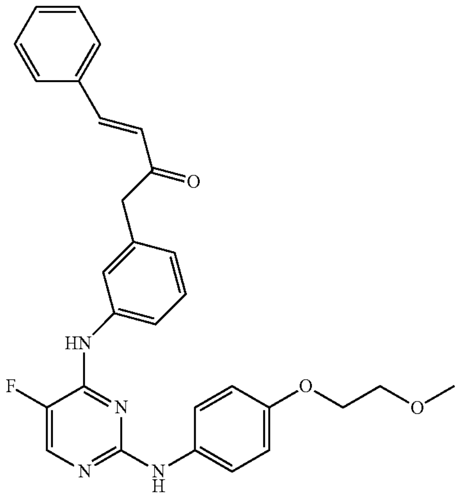

I-392

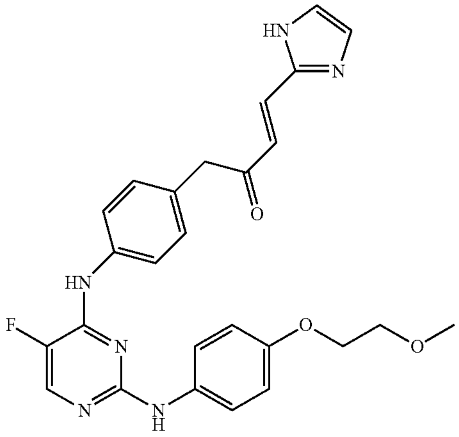

and

-continued

I-393

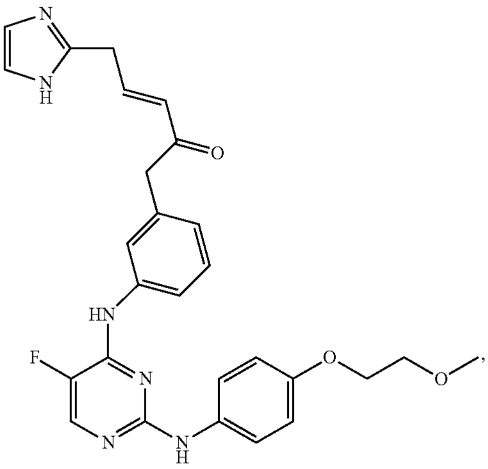

, or a pharmaceutically acceptable salt thereof.

2. The method according to claim 1, wherein the activity of the one or more of ErbB1 ErbB2, or ErbB4, or a mutant thereof, is inhibited irreversibly.

3. The method according to claim 2, wherein the activity of the one or more of ErbB1, ErbB2, or ErbB4, or a mutant thereof, is inhibited irreversibly by covalently modifying Cys797 of ErbB1, Cys805 of ErbB2 or Cys803 of ErbB4.

* * * * *

UNITED STATES PATENT AND TRADEMARK OFFICE

CERTIFICATE OF CORRECTION

PATENT NO. : 10,596,172 B2
APPLICATION NO. : 16/024514
DATED : March 24, 2020
INVENTOR(S) : Singh et al.

It is certified that error appears in the above-identified patent and that said Letters Patent is hereby corrected as shown below:

In the Claims

In Claim 1, Column 659, beginning at Line 15 and ending at Line 30, please delete the structure:

" 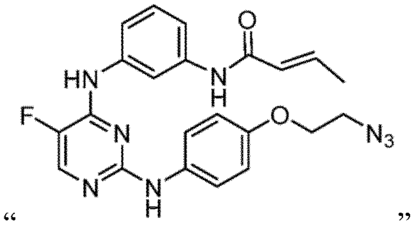 "

And insert the structure:

-- 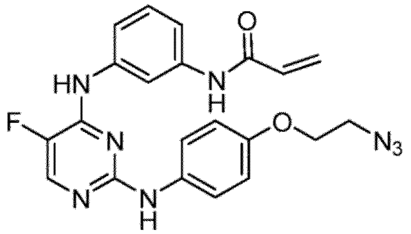 --

In Claim 1, Column 659, beginning at Line 32 and ending at Line 45, please delete the structure:

" 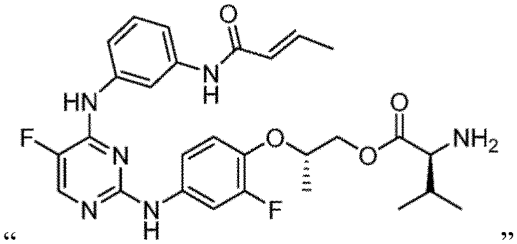 "

Signed and Sealed this
Sixteenth Day of February, 2021

Drew Hirshfeld
*Performing the Functions and Duties of the*
*Under Secretary of Commerce for Intellectual Property and*
*Director of the United States Patent and Trademark Office*

And insert the structure:
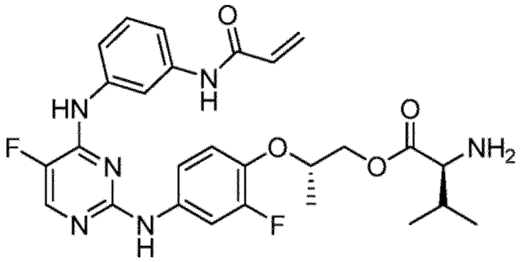
-- --